(12) United States Patent
Jahchan et al.

(10) Patent No.: US 12,378,311 B2
(45) Date of Patent: Aug. 5, 2025

(54) ANTI-MARCO ANTIBODIES AND USES THEREOF

(71) Applicant: Portsmouth Merger Sub II, LLC, Boston, MA (US)

(72) Inventors: Nadine Jahchan, San Carlos, CA (US); Michel Streuli, Atherton, CA (US); Xi Yang, Hillsborough, CA (US); Linda Liang, Mountain View, CA (US); Venkataraman Sriram, Berkeley, CA (US); Joshua Pollack, Richmond, CA (US); Kara Mojica, Dublin, CA (US); Vladislava Juric, San Mateo, CA (US); Linnea Haeggblom, San Francisco, CA (US); Leonard G. Presta, San Francisco, CA (US); Sayantan Mitra, Mountain View, CA (US)

(73) Assignee: Portsmouth Merger Sub II, LLC, Boston, MA (US)

( * ) Notice: Subject to any disclaimer, the term of this patent is extended or adjusted under 35 U.S.C. 154(b) by 0 days.

(21) Appl. No.: 18/068,237

(22) Filed: Dec. 19, 2022

(65) Prior Publication Data

US 2024/0084000 A1   Mar. 14, 2024

Related U.S. Application Data

(62) Division of application No. 17/529,927, filed on Nov. 18, 2021, now Pat. No. 11,572,407.

(60) Provisional application No. 63/244,662, filed on Sep. 15, 2021, provisional application No. 63/115,272, filed on Nov. 18, 2020.

(51) Int. Cl.
| | |
|---|---|
| *C07K 16/28* | (2006.01) |
| *A61K 39/00* | (2006.01) |
| *A61P 35/00* | (2006.01) |

(52) U.S. Cl.
CPC .............. *C07K 16/28* (2013.01); *A61P 35/00* (2018.01); *A61K 2039/505* (2013.01); *A61K 2039/507* (2013.01); *C07K 2317/21* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,916,766 | A | 6/1999 | Elshourbagy et al. |
| 6,197,931 | B1 | 3/2001 | Elshourbagy et al. |
| 8,597,946 | B2 | 12/2013 | Mule et al. |
| 10,882,917 | B2 | 1/2021 | Karlsson et al. |
| 2010/0227415 | A1 | 9/2010 | Winqvist et al. |
| 2012/0231023 | A1 | 9/2012 | Zurawski et al. |
| 2018/0000899 | A1 | 1/2018 | Francois et al. |
| 2018/0171021 | A1 | 6/2018 | Karlsson et al. |
| 2019/0263877 | A1 | 8/2019 | Yeung et al. |
| 2019/0336615 | A1 | 11/2019 | Thompson et al. |
| 2020/0071417 | A1 | 3/2020 | Loew et al. |
| 2020/0369773 | A1 | 11/2020 | Whitfield et al. |
| 2021/0000920 | A1 | 1/2021 | Quay |
| 2022/0153832 | A1 | 5/2022 | Jahchan et al. |

FOREIGN PATENT DOCUMENTS

| | | |
|---|---|---|
| EP | 3302558 A4 | 1/2019 |
| EP | 3759129 A1 | 1/2021 |
| WO | WO-2009114547 A2 | 9/2009 |
| WO | WO-2016/196612 A1 | 12/2016 |
| WO | WO-2017/062363 A1 | 4/2017 |
| WO | WO-2018/140831 A2 | 8/2018 |
| WO | WO-2018/195283 A1 | 10/2018 |
| WO | WO-2019/005641 A1 | 1/2019 |
| WO | WO-2019/036724 A2 | 2/2019 |
| WO | WO-2019/068007 A1 | 4/2019 |
| WO | WO-2019/126538 A1 | 6/2019 |
| WO | WO-2020/065406 A2 | 4/2020 |
| WO | WO-2020/0113274 A1 | 6/2020 |
| WO | WO-2020/142659 A2 | 7/2020 |
| WO | WO-2020/162696 A1 | 8/2020 |
| WO | WO-2020/191069 A1 | 9/2020 |
| WO | WO-2020/226633 A1 | 11/2020 |
| WO | WO-2020/252208 A2 | 12/2020 |
| WO | WO-2021/022218 A1 | 2/2021 |

OTHER PUBLICATIONS

Arredouani et al., "Scavenger Receptors SR-AI/II and MARCO limit pulmonary dendritic cell migration and allergic airway inflammation." The Journal of Immunology 178, No. 9 (2007): 5912-5920.

Arredouani et al., "The scavenger receptor MARCO is required for lung defense against pneumococcal pneumonia and inhaled particles." The Journal of experimental medicine 200, No. 2 (2004): 267-272.

Arredouani, "Is the scavenger receptor MARCO a new immune checkpoint?." Oncoimmunology 3, No. 10 (2014): e955709.

Bin et al., "Identification of uteroglobin-related protein 1 and macrophage scavenger receptor with collagenous structure as a lung-specific ligand-receptor pair." The Journal of Immunology 171, No. 2 (2003): 924-930.

Bowdish et al., "MARCO, TLR2, and CD14 are required for macrophage cytokine responses to mycobacterial trehalose dimycolate and *Mycobacterium tuberculosis*." PLoS pathogens 5, No. 6 (2009): e1000474.

Brown et al, "Silica-directed mast cell activation is enhanced by scavenger receptors." American journal of respiratory cell and molecular biology 36, No. 1 (2007): 43-52.

(Continued)

*Primary Examiner* — Ruixiang Li
(74) *Attorney, Agent, or Firm* — Goodwin Procter LLP

(57) ABSTRACT

Provided herein are anti-MARCO antibodies. Provided are also methods of generating and using anti-MARCO antibodies.

31 Claims, 80 Drawing Sheets

Specification includes a Sequence Listing.

(56) References Cited

OTHER PUBLICATIONS

Chen et al., "Defective microarchitecture of the spleen marginal zone and impaired response to a thymus-independent type 2 antigen in mice lacking scavenger receptors MARCO and SR-A." The Journal of Immunology 175, No. 12 (2005): 8173-8180.
Czerkies et al., "An interplay between scavenger receptor A and CD14 during activation of J774 cells by high concentrations of LPS." Immunobiology 218, No. 10 (2013): 1217-1226.
Dahl et al., "Protection against inhaled oxidants through scavenging of oxidized lipids by macrophage receptors MARCO and SR-AI/II." The Journal of clinical investigation 117, No. 3 (2007): 757-764.
Dorrington et al., "MARCO is required for TLR2-and Nod2-mediated responses to Streptococcus pneumoniae and clearance of pneumococcal colonization in the murine nasopharynx." The Journal of Immunology 190, No. 1 (2013): 250-258.
Eisinger et al., "Targeting a scavenger receptor on tumor-associated macrophages activates tumor cell killing by natural killer cells." Proceedings of the National Academy of Sciences 117, No. 50 (2020): 32005-32016.
Eisinger, "Revealing the secrets of MARCO: a target for cancer immunotherapy." PhD diss., Karolinska Institutet (Sweden), 2019, 84 pages.
Elomaa et al., "Cloning of a novel bacteria-binding receptor structurally related to scavenger receptors and expressed in a subset of macrophages." Cell 80, No. 4 (1995): 603-609.
Elomaa et al., "Structure of the human macrophage MARCO receptor and characterization of its bacteria-binding region." Journal of Biological Chemistry 273, No. 8 (1998): 4530-4538.
Elshourbagy et al., "Molecular characterization of a human scavenger receptor, human MARCO." European journal of biochemistry 267, No. 3 (2000): 919-926.
Georgoudaki et al., "Reprogramming tumor-associated macrophages by antibody targeting inhibits cancer progression and metastasis." Cell reports 15, No. 6 (2016): 2000-2011.
Ghosh et al., "MARCO regulates early inflammatory responses against influenza: a useful macrophage function with adverse outcome." American journal of respiratory cell and molecular biology 45, No. 5 (2011): 1036-1044.
Granucci et al., "The scavenger receptor MARCO mediates cytoskeleton rearrangements in dendritic cells and microglia." Blood 102, No. 8 (2003): 2940-2947.
Grolleau et al., "Inducible expression of macrophage receptor Marco by dendritic cells following phagocytic uptake of dead cells uncovered by oligonucleotide arrays." The Journal of Immunology 171, No. 6 (2003): 2879-2888.
Hamilton et al., "MARCO mediates silica uptake and toxicity in alveolar macrophages from C57BL/6 mice." Journal of Biological Chemistry 281, No. 45 (2006): 34218-34226.
Hirano et al., "Macrophage receptor with collagenous structure (MARCO) is a dynamic adhesive molecule that enhances uptake of carbon nanotubes by CHO-K1 cells." Toxicology and applied pharmacology 259, No. 1 (2012): 96-103.
Hirano et al., "Macrophage receptor with collagenous structure (MARCO) is processed by either macropinocytosis or endocytosis-autophagy pathway." PloS one 10, No. 11 (2015): e0142062.
Hornburg et al., "Single-cell dissection of cellular components and interactions shaping the tumor immune phenotypes in ovarian cancer." Cancer Cell (2021).
Jahchan et al., "Tuning the tumor myeloid microenvironment to fight cancer." Frontiers in immunology 10 (2019): 1611.
Jing et al., "Role of macrophage receptor with collagenous structure in innate immune tolerance." The Journal of Immunology 190, No. 12 (2013): 6360-6367.
Józefowsk et al., "Role of scavenger receptor MARCO in macrophage responses to CpG oligodeoxynucleotides." Journal of leukocyte biology 80, No. 4 (2006): 870-879.
Józefowski et al., Disparate regulation and function of the class A scavenger receptors SR-AI/II and MARCO. The Journal of Immunology 175, No. 12 (2005): 8032-8041.
Kangas et al., "Structure and chromosomal localization of the human and murine genes for the macrophage MARCO receptor." Genomics 58, No. 1 (1999): 82-89.
Kissick et al., "The scavenger receptor MARCO modulates TLR-induced responses in dendritic cells." PLoS One 9, No. 8 (2014): e104148.
Komine et al., "Examination of MARCO activity on dendritic cell phenotype and function using a gene knockout mouse." PloS one 8, No. 7 (2013): e67795.
Kraal et al., "The macrophage receptor MARCO." Microbes and infection 2, No. 3 (2000): 313-316.
La Fleur et al., "Expression of scavenger receptor MARCO defines a targetable tumor-associated macrophage subset in non-small cell lung cancer." International journal of cancer 143, No. 7 (2018): 1741-1752.
La Fleur et al., "Targeting MARCO and IL37R on Immunosuppressive Macrophages in Lung Cancer Blocks Regulatory T Cells and Supports Cytotoxic Lymphocyte Function." Cancer Research 81, No. 4 (2021): 956-967.
Lavin et al., "Innate immune landscape in early lung adenocarcinoma by paired single-cell analyses." Cell 169, No. 4 (2017): 750-765.
Matsushita et al., "Targeting MARCO can lead to enhanced dendritic cell motility and anti-melanoma activity." Cancer immunology, immunotherapy 59, No. 6 (2010): 875-884.
Mukhopadhyay et al., "SR-A/MARCO-mediated ligand delivery enhances intracellular TLR and NLR function, but ligand scavenging from cell surface limits TLR4 response to pathogens." Blood, The Journal of the American Society of Hematology 117, No. 4 (2011): 1319-1328.
Novakowski et al., "A naturally occurring transcript variant of MARCO reveals the SRCR domain is critical for function." Immunology and cell biology 94, No. 7 (2016): 646-655.
Ojala et al., "Crystal structure of the cysteine-rich domain of scavenger receptor MARCO reveals the presence of a basic and an acidic cluster that both contribute to ligand recognition." Journal of Biological Chemistry 282, No. 22 (2007): 16654-16666.
Palecanda et al., "Role of the scavenger receptor MARCO in alveolar macrophage binding of unopsonized environmental particles." The Journal of experimental medicine 189, No. 9 (1999): 1497-1506.
PCT/US2021/059955 International Preliminary Report on Patentability mailed Jun. 1, 2023, 16 pages.
PCT/US2021/059955 International Search Report and Written Opinion mailed Apr. 12, 2022, 21 pages.
Pikkarainen et al., "Expression of macrophage MARCO receptor induces formation of dendritic plasma membrane processes." Journal of Biological Chemistry 274, No. 16 (1999): 10975-10982.
Prokopec et al., "Cutting edge: Marginal zone macrophages regulate antigen transport by B cells to the follicle in the spleen via CD21." The Journal of Immunology 197, No. 6 (2016): 2063-2068.
Shi et al., "The Scavenger Receptor MARCO Expressed by Tumor-Associated Macrophages Are Highly Associated With Poor Pancreatic Cancer Prognosis." Frontiers in Oncology (2021): 4518.
Van der Laan et al., "Macrophage scavenger receptor MARCO: in vitro and in vivo regulation and involvement in the anti-bacterial host defense." Immunology letters 57, No. 1-3 (1997): 203-208.
Van der Laan et al., "Regulation and functional involvement of macrophage scavenger receptor MARCO in clearance of bacteria in vivo." The Journal of Immunology 162, No. 2 (1999): 939-947.
Xiao, Y., et al., Down-regulation of MARCO associates with tumor progression in hepatocellular carcinoma, Exp Cell Res, 383(2): 111542 (2019).
Xing et al., "Scavenger receptor MARCO contributes to macrophage phagocytosis and clearance of tumor cells." Experimental Cell Research 408, No. 2 (2021): 112862.

Anti-PD-1

PI-3009 + anti-PD-1

Controls

PI-3008 + anti-PD-1

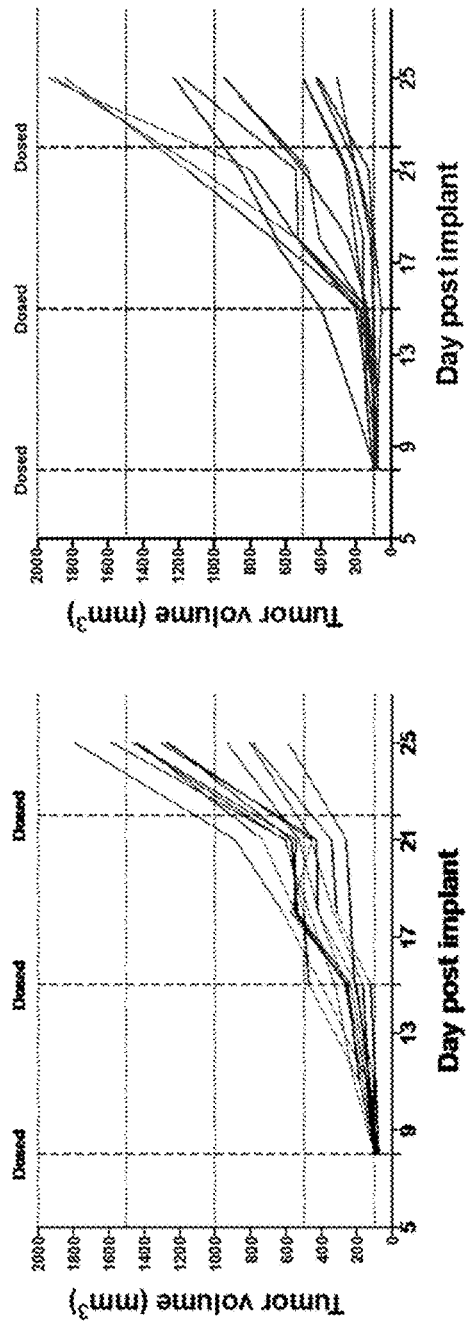
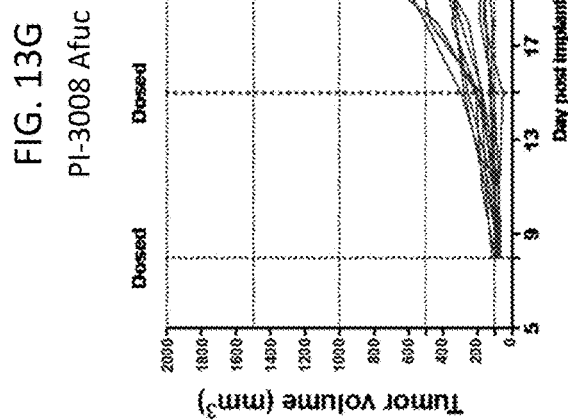
FIG. 13E Isotype
FIG. 13F PI-3008
FIG. 13G PI-3008 Afuc

FIG. 17A

```
seq              10         20         30         40         50
AbM              10         20         30         40         50  a
3061     EVQLVESGGGLVQPGSSLKLSCVAS KFTFSNYGMN WIRQAPKKGLEWIA LIYYNSNNKY
                                  *  *  *                    *  *  **
3-23*04  EVQLVESGGGLVQPGGSLRLSCAAS GFTFSSYAMS WVRQAPGKGLEWVS AISGSGGSTY
h3061-H1 EVQLVESGGGLVQPGGSLRLSCAAS KFTFSNYGMN WVRQAPGKGLEWVS LIYYNSNNKY
h3061-H2 EVQLVESGGGLVQPGGSLRLSCAAS KFTFSNYGMN WIRQAPGKGLEWIA LIYYNSNNKY
h3061-H3 EVQLVESGGGLVQPGGSLRLSCAAS GFTFSNYGMN WIRQAPGKGLEWIA LIYYNSNNKY
                                       #                     @ ## seq              60         70         80         90         100        110        120
AbM              60         70         80  abc    90                   110
3061     YADSVKGRFTISRDNSKNTLYLEMNSLRSEDTAMYYCAK SLTGGSDYFDS WGQGVMVTVSS
                              *       *      *                        **
3-23*04  YADSVKGRFTISRDNSKNTLYLQMNSLRAEDTAVYYCAK             WGQGTLVTVSS
h3061-H1 YADSVKGRFTISRDNSKNTLYLQMNSLRAEDTAVYYCAK SLTGGSDYFDS WGQGTLVTVSS
h3061-H2 YADSVKGRFTISRDNSKNTLYLQMNSLRAEDTAVYYCAK SLTGGSDYFDS WGQGTLVTVSS
h3061-H3 YADSVKGRFTISRDNSKNTLYLQMNSLRAEDTAVYYCAK SLTGGSDYFDS WGQGTLVTVSS
                                                      M                V @ isoaspartate formation substitutions: S/Q/A
asparagine deamidation substitutions: Q/S/A
```

FIG. 17B

```
seq              10         20         30         40         50
AbM              10         20         30         40         50
3061     DVQMTQSPSYLAASPGESVSISC KASKSIGTFLA WYQEKPEKTNKLLIY SGSTLQS
         *        *  * **  *                *   *  **
1-39*01  DIQMTQSPSSLSASVGDRVTITC RASQSISSYLN WYQQKPGKAPKLLIY AASSLQS
h3061-L1 DIQMTQSPSSLSASVGDRVTITC RASKSIGTFLA WYQQKPGKAPKLLIY SGSTLQS
         V                         K                E  TN seq              60         70         80         90         100
AbM              60         70         80         90         100
3061     GTPSRFSGSGSGTDFTLTIRNLEPEDFAVYYC QQHDEYPFT FGSGTKLEIK
                              **  *       *                 *
1-39*01  GVPSRFSGSGSGTDFTLTISSLQPEDFATYYC QQSYSTPP  FGQGTKLEIK
h3061-L1 GVPSRFSGSGSGTDFTLTISSLQPEDFATYYC QQHDEYPFT FGQGTKLEIK
               T
```

FIG. 18

```
seq              10         20         30         40         50
AbM         bbb     pp   bbb     b   bi bi  b   bi bi i     ii ibbi
3031        DIQMTQSPASLSTSLGETVSIEC LASEGISNDLA WYQQKSGKSPQLLIY AA
               *   *    * **   *        *         *            *

1-39*01     DIQMTQSPSSLSASVGDRVTITC RASQSISSYLN 
h3031-L1    DIQMTQSPSSLSASVGDRVTITC RASEGISNDLA WYQQKPGKAPKLLIY AA
h3031-L2    DIQMTQSPSSLSASVGDRVTITC RASEGISNDLA WYQQKPGKAPKLLIY AA
h3031-L3    DIQMTQSPSSLSASVGDRVTITC RASEGISNDLA WYQQKPGKAPKLLIY AA
h3031-L2b   DIQMTQSPSSLSASVGDRVTITC RASEGISNDLA WYQQKPGKAPKLLIY AA
h3031-L2c   DIQMTQSPSSLSTSVGDRVTITC RASEGISNDLA WYQQKPGKSPKLLIY AA
h3031-L2d   DIQMTQSPSSLSTSVGDRVTITC RASEGISNDLA WYQQKPGKSPKLLIY AA
                             T          L #         S seq              60         70         80         90        100
AbM           b        b    bbb   b     ib bib ibii-ib i  bbb
3031        GVPSRFSGSGSGTRYSLKISGMQPEDEADYFC QQSYSTPP   FGSGTKLEIK
              ***      *              **   *                   *

1-39*01     GVPSRFSGSGSGTDFTLTISSLQPEDFATYYC QQSYSTPP
h3031-L1    GVPSRFSGSGSGTDFTLTISSLQPEDFATYYC QQSYKYPLT FGQGTKLEIK
h3031-L2    GVPSRFSGSGSGTDYTLTISSLQPEDFATYYC QQSYKYPLT FGQGTKLEIK
h3031-L3    GVPSRFSGSGSGTDYTLTISSMQPEDFATYYC QQSYKYPLT FGQGTKLEIK
h3031-L2b   GVPSRFSGSGSGTDYTLTISSLQPEDFATYYC QQSYKYPLT FGQGTKLEIK
h3031-L2c   GVPSRFSGSGSGTDYTLTISSLQPEDFATYYC QQSYKYPLT FGQGTKLEIK
h3031-L2d   GVPSRFSGSGSGTDYTLTISSLQPEDEATYFC QQSYKYPLT FGQGTKLEIK
                                       E  F deamidation substitutions: Q/S/A/D
```

FIG. 21

```
humMARCO_SRCR   NSVSVRIVGSSNRGRAEVYYYSGTWGTICDDEWQNSDAIVFCRMLGYSKGRALYKVGAGTGQIWLDNVQCRGTESTLWSCTKNSWGHHDCSHEEDAGVECSV
murMARCO_SRCR   SFQRVRIMGGTNRGRAEVYYNNEWGTICDDDWDNDATVFCRMLGYSRGRALSSYGGGSGNIWLDNVNCRGTENSLWDCSKNSWGNHNCVHNEDAGVECS-
                **                   ***    *     * * *                   *             *  **    *   *   * mur_variant1    SFQRVRIMGGTNRGRAEVYYSGTWGTICDDDWDNDATVFCRMLGYSRGRALSSYGGGSGNIWLDNVNCRGTENSLWDCSKNSWGNHNCVHNEDAGVECS-
mur_variant2    SFQRVRIMGGTNRGRAEVYYNNEWGTICDDDEWQNSDATVFCRMLGYSRGRALSSYGGGSGNIWLDNVNCRGTENSLWDCSKNSWGNHNCVHNEDAGVECS-
mur_variant3    SFQRVRIMGGTNRGRAEVYYNNEWGTICDDDWDNDATVFCRMLGYSKGRALSSYGGGSGNIWLDNVNCRGTENSLWDCSKNSWGNHNCVHNEDAGVECS-
mur_variant4    SFQRVRIMGGTNRGRAEVYYNNEWGTICDDDWQNNDATVFCRMLGYSRGRALYKYGGGSGNIWLDNVNCRGTENSLWDCSKNSWGNHNCVHNEDAGVECS-
mur_variant5    SFQRVRIMGGTNRGRAEVYYNNEWGTICDDDWDNDATVFCRMLGYSRGRALSSYGGGSGNIWLDNVNCRGTESTLWSCTKNSWGNHNCVHNEDAGVECS-
mur_variant6    SFQRVRIMGGTNRGRAEVYYNNEWGTICDDDEWQNDATVFCRMLGYSRGRALSSYGGGSGNIWLDNVNCRGTENSLWDCSKNSWGNHHDCSHEEDAGVECS-
mur_variant7    NSVSVRIMGSSNRGRAEVYYNNEWGTICDDDWDNDATVFCRMLGYSRGRALSSYGGGSGNIWLDNVNCRGTENSLWDCSKNSWGNHNCVHNEDAGVECShumMARCO_SRCR   NSVSVRIVGSSNRGRAEVYYYSGTWGTICDDEWQNSDAIVFCRMLGYSKGRALYKVGAGTGQIWLDNVQCRGTESTLWSCTKNSWGHHDCSHEEDAGVECSV
murMARCO_SRCR   SFQRVRIMGGTNRGRAEVYYNNEWGTICDDDWDNDATVFCRMLGYSRGRALSSYGGGSGNIWLDNVNCRGTENSLWDCSKNSWGNHNCVHNEDAGVECS-
                **                   ***    *     * * *                   *             *  **    *   *   * hum-variant 1   NSVSVRIVGSSNRGRAEVYYYSGTWGTICDDEWQNSDAIVFCRMLGYSKGRALYKVGAGTGQIWLDNVQCRGTESTLWSCTKNSWGHHDCSHEEDAGVECSV
hum-variant 2   NSVSVRIVGSSNRGRAEVYYYSGTWGTICDDEWQNSDAIVFCRMLGYSRGRALYKVGAGTGQIWLDNVQCRGTESTLWSCTKNSWGHHDCSHEEDAGVECSV
hum-variant 3   NSVSVRIVGSSNRGRAEVYYYSGTWGTICDDEWQNSDAIVFCRMLGYSKGRALSSVGAGTGQIWLDNVQCRGTESTLWSCTKNSWGHHDCSHEEDAGVECSV
hum-variant 4   NSVSVRIVGSSNRGRAEVYYYSGTWGTICDDEWQNSDAIVFCRMLGYSKGRALYKVGAGTGQIWLDNVQCRGTENSLWDCSKNSWGHHDCSHEEDAGVECSV
hum-variant 5   NSVSVRIVGSSNRGRAEVYYYSGTWGTICDDEWQNSDAIVFCRMLGYSKGRALYKVGAGTGQIWLDNVQCRGTESTLWSCTKNSWGNHNCVHNEDAGVECSV
hum-variant 6   NSVSVRIVGSSNRGRAEVYYYSGTWGTICDDEWQNSDAIVFCRMLGYSKGRALYKVGAGTGQIWLDNVNCRGTESTLWSCSKNSWGHHDCSHEEDAGVECSV
hum-variant 7   SFQRVRIVGGTNRGRAEVYYYSGTWGTICDDEWQNSDAIVFCRMLGYSKGRALYKVGAGTGQIWLDNVQCRGTESTLWSCTKNSWGHHDCSHEEDAGVECSV
```

FIG. 22

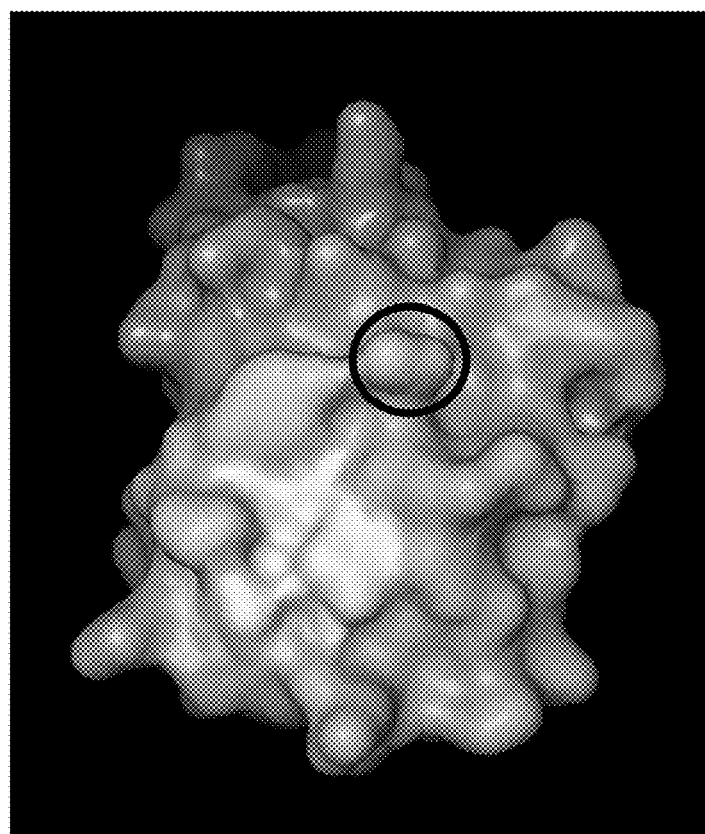
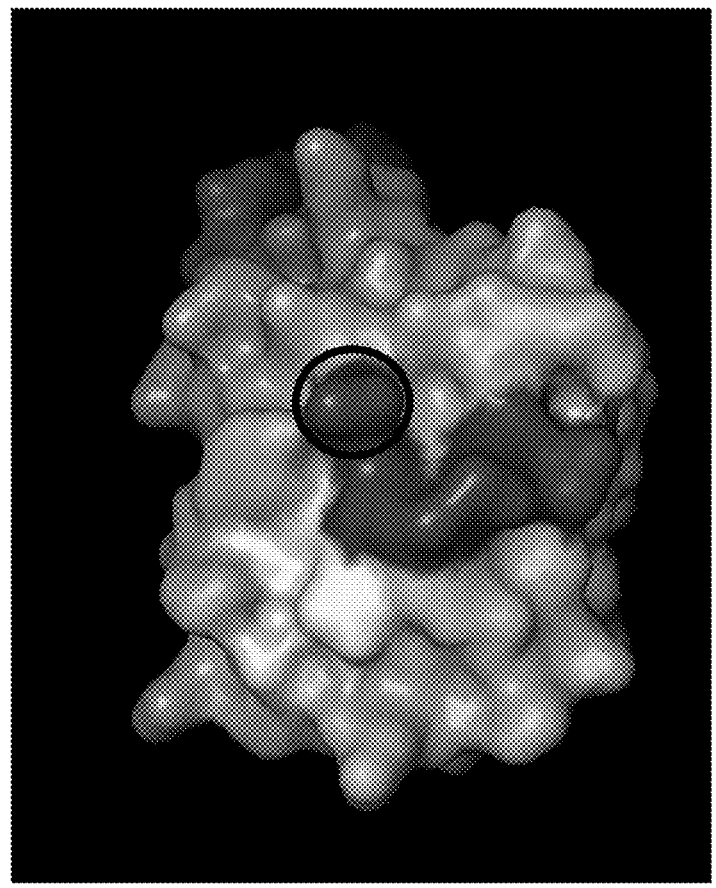
FIG. 24

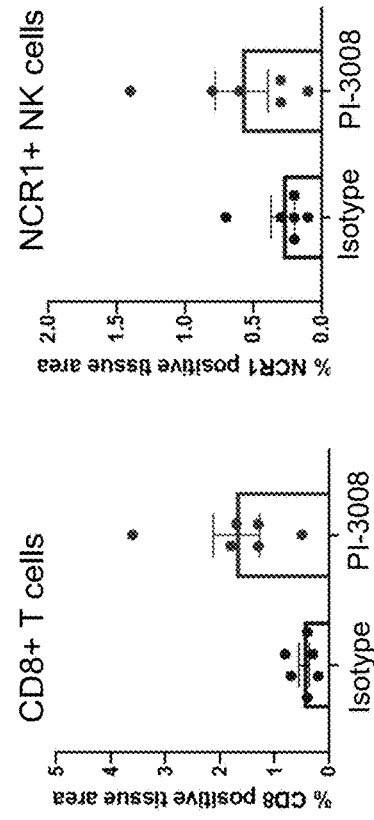
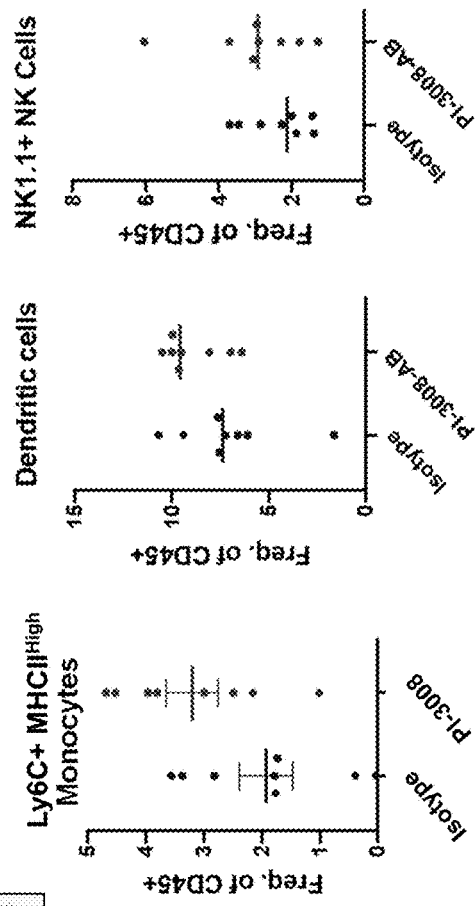
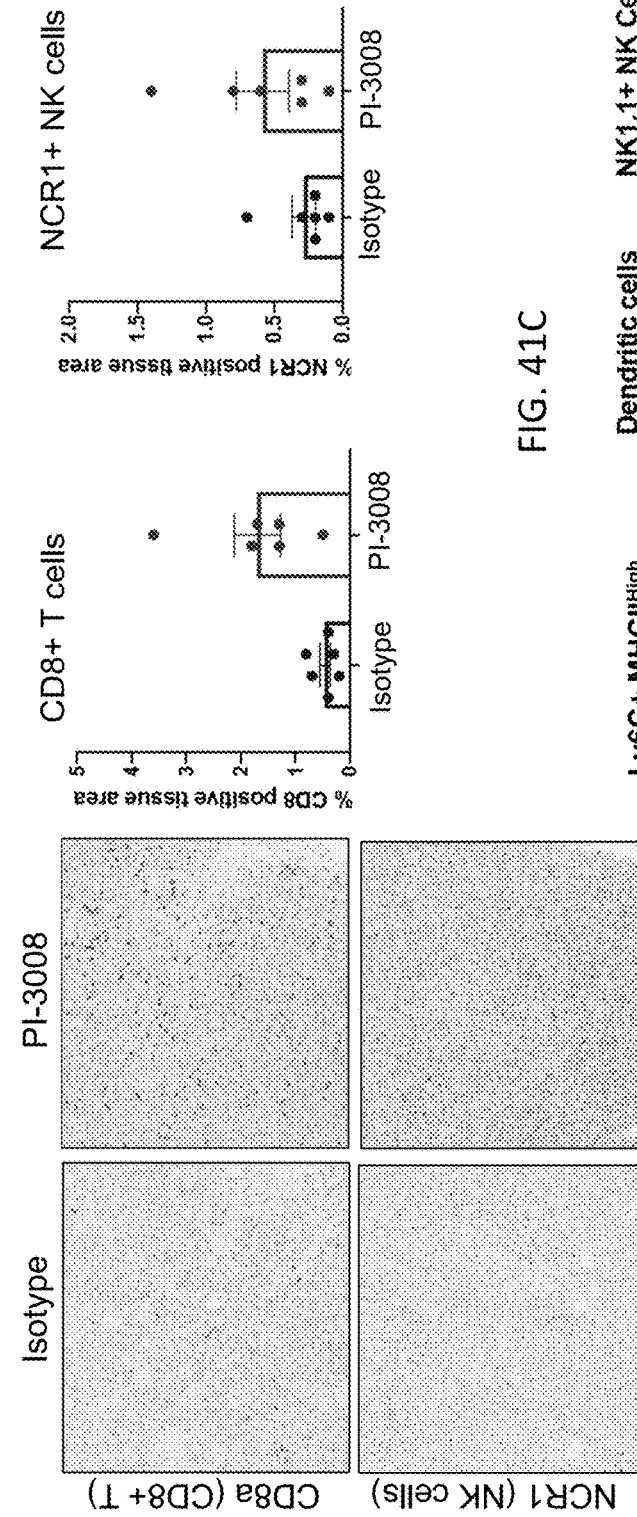
FIG. 41A
FIG. 41B
FIG. 41C

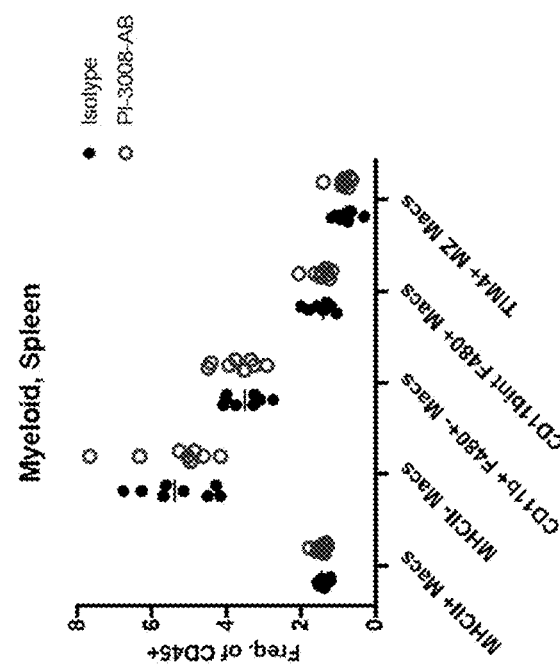
FIG. 44A Myeloid, Spleen
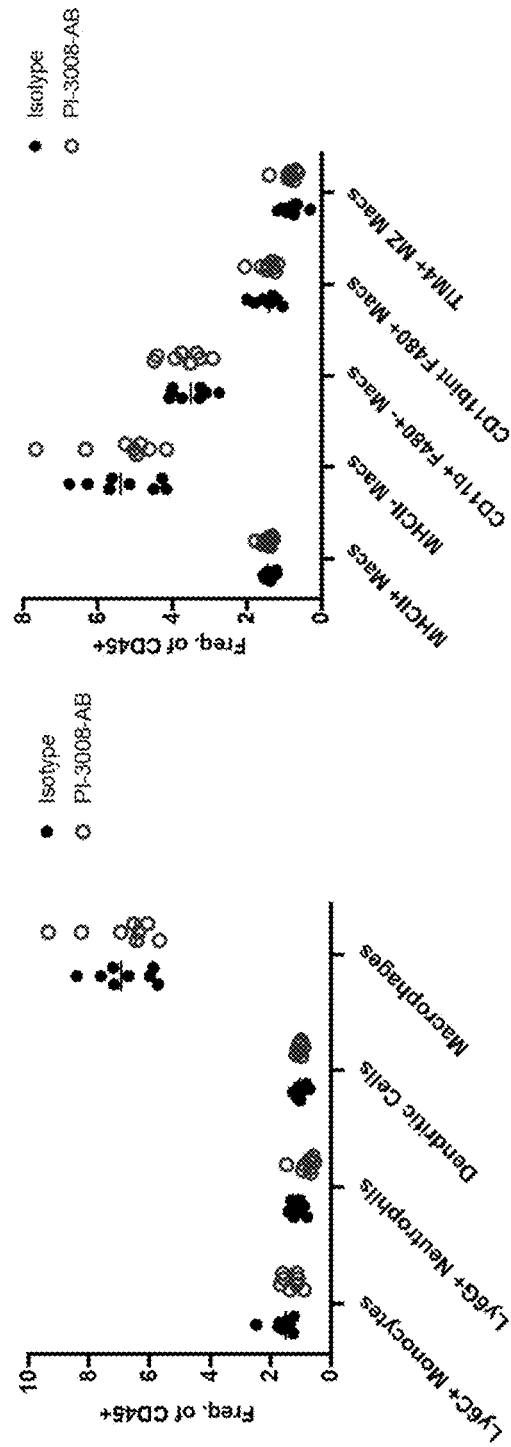
FIG. 44B Myeloid, Spleen
FIG. 44C Lymphoid, Spleen
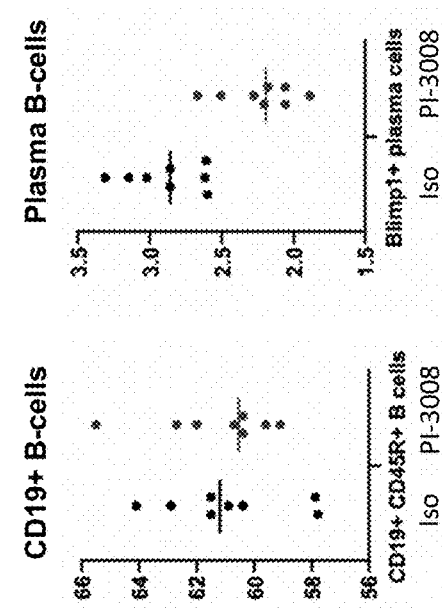
FIG. 44D
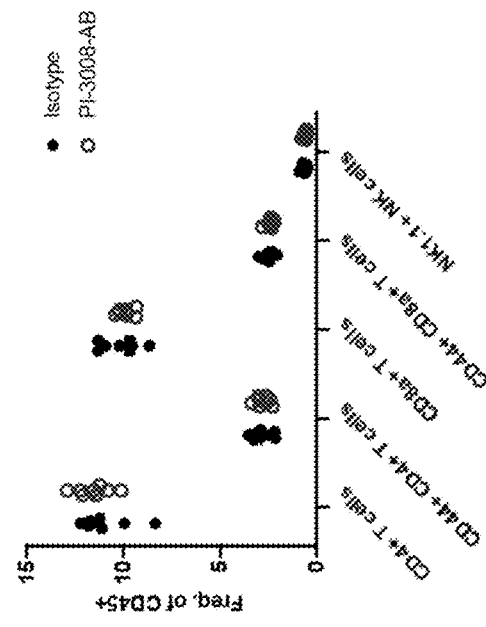

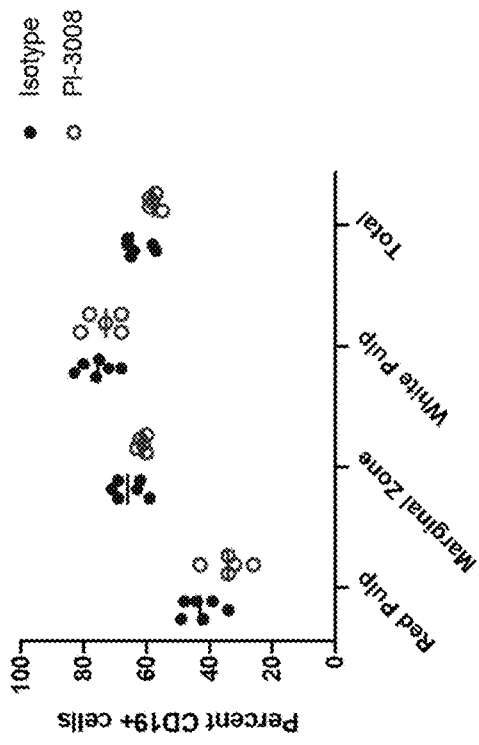
FIG. 48A MARCO
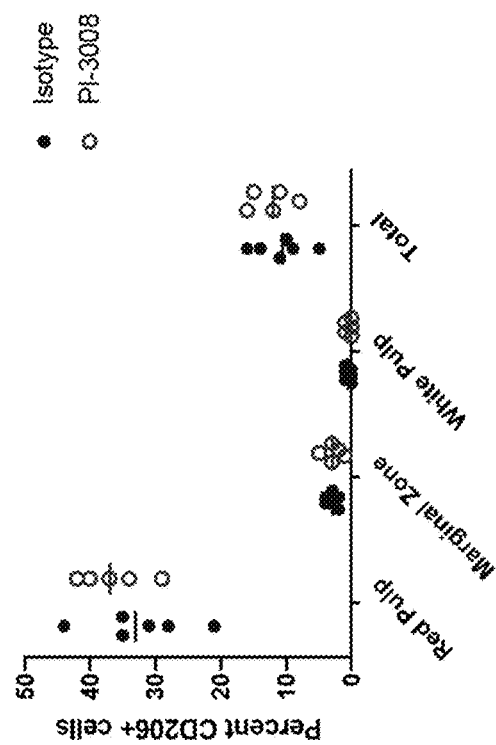
FIG. 48B CD19
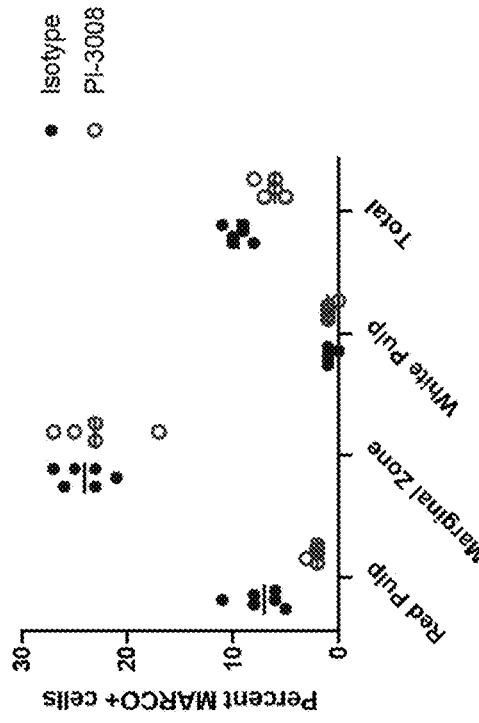
FIG. 48C CD8
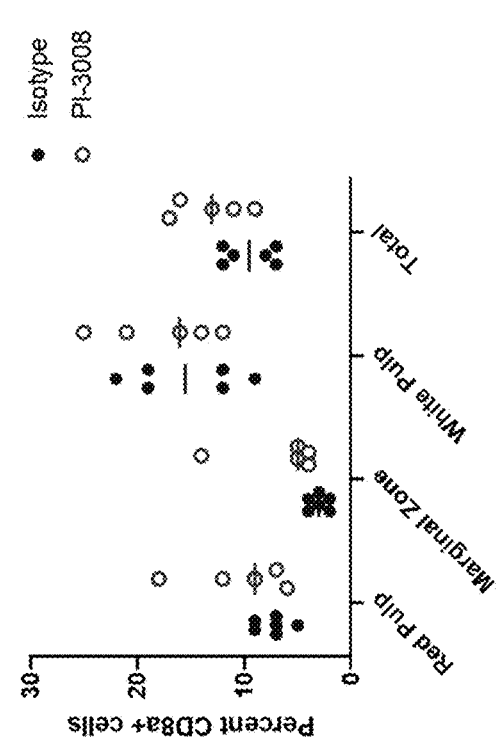
FIG. 48D CD206

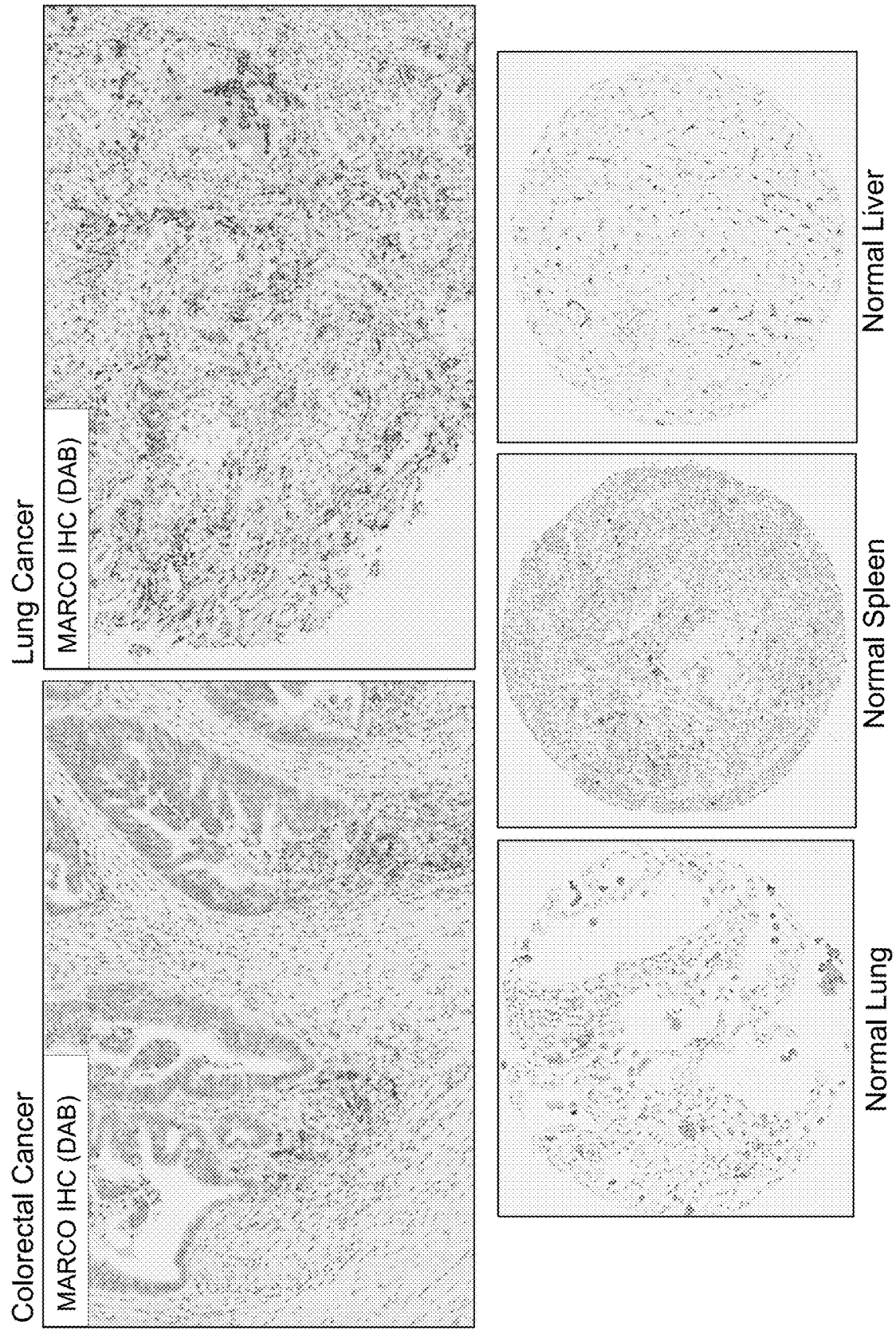

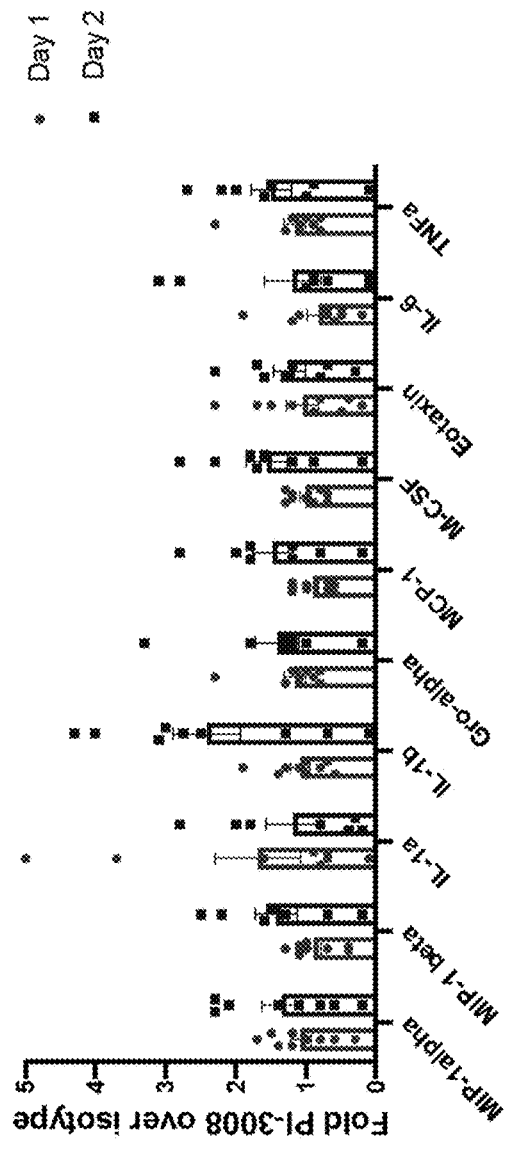
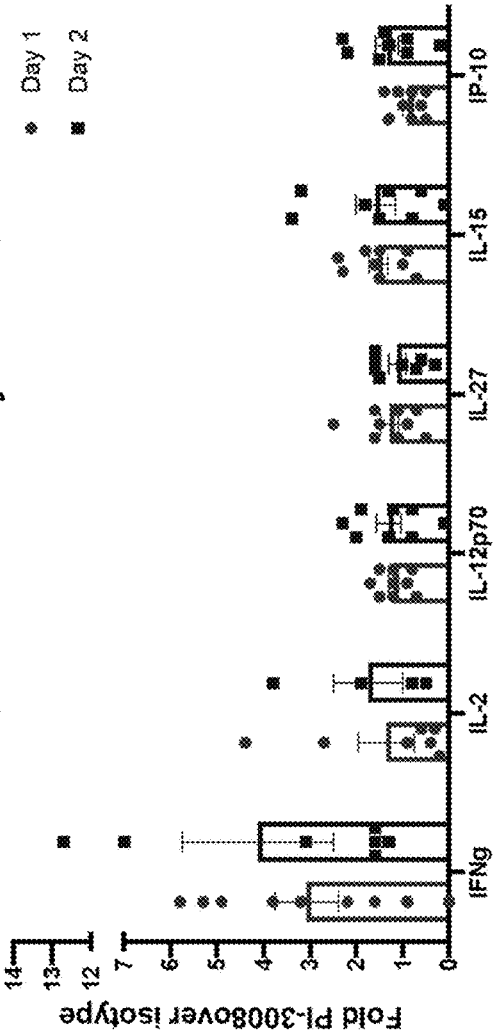
FIG. 58

ANTI-MARCO ANTIBODIES AND USES THEREOF

CROSS REFERENCE TO RELATED APPLICATIONS

This application is a divisional of U.S. application Ser. No. 17/529,927, filed Nov. 18, 2021, which claims priority to, and the benefit of, U.S. Application No. 63/115,272, filed Nov. 18, 2020, and U.S. Application No. 63/244,662, filed Sep. 15, 2021, each of which are hereby incorporated by reference in their entirety.

SEQUENCE LISTING

The instant application contains a Sequence Listing which has been submitted via Patent Center and is hereby incorporated by reference in its entirety. Said XML copy, created on May 9, 2023, is named PII-013D1_SL.xml, and is 763,317 bytes in size.

BACKGROUND

Myeloid populations of the tumor microenvironment prominently include monocytes and neutrophils (sometimes loosely grouped as myeloid-derived suppressor cells), macrophages, and dendritic cells. Although intra-tumoral myeloid populations, as a whole, have long been considered non-stimulatory or suppressive, it has more recently been appreciated that not all tumor-infiltrating myeloid cells are made equal.

Macrophage Receptor with Collagenous Structure (MARCO, also known as SCARA2; See HGNC: 6895 and NCBI: NM_006770.3 as available on May 8, 2020 via the NCBI website; herein incorporated by reference for all purposes) belongs to the class A scavenger receptor family and is expressed on peritoneal macrophages, as well as a subpopulation of macrophages in the spleen and lymph nodes (see Hirano S, PLoS ONE 2015: 10(11): e0142062). Recent studies have highlighted MARCO as a specific marker of TAMs in human cancer (Lavin et al., Cell; 2017: 169(4) 750-765). MARCO mediates macrophage internalization of unopsonized particles and microorganisms, such as bacteria (see Jing J, J Immunol 2013; 190:(12) 6360-6367). Recently, MARCO has been shown to be involved in the TLR-induced gene expression response in dendritic cells and may play a role in the inflammatory immune response (Kissick H T, PLoS oNE 2014; 9(8):2104148).

An unmet need exists for novel cancer therapeutic approaches that involve selectively removing, or re-programming or activating myeloid cells that are ineffective at stimulating immune cell responses (e.g., T-cells or NK cells), thereby enhancing the immune response within the tumor microenvironment.

SUMMARY

In some aspects, provided herein are isolated antibodies or antigen binding fragments thereof that binds to human Macrophage Receptor with Collagenous Structure (MARCO) (SEQ ID NO: 384).

In some embodiments, the antibody or antigen binding fragment thereof binds to a Scavenger Receptor Cysteine-Rich (SRCR) domain (residues 424-519 of SEQ ID NO: 384) of human MARCO.

In some aspects, provided herein are isolated antibodies or antigen binding fragments thereof that binds to a Scavenger Receptor Cysteine-Rich (SRCR) domain (residues 424-519 of SEQ ID NO: 384) of human Macrophage Receptor with Collagenous Structure (MARCO) (SEQ ID NO: 384).

In some embodiments, the antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYHVS (SEQ ID NO: 2), CDR-H2 comprises the sequence AIWTGGSIA (SEQ ID NO: 3), CDR-H3 comprises the sequence DLSDYYSSYTSFDY (SEQ ID NO: 4), CDR-L1 comprises the sequence ASEGISNDLA (SEQ ID NO: 431) or XASEGISNDLA (SEQ ID NO: 383), wherein X is arginine (R) or leucine (L), CDR-L2 comprises the sequence AASRLQD (SEQ ID NO: 8), and CDR-L3 comprises the sequence QQSYKYPLT (SEQ ID NO: 9).

In some embodiments, the antibody or antigen binding fragment thereof binds to at least one of the following residues: Q452, Y472, K473, E450, Q487, T499, H505, D507, S509, or E511 of MARCO (SEQ ID NO: 384).

In some embodiments, the antibody or antigen binding fragment comprises a chimeric, human, humanized, or rat antibody or antigen binding fragment.

In some embodiments, CDR-L1 comprises the sequence ASEGISNDLA (SEQ ID NO: 431).

In some embodiments, CDR-L1 comprises the sequence RASEGISNDLA (SEQ ID NO: 27).

In some embodiments, CDR-L1 comprises the sequence LASEGISNDLA (SEQ ID NO: 7).

In some embodiments, the VH sequence comprises the VH sequence set forth in SEQ ID NO: 61.

In some embodiments, the VH sequence comprises the VH sequence set forth in SEQ ID NO: 111.

In some embodiments, the VH sequence comprises a sequence selected from the sequences set forth in SEQ ID NO: 1, 11, 21, 31, 41, 51, 61, 71, 81, 91, 101, 111, 121, 131, 434, 444, and 474.

In some embodiments, the VL sequence comprises the VL sequence set forth in SEQ ID NO: 66.

In some embodiments, the VL sequence comprises the VL sequence set forth in SEQ ID NO: 116.

In some embodiments, the VL sequence comprises a sequence selected from the sequences set forth in SEQ ID NO: 6, 16, 26, 36, 46, 57, 66, 76, 86, 96, 106, 116, 126, 136, 439, 449, and 479.

In some embodiments, the VH sequence comprises the VH sequence set forth in SEQ ID NO: 61; and the VL sequence comprises the VL sequence set forth in SEQ ID NO: 66.

In some embodiments, the VH sequence comprises the VH sequence set forth in SEQ ID NO: 111; and the VL sequence comprises the VL sequence set forth in SEQ ID NO: 116.

In some embodiments, the VH sequence comprises a sequence selected from the sequences set forth in SEQ ID NO: 1, 11, 21, 31, 41, 51, 61, 71, 81, 91, 101, 111, 121, 131, 434, 444, and 474 and the VL sequence comprises a sequence selected from the sequences set forth in SEQ ID NO: 6, 16, 26, 36, 46, 57, 66, 76, 86, 96, 106, 116, 126, 136, 439, 449, and 479.

In some embodiments, the VH sequence comprises a sequence with at least 90%, 92%, 95%, 97%, 98%, or 99% identity to a sequence selected from the sequences set forth in SEQ ID NO: 1, 11, 21, 31, 41, 51, 61, 71, 81, 91, 101, 111, 121, 131, 434, 444, and 474 and/or the VL sequence comprises a sequence with at least 90%, 92%, 95%, 97%, 98%, or 99% identity to a sequence selected from the sequences set forth in SEQ ID NO: 6, 16, 26, 36, 46, 57, 66, 76, 86, 96, 106, 116, 126, 136, 439, 449, and 479.

In some embodiments, the antibody comprises a heavy chain sequence as set forth in SEQ ID NO: 65.

In some embodiments, the antibody comprises a heavy chain sequence as set forth in SEQ ID NO: 115.

In some embodiments, the antibody comprises a heavy chain sequence selected from the sequences set forth in SEQ ID NO: 5, 15, 125, 35, 45, 55, 65, 75, 85, 95, 105, 115, 125, 145, 438, 448, and 478.

In some embodiments, the antibody comprises a light chain sequence as set forth in SEQ ID NO: 70.

In some embodiments, the antibody comprises a light chain sequence as set forth in SEQ ID NO: 120.

In some embodiments, the antibody comprises a light chain sequence selected from the sequences set forth in SEQ ID NO: 10, 20, 30, 40, 50, 6, 70, 80, 90, 100, 110, 120, 130, 140, 443, 453, and 483.

In some embodiments, the antibody comprises a heavy chain sequence as set forth in SEQ ID NO: 65; and a light chain sequence as set forth in SEQ ID NO: 70.

In some embodiments, the antibody comprises a heavy chain sequence as set forth in SEQ ID NO: 115; and a light chain sequence as set forth in SEQ ID NO: 120.

In some embodiments, the antibody comprises a heavy chain sequence selected from the sequences set forth in SEQ ID NO: 5, 15, 125, 35, 45, 55, 65, 75, 85, 95, 105, 115, 125, 145, 438, 448, and 478; and a light chain sequence selected from the sequences set forth in SEQ ID NO: 10, 20, 30, 40, 50, 6, 70, 80, 90, 100, 110, 120, 130, 140, 443, 453, and 483.

In some embodiments, the antibody comprises a heavy chain sequence with at least 90%, 92%, 95%, 97%, 98%, or 99% identity to a sequence selected from the sequences set forth in SEQ ID NO: 5, 15, 125, 35, 45, 55, 65, 75, 85, 95, 105, 115, 125, 145, 438, 448, and 478; and/or a light chain sequence with at least 90%, 92%, 95%, 97%, 98%, or 99% identity to a sequence selected from the sequences set forth in SEQ ID NO: 10, 20, 30, 40, 50, 6, 70, 80, 90, 100, 110, 120, 130, 140, 443, 453, and 483.

In some aspects, provided herein are isolated antibodies or antigen binding fragments thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYAVN (SEQ ID NO: 232), CDR-H2 comprises the sequence WINTQTGKPT (SEQ ID NO: 233), CDR-H3 comprises the sequence DSYYYSSSLDY (SEQ ID NO: 234), CDR-L1 comprises the sequence ASAGISNDLA (SEQ ID NO: 432) or XASAGISNDLA (SEQ ID NO: 381), wherein X is arginine (R) or leucine (L), CDR-L2 comprises the sequence AASRLQD (SEQ ID NO: 238), and CDR-L3 comprises the sequence QQSYKYPWT (SEQ ID NO: 239).

In some embodiments, CDR-L1 comprises the sequence ASAGISNDLA (SEQ ID NO: 432).

In some embodiments, CDR-L1 comprises the sequence RASAGISNDLA (SEQ ID NO: 317).

In some embodiments, CDR-L1 comprises the sequence LASAGISNDLA (SEQ ID NO: 237).

In some embodiments, the VH sequence comprises the VH sequence as set forth in SEQ ID NO: 454.

In some embodiments, the VH sequence comprises a sequence selected from the sequences set forth in SEQ ID NO: 241, 311, 321, 331, 341, 351, 454, and 464.

In some embodiments, the VL sequence comprises the VL sequence as set forth in SEQ ID NO: 459.

In some embodiments, the VL sequence comprises a sequence selected from the sequences set forth in SEQ ID NO: 246, 316, 326, 336, 346, 356, 459, and 469.

In some embodiments, the VH sequence comprises the VH sequence as set forth in SEQ ID NO: 454; and the VL sequence comprises the VL sequence as set forth in SEQ ID NO: 459.

In some embodiments, the VH sequence comprises a sequence selected from the sequences set forth in SEQ ID NO: 241, 311, 321, 331, 341, 351, 454, and 464, and the VL sequence comprises a sequence selected from the sequences set forth in SEQ ID NO: 246, 316, 326, 336, 346, 356, 459, and 469.

In some embodiments, the VH sequence comprises a sequence with at least 90%, 92%, 95%, 97%, 98%, or 99% identity to a sequence selected from the sequences set forth in SEQ ID NO: 241, 311, 321, 331, 341, 351, 454, and 464; and/or the VL sequence comprises a sequence with at least 90%, 92%, 95%, 97%, 98%, or 99% identity to a sequence selected from the sequences set forth in SEQ ID NO: 246, 316, 326, 336, 346, 356, 459, and 469.

In some embodiments, the antibody comprises a heavy chain sequence as set forth in SEQ ID NO: 458.

In some embodiments, the antibody comprises a heavy chain sequence selected from the sequences set forth in SEQ ID NO: 245, 315, 325, 335, 345 355, 458, and 468.

In some embodiments, the antibody comprises a light chain sequence as set forth in SEQ ID NO: 463.

In some embodiments, the antibody comprises a light chain sequence selected from the sequences set forth in SEQ ID NO: 250, 320, 330, 340, 350, 360, 463, and 473.

In some embodiments, the antibody comprises a heavy chain sequence as set forth in SEQ ID NO: 458; and a light chain sequence as set forth in SEQ ID NO: 463.

In some embodiments, the antibody comprises a heavy chain sequence selected from the sequences set forth in SEQ ID NO: 245, 315, 325, 335, 345 355, 458, and 468; and a light chain sequence selected from the sequences set forth in SEQ ID NO: 250, 320, 330, 340, 350, 360, 463, and 473.

In some embodiments, the antibody comprises a heavy chain sequence with at least 90%, 92%, 95%, 97%, 98%, or 99% identity to a sequence selected from the sequences set forth in SEQ ID NO: 245, 315, 325, 335, 345 355, 458, and 468; and/or a light chain sequence with at least 90%, 92%, 95%, 97%, 98%, or 99% identity to a sequence selected from the sequences set forth in SEQ ID NO: 250, 320, 330, 340, 350, 360, 463, and 473.

In some aspects, provided herein are isolated antibodies or antigen binding fragments thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence KFTFSNYGMN (SEQ ID NO: 142), CDR-H2 comprises the sequence LIYYNSNNKY (SEQ ID NO: 143), CDR-H3 comprises the sequence SLTGGSDYFDS (SEQ ID NO: 144), CDR-L1 comprises the sequence ASKSIGTFLA (SEQ ID NO: 433) or XASKSIGTFLA (SEQ ID NO: 382), wherein X is arginine (R) or lysine (K), CDR-L2 comprises the sequence SGSTLQS (SEQ ID NO: 148), and CDR-L3 comprises the sequence QQHDEYPFT (SEQ ID NO: 149).

In some embodiments, CDR-L1 comprises the sequence ASKSIGTFLA (SEQ ID NO: 433).

In some embodiments, CDR-L1 comprises the sequence KASKSIGTFLA (SEQ ID NO: 147).

In some embodiments, CDR-L1 comprises the sequence RASKSIGTFLA (SEQ ID NO: 157).

In some embodiments, the VH sequence comprises a sequence selected from the sequences set forth in SEQ ID NO: 141, 151, 161, 171, 181, 191, 201, 211, and 221.

In some embodiments, the VL sequence comprises a sequence selected from the sequences set forth in SEQ ID NO: 146, 156, 166, 176, 186, 196, 206, 216, and 226.

In some embodiments, the VH sequence comprises a sequence selected from the sequences set forth in SEQ ID NO: 141, 151, 161, 171, 181, 191, 201, 211, and 221 and the VL sequence comprises a sequence selected from the sequences set forth in SEQ ID NO: 146, 156, 166, 176, 186, 196, 206, 216, and 226.

In some embodiments, the VH sequence comprises a sequence with at least 90%, 92%, 95%, 97%, 98%, or 99% identity to a sequence selected from the sequences set forth in SEQ ID NO: 141, 151, 161, 171, 181, 191, 201, 211, and 221 and/or the VL sequence comprises a sequence with at least 90%, 92%, 95%, 97%, 98%, or 99% identity to a sequence selected from the sequences set forth in SEQ ID NO: 146, 156, 166, 176, 186, 196, 206, 216, and 226.

In some embodiments, the antibody comprises a heavy chain sequence selected from the sequences set forth in SEQ ID NO: 145, 155, 165, 175, 185, 195, 205, 215, and 225.

In some embodiments, the antibody comprises a light chain sequence selected from the sequences set forth in SEQ ID NO: 150, 160, 170, 180, 190, 200, 210, 220, and 230.

In some embodiments, the antibody comprises a heavy chain sequence selected from the sequences set forth in SEQ ID NO: 145, 155, 165, 175, 185, 195, 205, 215, and 225 and a light chain sequence selected from the sequences set forth in SEQ ID NO: 150, 160, 170, 180, 190, 200, 210, 220, and 230.

In some embodiments, the antibody comprises a heavy chain sequence comprises a sequence with at least 90%, 92%, 95%, 97%, 98%, or 99% identity to a sequence selected from the sequences set forth in SEQ ID NO: 145, 155, 165, 175, 185, 195, 205, 215, and 225 and/or a light chain sequence comprises a sequence with at least 90%, 92%, 95%, 97%, 98%, or 99% identity to a sequence selected from the sequences set forth in SEQ ID NO: 150, 160, 170, 180, 190, 200, 210, 220, and 230.

In another aspect, provided herein are isolated antibodies or antigen binding fragments that bind to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYYLH (SEQ ID NO: 252), CDR-H2 comprises the sequence YINPNNAYTS (SEQ ID NO: 253), CDR-H3 comprises the sequence DTTDYYNLHFAY (SEQ ID NO: 254), CDR-L1 comprises the sequence LTSEGISNDLA (SEQ ID NO: 257), CDR-L2 comprises the sequence DASRLED (SEQ ID NO: 258), and CDR-L3 comprises the sequence QQSYKYPLT (SEQ ID NO: 259).

In some embodiments, the VH sequence comprises a sequence as set forth in SEQ ID NO: 251 or 261.

In some embodiments, the VL sequence comprises a sequence as set forth in SEQ ID NO: 256 or 266.

In some embodiments, the VH sequence comprises a sequence as set forth in SEQ ID NO: 251 or 261, and the VL sequence comprises a sequence s set forth in SEQ ID NO: 256 or 266.

In some embodiments, the VH sequence comprises a sequence with at least 90%, 92%, 95%, 97%, 98, or 99% identity to a sequence as set forth in SEQ ID NO: 251 or 261, and/or the VL sequence comprises a sequence with at least 90%, 92%, 95%, 97%, 98, or 99% identity to a sequence set forth in SEQ ID NO: 256 or 266.

In some embodiments, the antibody comprises a heavy chain sequence as set forth in SEQ ID NO: 255 or 265.

In some embodiments, the antibody comprises a light chain sequence as set forth in SEQ ID NO: 260 or 270.

In some embodiments, the antibody comprises a heavy chain sequence as set forth in SEQ ID NO: 255 or 265; and a light chain sequence as set forth in SEQ ID NO: 260 or 270.

In some embodiments, the antibody comprises a heavy chain sequence comprises a sequence with at least 90%, 92%, 95%, 97%, 98%, or 99% identity to a sequence as set forth in SEQ ID NO: 255 or 265; and a light chain sequence comprises a sequence with at least 90%, 92%, 95%, 97%, 98%, or 99% identity to a sequence as set forth in SEQ ID NO: 260 or 270.

In another aspect, provided herein are isolated antibodies or antigen binding fragments that bind to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYTLS (SEQ ID NO: 362), CDR-H2 comprises the sequence AIWGGDNTD (SEQ ID NO: 363), CDR-H3 comprises the sequence ELGGSFDY (SEQ ID NO: 364), CDR-L1 comprises the sequence KTSQNINKKLD (SEQ ID NO: 367), CDR-L2 comprises the sequence YTNNLQT (SEQ ID NO: 368), and CDR-L3 comprises the sequence YQYDSGFT (SEQ ID NO: 369).

In some embodiments, the VH sequence comprises a sequence as set forth in SEQ ID NO: 361 or 371.

In some embodiments, the VL sequence comprises a sequence as set forth in SEQ ID NO: 366 or 376.

In some embodiments, the VH sequence comprises a sequence as set forth in SEQ ID NO: 361 or 371, and the VL sequence comprises a sequence s set forth in SEQ ID NO: 366 or 376.

In some embodiments, the VH sequence comprises a sequence with at least 90%, 92%, 95%, 97%, 98, or 99% identity to a sequence as set forth in SEQ ID NO: 361 or 371, and/or the VL sequence comprises a sequence with at least 90%, 92%, 95%, 97%, 98, or 99% identity to a sequence set forth in SEQ ID NO: 366 or 376.

In some embodiments, the antibody comprises a heavy chain sequence as set forth in SEQ ID NO: 365 or 375; and a light chain sequence as set forth in SEQ ID NO: 370 or 380.

In some embodiments, the antibody comprises a heavy chain sequence comprises a sequence with at least 90%, 92%, 95%, 97%, 98%, or 99% identity to a sequence as set forth in SEQ ID NO: 365 or 375; and a light chain sequence comprises a sequence with at least 90%, 92%, 95%, 97%, 98%, or 99% identity to a sequence as set forth in SEQ ID NO: 370 or 380.

In some embodiments, the antibody is a monoclonal antibody, a neutral antibody, an antagonistic antibody, an agonist antibody, a polyclonal antibody, an afucosylated antibody, a human antibody, a humanized antibody, a chimeric antibody, a full-length antibody, and an scFv.

In some embodiments, the antibody is an scFv.

In some embodiments, the antibody is a monoclonal antibody.

In some embodiments, the antibody is a humanized antibody.

In some embodiments, the antibody is a human antibody.

In some embodiments, the antibody comprises an Fc region.

In some embodiments, the Fc region comprises a human Fc region.

In some embodiments, the antibody comprises an active human Fc region.

In some embodiments, the antibody comprises a heavy chain human constant region of a class selected from IgG, IgA, IgD, IgE, and IgM.

In some embodiments, the antibody comprises a human heavy chain constant region of the class IgG and a subclass selected from IgG1, IgG2, IgG3, and IgG4.

In some embodiments, the human Fc region comprises a wild-type, human IgG1 Fc region.

In some embodiments, the human Fc region comprises a wild-type, human IgG4 Fc region.

In some embodiments, the Fe region comprises one or more amino acid substitutions, wherein the one or more substitutions result in increased antibody half-life, increased ADCC activity, increased ADCP activity, increased CDC activity, decreased ADCC activity, decreased ADCP activity, or decreased CDC activity compared with an Fc region without the one or more substitutions.

In some embodiments, the Fc region binds an Fcγ Receptor selected from the group consisting of: FcγRI, FcγRIIa, FcγRIIb, FcγRIIc, FcγRIIIa, and FcγRIIIb.

In some embodiments, the antibody binds to human MARCO with a KD of less than or equal to about 0.5, 1, 2, 3, 4, 5, 6, or 7×10-9 M, as measured by surface plasmon resonance (SPR) assay.

In some embodiments, binding of the antibody to human MARCO is divalent cation dependent.

In some embodiments, binding of the antibody to human MARCO is divalent cation independent.

In some embodiments, the divalent cation comprises Ca2+ or Mg2+.

In some embodiments, the antibody binds an extracellular domain of human MARCO.

In some embodiments, the antibody binds to soluble MARCO.

In some embodiments, the antibody binds the SRCR domain of human MARCO, cynomolgus MARCO, or human and cynomolgus MARCO.

In some embodiments, the antibody binds the SRCR domain (residues 424-519 of SEQ ID NO: 384) of human MARCO.

In some embodiments, the antibody or antigen binding fragment thereof binds to at least one of: Q452, Y472, K473, E450, Q487, T499, H505, D507, S509, or E511 of MARCO (SEQ ID NO: 384).

In some embodiments, the antibody has receptor-ligand blocking activity.

In some embodiments, the antibody induces increased expression of at least one cytokine or chemokine upon contact with a cell as compared to an isotype control antibody, optionally as measured by a nucleic acid or protein assay.

In some embodiments, the at least one cytokine or chemokine comprises at least one of IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, upon cell contact the antibody induces increased NK cell activation, B cell regulation T cell proliferation, T cell activation, or T cell differentiation as compared to an isotype control antibody, optionally as measured by a nucleic acid or protein assay.

In some embodiments, upon cell contact the antibody induces IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1β and/or IL-18 secretion and/or phagocytosis as compared to an isotype control antibody.

In some embodiments, upon cell contact the antibody induces repolarization of myeloid M2-like TAMS to M1-like tumor associated macrophages (TAMs), and/or repolarization of mMDSCs to pro-inflammatory monocytes as compared to an isotype control antibody.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils, plasma B cells, marginal zone B cells, CD19+ B cells, MHCII− monocytes, and/or MHCII− macrophages as compared to an isotype control antibody.

In some embodiments, upon administration to a subject the antibody induces an increased anti-tumor memory response as compared to an isotype control antibody.

In some embodiments, a cell is a MARCO+ cell.

In some embodiments, the cell is a human MARCO+ cell.

In some embodiments, the MARCO+ cell is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the antibody binds to MARCO on the cell surface of a MARCO+ cell.

In some embodiments, the antibody: competes for binding to human MARCO with humanized PI-HX-3011, PI-HX-3031, PI-HX-3043, PI-HX-3061, PI-HX-3092 antibody; binds to human MARCO; binds to cynomolgus MARCO; binds to human and cynomolgus MARCO; binds to the SRCR domain of human MARCO; binds to the SRCR domain of cynomolgus MARCO; binds to the SRCR domain of human and cynomolgus MARCO; binds to human or cynomolgus MARCO in a divalent cation dependent manner; binds to human or cynomolgus MARCO in a divalent cation independent manner; stimulates MARCO signaling upon binding to a MARCO+ cell; induces one or more immune signaling pathways upon binding to a MARCO+ cell; induces cytokine or chemokine secretion upon binding to a MARCO+ cell, optionally wherein the cytokine or chemokine is IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin; induces increased NK cell activation, B cell regulation, T cell proliferation, T cell activation, or T cell differentiation upon binding to a MARCO+ cell; induces IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response; decreases a cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway; induces inflammasome activation as determined by IL-1β and/or IL-18 secretion and/or phagocytosis; induces repolarization of myeloid M2-like TAMs to M1-like TAMS, and/or repolarization of mMDSCs to pro-inflammatory monocytes; modulates B cells in the spleen upon binding to a MARCO+ cell; increases CD8+ T cells, CD4+ T cells, NK cells, dendritic cells, MHCII+ macrophages, MHCIIhigh monocytes, and/or MHCIImid monocytes in the spleen and/or tumor; increases macrophages, marginal zone macrophages, follicular B cells, and/or red pulp macrophages in the spleen and/or tumor; decreases TAMs, tumor associated neutrophils, plasma B cells, marginal zone B cells, CD19+ B cells, MHCII– monocytes, and/or MHCII– macrophages in the spleen and/or tumor; induces changes in cell adhesion, cytoskeletal, chemotaxis and cell migration upon binding to a MARCO+ cell; induces cell signaling pathways comprising adhesion, migration, chemotaxis cell cycle, T cell receptor, phagocytosis, autophagy, and wnt pathways upon binding to a MARCO+ cell; disables MARCO+ myeloid cells; or is capable of any combination above.

In some embodiments, the antibody is for use as a medicament.

In some embodiments, the antibody is for use in the treatment of a cancer or infection.

In some embodiments, the antibody is for use in the treatment of a cancer, wherein the cancer is selected from a solid tumor and a liquid tumor.

In another aspect, provided herein are isolated polynucleotides or sets of polynucleotides encoding the antibody described herein, a VH thereof, a VL thereof, a light chain thereof, a heavy chain thereof, or an antigen-binding portion thereof; optionally the isolated polynucleotide or set of polynucleotides is cDNA.

In another aspect, provided herein are vectors or set of vectors comprising the polynucleotide or set of polynucleotides.

In another aspect, provided herein are host cells comprising the polynucleotide or set of polynucleotides or the vector or set of vectors.

In another aspect, provided herein are methods of producing an antibody comprising expressing the antibody or antigen binding fragment thereof with the host cell and isolating the expressed antibody.

In another aspect, provided herein are pharmaceutical compositions comprising the isolated antibody or antigen binding fragment thereof and a pharmaceutically acceptable excipient.

In another aspect, provided herein are kits comprising the isolated antibody or antigen binding fragment thereof or a pharmaceutical composition and instructions for use.

In another aspect, provided herein are methods of increasing an immune response in a subject comprising administering to the subject a composition comprising an anti-human MARCO antibody or antigen binding fragment thereof.

In some embodiments, the composition comprises an antibody that binds to the SRCR domain (residues 424-519 of SEQ ID NO: 384) of human MARCO.

In some embodiments, the composition comprises the isolated antibody or the pharmaceutical composition.

In some embodiments, the antibody has receptor-ligand blocking activity.

In some embodiments, the increased immune response is an adaptive immune response.

In some embodiments, the increased immune response is an innate immune response.

In some embodiments, the increased immune response comprises increased expression of at least one cytokine or chemokine by a cell as compared to an isotype control antibody, optionally as measured by a nucleic acid or protein assay.

In some embodiments, the at least one cytokine or chemokine comprises at least one of IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, the increased immune response comprises increased NK cell activation, B cell regulation T cell proliferation, T cell activation, or T cell differentiation as compared to an isotype control antibody, optionally as measured by a nucleic acid or protein assay.

In some embodiments, upon cell contact the antibody induces In some embodiments, upon cell contact the antibody induces IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1β and/or IL-18 secretion and/or phagocytosis as compared to an isotype control antibody.

In some embodiments, upon cell contact the antibody induces repolarization of myeloid M2-like TAMs to M1-like TAMS, and/or repolarization of mMDSCs to pro-inflammatory monocytes as compared to an isotype control antibody.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils, plasma B cells, marginal zone B cells, CD19+ B cells, MHCII- monocytes, and/or MHCII- macrophages as compared to an isotype control antibody.

In some embodiments, the antibody induces an increased memory immune response.

In some embodiments, the cell is a MARCO+ cell.

In some embodiments, the cell is a human MARCO+ cell.

In some embodiments, the MARCO+ cells is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the antibody binds to MARCO on the cell surface of a MARCO+ cell.

In some embodiments, the subject is human.

In some embodiments, the subject has cancer.

In some embodiments, the cancer is a solid cancer.

In some embodiments, the cancer is a liquid cancer.

In some embodiments, the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

In some embodiments, the cancer is colon cancer, breast cancer, basal-like breast cancer, ovarian cancer, or gastric cancer.

In some embodiments, MARCO is expressed at a higher level on a tumor immune cell as compared to a non-tumor immune cell.

In some embodiments, IL-10 is expressed at a higher level on a tumor immune cell as compared to a non-tumor immune cell.

In another aspect, provided herein are methods of treating cancer in a subject, comprising administering to the subject a composition comprising an anti-human MARCO antibody or antigen binding fragment thereof.

In some embodiments, the composition comprises an antibody that binds to the SRCR domain (residues 424-519 of SEQ ID NO: 384) of human MARCO.

In some embodiments, the composition comprises the antibody disclosed herein or the pharmaceutical composition thereof.

In another aspect, provided herein are methods of treating cancer in a subject, comprising administering to the subject a composition comprising the anti-human MARCO antibody or antigen binding fragment thereof or a pharmaceutical composition thereof.

In some embodiments, the subject has previously received, is concurrently receiving, or will subsequently receive an immunotherapy.

In some embodiments, the immunotherapy is at least one of: a checkpoint inhibitor; a checkpoint inhibitor of T cells; and an anti-PD1 antibody.

In some embodiments, the immunotherapy comprises an anti-PD1 antibody.

In another aspect, provided herein are methods of treating cancer in a subject, comprising administering to the subject a composition comprising an anti-human MARCO antibody or antigen binding fragment thereof and an immunotherapy.

In some embodiments, the composition comprises an antibody that binds to the SRCR domain (residues 424-519 of SEQ ID NO: 384) of human MARCO.

In some embodiments, the composition comprises the antibody disclosed herein or the pharmaceutical composition thereof.

In some embodiments, the immunotherapy is at least one of: a checkpoint inhibitor; a checkpoint inhibitor of T cells; and an anti-PD1 antibody.

In some embodiments, the immunotherapy comprises an anti-PD1 antibody.

In some embodiments, the subject is human.

In some embodiments, the cancer is a solid cancer.

In some embodiments, the cancer is a liquid cancer.

In some embodiments, the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

In some embodiments, the cancer is colon cancer, breast cancer, basal-like breast cancer, ovarian cancer, or gastric cancer.

In some embodiments, MARCO is expressed at a higher level on a tumor immune cell as compared to a non-tumor immune cell.

In some embodiments, IL-10 is expressed at a higher level on a tumor immune cell as compared to a non-tumor immune cell.

In some embodiments, the antibody induces an increased anti-tumor memory response as compared to an isotype control antibody.

In some embodiments, the administration increases an immune response in the subject as compared to an isotype control antibody.

In some embodiments, the increased immune response is an adaptive immune response.

In some embodiments, the increased immune response is an innate immune response.

In some embodiments, the increased immune response comprises expression of at least one cytokine or chemokine by a cell as compared to an isotype control antibody, optionally as measured by a nucleic acid or protein assay.

In some embodiments, the at least one cytokine or chemokine comprises at least one of IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, the increased immune response comprises increased NK cell activation, B cell regulation T cell proliferation, T cell activation, or T cell differentiation as compared to an isotype control antibody, optionally as measured by a nucleic acid or protein assay.

In some embodiments, upon cell contact the antibody induces In some embodiments, upon cell contact the antibody induces IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1β and/or IL-18 secretion and/or phagocytosis as compared to an isotype control antibody.

In some embodiments, upon cell contact the antibody induces repolarization of myeloid M2-like TAMs to M1-like TAMS, and/or repolarization of mMDSCs to pro-inflammatory monocytes as compared to an isotype control antibody.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils (TANs), plasma B cells, marginal zone B cells, CD19+ B cells, MHCII− monocytes, and/or MHCII− macrophages as compared to an isotype control antibody.

In some embodiments, the cell is a MARCO+ cell.

In some embodiments, the cell is a human MARCO+ cell.

In some embodiments, the MARCO+ cell is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the antibody binds to MARCO on the cell surface of a MARCO+ cell.

In another aspect, provided herein are methods of disabling myeloid cells that express MARCO on the cell surface, comprising contacting the myeloid cells with an anti-human MARCO antibody or antigen binding fragment thereof.

In another aspect, provided herein are methods of disabling myeloid cells that express MARCO on the cell surface, comprising contacting the myeloid cells with the antibody described herein or the pharmaceutical composition thereof.

In some embodiments, the antibody disables the myeloid cells by at least one of ADCC activity, CDC activity, or ADCP activity, optionally wherein the antibody disables the myeloid cells by ADCC activity, optionally wherein the antibody disables the myeloid cells by CDC activity, and optionally wherein the antibody disables the myeloid cells by ADCP activity.

In some embodiments, the myeloid cell is a MARCO+ cell.

In some embodiments, the myeloid cell is a human MARCO+ cell.

In some embodiments, the myeloid cell is a monocyte, a monocytic Myeloid Derived Suppressor Cell (mMDSC), or a macrophage.

In some embodiments, the macrophage is a tumor associated macrophage (TAM) or a monocyte-derived macrophage (MDM).

In some embodiments, the myeloid cells are intratumoral or splenic myeloid cells.

In some embodiments, the contacting is in vitro or in vivo.

In some embodiments, the contacting occurs in vivo in a subject, optionally wherein the subject has cancer.

In some embodiments, the subject is a human.

In some embodiments, the cancer is a solid cancer.

In some embodiments, the cancer is a liquid cancer.

In some embodiments, the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

In some embodiments, the cancer is colon cancer, breast cancer, basal-like breast cancer, ovarian cancer, or gastric cancer.

In some embodiments, the contacting increases an immune response in the subject as compared to an isotype control antibody.

In some embodiments, the increased immune response is an adaptive immune response.

In some embodiments, the increased immune response is an innate immune response.

In some embodiments, the increased immune response comprises expression of at least one cytokine or chemokine by a cell as compared to an isotype control antibody, optionally as measured by a nucleic acid or protein assay.

In some embodiments, the at least one cytokine or chemokine comprises at least one of IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin.

In some embodiments, the increased immune response comprises increased NK cell activation, B cell regulation T cell proliferation, T cell activation, or T cell differentiation as compared to an isotype control antibody, optionally as measured by a nucleic acid or protein assay.

In some embodiments, upon cell contact the antibody IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response as compared to an isotype control antibody.

In some embodiments, upon cell contact the antibody decreases cell cycle pathway, cell survival, cell adhesion, Myc target pathway, E2F targets pathway, hypoxia pathway, mTOR signaling pathway, PI3K-AKT signaling pathway, Src signaling pathway, PKC signaling pathway, epithelial to mesenchymal transition signaling pathway, oxidative phosphorylation, or MAPK signaling pathway as compared to an isotype control antibody.

In some embodiments, upon cell contact the antibody induces inflammasome activation as determined by IL-1 and/or and IL-18 secretion and/or phagocytosis.

In some embodiments, upon cell contact the antibody induces repolarization of myeloid M2-like TAMs to M1-like TAMS, and/or repolarization of mMDSCs to pro-inflammatory monocytes.

In some embodiments, upon cell contact the antibody increases CD8+ T cells, CD4+ T cells, NK cells, dendritic cells, MHCII+ macrophages, MHCIIhigh monocytes, or MHCIImid monocytes as compared to an isotype control antibody.

In some embodiments, upon cell contact the antibody increases macrophages, marginal zone macrophages, follicular B cells, and/or red pulp macrophages in the spleen as compared to an isotype control antibody.

In some embodiments, upon cell contact the antibody decreases TAMs, tumor associated neutrophils, plasma B cells, marginal zone B cells, CD19+ B cells, MHCII- monocytes, and/or MHCII- macrophages as compared to an isotype control antibody.

In some embodiments, the subject has previously received, is concurrently receiving, or will subsequently receive an immunotherapy.

In some embodiments, the immunotherapy is at least one of: a checkpoint inhibitor; a checkpoint inhibitor of T cells; and an anti-PD1 antibody.

In some embodiments, the immunotherapy comprises an anti-PD1 antibody.

In some embodiments, of determining an expression level of MARCO protein in a sample from a subject comprising contacting the sample with an anti-MARCO antibody and performing an immunohistochemistry assay or a soluble MARCO assay.

In some embodiments, the assay is an immunohistochemistry assay and the antibody comprises RDM5, RDM9, PI-3010.15, PI-3010.25, or PI-3030.41.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 13E shows the tumor volumes in individual mice treated with isotype control antibody. FIG. 13F shows the tumor volumes in individual mice treated with fucosylated PI-3008. FIG. 13G shows the tumor volumes in individual mice treated with afucosylated PI-3008.

FIG. 17A shows a sequence comparison of PI-HX-3061 VH with a human VH framework sequence and three humanized VH sequences based on PI-HX-3061 (SEQ ID NOS 141, 511, 151, 161, and 171, respectively, in order of appearance). FIG. 17B shows a sequence comparison of PI-HX-3061 VL with a human VL framework sequence and one humanized VL sequences based on PI-HX-3061 (SEQ ID NOS 146, 512, and 156, respectively, in order of appearance).

FIG. 18 shows a sequence comparison of PI-HX-3031 VL with a human VL framework sequence and 6 humanized VL sequences based on PI-HX-3031 (SEQ ID NOS 6, 512, 26, 36, 46, 86, 96, and 106, respectively, in order of appearance).

FIG. 21 shows a sequence comparison of the wild type SRCR domain in human and mouse MARCO and the mutations made in the indicated murine and human recombinant variant proteins. FIG. 21 discloses SEQ ID NOS 513-521, 513-514, 522-527, and 503, respectively, in order of appearance.

FIG. 22 shows the amino acids residues of the wild type SRCR domain in human and mouse MARCO and the mutations made in the indicated recombinant variant proteins. FIG. 22 discloses SEQ ID NOS 513-514, 524, 526-527, 513, 520, and 514, respectively, in order of appearance.

FIG. 24 shows the overlapping SRCR epitope residue (circled) in murine SRCR (left, Q452) and human SRCR (right, D452).

FIG. 41A provides IHC images of CD8 T cells and NCR1 (NK cells) stained with DAB after administration of isotype control or PI-3008. FIG. 41B provides quantification of inflammatory monocyte infiltration (CD8+ T cells, NCR1+ NK cells) by flow cytometry. FIG. 41C provides quantification of $MHCII^{High}$ Ly6C+ monocytes, DC infiltration, and NK1.1 NK cells by flow cytometry.

FIG. 44A provides quantification of the indicated cell types in the spleen after treatment with isotype control antibody or PI-3008. FIG. 44B provides quantification of the indicated cell types in the spleen after treatment with isotype control antibody or PI-3008. FIG. 44C provides quantification of the indicated cell types in the spleen after treatment with isotype control antibody or PI-3008. FIG. 44D provides quantification of the indicated cell types in the spleen after treatment with isotype control antibody or PI-3008. In each figure, isotype samples are shown on the left of the pairs, PI-3008 samples are shown on the right of the pairs.

FIG. 48A provides quantification of the percentage positive cells per tissue compartment in the spleen after treatment with isotype control antibody or PI-3008. FIG. 48B provides quantification of the percentage positive cells per tissue compartment in the spleen after treatment with isotype control antibody or PI-3008. FIG. 48C provides quantification of the percentage positive cells per tissue compartment in the spleen after treatment with isotype control antibody or PI-3008. FIG. 48D provides quantification of the percentage positive cells per tissue compartment in the spleen after treatment with isotype control antibody or PI-3008. In each figure, isotype samples are shown on the left of the pairs, PI-3008 samples are shown on the right of the pairs.

FIG. 51A shows representative images of colorectal tumor tissue (left) and lung tumor tissue (right) stained with 2.5 µg/mL RDM5 using high pH (ER2) epitope retrieval conditions on the top panels. The bottom panels provide representative images of normal tissue cores from lung, spleen, and liver, stained with 2.5 µg/ml RDM5 using high pH (ER2) epitope retrieval conditions. The dark gay color indicates positive staining of myeloid cells expressing MARCO.

FIG. 58 shows that PI-3008 treatment induced the indicated cytokines and chemokines in tumors in the E0771 model at early timepoints.

DETAILED DESCRIPTION

Definitions

Figure 1:
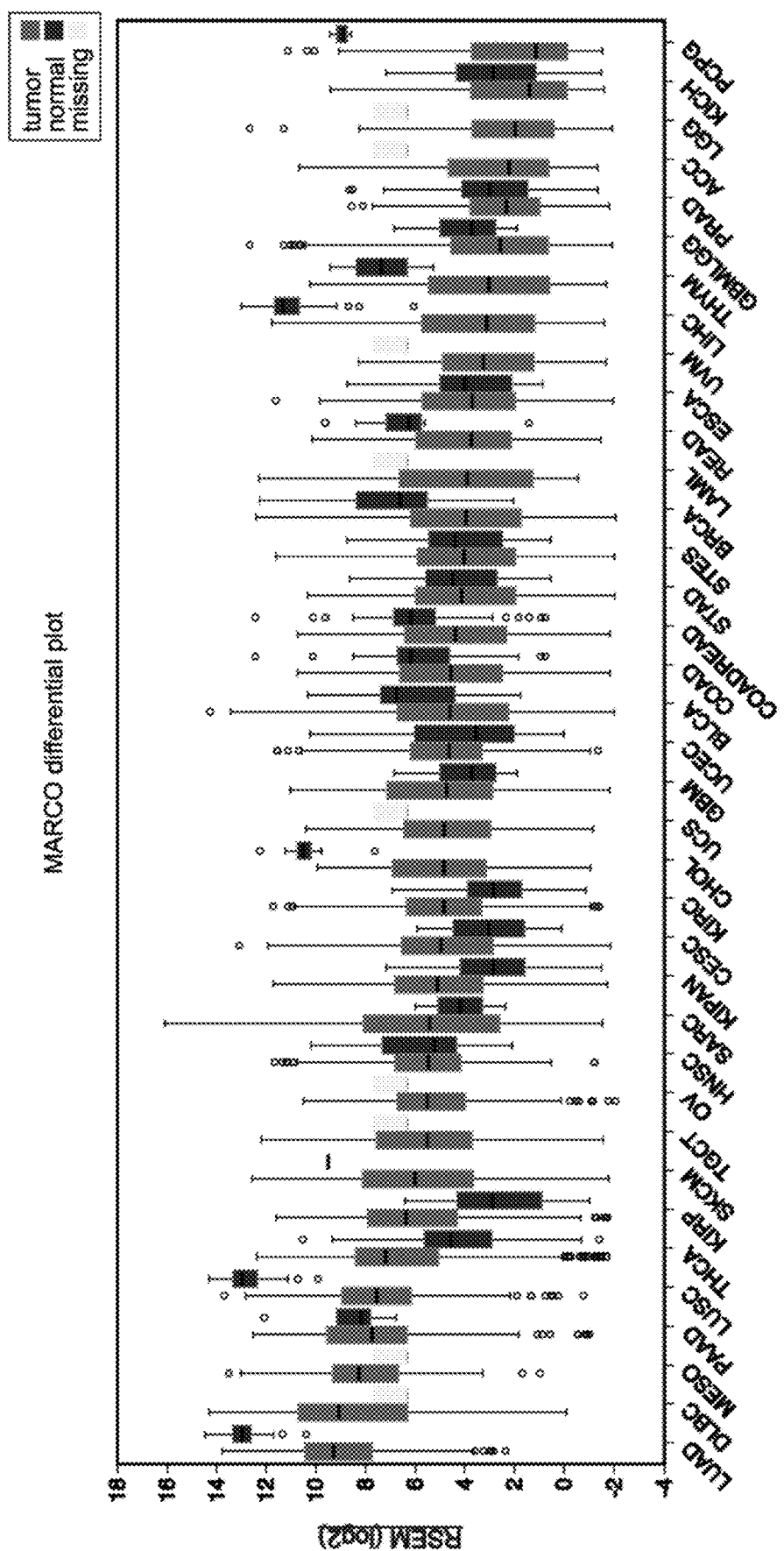
FIG. 1 shows the ordered MARCO mRNA expression in tumor (left bar) vs normal (right bar) tissue.

Terms used in the claims and specification are defined as set forth below unless otherwise specified.

The term "ameliorating" refers to any therapeutically beneficial result in the treatment of a disease state, e.g., a cancer disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

Abbreviations used in this application include the following:

It must be noted that, as used in the specification and the appended claims, the singular forms "a," "an" and "the" include plural referents unless the context clearly dictates otherwise.

Antibodies

Structure

The present application provides antibodies and compositions comprising an antibody which binds a MARCO protein. Such antibodies including antibodies that increase, enhance, or induce immune responses or kill, disable, or deplete myeloid cells.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

An exemplary immunoglobulin (antibody) structural unit is composed of two pairs of polypeptide chains, each pair having one "light" (about 25 kD) and one "heavy" chain (about 50-70 kD), e.g., a homodimer of a paired light chain and heavy chain. The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Pluckthun, J. Mol. Biol., 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinf.org.uk/abs/abnum/, and described in Abhinandan and Martin, Immunology, 2008, 45:3832-3839, incorporated by reference in its entirety.

TABLE A

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1 when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with ß-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain. In some cases, the Fc domain comprises an IgG1 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., Trends in Biochem. Sci., 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "epitope" means a portion of an antigen that specifically binds to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to MARCO variants with different point-mutations, or to chimeric MARCO variants. In some embodiments, the MARCO epitope is in the SRCR domain. In come embodiments, the MARCO epitope is in the collagen-like domain. In some embodiments, the anti-MARCO antibody or antigen binding fragment thereof binds the SRCR domain. In some embodiments, the anti-MARCO antibody or antigen binding fragment thereof binds the collagen-like domain.

A "multispecific antibody" is an antibody that comprises two or more different antigen-binding domains that collectively specifically bind two or more different epitopes. The two or more different epitopes may be epitopes on the same antigen (e.g., a single MARCO molecule expressed by a cell) or on different antigens (e.g., different MARCO molecules expressed by the same cell, or a MARCO molecule and a non-MARCO molecule). In some aspects, a multi-specific antibody binds two different epitopes (i.e., a "bispecific antibody"). In some aspects, a multi-specific antibody binds three different epitopes (i.e., a "trispecific antibody").

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP), receptor ligand blocking, agonism, or antagonism. An active Fc region is one that is capable of Fc-based effector functions such as ADCC, CDC, and/or ADCP.

Anti-MARCO antibodies can include those described herein such as the clones set forth in the tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment. A "MARCO antibody," "anti-MARCO antibody," or "MARCO-specific antibody" is an antibody, as provided herein, which specifically binds to the antigen MARCO. In some embodiments, the antibody binds the extracellular domain of MARCO. In certain embodiments, a MARCO antibody provided herein binds to an epitope of MARCO that is conserved between or among MARCO proteins from different species.

The term "chimeric antibody" or "chimera antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. The humanized antibody is less likely to induce an immune response, and/or induces a less severe immune response, as compared to the non-human species antibody, when it is administered to a human subject. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. Examples of how to make humanized antibodies can be found in U.S. Pat. Nos. 6,054,297, 5,886,152 and 5,877,293, each of which is incorporated by reference in its entirety. For further details, see Jones et al., Nature, 1986, 321:522-525; Riechmann et al., Nature, 1988, 332:323-329; and Presta, Curr. Op. Struct. Biol., 1992, 2:593-596, each of which is incorporated by reference in its entirety.

In some embodiments, the antibody comprises a rat MARCO antibody. In some embodiments, the antibody comprises a chimeric MARCO antibody. In some embodiments, the antibody comprises a humanized MARCO antibody. In some embodiments, the antibody comprises a human MARCO antibody.

In some embodiments, the humanized MARCO antibody VH sequence comprises at least one of 16G, 19R, 23A, 37V, 42G, 48V, 49S, 82Q, 88A, 93V, 114T, 115L, S16G, K19R, V23A, I37V, K42G, I48V, A49S, E82Q, S88A, M93V, V114T, or M115L as compared to a rat VH sequence as shown in SEQ ID NO: 141. In some embodiments, the humanized MARCO antibody VH sequence comprises at least one of G16, R19, A23, V37, G42, V48, S49, Q82, A88, V93, T114, L115, numbering according to EU Index. In some embodiments, the humanized MARCO antibody VH sequence comprises at least one of I38, I48, A49, S54, Q54, A54, G56, S56, Q56, A56, S57, Q57, or A57, numbering according to EU Index.

In some embodiments, the humanized MARCO antibody VL sequence comprises at least one of 21, 10S, 13S, 16V, 18D, 19R, 21T, 23T, 25R, 38Q, 41G, 43A, 44P, 50D, 51A, 53S, 55E, 58V, 76S, 77S, 79Q, 85T, 99Q, V2I, Y10S, A13S, P16V, E18D, S19R, S21T, S23T, K25R, E38Q, E41G, T43A, N44P, S50D, G51A, T53S, Q55E, T58V, R76S, N77S, E79Q, V85T, and S99Q, as compared to a rat VL sequence as shown in SEQ ID NO: 146. In some embodiments, the humanized MARCO antibody VL sequence comprises at least one of 12, S10, S13, V16, D18, R19, T21, T23, R25, Q38, G41, A43, P44, D50, A51, S53, E55, V58, S76, S77, Q79, T85, or Q99, numbering according to EU Index. In some embodiments, the humanized MARCO antibody VL sequence comprises at least one of V2, R24, K24, Q38, E38, A43, T43, N44, or P44, numbering according to EU Index.

In some embodiments, the humanized MARCO antibody VH sequence comprises at least one of 2V, 9A, I1V, 16A, 20V, 38R, 43Q, 46E, 62Q, 63K, 65Q, 66G, 68V, 69T, 70M, 71T, 72R, 73D, 76T, 78A, 79Y, 80M, 81E, 82L, 83S, 84S, 86R, 87S, 92V, 94Y, 96A, 114T, 115L, I2V, P9A, L11V, E16A, I20V, K38R, N43Q, K46E, D62Q, D63K, K65Q, Q66G, F68V, V69T, F70M, S71T, L72R, E73D, A76T, S78A, F79Y, L80M, Q81E, I82L, N83S, N84S, N86R, I87S, T92V, F94Y, T96A, V114T, M115L as compared to a rat VH sequence as shown in SEQ ID NO: 231. In some embodiments, the humanized MARCO antibody VH sequence comprises at least one of V2, A9, V11, A16, V20, R38, Q43, E46, Q62, K63, Q65, G66G, V68, T69, M70, T71, R72, D73, T76, A78, Y79, M80, E81, L82, S83, S84, R86, S87, V92, Y94, A96, T114, L115, numbering according to EU index.

In some embodiments, the humanized MARCO antibody VL sequence at least one of 9S, 15V, 17D, 18R, 20T, 22T, 24R, 40P, 43A, 45K, 70D, 72T, 73T, 76S, 77L, 82F, 84T, 86Y, 100Q, I06I, A9S, L15V, E17D, T18R, S20T, E22T, L24R, S40P, S43A, Q45K, R70D, S72T, K73T, D76S, M77L, E82F, D84T, F86Y, G100Q, L106I, as compared to a rat VL sequence as shown in SEQ ID NO: 236. In some embodiments, the humanized MARCO antibody VL sequence at least one of S9, V15, D17, R18, T20, T22, R24, P40, A43, K45, D70, T72, T73, S76, L77, F82, T84, Y86, Q100, or I106, numbering according to EU index.

In some embodiments, the humanized MARCO antibody VH sequence comprises at least one of 1E, 5Q, 13K, 16E, 48I, 61P, 62S, 67V, 68T, 76N, 79S, 82L, 83S, 85V, 86T, 87A, 88A, 92V, 116T, 117L, Q1E, K5Q, Q13K, Q16E, M48I, S61P, L62S, L67V, S68T, S76N, F79S, M82L, N83S, L85V, Q86T, T87A, E88A, T92V, V116T, or M117L, as compared to a rat VH sequence as shown in SEQ ID NO: 1. In some embodiments, the humanized MARCO antibody VH sequence comprises at least one of E1, Q5, K13, E16, I48, P61, S62, V67, T68, N76, S79, L82, S83, V85, T86, A87, A88, V92, T116, or L117, numbering according to EU index.

In some embodiments, the humanized MARCO antibody VL sequence comprises at least one of 9S, 13A, 15V, 17D, 18R, 20T, 22T, 24R, 40P, 43A, 45K, 56S, 70D, 71F, 72T, 74T, 77S, 78L, 92F, 94T, 96Y, 100Q, 9S, T13A, L15V, E17D, T18R, S20T, E22T, L24R, S40P, S43A, Q45K, D56S, R70D, Y71F, S72T, K74T, G77S, M78L, E92F, D94T, F96Y, or S100Q, as compared to a rat VL sequence as shown in SEQ ID NO: 6. In some embodiments, the humanized MARCO antibody VL sequence comprises at least one of S9, T13, A13, D17, R18, T20, T22, L24, R24, N31, S31, Q31, A31, D31, P40, A43, S43, I43, K45, D56, S56, D70, Y71, F71, T72, T74, S77, L78, M78, F83, E83, T85, Y87, F87, F92, T94, S100, or Q100, numbering according to EU index.

In one embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies. In one embodiment, all of the variable and constant domains are derived from human immunoglobulin sequences (a fully human antibody). These antibodies may be prepared in a variety of ways including through the immunization with an antigen of interest of a mouse that is genetically modified to express antibodies derived from human heavy and/or light chain-encoding genes.

In some embodiments, the antibodies provided herein comprise an antibody fragment. In some embodiments, the antibodies provided herein consist of an antibody fragment. In some embodiments, the antibodies provided herein consist essentially of an antibody fragment. In some embodiments, the antibody fragment is an Fv fragment. In some embodiments, the antibody fragment is a Fab fragment. In some embodiments, the antibody fragment is a F(ab')$_2$ fragment. In some embodiments, the antibody fragment is a Fab' fragment. In some embodiments, the antibody fragment is an scFv (sFv) fragment. In some embodiments, the antibody fragment is an scFv-Fc fragment. In some embodiments, the antibody fragment is a fragment of a single domain antibody.

Sequences of MARCO Antibodies

Table B provides the names and SEQ ID NOS of exemplary anti-MARCO antibodies provided herein.

TABLE B

| Name | Revised Name (if applicable) | Description | SEQ ID NOs |
|---|---|---|---|
| PI-HX-3031 | | parental rat hybridoma | 1-10 |
| PI-3010-AB | PI-3010 | hIgG1/chimeric PI-HX-3031 | 11-20 |
| PI-3011-AB | PI-3010.11 | humanized PI-HX-3031/3031-1 hIgG1 | 21-30 |
| PI-3012-AB | PI-3010.12 | humanized PI-HX-3031/3031-2 hIgG1 | 31-40 |
| PI-3013-AB | PI-3010.13 | humanized PI-HX-3031/3031-3 hIgG1 | 41-50 |
| PI-3014-AB | PI-3010.14 | humanized PI-HX-3031/3031-4 hIgG1 | 51-60 |
| PI-3015-AB | PI-3010.15 | humanized PI-HX-3031/3031-5 hIgG1 | 61-70 |
| PI-3020-AB | PI-3010.20 | chimeric PI-HX-3031- hIgG4 | 71-80 |
| PI-3022-AB | PI-3010.22 | humanized PI-HX-3031/3031-2 hIgG1 | 81-90 |
| PI-3023-AB | PI-3010.23 | humanized PI-HX-3031/3031-2 hIgG1 | 91-100 |
| PI-3024-AB | PI-3010.24 | humanized PI-HX-3031/3031-2 hIgG1 | 101-110 |
| PI-3025-AB | PI-3010.25 | humanized PI-HX-3031/3031-2 hIgG1 | 434-443 |
| PI-3026-AB | PI-3010.26 | humanized PI-HX-3031/3031-2 hIgG1 | 121-130 |
| PI-3027-AB | PI-3010.27 | humanized PI-HX-3031/3031-2 hIgG1 | 131-140 |
| PI-3046-AB | PI-3010.46 | humanized PI-HX-3031/3031-2 hIgG4 | 474-483 |
| PI-3048-AB | PI-3010.48 | humanized PI-HX-3031/3031-2 hIgG4 | 444-453 |
| PI-HX-3061 | | parental rat hybridoma | 141-150 |
| PI-3016-AB | | humanized PI-HX-3061/3061-1 hIgG1 | 151-160 |
| PI-3017-AB | | humanized PI-HX-3061/3061-2 hIgG1 | 161-170 |
| PI-3018-AB | | humanized PI-HX-3061/3061-3 hIgG1 | 171-180 |
| PI-3019-AB | | PI-HX-3061 mIgG2a chimera | 181-190 |
| PI-3028-AB | | PI-HX-3061 hIgG1 chimera | 191-200 |
| PI-3029-AB | | PI-HX-3061 hIgG4 chimera | 201-210 |
| PI-3032-AB | | humanized PI-HX-3061/3061-2 hIgG1 | 211-220 |
| PI-3033-AB | | humanized PI-HX-3061/3061-2 hIgG1 | 221-230 |
| PI-HX-3011 | | parental rat hybridoma | 231-240 |
| PI-3030-AB | PI-3030 | HX3011-h1 Chimera hIgG1 | 241-250 |
| PI-3036-AB | PI-3030.36 | humanized PI-HX-3011/3011-1 hIgG1 | 311-320 |
| PI-3037-AB | PI-3030.37 | humanized PI-HX-3011/3011-2 hIgG1 | 321-330 |
| PI-3038-AB | PI-3030.38 | humanized PI-HX-3011/3011-3 hIgG1 | 331-340 |
| PI-3039-AB | PI-3030.39 | humanized PI-HX-3011/3011-4 hIgG1 | 341-350 |
| PI-3040-AB | PI-3030.40 | humanized PI-HX-3011/3011-5 hIgG1 | 351-360 |
| PI-3041-AB | PI-3030.41 | humanized PI-HX-3011/3011-5 hIgG1 | 454-463 |
| PI-3047-AB | PI-3030.47 | humanized PI-HX-3011/3011-5 hIgG4 | 464-473 |
| PI-HX-3043 | | parental rat hybridoma | 251-260 |
| PI-3031-AB | | HX3043-h1 Chimera hIgG1 | 261-270 |
| PI-HX-3092 | | parental rat hybridoma | 361-370 |
| PI-3035 | | HX3092 (A mutation) - mIgG2a | 371-380 |

CDRs

In some embodiments, an isolated antibody or antigen binding fragment thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYHVS (SEQ ID NO: 2), CDR-H2 comprises the sequence AIWTGGSIA (SEQ ID NO: 3), CDR-H3 comprises the sequence DLSDYYSSYTSFDY (SEQ ID NO: 4), CDR-L1 comprises the sequence ASEGISNDLA (SEQ ID NO: 431) or XASEGISNDLA (SEQ ID NO: 383), wherein X is arginine (R) or leucine (L), CDR-L2 comprises the sequence AASRLQD (SEQ ID NO: 8), and CDR-L3 comprises the sequence QQSYKYPLT (SEQ ID NO: 9).

In some embodiments, CDR-L1 comprises the sequence LASEGISNDLA (SEQ ID NO: 7). In some embodiments, CDR-L1 comprises the sequence RASEGISNDLA (SEQ ID NO: 27). In some embodiments, CDR-L1 comprises the sequence ASEGISNDLA (SEQ ID NO: 431).

In some embodiments, an antibody provided herein comprises a CDR-H3 of SEQ ID NO: 4, a CDR-H2 of SEQ ID NO: 3, a CDR-H1 of SEQ ID NO: 2, a CDR-L3 of SEQ ID NO: 9, a CDR-L2 of SEQ ID NO: 8, and a CDR-L1 of SEQ ID NO: 7. In some embodiments, an antibody provided herein comprises a CDR-H3 of SEQ ID NO: 4, a CDR-H2 of SEQ ID NO: 3, a CDR-H1 of SEQ ID NO: 2, a CDR-L3 of SEQ ID NO: 9, a CDR-L2 of SEQ ID NO: 8, and a CDR-L1 of SEQ ID NO: 27. In some embodiments, an antibody provided herein comprises a CDR-H3 of SEQ ID NO: 4, a CDR-H2 of SEQ ID NO: 3, a CDR-H1 of SEQ ID NO: 2, a CDR-L3 of SEQ ID NO: 9, a CDR-L2 of SEQ ID NO: 8, and a CDR-L1 of SEQ ID NO: 431. In some embodiments, the CDR-H3 has at least about 50%, 75%, 80%, 85%, 90%, or 95% identity with a CDR-H3 of SEQ ID NO: 4, the CDR-H2 has at least about 50%, 75%, 80%, 85%, 90%, or 95% identity with a CDR-H2 of SEQ ID NO: 3, the CDR-H1 has at least about 50%, 75%, 80%, 85%, 90%, or 95% identity with a CDR-H1 of SEQ ID NO: 2, the CDR-L3 has at least about 50%, 75%, 80%, 85%, 90%, or 95% identity with a CDR-L3 of SEQ ID NO: 9, the CDR-L2 has at least about 50%, 75%, 80%, 85%, 90%, or 95% identity with a CDR-L2 of SEQ ID NO: 8, and the CDR-L1 has at least about 50%, 75%, 80%, 85%, 90%, or 95% identity with a CDR-L1 of SEQ ID NO: 431, 383, 7, or 27. In some embodiments, the CDR-H3 is a CDR-H3 of SEQ ID NO: 4, with up to 1, 2, 3, 4, 5, 6, 7, or 8 amino acid substitutions; the CDR-H2 is a CDR-H2 of SEQ ID NO: 3, with up to 1, 2, 3, 4, 5, 6, 7, or 8 amino acid substitutions; the CDR-H1 is a CDR-H1 of SEQ ID NO: 2, with up to 1, 2, 3, 4, or 5 amino acid substitutions; the CDR-L3 is a CDR-L3 of SEQ ID NO: 9, with up to 1, 2, 3, 4, or 5 amino acid substitutions; the CDR-L2 is a CDR-L2 of SEQ ID NO: 8, with up to 1, 2, 3, or 4 amino acid substitutions; and the CDR-L1 is a CDR-L1 of SEQ ID NO: 431, 383, 7, or 27 with up to 1, 2, 3, 4, 5, or 6 amino acid substitutions.

In some embodiments, an isolated antibody or antigen binding fragment thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYAVN (SEQ ID NO: 232), CDR-H2 comprises the sequence WINTQTGKPT (SEQ ID NO: 233), CDR-H3 comprises the sequence DSYYYSSSLDY (SEQ ID NO: 234), CDR-L1 comprises the sequence ASAGISNDLA (SEQ ID NO: 432) or XASAGISNDLA (SEQ ID NO: 381), wherein X is leucine (L) or arginine (R), CDR-L2 comprises the sequence AASRLQD (SEQ ID NO: 238), and CDR-L3 comprises the sequence QQSYKYPWT (SEQ ID NO: 239). In some embodiments, CDR-L1 comprises the sequence LASAGISNDLA (SEQ ID NO: 237). In some embodiments, CDR-L1 comprises the sequence RASAGISNDLA (SEQ ID NO: 317). In some embodiments, CDR-L1 comprises the sequence ASAGISNDLA (SEQ ID NO: 432).

In some embodiments, an antibody provided herein comprises a CDR-H3 of SEQ ID NO: 234, a CDR-H2 of SEQ ID NO: 233, a CDR-H1 of SEQ ID NO: 232, a CDR-L3 of SEQ ID NO: 239, a CDR-L2 of SEQ ID NO: 238, and a CDR-L1 of SEQ ID NO: 237. In some embodiments, an antibody provided herein comprises a CDR-H3 of SEQ ID NO: 234, a CDR-H2 of SEQ ID NO: 233, a CDR-H1 of SEQ ID NO: 232, a CDR-L3 of SEQ ID NO: 319, a CDR-L2 of SEQ ID NO: 318, and a CDR-L1 of SEQ ID NO: 317. In some embodiments, an antibody provided herein comprises a CDR-H3 of SEQ ID NO: 234, a CDR-H2 of SEQ ID NO: 233, a CDR-H1 of SEQ ID NO: 232, a CDR-L3 of SEQ ID NO: 239, a CDR-L2 of SEQ ID NO: 238, and a CDR-L1 of SEQ ID NO: 432. In some embodiments, the CDR-H3 has at least about 50%, 75%, 80%, 85%, 90%, or 95% identity with a CDR-H3 of SEQ ID NO: 234, the CDR-H2 has at least about 50%, 75%, 80%, 85%, 90%, or 95% identity with a CDR-H2 of SEQ ID NO: 233, the CDR-H1 has at least about 50%, 75%, 80%, 85%, 90%, or 95% identity with a CDR-H1 of SEQ ID NO: 232, the CDR-L3 has at least about 50%, 75%, 80%, 85%, 90%, or 95% identity with a CDR-L3 of SEQ ID NO: 239, the CDR-L2 has at least about 50%, 75%, 80%, 85%, 90%, or 95% identity with a CDR-L2 of SEQ ID NO: 238, and the CDR-L1 has at least about 50%, 75%, 80%, 85%, 90%, or 95% identity with a CDR-L1 of SEQ ID NO: 432, 237, 317, or 381. In some embodiments, the CDR-H3 is a CDR-H3 of SEQ ID NO: 234, with up to 1, 2, 3, 4, 5, 6, 7, or 8 amino acid substitutions; the CDR-H2 is a CDR-H2 of SEQ ID NO: 233, with up to 1, 2, 3, 4, 5, 6, 7, or 8 amino acid substitutions; the CDR-H1 is a CDR-H1 of SEQ ID NO: 232, with up to 1, 2, 3, 4, or 5 amino acid substitutions; the CDR-L3 is a CDR-L3 of SEQ ID NO: 239, with up to 1, 2, 3, 4, or 5 amino acid substitutions; the CDR-L2 is a CDR-L2 of SEQ ID NO: 238, with up to 1, 2, 3, or 4 amino acid substitutions; and the CDR-L1 is a CDR-L1 of SEQ ID NO: 432, 237, 317, or 381 with up to 1, 2, 3, 4, 5, or 6 amino acid substitutions.

In some embodiments, an isolated antibody or antigen binding fragment thereof that binds to human MARCO (SEQ ID NO: 363), comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GYTFTDYYLH (SEQ ID NO: 252), CDR-H2 comprises the sequence YINPNNAYTS (SEQ ID NO: 253), CDR-H3 comprises the sequence DTTDYYNLHFAY (SEQ ID NO: 254), CDR-L1 comprises the sequence LTSEGISNDLA (SEQ ID NO: 257), CDR-L2 comprises the sequence DASRLED (SEQ ID NO: 258), and CDR-L3 comprises the sequence QQSYKYPLT (SEQ ID NO: 259).

In some embodiments, an antibody provided herein comprises a CDR-H3 of SEQ ID NO: 254, a CDR-H2 of SEQ ID NO: 253, a CDR-H1 of SEQ ID NO: 252, a CDR-L3 of SEQ ID NO: 259, a CDR-L2 of SEQ ID NO: 258, and a CDR-L1 of SEQ ID NO: 257. In some embodiments, the CDR-H3 has at least about 50%, 75%, 80%, 85%, 90%, or 95% identity with a CDR-H3 of SEQ ID NO: 254, the CDR-H2 has at least about 50%, 75%, 80%, 85%, 90%, or 95% identity with a CDR-H2 of SEQ ID NO: 253, the CDR-H1 has at least about 50%, 75%, 80%, 85%, 90%, or 95% identity with a CDR-H1 of SEQ ID NO: 252, the CDR-L3 has at least about 50%, 75%, 80%, 85%, 90%, or 95% identity with a CDR-L3 of SEQ ID NO: 259, the CDR-L2 has at least about 50%, 75%, 80%, 85%, 90%, or 95% identity with a CDR-L2 of SEQ ID NO: 258, and the CDR-L1 has at least about 50%, 75%, 80%, 85%, 90%, or 95% identity with a CDR-L1 of SEQ ID NO: 257. In some embodiments, the CDR-H3 is a CDR-H3 of SEQ ID NO: 254, with up to 1, 2, 3, 4, 5, 6, 7, or 8 amino acid substitutions; the CDR-H2 is a CDR-H2 of SEQ ID NO: 253, with up to 1, 2, 3, 4, 5, 6, 7, or 8 amino acid substitutions; the CDR-H1 is a CDR-H1 of SEQ ID NO: 252, with up to 1, 2, 3, 4, or 5 amino acid substitutions; the CDR-L3 is a CDR-L3 of SEQ ID NO: 259, with up to 1, 2, 3, 4, or 5 amino acid substitutions; the CDR-L2 is a CDR-L2 of SEQ ID NO: 258, with up to 1, 2, 3, or 4 amino acid substitutions; and the CDR-L1 is a CDR-L1 of SEQ ID NO: 257, with up to 1, 2, 3, 4, 5, or 6 amino acid substitutions.

In some embodiments, an isolated antibody or antigen binding fragment thereof that binds to human MARCO (SEQ ID NO: 363), comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence KFTFSNYGMN (SEQ ID NO: 142), CDR-H2 comprises the sequence LIYYNSNNKY (SEQ ID NO: 143), CDR-H3 comprises the sequence SLTGGSDYFDS (SEQ ID NO: 144), CDR-L1 comprises the sequence ASKSIGTFLA (SEQ ID NO: 433) or XASKSIGTFLA (SEQ ID NO: 382), wherein X is lysine (K) or arginine (R), CDR-L2 comprises the sequence SGSTLQS (SEQ ID NO: 148), and CDR-L3 comprises the sequence QQHDEYPFT (SEQ ID NO: 149).

In some embodiments, CDR-L1 comprises the sequence KASKSIGTFLA (SEQ ID NO: 147). In some embodiments, CDR-L1 comprises the sequence RASKSIGTFLA (SEQ ID NO: 157). In some embodiments, CDR-L1 comprises the sequence ASKSIGTFLA (SEQ ID NO: 433).

In some embodiments, an antibody provided herein comprises a CDR-H3 of SEQ ID NO: 144, a CDR-H2 of SEQ ID NO: 143, a CDR-H1 of SEQ ID NO: 142, a CDR-L3 of SEQ ID NO: 149, a CDR-L2 of SEQ ID NO: 148, and a CDR-L1 of SEQ ID NO: 147. In some embodiments, an antibody provided herein comprises a CDR-H3 of SEQ ID NO: 144, a CDR-H2 of SEQ ID NO: 143, a CDR-H1 of SEQ ID NO: 142, a CDR-L3 of SEQ ID NO: 149, a CDR-L2 of SEQ ID NO: 148, and a CDR-L1 of SEQ ID NO: 157. In some embodiments, an antibody provided herein comprises a CDR-H3 of SEQ ID NO: 144, a CDR-H2 of SEQ ID NO: 143, a CDR-H1 of SEQ ID NO: 142, a CDR-L3 of SEQ ID NO: 149, a CDR-L2 of SEQ ID NO: 148, and a CDR-L1 of SEQ ID NO: 433. In some embodiments, the CDR-H3 has at least about 50%, 75%, 80%, 85%, 90%, or 95% identity with a CDR-H3 of SEQ ID NO: 144, the CDR-H2 has at least about 50%, 75%, 80%, 85%, 90%, or 95% identity with a CDR-H2 of SEQ ID NO: 143, the CDR-H1 has at least about 50%, 75%, 80%, 85%, 90%, or 95% identity with a CDR-H1 of SEQ ID NO: 142, the CDR-L3 has at least about 50%, 75%, 80%, 85%, 90%, or 95% identity with a CDR-L3 of SEQ ID NO: 149, the CDR-L2 has at least about 50%, 75%, 80%, 85%, 90%, or 95% identity with a CDR-L2 of SEQ ID NO: 148, and the CDR-L1 has at least about 50%, 75%, 80%, 85%, 90%, or 95% identity with a CDR-L1 of SEQ ID NO: 433, 382, 147, or 157. In some embodiments, the CDR-H3 is a CDR-H3 of SEQ ID NO: 144, with up to 1, 2, 3, 4, 5, 6, 7, or 8 amino acid substitutions; the CDR-H2 is a CDR-H2 of SEQ ID NO: 143, with up to 1, 2, 3, 4, 5, 6, 7, or 8 amino acid substitutions; the CDR-H1 is a CDR-H1 of SEQ ID NO: 142, with up to 1, 2, 3, 4, or 5 amino acid substitutions; the CDR-L3 is a CDR-L3 of SEQ ID NO: 149, with up to 1, 2, 3, 4, or 5 amino acid substitutions; the CDR-L2 is a CDR-L2 of SEQ ID NO: 148, with up to 1, 2, 3, or 4 amino acid substitutions; and the CDR-L1 is a CDR-L1 of SEQ ID NO: 433, 382, 147, or 157 with up to 1, 2, 3, 4, 5, or 6 amino acid substitutions.

In some embodiments, an isolated antibody or antigen binding fragment thereof that binds to human MARCO (SEQ ID NO: 384), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence GFSLTSYTLS (SEQ ID NO: 362), CDR-H2 comprises the sequence AIWGGDNTD (SEQ ID NO: 363), CDR-H3 comprises the sequence ELGGSFDY (SEQ ID NO: 364), CDR-L1 comprises the sequence KTSQNINKKLD (SEQ ID NO: 367), CDR-L2 comprises the sequence YTNNLQT (SEQ ID NO: 368), and CDR-L3 comprises the sequence YQYDSGFT (SEQ ID NO: 369).

In some embodiments, the CDR-H3 has at least about 50%, 75%, 80%, 85%, 90%, or 95% identity with a CDR-H3 of SEQ ID NO: 364, the CDR-H2 has at least about 50%, 75%, 80%, 85%, 90%, or 95% identity with a CDR-H2 of SEQ ID NO: 363, the CDR-H1 has at least about 50%, 75%, 80%, 85%, 90%, or 95% identity with a CDR-H1 of SEQ ID NO: 362, the CDR-L3 has at least about 50%, 75%, 80%, 85%, 90%, or 95% identity with a CDR-L3 of SEQ ID NO: 369, the CDR-L2 has at least about 50%, 75%, 80%, 85%, 90%, or 95% identity with a CDR-L2 of SEQ ID NO: 368, and the CDR-L1 has at least about 50%, 75%, 80%, 85%, 90%, or 95% identity with a CDR-L1 of SEQ ID NO: 367. In some embodiments, the CDR-H3 is a CDR-H3 of SEQ ID NO: 364, with up to 1, 2, 3, 4, 5, 6, 7, or 8 amino acid substitutions; the CDR-H2 is a CDR-H2 of SEQ ID NO: 363, with up to 1, 2, 3, 4, 5, 6, 7, or 8 amino acid substitutions; the CDR-H1 is a CDR-H1 of SEQ ID NO: 362, with up to 1, 2, 3, 4, or 5 amino acid substitutions; the CDR-L3 is a CDR-L3 of SEQ ID NO: 369, with up to 1, 2, 3, 4, or 5 amino acid substitutions; the CDR-L2 is a CDR-L2 of SEQ ID NO: 368, with up to 1, 2, 3, or 4 amino acid substitutions; and the CDR-L1 is a CDR-L1 of SEQ ID NO: 367 with up to 1, 2, 3, 4, 5, or 6 amino acid substitutions.

In some aspects, the amino acid substitutions are conservative amino acid substitutions. In some embodiments, the antibodies described herein are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477. In some aspects, the CDR-H3 has at least about 50%, 75%, 80%, 85%, 90%, or 95% identity with a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477. In some embodiments, the CDR-H3 is a CDR-H3 selected of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476. In some aspects, the CDR-H2 has at least about 50%, 75%, 80%, 85%, 90%, or 95% identity with a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476. In some embodiments, the CDR-H2 is a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 435, 445, 455, 465, or 475. In some aspects, the CDR-H1 has at least about 50%, 75%, 80%, 85%, 90%, or 95% identity with a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 435, 445, 455, 465, or 475. In some embodiments, the CDR-H1 is a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, and a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475. In some embodiments, the CDR-H3 has at least about 50%, 75%, 80%, 85%, 90%, or 95% identity with a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, the CDR-H2 has at least about 50%, 75%, 80%, 85%, 90%, or 95% identity with a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, and the CDR-H1 has at least about 50%, 75%, 80%, 85%, 90%, or 95% identity with a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475. In some embodiments, the CDR-H3 is a CDR-H3 of SEQ ID NO: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 437, 447, 457, 467, or 477, with up to 1, 2, 3, 4, 5, 6, 7, or 8 amino acid substitutions; the CDR-H2 is a CDR-H2 of SEQ ID NO: 3, 13, 23, 33, 43, 53, 63, 73, 83, 93, 103, 113, 123, 133, 143, 513, 163, 173, 183, 193, 203, 213, 223, 233, 243, 253, 263, 273, 283, 293, 303, 313, 323, 333, 343, 353, 363, 373, 376, 436, 446, 456, 466, or 476, with up to 1, 2, 3, 4, 5, 6, 7, or 8 amino acid substitutions; and the CDR-H1 is a CDR-H1 of SEQ ID NO: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372 435, 445, 455, 465, or 475, with up to 1, 2, 3, 4, or 5 amino acid substitutions. In some aspects, the amino acid substitutions are conservative amino acid substitutions.

In some embodiments, an antibody provided herein comprises a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482. In some aspects, the CDR-L3 has at least about 50%, 75%, 80%, 85%, 90%, or 95% identity with a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482. In some embodiments, the CDR-L3 is a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481. In some aspects, the CDR-L2 has at least about 50%, 75%, 80%, 85%, 90%, or 95% identity with a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481. In some embodiments, the CDR-L2 is a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480. In some aspects, the CDR-L1 has at least about 50%, 75%, 80%, 85%, 90%, or 95% identity with a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, or 383, 440, 450, 460, 470, or 480. In some embodiments, the CDR-L1 is a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480, with up to 1, 2, 3, 4, 5, 6, 7, or 8 amino acid substitutions.

In some aspects, the amino acid substitutions are conservative amino acid substitutions. In some embodiments, an antibody provided herein comprises a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, and a CDR-L2 of SEQ ID NO 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481. In some embodiments, an antibody provided herein comprises a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, and a CDR-L1 of SEQ ID NO: 77, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, or 383, 440, 450, 460, 470, or 480. In some embodiments, the CDR-L3 has at least about 50%, 75%, 80%, 85%, 90%, or 95% identity with a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, the CDR-L2 has at least about 50%, 75%, 80%, 85%, 90%, or 95% identity with a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, and the CDR-L1 has at least about 50%, 75%, 80%, 85%, 90%, or 95% identity with a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480. In some embodiments, the CDR-L3 is a CDR-L3 of SEQ ID NO: 9, 19, 29, 39, 49, 59, 69, 79, 89, 99, 109, 119, 129, 139, 149, 159, 169, 179, 189, 199, 209, 219, 229, 239, 249, 259, 269, 279, 289, 299, 309, 319, 329, 339, 349, 359, 369, 379, 442, 452, 462, 472, or 482, with up to 1, 2, 3, 4, or 5 amino acid substitutions; the CDR-L2 is a CDR-L2 of SEQ ID NO: 8, 18, 28, 38, 48, 58, 68, 78, 88, 98, 108, 218, 228, 238, 248, 258, 268, 278, 288, 298, 308, 318, 328, 338, 348, 358, 368, 378, 441, 451, 461, 471, or 481, with up to 1, 2, 3, or 4 amino acid substitutions; and the CDR-L1 is a CDR-L1 of SEQ ID NO: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 381, 382, 383, 440, 450, 460, 470, or 480, with up to 1, 2, 3, 4, 5, or 6 amino acid substitutions. In some aspects, the amino acid substitutions are conservative amino acid substitutions.

In some embodiments, an antibody provided herein comprises one to three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises two to three CDRs of a $V_H$ domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDR-H1 is a CDR-H1 of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, or 5 amino acid substitutions. In some embodiments, the CDR-H2 is a CDR-H2 of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, 5, 6, 7, or 8 amino acid substitutions. In some embodiments, the CDR-H3 is a CDR-H3 of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises two to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDR-L1 is a CDR-L1 of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474, with up to 1, 2, 3, 4, or 5 amino acid substitutions. In some embodiments, the CDR-L2 is a CDR-L2 of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, or 376 with up to 1, 2, 3, 4, 5, 6, 7, or 8 amino acid substitutions. In some embodiments, the CDR-L3 is a CDR-L3 of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474 with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, and one to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises two to three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, and two to three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some embodiments, an antibody provided herein comprises three CDRs of a VH domain selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, and three CDRs of a VL domain selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 434, 444, 454, 464, or 474. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

$V_H$ Domains

In some embodiments, an antibody or antigen binding fragment thereof provided herein comprises a $V_H$ sequence selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises a $V_H$ sequence of SEQ ID NO: 1. In some embodiments, an antibody provided herein comprises a $V_H$ sequence of SEQ ID NO: 21. In some embodiments, an antibody provided herein comprises a $V_H$ sequence of SEQ ID NO: 121. In some embodiments, an antibody provided herein comprises a $V_H$ sequence of SEQ ID NO: 181. In some embodiments, an antibody provided herein comprises a $V_H$ sequence of SEQ ID NO: 191. In some embodiments, an antibody provided herein comprises a $V_H$ sequence of SEQ ID NO: 221. In some embodiments, an antibody provided herein comprises a $V_H$ sequence of SEQ ID NO: 241. In some embodiments, an antibody provided herein comprises a $V_H$ sequence of SEQ ID NO: 261. In some embodiments, an antibody provided herein comprises a $V_H$ sequence of SEQ ID NO: 351. In some embodiments, an antibody provided herein comprises a $V_H$ sequence of SEQ ID NO: 371. In some embodiments, an antibody provided herein comprises a $V_H$ sequence of SEQ ID NO: 434. In some embodiments, an antibody provided herein comprises a $V_H$ sequence of SEQ ID NO: 444. In some embodiments, an antibody provided herein comprises a $V_H$ sequence of SEQ ID NO: 454. In some embodiments, an antibody provided herein comprises a $V_H$ sequence of SEQ ID NO: 464. In some embodiments, an antibody provided herein comprises a $V_H$ sequence of SEQ ID NO: 474.

In some embodiments, the $V_H$ sequence has at least 70%, 80%, or 90% identity with SEQ ID NO: 1, wherein any variation from SEQ ID NO: 1 does not occur within CDR-H1, CDR-H2, or CDR-H3. In some embodiments, the $V_H$ sequence has at least 70%, 80%, or 90% identity with SEQ ID NO: 21, wherein any variation from SEQ ID NO: 21 does not occur within CDR-H1, CDR-H2, or CDR-H3. In some embodiments, the $V_H$ sequence has at least 70%, 80%, or 90% identity with SEQ ID NO: 121, wherein any variation from SEQ ID NO: 121 does not occur within CDR-H1, CDR-H2, or CDR-H3. In some embodiments, the $V_H$ sequence has at least 70%, 80%, or 90% identity with SEQ ID NO: 181, wherein any variation from SEQ ID NO: 181 does not occur within CDR-H1, CDR-H2, or CDR-H3. In some embodiments, the $V_H$ sequence has at least 70%, 80%, or 90% identity with SEQ ID NO: 191, wherein any variation from SEQ ID NO: 191 does not occur within CDR-H1, CDR-H2, or CDR-H3. In some embodiments, the $V_H$ sequence has at least 70%, 80%, or 90% identity with SEQ ID NO: 221, wherein any variation from SEQ ID NO: 221 does not occur within CDR-H1, CDR-H2, or CDR-H3. In some embodiments, the $V_H$ sequence has at least 70%, 80%, or 90% identity with SEQ ID NO: 241, wherein any variation from SEQ ID NO: 241 does not occur within CDR-H1, CDR-H2, or CDR-H3. In some embodiments, the $V_H$ sequence has at least 70%, 80%, or 90% identity with SEQ ID NO: 261, wherein any variation from SEQ ID NO: 261 does not occur within CDR-H1, CDR-H2, or CDR-H3. In some embodiments, the $V_H$ sequence has at least 70%, 80%, or 90% identity with SEQ ID NO: 351, wherein any variation from SEQ ID NO: 351 does not occur within CDR-H1, CDR-H2, or CDR-H3. In some embodiments, the $V_H$ sequence has at least 70%, 80%, or 90% identity with SEQ ID NO: 371, wherein any variation from SEQ ID NO: 371 does not occur within CDR-H1, CDR-H2, or CDR-H3. In some embodiments, the $V_H$ sequence has at least 70%, 80%, or 90% identity with SEQ ID NO: 434, wherein any variation from SEQ ID NO: 434 does not occur within CDR-H1, CDR-H2, or CDR-H3. In some embodiments, the $V_H$ sequence has at least 70%, 80%, or 90% identity with SEQ ID NO: 444, wherein any variation from SEQ ID NO: 444 does not occur within CDR-H1, CDR-H2, or CDR-H3. In some embodiments, the $V_H$ sequence has at least 70%, 80%, or 90% identity with SEQ ID NO: 454, wherein any variation from SEQ ID NO: 454 does not occur within CDR-H1, CDR-H2, or CDR-H3. In some embodiments, the $V_H$ sequence has at least 70%, 80%, or 90% identity with SEQ ID NO: 464, wherein any variation from SEQ ID NO: 464 does not occur within CDR-H1, CDR-H2, or CDR-H3. In some embodiments, the $V_H$ sequence has at least 70%, 80%, or 90% identity with SEQ ID NO: 474, wherein any variation from SEQ ID NO: 474 does not occur within CDR-H1, CDR-H2, or CDR-H3.

In some embodiments, an antibody provided herein comprises a $V_H$ sequence having at least about 50%, 60%, 70%, 80%, 90%, 95%, or 99% identity to SEQ ID NO: 1. In some embodiments, an antibody provided herein comprises a $V_H$ sequence having at least about 50%, 60%, 70%, 80%, 90%, 95%, or 99% identity to SEQ ID NO: 21. In some embodiments, an antibody provided herein comprises a $V_H$ sequence having at least about 50%, 60%, 70%, 80%, 90%, 95%, or 99% identity to SEQ ID NO: 121. In some embodiments, an antibody provided herein comprises a $V_H$ sequence having at least about 50%, 60%, 70%, 80%, 90%, 95%, or 99% identity to SEQ ID NO: 181. In some embodiments, an antibody provided herein comprises a $V_H$ sequence having at least about 50%, 60%, 70%, 80%, 90%, 95%, or 99% identity to SEQ ID NO: 191. In some embodiments, an antibody provided herein comprises a $V_H$ sequence having at least about 50%, 60%, 70%, 80%, 90%, 95%, or 99% identity to SEQ ID NO: 221. In some embodiments, an antibody provided herein comprises a $V_H$ sequence having at least about 50%, 60%, 70%, 80%, 90%, 95%, or 99% identity to SEQ ID NO: 241. In some embodiments, an antibody provided herein comprises a $V_H$ sequence having at least about 50%, 60%, 70%, 80%, 90%, 95%, or 99% identity to SEQ ID NO: 261. In some embodiments, an antibody provided herein comprises a $V_H$ sequence having at least about 50%, 60%, 70%, 80%, 90%, 95%, or 99% identity to SEQ ID NO: 351. In some embodiments, an antibody provided herein comprises a $V_H$ sequence having at least about 50%, 60%, 70%, 80%, 90%, 95%, or 99% identity to SEQ ID NO: 371. In some embodiments, an antibody provided herein comprises a $V_H$ sequence having at least about 50%, 60%, 70%, 80%, 90%, 95%, or 99% identity to SEQ ID NO: 434. In some embodiments, an antibody provided herein comprises a V$_H$ sequence having at least about 50%, 60%, 70%, 80%, 90%, 95%, or 99% identity to SEQ ID NO: 444. In some embodiments, an antibody provided herein comprises a V$_H$ sequence having at least about 50%, 60%, 70%, 80%, 90%, 95%, or 99% identity to SEQ ID NO: 454. In some embodiments, an antibody provided herein comprises a V$_H$ sequence having at least about 50%, 60%, 70%, 80%, 90%, 95%, or 99% identity to SEQ ID NO: 464. In some embodiments, an antibody provided herein comprises a V$_H$ sequence having at least about 50%, 60%, 70%, 80%, 90%, 95%, or 99% identity to SEQ ID NO: 474.

In some embodiments, an antibody provided herein comprises a V$_H$ sequence having at least about 50%, 60%, 70%, 80%, 90%, 95%, or 99% identity to an illustrative V$_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474. In some embodiments, an antibody provided herein comprises a V$_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody or antigen binding fragment as described herein is encoded by the polynucleotide sequence as shown in any one of SEQ ID NOs: 385, 386, 387, 388, 389, 390, 391, 392, 393, 394, 395, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, or 426.

V$_L$ Domains

In some embodiments, an antibody or antigen binding fragment thereof provided herein comprises a V$_L$ sequence selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. In some embodiments, an antibody provided herein comprises a V$_L$ sequence of SEQ ID NO: 6. In some embodiments, an antibody provided herein comprises a V$_L$ sequence of SEQ ID NO: 26. In some embodiments, an antibody provided herein comprises a V$_L$ sequence of SEQ ID NO: 126. In some embodiments, an antibody provided herein comprises a V$_L$ sequence of SEQ ID NO: 186. In some embodiments, an antibody provided herein comprises a V$_L$ sequence of SEQ ID NO: 196. In some embodiments, an antibody provided herein comprises a V$_L$ sequence of SEQ ID NO: 226. In some embodiments, an antibody provided herein comprises a V$_L$ sequence of SEQ ID NO: 246. In some embodiments, an antibody provided herein comprises a V$_L$ sequence of SEQ ID NO: 266. In some embodiments, an antibody provided herein comprises a V$_L$ sequence of SEQ ID NO: 356. In some embodiments, an antibody provided herein comprises a V$_L$ sequence of SEQ ID NO: 376.

In some embodiments, the V$_L$ sequence has at least 70%, 80%, or 90% identity with SEQ ID NO: 6, wherein any variation from SEQ ID NO: 6 does not occur within CDR-L1, CDR-L2, or CDR-L3. In some embodiments, the V$_L$ sequence has at least 70%, 80%, or 90% identity with SEQ ID NO: 26, wherein any variation from SEQ ID NO: 26 does not occur within CDR-L1, CDR-L2, or CDR-L3. In some embodiments, the V$_L$ sequence has at least 70%, 80%, or 90% identity with SEQ ID NO: 126, wherein any variation from SEQ ID NO: 126 does not occur within CDR-L1, CDR-L2, or CDR-L3. In some embodiments, the V$_L$ sequence has at least 70%, 80%, or 90% identity with SEQ ID NO: 186, wherein any variation from SEQ ID NO: 186 does not occur within CDR-L1, CDR-L2, or CDR-L3. In some embodiments, the V$_L$ sequence has at least 70%, 80%, or 90% identity with SEQ ID NO: 196, wherein any variation from SEQ ID NO: 196 does not occur within CDR-L1, CDR-L2, or CDR-L3. In some embodiments, the V$_L$ sequence has at least 70%, 80%, or 90% identity with SEQ ID NO: 226, wherein any variation from SEQ ID NO: 226 does not occur within CDR-L1, CDR-L2, or CDR-L3. In some embodiments, the V$_L$ sequence has at least 70%, 80%, or 90% identity with SEQ ID NO: 246, wherein any variation from SEQ ID NO: 246 does not occur within CDR-L1, CDR-L2, or CDR-L3. In some embodiments, the V$_L$ sequence has at least 70%, 80%, or 90% identity with SEQ ID NO: 266, wherein any variation from SEQ ID NO: 266 does not occur within CDR-L1, CDR-L2, or CDR-L3. In some embodiments, the V$_L$ sequence has at least 70%, 80%, or 90% identity with SEQ ID NO: 356, wherein any variation from SEQ ID NO: 356 does not occur within CDR-L1, CDR-L2, or CDR-L3. In some embodiments, the V$_L$ sequence has at least 70%, 80%, or 90% identity with SEQ ID NO: 376, wherein any variation from SEQ ID NO: 376 does not occur within CDR-L1, CDR-L2, or CDR-L3. In some embodiments, the V$_L$ sequence has at least 70%, 80%, or 90% identity with SEQ ID NO: 439, wherein any variation from SEQ ID NO: 439 does not occur within CDR-L1, CDR-L2, or CDR-L3. In some embodiments, the V$_L$ sequence has at least 70%, 80%, or 90% identity with SEQ ID NO: 449, wherein any variation from SEQ ID NO: 449 does not occur within CDR-L1, CDR-L2, or CDR-L3. In some embodiments, the V$_L$ sequence has at least 70%, 80%, or 90% identity with SEQ ID NO: 459, wherein any variation from SEQ ID NO: 459 does not occur within CDR-L1, CDR-L2, or CDR-L3. In some embodiments, the V$_L$ sequence has at least 70%, 80%, or 90% identity with SEQ ID NO: 469, wherein any variation from SEQ ID NO: 469 does not occur within CDR-L1, CDR-L2, or CDR-L3. In some embodiments, the V$_L$ sequence has at least 70%, 80%, or 90% identity with SEQ ID NO: 479, wherein any variation from SEQ ID NO: 479 does not occur within CDR-L1, CDR-L2, or CDR-L3.

In some embodiments, an antibody provided herein comprises a V$_L$ sequence having at least about 50%, 60%, 70%, 80%, 90%, 95%, or 99% identity to SEQ ID NO: 6. In some embodiments, an antibody provided herein comprises a V$_L$ sequence having at least about 50%, 60%, 70%, 80%, 90%, 95%, or 99% identity to SEQ ID NO: 26. In some embodiments, an antibody provided herein comprises a V$_L$ sequence having at least about 50%, 60%, 70%, 80%, 90%, 95%, or 99% identity to SEQ ID NO: 126. In some embodiments, an antibody provided herein comprises a V$_L$ sequence having at least about 50%, 60%, 70%, 80%, 90%, 95%, or 99% identity to SEQ ID NO: 186. In some embodiments, an antibody provided herein comprises a V$_L$ sequence having at least about 50%, 60%, 70%, 80%, 90%, 95%, or 99% identity to SEQ ID NO: 196. In some embodiments, an antibody provided herein comprises a V$_L$ sequence having at least about 50%, 60%, 70%, 80%, 90%, 95%, or 99% identity to SEQ ID NO: 226. In some embodiments, an antibody provided herein comprises a V$_L$ sequence having at least about 50%, 60%, 70%, 80%, 90%, 95%, or 99% identity to SEQ ID NO: 246. In some embodiments, an antibody provided herein comprises a V$_L$ sequence having at least about 50%, 60%, 70%, 80%, 90%, 95%, or 99% identity to SEQ ID NO: 266. In some embodiments, an antibody provided herein comprises a V$_L$ sequence having at least about 50%, 60%, 70%, 80%, 90%, 95%, or 99% identity to SEQ ID NO: 356. In some embodiments, an antibody provided herein comprises a V$_L$ sequence having at least about 50%, 60%, 70%, 80%, 90%, 95%, or 99% identity to V$_L$ sequence of SEQ ID NO: 376. In some embodiments, an antibody provided herein comprises a V$_L$ sequence having at least about 50%, 60%, 70%, 80%, 90%, 95%, or 99% identity to V$_L$ sequence of SEQ ID NO: 439. In some embodiments, an antibody provided herein comprises a V$_L$ sequence having at least about 50%, 60%, 70%, 80%, 90%, 95%, or 99% identity to V$_L$ sequence of SEQ ID NO: 449. In some embodiments, an antibody provided herein comprises a V$_L$ sequence having at least about 50%, 60%, 70%, 80%, 90%, 95%, or 99% identity to V$_L$ sequence of SEQ ID NO: 459. In some embodiments, an antibody provided herein comprises a V$_L$ sequence having at least about 50%, 60%, 70%, 80%, 90%, 95%, or 99% identity to V$_L$ sequence of SEQ ID NO: 469. In some embodiments, an antibody provided herein comprises a V$_L$ sequence having at least about 50%, 60%, 70%, 80%, 90%, 95%, or 99% identity to V$_L$ sequence of SEQ ID NO: 479.

In some embodiments, an antibody provided herein comprises a V$_L$ sequence having at least about 50%, 60%, 70%, 80%, 90%, 95%, or 99% identity to an illustrative V$_L$ sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. In some embodiments, an antibody provided herein comprises a V$_L$ sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

V$_H$-V$_L$ Combinations

In some embodiments, an antibody or antigen binding fragment thereof provided herein comprises a V$_H$ sequence selected from SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474; and a V$_L$ sequence selected from SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479.

In some embodiments, an antibody provided herein comprises a V$_H$ sequence of SEQ ID NO: 1 and a V$_L$ sequence of SEQ ID NO: 6. In some embodiments, an antibody provided herein comprises a V$_H$ sequence of SEQ ID NO: 21 and a V$_L$ sequence of SEQ ID NO: 26. In some embodiments, an antibody provided herein comprises a V$_H$ sequence of SEQ ID NO: 121 and V$_L$ sequence of SEQ ID NO: 126. In some embodiments, an antibody provided herein comprises a V$_H$ sequence of SEQ ID NO: 181 and a V$_L$ sequence of SEQ ID NO: 186. In some embodiments, an antibody provided herein comprises a V$_H$ sequence of SEQ ID NO: 191 and a V$_L$ sequence of SEQ ID NO: 196. In some embodiments, an antibody provided herein comprises a V$_H$ sequence of SEQ ID NO: 221 and a V$_L$ sequence of SEQ ID NO: 226. In some embodiments, an antibody provided herein comprises a V$_H$ sequence of SEQ ID NO: 241 and a V$_L$ sequence of SEQ ID NO: 246. In some embodiments, an antibody provided herein comprises a V$_H$ sequence of SEQ ID NO: 261 and a V$_L$ sequence of SEQ ID NO: 266 In some embodiments, an antibody provided herein comprises a V$_H$ sequence of SEQ ID NO: 351 and a V$_L$ sequence of SEQ ID NO: 356. In some embodiments, an antibody provided herein comprises a V$_H$ sequence of SEQ ID NO: 371 and a V$_L$ sequence of SEQ ID NO: 376. In some embodiments, an antibody provided herein comprises a V$_H$ sequence of SEQ ID NO: 434 and a V$_L$ sequence of SEQ ID NO: 439. In some embodiments, an antibody provided herein comprises a V$_H$ sequence of SEQ ID NO: 444 and a V$_L$ sequence of SEQ ID NO: 449. In some embodiments, an antibody provided herein comprises a V$_H$ sequence of SEQ ID NO: 454 and a V$_L$ sequence of SEQ ID NO: 459. In some embodiments, an antibody provided herein comprises a V$_H$ sequence of SEQ ID NO: 464 and a V$_L$ sequence of SEQ ID NO: 469. In some embodiments, an antibody provided herein comprises a V$_H$ sequence of SEQ ID NO: 474 and a V$_L$ sequence of SEQ ID NO: 479.

In some embodiments, the V$_H$ sequence has at least 70%, 80%, or 90% identity with SEQ ID NO: 1 and wherein the variable region of the light chain has at least 70%, 80%, or 90% identity with SEQ ID NO: 6, wherein any variation from SEQ ID NO: 1 does not occur within CDR-H1, CDR-H2, or CDR-H3 and wherein any variation from SEQ ID NO: 6 does not occur within CDR-L1, CDR-L2, or CDR-L3. In some embodiments, the V$_H$ sequence has at least 70%, 80%, or 90% identity with SEQ ID NO: 21 and wherein the variable region of the light chain has at least 70%, 80%, or 90% identity with SEQ ID NO: 26, wherein any variation from SEQ ID NO: 21 does not occur within CDR-H1, CDR-H2, or CDR-H3 and wherein any variation from SEQ ID NO: 26 does not occur within CDR-L1, CDR-L2, or CDR-L3. In some embodiments, the V$_H$ sequence has at least 70%, 80%, or 90% identity with SEQ ID NO: 121 and wherein the variable region of the light chain has at least 70%, 80%, or 90% identity with SEQ ID NO: 126, wherein any variation from SEQ ID NO: 121 does not occur within CDR-H1, CDR-H2, or CDR-H3 and wherein any variation from SEQ ID NO: 126 does not occur within CDR-L1, CDR-L2, or CDR-L3. In some embodiments, the V$_H$ sequence has at least 70%, 80%, or 90% identity with SEQ ID NO: 181 and wherein the variable region of the light chain has at least 70%, 80%, or 90% identity with SEQ ID NO: 186, wherein any variation from SEQ ID NO: 181 does not occur within CDR-H1, CDR-H2, or CDR-H3 and wherein any variation from SEQ ID NO: 186 does not occur within CDR-L1, CDR-L2, or CDR-L3. In some embodiments, the $V_H$ sequence has at least 70%, 80%, or 90% identity with SEQ ID NO: 191 and wherein the variable region of the light chain has at least 70%, 80%, or 90% identity with SEQ ID NO: 196, wherein any variation from SEQ ID NO: 191 does not occur within CDR-H1, CDR-H2, or CDR-H3 and wherein any variation from SEQ ID NO: 196 does not occur within CDR-L1, CDR-L2, or CDR-L3. In some embodiments, the $V_H$ sequence has at least 70%, 80%, or 90% identity with SEQ ID NO: 221 and wherein the variable region of the light chain has at least 70%, 80%, or 90% identity with SEQ ID NO: 226, wherein any variation from SEQ ID NO: 221 does not occur within CDR-H1, CDR-H2, or CDR-H3 and wherein any variation from SEQ ID NO: 226 does not occur within CDR-L1, CDR-L2, or CDR-L3. In some embodiments, the $V_H$ sequence has at least 70%, 80%, or 90% identity with SEQ ID NO: 241 and wherein the variable region of the light chain has at least 70%, 80%, or 90% identity with SEQ ID NO: 246, wherein any variation from SEQ ID NO: 241 does not occur within CDR-H1, CDR-H2, or CDR-H3 and wherein any variation from SEQ ID NO: 246 does not occur within CDR-L1, CDR-L2, or CDR-L3. In some embodiments, the $V_H$ sequence has at least 70%, 80%, or 90% identity with SEQ ID NO: 261 and wherein the variable region of the light chain has at least 70%, 80%, or 90% identity with SEQ ID NO: 266, wherein any variation from SEQ ID NO: 261 does not occur within CDR-H1, CDR-H2, or CDR-H3 and wherein any variation from SEQ ID NO: 266 does not occur within CDR-L1, CDR-L2, or CDR-L3. In some embodiments, the $V_H$ sequence has at least 70%, 80%, or 90% identity with SEQ ID NO: 351 and wherein the variable region of the light chain has at least 70%, 80%, or 90% identity with SEQ ID NO: 356, wherein any variation from SEQ ID NO: 351 does not occur within CDR-H1, CDR-H2, or CDR-H3 and wherein any variation from SEQ ID NO: 356 does not occur within CDR-L1, CDR-L2, or CDR-L3. In some embodiments, the $V_H$ sequence has at least 70%, 80%, or 90% identity with SEQ ID NO: 371 and wherein the variable region of the light chain has at least 70%, 80%, or 90% identity with SEQ ID NO: 376, wherein any variation from SEQ ID NO: 371 does not occur within CDR-H1, CDR-H2, or CDR-H3 and wherein any variation from SEQ ID NO: 376 does not occur within CDR-L1, CDR-L2, or CDR-L3. In some embodiments, the $V_H$ sequence has at least 70%, 80%, or 90% identity with SEQ ID NO: 434 and wherein the variable region of the light chain has at least 70%, 80%, or 90% identity with SEQ ID NO: 439, wherein any variation from SEQ ID NO: 434 does not occur within CDR-H1, CDR-H2, or CDR-H3 and wherein any variation from SEQ ID NO: 439 does not occur within CDR-L1, CDR-L2, or CDR-L3. In some embodiments, the $V_H$ sequence has at least 70%, 80%, or 90% identity with SEQ ID NO: 444 and wherein the variable region of the light chain has at least 70%, 80%, or 90% identity with SEQ ID NO: 449, wherein any variation from SEQ ID NO: 444 does not occur within CDR-H1, CDR-H2, or CDR-H3 and wherein any variation from SEQ ID NO: 449 does not occur within CDR-L1, CDR-L2, or CDR-L3. In some embodiments, the $V_H$ sequence has at least 70%, 80%, or 90% identity with SEQ ID NO: 454 and wherein the variable region of the light chain has at least 70%, 80%, or 90% identity with SEQ ID NO: 459, wherein any variation from SEQ ID NO: 454 does not occur within CDR-H1, CDR-H2, or CDR-H3 and wherein any variation from SEQ ID NO: 459 does not occur within CDR-L1, CDR-L2, or CDR-L3. In some embodiments, the $V_H$ sequence has at least 70%, 80%, or 90% identity with SEQ ID NO: 464 and wherein the variable region of the light chain has at least 70%, 80%, or 90% identity with SEQ ID NO: 469, wherein any variation from SEQ ID NO: 464 does not occur within CDR-H1, CDR-H2, or CDR-H3 and wherein any variation from SEQ ID NO: 469 does not occur within CDR-L1, CDR-L2, or CDR-L3. In some embodiments, the $V_H$ sequence has at least 70%, 80%, or 90% identity with SEQ ID NO: 474 and wherein the variable region of the light chain has at least 70%, 80%, or 90% identity with SEQ ID NO: 479, wherein any variation from SEQ ID NO: 474 does not occur within CDR-H1, CDR-H2, or CDR-H3 and wherein any variation from SEQ ID NO: 479 does not occur within CDR-L1, CDR-L2, or CDR-L3.

In certain aspects, any of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474 can be combined with any of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. For example, SEQ ID NO: 11 can be combined with any of SEQ ID NO: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. As another example, SEQ ID NO: 16 can be combined with any of SEQ ID NO: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, or 371; and a $V_L$ sequence having at least about 50%, 60%, 70%, 80%, 90%, 95%, or 99% identity to an illustrative VL sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479. In some embodiments, an antibody provided herein comprises a VH sequence provided in SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 434, 444, 454, 464, or 474 with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a VL sequence provided in SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 439, 449, 459, 469, or 479, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, the percent homology of the variable heavy or variable light chain is to be calculated outside the CDRs. For instance, the percent homology can be calculated in the framework regions In some embodiments, an antibody or antigen binding fragment thereof comprises a heavy chain provided in SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478.

In some embodiments, an antibody or antigen binding fragment thereof comprises a light chain provided in SEQ ID NOs: 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483.

In certain aspects, any of SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478 can be combined with any of SEQ ID NOs: 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483.

In some embodiments, an antibody provided herein comprises a heavy chain sequence having at least about 50%, 60%, 70%, 80%, 90%, 95%, or 99% identity to an illustrative $V_H$ sequence provided in SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478; and a light chain sequence having at least about 50%, 60%, 70%, 80%, 90%, 95%, or 99% identity to an illustrative VL sequence provided in SEQ ID NOs 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483. In some embodiments, an antibody provided herein comprises a heavy chain sequence provided in SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 438, 448, 458, 468 or 478 with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a light chain sequence provided in SEQ ID NOs: 10, 20, 30, 40, 50, 60, 70, 80, 90, 100, 110, 120, 130, 140, 150, 160, 170, 180, 190, 210, 220, 230, 240, 250, 260, 270, 280, 290, 310, 320, 330, 340, 350, 360, 370, 380, 443, 453, 463, 473, or 483, with up to 1, 2, 3, 4, 5, 6, 7, 8, 9, 10, 11, 12, 13, 14, 15, 16, 17, 18, 19, 20, 21, 22, 23, 24, or 25 amino acid substitutions.

In some embodiments, an antibody or antigen binding fragment polynucleotide sequence comprises a signal sequence as shown in SEQ ID NOs: 427 or 430. In some embodiments, an antibody or antigen binding fragment polypeptide sequence comprises a signal sequence as shown in SEQ ID NOs: 428 or 429.

Fc Region

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

In some embodiments, an antibody is an IgG1 antibody.
In some embodiments, an antibody is an IgG3 antibody.
In some embodiments, an antibody is an IgG2 antibody.
In some embodiments, an antibody is an IgG4 antibody.

Modifications in the CH2 domain can affect the binding of FcRs to the Fc. A number of amino acid modifications in the Fc region are known in the art for selectively altering the affinity of the Fc for different Fc-gamma (Fcγ) receptors. In one embodiment, the Fc comprises one or more modifications to promote selective binding of Fc-gamma receptors.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC.

In certain embodiments, an antibody provided herein comprises an Fc region with one or more amino acid substitutions which improve ADCC.

In some embodiments, an antibody provided herein comprises one or more alterations that improves or diminishes C1q binding and/or CDC. See U.S. Pat. No. 6,194,551; WO 99/51642; and Idusogie et al., J. Immunol., 2000, 164:4178-4184; each of which is incorporated by reference in its entirety.

Thus, in one embodiment, an antibody described herein can include a dimeric Fc that comprises one or more amino acid modifications that confer improved effector function. In another embodiment, the antibody can be afucosylated to improve effector function.

Fc modifications reducing FcγR and/or complement binding and/or effector function are known in the art. Recent publications describe strategies that have been used to engineer antibodies with reduced or silenced effector activity (see Strohl, W R (2009), Curr Opin Biotech 20:685-691, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) *J. Mol. Biol.* 420: 204-219) describe specific modifications to reduce FcγR or complement binding to the Fc.

Methods of producing antibodies with little or no fucose on the Fc glycosylation site (Asn 297 EU numbering) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 Dec; 20 (12):1607-18.) Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies.

Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety).

Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In some aspects, an antibody provided herein comprises an IgG1 domain with reduced fucose content at position Asn 297 compared to a naturally occurring IgG1 domain. Such Fc domains are known to have improved ADCC. See Shields et al., J. Biol. Chem., 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., Biotech. Bioeng., 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

Examples of cell lines capable of producing defucosylated antibodies include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.,* 2004, 87: 614-622; Kanda et al., *Biotechnol. Bioeng.,* 2006, 94:680-688; and WO 2003/085107; each of which is incorporated by reference in its entirety).

In some embodiments, an antibody has antibody-dependent cellular phagocytosis (ADCP) activity. ADCP can occur when antibodies bind to antigens on the surface of pathogenic or tumorigenic target-cells. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell can be initiated. ADCP can be considered a form of ADCC.

In some embodiments, the antibodies are capable of forming an immune complex. For example, an immune complex can be a tumor cell covered by antibodies.

In some aspects, an anti-MARCO antibody does not substantially bind myeloid cells present outside of cancer tissue. In some aspects, an anti-MARCO antibody does not substantially bind stimulatory myeloid cells present in cancer tissue.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR and ScFv.

In some embodiments, antibodies are specific for surface antigens, such as MARCO protein. In some embodiments, therapeutic antibodies are specific for tumor antigens (e.g., molecules specifically expressed by tumor cells). In particular embodiments, the therapeutic antibodies may have human or non-human primate IgG1 or IgG3 Fc portions.

Binding

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. Crosslinking of an antigen target is a type of binding. In some embodiments, an anti-MARCO antibody crosslinks MARCO to MARCO on a MARCO+ cell.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

The term "$k_d$" ($\sec^{-1}$), as used herein, refers to the dissociation rate constant of a particular antibody-antigen interaction. This value is also referred to as the $k_{off}$ value.

The term "$k_a$" ($M^{-1} \times \sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular antibody-antigen interaction. $K_A = k_a/k_d$.

When used herein in the context of two or more antibodies, the term "competes with" or "cross-competes with" indicates that the two or more antibodies compete for binding to an antigen (e.g., MARCO). In one exemplary assay, MARCO is coated on a surface and contacted with a first MARCO antibody, after which a second MARCO antibody is added. In another exemplary assay, a first MARCO antibody is coated on a surface and contacted with MARCO, and then a second MARCO antibody is added. If the presence of the first MARCO antibody reduces binding of the second MARCO antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for MARCO and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [Internet], Updated Dec. 24, 2014 (ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

In some embodiments, an antibody provided herein binds human MARCO. In some embodiments, an antibody provided herein binds mouse MARCO. In some embodiments, an antibody provided herein binds rhesus macaque MARCO. In some embodiments, an antibody provided herein binds cynomolgus MARCO. In some embodiments, an antibody provided herein binds human, rhesus macaque, and/or cynomolgus MARCO.

In some embodiments, an antibody provided herein binds human MARCO with a $K_D$ of less than or equal to about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 3, 4, 5, 6, 7, 8, 9, or $10 \times 10^9$ M, as measured by Biacore assay. In some embodiments, the $K_D$ of the antibody provided herein is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, or 5-10×10$^9$ M, as measured by Biacore assay.

In some embodiments, the antibody provided herein binds human MARCO with a $K_D$ of less than or equal to about 2, 1.98, 1.95, 1.9, 1.85, 1.8, 1.75, 1.7, 1.65, 1.6, 1.55, 1.50, 1.45, or 1.4×10$^{-9}$ M, or less, as measured by Biacore assay. In some embodiments, the antibody provided herein binds human MARCO with a $K_D$ between 1.9-1.8, 1.8-1.7, 1.7-1.6, 1.6-1.5, or 1.9-1.5×10$^{-9}$ M as measured by Biacore assay. In some embodiments, the antibody provided herein binds human MARCO with a $K_d$ of less than or equal to about 10, 9.56, 9.5, 9.0, 8.88, 8.84, 8.5, 8, 7.5, 7.32, 7, 6.5, 6, 5.5, 5, 4.5, 4, 3.5, 3, 2.5, 2, 1.5, or 1×10$^{-4}$ (1/s), or less, as measured by Biacore assay. In some embodiments, the antibody provided herein binds human MARCO with a $K_d$ between 7-10, 7-8, 8-9, 9-10, 7-7.5, 7.5-8, 8.-8.5, 8.5-9, 9-9,5, or 9.5-10×10$^4$ (1/s) as measured by Biacore assay. In some embodiments, the antibody provided herein binds human MARCO with a $K_a$ of greater than or equal to about 4, 4.1, 4.2, 4.3, 4.4, 4.5, 4.6, 4.7, 4.8, 4.9, 45, 5.1, 5.2, 5.3, 5.4, 5.5, 5.6, 5.7, 5.8, 5.9, 6, 7, 8, 9, or 10×10$^5$ (1/Ms), or more, as measured by Biacore assay. In some embodiments, the antibody provided herein binds human MARCO with a $K_a$ between 4-7, 4-4.5, 4.5-5, 5-5.5, 5.5-6, 6-6.5, or 6.5-7, 7-8, 8-9, or 9-10×10$^5$ (1/Ms) as measured by Biacore assay.

In some embodiments, the antibody provided herein binds human MARCO with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds human MARCO with an EC50 between 0.6-1.4 nM as measured by measured by flow cytometry. In some embodiments, the antibody binds human MARCO with an EC50 of about 0.5, 0.6, 0.9, 1.1, 1.2, 1.3, 1.4, or 1.5 nM as measured by measured by flow cytometry.

In some embodiments, the antibody provided herein binds mouse MARCO with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds mouse MARCO with an EC50 between 0.6-1.4 nM as measured by measured by flow cytometry. In some embodiments, the antibody binds mouse MARCO with an EC50 of about 0.5, 0.6, 0.9, 1.1, 1.2, 1.3, 1.4, or 1.5 nM as measured by measured by flow cytometry.

In some embodiments, the antibody provided herein does not bind human MARCO with an EC50 great than or equal to 20 nM or more as measured by measured by flow cytometry. In some embodiments, the antibody provided herein does not bind mouse MARCO with an EC50 great than or equal to 3 nM or more as measured by measured by flow cytometry.

To screen for antibodies which bind to an epitope on a target antigen bound by an antibody of interest (e.g., MARCO), a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

Competition between antibodies can be determined by an assay in which an antibody under test inhibits or blocks specific binding of a reference antibody to a common antigen (see, e.g., Junghans et al., Cancer Res. 50:1495, 1990; Fendly et al. Cancer Research 50: 1550-1558; U.S. Pat. No. 6,949,245). A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to MARCO with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

In some embodiments, the antibody binds to the Scavenger Receptor Cysteine-Rich (SRCR) domain of MARCO.

In some embodiments, the antibody binds to an epitope on SRCR comprising at least one of residues Q452, Y472, or K473 of wild type human MARCO (SEQ ID NO: 363). In some embodiments, the antibody binds to an epitope on SRCR comprising at least one of residues H505, D507, S509, or E511 of wild type human MARCO (SEQ ID NO: 363). In some embodiments, the antibody binds to an epitope on SRCR comprising at least one of residues E450, Q452, Q487, or T499 of wild type human MARCO (SEQ ID NO: 363). In some embodiments, the antibody binds to an epitope on SRCR comprising at least one of residues E450, Q452, Q487, T499, H505, D507, S509, or E511 of wild type human MARCO (SEQ ID NO: 363).

In some embodiments, the antibody or antigen binding fragment thereof binds to at least one of the following residues: Q452, Y472, K473, E450, Q487, T499, H505, D507, S509, or E511 of MARCO listed in SEQ ID NO: 363. In some embodiments, the antibody or antigen binding fragment thereof binds to at least two, three, four, five, six, seven, eight, nine, or ten of the following residues: Q452, Y472, K473, E450, Q487, T499, H505, D507, S509, or E511 of SEQ ID NO: 363. In some embodiments, the antibody or antigen binding fragment thereof binds to at least two of the following residues: Q452, Y472, K473, E450, Q487, T499, H505, D507, S509, or E511 of SEQ ID NO: 363. In some embodiments, the antibody or antigen binding fragment thereof binds to at least three of the following residues: Q452, Y472, K473, E450, Q487, T499, H505, D507, S509, or E511 of SEQ ID NO: 363. In some embodiments, the antibody or antigen binding fragment thereof binds to at least four of the following residues: Q452, Y472, K473, E450, Q487, T499, H505, D507, S509, or E511 of SEQ ID NO: 363.

In some embodiments, the antibody or antigen binding fragment thereof binds to at least Q452. In some embodiments, the antibody or antigen binding fragment thereof binds to at least Y472. In some embodiments, the antibody or antigen binding fragment thereof binds to at least K473. In some embodiments, the antibody or antigen binding fragment thereof binds to at least E450. In some embodiments, the antibody or antigen binding fragment thereof binds to at least Q487. In some embodiments, the antibody or antigen binding fragment thereof binds to at least T499. In some embodiments, the antibody or antigen binding fragment thereof binds to at least H505. In some embodiments, the antibody or antigen binding fragment thereof binds to at least D507. In some embodiments, the antibody or antigen binding fragment thereof binds to at least S509. In some embodiments, the antibody or antigen binding fragment thereof binds to at least E511.

Function

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc. Natl. Acad. Sci. (USA) 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

In some embodiments, an antibody is an agonistic antibody. An agonistic antibody can induce (e.g., increase) one or more activities or functions of MARCO-expressing cells after the antibody binds a MARCO protein expressed on the cell. The agonistic antibody may bind to and activate MARCO-expressing cells, causing changes in proliferation of the cell or modifying antigen presentation capabilities. The agonistic antibody may bind to and activate MARCO-expressing cells, triggering intracellular signaling pathways that lead to modified cell growth or apoptosis.

In some embodiments, an antibody is an antagonistic antibody. An antagonistic antibody can block (e.g. decrease) one or more activities or functions of MARCO-expressing cells after the antibody binds a MARCO protein expressed on the cell. For example, the antagonist antibody may bind to and block ligand binding to one or more MARCO proteins, preventing differentiation and proliferation of the cell or modifying antigen presentation capabilities. The antagonist antibody may bind to and prevent activation of a MARCO protein by its ligand, modifying intracellular signaling pathways that contribute to cell growth and survival.

In some embodiments an antibody is a depleting antibody. A depleting antibody is one that would kill a MARCO-expressing cell upon contact through the antibody's interaction with other immune cells of molecules. For example, antibodies, when bound to cells bearing MARCO proteins, could engage complement proteins and induce complement-dependent cell lysis. Antibodies, when bound to cells bearing MARCO proteins, could also trigger neighboring cells bearing Fc receptors to kill them by antibody-dependent cellular cytotoxicity (ADCC).

In some embodiments, an antibody is a neutralizing antibody, and the antibody neutralizes one or more biological activities of MARCO-expressing cells. In some embodiments, MARCO protein is expressed on the surface of MARCO-expressing cells and the antibody recognizes the extracellular domain of MARCO protein.

In some embodiments an antibody is selective for MARCO-expressing cells (preferentially binds to MARCO). In certain embodiments, an antibody that selectively binds to MARCO-expressing cells has a dissociation constant (Kd) of range of 0.0001 nM to 1 μM. In certain embodiments, an antibody specifically binds to an epitope on a MARCO protein that is conserved among the protein from different species. In another embodiment, selective binding includes, but does not require, exclusive binding.

In one embodiment an anti-MARCO antibody bound to its target is responsible for causing the in vivo depletion of MARCO-expressing cells to which it is bound. In some embodiments, effector proteins induced by clustered antibodies can trigger a variety of responses, including release of inflammatory cytokines, regulation of antigen production, endocytosis, or cell killing. In one embodiment the antibody is capable of recruiting and activating complement or mediating antibody-dependent cellular cytotoxicity (ADCC) in vivo, or mediating phagocytosis by binding Fc receptors in vivo. The antibody may also deplete MARCO-expressing cells by inducing apoptosis or necrosis of the MARCO-expressing cell upon binding.

In some embodiments the disabling of MARCO-expressing cells is in vitro and is achieved: a) by killing of the MARCO-expressing cells; b) magnetic bead depletion of the MARCO-expressing cells; or c) Fluorescence-activated cell sorting (FACS) sorting of the MARCO-expressing cells.

In some embodiments, an antibody is bound to, or conjugated to an effector molecule. In particular embodiments, an antibody is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

In certain embodiments an antibody is conjugated to a drug, e.g., a toxin, a chemotherapeutic agent, an immune modulator, or a radioisotope. Several methods of preparing ADCs (antibody drug conjugates) are known in the art and are described in U.S. Pat. No. 8,624,003 (pot method), U.S. Pat. No. 8,163,888 (one-step), and U.S. Pat. No. 5,208,020 (two-step method), for example. An antibody or antigen-binding fragment thereof can be conjugated to at least one agent including a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody, and a second antibody fragment that is antigen binding.

In some embodiments, an antibody modulates an immune response. In some embodiments, an antibody increases an immune response. In some embodiments, an antibody enhances or initiates an immune response.

Method of Treating Cancer

In another aspect, the invention provides methods of treating an immune-related condition (e.g., cancer) in an individual comprising administering to the individual an effective amount of a composition comprising an anti-MARCO antibody. In another aspect, the invention provides methods of enhancing an immune response in an individual comprising administering to the individual an effective amount of a composition comprising an anti-MARCO antibody.

In some embodiments, the methods provided herein are useful for the treatment of an immune-related condition in an individual. In one embodiment, the individual is a human.

In some embodiments, the methods provided herein (such as methods of enhancing an immune response) are useful for the treatment of cancer and as such an individual receiving the anti-MARCO antibody has cancer. In some embodiments, the cancer is a solid cancer. In some embodiments, the cancer is a liquid cancer. In some embodiments, the cancer is immunoevasive. In some embodiments, the cancer is immunoresponsive. In some embodiments, the cancer expresses IL-10. In some embodiments, the cancer is a hypoxic cancer. In particular embodiments, the cancer is selected from the group consisting of lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancers. In some embodiments, the cancer is colon cancer, breast cancer, basal-like breast cancer, ovarian cancer, or gastric cancer.

In some embodiments, the treatment results in a decrease in the cancer volume or size. In some embodiments, the treatment is effective at reducing a cancer volume as compared to the cancer volume prior to administration of the antibody. In some embodiments, the treatment results in a decrease in the cancer growth rate. In some embodiments, the treatment is effective at reducing a cancer growth rate as compared to the cancer growth rate prior to administration of the antibody. In some embodiments, the treatment is effective at eliminating the cancer.

In some embodiments, MARCO is expressed at a higher level in the cancer as compared to a non-cancer cell. In some embodiments, IL-10 is expressed at a higher level in the cancer as compared to a non-cancer cell. Levels of MARCO and/or IL-10 can be assessed by any technique known in the field, including, but not limited to, protein assays or nucleic acid assays such as FACS, Western blot, ELISA, immunoprecipitation, immunohistochemistry, monoplex immunohistochemistry, multiplex immunohistochemistry, flow cytometry, immunofluorescence, radioimmunoassay, dot blotting, immunodetection methods, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, Luminex, MSD, and FISH, and combinations thereof.

Combination Therapies

For the treatment of cancer, the anti-MARCO antibody may be combined with one or more antibodies that inhibit immune checkpoint proteins. Of particular interest are immune checkpoint proteins displayed on the surface of a tumor cell. The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279), are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD-1 are PD-1 ligand 1 (PD-L1; also known as B7-H1 and CD274) and PD-L2 (also known as B7-DC and CD273). PD-L1 is expressed on cancer cells and through binding to its receptor PD-1 on T cells it inhibits T cell activation/function. Inhibitors that block the interaction of PD-1 with its cognate ligands on the cancer cells, PD-L1 and PD-L2, can result in both increased T cell activation and function, and prevent cancer cells from evading the immune system.

In some embodiments, the immunotherapy is an agent that interferes with PD-1 and PD-L1 or PD-L2 binding. In some embodiments, the immunotherapy is an anti-PD1 antibody. In some embodiments, the immunotherapy is an anti-PD-L1 antibody. In some embodiments, the immunotherapy is an anti-PD-L2 antibody.

Various PD-1, PD-L1, and PD-L2 antibodies are known in the art. In some embodiments, the additional therapeutic agent is at least one of: Atezolizumab (PD-L1), Avelumab (PD-L1), Durvalumab (PD-L1), Nivolumab (PD-1), Pembrolizumab (PD-1), Cemiplimab (PD-1), Ipilimumab (CTLA-4), Tremelimumab (CTLA-4), or any combination thereof.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent.

Method of Immune Modulation

Immunosuppressive M2-like MARCO expressing cells, such as MARCO+ tumor associated macrophages (TAMs), and MARCO+ mMDSCs, are upregulated in IL-10 enriched and hypoxic tumor micro environments (TME). These cells suppress immune cytotoxic activity. Immunosuppression also leads to increased angiogenesis and metastasis.

Anti-MARCO antibodies can activate intra-tumor immunity at least by mediating repolarization of MARCO+ myeloid M2-like TAMs to M1-like TAMs, and repolarization of mMDSCs to pro-inflammatory monocytes. This repolarization can lead to production of cytokines, chemokines, and activation receptors, which in turn leads to activation of T cells, B cells, and NK cells. The repolarization of myeloid M2-like TAMs and mMDSCs can activate T cells, B cells, and NK cells. Once activated, these NK cells, CD8+ T cells, M1-like TAMs and inflammatory monocytes can induce tumor destruction. In addition, the anti-tumor immunity can be modulated by decreasing the M2-like TAMs and immunosuppressive mMDSCs. Anti-tumor immunity may also be mediated by increased antigen presentation and activation of cells in the spleen and lymph nodes. Binding of the anti-MARCO antibody to medullary cord macrophages (MCMs) can induce changes in adhesion and motility in the lymph node, and binding of the anti-MARCO antibody to marginal zone macrophages (MZMs) in the spleen can lead to changes in adhesion and motility, leading to potential B cell activation.

In some embodiments, repolarization of MARCO+ cells is observed by rapid modulation of phospho-signaling cascades involved in molecular association, enzymatic activity, transcription, translation, and pro-inflammatory signaling (Src, SYK, NF-kB, PI3K/AKT, TLR, STAT6, IL2RA, CAMK, PKC, Raf1, TPL2, MAPKs, cell cycle, survival, cell adhesion and migration, cytoskeletal rearrangement); changes in phagocytosis, adhesion, motility, and chemotaxis; activation of NF-kB reporter activity as single agent and in combination with TLRs agonists; induction of secretion of pro-inflammatory cytokines and chemokines, including but not limited to, IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, eotaxin; and increasing inflammasome activation and phagocytosis.

Methods of administration of a MARCO antibody as described herein can result in modulation of an immune response. Modulation can be an increase or decrease in an immune response. In some embodiments, modulation is an increase in an immune response.

In one aspect, administration of a MARCO antibody as described herein can result in induction of pro-inflammatory molecules, such as cytokines, chemokines, or expression of myeloid activation receptors by myeloid cells. Generally, induced pro-inflammatory molecules are present at levels greater than that achieved with isotype control. In some embodiments, the myeloid cells are MARCO-expressing (MARCO+) cells. In some embodiments, the MARCO+ myeloid cell is a monocyte or a macrophage. In some embodiments, the MARCO+ macrophage is a tumor associated macrophage (TAM) or a monocyte-derived macrophage (MDM). Such pro-inflammatory molecules in turn result in activation of anti-tumor immunity, including, but not limited to, T cell activation, T cell proliferation, T cell differentiation, M1-like macrophage activation, B cell regulation, and NK cell activation. Thus, the administration of an anti-MARCO antibody can induce multiple anti-tumor immune mechanisms that lead to tumor destruction.

In another aspect, provided herein are methods of increasing an immune response in an individual comprising administering to the individual an effective amount of a composition comprising an anti-MARCO antibody or antigen-binding fragment thereof. In some embodiments, the method of increasing an immune response in a subject comprises administering to the subject an antibody that binds to the SRCR domain of human MARCO (SEQ ID NO: 363). In some embodiments, the method of increasing an immune response in a subject comprises administering to the subject an antibody that competes for binding to human MARCO (SEQ ID NO: 363) with a reference antibody. In some embodiments, the method of increasing an immune response in a subject comprises comprising administering to the subject an antibody that competes for binding to human MARCO (SEQ ID NO: 363), wherein the antibody binds at least one of residues Q452, Y472, and K473 of human MARCO (SEQ ID NO: 363). In some embodiments, the method of increasing an immune response in a subject comprises comprising administering to the subject an antibody that competes for binding to human MARCO (SEQ ID NO: 363), wherein the antibody binds at least one of residues E450, Q452, Q487, and T499 of human MARCO (SEQ ID NO: 363). In some embodiments, the method of increasing an immune response in a subject comprises comprising administering to the subject an antibody that competes for binding to human MARCO (SEQ ID NO: 363), wherein the antibody binds at least one of residues H505, D507, S509, or E511 of human MARCO (SEQ ID NO: 363).

In some embodiments, the antibody is present in a pharmaceutical composition further comprising a pharmaceutically acceptable excipient.

In any and all aspects of increasing an immune response as described herein, any increase or decrease or alteration of an aspect of characteristic(s) or function(s) is as compared to a cell not contacted with an anti-MARCO antibody.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response. In some embodiments, the immune response is started or initiated by administration of an anti-MARCO antibody. In some embodiments, the immune response is enhanced by administration of an anti-MARCO antibody.

In another aspect, the present application provides methods of contacting a cell with an anti-MARCO antibody, which results in the modulation of the immune function of the cell. The modulation can be increasing an immune response or reprogramming of MARCO-expressing cells. In some embodiments, the modulation is an increase in immune function. In some embodiments, the modulation of function leads to the activation of MARCO-expressing myeloid cells. In some embodiments, the modulation of function leads to the reprogramming of MARCO-expressing myeloid cells.

In some embodiments, the cells are myeloid cells. In some embodiments, the cells are MARCO-expressing cells (MARCO+ cells). In some embodiments, the MARCO+ cells are one or more of monocytes, macrophages, tumor associated macrophage (TAM), and monocyte-derived macrophages (MDM). In some embodiments, the MARCO+ cell is a monocyte. In some embodiments, the MARCO+ cell is a macrophage. In some embodiments, the MARCO+ cell is a tumor associated macrophage (TAM). In some embodiments, the MARCO+ cell is a monocyte-derived macrophage (MDM). In some embodiments, contacting a MARCO-expressing cell with a MARCO antibody induces activation of the cell.

In some embodiments, the modulation of function of the MARCO+ cells leads to an increase in the cells' abilities to stimulate both native and activated CD8+ T-cells, for example, by increasing the ability of MARCO-expressing cells to cross-present tumor antigen on MHCI molecules to naive CD8+ T-cells or by increasing cytokine or chemokine secretion by the MARCO-expressing cells. In some embodiments, the modulation of function of the MARCO+ cells leads to an increase in the cells' abilities to stimulate both native and activated CD4+ T-cells, for example, by increasing the ability of MARCO-expressing cells to cross-present tumor antigen on MHCII molecules to naive CD4+ T-cells. In some embodiments, the modulation of function enhances or increases the cells' ability to produce cytokines, chemokines, or costimulatory or activating receptors. In some embodiments, the modulation increases the T-cell stimulatory function of the MARCO+ cell, including, for example, the cells' abilities to trigger T-cell receptor (TCR) signaling, T-cell proliferation, or T-cell cytokine production.

In some embodiments, the increased immune response is secretion of cytokines and chemokines. In some embodiments, the MARCO antibody has agonist activity. In some embodiments, the MARCO antibody induces increased expression of at least one cytokine or chemokine in a cell as compared to an isotype control antibody. In some embodiments, the MARCO antibody induces increased expression of at least one pro-inflammatory cytokine or chemokine in a cell as compared to an isotype control antibody. In some embodiments, the at least one cytokine or chemokine is selected from the group consisting of: IL-1α, IL-1β, IL-2, IL-4, IL-6, IL7R, IL-12, IL12-p70, IL-15, IL-18, IL-27, IP-10, IFN-γ, TNFα, MIP1-α, MIP1-β, MIP-2, CSF2, CSF3, G-CSF, M-CSF, CCL3, CCL4, CCL5, CCL20, CCL24, CXCL1, CXCL3, CXCL8, CXCL9, CXCL10, CXCL12, gro-alpha, MCP-1, MCP-3, LIF, or eotaxin. In some embodiments, the cytokine or chemokine is IL-2. In some embodiments, the cytokine or chemokine is IL-12. In some embodiments, the cytokine or chemokine secretion is increased between about 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody. In some embodiments, the chemokine is IL-2 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody. In some embodiments, the cytokine is IL-12 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody.

In some embodiments, the MARCO antibody induces decreased expression of at least one gene in a cell as compared to an isotype control antibody. In some embodiments, the at least one gene is ALK, MPB, TMEM37, NHSL2, or SLC46A2. In some embodiments, the gene is decreased between about 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody.

In some embodiments, the MARCO antibody induces inflammasome activation as compared to an isotype control antibody. Inflammasome activation can be determined by measuring IL-1β and/or IL-18 secretion.

In some embodiments, the MARCO antibody induces repolarization of myeloid M2-like TAMs to M1-like TAMS, and/or repolarization of mMDSCs to pro-inflammatory monocytes as compared to an isotype control antibody.

In some embodiments, the MARCO antibody increases CD8+ T cells, CD4+ T cells, NK cells, dendritic cells, MHCII$^{high}$ monocytes, MHCII$^{mid}$ monocytes, marginal zone macrophages, follicular B cells, and/or red pulp macrophages as compared to an isotype control antibody.

In some embodiments, upon cell contact the antibody decreases TAMs, neutrophils, marginal zone B cells, CD19+ B cells, and/or MHCII− monocytes, as compared to an isotype control antibody.

In some embodiments, the MARCO antibody modulates motility and/or phagocytosis changes by altering cytoskeletal, actin and muscles, and cell-adhesion related pathways in the tumor. In some embodiments, the MARCO antibody results in a pro-inflammatory activation within the TME, comprising M2 to M1 macrophage reprogramming, an increase in the phagocytosis and/or inflammasome, activation of NK cells, and/or activation of T cells.

In some embodiments, the MARCO antibody modulates cell signaling, cell adhesion, cytoskeletal, and motility changes in the lymph nodes. In some embodiments, the MARCO antibody binds to medullary cord macrophages in the lymph nodes and modulates cell adhesion and motility.

In some embodiments, the MARCO antibody modulates cell adhesion, cytoskeletal, migration, motility, cell signaling, and B cell activation in the spleen. In some embodiments, the MARCO antibody binds to marginal zone macrophages in the spleen and modulates cell adhesion, motility, and B cell activation.

In some embodiments, the modulation increases cell adhesion, cytoskeletal, and cell migration as compared to an isotype control antibody. In some embodiments, the modulation induces B cell maturation in the spleen as compared to an isotype control antibody. In some embodiments, the modulation induces cell signaling pathways comprising cell cycle, T cell receptor, phagocytosis, autophagy, and wnt pathways as compared to an isotype control antibody.

In some embodiments, the enhanced immune response is anti-tumor immune cell recruitment and activation.

In some embodiments, the antibody induces a memory immune response as compared to an isotype control antibody. In general, a memory immune response is a protective immune response upon a subsequent exposure to pathogens or antigens that the immune system encountered previously. Exemplary memory immune responses include the immune response after infection or vaccination with an antigen. In general, memory immune responses are mediated by lymphocytes such as T cells or B cells. In some embodiments, the memory immune response is a protective immune response to cancer, including cancer cell growth, proliferation, or metastasis. In some embodiments, the memory immune response inhibits, prevents, or reduces cancer cell growth, proliferation, or metastasis.

In some embodiments, the MARCO antibody induces or increases at least one of the following pathways or a gene associated with: B cell maturation in the spleen, the actin mediated cell contraction pathway, the kinase activation and activity pathway, the Toll-like receptor signaling pathway, the TLR 4 and 9 pathways, GTPase binding and activity, and/or the RAS-Rho signal transduction pathways, as compared to isotype antibody. In some embodiments, the MARCO antibody induces or increases at least one of the following pathways or a gene associated with: the humoral immune response, NK mediated immunity, NK activation, IL-2 and IL-12 production, cell killing, regulation of effector process, T cell proliferation, activation, differentiation, chemotaxis and migration, cell-cell adhesion, phagocytosis, and/or myeloid differentiation, as compared to isotype antibody.

In some embodiments, the MARCO antibody induces or increases at least one of the following pathways or a gene associated with: Natural Killer cell mediated cytotoxicity, T cell receptor signaling pathway, JAK/STAT signaling pathway, cytokine-cytokine receptor interaction, Intestinal immune network for IgA production, leukocyte trans-endothelial migration, chemokine signaling pathway, hematopoietic cell lineage, type II diabetes mellitus, and Fc-epsilon RI signaling pathway, as compared to isotype antibody. In some embodiments, the MARCO antibody decreases or suppresses at least one of the following pathways or a gene associated with: homologous recombination, Alzheimer's disease, RNA polymerase, arginine and proline metabolism, citrate cycle (TCA cycle), porphyrin and chlorophyll metabolism, valine, leucine, and isoleucine degradation, biosynthesis of unsaturated fatty acids, N-glycan biosynthesis, and aminoacyl tRNA biosynthesis, as compared to isotype antibody.

In some embodiments, the MARCO antibody induces or increases at least one of the following pathways or a gene associated with: cytokine-cytokine receptor interaction, Natural Killer cell mediated cytotoxicity, primary immunodeficiency, chemokine signaling pathway, hematopoietic cell lineage, JAK/STAT signaling pathway, T cell receptor signaling pathway, Intestinal immune network for IgA production, neuroactive ligand receptor interaction, and Fc-epsilon RI signaling pathway, as compared to isotype antibody. In some embodiments, the MARCO antibody decreases or suppresses at least one of the following pathways or a gene associated with: glycolysis gluconeogenesis, propanoate metabolism, proteasome, citrate cycle TCA cycle, cardiac muscle contraction, Alzheimer's disease, Huntington's disease, oxidative phosphorylation, ribosome, and Parkinson's disease, as compared to isotype antibody.

In some embodiments, the MARCO antibody induces or increases at least one of the following pathways or a gene associated with: phosphatidylinositol signaling system, focal adhesion, inositol phosphate metabolism, axon guidance, adherens junction, pathways in cancer, regulation of actin cytoskeleton, progesterone mediated oocyte maturation, ERBB signaling pathway, and Wnt signaling pathway, as compared to isotype antibody. In some embodiments, the MARCO antibody decreases or suppresses at least one of the following pathways or a gene associated with: aminoacyl tRNA biosynthesis, lysosome, histidine metabolism, drug metabolism cytochrome p450, proteasome, Alzheimer's disease, Huntington's disease, Parkinson disease, oxidative phosphorylation, and ribosome, as compared to isotype antibody.

In some embodiments, the MARCO antibody induces or increases at least one of the following pathways or a gene associated with: focal adhesion, phosphatidylinositol signaling system, neurotrophin signaling pathway, insulin signaling pathway, inositol phosphate metabolism, MAPK signaling pathway, pathways in cancer, regulation of actin cytoskeleton, ERBB signaling pathway, and adherens junction, as compared to isotype antibody. In some embodiments, the MARCO antibody decreases or suppresses at least one of the following pathways or a gene associated with: metabolism of xenobiotics by cytochrome p450, hematopoietic cell lineage, lysosome, Alzheimer's disease, proteasome, cytokine-cytokine receptor interaction, Huntington's disease, Parkinson's disease, oxidative phosphorylation, and ribosome, as compared to isotype antibody.

In some embodiments, the MARCO antibody induces or increases at least one of the following pathways or a gene associated with: ECM receptor interaction, focal adhesion, tight junction, adheres junction, proteasome, complement and coagulation cascades, cell adhesion molecules and CAMs, pathways in cancers, arrhythmogenic right ventricular cardiomyopathy ARVC, Wnt signaling pathway, regulation of actin skeleton, axon guidance, Huntington's disease, pathogenic *Escherichia coli* infection, Alzheimer's disease, leukocyte transendothelial migration, cytokine-cytokine receptor interaction, basal cell carcinoma, melanogenesis, and hedgehog signaling pathway, as compared to isotype antibody. In some embodiments, the MARCO antibody decreases or suppresses at least one of the following pathways or a gene associated with: cell cycle, aminoacyl tRNA biosynthesis, mismatch repair, glycosylphosphatidylinositol GPI anchor biosynthesis, glycerophospholipid metabolism, and homologous recombination, as compared to isotype antibody.

In some embodiments, the MARCO antibody induces or increases at least one of the following pathways or a gene associated with: cell cycle, proteasome, T cell receptor signaling pathway, DNA replication, ubiquitin mediated proteolysis, regulation of actin cytoskeleton, adherens junction, pathogenic *Escherichia coli* infection, basal transcription factors, pentose phosphate pathway, Fc gamma R mediated phagocytosis, neurotrophin signaling pathway, regulation of autophagy, glycolysis gluconeogenesis, oocyte meiosis, chronic myeloid leukemia, citrate cycle TCA cycle, Wnt signaling pathway, P53 signaling pathway, and natural killer cell mediated cytotoxicity, as compared to isotype antibody. In some embodiments, the MARCO antibody decreases or suppresses at least one of the following pathways or a gene associated with: ABC transporters, glycosylphosphatidylinositol GPI anchor biosynthesis, RNA polymerase, ribosome, arachidonic acid metabolism, glycerophospholipid metabolism, as compared to isotype antibody.

In some embodiments, the MARCO antibody induces IL-2-STAT5 signaling, NF-kB signaling, TLR signaling, adhesion and motility signaling, cytoskeletal rearrangement signaling, TNFα signaling via NF-kB, IL-6-JAK-STAT3 signaling, SYK signaling, MAPK signaling, TPL2 signaling, calcium signaling, an IFNγ response, or an IFNα response, an complement, inflammatory response pathway, or allograft rejection pathways as compared to an isotype control antibody.

In some embodiments, the MARCO antibody decreases oxidative phosphorylation, mTOR signaling, unfolded protein response, cholesterol homeostasis, fatty acid metabolism, myc targets, glycolysis pathways, a cell cycle pathway, cell survival, cell adhesion, E2F targets pathway, hypoxia, PI3K-AKT signaling pathway, Src signaling pathway, PKC signaling pathway, epithelial to mesenchymal transition signaling pathway, oxidative phosphorylation, or MAPK signaling pathways as compared to an isotype control antibody.

In some embodiments, the MARCO antibody induces increased expression of at least one pro-inflammatory or activation gene in a cell in the tumor as compared to an isotype control antibody. In some embodiments, the MARCO antibody induces or increases expression of at least one of the following genes: Klrk1, Nrc1, Prf1, Cd40, Cd8α, Nod2, Tlr4, Tnf, Nlrp3, Cd274, Clec9α, Cd200r3, Il-27, Cxcl9, Cxcl10, or Cxcl12.

In some embodiments, the MARCO antibody increases CD8+ T cells, CD4+ T cells, NK cells, dendritic cells, MHCII+ macrophages, MHCIIhigh monocytes, and/or MHCIImid monocytes in the spleen and/or tumor.

In some embodiments, the MARCO antibody increases macrophages, marginal zone macrophages, follicular B cells, and/or red pulp macrophages in the spleen and/or tumor.

In some embodiments, the MARCO antibody decreases TAMs, tumor associated neutrophils, plasma B cells, marginal zone B cells, CD19+ B cells, MHCII− monocytes, and/or MHCII− macrophages in the spleen and/or tumor.

In some embodiments, the expression level of the chemokine, cytokine, gene, or pathway is detected by a nucleic acid or protein assay. Exemplary nucleic acid or protein assays include, but are not limited to, FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof.

In some embodiments, the MARCO antibody induces changes in cell adhesion, cytoskeletal, chemotaxis and cell migration upon binding to a MARCO+ cell.

In some embodiments, the antibody crosslinks MARCO to MARCO on the cell surface of a MARCO+ cell. In some embodiments, the contacting is in vitro. In some embodiments, the contacting is in vivo. In some particular embodiments, the contacting is in vivo in a human. In some embodiments, the contacting is effected by administering an anti-MARCO antibody. In some embodiments, the individual receiving the antibody (such as a human) has cancer.

Methods of Disabling, Killing, or Depleting MARCO-Expresssing Cells

In one aspect, the present application provides methods of contacting cells with an anti-MARCO antibody, such as a human or humanized antibody, which results in the disabling of the MARCO-expressing cells. Disabling MARCO-expressing cells also encompasses killing and/or depleting MARCO-expressing cells.

In another aspect, the present application provides methods of contacting MARCO-expressing cells with an anti-MARCO antibody, which results in the disabling of the MARCO-expressing cells.

In some embodiments, the MARCO-expressing are myeloid cells. In some embodiments, the MARCO-expressing are one or more of monocytes or macrophages. In some embodiments, the MARCO-expressing cells are one or more of TAM cells and monocyte-derived macrophages (MDM). In some embodiments, the MARCO-expressing cells are monocytic Myeloid Derived Suppressor Cells (mMDSC).

In some embodiments, the present application provides methods of disabling MARCO-expressing cells, comprising contacting the MARCO-expressing cells with a MARCO antibody, thereby killing the MARCO-expressing cells. Disabling refers to rendering a cell partially or completely non-functional. In some embodiments, the disabling of the cells leads to inducing growth arrest in the cells. In some embodiments, the disabling of the cells leads to apoptosis in the cells. In some embodiments, the disabling of the cells leads to lysis of the cells, as for example by complement dependent cytotoxicity (CDC) or antibody-dependent cell cytotoxicity (ADCC). In some embodiments, the disabling of the MARCO-expressing cells leads to necrosis in the cells. In some embodiments, the disabling of the MARCO-expressing cells leads to inducing growth arrest in the cells. In some embodiments, the disabling of the MARCO-expressing cells leads to inactivating the cells. In some embodiments, the disabling of the MARCO-expressing cells leads to neutralizing the activity of a MARCO protein in the cells. In some embodiments, the disabling of the MARCO-expressing cells leads to reduction in proliferation of the cells. In some embodiments, the disabling of MARCO-expressing cells leads to differentiation of the cells.

In some embodiments, the disabling of the MARCO-expressing leads to a decrease in the cells' ability to act as inhibitory antigen presenting cells or leads to an increase in the cells' ability to act as activating antigen-presenting cells. In some embodiments, the disabling of the MARCO-expressing cells leads to the mislocalization of the cells within tumor tissue or tumor microenvironment (TME). In some embodiments, the disabling of the MARCO-expressing cells leads to an altered spatial organization of the cells within tumor tissue or tumor microenvironment. In some embodiments, the disabling of the MARCO-expressing cells leads to an altered temporal expression of the cells within tumor tissue or TME. In some embodiments, the method further comprises removing the MARCO-expressing cells.

In any and all aspects of disabling MARCO-expressing cells as described herein, any increase or decrease or alteration of an aspect of characteristic(s) or function(s) is as compared to a cell not contacted with an anti-MARCO antibody.

In another aspect, the present application provides methods of contacting MARCO-expressing cells with an anti-MARCO antibody, which results in the modulation of function of the MARCO-expressing cells. The modulation can be any one or more of the following. In some embodiments the MARCO-expressing cells are one or more of monocytes, macrophages, TAMs, and MDMs. In some embodiments, the modulation of function of the cells leads to an increase in the cells' abilities to stimulate both native and activated CD8+ T-cells, for example, by increasing the ability of MARCO-expressing cells to cross-present tumor antigen on MHCI molecules to naive CD8+ T-cells. In some embodiments, the modulation of function of the MARCO-expressing cells leads to an increase in the cells' abilities to stimulate both native and activated CD4+ T-cells, for example, by increasing the ability of MARCO-expressing cells to cross-present tumor antigen on MHCII molecules to naive CD4+ T-cells. In some embodiments, the modulation increases the T-cell stimulatory function of the myeloid cells, including, for example, the cells' abilities to trigger T-cell receptor (TCR) signaling, T-cell proliferation, or T-cell cytokine production. In some embodiments, the modulation of function enhances or increases the cells' ability to produce cytokines, chemokines, or costimulatory or activating receptors.

In any and all aspects of decreasing the function of MARCO-expressing cells as described herein, any increase or decrease or alteration of an aspect of characteristic(s) or function(s) is as compared to a cell not contacted with an anti-MARCO antibody.

In some embodiments, the present application provides methods of killing (also referred to as inducing cell death) MARCO-expressing cells, comprising contacting the MARCO-expressing cells with an anti-MARCO antibody, thereby killing the MARCO-expressing cells. In some embodiments the killing is increased relative to MARCO-expressing cells that have not been contacted with an anti-MARCO antibody. In some embodiments, the contacting induces apoptosis in the MARCO-expressing cells. In some embodiments, the MARCO-expressing cells are in a population of immune cells comprising MARCO-expressing cells and non-MARCO expressing cells. In some embodiments, the method further comprises removing the MARCO-expressing cells. In some embodiments, 10%-100% of the cells are killed. In some embodiments, at least 10%, 20%, 30%, 40%, 50%, 60%, 70%, 80%, 90% or 100% of the cells are killed.

In some embodiments, the MARCO-expressing cells are reduced in number. In some embodiments, the MARCO-expressing cells are killed, for example by necrosis, or apoptosis. In some embodiments, the MARCO-expressing cells are induced to undergo growth arrest. In some embodiments, the MARCO-expressing cells no longer proliferate. In some embodiments the spatial localization of the MARCO-expressing cells is altered, and the ratio is increased in a particular region of the TME. In some embodiments the temporal expression of the MARCO-expressing cells is altered, and the ratio is increased during a particular time during the development of the tumor.

Additional Methods
Determining Expression of MARCO

Also provided herein are methods of treating a cancer or modulating an immune response in an individual comprising: determining or having determined the expression of MARCO in the subject; and administering or having administered to the subject an isolated antibody or antigen binding fragment that binds to MARCO.

In some embodiments, the method further comprises determining or having determined the expression level of MARCO in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level of MARCO comprises the mRNA expression level of MARCO. In some embodiments, the expression level of MARCO comprises the protein expression level of MARCO. In some embodiments the expression level of MARCO is detected in the sample using a method selected from the group consisting of FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof.

In some aspects, provided herein are methods of determining an expression level of MARCO protein in a sample from a subject comprising contacting the sample with an anti-MARCO antibody and performing an immunohistochemistry assay. In some embodiments, the antibody comprises RDM5, RDM9, PI-3010.15, PI-3010.25, or PI-3030.41.

In embodiments described herein for detection and/or quantification, the anti-MARCO antibody binds to the MARCO protein, but does not necessarily have to effect a biological response, such as ADCC, although it may have an effect on a biological response. In some embodiments, the antibody binds to soluble MARCO.

In another aspect, the present invention provides methods for identifying an individual who may respond to immunotherapy (e.g. with an anti-MARCO antibody) for the treatment of an immune-related condition (e.g. cancer) comprising: detecting the expression level of MARCO in a biological sample from the individual; and determining based on the expression level of MARCO, whether the individual may respond immunotherapy, wherein an elevated level of MARCO in the individual relative to that in a healthy individual indicates that the individual may respond to immunotherapy. In some embodiments, the MARCO expression in the individual has already been determined. In some embodiments, these methods may also be used for diagnosing an immune-related condition (e.g. cancer) in the individual and are based the expression level of MARCO, wherein an elevated level of MARCO in the individual relative to that in a healthy individual indicates that the individual suffers from cancer. In some embodiments, the expression level of MARCO comprises the mRNA expression level of MARCO. In other embodiments, the expression level of MARCO comprises the protein expression level of MARCO. In some embodiments the expression level of MARCO is detected in the sample using a nucleic acid or protein assay. Exemplary a nucleic acid or protein assays include, but are not limited to, FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof. In these embodiments, the anti-MARCO antibody binds to the MARCO protein, but does not necessarily have to effect a biological response, such as ADCC. In some embodiments the biological sample is derived from a tumor tissue. In some embodiments the biological sample includes, but is not limited to a body fluid, a tissue sample, an organ sample, urine, feces, blood, saliva, CSF and any combination thereof.

In some embodiments, the assay is an immunohistochemistry assay and the antibody comprises RDM5, RDM9, PI-3010.15, PI-3010.25, or PI-3030.41.

Method of Administration

In some embodiments, the anti-MARCO antibody is administered intravenously, intramuscularly, subcutaneously, topically, orally, transdermally, intraperitoneally, intraorbitally, by implantation, by inhalation, intrathecally, intraventricularly, or intranasally. An effective amount of the anti-MARCO antibody may be administered for the treatment of cancer. The appropriate dosage of the anti-MARCO antibody may be determined based on the type of cancer to be treated, the type of the anti-MARCO antibody, the severity and course of the cancer, the clinical condition of the individual, the individual's clinical history and response to the treatment, and the discretion of the attending physician.

Method of Preparation

Antibodies described herein can be produced using recombinant methods and compositions, e.g., as described in U.S. Pat. No. 4,816,567.

In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antibody is provided, wherein the method comprises culturing a host cell comprising nucleic acid encoding the antibody, as provided above, under conditions suitable for expression of the antibody, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp2O, CV-1, VERO-76, HeLa, HepG2, Per.C6, or BHK.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, Methanococcus jannaschii, *Methanobacterium* thermoautotrophicum, *Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments is the method of producing an antibody in stable mammalian cells as described herein wherein the expression product of the at least one stable mammalian cell comprises a larger percentage of the desired glycosylated antibody as compared to the monomeric heavy or light chain polypeptides, or other antibodies.

In some embodiments is the method of producing a glycosylated antibody in stable mammalian cells described herein, said method comprising identifying and purifying the desired glycosylated antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, Ni+2 affinity chromatography if a His-tag is employed or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the use of the antibodies. In some instances no purification is necessary.

In certain embodiments the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

Pharmaceutical Compositions

Methods for treatment of immune-related diseases (e.g., cancer) are also encompassed by the present invention. Said methods of the invention include administering a therapeutically effective amount of an anti-MARCO antibody or antigen-binding fragment. The MARCO antibody or antigen-binding fragment can be formulated in pharmaceutical compositions. These compositions can comprise, in addition to one or more of the anti-MARCO antibodies or antigen-binding fragments, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody, or antigen-binding fragment or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

Additional Embodiments

In one aspect, provided herein are isolated antibodies or antigen binding fragments thereof that binds to human Macrophage Receptor with Collagenous Structure (MARCO) (SEQ ID NO: 384) and competes for binding with a reference antibody, wherein the reference antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:

CDR-H1 comprises the sequence GFSLTSYHVS (SEQ ID NO: 2),
CDR-H2 comprises the sequence AIWTGGSIA (SEQ ID NO: 3),
CDR-H3 comprises the sequence DLSDYYSSYTSFDY (SEQ ID NO: 4),
CDR-L1 comprises the sequence ASEGISNDLA (SEQ ID NO: 431) or XASEGISNDLA
(SEQ ID NO: 383), wherein X is arginine (R) or leucine (L),
CDR-L2 comprises the sequence AASRLQD (SEQ ID NO: 8), and
CDR-L3 comprises the sequence QQSYKYPLT (SEQ ID NO: 9).

In some embodiments, CDR-L1 comprises the sequence ASEGISNDLA (SEQ ID NO: 431).

In some embodiments, CDR-L1 comprises the sequence RASEGISNDLA (SEQ ID NO: 27).

In some embodiments, the VH sequence comprises the VH sequence set forth in SEQ ID NO: 61; and the VL sequence comprises the VL sequence set forth in SEQ ID NO: 66.

In some embodiments, the VH sequence comprises the VH sequence set forth in SEQ ID NO: 111; and the and the VL sequence comprises the VL sequence set forth in SEQ ID NO: 116.

In some embodiments, the VH sequence comprises the VH sequence set forth in SEQ ID NO: 1, 11, 21, 31, 41, 51, 61, 71, 81, 91, 101, 111, 121, 131, 434, 444, or 474.

In some embodiments, the VL sequence comprises the VL sequence set forth in SEQ ID NO: 6, 16, 26, 36, 46, 57, 66, 76, 86, 96, 106, 116, 126, 136, 439, 449, or 479.

In some embodiments, the VH sequence comprises the VH sequence set forth in SEQ ID NO: 1, 11, 21, 31, 41, 51, 61, 71, 81, 91, 101, 111, 121, 131, 434, 444, or 474; and the VL sequence comprises the VL sequence set forth in SEQ ID NO: 6, 16, 26, 36, 46, 57, 66, 76, 86, 96, 106, 116, 126, 136, 439, 449, or 479.

In some embodiments, the antibody comprises a heavy chain sequence as set forth in SEQ ID NO: 65; and a light chain sequence as set forth in SEQ ID NO: 70.

In some embodiments, the antibody comprises a heavy chain sequence as set forth in SEQ ID NO: 115; and a light chain sequence as set forth in SEQ ID NO: 120.

In some embodiments, the antibody comprises a heavy chain sequence selected from the sequences set forth in SEQ ID NO: 5, 15, 125, 35, 45, 55, 65, 75, 85, 95, 105, 115, 125, 145, 438, 448, and 478 and a light chain sequence selected from the sequences set forth in SEQ ID NO: 10, 20, 30, 40, 50, 6, 70, 80, 90, 100, 110, 120, 130, 140, 443, 453, and 483.

In some embodiments, the VH sequence consists of the VH sequence set forth in SEQ ID NO: 61; and the VL sequence consists of the VL sequence set forth in SEQ ID NO: 66.

In some embodiments, the VH sequence consists of the VH sequence set forth in SEQ ID NO: 111; and the and the VL sequence consists of the VL sequence set forth in SEQ ID NO: 116.

In some embodiments, the VH sequence consists of the VH sequence selected from the sequences set forth in SEQ ID NO: 1, 11, 21, 31, 41, 51, 61, 71, 81, 91, 101, 111, 121, 131, 434, 444, or 474; and the VL sequence consists of the VL sequence selected from the sequences set forth in SEQ ID NOs: 6, 16, 26, 36, 46, 57, 66, 76, 86, 96, 106, 116, 126, 136, 439, 449, or 479.

In some embodiments, the antibody comprises a heavy chain and a light chain, wherein the sequence of the heavy chain consists of the heavy chain sequence set forth in SEQ ID NO: 65 and the sequence of the light chain consists of the light chain sequence set forth in SEQ ID NO: 70.

In some embodiments, the antibody comprises a heavy chain and a light chain, wherein the sequence of the heavy chain consists of the heavy chain sequence set forth in SEQ ID NO: 115 and the sequence of the light chain consists of the light chain sequence set forth in SEQ ID NO: 120.

In some embodiments, the antibody comprises a human Fc region.

In some embodiments, the human Fc region is a wild-type human IgG1 Fc.

In some embodiments, the antibody comprises a wild type human IgG1 Fc, and wherein the VH sequence comprises the VH sequence set forth in SEQ ID NO: 61, and the VL sequence comprises the VL sequence set forth in SEQ ID NO: 66.

In some embodiments, the antibody comprises a wild type human IgG1 Fc, and wherein the VH sequence comprises the VH sequence set forth in SEQ ID NO: 111, and the VL sequence comprises the VL sequence set forth in SEQ ID NO: 116.

In some embodiments, the antibody binds to human MARCO with a KD of less than or equal to about 0.5, 1, 2, 3, 4, 5, 6, or 7×10-9 M, as measured by surface plasmon resonance (SPR) assay.

In some embodiments, the antibody is humanized.

In one aspect, provided herein are methods of producing an antibody comprising expressing the antibody as disclosed herein from a host cell and isolating the expressed antibody.

In one aspect, provided herein are pharmaceutical compositions comprising the antibody as disclosed herein and a pharmaceutically acceptable excipient.

In one aspect, provided herein are kits comprising the antibody as disclosed herein and instructions for use.

In one aspect, provided herein are isolated antibodies or antigen binding fragments thereof that binds to human MARCO (SEQ ID NO: 384) and competes for binding with a reference antibody, wherein the reference antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
  CDR-H1 comprises the sequence GYTFTDYAVN (SEQ ID NO: 232),
  CDR-H2 comprises the sequence WINTQTGKPT (SEQ ID NO: 233),
  CDR-H3 comprises the sequence DSYYYSSSLDY (SEQ ID NO: 234),
  CDR-L1 comprises the sequence ASAGISNDLA (SEQ ID NO: 432) or XASAGISNDLA (SEQ ID NO: 381), wherein X is arginine (R) or leucine (L),
  CDR-L2 comprises the sequence AASRLQD (SEQ ID NO: 238), and
  CDR-L3 comprises the sequence QQSYKYPWT (SEQ ID NO: 239).

In one aspect, provided herein are methods of treating cancer in a subject, comprising administering to the subject an antibody that competes for binding to human MARCO (SEQ ID NO: 384) with a reference antibody, wherein the reference antibody comprises a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
  CDR-H1 comprises the sequence GFSLTSYHVS (SEQ ID NO: 2),
  CDR-H2 comprises the sequence AIWTGGSIA (SEQ ID NO: 3),
  CDR-H3 comprises the sequence DLSDYYSSYTSFDY (SEQ ID NO: 4),
  CDR-L1 comprises the sequence ASEGISNDLA (SEQ ID NO: 431) or XASEGISNDLA (SEQ ID NO: 383), wherein X is arginine (R) or leucine (L),
  CDR-L2 comprises the sequence AASRLQD (SEQ ID NO: 8), and
  CDR-L3 comprises the sequence QQSYKYPLT (SEQ ID NO: 9).

In some embodiments, the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator.

In some embodiments, the immunotherapy is an anti-PD1 antibody, an anti-PDL1 antibody, or an anti-CTLA4 antibody.

In one aspect, provided herein are methods of increasing an immune response in a subject, comprising administering to the subject an antibody that competes for binding to human MARCO (SEQ ID NO: 384) with a reference antibody, wherein the reference antibody comprises a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
  CDR-H1 comprises the sequence GFSLTSYHVS (SEQ ID NO: 2),
  CDR-H2 comprises the sequence AIWTGGSIA (SEQ ID NO: 3),
  CDR-H3 comprises the sequence DLSDYYSSYTSFDY (SEQ ID NO: 4),
  CDR-L1 comprises the sequence ASEGISNDLA (SEQ ID NO: 431) or XASEGISNDLA (SEQ ID NO: 383), wherein X is arginine (R) or leucine (L),
  CDR-L2 comprises the sequence AASRLQD (SEQ ID NO: 8), and
  CDR-L3 comprises the sequence QQSYKYPLT (SEQ ID NO: 9).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3$^{rd}$ Ed. (Plenum Press) Vols A and B (1992).

Example 1: MARCO is Expressed in Multiple Tumor Types

MARCO Bulk RNA Expression in Multiple Cancer Types

MARCO mRNA expression in tumor and normal tissues across all indications in The Cancer Genome Atlas (TCGA) was generated by the BROAD Institute gene expression viewer on firebrowse.org.

Ordered MARCO mRNA expression in tumor (left bar) vs normal (right bar) tissue is shown in FIG. 1. The x-axis lists the following tumor types: ACC, adrenocortical carcinoma; BLCA, bladder urothelial carcinoma; BRCA, breast invasive carcinoma; CESC, cervical squamous cell carcinoma and endocervical adenocarcinoma; CHOL, cholangiocarcinoma; COAD, colon adenocarcinoma; COADREAD, colon adenocarcinoma and rectum adenocarcinoma; DLBC, diffuse large b-cell lymphoma; ESCA, esophageal carcinoma; GBM, glioblastoma multiforme; GBMLGG, glioblastoma multiforme and lower grade glioma; HNSC, head and neck squamous cell carcinoma; KICH, kidney chromophobe; KIRC, kidney renal clear cell carcinoma; KIRP, kidney renal papillary cell carcinoma; KIPAN, pan-kidney cohort (KICH+KIRC+KIRP); LAML, acute myeloid leukemia; LGG, brain lower grade glioma; LIHC, liver hepatocellular carcinoma; LUAD, lung adenocarcinoma; LUSC, lung squamous cell carcinoma; MESO, mesothelioma; OV, ovarian serous cystadenocarcinoma; PAAD, pancreatic adenocarcinoma; PCPG, pheochromocytoma and paraganglioma; PRAD, prostate adenocarcinoma; READ, rectum adenocarcinoma; SARC, sarcoma; SKCM, skin cutaneous melanoma; STAD, stomach adenocarcinoma; STES, stomach and esophageal cancer; TGCT, testicular germ cell tumors; THYM, thymoma; THCA, thyroid carcinoma; UCS, uterine carcinosarcoma; UCEC, uterine corpus endometrial carcinoma; UVM, uveal melanoma. The y-axis represents log 2-transformed values of transcript abundance from RNA-seq data, quantified using RNAseq by Expectation-Maximization (RSEM).

MARCO Expression in Primary Tumors by scRNA-Seq

Single Cell RNA Sequencing (scRNA-Seq)

1 mL of frozen, dissociated tumor cells from various tumors were purchased from Discovery Life Sciences. The frozen pellet was thawed in a 37 C water bath and gradually diluted with 25 mL of warm RPMI containing 10% FBS and 10 mM HEPES, and centrifuged for 5 min at 550 rcf. The cell pellet was stained with anti-CD45-PE (clone HI30, Biolegend). DAPI⁻, CD45⁺ cells were sorted on a BD FACSAria Fusion. After sorting, cells were washed with 3 mL of 0.04% BSA/PBS three times and resuspended at 5×10$^5$ cells/mL. The cells were loaded into a Chromium Chip B for a targeted cell encapsulation of 10,000 cells, and placed into the Chromium Controller (10× Genomics, Single Cell 3' v3 Reagent Kit). Post GEM-RT cleanup, cDNA amplification and library construction were performed according to the Single Cell 3' v3 user manual from 10× Genomics. The libraries were sequenced on a NovaSeq by MedGenome Inc.

Single Cell Data Processing

Sequencing data was processed using 10× Genomics Cell Ranger v3.0.2 pipeline. MedGenome Inc. provided fastq files for each sample by converting raw, Illumina bcl files into fastq files using the Cell Ranger subroutine mkfastq. Afterwards, Cell Ranger count was run, which utilizes STAR (Dobin et al., 2013) to align reads against the GRCh38 human reference genome. After filtering reads with redundant unique molecular identifiers (UMI), count generated gene-cellular barcode files (filtered_feature_bc_matrix folder consisting of barcodes.tsv, features.tsv, and matrix.mtx). Both mkfastq and count were run with default parameters.

Cellular Identification, Clustering, and Visualization

For each sample, the filtered_feature_bc_matrix files were passed to the R (v. 3.6.0) software package Seurat (Satija et al., 2015) (https://satijalab.org/seurat) (v2.3.4) for all downstream analyses. The features.tsv file was renamed to genes.tsv to be compatible with the Read10× function. Data was filtered for cells that expressed a minimum of 200 genes, all genes were expressed in at least 3 cells, and had no more than 8500 UMI. Cells that contained >20% of reads associated with mitochondrial genes and >45% of reads associated with ribosomal genes were removed. Count data was then log transformed and scaled using each remaining cell's UMI count and proportion of mitochondrial and ribosomal genes as nuisance factors (implemented in Seurat's ScaleData function) to correct for any remaining unwanted effects in downstream clustering and differential expression analyses. For each sample, principal component (PC) analysis was performed on a set of highly variable genes defined by Seurat's FindVariableGenes function. Genes associated with the resulting top PCs (chosen by visual inspection of scree plots) were then used for graph-based cluster identification and subsequent dimensionality reduction using t-distributed stochastic neighbor embedding (tSNE). Cluster-based marker identification and differential expression were performed using Seurat's FindAllMarkers for all between-cluster comparisons. Graphs were plotted using built-in visualization functions in Seurat (TSNEPlot, FeaturePlot).

MARCO is predominantly expressed in human tumor monocytes and macrophages as determined by the scRNA-seq analysis (data not shown). Tumor cells from lung cancer, kidney (RCC) cancer, ovarian cancer, colorectal cancer, and head and neck cancer all showed expression of MARCO on monocytes and macrophages.

MARCO RNA Expression is Induced by IL-10

Differentiated human macrophages were polarized by adding the following cytokines to the media for 24 hours at 37 C: 50 ng/ml lipopolysaccharide (LPS) (InvivoGen), 25 ng/ml recombinant human IFN-γ (PeproTech), LPS+ IFN-γ, IL-4, IL-10, TGF-β, TGF-β+, or IL-10. The media was then removed and macrophages lysed in 300 μl of RLT buffer+ BME, followed by RNA extraction using the Qiagen kit. The mRNA quantity and quality were assessed by Nanodrop and the Agilent Bioanalyzer before sending the samples to Medgenome for library preparation and RNAseq. MARCO mRNA expression in each of the polarization conditions was then extracted from the RNAseq analysis and plotted in log 2 CPM units.

Figure 2:
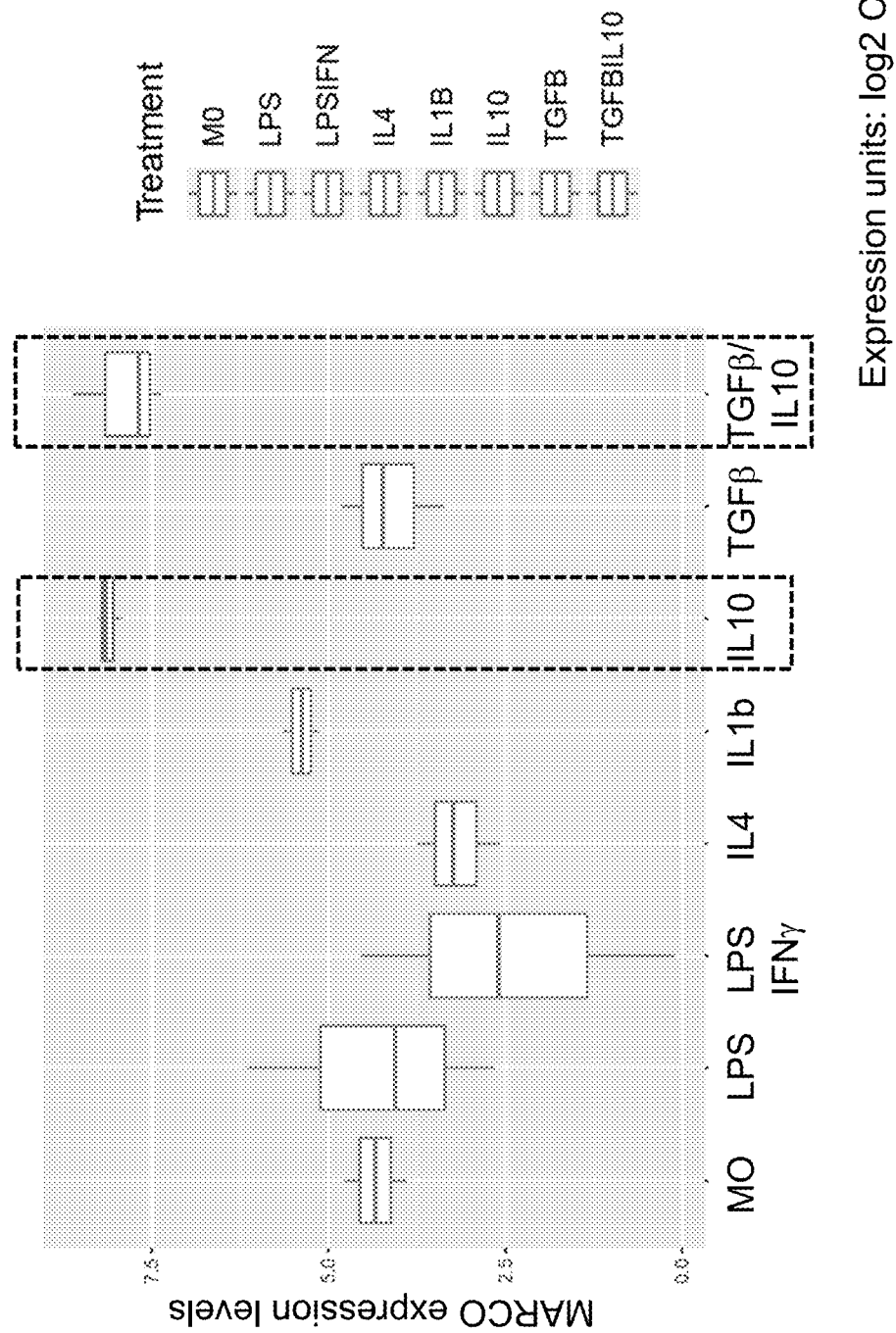
FIG. 2 shows that MARCO RNA expression was induced by IL-10 in Human Monocyte-derived Macrophages (MDMs).

As shown in FIG. 2, MARCO RNA expression was induced by IL-10 in Human Monocyte-derived Macrophages (MDMs)

IL10 and MARCO Expression Correlate Across Indications

All single indication, Level 2, RNAseq data from TCGA were downloaded from the Broad Institute using firehose_get. RSEM values for MARCO, IL-10, PTPRC (CD45), and TREM2 expression from tumor samples were converted to log 2 counts per million. Per-indication, median values for MARCO and IL10 expression were plotted in R. Dot size was scaled by the degree of IL10-MARCO Spearman rank correlation. The matrix of per-indication, median expression values for the genes listed above was transformed into a matrix of Spearman correlations and plotted as a heatmap using the pheatmap package in R.

Figure 3B:
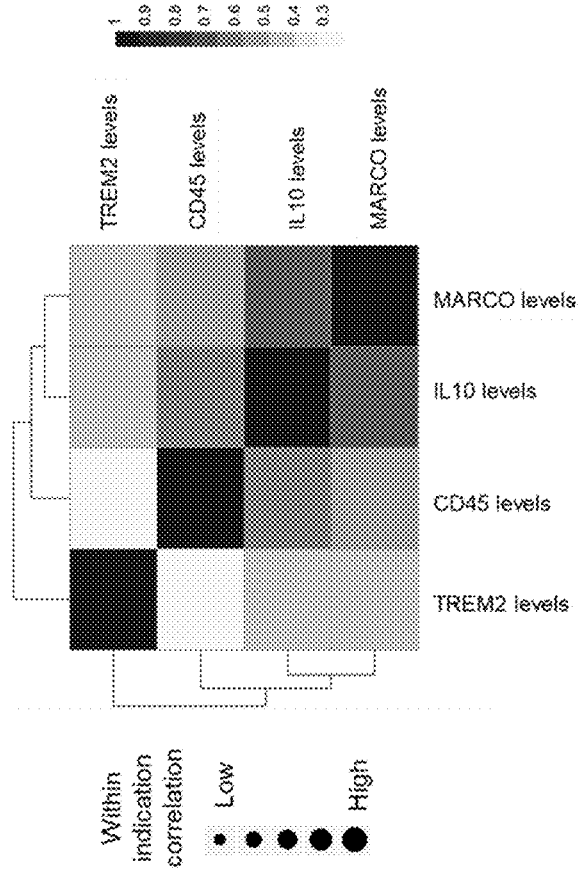
FIG. 3B shows a heat map of the correlation between TREM2 expression, CD45 expression, IL-10 expression, and MARCO expression.
Figure 3A:
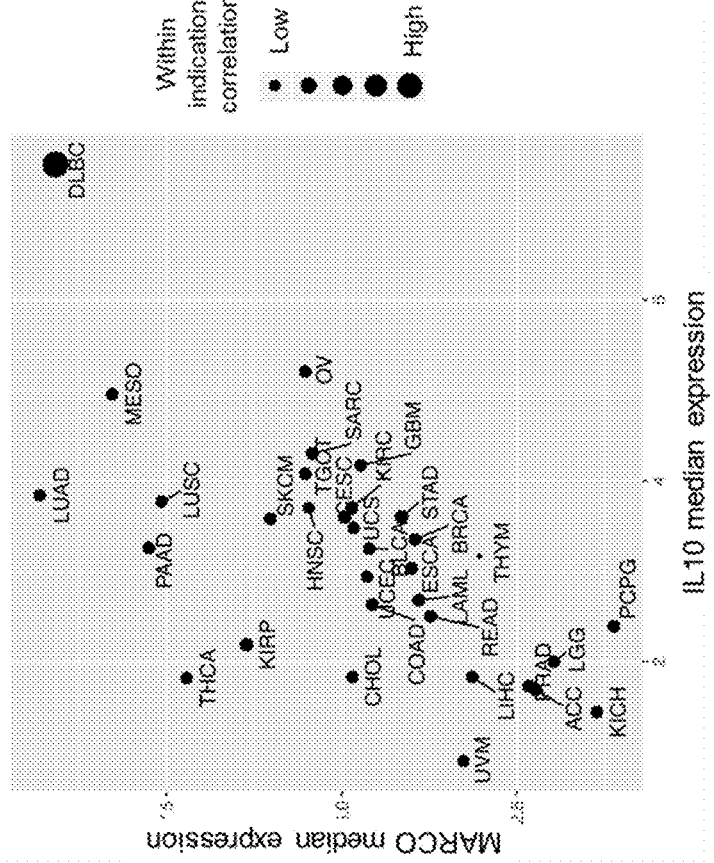
FIG. 3A shows the correlation of MARCO and IL-10 expression in various tumor types.

FIG. 3A shows the correlation of MARCO and IL-10 expression in various tumor types, and FIG. 3B shows a heat map of the correlation between TREM2 expression, CD45 expression, IL-10 expression, and MARCO expression. As shown in FIGS. 3A and 3B, IL10 and MARCO expression are well correlated across cancer indications.

MARCO Expression and Correlation with Patient Survival in Different Indications

In Colorectal Cancer (CRC)

Figure 4A:
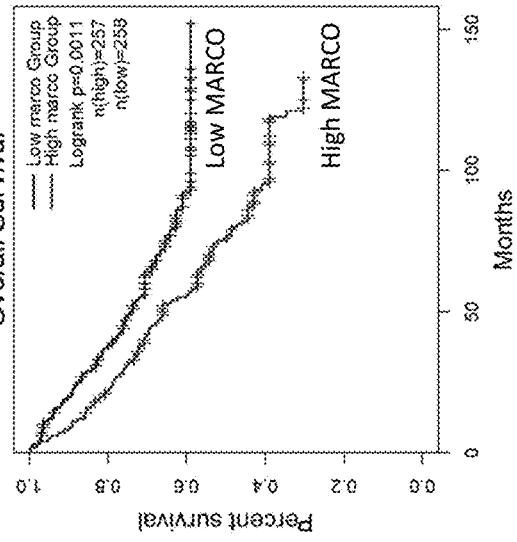
FIG. 4A shows that MARCO expression is inversely correlated with patient survival probability in CRC.

Prenormalized MARCO expression profiles and associated clinical data across 55 colorectal tumors were downloaded from NCBI's GEO website (accession GSE17537). Expression profiles were divided into two cohorts based on median level of MARCO. Kaplan-Meier survival curves were plotted for each cohort and the associated logrank test was carried using the survival and survminer packages in R. As shown in FIG. 4A, MARCO expression inversely correlated with patient survival probability in CRC; higher MARCO expression correlated with lower patient survival probability and lower MARCO expression correlated with higher patient survival probability.

In Renal Cell Carcinoma (RCC)

Survival associations of two cohorts of kidney cancer (renal cell carcinoma) from TCGA based on median split of MARCO mRNA expression generated by the Gene Expression Profiling Interactive Analysis (GEPIA2) viewer at http://gepia2.cancer-pku.cn/#index.

Figure 4B:
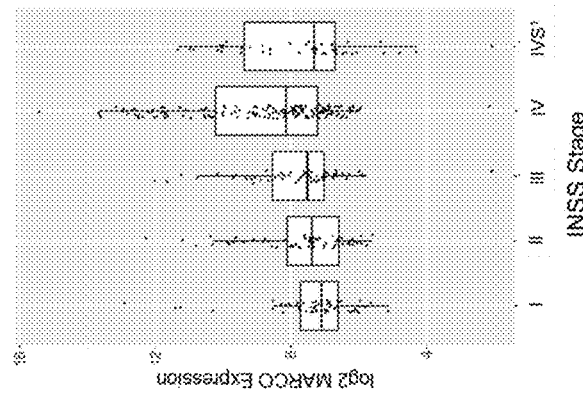
FIG. 4B shows that MARCO expression is inversely correlated with patient survival probability in RCC.

As shown in FIG. 4B, MARCO expression is inversely correlated with patient survival probability in RCC; higher MARCO expression correlated with lower patient survival probability and lower MARCO expression correlated with higher patient survival probability in RCC.

In Neuroblastoma

Pre-normalized MARCO expression profiles and associated clinical data across 498 neuroblastoma tumors were downloaded from NCBI's GEO website (accession GSE62564). Expression profiles were divided into two cohorts based on median level of MARCO. Kaplan-Meier survival curves were plotted for each cohort and the associated logrank test was carried using the survival and survminer packages in R.

Figure 4C:
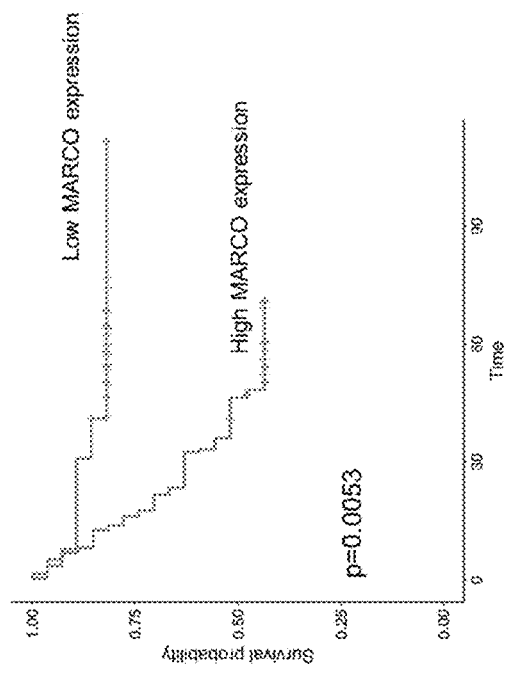
FIG. 4C shows that MARCO expression is inversely correlated with patient survival probability in neuroblastoma.

As shown in FIG. 4C, MARCO expression is inversely correlated with patient survival probability in neuroblastoma; higher MARCO expression correlated with lower patient survival probability and lower MARCO expression correlated with higher patient survival probability in neuroblastoma.

Figure 4D:
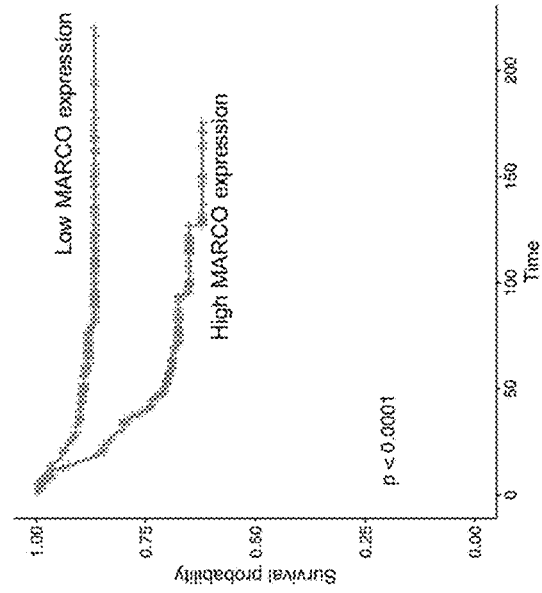
FIG. 4D shows that MARCO expression increased as function of disease severity in neuroblastoma, according to INSS stage.

Prenormalized MARCO expression profiles and associated clinical data across 394 neuroblastoma tumors were downloaded from NCBI's GEO website (accession GSE120572). MARCO expression profiles were plotted for all samples with an identified INSS Stage. Statistics for paired comparisons were generated using the Wilcoxon Rank Sum Test in R. As shown in FIG. 4D, MARCO expression increased as function of disease severity in neuroblastoma, according to INSS stage.

In Basal-Like Breast Cancer

MARCO expression from TCGA across PAM50 subtyping of human breast cancer generated by the Gene Expression Profiling Interactive Analysis (GEPIA2) viewer at gepia2.cancer-pku.cn/#index. METABRIC expression profiling and associated clinical data was downloaded from cBioPortal at cbioportal.org. Normalized MARCO expression profiles were plotted in R across cohorts based on PAM50 subtyping. Statistics for paired comparisons were generated using the Wilcoxon Rank Sum Test in R.

Figure 5:
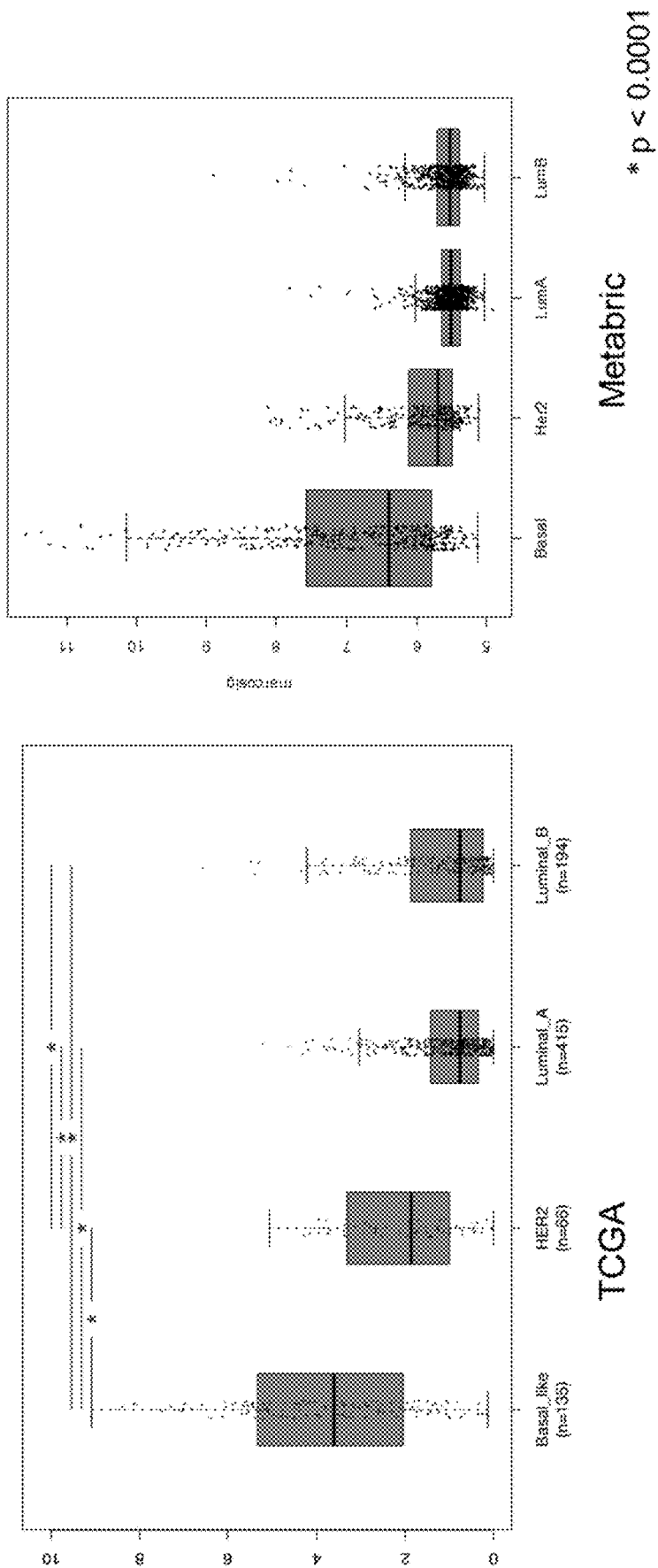
FIG. 5 shows that MARCO is upregulated in basal-like breast cancer relative to other breast cancer subtypes.

As shown in FIG. 5, MARCO is upregulated in basal-like breast cancer relative to other breast cancer subtypes. The left panel shows the MARCO expression from TCGA, the right panel shows the MARCO expression from METABRIC.

MARCO is highly expressed on a population of intratumoral intermediate monocytes. Gene signatures of immune desert and exclusion were upregulated in the MARCO+ cluster. Aggregated TAMs and monocytes derived from single cell sequencing of human immune cells from bladder, breast, colorectal, endometrial, gastric, head and neck, kidney, lung, and ovarian tumors yielded a single cluster with substantially elevated MARCO expression in transitioning monocytes (cluster 2). Gene Set Enrichment Analysis (GSEA) of Hallmark pathways (MARCO-rich cluster 2 vs. all other macrophages and monocytes) showed that MARCO expression was associated with immunosuppressive, matrix-associated gene sets (e.g., angiogenesis, EMT) and downregulated for inflammatory, interferon-based pathways. Significant (FDR<0.05) pathways identified that were upregulated in MARCO+ cells were glycolysis, oxidative phosphorylation, epithelial mesenchymal transition, hypoxia, xenobiotic metabolism, angiogenesis, cholesterol homeostasis, adipogenesis, fatty acid metabolism, reactive oxygen species pathway, and mTORC1 signaling. Significant (FDR<0.05) pathways identified that were downregulated in MARCO+ cells were allograft rejection, TGF-b signaling, KRAS signaling DN, TNFα signaling vi NF-kB, IFNγ response, and IFNα response.

Example 2: Production and Characterization of Anti-Human MARCO Antibodies

First Generation of Hybridomas

An antibody campaign was performed at Antibody Solutions (Sunnyvale, CA) with two Rapid campaigns on 3 Balb/c mice each and one standard campaign on 4 Balb/c mice using a human MARCO His-tagged extracellular domain (His-ECD 147-520, using residues 147-419 of the Collagen-like domain (CLD) and residues 424-520 of the Scavenger Receptor Cysteine-Rich (SRCR) domain, Pi-114) as the immunogen. The rapid immunization program consisted of 10 injections, 2× a week, utilizing the footpad as the route. The standard immunization program consisted of 5 injections over the course of 12 weeks, utilizing the subQ as the route. Rapid 1 campaign included TLR+anti-CTLA4 for adjuvants while Rapid 2 campaign included TLR+anti-GITR. The mouse serum was tested at different timepoints for antigen titer by ELISA. Spleen and lymph nodes from the mouse from Rapid 1 campaign with the highest titer were fused and the hybridoma library was created to provide an immortal population of antibody producing cells representing the stimulated B-cell population responding to the antigen. Single cell cloning by FACS sorting was performed to generate single clones hybridomas for monoclonal antibody cultures. 2,880 clones were then screened by dual flow cytometry for binding to mouse and human 293T overexpressing MARCO cell lines and using a GFP expressing cell line (GFP-293T) as the negative control for no binding. 33 clones were identified from the primary screen with cross-reactivity to both human and mouse MARCO and with no to low background binding and were additionally screened by ELISA on the MARCO human antigen Pi-114. Hybridoma supernatants from the 33 clones were checked for cell binding by flow cytometry.

Generation of Stably Overexpressing Cell Lines

Mouse and human MARCO DNA sequences were cloned in the pLenti-GIII-CMV-GFP-2A-Puro lentiviral vector at Abmgood (Vancouver, Canada) and amplified using standard bacterial transformation protocols using E. coli DH5-alpha strains to produce high yields of plasmid for lentiviral packaging. Viral particles from the empty GFP control vector, Human MARCO, and mouse MARCO cloned lentiviral vectors were produced and packaged in 293T cells and concentrated for high titers. 293T cells were used as the target cells for infection using the virus provided by Abmgood following their protocols and guidelines. Puromycin was used to select for infected pools and single clones expressing homogeneous high levels of Mouse MARCO (293T_MuMARCO), human MARCO (293T_HuMARCO), and GFP (293T_GFP) were expanded.

pD2109-CMV-puromycin lentiviral backbone was subsequently generated to clone additional MARCO plasmids without and with IRES-GFP: Human MARCO full length with GFP (plasmid 3012) and without GFP (plasmid 3010), Mouse MARCO full length with GFP (plasmid 3013) and without GFP (plasmid 3011), Cynomolgus MARCO (cyno MARCO) full length with GFP (plasmid 3021) and without GFP (plasmid 3014), Human MARCO CLD only (1-419, plasmid 3022), and the chimera Mouse MARCO CLD-human MARCO SRCR with IRES-GFP (plasmid 3020). 293FT cells from Sigma were transfected with the above constructs using Fugene to produce lentiviral particles and subsequently transduce 293T cells. Puromycin was used to select the positive clones, which were expanded to generate the following stable pools of cells for in vitro use: 3010 (Hu_MARCO), 3012 (Hu_MARCO_GFP), 3011 (Mu_MARCO), 3013 (Mu_MARCO_GFP), 3014 (Cy_MARCO), 3021 (Cy_MARCO_GFP), 3020 (Mu-CLD_HuSRCR_GFP), and 3022 (Hu_MARCO_CLD).

Characterization of Binding of the Anti-MARCO Hybridomas and Anti-MARCO Antibodies to Cell Surface Expressed MARCO HEK293T cells expressing human MARCO (293T_HuMARCO), mouse MARCO (293T_MuMARCO), cyno MARCO (CyMARCO), and GFP-expressing control cell line (293T_GFP) were maintained in DMEM (Gibco) with 10% FBS at 37° C. Cells were counted and then harvested by centrifugation at 400×g for 5 minutes (min). Supernatants were removed and cell pellets were resuspended in $Ca^{2++}$ and $Mg^{2++}$ Dulbecco's phosphate-buffered saline (D-PBS) at $1 \times 10^6$ cells/ml. 100,000 cells/well were plated onto U-bottom 96-well plates for staining and all centrifugation steps were performed at 1500 rpm at 4° C. for 5 min and samples were kept protected from light throughout the protocol. Cells were pelleted and resuspended in 100 µl of Zombie NIR viability dye (BioLegend) prepared by diluting Zombie NIR dimethyl sulfoxide (DMSO) stock 1000-fold in D-PBS. Cells were stained by incubation for 10 min at room temperature (RT) in the dark, followed by quenching the staining reaction with the addition of 100 µl of Staining Medium (D-PBS containing 2% FBS and 2 mM ethylenediaminetetraacetic acid (EDTA). Cells were pelleted and resuspended in 100 µl of the different antibodies and hybridomas supernatants needed for screening and corresponding isotype controls in freshly prepared staining medium, such as PI-M014 and mIgG2b isotype. All mAbs were tested at the final top concentration of 100 nM (15 µg/ml) followed by an 8-point three-fold serial dilution, including 0 mg/ml control. Staining was carried out for 1 hour (hr) on ice, followed by 2 washes in Staining Medium. Cells were then pelleted and resuspended in 100 ul of allophycocyanin (APC)-conjugated goat anti-mouse IgG (Fc-specific) secondary antibody, prepared by 500-fold dilution of the antibody stocks in Staining Medium, and incubated for 30 min on ice. Plates were then washed two times with Staining Medium, followed by resuspension in 150 ul of the same buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8). Half-maximal effective concentrations ($EC_{50}$) were calculated based on geometric mean fluorescence intensities (gMFI). In case when the plates were not able to be analyzed on the cytometer, cells were pelleted after the washes and fixed in 100 µl of 2% paraformaldehyde (PFA), prepared by diluting the 16% (w/v) stock (Thermo Fisher) in DPBS, for 15 min at RT. Cells were then pelleted and the fixative was removed, followed by resuspension in 150 µl of Staining Medium and stored at 4° C. until acquisition on the flow cytometer.

Figure 6A:
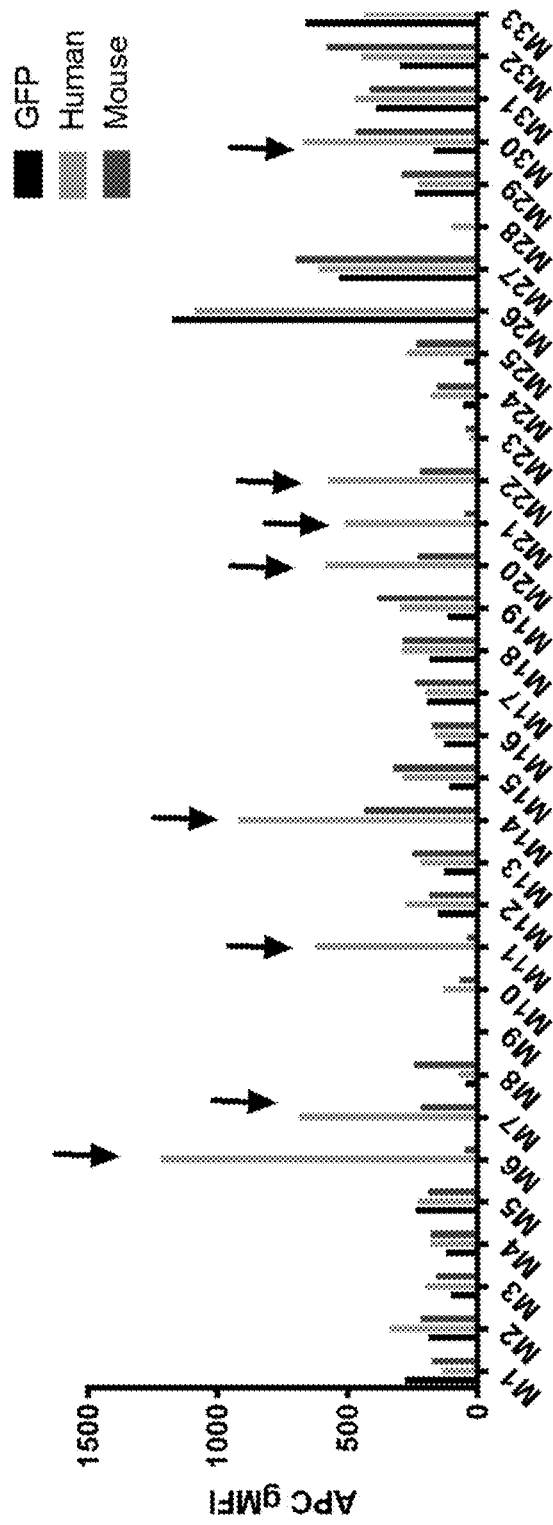
FIG. 6A shows the binding of 33 anti-human MARCO antibodies to GFP-239T control cells (left bar), cells expressing human MARCO (middle bar), or cells expressing mouse MARCO (right bar).
Figure 6B:
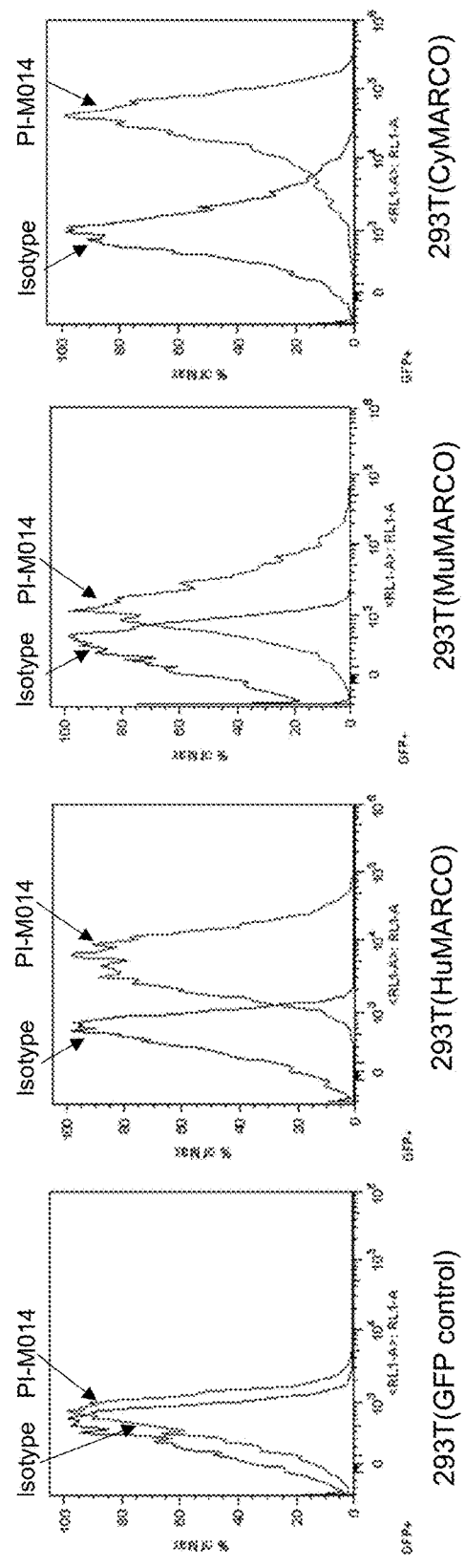
FIG. 6B shows flow cytometry histograms of one MARCO antibody, PI-M014, binding to cells expressing huMARCO, muMARCO, and CynoMARCO, as compared to control cells (GFP control).
Figure 6C:
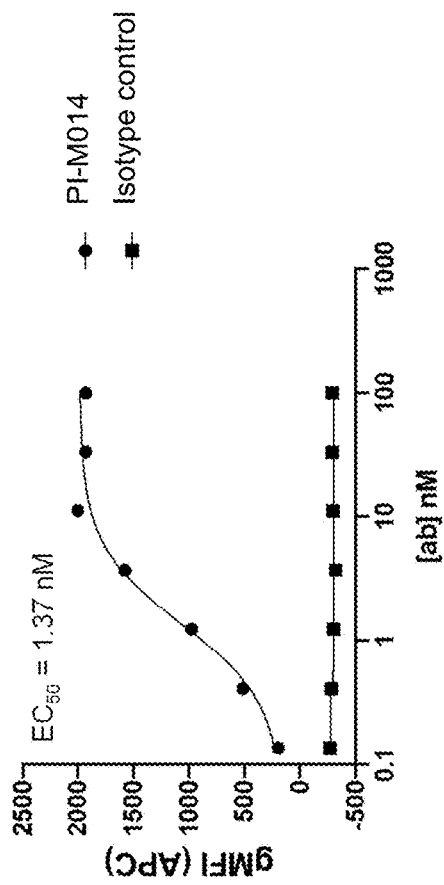
FIG. 6C shows a titration of PI-M014 and isotype control antibody binding to cells expressing huMARCO.

FIG. 6A shows the binding of the 33 antibodies to GFP-239T control cells (left bar), or cells expressing human MARCO (middle bar) or mouse MARCO (right bar). FIG. 6B shows flow cytometry histograms of one MARCO antibody, PI-M014, binding to cells expressing huMARCO, muMARCO, and CynoMARCO, as compared to control cells (GFP control). FIG. 6C shows a titration of PI-M014 and isotype control antibody binding to cells expressing huMARCO. PI-M014 bound to huMARCO with an EC50 of 1.37 nM.

Characterization of Binding of the Anti-MARCO Hybridomas and Anti-MARCO Antibodies to Recombinant MARCO by ELISA Hybridomas from Antibody Solutions or the anti-MARCO antibodies were screened by enzyme-linked immunosorbent assay (ELISA) on recombinant human MARCO protein (Pi-114 His tag). Briefly, 96-well plates (Biolegend) were coated with 1 ug/well of recombinant MARCO protein, overnight in D-PBS. Plates were washed 3× with PBS/0.1% TWEEN-20/2 mM EDTA (ELISA wash buffer) and blocked with 1% BSA for 2 hrs at RT. Antibodies were incubated for 1 h at RT at the final top concentration of 5 µg/ml followed by an 8-point three-fold serial dilution in PBS, including 0 mg/ml control. Plates were washed as above and incubated with goat anti-mouse IgG F(ab')2 Fragment-HRP conjugated secondary antibody (Jackson Immuno) at 1:5000 dilution for 1 hr at room temperature. Plates were washed 4 times in the above ELISA wash buffer and developed with TMB substrate for 10 min (Thermo) and stopped with TMB Stop Solution (1M $H_3PO_4$ Phosphoric Acid), and the A450 determined using a plate reader (SpectraMax i3x).

MARCO Antibody Kinetics Characterization by SPR

Surface plasmon resonance (SPR) was performed on the BIAcore™ T200 (GE Healthcare) instrument and all data were collected at 25° C. using multi cycle kinetics. An anti-mouse Fc mAb (GE Healthcare) was immobilized on a CM4 biosensor chip (GE Healthcare) using amine coupling chemistry with 4500 RUs as target for immobilization of the mAb. Serial dilution of were made in mobile buffer containing 10 mM HEPES pH 7.4, 150 mM NaCl, 3 mM EDTA and 0.05% (v/v) surfactant P20. Anti-mouse Fc mAb was used to capture select monoclonal antibodies against human MARCO antigen (ligand). The anti-MARCO antibodies tested were PI-M014, PI-M015, PI-M017, and PI-M018.

The interacting analyte used was N-terminally polyhistidine tagged human MARCO ECD (147-520) termed PI-RG-3000 The following range of antibody concentrations was injected into flow cells: 0.625 nM, 1.25 nM, 2.5 nM, 5 nM and 10 nM. A flow rate of 30 L/min, with an association and dissociation time of 90 and 600 seconds, respectively. After each cycle (comprising of the antigen capture, antibody association and dissociation phases), the cell surface was regenerated by injecting 10 mM glycine HCl buffer pH 1.7 for 100 seconds at 50 L/min flowrate. Kinetic evaluation was performed using BIAevaluation 3.1 software to determine single cycle and multi cycle kinetics.

PI-M014 monomer had a $K_D$ of 3.91 nM in a single SPR cycle, and a $K_D$ of 1.32 nM in a multi cycle assay. PI-M015 monomer had a $K_D$ of 0.39 nM in a multi cycle assay. PI-M017 monomer had a $K_D$ of 0.96 nM in a multi cycle assay. PI-M018 monomer had a $K_D$ of 1.65 nM in a multi cycle assay.

MARCO Cell Surface Expression on Human Monocyte Derived Macrophages

Frozen human peripheral blood $CD14^+$ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM 2-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of $12-15 \times 10^6$ cells in 15 cm dish. At day 3 of differentiation, media was replenished with the addition of fresh M-CSF. After 7 days of differentiation, macrophages were gently harvested non-enzymatically using a sterile cell scraper (Nunc) into FACS buffer (D-PBS containing 2 mM EDTA and 0.5% (w/v) bovine serum albumin (BSA) (Sigma)) followed by centrifugation at 400×g for 5 min at ~20° C.

Cells were counted and seeded onto 96-well plates at 250,000 cells per well. 100 ul of Zombie NIR viability dye (BioLegend), prepared by diluting the stock 1000-fold in D-PBS, was added to each well and incubated for 10 min at RT in the dark. The reaction was quenched by addition of 150 ul of FACS buffer, followed by centrifugation at 400×g for 5 min at 4° C. Cells were then incubated in 100 ul of blocking solution, containing 2.5% mouse and 2.5% rat serum and human TruStain FcX (BioLegend) diluted 50-fold in Fc receptor blocker (Innovex Biosciences), for 20 min in the dark. Cells were then washed and resuspended in 100 μl of the different antibodies needed for screening and corresponding isotype controls in freshly prepared in FACS buffer (PI-M014, PI-M015, PI-M017, PI-M018, mouse IgG2a and mouse IgG2b all APC-conjugated with the Thermo Fisher conjugation kit). mAbs were tested in single point concentrations (3.33 μg/ml for PI-M014 or 5 μg/ml for the other mAbs) and primary incubation was carried out for 20-30 min on ice, followed by 2 washes in FACS buffer. Cells were resuspended in 150 ul of the same buffer for acquisition on the flow cytometer (Attune NxT, Life Technologies). Flow cytometry data were analyzed using FlowJo software and data were processed and further analyzed in Microsoft Excel and GraphPad Prism software.

Figure 6D:
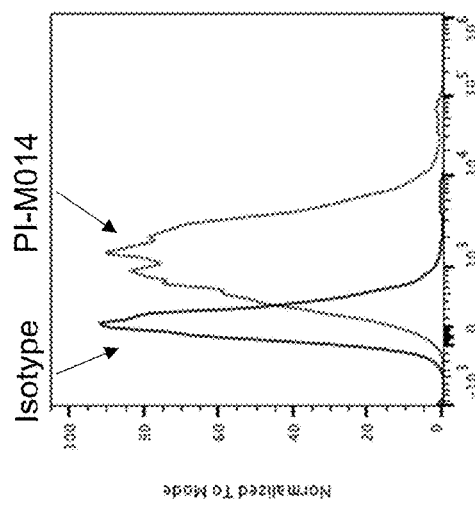
FIG. 6D shows a flow cytometry histogram of PI-M014 binding to human monocyte-derived macrophages.

PI-M014 bound to human monocyte-derived macrophages, as shown in FIG. 6D.

Mouse Antibody-Dependent Cellular Phagocytosis (ADCP) Assay

Bone marrow derived macrophages were generated as demonstrated previously, using 25 ng/ml of murine CSF-1 (Peprotech) for differentiation. On day 6 of culture, 25 ng/ml of murine IFN-γ (peprotech) was added to the BMDM culture for 18 hours. The following day, cells were stimulated with 200 ng/ml LPS (invivogen) for 2 hours before use in ADCP assay. IFN-γ/LPS-induced BMDM served as effector cells and the GFP+HEK293T cells transduced with human MARCO (293T Hu_MARCO) or control (293T_GFP) were targets. After harvest, effector BMDM were stained with Cell-Trace Violet dye (invitrogen) for 20 minutes at 37° C. 50,000 target cells were plated in 96-well U-bottom plates and co-incubated with anti-MARCO mAbs or corresponding isotype (PI-M014 to PI-M018). Antibodies were serially diluted and prepared in media for 30 minutes at 37° C. Effector cells were then added to Antibody-Target plates at a 3:1 ratio (150,000 effectors to 50,000 targets) and incubated for 2 hours at 37° C. Following incubation, cells were viability stained using Zombie NIR (BioLegend) then fixed using 2% Paraformaldehyde (Invitrogen) for 20 minutes at room temperature prior to being run on an Attune NXT flow cytometer (ThermoFisher). ADCP activity was assessed based on double-positivity of Cell Trace Violet and GFP levels, gated downstream of live cells.

Incubation of target cells with PI-M015 and PI-M017 both induced ADCP activity by effector cells. The results are summarized in Table 1, below.

HuMARCO Antibody Epitope Binning

The ForteBio Blitz label free system was used to analyze the epitopes for the anti-MARCO antibodies.

For the tandem format, N-terminal his-tagged MARCO protein was loaded onto the ForteBio anti-his probe followed by baseline and then association with the first antibody. Following binding of the first antibody, a second antibody was added and the association of the second set of antibodies was measured. Any additional binding observed for the second antibody, measured as an increased signal indicates that the second antibody bound to a different epitope than the first antibody.

Figure 7:
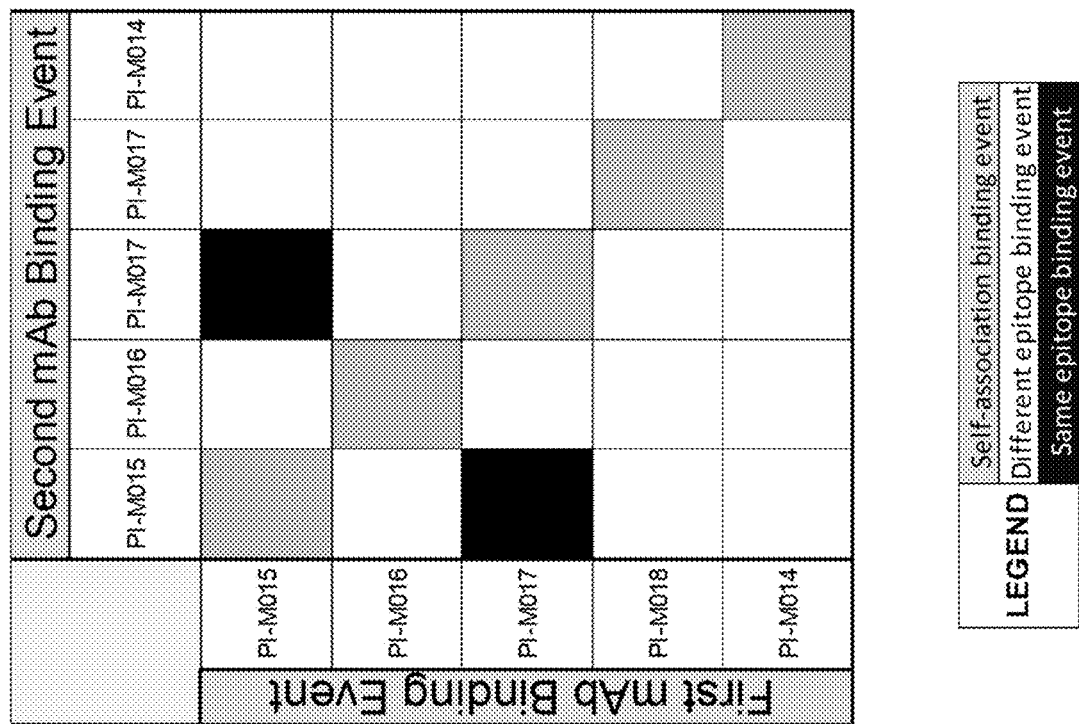
FIG. 7 shows a summary of the binding competition assay and that PI-M015 and PI-M017 competed with each other for binding to the MARCO antigen, indicating they bound to the same MARCO epitope.

PI-M015 and PI-M017 competed with each other for binding to the MARCO antigen, indicating they bind to the same MARCO epitope (FIG. 7). All other antibodies bound to different epitopes and did not compete with any other antibody for binding to MARCO.

However, the antibodies only bound to the CLD domain of human MARCO and did not bind to the SRCR domain of human MARCO.

MARCO Expression on Primary Human DTCs Tumors and Peripheral Blood Leukocytes (PBLs)

MARCO expression was assessed in the microenvironment of human tumors from three indications by flow cytometry, ovarian cancer and gastric cancer, using the newly developed human MARCO antibodies. Tumor tissues were previously dissociated as "dissociate tumor cells" (DTCs) and snap frozen (Folio Conversant). DTCs were thawed following the manufacturer's guidelines and were counted to assess total viable cells. PBLs were isolated from buffy coats (two donors from Stanford Blood Center). The single cell suspensions from DTCs and PBLs were diluted in PBS (Gibco), washed once, and stained with Zombie NIR (Biolegend) to determine cell viability. Fc receptors were also blocked with a combination of human serum (Jackson Immunoresearch), human FcX (Biolegend), and a peptide-based FcR block solution (Innovex Biosciences). After incubation with FcR blocking reagents, surface receptors on the DTCs were stained with a flow cytometry cocktail encompassing markers for major intratumoral immune subsets as well as isotypes control (5 µg/ml mIgG2a or mIgG2b or Rat IgG2a) and anti-human MARCO antibodies directly conjugated (5 µg/ml PI-M017 or PI-M018 or PI-HX-3031). Cells were also fixed and permeabilized (True-Nuclear Transcription Buffer Set, Biolegend) in order to determine intracellular CD68 expression. PBLs were stained with a flow cytometry cocktail encompassing markers for major blood immune subsets as well as the isotype control (10 µg/ml hIgG1-conjugated with PE Zenon labeling) and anti-human MARCO antibodies (10 µg/ml PI-3010, PI-3030, and PI-3031-conjugated with PE Zenon labeling). Data from DTCs and PBLs was acquired using an Attune NxT analyzer (ThermoFisher) and analyzed using FlowJo (BD Biosciences).

Figures 8A, 8B:
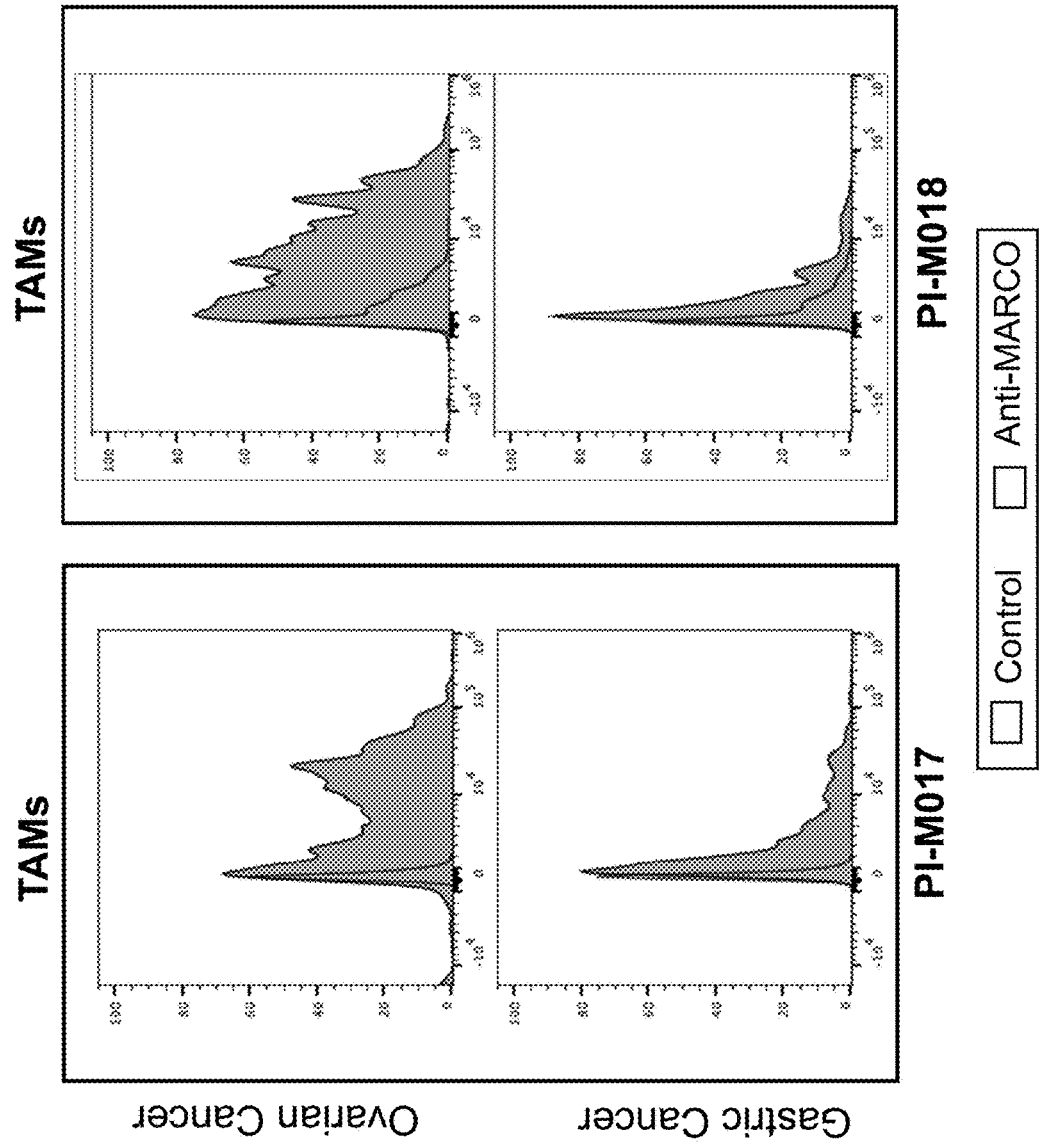
FIG. 8A shows that MARCO is expressed in human MDMs.
FIG. 8B shows that MARCO is expressed in tumor associated macrophages (TAMs) from primary human tumor samples (gastric cancer and ovarian cancer).

FIGS. 8A and 8B show that MARCO is expressed in human MDMs (FIG. 8A) and tumor associated macrophages (TAMs) from primary human tumor samples (gastric cancer and ovarian cancer, FIG. 8B). In FIGS. 8A and 8B, the right peak(s) indicates MARCO antibody PI-M018 or PI-M017 binding and staining, while the left peak indicates isotype mIgG2a binding.

A summary of the binding and functional characterization of selected antibodies from the first antibody campaign is shown in Table 1.

Hybridoma Generation

Lymph node cells were harvested from immunized rats and single cell suspensions generated. Lymphocytes were fused with the myeloma cell line, SP2/0-Ag 14 (ATCC) using electrofusion with the BTX EC2000+ electrofusion apparatus (Harvard Bioscience). Fused cells were plated into 96-well flat-bottom plates (Corning) and recovered overnight in Clona-Cell Medium E containing HT (Stem Cell Technologies). The following day, aminopterin (Sigma) was added to the cultures to a 1× final concentration. Fusions were fed on day 6 and day 8, and screened on day 11.

Hybridoma Screening

Hybridomas were screened by enzyme-linked immunosorbent assay (ELISA) on either recombinant mouse MARCO protein or recombinant human MARCO protein depending on the immunization. Briefly, 96-well Maxisorp plates (Nunc) were coated with 0.1 ug/well of recombinant MARCO protein, overnight in DPBS containing Ca2+ and Mg2+ (Gibco Cat #14040117)-. Plates were washed 3× with PBS/0.05% TWEEN-20 and blocked with PBS/Ca2+ containing 2% fetal bovine serum. Hybridoma supernatants were added 1:1 to the wells with PBS/Ca2+/2% FBS buffer

TABLE 1

| Anti-huMARCO mAb | Isotype | Epitope bin and map | $K_D$ (nM) | Endogenous cell binding | Human $EC_{50}$ 293T (HuMARCO) (nM) | Cyno $EC_{50}$ 293T (CyMARCO) (nM) | Mouse $EC_{50}$ 293T (MuMARCO) (nM) | ADCP/ADCC in BMDM assay in vitro |
|---|---|---|---|---|---|---|---|---|
| PI-M014 | mIgG2b | 4 (CLD) | 1.32 | + | 7.861 | 11.07 | 41.57 | No |
| PI-M015 (RDM1) | mIgG2a | 1 (CLD) | 0.39 | + | 1.606 | 1.206 | NB | Yes |
| PI-M017 (RDM7) | mIgG2a | 1 (CLD) | 0.96 | + | 1.59 | 1.522 | NB | Yes |
| PI-M018 (RDM9) | mIgG2b | 3 (CLD) | 1.65 | + | 1.851 | 45.4 | NB | No |

*NB: No binding

Example 3: Production and Characterization of Anti-Mouse MARCO Antibodies

Materials and Methods

Immunization for Generating Anti-Mouse Marco Antibodies

Rat anti-mouse MARCO hybridomas were generate by immunizing Sprague Dawley rats with recombinant N-terminal-his-tagged mouse MARCO protein produced at Pionyr, using Sigma Adjuvant System (SAS) alone or alternating with mouse MARCO expressing HEK293 cells, also in SAS. The sequence of the recombinant N-terminal-his-tagged mouse MARCO protein used is shown below. Recombinant mouse MARCO protein was analyzed by SDS-PAGE and using size exclusion chromatography to confirm that the protein molecular weight was correct.

Rats were immunized twice weekly in the hock at Antibody Solutions (Santa Clara, CA) and serum titers tested at day 21 by ELISA. Rats with sufficient serum antibody titers to mouse MARCO were chosen for electrofusion to generate hybridomas. Two final boosts were given on days −3 and −2 prior to harvest in phosphate buffered saline (PBS).

The mouse MARCO mAb RDM-9514 was purchased from R&D biosystems (CUST017 MABP, Clone 57914) as a custom purified hybridoma clone, raised in rat against NS0-derived recombinant mouse MARCO Gln70-Ser518.

and incubated at room temperature for 1 hour. Plates were washed as above and incubated with goat anti-rat IgG-HRP conjugated secondary antibody (Jackson Immuno) or mouse anti-rat IgG (1, 2a, 2b) HRP conjugated antibodies (Southern Biotech) for 1 hr at room temperature. Plates were washed and developed with TMB substrate (Thermo) and stopped with TMB Stop Solution (Suromodics), and the A450 determined using a platereader (Tecan). Hybridomas producing anti-MARCO antibodies were transferred to a 24-well plate and the supernatant from positive clones re-tested for MARCO reactivity and further tested in additional binding assays. Hybridomas were screened on recombinant human MARCO, recombinant mouse MARCO, and control recombinant his-tagged protein to eliminate any non-specific or his-tag specific clones and also tested on mouse MSR1 (R&D Systems) or human MSR1 (R&D Systems) to check for cross-reactivity to related scavenger receptor proteins. Hybridomas were also tested for binding to two chimeric proteins, N-terminal recombinant human MARCO SRCR/mouse CLD protein and N-terminal recombinant mouse MARCO SRCR/human CLD protein to determine the domain on the MARCO protein for which antibodies were specific. The sequences for the recombinant proteins used in these studies is below:

N-terminal his-tagged mouse MARCO protein:
(SEQ ID NO: 484)
HHHHHHHHGERGSPGPKGAPGAPGIPGLPGPAAEKGEKGAAGRDGTPGVQ

GPQGPPGSKGEAGLQGLTGAPGKQGATGAPGPRGEKGSKGDIGLTGPKGE

HGTKGDKGDLGLPGNKGDMGMKGDTGPMGSPGAQGGKGDAGKPGLPGLAG

SPGVKGDQGKPGVQGVPGPQGAPGLSGAKGEPGRTGLPGPAGPPGIAGNP

GIAGVKGSKGDTGIQGQKGTKGESGVPGLVGRKGDTGSPGLAGPKGEPGR

VGQKGDPGMKGSSGQQGQKGEKGQKGESFQRVRIMGGTNRGRAEVYYNNE

WGTICDDDWDNNDATVFCRMLGYSRGRALSSYGGGSGNIWLDNVNCRGTE

NSLWDCSKNSWGNHNCVHNEDAGVECS

N-terminal his tagged chimeric MARCO protein
(human SRCR/mouse CLD domains):
(SEQ ID NO: 485)
HHHHHHHHKGERGSPGPKGAPGAPGIPGLPGPAAEKGEKGAAGRDGTPGV

QGPQGPPGSKGEAGLQGLTGAPGKQGATGAPGPRGEKGSKGDIGLTGPKG

EHGTKGDKGDLGLPGNKGDMGMKGDTGPMGSPGAQGGKGDAGKPGLPGLA

GSPGVKGDQGKPGVQGVPGPQGAPGLSGAKGEPGRTGLPGPAGPPGIAGN

PGIAGVKGSKGDTGIQGQKGTKGESGVPGLVGRKGDTGSPGLAGPKGEPG

RVGQKGDPGMKGSSGQQGQKGEKGQKGENSVSVRIVGSSNRGRAEVYYSG

TWGTICDDEWQNSDAIVFCRMLGYSKGRALYKVGAGTGQIWLDNVQCRGT

ESTLWSCTKNSWGHHDCSHEEDAGVECSV

N-terminal his tagged chimeric MARCO protein
(mouse SRCR/human CLD domains):
(SEQ ID NO: 486)
HHHHHHKGEQGAPGLQGHKGAMGMPGAPGPPGPPAEKGAKGAMGRDGATG

PSGPQGPPGVKGEAGLQGPQGAPGKQGATGTPGPQGEKGSKGDGGLIGPK

GETGTKGEKGDLGLPGSKGDRGMKGDAGVMGPPGAQGSKGDFGRPGPPGL

AGFPGAKGDQGQPGLQGVPGPPGAVGHPGAKGEPGSAGSPGRAGLPGSPG

SPGATGLKGSKGDTGLQGQQGRKGESGVPGPAGVKGEQGSPGLAGPKGAP

GQAGQKGDQGVKGSSGEQGVKGEKGERGESFQRVRIMGGTNRGRAEVYYN

NEWGTICDDDWDNNDATVFCRMLGYSRGRALSSYGGGSGNIWLDNVNCRG

TENSLWDCSKNSWGNHNCVHNEDAGVECS

Cell Binding

Clones positive for binding to MARCO by ELISA were tested for binding to cell surface MARCO by staining human MARCO-293 cells, mouse MARCO-293 cells, or control 293 cells and testing by flow cytometry using the Intellicyt iQue flow cytometer.

Hybridomas that were positive for binding to MARCO by ELISA and to cell surface MARCO by flow cytometry were chosen for subcloning and purification.

Hybridoma Subcloning and Purification

Subcloning of parental hybridomas was performed by single cell sorting on the FACSAria. Single cells were sorted into flat-bottom 96-well tissue culture plates into Clona-Cell Medium E. Single cells were cultured for 7-9 days and then assayed for anti-MARCO specific clones by ELISA, as described above.

Monoclonal hybridomas were then culture for purification by growth in serum-free expansion medium (AOF, Stem Cell Technologies) and purified using either protein A or protein G.

Hybridoma Antibody Variable Region Sequences Generation

Total RNA was extracted from (104 to 106) monoclonal hybridoma cells using the RNeasy purification kit (Qiagen Cat #74134), then reverse transcription (RT) was performed to synthesize cDNA using Maxima H Minus First Strand cDNA Synthesis Kit (Thermofisher Cat #K1651) and reverse gene specific primers (GSP1). cDNA was purified to remove GSP and enzymes in the RT reaction using the QIAquick PCR Purification Kit (Qiagen Cat #28104). Terminal Deoxynucleotidyl Transferase was used to add a string of oligo-dA to the 3' end of the cDNA (Thermo Scientific Cat #10533065), the product was purified again (QIAquick PCR Purification Kit Cat #28104) before amplification. PCR was then carried out using a second gene specific primer (GSP2) and the Oligo-dT forward primer that binds the Oligo-dA tail previously added to the 3' ends of the cDNAs. PCR products were sequenced. In cases where sequences of insufficient quality were generated from PCR products, the PCR products were TOPO cloned and transformed into E. coli, and single colonies processed for sequencing.

The primers used are listed below:

GSP1-mk:
(SEQ ID NO: 487)
TTGTCGTTCACTGCCATCAATC

GSP2-mk:
(SEQ ID NO: 488)
ACATTGATGTCTTTGGGGTAGAAG

GSP1-mHC:
(SEQ ID NO: 489)
AGCTGGGAAGGTGTGCACAC

GSP2-mHC:
(SEQ ID NO: 490)
GGGATCCAGAGTTCCAGGTC

GSP1-rk:
(SEQ ID NO: 491)
GT GAG GAT GAT GTC TTA TGA ACA

GSP2-rk:
(SEQ ID NO: 492)
GCCATCAATCTTCCACTTGACAC

GSP1-rHC:
(SEQ ID NO: 493)
GAG ATG STT TTC TCG ATG GG

GSP2-rHC:
(SEQ ID NO: 494)
GS GGG AAG ATG AAG ACA GAT G

Calcium Dependency ELISA Assay

The purpose of this assay was to determine the calcium dependency for binding to MARCO by the anti-MARCO antibodies. This assay can apply to both hybridoma supernatant and purified antibodies.

0.05 µg/ml of the human or mouse MARCO recombinant proteins were coated on 4 Nunc-Immuno™ MicroWell plates using the following conditions: in DPBS with Ca2+ (Gibco Cat #14040117), in DPBS without Ca2+(Gibco Cat #14190136) with 2 mM EDTA (Invitrogen Cat #15575020)-Plate B, in DPBS without Ca2+ with 10 mM EDTA, and in DPBS without Ca2+ with 50 mM EDTA.

After the plates were incubated at room temperature for 1 hour or 4° C. overnight, the plates were wash 3 times with ELISA wash buffer (PBS/0.05% TWEEN-20), then hybridoma supernatant (1:5 dilution) or purified antibody (1 ug) was diluted in DPBS/Ca2+/2% FBS, DPBS without Ca2+/2 mM EDTA/2% FBS, DPBS without Ca2+/10 mM EDTA/2% FBS, and DPBS without Ca2+/50 mM EDTA/2% FBS. Plates again were incubated at room temperature for 1 hour.

Plates were washed as above and incubated with goat anti-mouse IgG-HRP (Jackson) or a mixture of mouse anti-rat IgG-HRP (1+2a+2b) 1:1:1 (SouthemBiotech Cat #3060-05, 3065-05, 3070-05) diluted 1:5000 for 1 hr at room temperature in the 4 different buffers as above. Plates were then washed and developed with TMB substrate (Thermofisher) and stopped with TMB Stop Solution (Surmodics), and read at A450 using a Tecan plate reader.

Kinetics and Epitope Binning Using the ProbeLife Gator Instrument

The Probe-Life Gator™ label free system was used to analyze binding kinetics and epitopes for the anti-MARCO antibodies.

The kinetics assay used either anti-mouse Fc or anti-human Fc probes to capture the anti-MARCO antibodies onto the probe, and then a five-step kinetic protocol was used to measure the affinity of the antibodies to the antigen, including the following steps: baseline, loading, baseline, association, and dissociation. The kinetics buffer (K buffer) provided by ProbeLife was used to establish the baseline for 60 seconds, and then the anti-mFec or anti-hFc probes were loaded with 200 nM of the antibodies for 120 s until the capture reached saturation, measurement of the baseline in K buffer was performed for another 60 s, followed by the association step using 200 nM antigen (human MARCO, mouse MARCO or cyno MARCO), and the dissociation step performed in K buffer for 5-10 minutes. The assay was done at 37° C. to maximize antibody:antigen dissociation.

For epitope binning of the antibodies, both tandem and sandwich formats were used.

For tandem format, 200 nM of the N-terminal his-tagged MARCO protein was loaded onto ProbeLife anti-his probe for 120 s or until binding reached saturation, followed by baseline for 60 s and then association with the first set of saturating antibodies loaded at 200 nM. Following binding of the first antibody, a second antibody was added at 100-200 nM) and the association of the second set of antibodies was measured. Any additional binding observed for the second antibody, measured as an increased signal indicates that the second antibody bound to a different epitope than the first antibody.

For sandwich assay format, the first antibody at 200 nM was loaded onto anti-mFc or anti-hFc probes for 120 s, followed by a baseline step, and then association with MARCO antigen (200 nM) for 120 s. Association of the second antibody at 200 nM was then measured for 120 s to determine if there was additional binding. In this format, where the first antibody was at low concentration, additional isotype control antibody was added after the first association in order to saturate free binding sites on the probe. All probes and buffers were directly ordered from ProbeLife.

MARCO Staining on BMDMs with the Anti-Mouse MARCO Hybridomas

Femurs and tibias from three female C57BL/6 mice (Jackson Laboratories) were cleaned and crushed in Staining Medium (0.5% (w/v) BSA (Sigma) and 2 mM EDTA in D-PBS) using a mortar and pestle. Samples were then passed through a 40 um filter, washed with D-PBS and pelleted at 400×g for 5 min at RT. Cell pellets were resuspended in 5 ml of BD Pharm Lyse buffer (BD Biosciences) and red blood cell lysis was carried out at RT for 5 min, followed by quenching with 10 volumes of Staining Medium. Cells were pelleted at 400×g for 5 min at RT and resuspended in Macrophage Medium composed of Iscove's modified Dulbecco Medium supplemented with 10% (v/v) fetal bovine serum (FBS) (HyClone) and antibiotic-antimycotic solution (Gibco), at the density of 15×106 cells/ml in 15 cm plates. These bone marrow mononuclear cells were stimulated with 25 ng/ml of mouse macrophage colony-stimulating factor (M-CSF) (PeproTech) for 7 days to generate M0-macrophages and differentiated into M1-like by supplementing the medium with LPS at 100 ng/ml on day 6 and into M2-like macrophages by adding 20 ng/ml of IL-10. After 18 hours of incubation at 37 C with polarizing cytokines, M0, M1, and M2-like macrophages were rinsed with DPBS and incubated in 6 ml of 2 mM EDTA for 10 minutes to promote cell detachment. Cells were gently scraped into an additional 6 ml of the Staining Medium described above, counted and seeded onto 96-well plates at 250,000 cells per well. 100 ul of Zombie NIR viability dye (BioLegend), prepared by diluting the stock 1000-fold in D-PBS, was added to each well and incubated for 10 min at RT in the dark. The reaction was quenched by addition of 150 ul of Staining Medium, followed by centrifugation at 400×g for 5 min at 4° C. Cells were then incubated in 100 ul of blocking solution, containing 2.5% mouse and 2.5% rat serum and mouse TruStain FcX PLUS (BioLegend) diluted 50-fold in Fc receptor blocker (Innovex Biosciences), for 20 min in the dark. Cells were then washed and resuspended in 100 μl of the different antibodies and hybridomas needed for screening and corresponding isotype controls in freshly prepared FACS buffer containing 2% FBS in DPBS with Ca2+ (RDM-9514, HX-3012, HX-3014, HX-3016, HX-3017, Rat IgG2a and Rat IgG1 all PE-conjugated with the PE Lightning kit). RDM-9514 was tested at the final top concentration of 10 μg/ml followed by an 8-point three-fold serial dilution in PBS the highest dose of 10 μg/ml. The internal hybridomas were tested at the single point concentrations of 5 μg/ml. Staining was carried out for 20-30 min on ice, followed by 2 washes in FACS buffer. Cells were resuspended in 150 ul of the same buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8). Data was plotted as Delta gmfi between the antibody and corresponding isotype. In case when the plates were not able to be analyzed on the cytometer, cells were pelleted after the washes and fixed in 100 μl of 2% paraformaldehyde (PFA), prepared by diluting the 16% (w/v) stock (Thermo Fisher) in DPBS, for 15 min at RT. Cells were then pelleted and the fixative was removed, followed by resuspension in 150 μl of Staining Medium and stored at 4° C. until acquisition on the flow cytometer.

MARCO Staining on Tumors with Anti-Mouse MARCO PE Conjugated mAbs

Py8119 and CT26 tumors were harvested from mice when they reached a volume of ~400 mm3. Fat and fibrous material were removed from the tumors by dissection. The tumors were then weighed and processed for single-cell suspension by a combination of mechanical and enzymatic dissociation. After mincing the tissues, tumors were enzymatically digested using an optimized enzyme cocktail (Miltenyi Biotec, Tumor Dissociation Kit, mouse 130-096-830) with gentleMACS C tubes (Miltenyi Biotec, 130-093-235) in a gentleMACS Octo Dissociator (Miltenyi Biotec, 130-095-937). After dissociation, the sample was applied to a filter to remove any remaining larger particles. Single cell suspension of tumor tissues was surface stained using a panel of antibodies for flow cytometry. The antibody panel for evaluating myeloid subsets included antibodies specific for CD45, XCR1, F4/80, CD64, CD11c, Ly6C, CD11b, Ly6G, CD24, MHC class II as well as lineage markers in the dump channel (CD45R, CD90.2, CD3e, NKp46, CD19, Siglec F). The antibody panel for evaluating lymphoid subsets included antibodies specific for CD45, CD4, CD25, B220, NKp46, CD44, CD90.2, CD8a, CD11b, and CD49b. The anti-MARCO antibodies used to stain the mouse tumors were RDM-9514, PI-HX-3012, PI-HX-3021, PI-HX-3016, PI-HX-3017, rat IgG1 and rat IgG2a isotypes at 5 µg/ml. All data were collected on an Attune flow cytometer (Thermo Fisher) and analyzed using FlowJo software.

LDL Competition Assay on Mouse and Human Recombinant MARCO

A high-binding, 96-well MSD plate was coated with 4 µg/ml mouse MARCO or 4 µg/ml human MARCO (R&D biosystems). After the plate was blocked with PBST and 5% BSA for an hour, titrated anti-mouse or anti-human MARCO antibodies were added to the plate and incubated for 30 minutes. Biotinylated hLDL (860 pM or 2 µg/ml) were added to the antibody, and the antibody/LDL mixture was incubated for an hour to allow the mixture to reach binding equilibrium. The plates were washed and bound biotinylated LDL was detected with Sulfo-tagged streptavidin that generates an electrocheminlumenscent signal when read buffer is added and electricity is applied to the electrodes in the MSD plate. IC50's were calculated using a 4-parameter curve fit in GraphPad Prism software.

Results

Multiple antibodies that bound to the SRCR domain of mouse MARCO were generated and characterized. 909 candidate antibodies were identified in the primary ELISA screen using purified mouse MARCO, human MARCO, mouse CLD-human SRCR, human-CLD-mouse-SRCR, and mouse MSR1. Secondary screening of binding to 293T cells expressing mouse MARCO or GFP control resulted in 275 candidates. Screening of binding on endogenous mouse BMDMs resulted in 40 candidates. A final screen for just SRCR binders resulted in 20 candidates. The candidates were screened for additional biophysical characteristics. The biophysical characterization of the top anti-mouse MARCO antibodies generated is shown in Table 2. These antibodies showed no binding to 293T HuMARCO cells or 293T CyMARCO cells. The sequences of selected mouse MARCO antibodies are shown in the sequence listing table. The CDRs were defined using the AbM definition.

| Anti-muMARCO mAb | Isotype | SRCR Bin (CDR3 sequence) | Epitope Bin | Biacore $K_{on}$ (1/Ms) | Biacore $K_{off}$ (1/s) | Mouse $EC_{50}$ 293T (MuMAR (nM) | $EC_{50}$ LDL competition assay (nM) | MSR1 binding | Binding to BMDM |
|---|---|---|---|---|---|---|---|---|---|
| RDM-9514 | Rat IgG1 | 11 | 2 | 1.36E+05 | 6.95E−07 | 0.83-0.86 | 0.38 | − | + |
| PI-HX-3001 (PI-3006) | Rat IgG2a | 1 | 2 | 1.88E+05 | 7.89E−07 | 0.48-1.09 | 0.4 | − | NA |
| PI-HX-3003 | Rat IgG2a | 8 | 2 | 2.16E+05 | 5.40E−07 | 1.00 | 0.23 | +/− | + |
| PI-HX-3004 | Rat IgG2a | 10 | 2 | 3.45E+05 | 3.58E−08 | 0.92 | 0.17 | +/− | NA |
| PI-HX-3012 | Rat IgG2a | 1 | 2 | 1.54E+05 | 2.48E−07 | 0.80 | 0.17 | − | + |
| PI-HX-3013 | Rat IgG2a | 2 | 2 | 2.40E+05 | 4.50E−07 | 0.34 | 0.36 | +/− | + |
| PI-HX-3021 (PI-3007) | Rat IgG2a | 3 | 2 | 1.91E+05 | 2.11E−05 | 0.47-0.75 | 0.25 | − | + |
| PI-HX-3016 (PI-3008) | Rat IgG1 | 1 | 2 | 1.84E+05 | 1.27E−06 | 0.36-0.59 | 0.34 | − | + |
| PI-HX-3017 (PI-3009) | Rat IgG1 | 6 | 2 | 1.55E+05 | 2.35E−07 | 0.66-1.30 | 0.14 | − | + |

Figure 9:
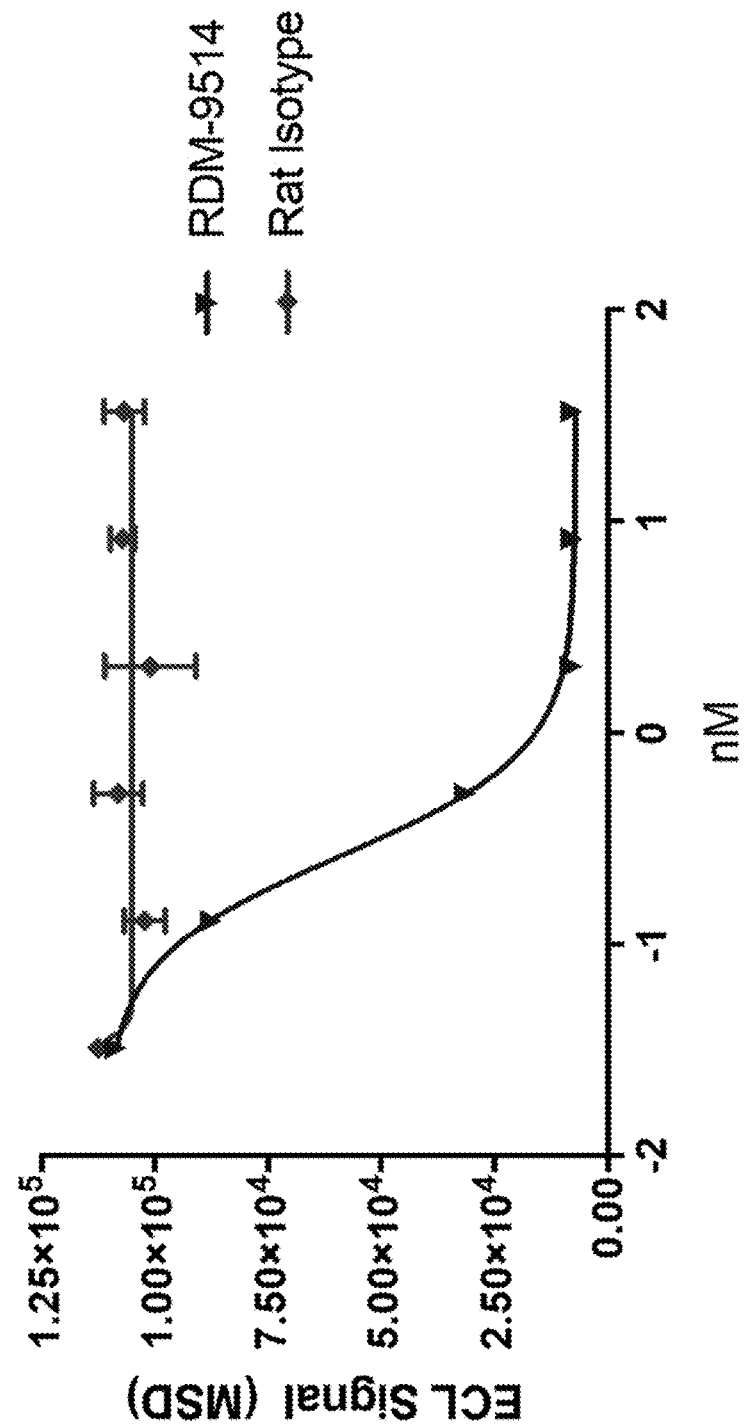
FIG. 9 shows that RDM-9514 also blocked LDL binding to MARCO in a dose dependent manner.
Figure 10A:
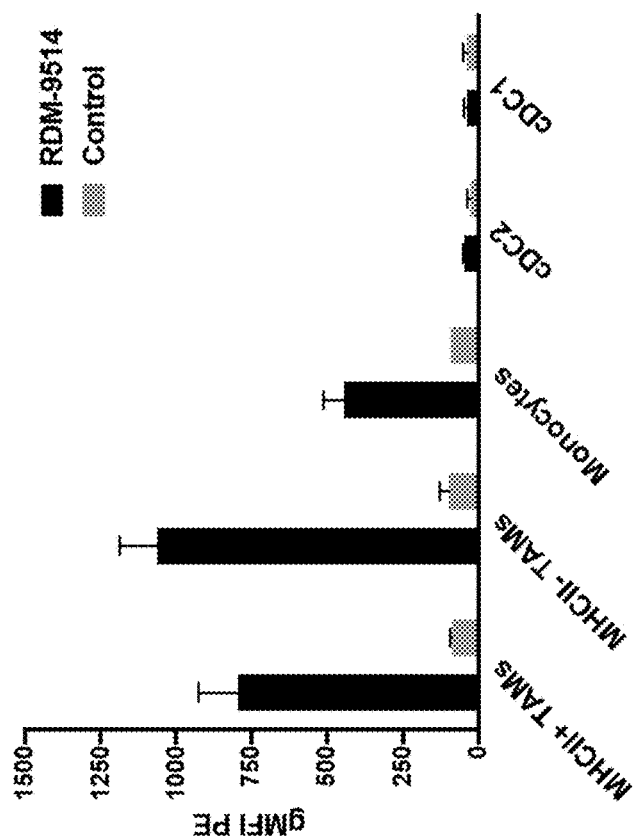
FIG. 10A shows that RDM-9514 bound to surface expressed MARCO on MHCII$^{high}$ TAMs and MHCII$^{low}$ TAMs isolated from CT26 tumors and Py8119 tumors.
Figure 10B:
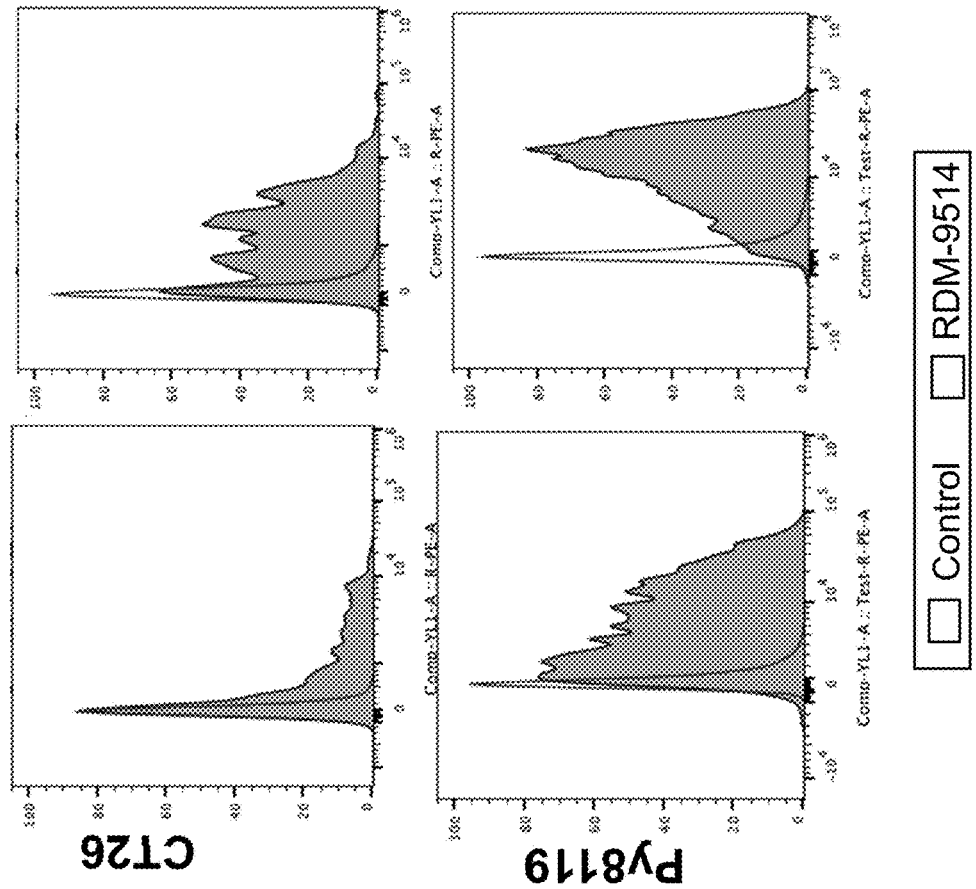
FIG. 10B shows that MARCO is expressed on TAMs and monocytes in the CT26 syngeneic tumor model.

RDM-9514 bound to the SRCR domain of MARCO. RDM-9514 also blocked LDL binding to MARCO in a dose dependent manner (FIG. 9) and bound to surface expressed MARCO on MHCII$^{high}$ TAMs and MHCII$^{low}$ TAMs isolated from CT26 tumors and Py8119 tumors (FIG. 10A). Staining with mouse antibody RDM-9514 also showed that MARCO is expressed on TAMs and monocytes in the CT26 syngeneic tumor model (FIG. 10B).

Figure 11B:
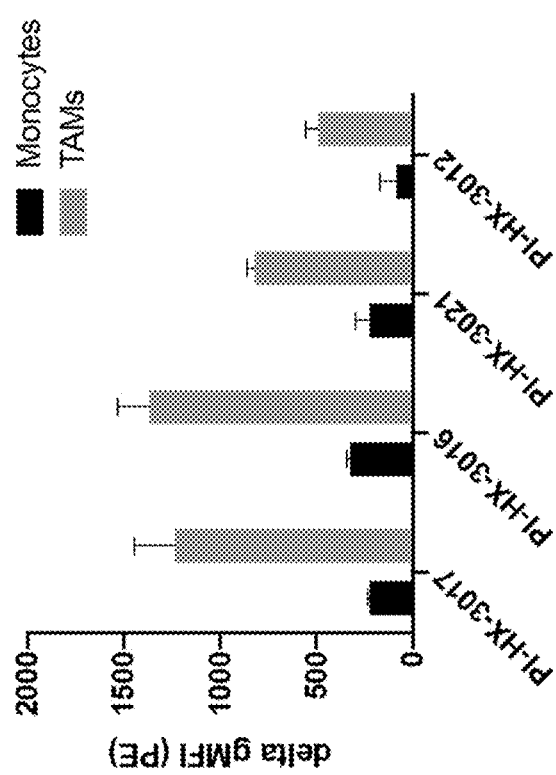
FIG. 11B shows that the same antibodies also bound to MARCO on TAMs (right bar) and monocytes (left bar) isolated from tumors in the CT26 syngeneic tumor model (n=2).
Figure 11A:
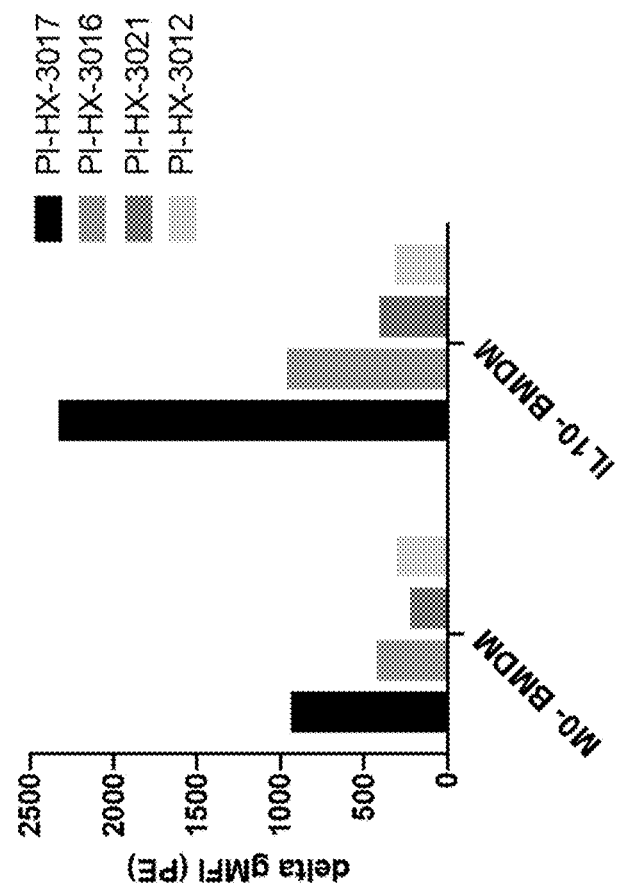
FIG. 11A shows that anti-mouse MARCO antibodies PI-HX-3017 (left bar, renamed PI-3009), PI-HX-3016 (middle left bar, renamed PI-3008), PI-HX-3021 (middle right bar, renamed PI-3007) and PI-HX-3012 (right bar) each bound to mouse BMDMs.

MARCO expression on mouse BDMDs after macrophage and IL-10 polarization was also assessed with the newly generated mouse MARCO antibodies. PI-HX-3017 (left bar, renamed PI-3009), PI-HX-3016 (middle left bar, renamed PI-3008), PI-HX-3021 (middle right bar, renamed PI-3007) and PI-HX-3012 (right bar) each bound to mouse BMDMs (FIG. 11A). The same antibodies also bound to MARCO on TAMs (right bar) and monocytes (left bar) isolated from tumors in the CT26 syngeneic tumor model (FIG. 11B, n=2).

Example 4: In Vivo Efficacy of Anti-Mouse MARCO Antibodies in Mono and Combination Therapy Materials and Methods In Vivo Combination Therapy with PD-1 Antibody in CT26 Syngeneic Model Antibodies for in vivo use were all tested for endotoxin and used at or below 0.2 EU/mg protein. Anti-PD-1 [clone RMP1-14] in a mouse IgG1 D265A format was obtained. Mouse IgG1 [clone MOPC-21] and mouse IgG2a [clone C1.18.4] isotype controls were obtained. PI-3006, PI-3007, PI-3008, and PI-3009 were produced in HEK293 cells and evaluated for monodispersity and purity by SEC and CE-SDS as well as endotoxin tested. Antibodies were also tested for binding to mouse MARCO overexpressing 293T cells and for lack of binding to the parental 293T cells by flow cytometry.

Female BALB/c mice at about eight weeks of age were obtained from Taconic Biosciences (Rensselaer, NY). Mouse tumor cell line CT26.WT (CRL-2638) was obtained from American Type Culture Collection (ATCC), and cultured according to their guidelines. Low passage cells were resuspended at 1×10$^7$ cells/ml in serum-free 1×DPBS (Gibco). The tumor cell suspension was subcutaneously injected on the shaved lower right ventral flank of BALB/c mice under isoflurane anesthesia. Tumor volume growth was monitored twice a week via perpendicular tumor diameter measurements and calculated using the formula (mm$^3$)=0.5× (length)×(width)$^2$. Six treatment groups were randomly assigned with 10 animals each when tumors reached an average of 97 mm$^3$. For drug treatments, mice were dosed intraperitoneally once every 5 days for 4 doses total (Q5Dx 4) with anti-mouse isotype control IgG2a (Clone C1.18.4) at 15 mg/kg, anti-mouse isotype control IgG1 (Clone MOPC-21) at 5 mg/kg, anti-mouse PD-1 (clone RMP1-14 recombinantly produced as mouse IgG1 D265A format and called PI-0004-AB) at 5 mg/kg alone or in combination with the anti-mouse MARCO antibodies (PI-3006, PI-3007, PI-3008, and PI-3009) at 10 mg/kg. All studies were conducted in accordance with the Explora Biolabs institutional animal care and use committee under the protocol EB17-010. Mice were housed under conditions outlined in the NIH Guide for Care and Use of Laboratory Animals in compliance with the USDA Laboratory Animal Welfare Act. The animals were allowed ad libitum access to Lab Diet rodent chow and water. Mice were monitored a minimum of twice per week by the investigator or veterinary staff for clinical abnormalities which may require euthanasia. Mice showing a net body weight loss >20% compared to baseline weight measurement were euthanized.

Anti-Tumor Immune Memory Assay

BALB/c mice that were tumor-free from the CT26 tumor model study with the anti-MARCO antibodies plus anti-PD-1 antibody treatment as described above were re-challenged with 1×10$^6$ CT26 tumor cells on the left ventral flank. EMT6 cells were injected subcutaneously on the opposite right ventral flank as a control cell line to track for tumor growth during the study period. No additional treatment was provided to the mice during the study period. Tumor volume was measured for 35 days after the re-challenge implant.

Figure 15A:
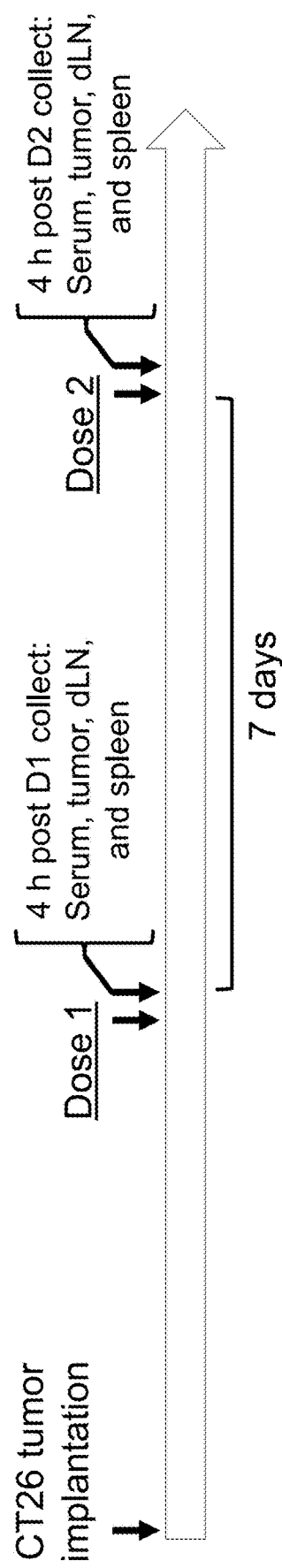
FIG. 15A shows a timeline of the PD study.

Pharmacodynamics (PD) and In Vivo Anti-MARCO Antibody Single Agent Efficacy in CT26 Model Female BALB/c mice at about eight weeks of age were obtained from Taconic Biosciences (Rensselaer, NY). Mouse tumor cell line CT26.WT (CRL-2638) was obtained from American Type Culture Collection (ATCC), and cultured according to their guidelines. Low passage cells were resuspended at 1×107 cells/ml in serum-free 1×DPBS (Gibco). The tumor cell suspension was subcutaneously injected on the shaved lower right ventral flank of BALB/c mice under isoflurane anesthesia. Tumor volume growth was monitored twice a week via perpendicular tumor diameter measurements and calculated using the formula (mm$^3$)=0.5× (length)×(width)$^2$. Two treatment groups were randomly assigned with 10 animals each when tumors reached an average of 109 mm$^3$. For drug treatments, mice were dosed iv once every 7 days (Q7D) with anti-mouse isotype control IgG2a (Clone C1.18.4) and anti-mouse MARCO antibody (PI-3008) at 10 mg/kg. All studies were conducted in accordance with the Explora Biolabs institutional animal care and use committee under the protocol EB17-010. Mice were housed under conditions outlined in the NIH Guide for Care and Use of Laboratory Animals in compliance with the USDA Laboratory Animal Welfare Act. The animals were allowed ad libitum access to Lab Diet rodent chow and water. Mice were monitored a minimum of twice per week by the investigator or veterinary staff for clinical abnormalities which may require euthanasia. Mice showing a net body weight loss >20% compared to baseline weight measurement were euthanized. A schematic of the study time line is shown in FIG. 15A.

Pharmacokinetics (PK) Assay

The mouse MARCO PK assay was used for quantification of drug antibody levels in mouse serum. A high-binding 96-well MSD plate was coated with 2 µg/ml mMARCO (PI-RG-3016). After blocking for an hour with blocking buffer (PBST, 5% BSA (PBS, 0.01% Tween-20, BSA), a standard curve and diluted serum samples were added to the plate and incubated for 2 hours on a plate shaker. Both the samples and the standard curve were normalized to a final concentration of 5% mouse serum. The plate was washed in DPBS++ (Gibco), 0.05% Tween-20, 1% BSA, and the bound MARCO antibody was detected using a sulfo-tagged anti-mouse IgG2a (Jackson Immuno). The sulfo tagged antibody generates an electrochemiluminescent signal when read buffer was added and electricity was applied to the electrodes in the MSD plate. Antibody levels in the serum samples are quantitated by interpolating from the standard curve using a 4-parameter curve fit in the MSD software.

RNAseq and Pathway Analysis of the Tumors, LNs, and Spleens from the CT26 PD Study The first timepoint for PD takedown was 4 h following iv dosing of the antibodies. Blood (serum), spleen, tumor, and tumor draining lymph nodes from each mouse was harvested and tissues snap frozen in liquid nitrogen. The second timepoint was 4 h after the second iv dosing of the antibodies, which occurred 6 days after the first iv dose. Blood (serum), spleen, tumor, and tumor draining lymph nodes from each mouse was harvested and tissues snap frozen in liquid nitrogen. Snap frozen samples were shipped to Medgenome Inc. for tissue homogenization using the Biospec Beadbeater in buffer RLT+BME and RNA extraction using the Qiagen All Prep kit and Biospec Beadbe. The mRNA quantity and quality were assessed by Nanodrop and the Agilent Bioanalyzer before moving to library preparation and RNAseq analysis to determine changes in gene expression induced by MARCO at the early and late PD timepoints. Differentially expressed genes (upregulated and downregulated) with FDR (<0.05) and cpm>2 cutoffs were generated and GSEA pathway analysis was performed and plotted using Cytoscape, KEGG, and Hallmarks analyses. The IgV genes observed in the differentially expressed gene list from the spleens treated with PI-3008 at 4 h were plotted using a heatmap.

Afucosylated Antibody Assay

Afucosylated PI-3008 with an mIgG2a mouse Fc was generated and tested in vivo. Fucosylated PI-3008 antibody and an mIgG2a isotype antibody were used as controls.

CT26 tumor cells (1×10$^4$6 cells per mouse) were implanted on Day 0. Afucosylated PI-3008 antibody IV (10 mg/kg; Q7dx3) dosing was initiated when tumors reached an average of ~100 mm3 in volume.

Effector Dead Antibody Assay

An N297A mutation was engineered in the mouse IgG2a Fc of PI-3008 to generate an effector dead mAb, PI-3021. PI-3008 and effector dead PI-3021 were tested alone and in combination with anti-PD-1 antibody in the CT26 mouse model. Balb/c female mice were inoculated subcutaneously with syngeneic CT26 tumor cells (1×10$^4$6 cells per mouse) on Day 0, and dosed with PI-3008 (WT Fc; 10 mg/kg), PI-3021 (Effector dead; 10 mg/kg), anti-PD-1 (5 mg/kg), and appropriate isotype controls (10 mg/kg) as single agent or in combination with anti-PD1 (N=10/group) was initiated when tumor volumes reached an average of ~100 mm3.

Animals were dosed intraperitoneally every 5 days, for total of four doses. Tumor volumes were monitored over time and presented as averages per group, individual tumor volumes at the end of study, or as % TGI.

Results

Figure 12:
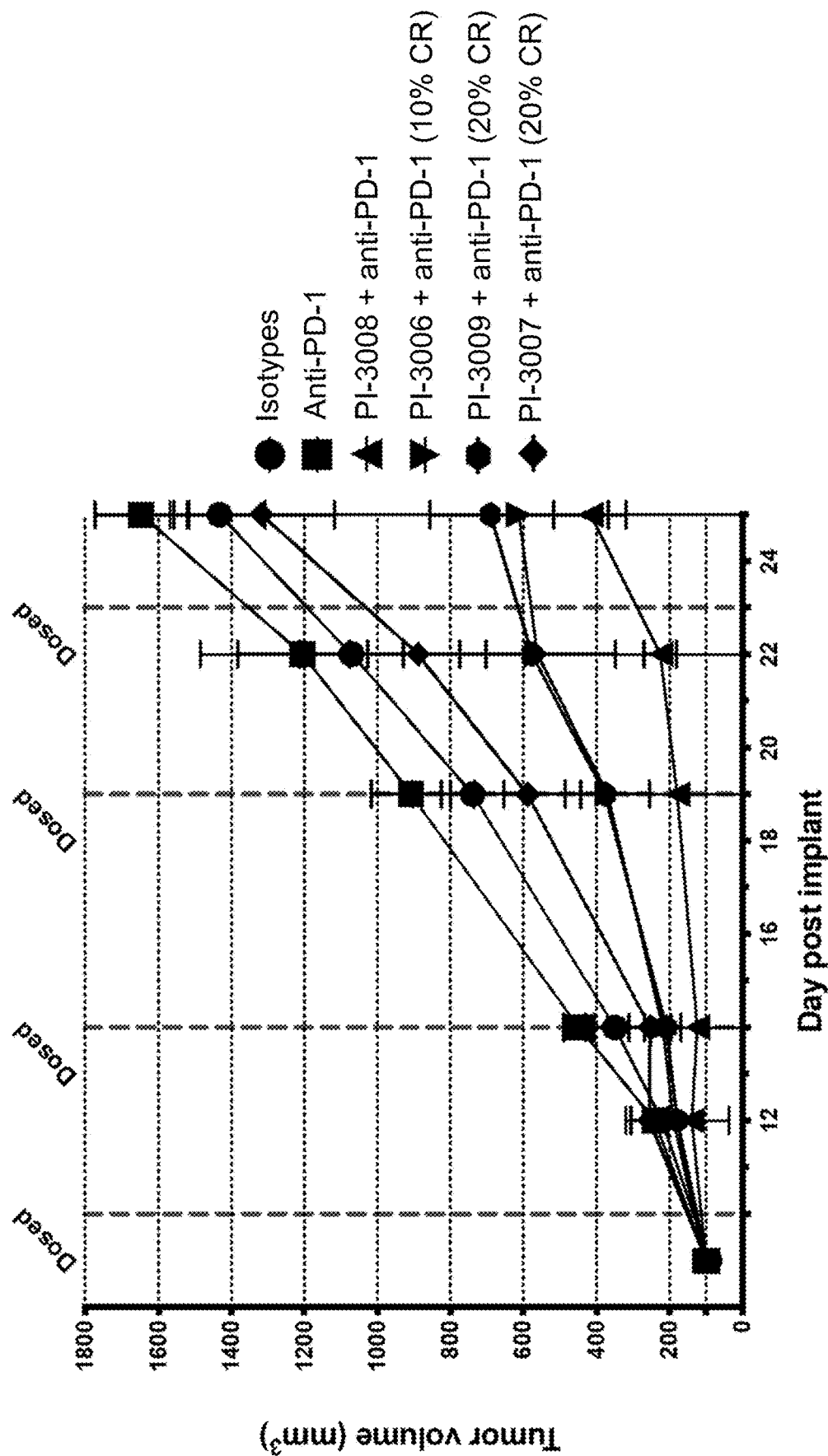
FIG. 12 shows the tumor volume in mice groups treated with isotype antibody; PD-1 antibody only; or PI-3008 plus PD-1 antibodies, PI-3007 plus PD-1 antibodies, PI-3009 plus PD-1 antibodies, and PI-3007 plus PD-1 antibodies.

The mouse anti-MARCO antibodies demonstrated significant anti-tumor efficacy in the CT26 model in combination with an anti-PD-1 antibody. FIG. 12 shows the tumor volume in mice groups treated with isotype antibody; PD-1 antibody only; or PI-3008 plus PD-1 antibodies, PI-3007 plus PD-1 antibodies, PI-3009 plus PD-1 antibodies, and PI-3007 plus PD-1 antibodies. PI-3006 and PD-1 antibodies resulted in 10% cancer remission (CR), while PI-3007 and PI-3009 in combination with PD-1 antibodies resulted in 20% CR. PI-3008 had the best response and TGI overall. FIG. 13A-D show the responses in the individual mice after treatment with isotype control, anti-PD-1, PI-3008+PD-1 antibodies, or PI-3009+PD-1 antibodies. PI-3008 (FIG. 13C) and PI-3009 (FIG. 13D) demonstrated the best anttumor efficacy in combination with the anti-PD-1 antibody.

Afucosylated Antibody Assay

Figure 13B:
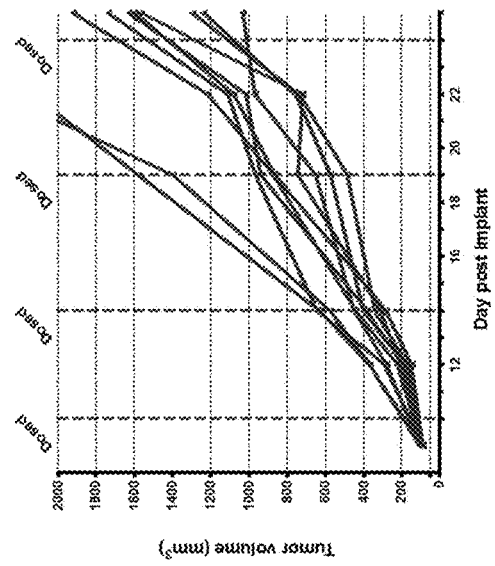
FIG. 13B shows the tumor volumes in individual mice treated with anti-PD-1 antibody.
Figure 13D:
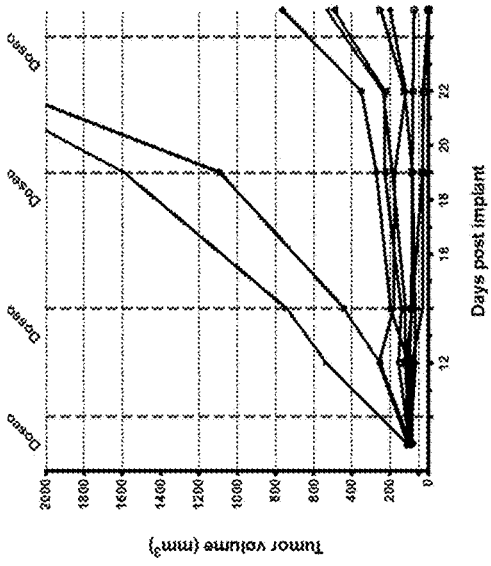
FIG. 13D shows the tumor volumes in individual mice treated with PI-3009 and anti-PD-1 antibody.
Figure 13A:
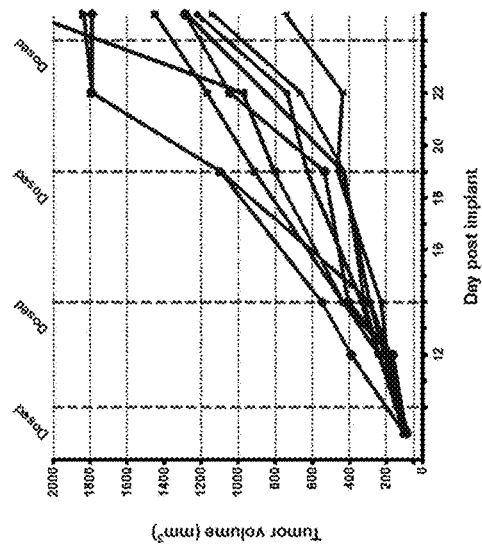
FIG. 13A shows the tumor volumes in individual mice treated with isotype control antibody.
Figure 13C:
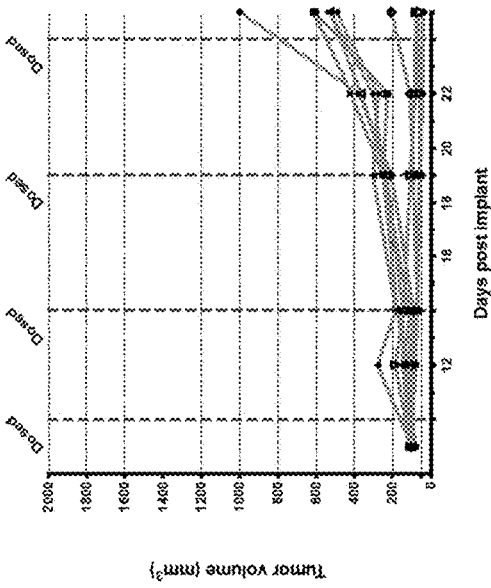
FIG. 13C shows the tumor volumes in individual mice treated with PI-3008 and anti-PD-1 antibody.
Figure 13H:
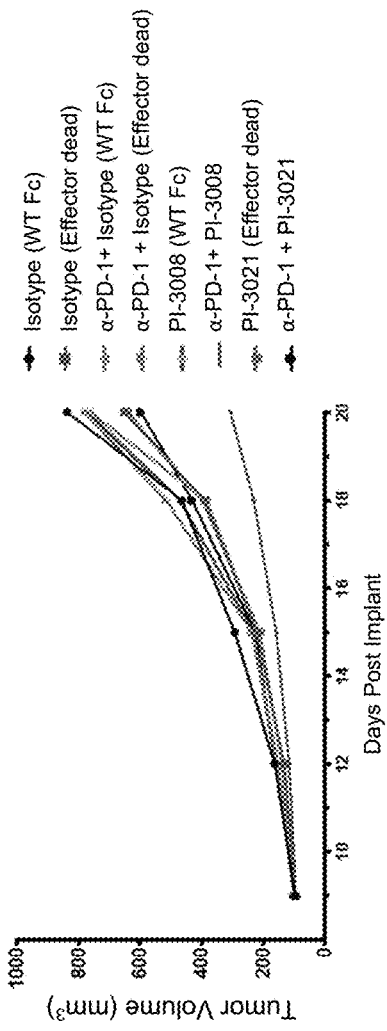
FIG. 13H shows the tumor volumes in mice treated with the indicated antibody.
Figure 13I:
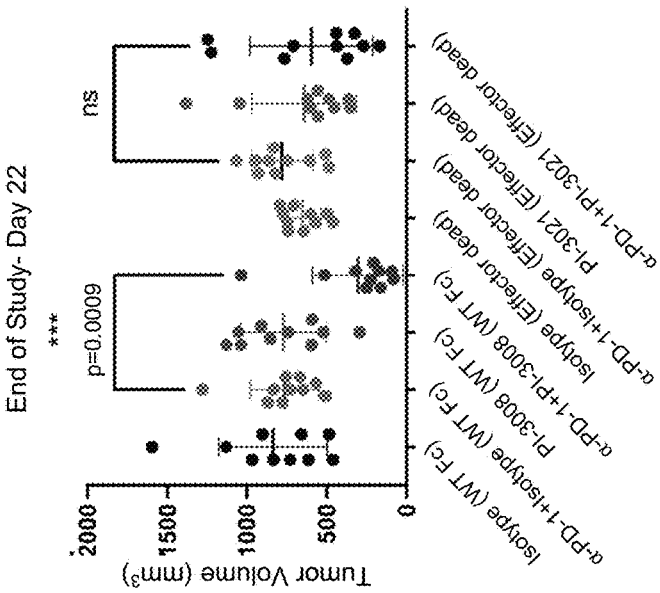
FIG. 13I shows the shows the tumor volumes in mice treated with the indicated antibody
Figure 13K:
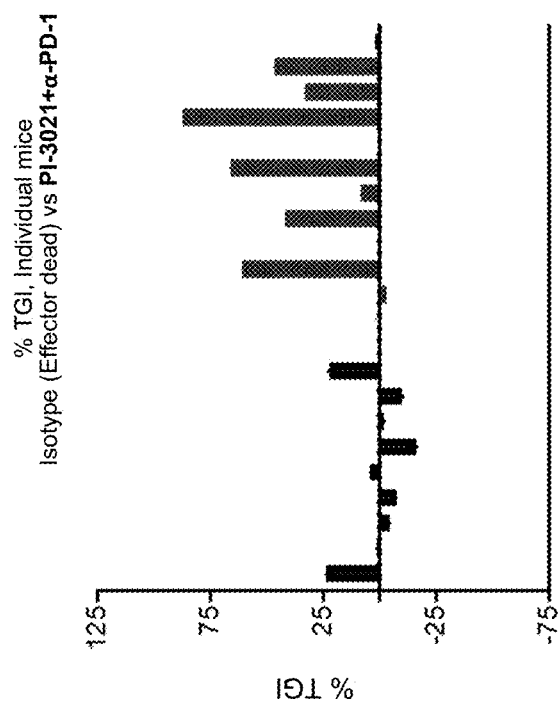
FIG. 13K shows the shows the percentage of tumor growth inhibition (% TGI) in mice treated with isotype control antibody (effector dead Fc) as compared to dead Fc PI-3021 and PD-1 antibody.
Figure 13J:
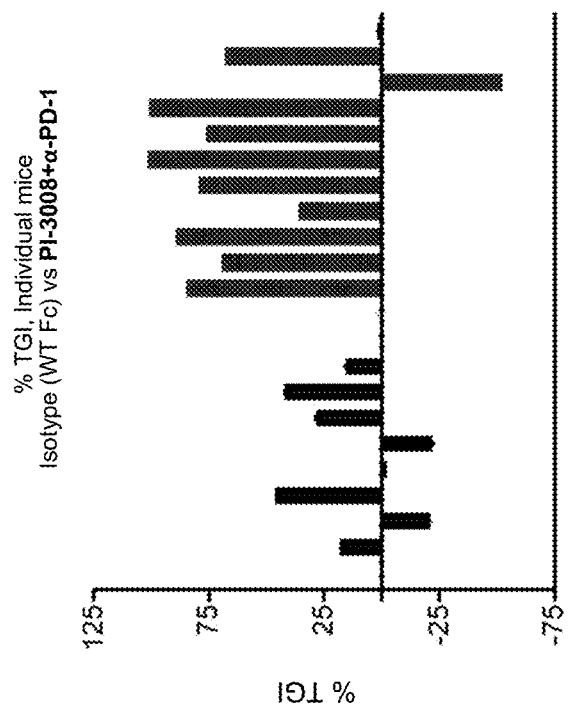
FIG. 13J shows the percentage of tumor growth inhibition (% TGI) in mice treated with isotype control antibody (wt Fc) as compared to wt Fc PI-3008 and PD-1 antibody.

PI-3008 demonstrated better single agent (monotherapy) anti-tumor activity than the Fc enhanced variant (PI-3008-Afuc). Afucosylated PI-3008 did not show appreciable monotherapy when compared to fucosylated PI-3008 (FIGS. 13E, 13F, and 13G). Without wishing to be bound by theory, this data suggests that enhanced Fc mediated engagement is not required for monotherapy Effector Dead Antibody Assay The effector dead PI-3008 (PI-3021) also did not result in increased anti-tumor efficacy. Anti-tumor efficacy of PI-3008 in combination with anti-PD-1 was robust and more pronounced than that of PI-3021/anti-PD-1 combination (FIG. 13H). In the CT26 model, PI-3021 in combination with anti-PD1 did not lead to same level anti-tumor activity as observed with PI-3008 (FIG. 13H). At the end of study, day 22, PI-3008 had significant reduction in tumor volume compared to anti-PD-1 alone while PI-3021 did not reach statistical significance (FIG. 13I). In addition, percentage of tumor growth inhibition (% TGI) was higher in PI-3008 compared to PI-3021 in individual mice treated with combination therapy (FIGS. 13J and 13K). Finally, mouse BMDMs treated in vitro with PI-3021 did not show activation of the pro-inflammatory pathways as seen with PI-3008 after 4 hr of treatment (data not shown). Without wishing to be bound by theory, this data suggests that PI-3008 with a fucosylated Fc is the optimal Fc format for the desired anti-tumor activity in vivo in in the anti-PD-1 resistant CT26 mouse model. However, PI-3021 demonstrated equal anti-tumor activity as PI-3008 in the E0771 anti-PD1 sensitive model (Example 11 and FIG. 38), suggesting that anti-MARCO antibody activity could also be due to target activity on MARCO in addition to Fc-mediated signaling.

Figure 14:
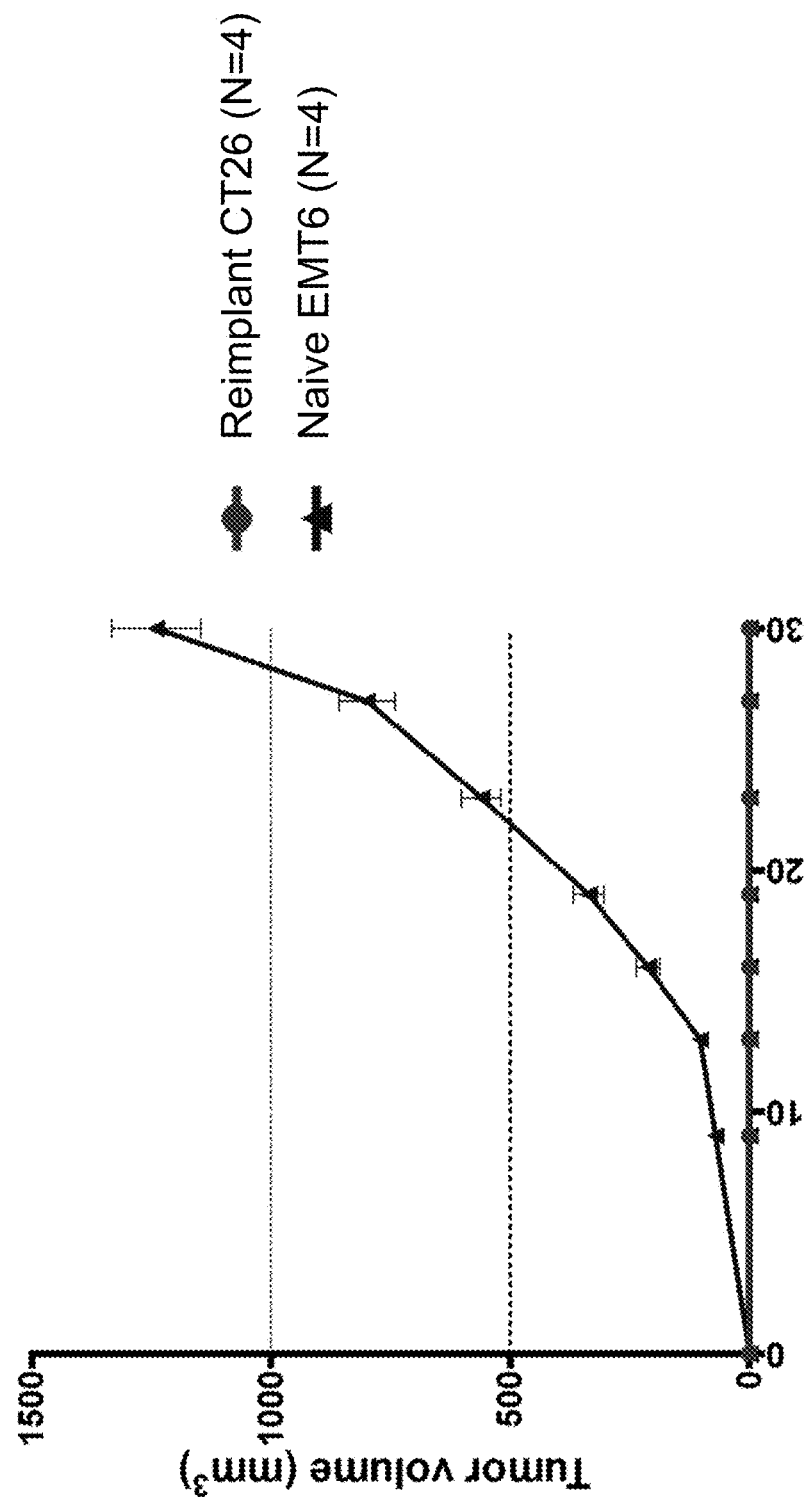
FIG. 14 shows the tumor volume of re-implanted CT26 tumor cells and EMT6 cells in mice that had been previously treated with anti-MARCO and anti-PD-1 antibodies.

Anti-MARCO and PD-1 combination treatment also resulted in long-term, anti-tumor immune memory after CT26 tumor challenge (FIG. 14). The mice that were tumor free after the first treatment of anti-MARCO antibodies were re-implanted with CT26 tumor cells, or EMT6 tumor cells. As shown in FIG. 14, no growth of the re-implanted CT26 tumor cells was observed in the mice that had been previously treated with anti-MARCO and anti-PD-1 antibodies.

Figure 15C:
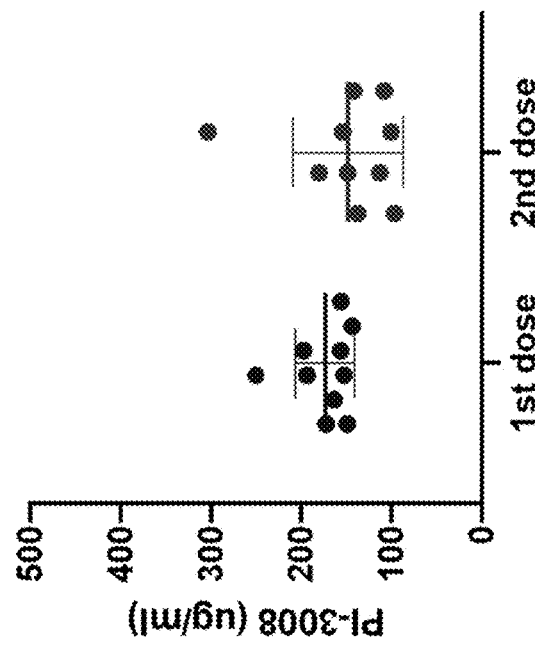
FIG. 15C shows quantification of the PI-3008 antibody in the mice after the first and second dose.
Figure 15B:
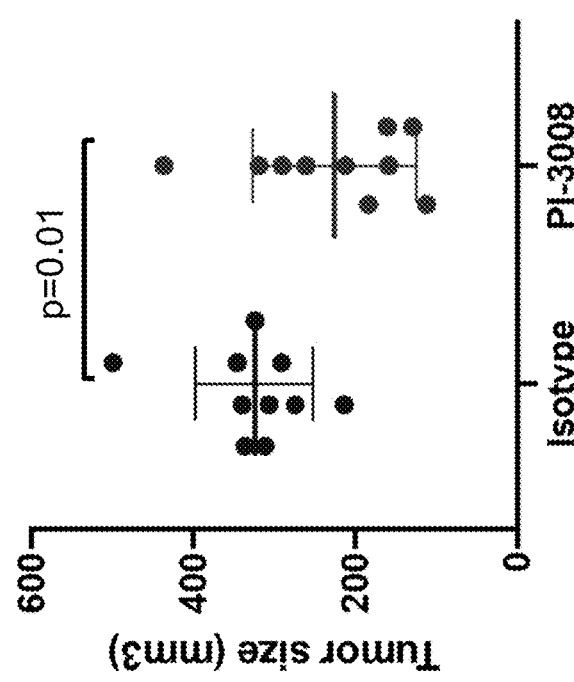
FIG. 15B shows CT26 tumor volume in mice treated with isotype antibody or PI-3008.

The pharmacodynamics (PD) and anti-tumor efficacy of one anti-MARCO antibody, PI-3008, was also assessed in the CT26 colorectal tumor model as single agent monotherapy (FIG. 15A-15C). The PI-3008 anti-MARCO antibody demonstrated significant monotherapy in the CT26 model. FIG. 15A shows a timeline of the PD study. FIG. 15B shows that treatment with PI-3008 reduced mouse tumor size 6 days after the first dose, as compared to isotype control antibody. FIG. 15C shows quantification of the PI-3008 antibody in the mice after the first and second dose.

Molecular profiling analysis of CT26 tumors was also performed on samples taken 4 hours after the first and second dose of PI-3008 and isotype antibodies. The anti-MARCO antibody activated multiple immune pathways. After dose 1, genes in the actin mediated cell contraction pathway were upregulated, with a pathway FDR<0.1. 4 hours after the second dose, genes in kinase activation and activity pathway, Toll-like receptor signaling pathway, TLR 4 and 9 pathways, GTPase binding and activity, and RAS-Rho signal transduction pathways were upregulated. After both the first and second dose, the following pathways were upregulated: humoral immune response, NK mediated immunity, NK activation, IL-2 and IL-12 production, cell killing, regulation of effector process, T cell proliferation, activation, differentiation, chemotaxis and migration, cell-cell adhesion, phagocytosis, and myeloid differentiation.

The KEGG pathways induced by anti-MARCO antibody in the CT26 tumors in vivo were determined. After dose 1, the top 10 most differentially upregulated pathways were: Natural Killer cell mediated cytotoxicity, T cell receptor signaling pathway, JAK/STAT signaling pathway, cytokine-cytokine receptor interaction, Intestinal immune network for IgA production, leukocyte trans-endothelial migration, chemokine signaling pathway, hematopoietic cell lineage, type II diabetes mellitus, and Fc-epsilon RI signaling pathway. After dose 1, the top 10 most differentially downregulated pathways were: homologous recombination, Alzheimer's disease, RNA polymerase, arginine and proline metabolism, citrate cycle (TCA cycle), porphyrin and chlorophyll metabolism, valine, leucine, and isoleucine degradation, biosynthesis of unsaturated fatty acids, N-glycan biosynthesis, and aminoacyl tRNA biosynthesis.

After dose 2, the top 10 most differentially upregulated pathways in the CT26 tumors were: cytokine-cytokine receptor interaction, Natural Killer cell mediated cytotoxicity, primary immunodeficiency, chemokine signaling pathway, hematopoietic cell lineage, JAK/STAT signaling pathway, T cell receptor signaling pathway, Intestinal immune network for IgA production, neuroactive ligand receptor interaction, and Fc-epsilon RI signaling pathway. After dose 2, the top 10 most differentially downregulated pathways were: glycolysis gluconeogenesis, propanoate metabolism, proteasome, citrate cycle TCA cycle, cardiac muscle contraction, Alzheimer's disease, Huntington's disease, oxidative phosphorylation, ribosome, and Parkinson's disease.

The KEGG pathways induced by anti-MARCO antibody in the tumor draining lymph nodes in vivo were also determined. After dose 1, the top 10 most differentially upregulated pathways were: phosphatidylinositol signaling system, focal adhesion, inositol phosphate metabolism, axon guidance, adherens junction, pathways in cancer, regulation of actin cytoskeleton, progesterone mediated oocyte maturation, ERBB signaling pathway, and Wnt signaling pathway. After dose 1, the top 10 most differentially downregulated pathways were: aminoacyl tRNA biosynthesis, lysosome, histidine metabolism, drug metabolism cytochrome p450, proteasome, Alzheimer's disease, Huntington's disease, Parkinson disease, oxidative phosphorylation, and ribosome.

After dose 2, the top 10 most differentially upregulated pathways in the tumor draining lymph nodes were: focal adhesion, phosphatidylinositol signaling system, neurotrophin signaling pathway, insulin signaling pathway, inositol phosphate metabolism, MAPK signaling pathway, pathways in cancer, regulation of actin cytoskeleton, ERBB signaling pathway, and adherens junction. After dose 2, the top 10 most differentially downregulated pathways were: metabolism of xenobiotics by cytochrome p450, hematopoietic cell lineage, lysosome, Alzheimer's disease, proteasome, cytokine-cytokine receptor interaction, Huntington's disease, Parkinson's disease, oxidative phosphorylation, and ribosome.

The KEGG pathways induced by anti-MARCO antibody in the spleen in vivo were also determined. After dose 1, upregulated pathways included: ECM receptor interaction, focal adhesion, tight junction, adheres junction, proteasome, complement and coagulation cascades, cell adhesion molecules and CAMs, pathways in cancers, arrhythmogenic right ventricular cardiomyopathy ARVC, Wnt signaling pathway, regulation of actin skeleton, axon guidance, Huntington's disease, pathogenic *Escherichia coli* infection, Alzheimer's disease, leukocyte transendothelial migration, cytokine-cytokine receptor interaction, basal cell carcinoma, melanogenesis, and hedgehog signaling pathway. Downregulated pathways included: cell cycle, aminoacyl tRNA biosynthesis, mismatch repair, glycosylphosphatidylinositol GPI anchor biosynthesis, glycerophospholipid metabolism, and homologous recombination.

After dose 2, upregulated pathways in the spleen included: cell cycle, proteasome, T cell receptor signaling pathway, DNA replication, ubiquitin mediated proteolysis, regulation of actin cytoskeleton, adherens junction, pathogenic *Escherichia coli* infection, basal transcription factors, pentose phosphate pathway, Fc gamma R mediated phagocytosis, neurotrophin signaling pathway, regulation of autophagy, glycolysis gluconeogenesis, oocyte meiosis, chronic myeloid leukemia, citrate cycle TCA cycle, Wnt signaling pathway, P53 signaling pathway, and natural killer cell mediated cytotoxicity. Downregulated pathways included: ABC transporters, glycosylphosphatidylinositol GPI anchor biosynthesis, RNA polymerase, ribosome, arachidonic acid metabolism, glycerophospholipid metabolism.

Figure 16A:
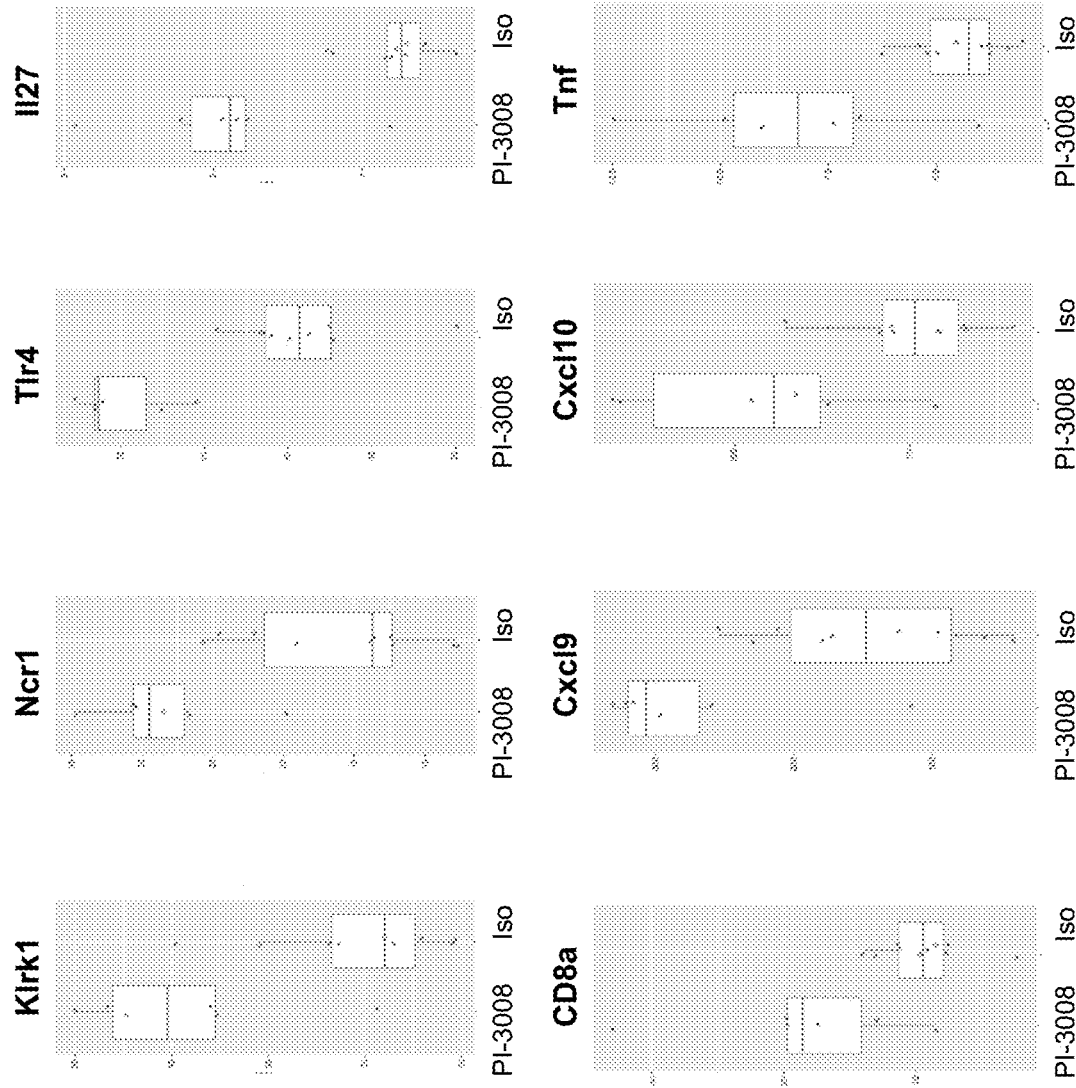
FIG. 16A show pro-inflammatory molecule expression within the TME of CT26 mice treated with PI-3008.
Figure 16B:
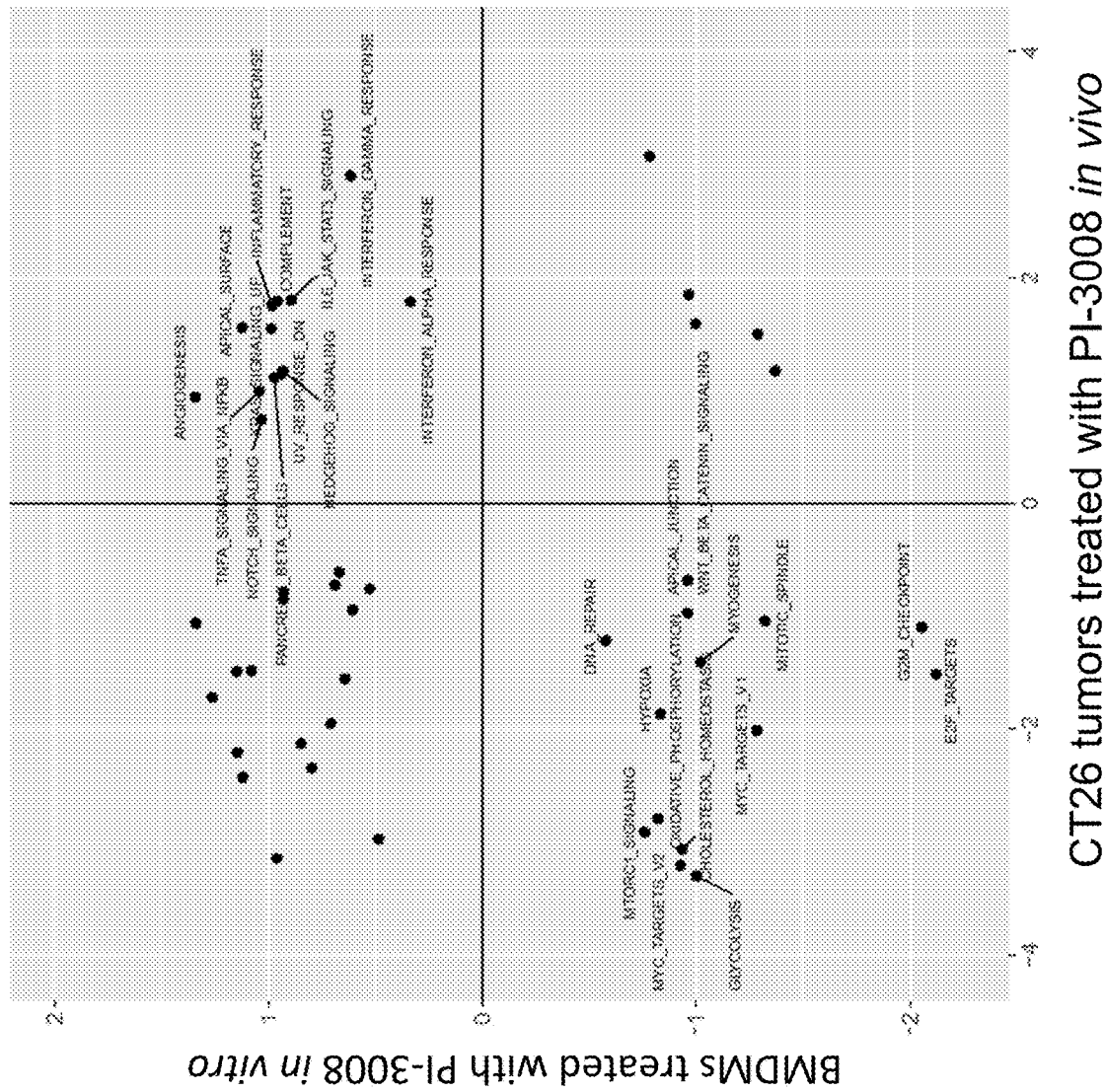
FIG. 16B shows a comparison of the genes upregulated in BMDMs and CT26 tumors after in vitro or in vivo treatment with PI-3008.

A more in depth analysis of the differentially expressed genes in the PI-3008-treated CT26 tumors after dose 1 and dose 2 was also performed. Genes associated with NK cells, such as Klrk1, Nrc1, and Prf1; genes associated with pro-inflammatory and immune activation, such as Cd40, Cd8α, Nod2, Tlr4, Tnf, Nlrp3, Cd274, Clec9α, and Cd200r3; and pro-inflammatory cytokines, such as I1-27, Cxcl9, Cxcl10, and Cxcl12 were upregulated. FIG. 16A shows the expression levels of Klrk1, Nrc1, Tlr4, I1-27, Cd8a, Cxcl9, Cxcl10, and Tnf in the CT26 tumor microenvironment after treatment with PI-3008 or an isotype control antibody. In each case, treatment with PI-3008 increased expression of the gene. FIG. 16B shows a comparison of the genes upregulated in BMDMs and CT26 tumors after treatment with PI-3008.

In addition, anti-Marco antibody 3008 upregulated IG-V genes in CT26 spleens after the first dose. 154 annotated IG-V genes with CPM>1 are known. All of the 154 annotated IG-V genes were upregulated with PI-3008 treatment, while 138/154 were differentially expressed with an FDR<0.05. Thus, polyclonal expansion of plasma cells or activated B-cells in the Marginal Zone in the spleen may be occurring upon anti-MARCO antibody treatment to activate self-antigens or tumor antigens, such as NK activation.

Example 5: Production and Characterization of Additional Anti-Human MARCO Antibodies Materials and Methods A further antibody campaign to develop antibodies that bind to the SRCR domain of human MARCO was performed.

Immunization for Generating Anti-Human MARCO Antibodies

Rat anti-human MARCO hybridomas were generated by immunizing Sprague Dawley rats with recombinant N-terminal-his tagged human MARCO protein in Sigma Adjuvant System (SAS) alone or alternating with human MARCO expressing HEK 293 cells. The recombinant N-terminal his-tagged human MARCO protein comprised residues 147-520 of human MARCO. The recombinant human MARCO protein was quality control for proper folding and trimer formation. In contrast, the human MARCO protein (Pi 114) previously used for the unsuccessful anti-human MARCO campaign described in Example 2 consisted of a modified MARCO ECD domain comprising residues 147-419 of the CLD domain and residues 424-520 of the SRCR domain.

Rats were immunized twice weekly in the hock and serum titers tested at day 21 at Antibody Solutions (Santa Clara, CA). Rats with sufficient serum antibody titers to human MARCO were chosen for electrofusion to generate hybridomas. Two final boosts were given on days −3 and −2 prior to harvest Immunizations in phosphate buffered saline (PBS).

Hybridoma Generation and Screening

Hybridoma generation and screening assays for human MARCO antibodies were performed as described in Example 3.

Cell Binding

Cell binding assays for human MARCO antibodies were performed as described in Example 3.

Hybridoma Subcloning and Purification

Hybridoma subcloning and purification for human MARCO antibodies were performed as described in Example 3.

Hybridoma Antibody Variable Region Sequences Generation

Hybridoma antibody variable region sequences for human MARCO antibodies were generated as described in Example 3.

Chimeric and Humanized Antibody Generation

Chimeric antibodies were made by replacing the rat IgG1 or IgG2a Fc domain with human IgG1 or IgG4 domains.

Humanized antibodies were also synthesized from the rat parental hybridomas.

The VH and VL sequences of the rat hybridomas were compared to libraries of known human germline sequences on the NCBI website (ncbi.nlm.nih.gov/igblast/; Ye, J. et al. Nucleic Acids Research 41:W34-W40 (2013)). The databases used were IMGT human VH genes (F+ORF, 273 germline sequences) and IMGT human VLkappa genes (F+ORF, 74 germline sequences) as used by the NCBI IgBLAST program. The acceptor human germline was chosen from those closest in sequence to the parental antibody.

Human germline IGHV1-46(allele 1) was chosen as the acceptor sequence and the human heavy chain IGHJ4 (allele 1) joining region (J gene) was chosen from human joining region sequences compiled at IMGT® the international ImMunoGeneTics information System® imgt.org (founder and director: Marie-Paule Lefranc, Montpellier, France).

Human germline IGKV1-39(allele 1) was chosen as the acceptor sequence and human light chain IGKJ2(allele 1) joining region (J gene) was chosen from human joining region sequences compiled at IMGT® the international ImMunoGeneTics information System® imgt.org (founder and director: Marie-Paule Lefranc, Montpellier, France). Sequence alignments of the HX-3061 rat parental and humanized VH and VL sequences are shown in FIGS. 17A and 17B, respectively. Sequence alignments of the HX-3031 rat parental and humanized VL sequences are shown in FIG. 18.

Additional back mutations were made in the humanized antibody VH derived from the HX-3061 hybridoma and the VL derived from the HX-3031 hybridoma. The back mutations made in the HX-3061 VH were: V37I, V48I, and S49A, based on the human framework VH sequence. The back mutations made in the HX-3031 VL were: A13T, A43P, S56D, F71Y, L78M, F83E, and Y87F, based on the human framework VL sequence.

CDRs were defined according to the AbM definition (bioinf.org.uk/abs/for a table comparing CDR definitions).

Calcium Dependency ELISA Assay

The calcium dependency ELISA assay was performed as described in Example 3.

Kinetics and Epitope Binning Using the ProbeLife Gator Instrument

Kinetics and epitope binning analysis of the newly generated anti-human MARCO antibodies was performed as described in Example 3.

LDL Competition Assay on Mouse and Human Recombinant Marco

LDL competition assay on mouse and human recombinant MARCO was performed as described in Example 3.

MARCO Bacteria Competition Assay 293T cells expressing human or mouse MARCO were harvested along with the parental 293T cells. Zombie NIR viability dye (BioLegend) was prepared by diluting the stock 1000-fold in D-PBS and added to the cells. The cells were incubated with the dye for 10 min at RT in the dark. The reaction was quenched by adding 1 m of 4× Staining buffer (2% FBS in DBPS containing $Ca^{2+}$), followed by centrifugation at 400×g for 5 min at 4° C. Cells were then plated in V-shaped 96 well plates at a density of 100,000 cells. A488-fluorescently labeled bacteria (E. coli from Invitrogen) was added at 10 μg/ml with the anti-human or anti-mouse antibodies of interest for a 30 min incubation at 37 C. Plates were then washed twice followed by resuspension in 100 ul of staining buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8).

Results

Primary screening of anti-human MARCO antibodies via ELISA screening for binding to human MARCO resulted in 304 candidates. A secondary screening 304 candidate antibodies were identified in the primary ELISA screen using purified human MARCO. Secondary screening of binding to 293T cells expressing human, cyno, and mouse MARCO or GFP control cells resulted in 138 candidates. An additional secondary screen for SRCR verus CLD binding was also performed via ELISA. 90 SRCR binding antibodies and 47 CLD binding antibodies were identified. Candidate antibodies were then screened for binding on endogenous cells, binding kinetics, LDL competition, and binding to human MSR1. 42 candidate antibodies were identified, 37 SRCR binding antibodies and 5 CLD binding antibodies. Of these, 11 candidate anti-human MARCO antibodies were identified with good binding characteristics. The sequences of selected human MARCO antibodies are shown in the sequence listing table. The CDRs are defined using the AbM definition.

The characterization of the rat hybridoma anti-human MARCO antibodies generated are shown in Table 3.

TABLE 3

| Anti-huMARCO mAb | Isotype | Bin | Ca2+/Mg2+ req for binding | $K_{on}$ (1/Ms) | $K_{off}$ (1/s) | Human $EC_{50}$ 293T (HuMARCO) (nM) | Cyno $EC_{50}$ 293T (CyMARCO) (nM) | $EC_{50}$ LDL competition assay (nM) | MSR1 binding |
|---|---|---|---|---|---|---|---|---|---|
| PI-HX-3011 | Rat IgG2a | 3 | + | 4.01E+05 | 9.14E−04 | 0.096 | 0.094 | NA | − |
| PI-HX-3023 | Rat IgG2a | 2 | +/− | 2.27E+05 | 4.75E−04 | 0.451 | 0.071 | 1.5 | − |
| PI-HX-3026 | Rat IgG2a | 2 | + | 2.42E+05 | 6.01E−04 | 0.23 | 0.162 | 1.3 | − |
| PI-HX-3028 | Rat IgG2a | 2 | +/− | 2.42E+05 | 4.79E−04 | 0.332 | 0.144 | 1.5 | − |
| PI-HX-3031 | Rat IgG2a | 3 | + | 4.43E+05 | 7.98E−04 | 0.141 | 0.046 | NA | − |
| PI-HX-3033 | Rat IgG2a | 2 | + | 2.70E+05 | 8.07E−04 | 0.272 | 0.067 | NA | − |
| PI-HX-3040 | Rat IgG2a | 3 | + | 2.41E+05 | 6.72E−04 | 0.229 | 0.107 | 2.9 | − |
| PI-HX-3041 | Rat IgG2a | 3 | + | 3.08E+05 | 7.96E−04 | 0.215 | 0.110 | NA | − |
| PI-HX-3043 | Rat IgG2a | 3 | + | 2.33E+05 | 8.49E−04 | 0.438 | 0.067 | 3.4 | − |
| PI-HX-3047 | Rat IgG2a | 1 | − | 4.84E+05 | 6.55E−04 | 0.326 | 0.100 | NA | − |
| PI-HX-3061 | Rat IgG2a | 4 | − | | | 0.49 | 0.45 | 8.2 | − |

Five of the eleven candidate anti-MARCO antibodies were selected for further development based on CDR sequence analysis: PJ-HX-3011, PJ-HX-3031, PJ-HX-3043, PT-HX-3061, and PI-HX-3092. Human chimeric antibodies were made by exchanging the rat IgG2a Fc region with human IgG1 (for PI-HX-3011 and PJ-HX-3043) or both IgG1 and IgG4 (for PI-3031 ad PJ-HX-3061). Additional chimeric antibodies were also made by exchanging the rat IgG2a Fc region with mouse IgG2a (for PJ-HX-3036, and PJ-HX-3092). Further humanization of the VH and VL frameworks was performed on antibodies derived from the PI-HX-3011, PJ-HX-3031, and PJ-HX-3061 rat parental antibodies.

Table 4 provides a summary of the selected rat parental antibodies, the chimeric antibodies, and the humanized antibodies generated.

TABLE 4

| Name | Revised Name (if applicable) | Description | SEQ ID NOs |
|---|---|---|---|
| PI-HX-3031 | | parental rat hybridoma | 1-10 |
| PI-3010-AB | PI-3010 | hIgG1/chimeric PI-HX-3031 | 11-20 |
| PI-3011-AB | PI-3010.11 | humanized PI-HX-3031/3031-1 hIgG1 | 21-30 |
| PI-3012-AB | PI-3010.12 | humanized PI-HX-3031/3031-2 hIgG1 | 31-40 |
| PI-3013-AB | PI-3010.13 | humanized PI-HX-3031/3031-3 hIgG1 | 41-50 |
| PI-3014-AB | PI-3010.14 | humanized PI-HX-3031/3031-4 hIgG1 | 51-60 |
| PI-3015-AB | PI-3010.15 | humanized PI-HX-3031/3031-5 hIgG1 | 61-70 |
| PI-3020-AB | PI-3010.20 | chimeric PI-HX-3031-hIgG4 | 71-80 |
| PI-3022-AB | PI-3010.22 | humanized PI-HX-3031/3031-2 hIgG1 | 81-90 |
| PI-3023-AB | PI-3010.23 | humanized PI-HX-3031/3031-2 hIgG1 | 91-100 |
| PI-3024-AB | PI-3010.24 | humanized PI-HX-3031/3031-2 hIgG1 | 101-110 |
| PI-3025-AB | PI-3010.25 | humanized PI-HX-3031/3031-2 hIgG1 | 434-443 |
| PI-3026-AB | PI-3010.26 | humanized PI-HX-3031/3031-2 hIgG1 | 121-130 |
| PI-3027-AB | PI-3010.27 | humanized PI-HX-3031/3031-2 hIgG1 | 131-140 |
| PI-3046-AB | PI-3010.46 | humanized PI-HX-3031/3031-2 hIgG4 | 474-483 |
| PI-3048-AB | PI-3010.48 | humanized PI-HX-3031/3031-2 hIgG4 | 444-453 |
| PI-HX-3061 | | parental rat hybridoma | 141-150 |
| PI-3016-AB | | humanized PI-HX-3061/3061-1 hIgG1 | 151-160 |
| PI-3017-AB | | humanized PI-HX-3061/3061-2 hIgG1 | 161-170 |
| PI-3018-AB | | humanized PI-HX-3061/3061-3 hIgG1 | 171-180 |
| PI-3019-AB | | PI-HX-3061 mIgG2a chimera | 181-190 |
| PI-3028-AB | | PI-HX-3061 hIgG1 chimera | 191-200 |
| PI-3029-AB | | PI-HX-3061 hIgG4 chimera | 201-210 |
| PI-3032-AB | | humanized PI-HX-3061/3061-2 hIgG1 | 211-220 |
| PI-3033-AB | | humanized PI-HX-3061/3061-2 hIgG1 | 221-230 |
| PI-HX-3011 | | parental rat hybridoma | 231-240 |
| PI-3030-AB | PI-3030 | HX3011-h1 Chimera hIgG1 | 241-250 |
| PI-3036-AB | PI-3030.36 | humanized PI-HX-3011/3011-1 hIgG1 | 311-320 |
| PI-3037-AB | PI-3030.37 | humanized PI-HX-3011/3011-2 hIgG1 | 321-330 |
| PI-3038-AB | PI-3030.38 | humanized PI-HX-3011/3011-3 hIgG1 | 331-340 |
| PI-3039-AB | PI-3030.39 | humanized PI-HX-3011/3011-4 hIgG1 | 341-350 |
| PI-3040-AB | PI-3030.40 | humanized PI-HX-3011/3011-5 hIgG1 | 351-360 |
| PI-3041-AB | PI-3030.41 | humanized PI-HX-3011/3011-5 hIgG1 | 454-463 |
| PI-3047-AB | PI-3030.47 | humanized PI-HX-3011/3011-5 hIgG4 | 464-473 |
| PI-HX-3043 | | parental rat hybridoma | 251-260 |
| PI-3031-AB | | HX3043-h1 Chimera hIgG1 | 261-270 |
| PI-HX-3092 | | parental rat hybridoma | 361-370 |
| PI-3035 | | HX3092 (A mutation) - mIgG2a | 371-380 |

The newly generated rat hybridoma anti-human MARCO antibodies were characterized as previously described. The characterization of the rat parental antibodies HX-3031 and HX-3061 is shown in Table 5. Neither antibody bound to MSR1. Binding kinetics were determined via Multi Cycle Kinetics analysis using the huMARCO antigen as previously described.

TABLE 5

| Anti-hu MARCO) mAb | Bin | Ca2+/ Mg2+ req for binding | $EC_{50}$ (raIgG2a) ELISA (hu/SRCR/cyn) | $K_D$ (M) Hu | $K_D$ (M) Cyno | Human $EC_{50}$ 293T (Hu MARCO) (nM) | Cyno $EC_{50}$ 293T (Cy MARCO) (nM) | Mouse $EC_{50}$ 293T (Mu MARCO) (nM) | $EC_{50}$ Bac competition assay (nM) | $EC_{50}$ LDL competition assay (nM) |
|---|---|---|---|---|---|---|---|---|---|---|
| PI-HX-3031 | 3 | + | 0.13/0.15/0.14 | 9.13E−11 | 1.09E−10 | 0.56 | 0.51 | nb | 0.18 | 6.2 |
| PI-HX-3061 | 4 | − | 0.24/0.24/0.23 | 2.56E−10 | 1.19E−10 | 0.49 | 0.45 | 1.52 | 0.52 | 8.2 |

One anti-huMARCO antibody (PI-HX-3061) was determined to be cross reactive with human and mouse MARCO.

Figure 19:
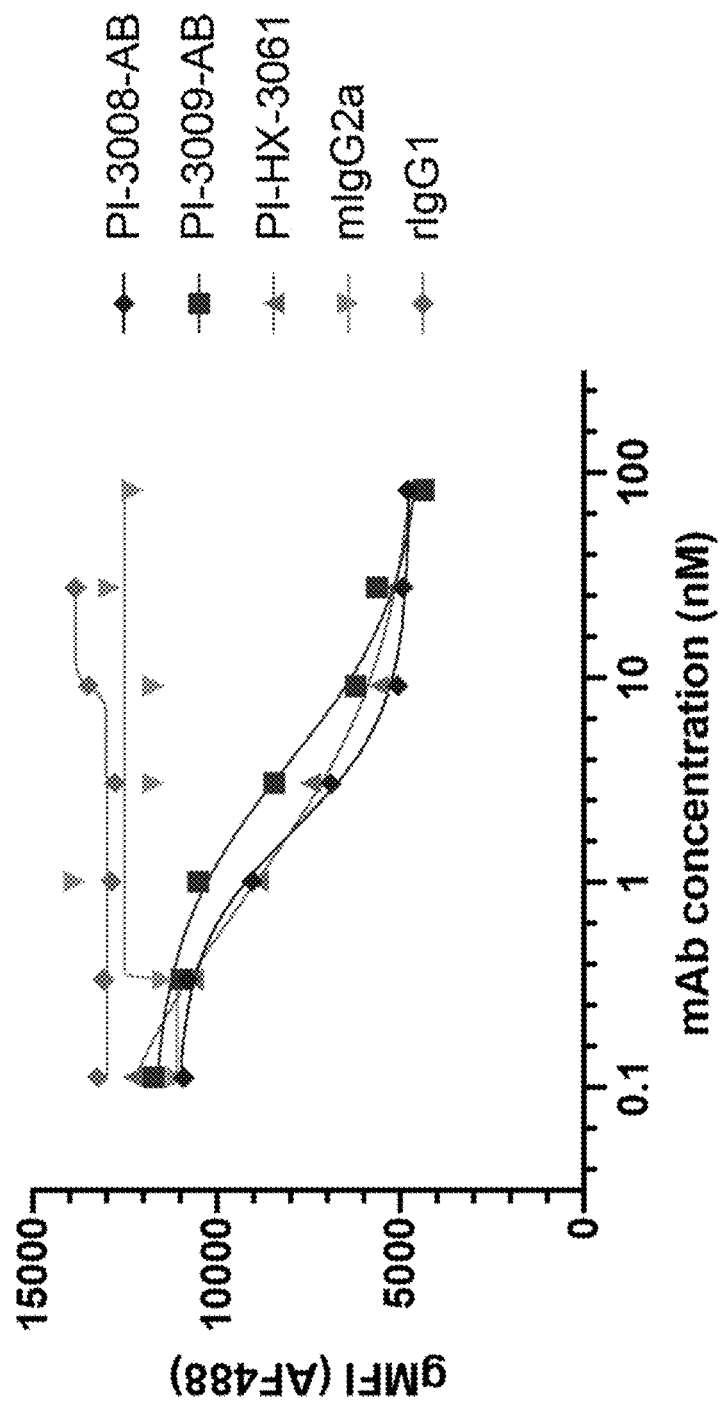
FIG. 19 shows the geometric mean fluorescent intensity (gMFI) of cells incubated with anti-MARCO antibodies and AF488 fluorescent bacteria in a competition assay. Pre-incubation of the cells with anti-MARCO antibodies reduced the bacteria binding and fluorescent signal in a dose dependent manner.

Three antibodies, two ani-mouse MARCO antibodies, PI-3008 and PI-3009, and the cross reactive anti-human MARCO antibody PI-HX-3061, were further characterized in a bacterial binding assay. As shown in FIG. 19, incubation of muMARCO 293T cells with increasing concentrations of each of PI-3008, PI-3009, or PI-HX-3061 decreased bacterial binding in a dose dependent manner, while incubation with isotype controls rat IgG1 or mouse IgG2a did not affect bacteria binding to the cells.

A comparison of the physical properties of PI-3008, PI-3009, and PI-HX-3061 is provided in Table 6.

TABLE 6

| Anti-muMARCO mAb | Mouse bin | Ca2+/Mg2+ req for binding | Biacore $K_D$ (nM) | Mouse $EC_{50}$ 293T(muMARCO) (nM) | $EC_{50}$ Bac competition assay (nM) | MSR1 binding | Binding to BMDM | Binding to TAMs in vivo |
|---|---|---|---|---|---|---|---|---|
| PI-3008 | 2 | Yes | <0.02 | 1.097 | 1.81 | – | + | + |
| PI-3009 | 4 | Yes | <0.02 | TBD | 3.84 | – | + | + |
| PI-HX-3061 (Cross-reactive) | 5 | No | <0.02 | 2.526 | 0.85 | – | + | TBD |

ELISA screening of selected rat hybridoma parental antibodies with 4 EDTA concentrations on recombinant human MARCO showed differential dependency on divalent cations for binding to MARCO with the various anti-MARCO antibodies and different epitopes. The results are shown in Table 7.

TABLE 7

| | Clone ID | EDTA [Conc] | | | |
|---|---|---|---|---|---|
| | | 0 | 2 mM | 10 mM | 50 mM |
| SRCR | PI-HX-3010 | 0.9525 | 0.8158 | 0.101 | 0.1055 |
| | PI-HX-3011 | 1.1743 | 0.0636 | 0.0811 | 0.082 |
| | PI-HX-3047 | 0.9688 | 1.2065 | 0.9205 | 0.9986 |
| | PI-HX-3031 | 1.3709 | 0.0678 | 0.0589 | 0.0754 |
| | PI-HX-3043 | 1.1971 | 0.0595 | 0.06 | 0.1002 |
| CLD | PI-HX-3049 | 1.1909 | 1.1447 | 1.0708 | 1.1915 |
| | PI-HX-3048 | 1.1987 | 1.2159 | 1.0695 | 1.2002 |

Select human chimera and further humanized antibodies were also characterized for species binding specificity, divalent cation binding requirement, SRCR and CLD domain binding kinetics, and cell binding.

Figure 52:
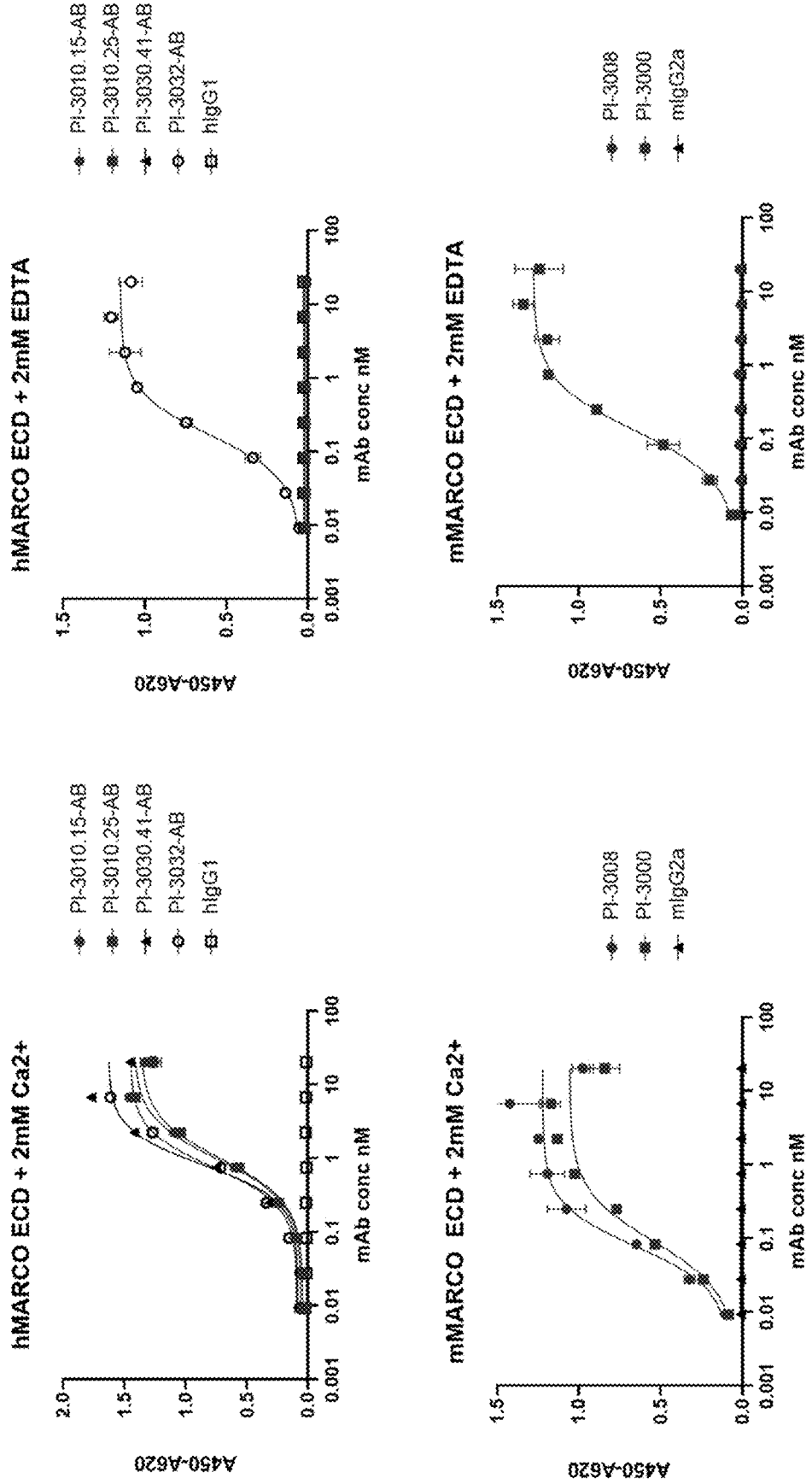
FIG. 52 shows that binding of some anti-MARCO antibodies to MARCO was calcium dependent.

As shown in FIG. 52, binding of some anti-MARCO antibodies to MARCO was calcium dependent. Addition of 2 mM EDTA abrogated binding of PI-3010.15, PI-3010.25, and PI-3030.41 to MARCO while the binding of a calcium independent mAb, PI-3032 was not affected. The surrogate anti-mouse MARCO mAb, PI-3008-AB also bound to mouse MARCO in a calcium dependent manner. Addition of 2 mM EDTA abrogated binding, while a calcium independent anti-mouse MARCO mAb, PI-3000 was not affected.

A summary of the characterization results for PI-3010 (hIgG1), PI-3030 (hIgG1), and PI-3031 (hIgG1) are shown in Table 8.

TABLE 8

| Anti-huMARCO mAb | Specificity | $Ca^{2+}$ dependent binding | $K_D$ (nM) Human | $K_D$ (nM) Cyno | $K_{off}$ (1/s) ProbeLife | $EC_{50}$ (nM) OVX Human | $EC_{50}$ (nM) OVX HuSRCR-mouse CLD | $EC_{50}$ (nM) OVX Cyno | Binding to PBLs |
|---|---|---|---|---|---|---|---|---|---|
| PI-3010-AB (hIgG1) | hu/cy | Yes | 0.43–0.64 | 0.26 | 2.34E–03 | 0.68 | 0.25 | 0.34 | No |
| PI-3030-AB (hIgG1) | hu/cy | Yes | 0.44 | n.d. | 3.51E–03 | 0.55 | 0.17 | 0.38 | No |
| PI-3031-AB (hIgG1) | hu/cy | Yes | 0.60 | n.d. | 2.81E–03 | 1.6 | 1.071 | 1.092 | No |

Results for the PI-3031 (hIgG1) chimera and two further humanized antibodies based on the PI-3031 chimera are shown in Table 9.

TABLE 9

| mAb | SRCR Epitope | $Ca^{2+}$ dep | $EC_{50}$ (raIgG2a) ELISA (hu/SRCR/cyn) | $K_D$ (M; sc) Human | $K_D$ (M; sc) Cyno | $EC_{50}$ (nM) OVX Human | $EC_{50}$ (nM) OVX Cyno | $EC_{50}$ Bac (nM) Cell-based | MSRI Binding |
|---|---|---|---|---|---|---|---|---|---|
| PI-3031-chi (PI-3010) | Bin 3 | Yes | 0.04/0.12/0.07 | 4.30E–10 | 2.59E–10 | 0.68 | 1.48 | 0.44 | – |
| PI-3031-h2 (PI-3012) | Bin 3 | Yes | 0.08/0.27/0.07 | 1.13E–09 | 7.35E–10 | 0.57 | 1.40 | 0.12 | – |
| PI-3031-h5 (PI-3015) | Bin 3 | Yes | 0.08/0.25/0.09 | 9.11E–10 | 6.11E–10 | 0.86 | 1.73 | 0.50 | – |

Figure 20A:
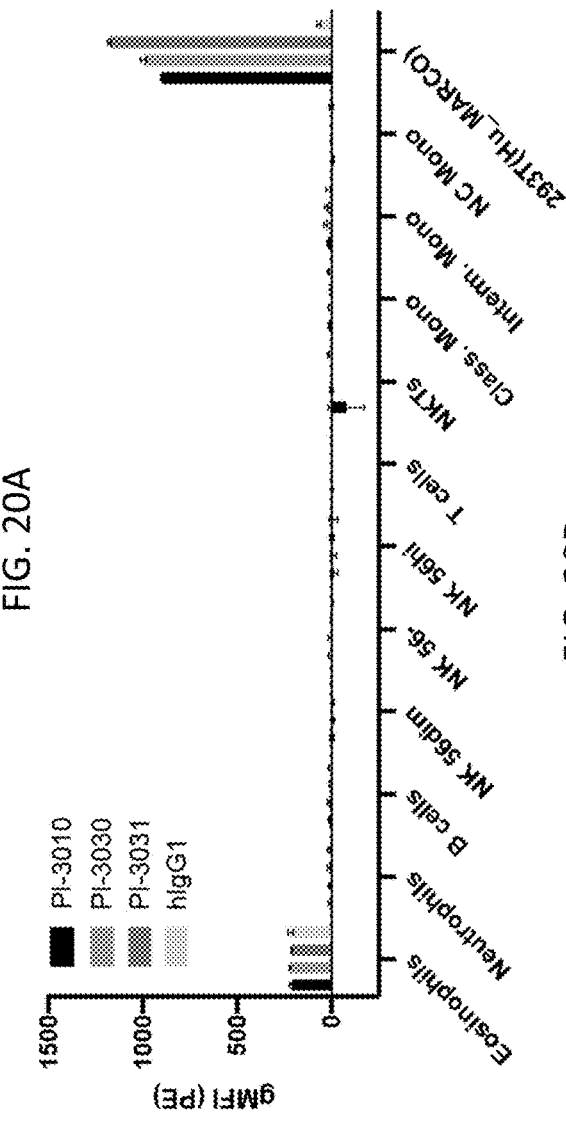
FIG. 20A shows binding of the chimera antibodies bound to 293T cells overexpressing MARCO but not to the immune cells present in PBLs (peripheral blood leukocytes). The eosinophil binding was non-specific across all tested antibodies including the hIgG1 isotype control. PI-3010 is shown on the left, PI-3030 is shown on the left middle, PI-3031 is shown on the right middle, and isotype control hIgG1 is shown on the right.
Figure 20B:
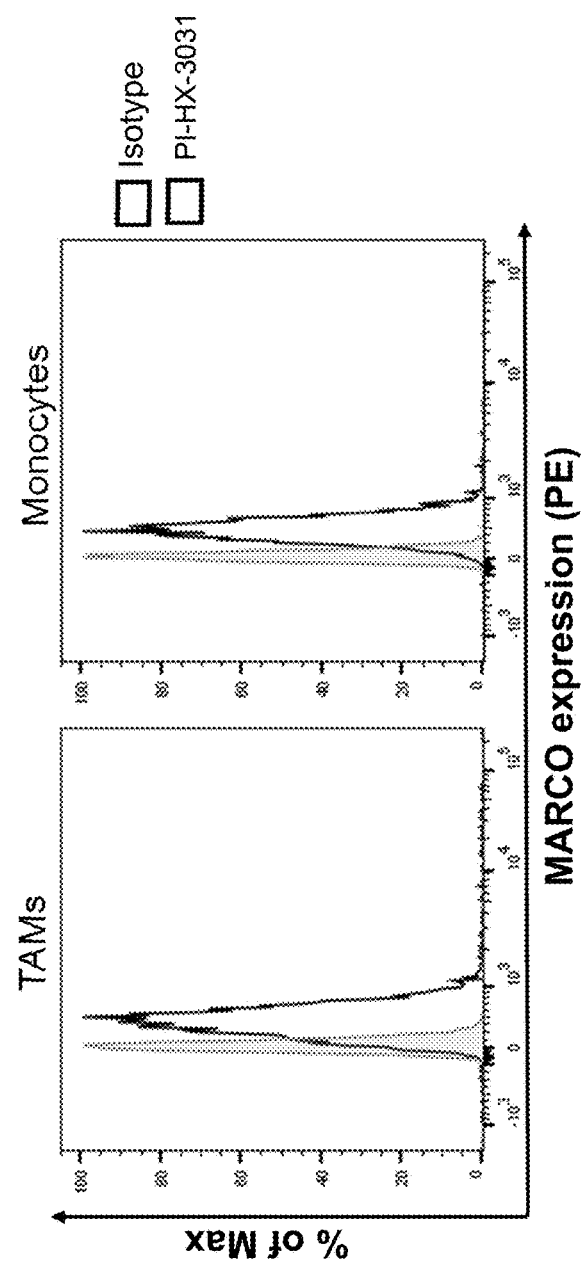
FIG. 20B shows binding of PI-HX-3031 on TAMs and monocytes from an endometrial cancer (primary human tumor). Antibody binding is the right peak, isotype control binding is the left peak.

The chimera antibodies PI-3010, PI-3030, and PI-3031 were also assessed for PBL binding. As shown in FIG. 20A, the chimera antibodies bound to 293T cells overexpressing MARCO but not to the immune cells present in PBLs. The binding to eosinophils was non-specific across all tested antibodies including the hIgG1 isotype control. PI-3010 is shown on the left, PI-3030 is shown on the left middle, PI-3031 is shown on the right middle, and isotype control hIgG1 is shown on the right. Binding of PI-HX-3031 in immune cells from Endometrial cancer (primary human tumor) was also assessed. As shown in FIG. 20B, the antibody bound to TAMs and monocytes from the tumor sample. Antibody binding is the right peak, isotype control binding is the left peak.

Example 6: Epitope Mapping by Surface Residues Swapping

Materials and Methods

Mouse MARCO SRCR crystal structure (PDB Entry 2OY3) was used to design the constructs. Mouse and human MARCO SRCR sequences were aligned and different residues on the protein surface were swapped with each other in clusters. N-term his tag and CLD domain were added to the SRCR sequences to produce recombinant proteins. The sequences for the recombinant proteins used in these studies are listed below. Bold and underlined residues are the swapped epitope residues:

```
hMARCO(His-CLD-SRCR) (RG3033)
                              (SEQ ID NO: 495)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDEWQNSDAIVFCRMLGYSKGRALYKVGAGTGQIWLDNVQCRG
TESTLWSCTKNSWGHHDCSHEEDAGVECSV* hVar1 (RG3034)
                              (SEQ ID NO: 496)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYN
NEWGTICDDEWQNSDAIVFCRMLGYSKGRALYKVGAGTGQIWLDNVQCRG
TESTLWSCTKNSWGHHDCSHEEDAGVECSV* hVar2 (RG3035)
                              (SEQ ID NO: 497)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDDWDNNDAIVFCRMLGYSRGRALYKVGAGTGQIWLDNVQCRG
TESTLWSCTKNSWGHHDCSHEEDAGVECSV* hVar3 (RG3036)
                              (SEQ ID NO: 498)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDEWDNSDAIVFCRMLGYSKGRALSSVGAGTGQIWLDNVQCRG
TESTLWSCTKNSWGHHDCSHEEDAGVECSV* hVar4 (RG3037)
                              (SEQ ID NO: 499)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDEWQNSDAIVFCRMLGYSKGRALYKVGAGTGQIWLDNVQCRG
TENSLWDCSKNSWGHHDCSHEEDAGVECSV* hVar5 (RG3038)
                              (SEQ ID NO: 500)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
GTWGTICDDEWQNSDAIVFCRMLGYSKGRALYKVGAGTGQIWLDNVQCRG
TESTLWSCTKNSWGNHNCVHNEDAGVECSV* hVar6 (RG3039)
                              (SEQ ID NO: 501)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGENSVSVRIVGSSNRGRAEVYYS
```

```
GTWGTICDDDWDNSDAIVFCRMLGYSKGRALYKVGAGTGQIWLDNVNCRG
TESTLWSCSKNSWGHHDCSHEEDAGVECSV* hVar7 (RG3040)
                                       (SEQ ID NO: 502)
HHHHHHKGEQGAPGLQGHKGAMGMPGAPGPPGPPAEKGAKGAMGRDGATG
PSGPQGPPGVKGEAGLQGPQGAPGKQGATGTPGPQGEKGSKGDGGLIGPK
GETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPG
SPGATGLKGSKGDTGLQGQQGRKGESGVPGPAGVKGEQGSPGLAGPKGAP
GQAGQKGDQGVKGSSGEQGVKGEKGERGESFQRVRIVGGTNRGRAEVYYS
GTWGTICDDEWQNSDAIVFCRMLGYSKGRALYKVGAGTGQIWLDNVQCRG
TESTLWSCTKNSWGHHDCSHEEDAGVECSV* mMARCO (RG3016)
                                       (SEQ ID NO: 484)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYNNE
WGTICDDDWDNNDATVFCRMLGYSRGRALSSYGGGSGNIWLDNVNCRGTE
NSLWDCSKNSWGNHNCVHNEDAGVECS mVar1 (RG3026)
                                       (SEQ ID NO: 504)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYSGT
WGTICDDDWDNNDATVFCRMLGYSRGRALSSYGGGSGNIWLDNVNCRGTE
NSLWDCSKNSWGNHNCVHNEDAGVECS* mVar2 (RG3027)
                                       (SEQ ID NO: 505)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYNNE
WGTICDDEWQNSDATVFCRMLGYSKGRALSSYGGGSGNIWLDNVNCRGTE
NSLWDCSKNSWGNHNCVHNEDAGVECS* mVar3 (RG3028)
                                       (SEQ ID NO: 506)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYNNE
WGTICDDDWQNNDATVFCRMLGYSRGRALYKYGGGSGNIWLDNVNCRGTE
NSLWDCSKNSWGNHNCVHNEDAGVECS* mVar4 (RG3029)
                                       (SEQ ID NO: 507)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYNNE
WGTICDDDWDNNDATVFCRMLGYSRGRALSSYGGGSGNIWLDNVNCRGTE
STLWSCTKNSWGNHNCVHNEDAGVECS* mVar5 (RG3030)
                                       (SEQ ID NO: 508)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYNNE
WGTICDDDWDNNDATVFCRMLGYSRGRALSSYGGGSGNIWLDNVNCRGTE
NSLWDCSKNSWGHHDCSHEEDAGVECS* mVar6 (RG3031)
                                       (SEQ ID NO: 509)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGESFQRVRIMGGTNRGRAEVYYNNE
WGTICDDEWQNNDATVFCRMLGYSRGRALSSYGGGSGNIWLDNVQCRGTE
NSLWDCTKNSWGNHNCVHNEDAGVECS* mVar7 (RG3032)
                                       (SEQ ID NO: 510)
HHHHHHHHGERGSPGPKGAPGAPGIPGLPGPAAEKGEKGAAGRDGTPGVQ
GPQGPPGSKGEAGLQGLTGAPGKQGATGAPGPRGEKGSKGDIGLTGPKGE
HGTKGDKGDLGLPGNKGDMGMKGDTGPMGSPGAQGGKGDAGKPGLPGLAG
SPGVKGDQGKPGVQGVPGPQGAPGLSGAKGEPGRTGLPGPAGPPGIAGNP
GIAGVKGSKGDTGIQGQKGTKGESGVPGLVGRKGDTGSPGLAGPKGEPGR
VGQKGDPGMKGSSGQQGQKGEKGQKGENSVSVRIMGSSNRGRAEVYYNNE
```

-continued

WGTICDDDWDNNDATVFCRMLGYSRGRALSSYGGGSGNIWLDNVNCRGTE

NSLWDCSKNSWGNHNCVHNEDAGVECS*

Sequence comparisons of the wild type human and mouse SRCR domain, and the mouse and human variant sequences made are shown in FIG. 21.

Binding Kinetics Using the ProbeLife Gator Instrument

The Probe-Life Gator™ label free system was used to analyze binding of the top anti-human and anti-mouse antibodies to the mouse/human SRCR antigen variants.

The kinetics assay used either anti-mouse Fc or anti-human Fc probes to capture the anti-MARCO antibodies onto the probe, and then a five-step kinetic protocol was used to measure the affinity of the antibodies to the different variant antigens described above, including the following steps: baseline, loading, baseline, association, and dissociation. The kinetics buffer (K buffer) provided by ProbeLife was used to establish the baseline for 60 seconds, and then the anti-mFec or anti-hFc probes were loaded with 200 nM of the antibodies for 120 s until the capture reached saturation, measurement of the baseline in K buffer was performed for another 60 s, followed by the association step using 200 nM antigen (human SRCR MARCO variants and mouse SRCR MARCO variants), and the dissociation step performed in K buffer for 5-10 minutes. The assay was done at 37° C. to maximize antibody:antigen dissociation.

Antibodies used for loading were PI-3010, PI-3008, PI-3019, PI-3030, PI-3031, and PI-3035. PI-3008, PI-3010, and PI-3030 are Ca2+ dependent binders, while PI-3019, and PI-3035 are Ca2+ independent binders. PI-3019 and PI-3035 also have cross reactivity with both human and mouse MARCO.

Results

Figure 22:
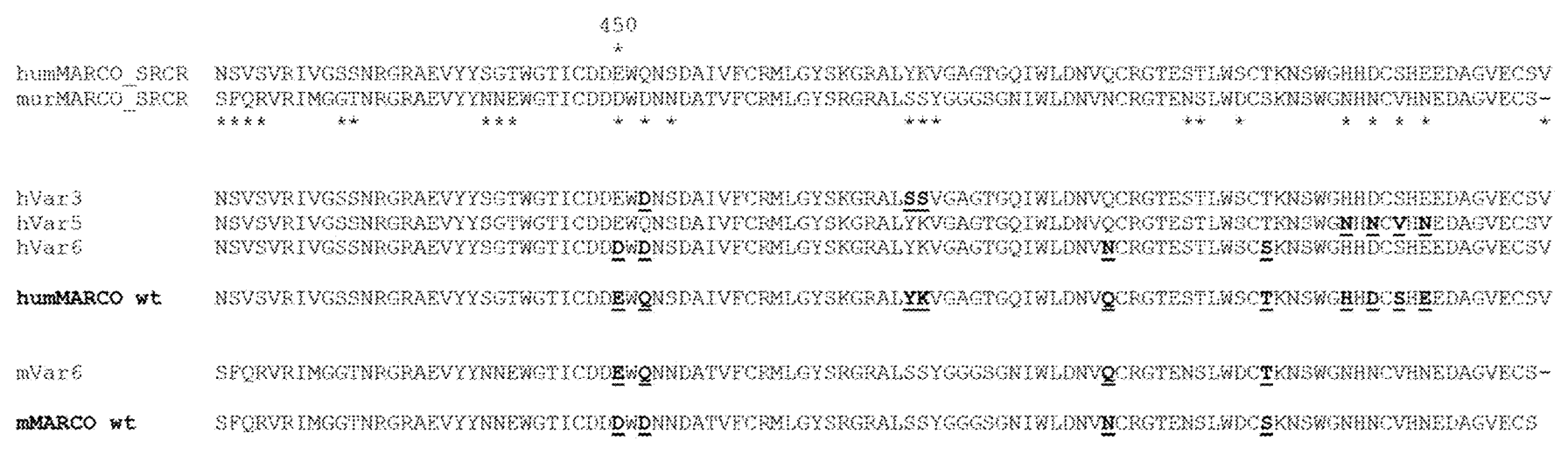

PI-3008 binding to mMARCO was most affected by the mutations in mVar2, mVar 3, mVar 4, mVar, 5, and mVar6 (data not shown). However, binding of PI-3008 to mMARCO SRCR was the most affected by the mutations in mVar6, and thus the altered residues in mVar6 are likely part of the mMARCO epitope (D450, D452, N487, S499 of mouse MARCO). The mutations in mVar 1 and mVar 7 had minimal adverse effect on PI-3008 binding to mMARCO. A sequence comparison of wild type (wt) mMARCO SRCR domain and the mVar6 sequence is shown in FIG. 22.

The cross reactive antibodies with Ca2+ independent binding, PI-3019 and PI-3035, were tested with both the mouse and human MARCO variants. PI-3019 was most adversely affected by the mutations in hVar3 (Q452D, Y472S, and K473S of human MARCO), while PI-3035 was adversely affected by hVar5 and hVar6 (data not shown). Similar binding reductions were seen with mVar3 for PI-3019 and mVar 3 and mVar 5 for PI-3035. A sequence comparison of wild type (wt) hMARCO SRCR domain and the hVar3, hVar5, and hVar6 sequences are shown in FIG. 22. The bolded and underlined amino acids were mutated as compared to wild type human or mouse MARCO.

The human-only and Ca2+ dependent antibodies PI-3010, PI-3030, and PI-3031 all showed significantly reduced binding with hVar3 (data not shown). Thus, hVar3 affected binding of PI-3010, PI-3030, PI-3031 and PI-3019, while hVar5 and hVar6 affected binding of PI-3035.

A summary of the antibody binding and cation dependence is shown in Table 10.

TABLE 10

| Antibody | Variant Reduced Binding | Species binding | Ca+ Dependent? |
| --- | --- | --- | --- |
| PI-3010 (HX-3031) | hVar3 | Human/Cyno | + |
| PI-3030 (HX-3011) | hVar3 | Human/Cyno | + |
| PI-3033 (HX-3043) | hVar3 | Human/Cyno | + |
| PI-3019 (HX-3061) | hVar3 | Human/Cyno/Mouse | − (independent) |
| PI-3035 (HX-3092) | hVar5, hVar6 | Human/Cyno/Mouse | − (independent) |
| PI-3008 | mVar6 | Mouse | + |

Figure 23:
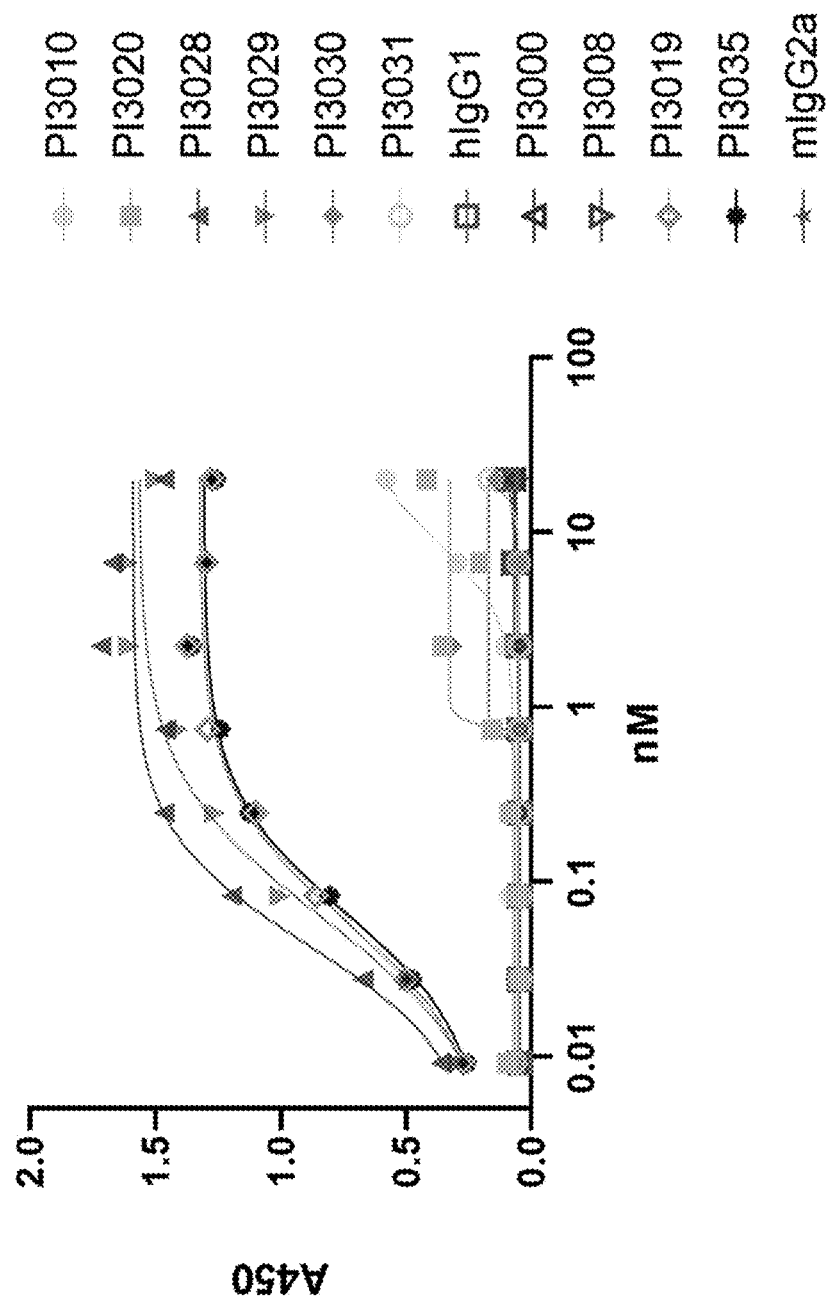
FIG. 23 shows binding of the indicated antibody to recombinant human SRCR MARCO hVar3 protein.

Binding of various human antibodies to hVar3 as measured by ELISA are shown in FIG. 23. hIgG1 and mIgG2a were used as antibody controls. PI-3008 and PI-300 were used as negative controls. Antibodies with single reactivity to human MARCO (PI-3010, PI-3020, PI-3030, PI-3031) did not bind to hVar3, while antibodies derived from the cross reactive HX-3061 hybridoma (PI-3028, PI-3029, PI-319) or HX-3092 (PI-3035) bound to hVar3.

To confirm the importance of the residues identified in hVar3 (Q452, Y472, and K473) as the binding epitope for the single reactive hMARCO antibodies, PI-3010 was bound to both hVar3, which has mutant Q452D, Y472S, and K473S residues, and mVar3, which has the same residues as the wild type human MARCO, Q452, Y472, and K473. The binding of PI-3010 was lost on the hVar3, but restored on mVar3 (data not shown). This confirmed that at least one, some, or all of residues Q452, Y472, and K473 are likely part of the MARCO epitope for the antibodies generated against human MARCO derived from HX-3011, HX-3043, HX-3031, and HX-3061 (e.g., those including, but not limited to, PI-3010, PI-3020, PI-3030, PI-3031, PI-3019, and PI-3033). These residues are also near the D447 D448 E511 acidic cluster on MARCO.

The residues that were mutated in hVar5 that affected binding of PI-3035 were H505, D507, 5509, and E511. The residues that were mutated in hVar6 that affected binding of PI-3035 were E450, Q452, Q487, and T499. Thus, at least one, some, or all of residues E450, Q452, Q487, T499, H505, D507, 5509, and E511 likely represent another binding epitope for antibodies derived from HX-3092 (e.g., those including, but not limited to, PI-3035).

The mouse and human antibodies have overlapping epitopes in the SRCR domain, with one overlapping residue, Q452 for the human SRCR and D452 for mouse SRCR, shown in FIG. 24. The overlapping residue is circled on both the mouse SRCR domain on the left and the human SRCR domain on the right.

Example 7: Non-Human Primate Pharamacokinetics Study

To assess drug exposure and safety of the humanized drug candidates, two pharmacokinetic (PK) assays, total and free (ligand binding), were developed to quantify PI-3025-AB2 (IgG1 format) and PI-3048-AB (IgG4 format) antibody concentrations in an exploratory single dose non-human primate (NHP) PK and tolerability study. The single dose study consisted of four animals (1 male and 1 female per group) dosed at 10 mg/kg with PI-3025-AB2 (IgG1) and PI-3048-AB (IgG4). Table 11 shows the study design.

TABLE 11

| Group | Test Material | Dose Level (mg/kg) | Dose Vol. (ml/kg) | Dose Conc. (mg/ml) | No. animals Males | Females |
|---|---|---|---|---|---|---|
| 1 | Control Article | 0 | 2 | 0 | 1 | 1 |
| 2 | PI-3025-AB2 | 10 | 2 | 5 | 1 | 1 |
| 3 | PI-3048-AB | 10 | 2 | 5 | 1 | 1 |

Ligand Binding Assay

A standard MSD Plate (Meso Scale Discovery, Catalog #L15XA-3) was coated with recombinant human MARCO protein at 1 μg/mL. The plate was incubated at room temperature for 60 min and then washed. The plate was then blocked with 5% bovine serum albumin (BSA) for 60 min at room temperature.

PI-3025-AB2 and PI-3048-AB protein standards and quality control samples, and animal samples were diluted in buffer (PBS/0.5% BSA/0.05% Tween+Ca2+/Mg2+) and added to the coated plate in salt buffer. The plate was incubated for 60 min at room temperature and washed. 0.5 μg/mL of the detection antibody, anti-human IgG CH2 (Thermo Fisher, Catalog #MA5-16929) was added and the plate incubated for 60 min at room temperature. The plate was washed and 1× Read Buffer (Meso Scale Discovery, Catalog #R92TC-1) was added to the MSD plate. The plate was read on an MSD Sector Imager.

Total PK Assay Format

A streptavidin MSD plate (Meso Scale Discovery, Catalog #L15SA-1) was coated with biotinylated anti-human kappa antibody (Invitrogen, Catalog #SA1-19155) at 1 μg/mL. The plate was incubated at room temperature for 60 min and then washed. PI-3025-AB2 and PI-3048-AB protein standards and quality control samples, and animal samples were diluted in buffer (PBS/0.5% BSA/0.05% Tween+Ca2+/Mg2+) and added to the coated plate in salt buffer. The plate was incubated for 60 min at room temperature and washed. 0.5 μg/mL of the detection antibody, anti-human IgG CH2 (Thermo Fisher, Catalog #MA5-16929) was added and the plate incubated for 60 min at room temperature. The plate was washed and 1× Read Buffer (Meso Scale Discovery, Catalog #R92TC-1) was added to the MSD plate. The plate was read on an MSD Sector Imager.

Results

The single dose study demonstrated that PI-3025 and PI-3048 antibodies have an acceptable PK and were well tolerated. Both total and free assay formats measured similar drug concentrations for each antibody.

Figure 25A:
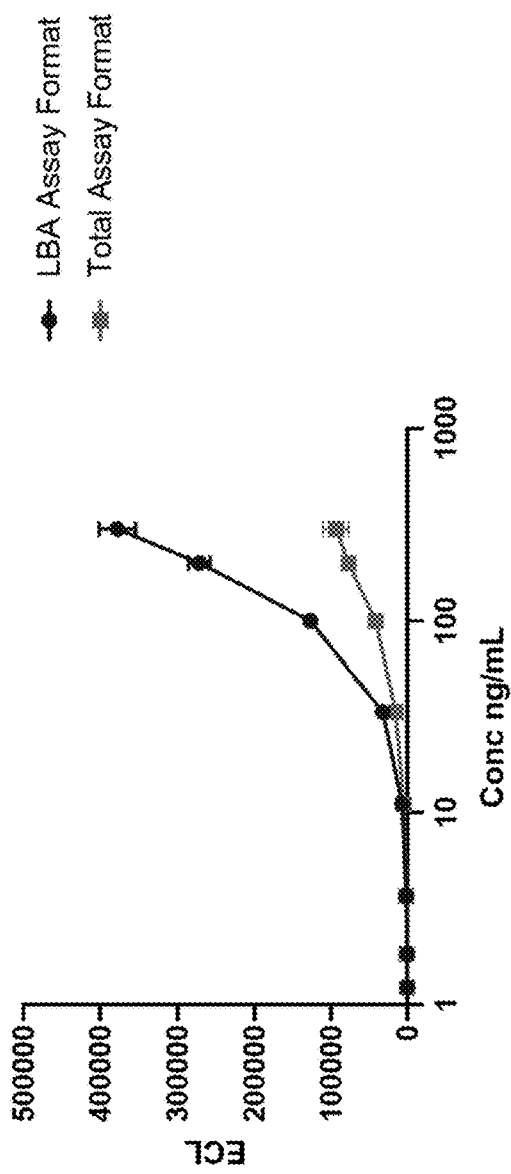
FIG. 25A shows the PK standard calibration curve for PI-3025.

The PK calibration curve for PI-3025-AB2 is shown in FIG. 25A and Table 12.

TABLE 12

| | LBA Assay Format | | | Total Assay Format | | |
|---|---|---|---|---|---|---|
| Nominal Conc. ng/ml | Detected Mean Conc. (ng/ml) | Calc. Mean Conc. CV | % Recovery Mean | Detected Mean Conc. (ng/ml) | Calc. Mean Conc CV | % Recovery Mean |
| 240 | 233 | 5 | 94 | 280 | 10 | 116 |
| 100 | 109 | 5 | 106 | 120 | 3 | 120 |
| 50 | 46 | 5 | 96 | 56 | 0 | 111 |
| 10 | 9 | 5 | 89 | 10 | 5 | 100 |
| 5 | 4 | 3 | 77 | 5 | 6 | 91 |

Figure 25B:
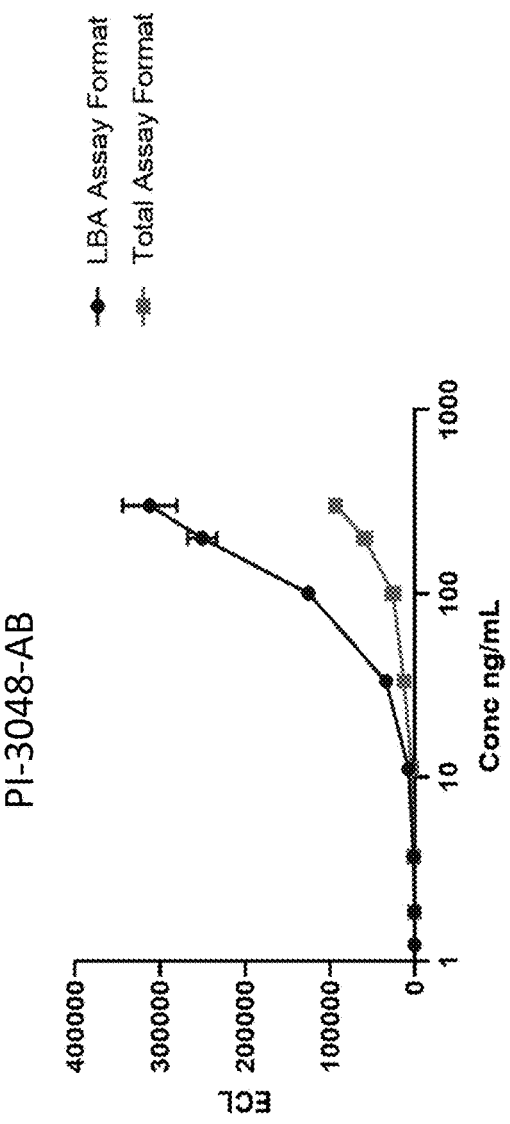
FIG. 25B shows the PK standard calibration curve for PI-3048.

The PK calibration curve for PI-3048-AB is shown in FIG. 25B and Table 13.

TABLE 13

| | LBA Assay Format | | | Total Assay Format | | |
|---|---|---|---|---|---|---|
| Nominal Conc. ng/ml | Detected Mean Conc. (ng/ml) | Calc. Mean Conc. CV | % Recovery Mean | Detected Mean Conc. (ng/ml) | Calc. Mean Conc CV | % Recovery Mean |
| 240 | 217 | 4.1 | 88 | 295 | 0 | 123 |
| 100 | 98 | 0.8 | 97 | 88 | 21 | 88 |
| 50 | 47 | 2.2 | 94 | 58 | 9 | 116 |
| 10 | 10 | 1.8 | 99 | 10 | 16 | 104 |
| 5 | 4 | 2.4 | 85 | 6 | 3 | 129 |

The PK assays were successfully developed to measure drug concentrations in the exploratory NHP study. The PK assay range was 1.85 ng/mL to 300 ng/mL (in assay) with a minimum required dilution (MRD) of 20. The LLOQ was 1.85 ng/mL and the ULOQ was 240 ng/mL. The quality controls (QCs) ranged from 5 ng/mL to 240 ng/mL.

Figure 26A:
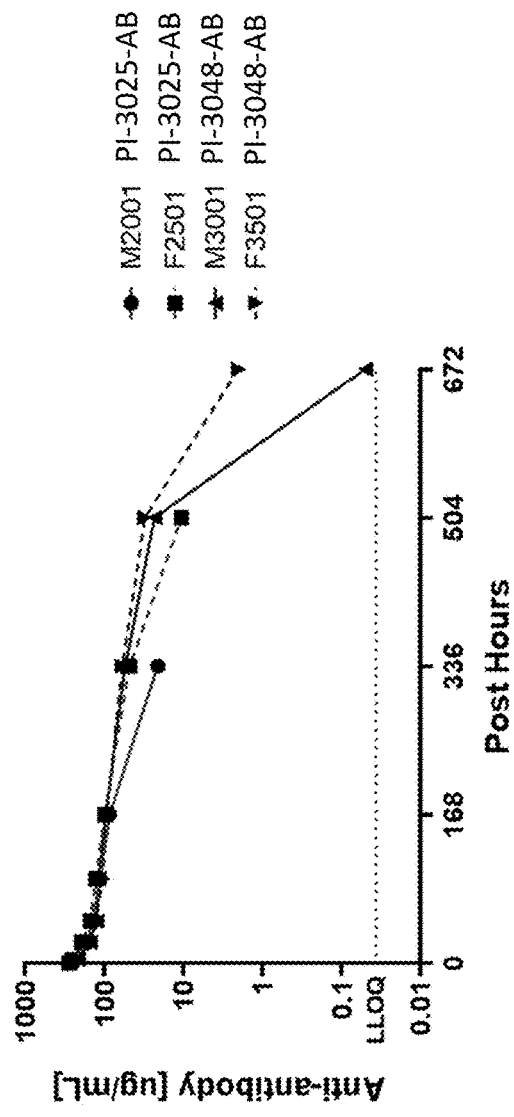
FIG. 26A shows the concentration-time profile of PI-3025 and PI-3048 in the ligand binding PK assay.
Figure 26B:
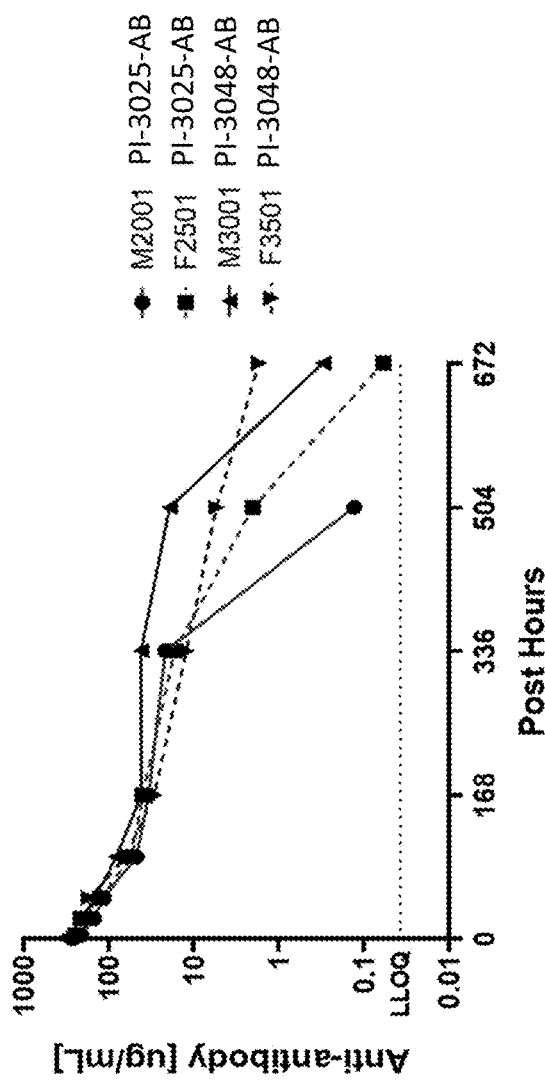
FIG. 26B shows the concentration-time profile of PI-3025 and PI-3048 in the total PK assay.

The in vivo ligand binding PK assay results are shown in FIG. 26A. PI-3025-AB2 showed no detectable drug levels post Day 21 (504 hr) in the ligand binding assay (FIG. 26A). PI-3048-AB was detected up to Day 28 (672 hr) in the ligand binding assay (FIG. 26A). The in vivo total PK assay results are shown in FIG. 26B. PI-3025-AB2 was detected up to Day 21 (504 hr) and Day 28 (672 hr) (FIG. 26B). PI-3048-AB was detected up to Day 28 (672 hr) (FIG. 26B). Animals dosed with PI-3048-AB showed slightly better exposure than dosed with PI-3025-AB2.

The PK results for PI-3025-AB2 and PI-3048-AB were comparable using both the total and free assay. PI-3025-AB2 and PI-3048-AB antibodies had an acceptable tolerability and good exposure following the single dose study.

Example 8: Additional Characterization of Anti-Human MARCO Antibodies

Materials and Methods

Anti-MARCO antibody cell binding, SPR binding kinetics ($K_D$) and macrophage binding were performed as previously described in Examples 2 and 5.

Ligand Binding Block Assay 293T cells expressing human MARCO were harvested along with the parental 293T cells. Zombie NIR viability dye (BioLegend), prepared by diluting the stock 1000-fold in D-PBS, was added to the cells and incubated for 10 min at RT in the dark. The reaction was quenched by adding 1 m of 4× Staining buffer (2% FBS in DBPS containing Ca2+), followed by centrifugation at 400×g for 5 min at 4° C. Cells were then plated in V-shaped 96 well plates at a density of 100,000 cells. A488-fluorescently labeled bacteria (E. coli from Invitrogen) was added at 10 μg/ml with the anti-human MARCO antibodies of interest for a 30 min incubation at 37 C. Plates were then washed twice followed by resuspension in 100 ul of staining buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8).

T-Cell Binding Assay

A standard flow binding assay using Jurkat T-cells obtained from ATCC was performed. 100,000 cells/well of Jurkat T cells were plated onto U-bottom 96-well plates for staining and all centrifugation steps were performed at 1500 rpm at 4° C. for 5 min and samples were kept protected from light throughout the protocol. Cells were pelleted and resuspended in 100 μl of Zombie NIR viability dye (BioLegend) prepared by diluting Zombie NIR dimethyl sulfoxide (DMSO) stock 1000-fold in D-PBS. Cells were stained by incubation for 10 min at room temperature (RT) in the dark, followed by quenching the staining reaction with the addition of regular Medium containing 10% FBS. Cells were pelleted and resuspended in 100 μl of the different anti-human MARCO antibodies and the corresponding hIgG1 and hIgG4 isotype controls in freshly prepared staining medium (2% FBS in DBPS containing Ca2+). All mAbs were tested at the final top concentration of 100 nM (15 μg/ml) followed by an 8-point three-fold serial dilution, including 0 mg/ml control. Staining was carried out for 1 hour (hr) on ice, followed by 2 washes in Staining Medium. Cells were then pelleted and resuspended in 100 ul of allophycocyanin (APC)-conjugated goat anti-mouse IgG (Fc-specific) secondary antibody, prepared by 500-fold dilution of the antibody stocks in Staining Medium, and incubated for 30 min on ice. Plates were then washed two times with Staining Medium, followed by resuspension in 150 ul of the same buffer for acquisition on the flow cytometer (Attune NxT, Life Technologies). Flow cytometry data were analyzed using FlowJo software (version 10.6.1) and data were processed and further analyzed in Microsoft Excel and GraphPad Prism software (version 8). Half-maximal effective concentrations (EC50) were calculated based on geometric mean fluorescence intensities (gMFI).

mAb Thermal Stability Assessment Using Dynamic Light Scattering (DLS)

Dynamic light scattering takes advantage of the Brownian motion of particles in solution or suspension to measure their size. The rate of fluctuation corresponds directly to the diffusion rate of the scattering particles. Larger particles diffuse more slowly, leading to slow optical fluctuations, while smaller particles diffuse more rapidly, leading to fast optical fluctuations. The diffusion coefficient of the particles can be determined from the autocorrelation analysis on the raw optical signals and fitting the resulting autocorrelation function. The particle size is then determined from the diffusion coefficient using the Stokes-Einstein equation.

DLS measurements were made using the Dynapro plate reader III (Wyatt Technology). Antibodies to be evaluated were diluted in 1xPBS (Gibco catalog #14190-144), filtered through a 0.02 um filter to remove particulate matter and large aggregates, to a final concentration of 1-2 mg/mL. Twenty-five microliters of the antibody solution was added to wells of a 384 well plate (Aurora catalog #ABA210100A), followed by 5 uL of silicone oil (Alfa Aesar catalog #A12728). The plate was covered and centrifuged at 1000xg for 1 min to ensure removal of air bubbles. The plate was then loaded on the DLS instrument, and data collected using the following setup along with default instrument settings.

The initial temperature was set at 25° C., followed by a steady increase in temperature by 1° C./min up to 85° C. with enabled auto attenuation of laser intensity. Continuous measurements were made for each well to determine the diffusion coefficient and hydrodynamic radii. The temperature onset for aggregation (Tagg) value was obtained by using the integrated Dynamics7.1 software, which analyzed changes in radii corresponding to change in temperature and identified the temperature corresponding to increase in hydrodynamic radius as the Tagg.

mAb Thermal Stability Assessment Using Differential Scanning Fluorimetry (DSF)

DSF was carried out with the QuantStudio5 real-time PCR instrument (Life Technologies) using the protein thermal shift Protein Thermal Shift™ Dye Kit (Life Technologies Catalog #4461146) following manufacturer protocols. MicroAmp 384-well plates (Thermo Fisher catalog #AB1384/W) were used with 20 μL sample per well. Monoclonal antibodies were diluted to a 1 mg/mL concentration in the respective formulation buffer, and samples were prepared as follows: five microliters of Protein Thermal Shift™ Buffer, 12.5 μL of the antibody (1 mg/mL) or buffer (negative control), and 2.5 μL of Diluted Protein Thermal Shift™ Dye (8×) were added together for a total volume of 20.0 μL for each reaction. SYPRO Orange was diluted 125-fold from the 1000× concentrated stock solution to the working dye solution in the provided thermal shift buffer prior to addition to the reaction mixture. To prevent bleaching, the working solution of SYPRO Orange was added to the reaction mixture just prior to the experiment. Each sample was measured in quadruplicate. Thermal denaturation was carried out by increasing the temperature from 25° C. to 95° C. at a rate of 0.017° C. per second. Fluorescence intensity (excitation at 490 nm and emission with the use of a ROX filter at 600 to 630 nm) was collected at 0.07° C. intervals and analyzed with Protein Thermal Shift Software (Life Technologies), using the first derivative approach to calculate Tm. In this method, Tm is the temperature corresponding to the maximum value of the first derivative of the DSF melting curve.

Immune Pathway Activation in Human Dissociated Tumor Cells (DTCs)

Dissociated Tumor Cells (DTCs) from four NSCLC patients were purchased from DLS and thawed per manufacturer's recommendation. Cells were counted and plated at around 2M cells per 24 well in 3 wells in Ex vivo media with anti-anot but no serum. 5 μg/ml of R&D, RDM5 and RDM9, PI-3030, and hIgG1 (ultra-LEAF) were added to each well containing 1 ml of media. Four hours later at 37 C, cells were collected in 15 ml canonical tubes and centrifuged at 400×g for 5 min at 4° C. Each pellet was resuspended in 600 ul of RLT buffer with B-mercapthoethanol (at 1:100 dilution).

Total RNA was isolated from the above DTCs samples using the Qiagen RNeasy Mini kit and control treated human and submitted for high-throughput RNA sequencing. Libraries were prepared using Illumina's TruSeq Stranded mRNA kit and sequenced on an Illumina Novaseq 6000. Subsequent data was aligned to the human genome (GRCh38.p12) and per-gene expression values were tabulated using the STAR aligner. The resulting expression matrices were used as input for differential expression analysis using DESeq2. Resulting fold changes from PI-3010 vs control comparisons for all protein coding genes were submitted to Gene Set Enrichment Analysis (GSEA) software, using the preRanked test, available from the Broad Institute at https://www.gsea-msigdb.org/gsea/index.jsp. MSigDB's Hallmark pathways were assessed and resulting Normalized Enrichment Scores were plotted using ggplot2 in R. FDR values were determined via permutation test implanted within GSEA using standard parameters.

Proinflammatory Signature in Human Suppressive Macrophages (M2c)

Four Frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (Hy-Clone), 1 mM sodium pyruvate, non-essential amino-acids, 2 mM L-glutamine, 55 uM β-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 500,000 cells per well in 24 well plates. At day 3 of differentiation, media was replenished with the addition of fresh M-CSF. Differentiated human macrophages were polarized by adding the following cytokines to the media for 24 hours at 37 C: M0 (no cytokine addition) and 25 ng/ml of recombinant human IL-10 (M2 condition) for 24 hours at 37 C. On day 7, the media was aspirated and cells washed gently. Fresh complete RPMI 1640 medium macrophage medium with 5 µg/ml of PI-3010.15, PI-3030.41, and hIgG1 (Ultra-LEAF from Biolegend) were added to each well from the above 2 conditions. 4 hours later, media was aspirated and cells lysed in RLT buffer with β-mercaptoethanol (at 1:100 dilution).

Total RNA was isolated from the IL-10 polarized hMDMs using Qiagen RNeasy Mini kit and submitted for high-throughput RNA sequencing. Libraries were prepared using Illumina's TruSeq Stranded mRNA kit and sequenced on an Illumina Novaseq 6000. Subsequent data was aligned to the human genome (GRCh38.p12) and per-gene expression values were tabulated for all MDM using the STAR aligner. The resulting expression matrices were used as input for differential expression analysis using DESeq2. Resulting fold changes from PI-3010.15 vs control comparisons for all protein coding genes were submitted to Gene Set Enrichment Analysis (GSEA) software, using the preRanked test, available from the Broad Institute at www.gsea-msigdb.org/gsea/index.jsp. MSigDB's Hallmark pathways were assessed and resulting Normalized Enrichment Scores were plotted using ggplot2 in R. FDR values were determined via permutation test implanted within GSEA using standard parameters.

Hallmark Pathways: PI-3008 Treated BMDMs vs PI-3008 Treated CT26 Tumors

Individual femurs and tibias from four females BALB/c mice were cleaned and crushed in Macrophage Medium composed of Iscove's modified Dulbecco Medium supplemented with 10% (v/v) fetal bovine serum (FBS) (HyClone) and antibiotic-antimycotic solution (Gibco), using a mortar and pestle. Samples were then passed through a 40 um filter, washed with media and pelleted at 400×g for 5 min at RT. Cell pellets were resuspended in 5 ml of BD Pharm Lyse buffer (BD Biosciences) and red blood cell lysis was carried out at RT for 5 min, followed by quenching with 10 volumes of Macrophage Medium. Cells were pelleted at 400×g for 5 min at RT and resuspended in Macrophage Medium at the density of 500,000 cells per well in 24 well plates. These bone marrow mononuclear cells were stimulated with 25 ng/ml of mouse macrophage colony-stimulating factor (M-CSF) (PeproTech) for 6 days to generate M0-macrophages and polarized into M1-like and M2-like macrophages by supplementing the medium with LPS (1 ng/ml) and mouse IL-10 at 20 ng/ml respectively for 24 hours at 37 C.

On day 7, the media was aspirated and cells washed gently with macrophage medium. Fresh media with 5 ug/ml of PI-3008 or its mIgG2a isotype control was added to each well from the three conditions: M0, M1, and M2. 4 hours later, media was aspirated and cells lysed in RLT buffer with B-mercapthoethanol (at 1:100 dilution).

Total RNA was isolated from these BMDMs using the Qiagen RNeasy Mini kit and CT26 tumors (previously described for FIGS. 12C-12H) and submitted for high-throughput RNA sequencing. Libraries were prepared using Illumina's TruSeq Stranded mRNA kit and sequenced on an Illumina Novaseq 6000. Subsequent data was aligned to the murine genome (GRCm38.p6) and per-gene expression values were tabulated for all BMDM samples and CT26 samples, respectively, using the STAR aligner. The resulting expression matrices were used as input for differential expression analysis using DESeq2. Resulting fold changes from PI3008 vs control comparisons (from both BMDM and CT26 subsets) for all protein coding genes were submitted to Gene Set Enrichment Analysis (GSEA) software, using the preRanked test, available from the Broad Institute at gsea-msigdb.org/gsea/index.jsp. MSigDB's Hallmark pathways were assessed for both the BMDM and CT26 comparisons and resulting Normalized Enrichment Scores were plotted using ggplot2 in R.

Cytokine qPCR Assay

Two frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (Hy-Clone), 1 mM sodium pyruvate, non-essential amino-acids, 2 mM L-glutamine, 55 uM β-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 500,000 cells per well in 24 well plates. At day 3 of differentiation, media was replenished with the addition of fresh M-CSF. Differentiated human macrophages were polarized on day 6 by adding 25 ng/ml of recombinant human IL-10 (M2 condition) for 24 hours at 37 C. On day 7, the media was aspirated and cells washed gently. Fresh complete RPMI 1640 macrophage medium with 5 µg/ml of PI-3010.15 (PI-3015), PI-3010.25 (PI-3025), PI-3030.41 (PI-3041), or hIgG1 isotype control (Ultra-LEAF from Biolegend) and 5 µg/ml of PI-3010.46 (PI-3046), PI-3030.47 (PI-3047), PI-3010.48 (PI-3048), or hIgG4 isotype control (Ultra-LEAF from Biolegend) were added to the corresponding wells. 4 hours later, media was collected into 96 well plates for Luminex cytokine secretion and cells lysed in RLT buffer with β-mercapthoethanol (at 1:100 dilution). Total RNA was isolated from the IL-10 polarized hMDMs using Qiagen RNeasy Mini kit and 250 ng of RNA was made into single strand DNA using the High-capacity cDNA Reverse Transcription kit (Applied Biosystems). qPCR was performed using the 5 ul of SYBR green mix and primers specific to IL-6, IL-1b, IL10, TNFa, CXCL10, IL18, CCL20, CCL24, IL1A. The endogenous housekeeping primers tested were GAPDH and RPL37A. The plates were ran on the QuantStudio 5 qPCR machine from Thermo Fisher.

This cytokine expression qPCR assay was repeated in multiple hMDMs donors and different runs with titrating down the concentration of the hIgG1 lead antibodies to be 1 ug/ml compared to hIgG1 isotype (PI-0003). In addition, this assay was used to confirm the activation of the pro-inflammatory gene signature The expression of IL-6, TNFa, IL-1b, IL10, IL18, CCL20, CCL24, CXCL8, IL1A was assessed for pro-inflammatory activation was tested in all assays.

In addition this assay was used to confirm the activation of the pro-inflammatory gene signature downstream of PI-3010.15-AB in THP-1 monocytic cells overexpressing human full length MARCO.

The qPCR analysis was done by calculating the fold changes of the treated samples over the corresponding isotype control using the 2^-(ddCT). Each gene CT value was normalized to the CT value of the endogenous control used (such as GAPDH or RPL37A).

Human Cytokine and chemokines secretion by MSD 200 ul of Supernatant collected from hMDMs cells treated with the human anti-MARCO PI-3010.15, PI-3010.25, and PI-3030.41 and isotype were evaluated for cytokine levels using the V-PLEX human proinflammatory panel 1 human kit measuring 10 cytokines (MSD, Cat. No. K15049D) and the V-PLEX human chemokine panel 1 human kit measuring 10 chemokines (MSD, Cat. No. K15049D) from Meso Scale Discovery (MSD, Cat. No. K15047D) or a customized human PrecartaPlex 26-plex kit from Thermo Fisher (Cat. No. PPX-26-MX-3222A). The MSD multiplex assay plates were precoated with capture antibodies. Samples for analysis or kit standards were added at a volume of 50 µl per well after pre-diluting the original sample with assay diluent. The plates were washed after a two-hour incubation at room temperature with agitations.

For the V-PLEX assay, sulfo-tagged detection antibodies were added and incubated for another two hours at room temperature with agitations. Following the incubation, plates were washed once again. 2× Read Substrate was added and plates were read on MSD reader. All data were analyzed by MSD Discovery Workbench® Software 4.0.

For the customized human 26-plex kit, biotinylated labeled detection antibodies were added and incubated for one hour at room temperature with agitations. Plates were washed. PE (Phycoerythrin)-labeled Streptavidin were added and incubated for 30 min at room temperature with agitations. After the plates were washed, Luminex reading buffer was added and plates were read on Luminex 200 analyzer. All data were analyzed by xPONENT Software.

Results

DNA sequences for the heavy and light chain of antibodies PI-3010.15, PI-3010.25, and PI-3030.41 were codon optimized and incorporated into proprietary vectors at Atum (Newark, CA). The heavy and light chain encoding vectors were transfected in CHO cells at 2 L scale, followed by purification using MabSelect Sure Protein A resin. Both candidates showed high titers and <5% aggregates post Protein A purification. Data are summarized in Table 14

TABLE 14

| Antibody | Germline | Isotype | Expression CHO - transient (mg/L) | Theoretical pI | % Monomer (post Protein A) |
|---|---|---|---|---|---|
| PI-3010.15-H1 | IGHV1-46 IGKV1-39 | hIgG1 | 585 | 8.45 | >95 |
| PI-3010.25-H1 | IGHV1-46 IGKV1-39 | hIgG1 | 818 | 8.11 | >95 |
| PI-3030.41-H1 | IGHV1-59 IGKV1-39 | hIgG1 | 868 | 8.44 | >95 |

Binding of PI-3010.15, PI-3010.25, and PI-3030.41 was assessed by Biacore on recombinant human and cynomolgus MARCO protein and demonstrated high affinity binding to both human and cynoMARCO, with the affinity of binding to cynoMARCO within 2-3 fold of the human MARCO affinity.

Flow cytometry was used to assess the binding of the antibodies to human and cynomolgus MARCO expressing cell lines, including MARCO transfectants in HEK 293T cells and human monocyte derived macrophages (MDM) expressing endogenous MARCO. The antibodies bound to human and cynoMARCO with comparable EC50s and bound to endogenous MARCO on human MDMs with high affinity. No off-target binding was observed to parental HEK 293T cells that did not express MARCO or to Jurkat T cells by flow cytometry (Table 15 and FIG. 53).

TABLE 15

| Humanized mAb | EC50 OVX Cell binding (nM) (hu/cyn) | $K_D$(nM) Human | $K_D$(nM) Cyno | $K_{off}$(1/s) Human | Binding on human macrophages | Block ligand(s) binding | Binding to T-cells |
|---|---|---|---|---|---|---|---|
| PI-3010.15 PI-3015 (hIgG1) | 0.798/1.16 | 0.51 | 1.65 | 2.94E−04 | + | + | − |
| PI-3010.46 PI-3046 (hIgG4) | 0.821/1.07 | 0.78 | 1.10 | 3.71E−04 | + | | − |
| PI-3010.25 PI-3025 (hIgG1) | 0.790/1.01 | 1.09 | 1.79 | 4.30E−04 | + | + | − |
| PI-3010.48 PI-3048 (hIgG4) | 0.721/2.39 | 1.05 | 1.81 | 3.86E−04 | + | | − |
| PI-3030.41 PI-3041 (hIgG1) | 0.704/1.028 | 0.82 | 1.12 | 3.34E−04 | + | + | − |
| PI-3030.47 PI-3047 (hIgG4) | 0.796/1.39 | 0.72 | 0.79 | 3.37E−04 | + | | − |

Thermal stability assessment to determine the temperature for melting (Tm1) and aggregation (Tagg) using differential scanning fluorimetry (DSF) and dynamic light scattering (DLS) respectively showed that all 3 antibodies have acceptable and similar properties. In addition, all 3 antibodies were soluble and stable up to 30 mg/ml as determined by size exclusion chromatography (SEC) and DLS in citrate and histidine buffers ranging between pH 5.0-6.5. A summary of the data is shown in Table 16 below.

TABLE 16

| | Analysis Method | PI-3010.25 (PI-3025) (hIg1) | PI-3010.48 (PI-3048) (hIg4) | PI-3010.15 (PI-3015) (hIg1) | PI-3010.46 (PI-3046) (hIg4) | PI-3030.41 (PI-3041) (hIg1) | PI-3030.47 (PI-3047) (hIg4) |
|---|---|---|---|---|---|---|---|
| Binding affinity to human MARCO (KD) | Biacore (SPR, nM) | 1.09 | 1.05 | 0.51 | 0.78 | 0.82 | 0.72 |
| Thermal Stability (PBS) | Tm1 (DSF, °C.) | 68 | 65 | 68 | 64 | 68 | 64 |
| Thermal Stability (PBS) | Tagg (DLS, °C.) | 83 | 73 | 78 | 72 | 78 | 71 |
| Solubility (30 mg/mL) | SEC, DLS | Soluble and stable up to 30 mg/mL in citrate and acetate buffers, pH 5.0-6.0 | | | | | |

Figure 27:
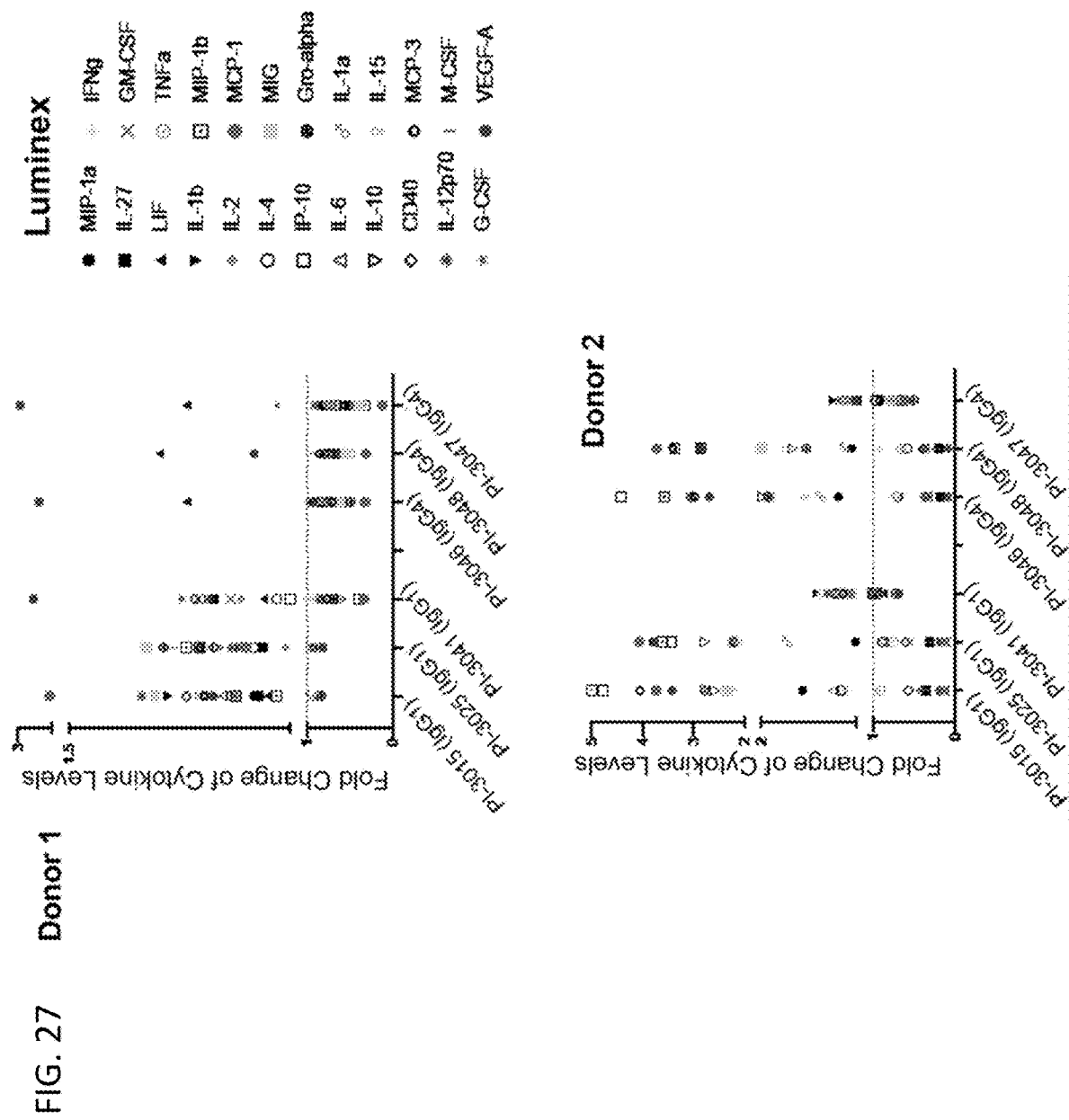
FIG. 27 provides cytokine and other relevant gene expression (MIP-1α, IL-27, LIF, IL-1β, IL-2, IL-4, IP-10, IL-6, IL-10, CD40, IL-12p70, G-CSF, IFNγ, GM-CSF, TNFα, MIP-10, MCP-1, MIG, gro-alpha, IL-1α, IL-15, MCP-3, M-CSF, and VEGF-A) in hMDMs from two different donors after treatment with anti-MARCO antibody.

Cytokine expression induced by human anti-MARCO antibodies in hMDMs was also assessed. As shown in Table 17, all of PI-3010.15, PI-3010.46, PI-3010.25, PI-3010.48, PI-3030-41, and PI-3030.47 induced expression of the indicated cytokine genes in Donor 1. Cytokine and other relevant gene expression (MIP-1α, IL-27, LIF, IL-10, IL-2, IL-4, IP-10, IL-6, IL-10, CD40, IL-12p70, G-CSF, IFNγ, GM-CSF, TNFα, MIP-10, MCP-1, MIG, gro-alpha, IL-1α, IL-15, MCP-3, M-CSF, and VEGF-A) in hMDMs from two different donors (Donor 1 and Donor 2) is also shown in FIG. 27.

TABLE 17

Gene fold induction over corresponding isotype

| Donor 1 | IL-6 | TNFα | CXCL10 | IL18 | CCL20 | IL1A |
|---|---|---|---|---|---|---|
| PI-3010.15 IgG1 | 1.3 | 2.2 | 1.5 | 1.8 | 1.4 | 2.4 |
| PI-3010.46 IgG4 | 1.8 | 1.9 | 1 | 1.8 | 1.7 | 3.6 |
| PI-3010.25 IgG1 | 1.2 | 2.5 | 1.5 | 3.9 | 1.5 | 4.1 |
| PI-3010.48 IgG4 | 1 | 2.1 | 0.9 | 1.5 | 1.3 | 3.6 |
| PI-3030.41 IgG1 | 1.3 | 3.2 | 1.9 | 4.3 | 1.6 | 7.8 |
| PI-3030.47 IgG4 | 2 | 3.2 | 1.8 | 1.3 | 1.8 | 6.6 |

Figure 28:
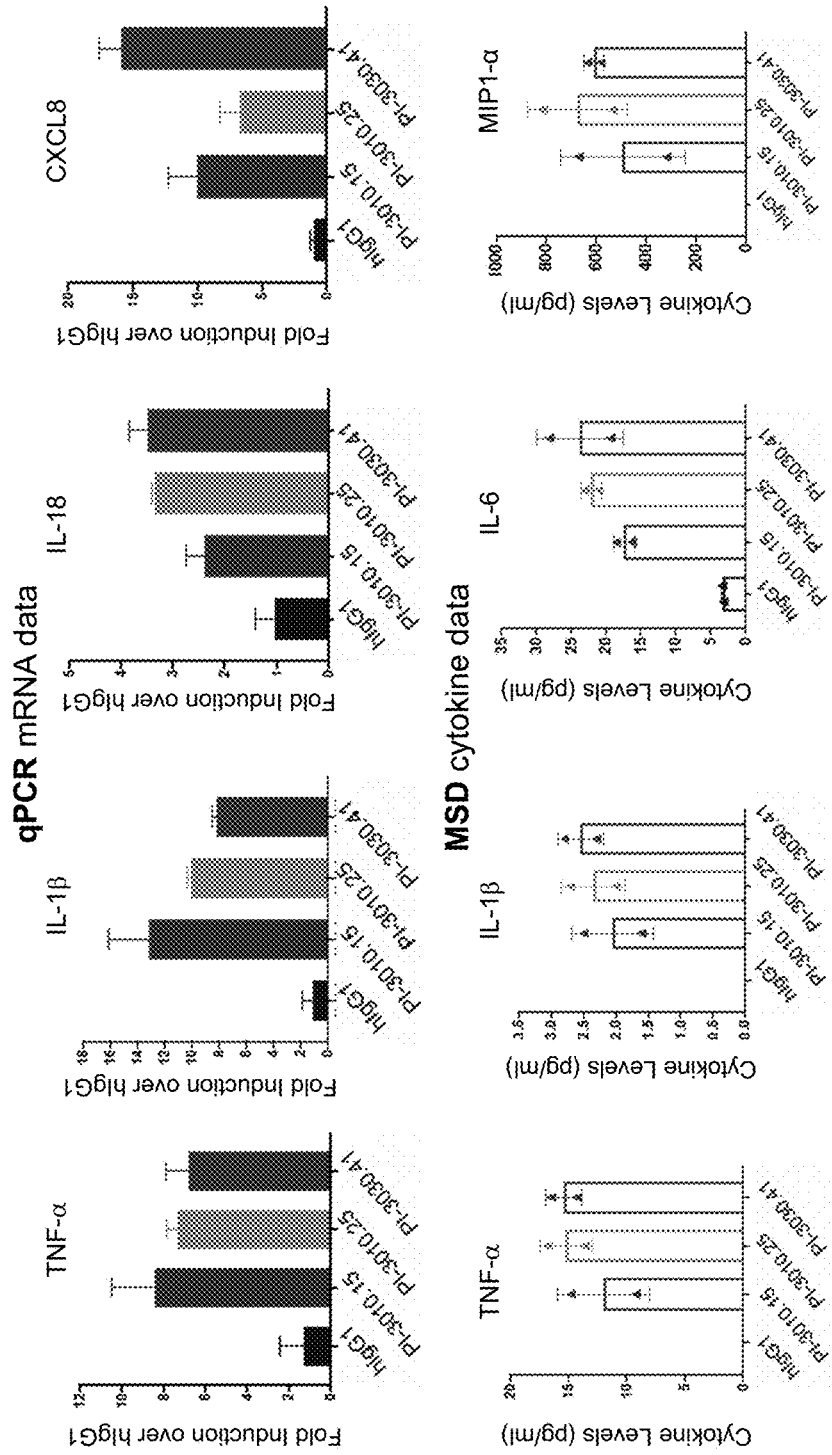
FIG. 28 provides the qPCR mRNA expression data for the indicated genes after treatment with PI-3010.15, PI-3010.25, PI-3030.41, or the hIgG1 control.

FIG. 28 provides the qPCR mRNA data (TNFα, IL-1 (3, IL-18, and CXCL8) and MSD cytokine data (TNFα, IL-10, IL-6, MIP1-α) for PI-3010.15, PI-3010.25, and PI-3030.41 as well as the hIgG1 control. qPCR mRNA analysis of pro-inflammatory genes was plotted as fold induction over the hIgG1 control isotype of one representative donor (top row). Data is presented as mean values of technical duplicates ±standard deviation (SD). Cytokine secretion was also measured by MSD and data plotted for the levels (pg/ml) of representative pro-inflammatory cytokines and chemokines levels (bottom row). Data is presented as mean values of technical duplicates of the same representative donor ±standard deviation (SD).

Figure 29:
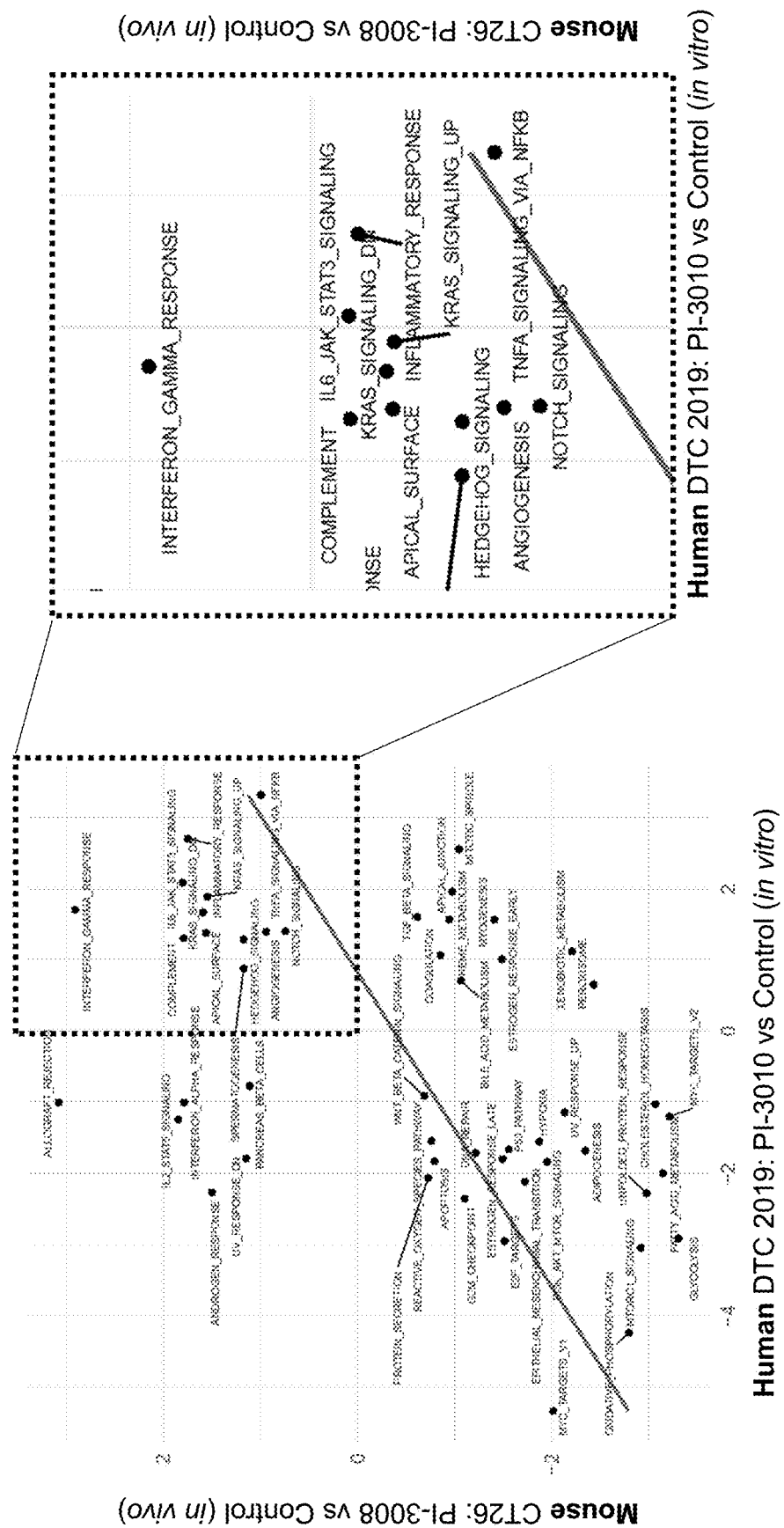
FIG. 29 shows that human and mouse MARCO mAbs drive similar pathway regulation.

PI-3010.15 hIgG1 control treated human disassociated tumor cells and P13008/control treated CT26 tumors were processed as described above (FIG. 16B). GSEA derived Normalized Enrichment Scores from both experiments were plotted using ggplot2 in R. As shown in FIG. 29, human and mouse MARCO mAbs drive similar pathway regulation.

Figure 30:
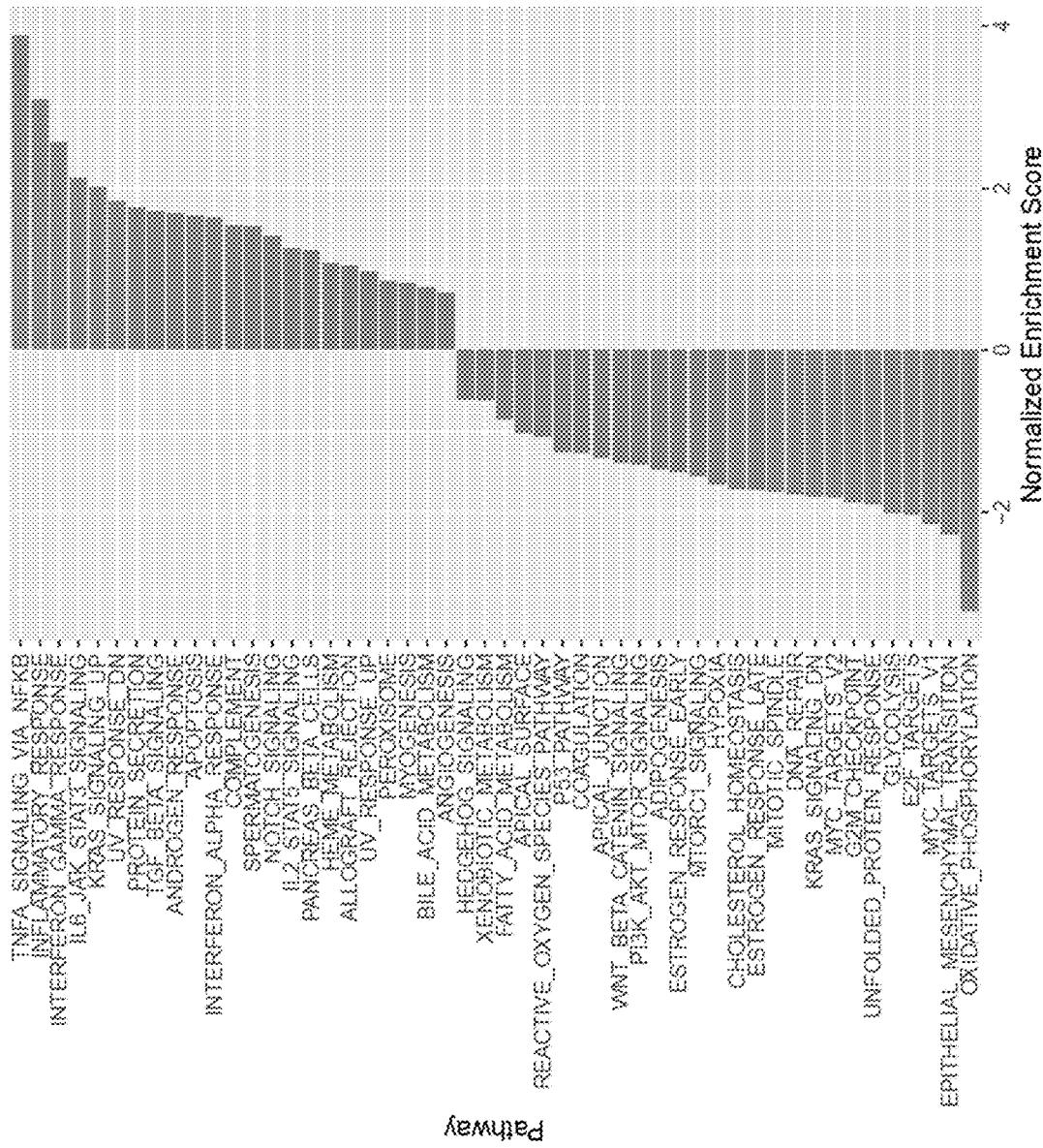
FIG. 30 shows the top immune activation genes and pathways increased by anti-MARCO antibody in hDTCs include IL-2-STAT5 signaling, TNFα signaling via NF-kB, IL-6-JAK-STAT3 signaling, the inflammatory response, IFNγ response, and IFNα response.

PI-3010.15 activated anti-tumor immune pathways in human dissociated tumor cells (DTCs) (FIG. 30). The top immune activation genes and pathways increased by anti-MARCO antibody in hDTCs including IL-2-STAT5 signaling, TNFα signaling via NF-kB, IL-6-JAK-STAT3 signaling, the inflammatory response, IFNγ response, and IFNα response (FIG. 30). These pathways were also upregulated by PI-3008 in mouse tumor cells and BMDMs as shown in Example 4. The pathways decreased by anti-MARCO antibody in hDTCs included hypoxia, apical junctions, Myc targets, PI3K-AKT-mTOR, E2F targets and oxidative phosphorylation. These pathways were also downregulated by PI-3008 in mouse tumor cells and BMDMs as shown in Example 4. Pathways were defined using the Hallmark pathway set.

Figure 31:
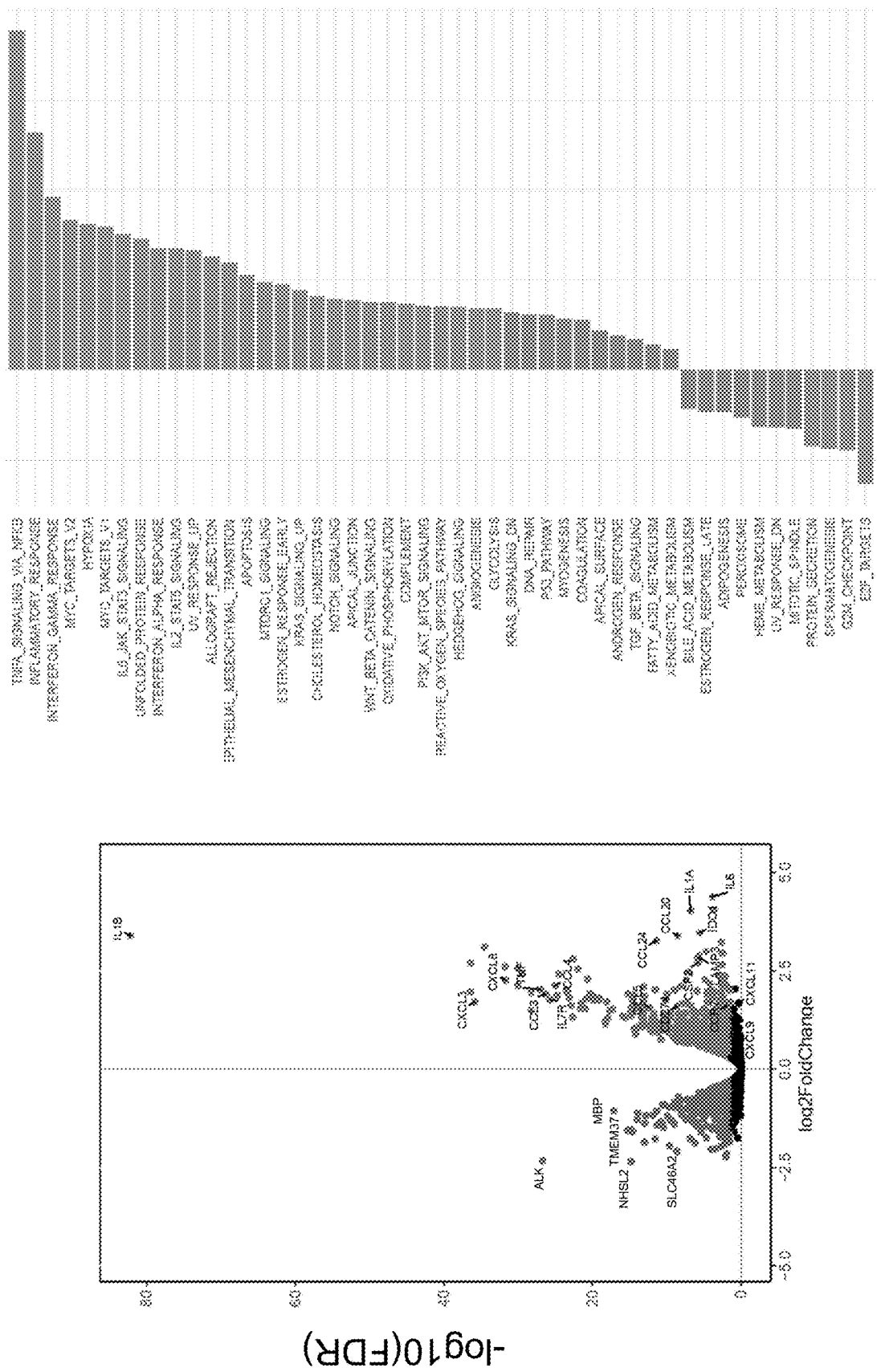
FIG. 31 shows that PI-3010.15 induced a pro-inflammatory signature in human suppressive macrophages (M2c).

PI-3010.15 also induced a pro-inflammatory signature in human suppressive macrophages (M2c) (FIG. 31). Upregulated cytokines and genes were CXCL3, CXCL8, TNFα, CCL3, IL7R, CCL4, CCL5, CCL24, CCL20, IL-1α, IL-6, IDO, CD274, SF2, LAMP3, CCR7, CXCL11, and CXCL9. Down regulated cytokines and genes were ALK, MPB, TMEM37, NHSL2, SLC46A2. Upregulated pathways were TNFa signaling via NF-kB, inflammatory response, INFg response, Myc targets, hypoxia, IL6/JAK/STAT3 signaling, IFNa response, unfolded protein response, IL2/STAT5 signaling, UV response, allograft rejection, epithelial mesenchymal rejection, apoptosis, mTORC1 signaling, estrogen response early, KRAS signaling up, cholesterol homeostasis, notch signaling, apical junction, wnt beta catenin signaling, oxidative phosphorylation, complement, PI3k Akt mTOR signaling, reactive oxygen species pathway, hedgehog signaling, angiogenesis, glycolysis, KRAS signaling DN, DNA repair, p53 pathway, myogenesis, coagulation, apical surface, androgen response, TGFβ signaling, fatty acid metabolism, and xenobiotic metabolism.

Pathways down regulated were bile acid metabolism, estrogen response late, adipogenesis, peroxisome, heme metabolism, UV response DN, mitotic spindle, protein secretion, spermatogenesis, G2M checkpoint, and E2F targets. The key pro-inflammatory genes and pathways induced by PI-3010.15 in M2c hMDMs included IL-2-STAT5 signaling, TNFα signaling via NF-kB, IL-6-JAK-STAT3 signaling, the inflammatory response, IFNγ response, and IFNα response. Pathways were defined using the Hallmark pathway set. Similar pathways were induced in BMDMs treated with PI-3008.

Figure 32:
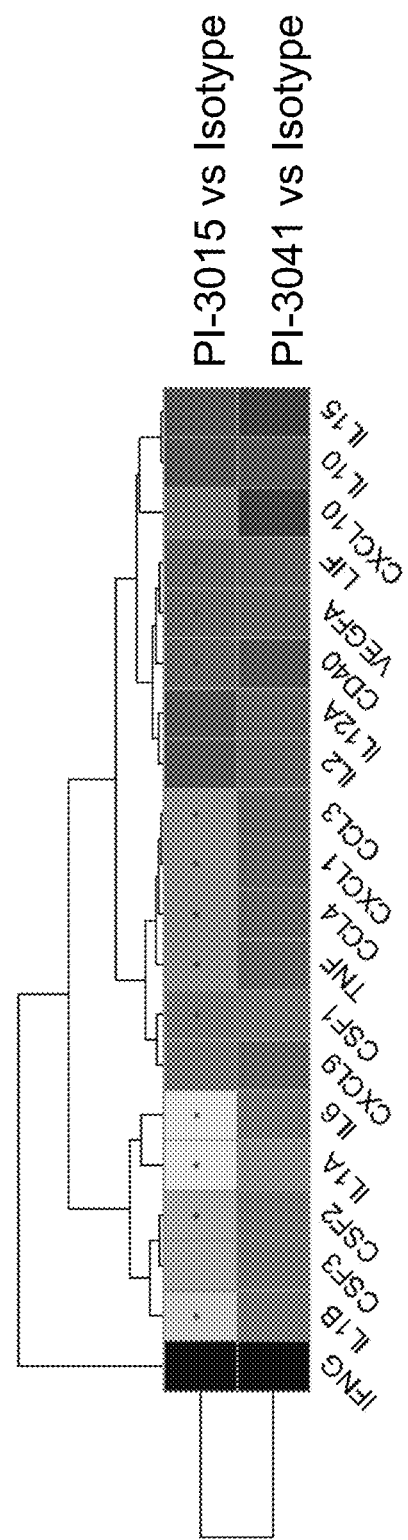
FIG. 32 provides a comparison of the indicated cytokine expression fold change induced by PI-3010.15 and PI-3030.41.

A comparison of the fold change induced in cytokine expression by PI-3010.15 and PI3030.41 is shown in FIG. 32. PI-3010.15 induced higher levels of IL-1β, CSF3, CSF2, IL-1α, IL-6, TNFα, CCL4, CXCL1, CCL3, and CXCL10 as compared to PI-3030.41.

Tables 18 and 19 provide a comparison summary of a selection of anti-MARCO antibodies and characteristics. (−) indicates no difference between antibodies, (+) indicates an advantage.

TABLE 18

| Criteria/Test | PI-3010.15 | P-3010.25 | P-3030.41 |
|---|---|---|---|
| $K_D$ human (avid) | − | − | − |
| $K_D$ cyno (avid) | − | − | − |
| ELISA binding | − | − | − |
| Calculated (In silico) sequence liability | Oxidation (low) Deamidation (low) + | Deamidation (low) Isomerization (high) | Deamidation (low) Isomerization (high) |
| Observed liabilities (forced degradation) | Oxidation (low) + | Isomerization (low) | Deamidation (lhigh) Isomerization (high) |
| Aggregation (SEC, DLS, HIC from transient expression) | + | + | |
| Aggregation (SEC from Lonza stable pooled transfected materials) | + | + | |
| Thermal Stress (DLS, DSF) | − | − | − |
| Stability over time (DLS, SEC, SPR) | + | | |
| Deamidation and Isomerization Risk | + | | |
| Functional in vitro assays | + | | |

TABLE 19

| In vitro assays | PI-3010.15 | PI-3010.25 | PI-3030.41 |
|---|---|---|---|
| Binding to overexpressed cells and absence of binding on negative cells | − | − | − |
| Compete for the binding of ligands to the SRCR domain | − | − | − |
| Cell surface expression in hMDMs and THP1 cells polarized with IL-10 | + | | |
| RNAseq in DTCs | + | + | |
| RNAseq in hMDMs | + | Not tested | |
| qPCR for gene expression in hMDMs | − | − | − |
| Cytokine secretion assay by MSD and/or Luminex | − | − | − |
| Increase Inflammasome in hMDMs | + | | |
| NF-κB reporter assay in THP1-Blue ™ NF-κB Cells | + | + | |
| Mild Increase in Phagocytosis | + | + | |

In order to determine if any potential liabilities exist in the sequences of three selected antibodies, Sentinel APART algorithm (Lonza) was used for in-silico sequence analysis of the candidates. Points of concern that were flagged by in-silico analysis were: increased hydrophobicity, aggregation propensity, aspartate isomerization, and oxidation liability. Previous in silico assessment showed similar liabilities that were flagged but proved to be minor liabilities when tested under various stress conditions and forced degradation assays. Table 20 below shows a summary of the experimental data in comparison with the theoretical data.

TABLE 20

| Antibody | Aggregation | | Deamidation | | Isomerization/Fragmentation | | Oxidation | |
|---|---|---|---|---|---|---|---|---|
| | Calculated (in silico) | Observed (HIC) | Calculated (in silico) | Observed (HIC) | Calculated (in silico) | Observed (HIC) | Calculated (in silico) | Observed (HIC) |
| PI-3010.15 | High | Low | 0 (1) | 0 (0) | 0 (0) | 0 (0) | 0 (2) | 0 (2) |
| PI-3010.25 | High | Low | 0 (1) | 0 (0) | 1 (0) | 0 (1) | 0 (1) | 0 (0) |
| PI-3030.41 | High | Low | 0 (2) | 1 (1) | 2 (0) | 1 (1) | 0 (3) | 0 (0) |

Total hydrophobicity of lead candidates was evaluated using hydrophobic interaction chromatography (HIC). Longer retention time indicates more hydrophobicity. An anti-TREM1 antibody was used as a positive control in this assay. The PI-3010.15, PI-3010.25 and PI-3030.41 antibodies all showed hydrophobicity in the range expected for antibodies (Table 21). High levels of main peak % indicate fewer modifications and lower retention time corresponds to lower hydrophobicity.

TABLE 21

| Sample Number | Main Peak (%) | Retention Time (min) |
|---|---|---|
| PI-3010.15 | 88.7 | 15.7 |
| PI-3010.25 | 95.8 | 15.6 |
| PI-3030.41 | 70.7 | 11.5 |

A forced degradation study to understand liabilities of selected antibodies was conducted. PI-3010.15-H1, PI-3010.25-H1 and PI-3030.41-H1 samples were incubated under stress conditions (oxidation, low pH, and high pH) and analyzed by peptide mapping (LC-MS/MS) to identify protein modifications in the mAbs. The focus was on the analysis of isomerization and oxidation liabilities. In addition, other parameters were used to assess the stability of each antibody at the various stress conditions (Table 22).

TABLE 22

| Sample | Source | Isoytpe | Conc (mg/mL) | Condition | Time | Readout |
|---|---|---|---|---|---|---|
| PI-3010.25 | CHO-ATUM | hIgG1 | 8.4 | 4° C. (PBS control) | 2 weeks | Nanodrop (A280) |
| PI-3010.41 | CHO-ATUM | hIgG1 | 9.5 | 40° C. (PBS) | | SEC (aggregation) |
| PI-3010.15 | CHO-ATUM | hIgG1 | 10.5 | 40° C. (pH 5.5) | | DLS (Tagg, size) |
| | | | | 40° C. (pH 8.5) | | DSF (domain stability) |
| | | | | 40° C. (PBS) + AAPH (6 hrs) | | LC-MS (peptide mapping to detect modifications) |
| | | | | 25° C. (pH 3.5) | | Charge variant analysis |
| | | | | | | Biacore (binding) |

Isomerization

PI-3010.15 was incubated at the following conditions: 40° C. in PBS for 2 weeks, control in PBS at −80° C., 40° C. (PBS)+1 mM AAPH for 6 h, and 40° C. in pH 5.5 sodium acetate for 2 weeks. Post treatment the samples were analyzed by LC-MS/MS which identified the % modification on isolated peptides derived from the antibody after trypsin digest.

LC/MS peptide mapping was done on PI-3010.15 after incubation at low pH for extended periods to identify potential hotspots. PI-3010.15 did not show any Isoaspartate (IsoAsp), deamidation or succinimide formation. PI-3010.25 showed IsoAsp formation in residue D56 of light chain (>2%, only under pH 5.5, 40° C.) and D72 of heavy chain (3.7% at pH 3.5) while PI-3030.41 showed IsoAsp in D56 of light chain (>2.7%, under pH 5.5, 40° C.) and succinimide at residue N52 of heavy chain (6-9% under all conditions, including control).

Oxidation:

PI-3010.15 was incubated at the following conditions: control in PBS at −80° C., 40° C. (PBS)+1 mM AAPH for 6 h, 0.5 and 1.5% H2O2 in PBS for 24 h, which was compared to a previous experiment at 40° C. (PBS)+1 mM AAPH for 6 h. Post treatment the samples were analyzed by LC-MS/MS which identified the % modification on isolated peptides derived from the antibody after trypsin digest.

PI-3010.15 showed oxidation of Met-48 and Trp-52 with AAPH and H2O2 treatment. Trp-52 was flagged as a potential liability in the in-silico assessment. Met-48 residue is expected to be buried in the structure, and not solvent accessible. It was not possible to unambiguously assign oxidation liability to either residue as they are found as part of the same peptide during LC-MS/MS analysis.

Binding of the stressed samples to recombinant human MARCO was assessed by Biacore. The binding of the stressed samples had similar KDs and Rmax levels compared to the control conditions suggesting that binding potency was not significantly affected (Table 23), including various oxidized stress samples from PI-3010.15 (Table 24).

TABLE 23

Binding to MARCO

| Antibody | Control | | 40° C. 2 week | | Deamidation (40° C. 2 week) | | Isomerization/ Fragmentation | | Oxidation (1 mM AAPH, 6 hrs) | |
|---|---|---|---|---|---|---|---|---|---|---|
| | $K_D$ (nM) | Rmax | $K_D$ (nM) | Rmax | $K_D$ (nM) | Rmax | $K_D$ (nM) | Rmax | $K_D$ (nM) | Rmax |
| PI-3010.15 | 1.2 | 131.7 | 1.2 | 103.8 | 1.24 | 111.3 | 1.24 | 108.6 | 1.29 | 104.5 |
| PI-3010.25 | 0.54 | 63.2 | 0.58 | 62.2 | 0.66 | 62.4 | 0.66 | 62.4 | | |
| PI-3030.41 | 0.24 | 62 | 0.36 | 54.3 | 0.39 | 54.8 | 0.34 | 48.9 | | |

TABLE 24

Oxidation

| Antibody | Control | | 0.5% H2O2 (24 hr, RT) | | 1.5% H2O2 (24 hr, RT) | | 1 mM AAPH, 6 hrs 40° C.) | |
|---|---|---|---|---|---|---|---|---|
| | $K_D$ (nM) | Rmax | $K_D$ (nM) | Rmax | $K_D$ (nM) | Rmax | $K_D$ (nM) | Rmax |
| PI-3010.15 | 0.97 | 111.7 | 1.05 | 97.1 | 1.07 | 109.5 | 1.10 | 97.6 |

The 3 antibodies (PI-3010.15, PI-3010.25, and PI-3030.41) were successfully concentrated up to 30 mg/mL in the following buffers in pH range 5.0-6.0 without any other excipients. PBS was used a control. The antibodies were incubated at 4° C. overnight prior to the following analyses: % aggregation by SEC-HPLC; Size (radius) and polydispersity using DLS; Thermal stability [Tagg (DLS), Tm (DSF)]; Colloidal stability (kd) by SLS.

PI-3010.25 was concentrated in the following buffers (Table 25).

TABLE 25

| Buffer | pH | mAb Concentration (mg/mL) for PI-3010.25 |
|---|---|---|
| 10 mM Histidine HCl | 6.0 | 27.1 |
| 10 mM Histidine HCl | 5.5 | 36.4 |
| 10 mM Sodium Citrate | 6.0 | 33.2 |
| 10 mM Sodium Citrate | 5.5 | 35.8 |
| 10 mM Sodium Citrate | 5.0 | 29.7 |
| 10 mM Sodium Acetate | 5.5 | 33.4 |
| 10 mM Sodium Acetate | 5.0 | 36.1 |
| PBS (control) | 7.4 | 30.4 |

PI-3010.25 could be concentrated to 30 mg/mL without increase in HMW aggregates.

Example 9: Anti-MARCO Antibody Induces Inflammasome Activation

Materials and Methods

Inflammasome Assay in mBMDMs

Femurs and tibias from three females C57BL/6 mice and three females BALB/c were cleaned and crushed in Staining Medium (0.5% (w/v) BSA (Sigma) and 2 mM EDTA in D-PBS) using a mortar and pestle. Samples were then passed through a 40 um filter, washed with D-PBS and pelleted at 400×g for 5 min at RT. Cell pellets were resuspended in 5 ml of BD Pharm Lyse buffer (BD Biosciences) and red blood cell lysis was carried out at RT for 5 min, followed by quenching with 10 volumes of Staining Medium. Cells were pelleted at 400×g for 5 min at RT and resuspended in Macrophage Medium composed of Iscove's modified Dulbecco Medium supplemented with 10% (v/v) fetal bovine serum (FBS) (HyClone) and antibiotic-antimycotic solution (Gibco), at the density of 15×10^6 cells/ml in 15 cm plates. These bone marrow mononuclear cells were stimulated with 25 ng/ml of mouse macrophage colony-stimulating factor (M-CSF) (PeproTech) for 7 days to generate M0-macrophages and differentiated into M2-like by supplementing the medium with mouse IL-1b at 20 ng/ml on day 6 for 24 hours at 37 C. On day 7, macrophages were rinsed with DPBS and incubated in 6 ml of 2 mM EDTA for 10 minutes to promote cell detachment. Cells were gently scraped into an additional 6 ml of the Staining Medium described above, counted and seeded onto 96-well plates at 100,000 cells per well.

After 30 minutes to 1 h at 37 C to allow the cells to attach, BMDMs were treated with 5 µg/ml of the anti-mouse MARCO antibody PI-3008 and its corresponding isotype control mIgG2a. After 3 hours of incubation with the antibodies, LPS (tested 0.5 and 50 ng/ml) was added to prime the inflammasome pathway for an additional 2.5 hours. ATP (5 mM) was then added for 30 minutes to activate the inflammasome and induce cytokine secretion of IL-1β that was measured by MSD. Sidak's multiple comparisons test was used to calculate statistical significance of secreted IL-1β fold change over untreated isotype (no LPS and no ATP). Sidak's multiple comparisons test, **P<0.01.

Inflammasome Assay in hMDMs

Frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM 2-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 12-15×10^6 cells in 15 cm dish. At day 3 of differentiation, media was replenished with the addition of fresh M-CSF. Differentiated human macrophages were polarized by adding the following cytokines to the media for 24 hours at 37 C: 100 ng/ml of IFNγ (M1 condition) and 25 ng/ml of recombinant human IL-10 (M2 condition) for 24 hours at 37

C. On day 7, polarized macrophages were gently harvested non-enzymatically using a sterile cell scraper (Nunc) into FACS buffer (D-PBS containing 2 mM EDTA and 0.5% (w/v) bovine serum albumin (BSA) (Sigma)) followed by centrifugation at 400×g for 5 min at −20° C.

Cells were counted and seeded onto 96-well plates at 100,000 cells per well. After 30 minutes to 1 h at 37° C. to allow the cells to attach, hMDMs were treated with 5 µg/ml of the anti-human MARCO antibodies PI-3010.15, PI-3010.25 (PI-3025), PI-3030.41 (PI-3041), and PI-3010.48 (PI-3048) and their corresponding isotypes controls hIgG1 and hIgG4 (Ultra-leaf from Biolegend). After 3 hours of incubation with the antibodies, LPS (tested 0.1 and 1 µg/ml) was added to prime the inflammasome pathway for an additional 2.5 hours. ATP (5 mM) was then added for 30 minutes to activate the inflammasome and induce cytokine secretion of IL-1 that was measured by MSD. Tukey's multiple comparison test was used to calculate statistical significance of secreted IL-10 fold change over untreated (no LPS and no ATP) hIgG1. Tukey's multiple comparisons test (*P<0.05; *P<0.0006, **P<0.0001).

E. coli Phagocytosis Assay

Human monocyte-derived macrophages (MDM) were generated by culturing CD14+ human monocytes in RPMI 1640 medium (Gibco) supplemented with 10% Fetal Bovine Serum (Gibco), 1% ß-mercaptoethanol (ThermoFisher), 1× non-essential amino acids (Gibco), 1× Sodium Pyruvate (Gibco), 1× GlutaMax (Gibco), 1× anti-anti (Gibco), 50 ng/ml of M-CSF (Peprotech) in 15 cm plate. Medium was refreshed after 3 days. On day 6 of culture, 100 ng/ml of human IFN-g (Peprotech)+50 ng/ml of LPS (Invivogen) or 25 ng/ml of IL-10 (Peprotech) were added to the culture. The following day, cells were harvested, and 200,000 cells were plated per well of 96-well flat bottom plate and incubated with a dose titration of PI-3101.15, PI-3010.25 or PI-3030.41 and isotype control antibody for 2 hours at 37° C. and 5% CO2 to allow cells to adhere.

To measure phagocytosis, the Vybrant Phagocytosis Assay Kit (Molecular Probes) was used. After the 2-hour antibody incubation, media was removed, and cells were incubated with E. coli fluorescent BioParticles solution for 2 hours at 37° C. and 5% CO2. The particles solution was removed and replaced by the trypan blue solution. After 1 min incubation at room temperature, the solution was removed, and fluorescence was measured using 480 nm for excitation and 520 nm emission wavelengths on the Tecan microplate plate reader.

Results

Figure 33A:
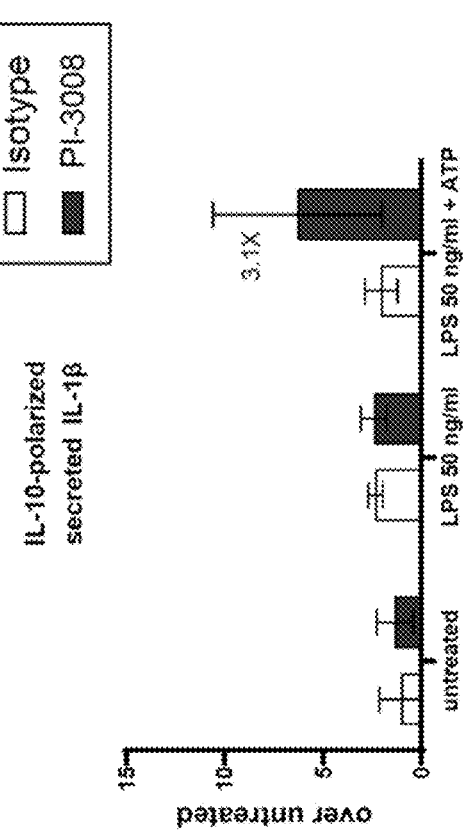
FIG. 33A shows that PI-3008 induced statistically significant IL-10 secretion by the inflammasome in non-polarized macrophages from C57BL/6 mice.
Figure 33B:
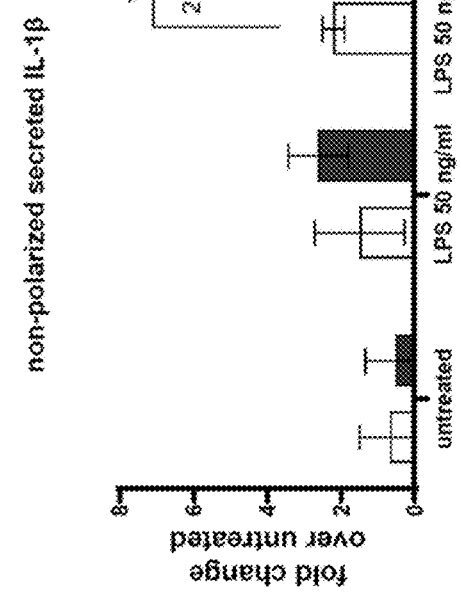
FIG. 33B shows that PI-3008 induced statistically significant IL-10 secretion by the inflammasome in IL-10 polarized macrophages from C57BL/6 mice
Figure 33C:
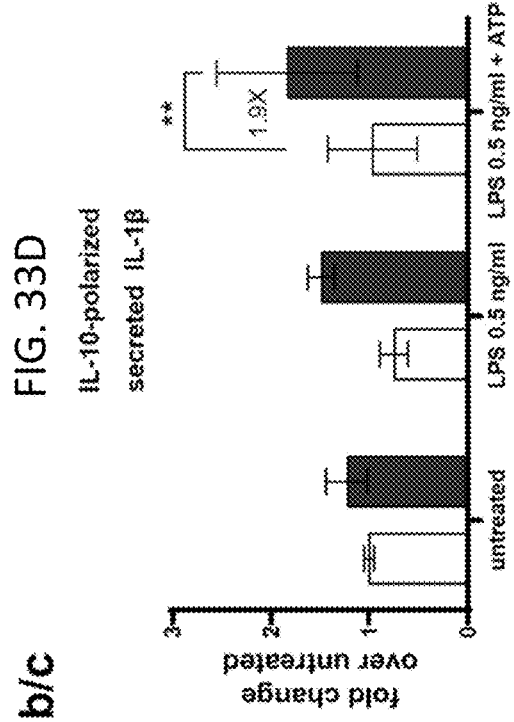
FIG. 33C shows that PI-3008 induced statistically significant IL-1 secretion by the inflammasome in non-polarized macrophages from Balb/c mice.
Figure 33D:
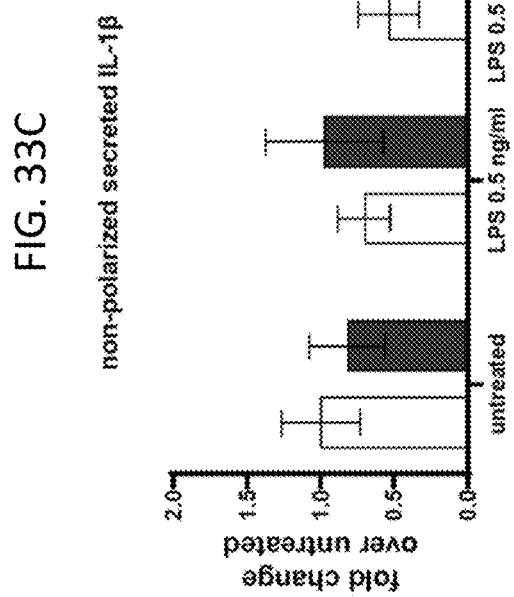
FIG. 33D shows that PI-3008 induced statistically significant IL-1 secretion by the inflammasome in IL-10 polarized macrophages from Balb/c mice.

PI-3008 induced statistically significant IL-1β secretion by the inflammasome in both non-polarized macrophages (FIGS. 33A and 33C) and IL-10 polarized macrophages (FIGS. 33B and 33D). This effect was observed in two separate murine lineages, C57BL/6 mice (FIGS. 33A and 33B) and Balb/c mice (FIGS. 33C and 33D). Thus, PI-3008 enhances and increases inflammasome activation in mouse BMDMs.

Figures 34A, 34B:
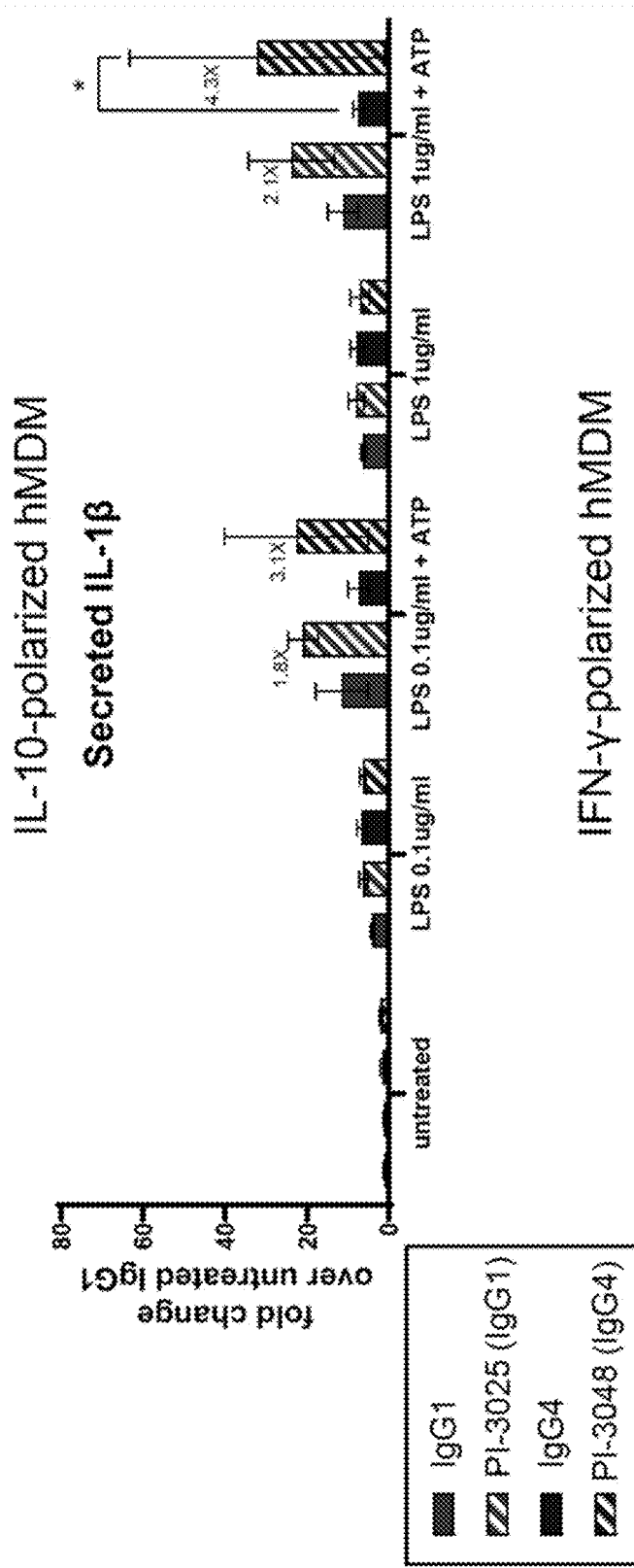
FIG. 34A shows that PI-3025 (IgG1 format) and PI-3048 (IgG4 format) induced statistically significant IL-1 secretion in IL-10 polarized macrophages after incubation with 0.1 μg/ml LPS+ATP and 1 μg/ml LSP+ATP.
FIG. 34B shows that PI-3048 induced IL-10 secretion after treatment with 1 μg/ml LPS+ATP. Bars for PI-3025 are shown second from the left in each grouping, bars for PI-3048 are shown on the right in each grouping.
Figure 35:
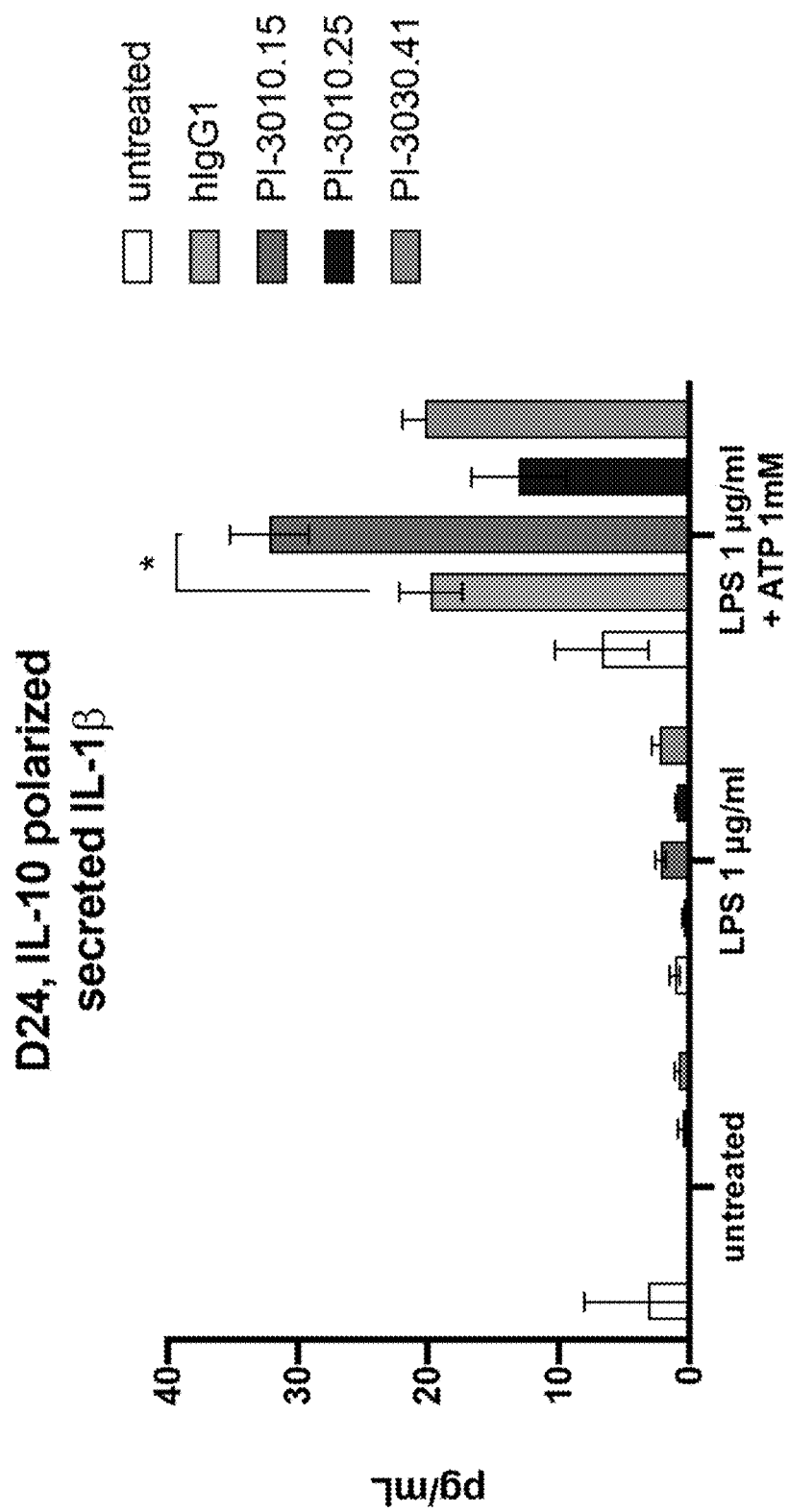
FIG. 35 shows that of PI-3010.15, PI-3010.25, and PI-3030.41 induced IL-1 production when treated with LPS and ATP compared to the untreated condition

A similar results was observed in human MDMs (FIGS. 34A, 34B, and 35). Both PI-3010.25 (IgG1 format) and PI-3010.48 (IgG4 format) induced statistically significant IL-10 secretion in IL-10 polarized macrophages after incubation with 0.1 µg/ml LPS+ATP and 1 µg/ml LSP+ATP (FIG. 34A). In IFN-γ polarized hMDMs, PI-3025 induced IL-10 secretion after incubation with 0.1 µg/ml LPS+ATP, while PI-3010.48 induced IL-10 secretion after treatment with 1 µg/ml LPS+ATP (FIG. 34B). Bars for PI-3010.25 are shown second from the left in each grouping, bars for PI-3010.48 are shown on the right in each grouping.

In a separate assay, all of PI-3010.15, PI-3010.25, and PI-3030.41 induced IL-10 production when treated with LPS and ATP compared to the untreated condition (FIG. 35), indicating that anti-human MARCO antibodies induce inflammasome activation.

The percent induction of phagocytosis by PI-3010.15, PI-3101.25, and PI-3030.41 in the IL-10 hMDM donor cells is provided in Table 26.

TABLE 26

| Antibody | Isotype | Phagocytosis |
| --- | --- | --- |
| PI-3010.25 | IgG1 | 90% |
| PI-3010.15 | IgG1 | 88% |
| PI-3030.41 | IgG1 | 50% |

PI-3010.25 and PI-3010.15 showed more consistent phagocytosis induction across multiple donors when hDMMs were polarized with IL-10.

Example 10: In Vivo Monotherapy Efficacy of Anti-Mouse MARCO Antibodies in EMT6 Model Methods EMT6 breast cancer tumor cells (1×10^6 cells per mouse) were implanted on Day 0, and dosing (10 mg/kg; Q5dx4; ip) was initiated when tumors reached an average volume of ~90 mm3. Animals were dosed intraperitoneally every 5 days, for total of four doses. Tumor volumes were monitored over time and presented as averages per group, individual tumor volumes at the end of study, or as % TGI.

Results

Figure 36:
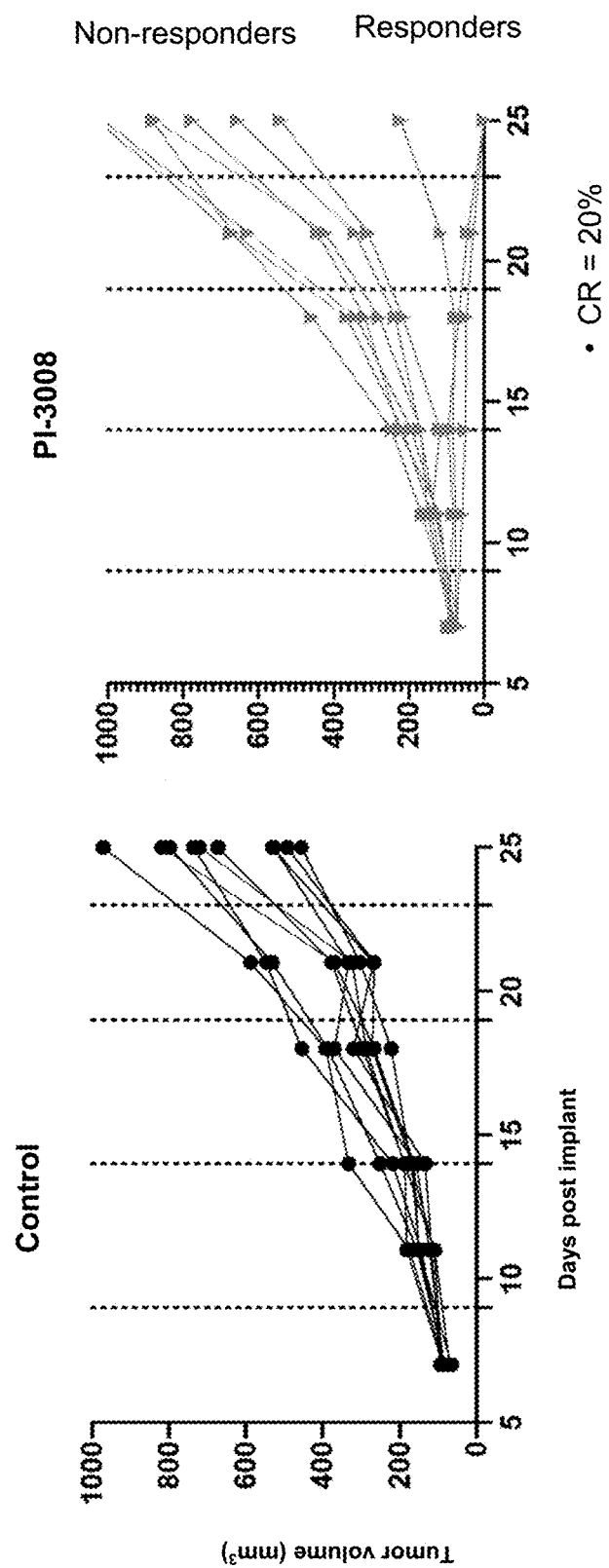
FIG. 36 shows that PI-3008 demonstrated anti-tumor activity as a single agent in the EMT6 model. Tumor volumes in isotype control antibody treated mice are shown in the right panel, tumor volumes in PI-3008 antibody treated mice are shown in the left panel. The PI-3008 treated mice grouped into responders and non-responders.

PI-3008 demonstrated anti-tumor activity as a single agent in the EMT6 model (FIG. 36). In some groups, up to a 20% complete response (CR) was achieved (responders).

Example 11: In Vivo Monotherapy Efficacy of Anti-Mouse MARCO Antibodies in E0771 Model Methods E0771 Syngeneic Mouse Model The mouse studies were performed under the guidance of and approved by the Institutional Animal Care and Use Committee of Explora BioLabs, South San Francisco, CA.

Eight to ten-week old female C57/BL6 mice (Taconic) were implanted with subconfluent E0771 cells (ATCC) grown in log-phase. One million tumor cells resuspended in serum-free media with Matrigel were implanted orthotopically in the mammary fat pad of the mice under isoflurane anesthesia. When the majority of tumors were between 110-120 cubic millimeters (mm3), mice were randomized into the treatment groups (PI-3008-AB and PI-0002 mIgG2a isotype) before initiation of treatment.

PD Study

Mice randomized in 2 groups were dosed intraperitoneally with 10 mg/kg of PI-3008-AB or PI-0002-AB (isotype) based on group average body weight for each group. Tumor volume was calculated using the formula [length×(width) 2]/2 after measuring two orthogonal diameters using digital calipers. At three different timepoints (2 days after 1 dose, 5 days after 1 dose, 24 hours after second dose Q5dx2), 15 mice per group were sacrificed and tumor, spleen and blood were collected. 9 animals were used for flow cytometry processing of tumors and spleen, and 6 mice were used for IHC evaluation of tumors and spleen. Tumor volumes were monitored over time and presented as averages per group, individual tumor volumes at the end of study, or as % TGI.

Effector Dead Antibody Efficacy

The effector dead anti-MARCO antibody, PI-3021 (PI-3008 with an N297A mutation) was also assessed in the E0771 model. Mice were dosed as described in Example 4. Briefly, 10 mice per group, IP dosing initiated when tumors were ~100 mm$^3$. Dosing was 10 mg/kg; Q5dx4. mIgG2a isotypes of both PI-3008 and the effector dead PI-3021 were used. An anti-PD-1 antibody was also used.

PK/PD Efficacy in E0771 Syngeneic Mouse Model

Figure 39A:
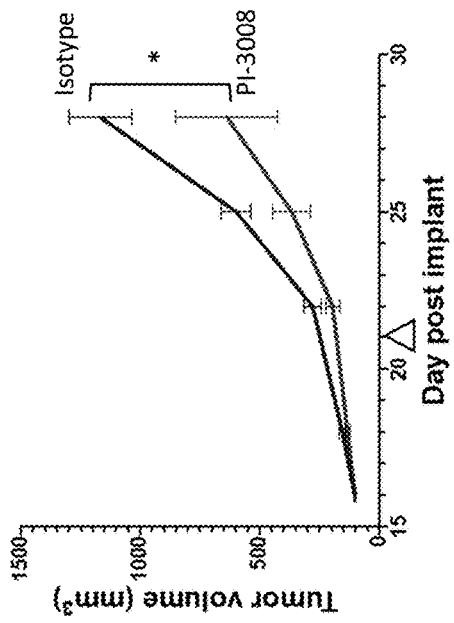
FIG. 39A provides a schematic of the E0771 PD/PK/efficacy study timeline.

To determine PK-PD-efficacy relationships, the E0771 orthotopic breast cancer model was used since PI-3008 elicited monotherapy in this model. The study design included a PD arm where tumors and spleens were collected 24 hr after the second dose, and a "PK" arm to determine PI-3008 serum levels. A schematic of the study timeline is shown in FIG. 39A.

C57BL/6 female mice were injected into mammary fat pad with syngeneic E0771 tumor cells (5×105 cells per mouse) on Day 0, and dosing with PI-3008 or isotype controls (10 mg/kg, N=10/group) was initiated when tumor volumes reached an average of ~100 mm3. Animals were dosed intraperitoneally every 5 days, for total of four doses. A subset of animals was sampled 24 hr after the second dose for the assessment of PD changes in tumors and spleens. Additional PD takedown were done at 2 days and 5 days after first dose. Tissues sampled were tumors, spleens, and blood via Luminex and flow cytometry.

The rest of the animals were monitored for anti-tumor efficacy and were sampled at end of study for drug exposure analysis. The endpoint PD assays included flow cytometry profiling on the tumors and spleens to determine changes in myeloid and lymphoid composition, measurement of cytokines/chemokines in tumor and spleen, and assessment of CD8 T cells, NK cells, MARCO cells, and CD19 B cells frequencies and tissue distribution by IHC (monoplex and multiplex).

Flow Cytometry Assay

Mouse tumor tissue was harvested and placed in ice cold RPMI-1640 (Invitrogen) media. Tumors were enzymatically dissociated using the Mouse Tumor Dissociation Kit (Miltenyi) according to the manufacturer's recommendation. Following dissociation, single cell suspensions were pelleted and tumor supernatant was collected, spun at high speed to remove insoluble material, enzymatically inactivated using Halt™ Protease Inhibitor Cocktail (Thermo Scientific) and promptly frozen at −80deg C. until downstream analysis was performed. Cell pellets were resuspended in stain media (DPBS/1% BSA/2 mM EDTA) and passed through a 100 uM filter to remove undissociated material. Single cell suspensions were counted on a ViCell XR (Beckman Coulter) and plated in 96-well V bottom plates for flow cytometric staining.

Cells were incubated with Zombie NIR (BioLegend), followed by FcgR block using a combination cocktail of TruStain FcX PLUS (Biolegend), Mouse Serum, Rat Serum, Hamster Serum (Jackson Immuno Research), all prepared in Fc Receptor Blocker (Innovex). Cell surface proteins were stained for 30 minutes on ice, followed by either a secondary stain step or fixation with 1% PFA overnight at 4° C. For staining intracellular proteins, cells were fixed and permeabilized with the FoxP3/Transcription Factor Staining Buffer Set (Thermo Fisher Scientific). Intracellular antibodies were prepared in permeabilization buffer with 2% rat serum and cells were incubated for at least 30 minutes at room temperature. Cells were run on an Attune NXT (ThermoFisher). Flow cytometric analysis was performed using FlowJo (Beckton Dickinson).

The flow antibodies used for each panel are described in Table 27 below and were prepared by adding the appropriate antibodies to the FACS buffer containing Ca2+/Mg2+PBS and 2% FBS.

TABLE 27

| Immune Population | Cell Surface Markers |
|---|---|
| Neutrophils | Ly6G+ |
| Monocytes | Ly6G−/Ly6C+ and sub-gating on MHCII−, MHCII$^{int}$, MHCII$^{high}$ |
| TAMs | CD11b+/F4/80+ and sub-gating on MHCII−, MHCII$^{int}$, MECII$^{high}$ |
| DCs | F4/80−/CD11c+/MHC-II+ |
| CD4+ T cell | CD90.2+/CD8−/CD4 |
| CD8+ T cell | CD90.2+/CD4−/CD8+ |
| NK cell | CD90.2+/CD4−/CD8−/NK1.1+ |
| Memory B cells | CD90.2− /CD45R+/CD19+ |
| Plasma B cells | CD 90.2− /CD45R+/CD19$^{Low}$/Blimp1+ |
| Marginal Zone B cells | CD90.2− /CD45R+/CD21+/CD35$^{mid}$/CD23+ |
| Follicular B cells | CD90.2− /CD45R+/CD21+/CD35$^{high}$ |
| Spleen macrophages | CD11b+/F4/80+ and sub-gating on MHCII− and MHCII+ |
| Red pulp macrophages | CD11b+/F4/80+/CD206+ |
| Marginal zone macrophages | CD11b$^{int}$/F480+ And/or CD11 CD11b$^{int}$/F480+/TIM4+ |
| Non marginal zone macrophages | All CD11b/F480+ populations for the exception of CD11b$^{int}$/F480+ marginal zone |

Receptor Occupancy (RO) Assay

For the tumor/spleen myeloid and blood flow cytometry antibody panels, the PI-3008 antibody conjugated with PE at BioLegend or the mIgG2a-PE from BioLegend were added to the staining cocktail at 10 µg/ml to assess receptor occupancy (RO) in the various myeloid cells in the tumors, spleen, and blood.

In Vivo Serum Concentrations

Serum levels of anti-mouse MARCO mAbs were determined using a standard ligand-binding ELISA (LBA) format with coated recombinant extracellular domain (ECD) mouse MARCO His-tagged fusion construct protein. PI-3008 mAb levels in the serum of CT26 tumor-bearing mice were assessed for multiple studies and various timepoints. For the PD study, PI-3008 was measured 4 h after the first IV dose and 4 h after the second IV dose, 7 days apart.

In vivo antibody serum levels in the CT26 combination studies with anti-MARCO antibody and anti-PD-1 antibody were also assessed for comparison. PI-3008 and PD-1 were dosed IP at 10 mg/kg or 5 mg/kg at Q5d X4 in the CT26 efficacy study (Example 4). The serum samples for PI-3008 and PD-1 concentration determinations were collected before the third dose (pre dose) and 24 hr after the final dose (post dose).

Mouse Cytokine and Chemokine Secretion by Luminex

Mouse plasma, spleen supernatants, or tumor supernatants were evaluated for cytokine levels using ProcartaPlex Multiplex Immunoassay from ThermoFisher Scientific (Cat #PPX-25-MX47WJ7). The kit uses color coded beads for measurement of multiple cytokines via Luminex xMAP technology. The beads are internally dyed with different proportions of red and infrared fluorophores that correspond to distinct spectral regions. For the experiment, 50 µl of magnetic capture beads are first added to the plate. Samples for analysis or kit standards were added at 25 µl per well volume and an equal amount of universal assay buffer was added to adjust the matrix. Following a two-hour incubation at room temperature, the beads are captured on a magnetic plate and were then washed followed by the addition of 25 µl/well of detection antibody. Following a one-hour incubation at room temperature, the beads were washed again and streptavidin phycoerythrin (SAPE) was added at 50 µl/well. After a final one-hour incubation, the beads were washed and 120 µl/well of read buffer was added. The plate was run on the Luminex 200 Instrument. Data was analyzed using Luminex Xponent software v4.3 and analytes levels in pg were normalized to the tumor or spleen weight. Cytokine/chemokine data was presented as fold changes of PI-3008 treated supernatants over the average of the isotype treated supernatants for each analyte.

Detection of IgG/IgM in Mouse Tissue and Serum

25 µL/well of Diluent 100 (MSD, Catalog R50AA-4) was added to the pre-coated plate with capture antibodies (MSD, Catalog #K15183B-1 and K15203D-1). The plate was incubated at room temperature for 30 min with vigorous shaking. Standards (Mouse Isotyping Panel 1, MSD Catalog #K15183B-1) and samples were diluted in Diluent 100 (MSD, Catalog #R50AA-4) and added to the coated plate. The plate was incubated for 120 min with vigorous shaking at room temperature and washed. 25 µL of 1× detection antibody solution was added to each well, and the plate was incubated for 120 min with vigorous shaking at room temperature. The plate was washed and 2× Read Buffer (MSD, Catalog #R92TC-3) was added to the MSD plate. The plate was read on an MSD Sector Imager. The IgG/IgM assay range for the Mouse Isotyping Panel was 24 µg/mL to 100,000 µg/mL. The LLOQ was 97.7 µg/mL and the ULOQ was 100,000 µg/mL. The IgG levels in mouse tissue samples ranged from 0.8 µg/mL to 1 µg/mL. The IgM levels in Mouse Tissue samples ranged from 0.2 µg/mL to 1 µg/mL. The IgG levels in mouse serum samples ranged from 41 µg/mL to 56 µg/mL. The IgM levels in mouse serum samples ranged from 15 µg/mL to 24 µg/mL.

Histology of Mouse Tissues and Antibody Staining in a Monoplex DAB IHC Assay

Animals were euthanized as per the institutionally approved standard operating procedure (SOP) for CO2 asphyxiation followed by cervical dislocation. Animals were sprayed with 70% ethanol to ensure sterility and reduce airborne allergens. Tumors and spleens were then collected in 10% Neutral Buffered Formalin (VWR, 16004). Formalin was removed 24 hrs later and tumors and spleen were transferred to 70% ethanol.

All tumors and spleens were shipped to Cureline (Brisbane, CA). Cureline performed histology based on their institutional SOP and fully automated workflow. Larger tumors were cut in half and smaller tumor were left intact and were then processed, embedded in paraffin, and cut into 5 µm thin sections. Spleens were cut cross sectionally and were then processed, embedded in paraffin, and cut into 3 µm thin sections.

CD8a (Cell Signaling, 98941S) immunohistochemistry (IHC) was performed using a Bond Rx autostainer (Leica Biosystems) with Heat-Induced Epitope Retrieval (HIER) at pH 9.0 for 20 minutes. The CD8a primary antibody (98941S, Cell Signaling Technologies, diluted for use at 3.2 µg/ml) and Bond Polymer Refine Detection (Leica Biosystems) were used according to manufacturer's protocol. Both spleen and tumor tissues were stained. Marco (Abcam, ab239369) IHC was performed using a Bond Rx autostainer (Leica Biosystems) with HIER at pH 6.0 for 20 minutes. The Marco primary antibody (ab239369, Abcam, diluted for use at 1.5 µg/ml) and Bond Polymer Refine Detection (Leica Biosystems) were used according to manufacturer's protocol. Both spleen and tumor tissues were stained.

NCR1 IHC was performed using a Bond Rx autostainer (Leica Biosystems) with HIER at pH 9.0 for 20 minutes. The NCR1 primary antibody (ab233558, Abcam, diluted for use at 1.25 µg/ml) and Bond Polymer Refine Detection (Leica Biosystems) were used according to manufacturer's protocol. Both spleen and tumor tissues were stained.

CD19 (Abcam, ab245235) IHC was performed using a Bond Rx autostainer (Leica Biosystems) with HIER at pH 9.0 for 20 minutes. The CD19 primary antibody (ab245235, Abcam, diluted for use at 0.91 µg/ml) and Bond Polymer Refine Detection (Leica Biosystems) were used according to manufacturer's protocol. Both spleen and tumor tissues were stained.

CD206 (MRC1; Invitrogen, PA5-114370) IHC was performed using a Bond Rx autostainer (Leica Biosystems) with HIER at pH 9.0 for 20 minutes. The CD206 primary antibody (PA5-114370, ThermoFisher Scientific, diluted for use at 0.5 µg/ml for spleen and 1 µg/ml for tumor) and Bond Polymer Refine Detection (Leica Biosystems) were used according to manufacturer's protocol. Both spleen and tumor tissues were stained.

After staining, sections were rinsed in dH2O and mounted with Xylene and Cytoseal XYL (ThermoFisher Scientific) mounting medium. Whole slide scanning (40×) was performed on an Aperio AT2 (Leica Biosystems) and all scans were deposited electronically on the Pionyr Pathcore webpage.

CD8a, MARCO, NCR1, CD19 and CD206 Quantification

The tissue sections were analyzed using the image analysis software HALO v3.3.2541.202 (Indica Labs). The images were imported into the HALO database, and brush annotation tool was used to identify the area for analysis (labelled layer 1). The entire spleen and tumor tissue areas were included, excluding any artifact staining, folds, necrotic regions, glass, or skin regions using the scissor annotation tool. IHC analysis was performed on each annotation layer for all markers separately (CD8a, MARCO, NCR1, CD19 and CD206) using the Indica Labs-Area Quantification v2.1.11 algorithm. The algorithm was set to detect the blue pixels from the hematoxylin stain, and brown pixels from the DAB IHC stain. The data was exported as an excel file and the % positive DAB staining over total annotated area was collected for each individual marker and was used to plot the data in prism.

Multiplex Immunofluorescent (IF) Staining and Image Analysis

FFPE sections from mouse spleens and tumors were stained using 5-plex IF panels. Spleens from 6 PI-3008 treated, and 6 isotype treated mice, and tumors from 4 PI-3008 treated, and 4 isotype treated mice were stained and analyzed. All IHC antibodies included in the multiplex mouse spleen panel and the mouse tumor (E0771) panel were first optimized by DAB IHC on FFPE mouse spleen and tumor sections (E0771 tumors). Optimal antibody concentrations and staining conditions were then considered when developing the multiplex panels. Antibodies used were: CD8a from Cell Signaling, 98941S; MARCO from Abcam, ab239369; CD19 from Abcam, ab245235, CD206 (MRC1) from Invitrogen; PA5-114370; NCR1 from Abcam ab233558; and nuclei from Akoya, SKU FP1490.

Sections were subjected to 4 sequential rounds of staining with each primary antibody followed by a secondary HRP-conjugated polymer, and signal amplification using TSA-Opal fluorophores. A heat-induced epitope retrieval step was performed after each round of staining to remove the primary-secondary-HRP complexes. The slides were then counterstained with Spectral DAPI and mounted using anti-fade mounting medium.

Figure 37:
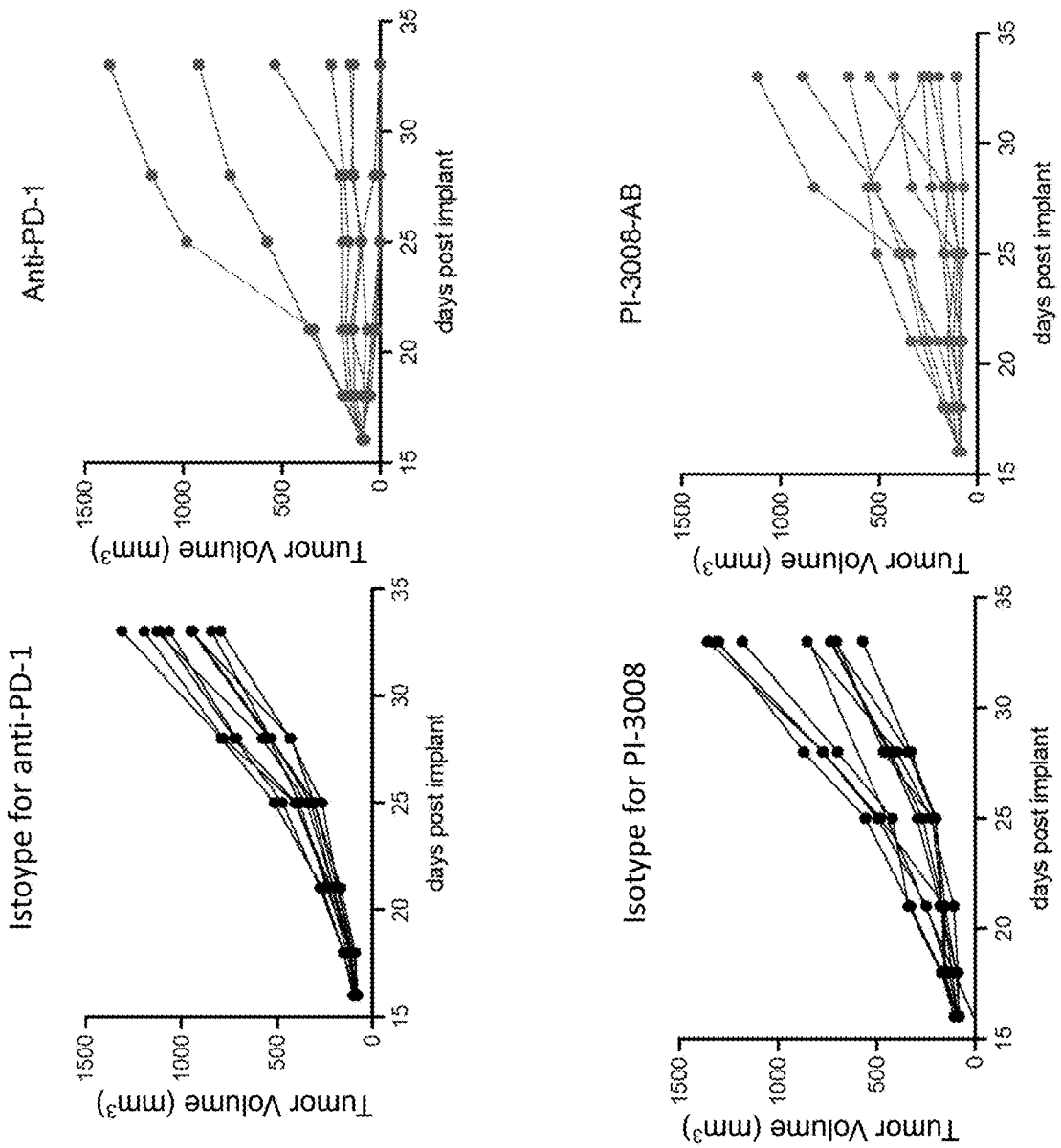
FIG. 37 shows that PI-3008 demonstrated anti-tumor activity as a single agent in the E0771 model. Tumor volumes in isotype control antibody treated mice are shown in the top right and bottom right panels, tumor volumes in PD-1 antibody treated mice are shown in the top left panel, and tumor volumes in PI-3008 antibody treated mice are shown in the bottom left panel.
Figure 38B:
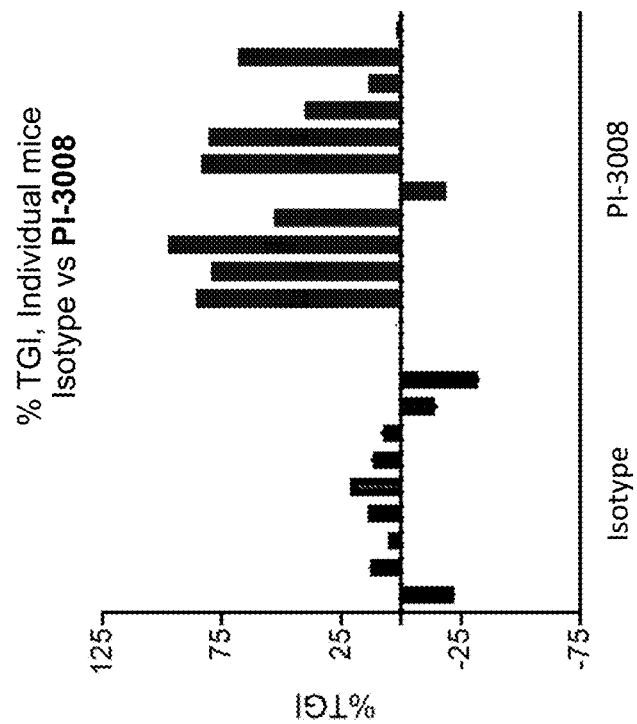
FIG. 38B shows the percentage of tumor growth inhibition (TGI) for isotype antibody and PI-3008.
Figure 38A:
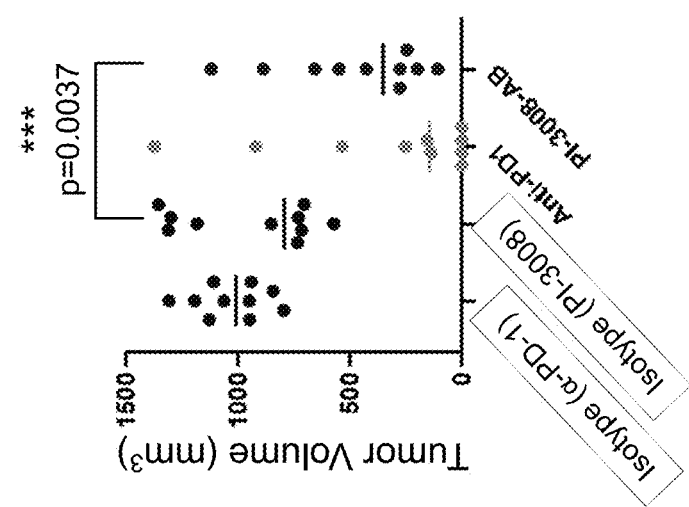
FIG. 38A shows that the mice dosed with PI-3008 showed a statistically significant reduction in tumor volume as compared to isotype controls (p=0.0037).

Stained slides were imaged using the Vectra 3 imaging system (Akoya Biosciences). After a low magnification scan, regions of interest (ROI) were stamped by using the Phenochart viewer (Akoya Bioscience) and these stamps were subsequently scanned at a higher resolution (20×). Four stamps per spleen section were selected by choosing regions where representative white pulp, red pulp and marginal zone areas were included. In the tumor sections, stamps were selected to cover the majority of the tumor area, purposely selecting edge regions and center regions to facilitate comparative analysis of these tumor areas. The acquired ROI image files were opened in InForm (Akoya Biosciences) and there spectrally unmixed followed by removal of auto fluorescent staining. Image analysis was performed in InForm by first manually segmenting the spleen tissue into red pulp, white pulp, and marginal zone. Glass regions were excluded from analysis. Tumor tissues were manually segmented to just include tumor and exclude skin, glass, and necrotic regions. Nuclei were identified and segmented using the DAPI counterstain, followed by training of the cell phenotyping algorithm for the identification of the cell types of interest. The data generated by InForm was then loaded into R studio and using the phenoptrReports package (Akoya Biosciences) from which data including cell counts, cell percentages, cell densities, and nearest neighbor analysis for the different tissue compartments was generated Results PI-3008-AB also demonstrated anti-tumor activity as single agent in the orthotopic E0771 model as compared to isotype control antibodies (FIG. 37). At the end of the study on day 33, mice dosed with PI-3008 showed a statistically significant reduction in tumor volume as compared to isotype controls (p=0.0037) (FIG. 38A). The percentage of tumor growth inhibition (TGI) is shown in FIG. 38B for isotype antibody and PI-3008.

Figure 38C:
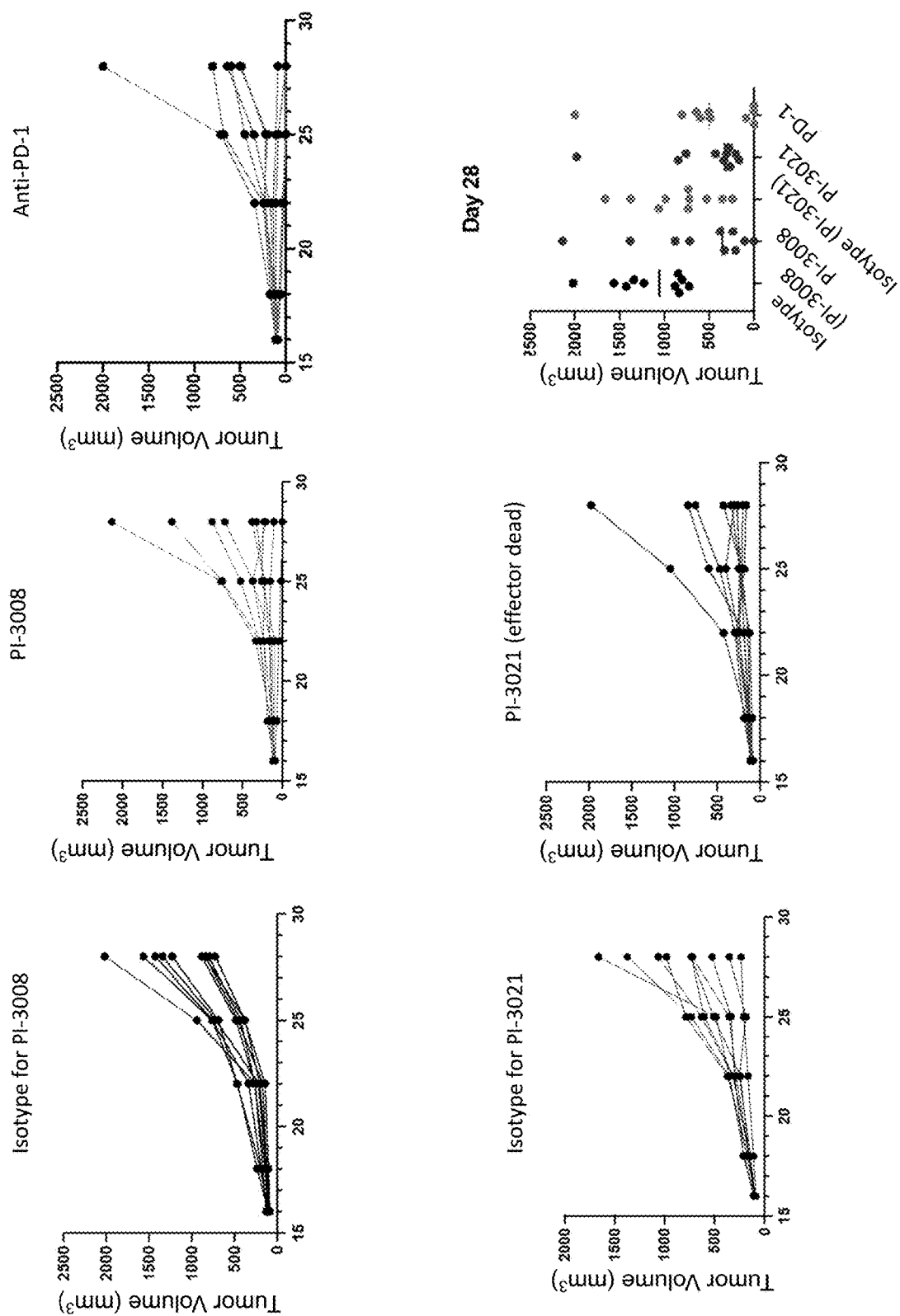
FIG. 38C shows that PI-3008 and effector dead PI-3021 both have anti-tumor activity in the E0771 model.

In addition, both PI-3008 and effector dead PI-elicited similar single agent activity in the orthotopic E0771 Model (FIG. 38C). Individual panels show the tumor volume in individual mice after treatment with the indicated antibody or isotypes control. The upper right panel shows the tumor valiums in each mouse at Day 28. The lower right panel shows the antibody concentration in serum for PI-3008 and PI-3021.

PK-PD-Efficacy Assay

Figure 39B:
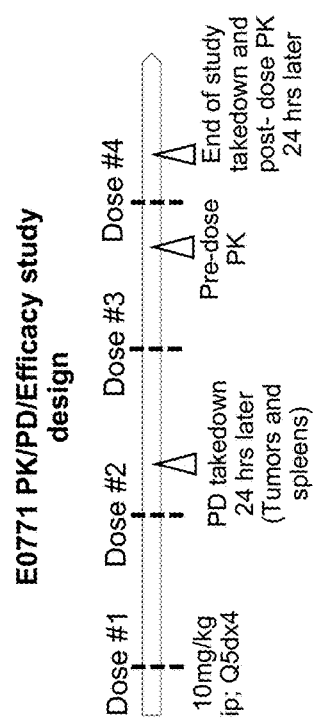
FIG. 39B shows the tumor volume in isotype control treated mice and PI-3008 treated mice over the course of the study.
Figure 39C:
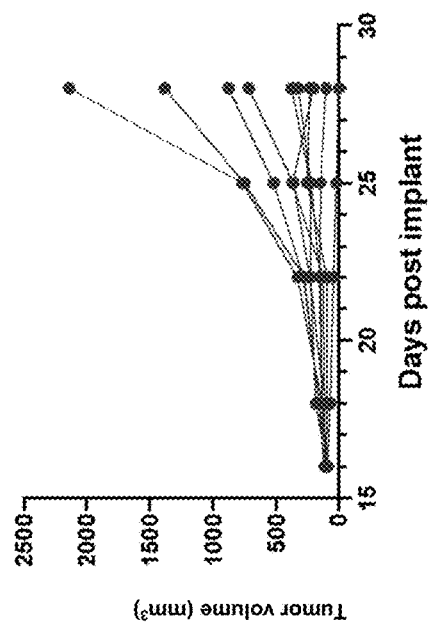
FIG. 39C provides individual tumor volumes in the isotype control mice.
Figure 39D:
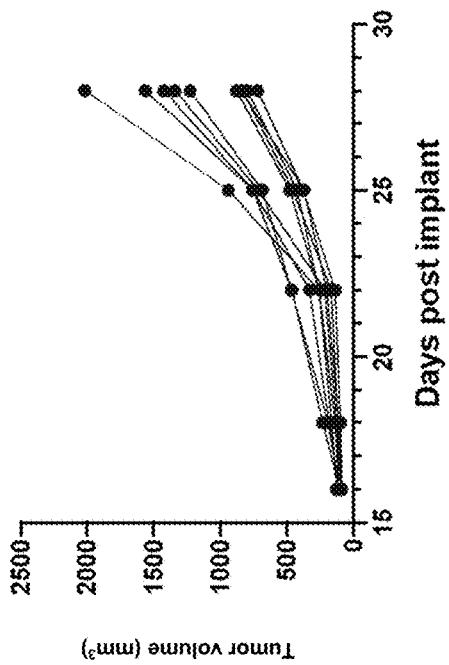
FIG. 39D provides individual tumor volumes in the PI-3008 mice.
Figure 39F:
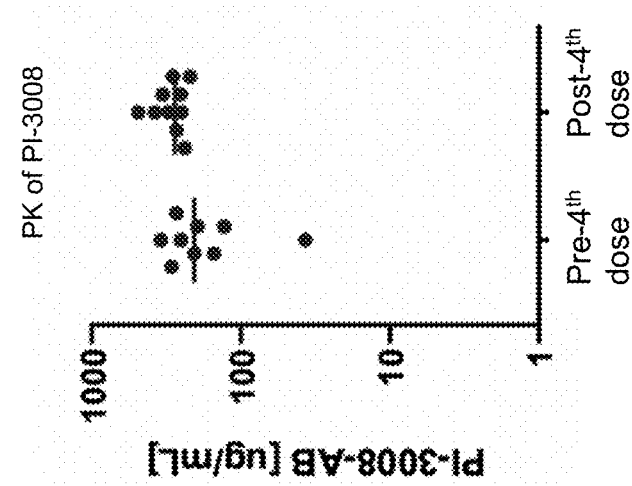
FIG. 39F provides the serum levels of PI-3008.
Figure 39E:
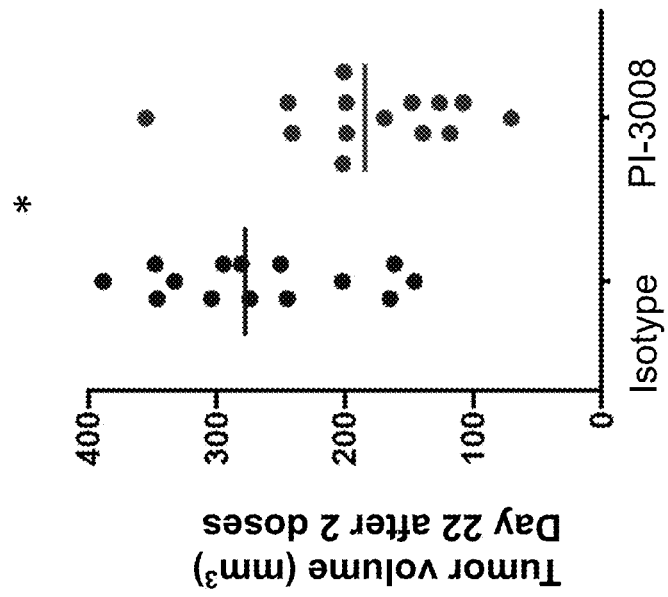
FIG. 39E provides the final tumor volumes at Day 28.

The in vivo PK-PD study in E0771 showed that PI-3008 elicited single agent activity compared to the isotype antibody after 4 doses of treatment. Significant differences in tumor size was observed starting at the second dose (FIG. 39B). Individual tumor volumes in the isotype control mice are provided in FIG. 39C. Individual tumor volumes in the PI-3008 mice on are provided in FIG. 39D. The final tumor volumes at Day 28 are provided in FIG. 39E. In addition, the serum levels of PI-3008 maintained robust exposure until the end of the study (FIG. 39F).

Figure 40B:
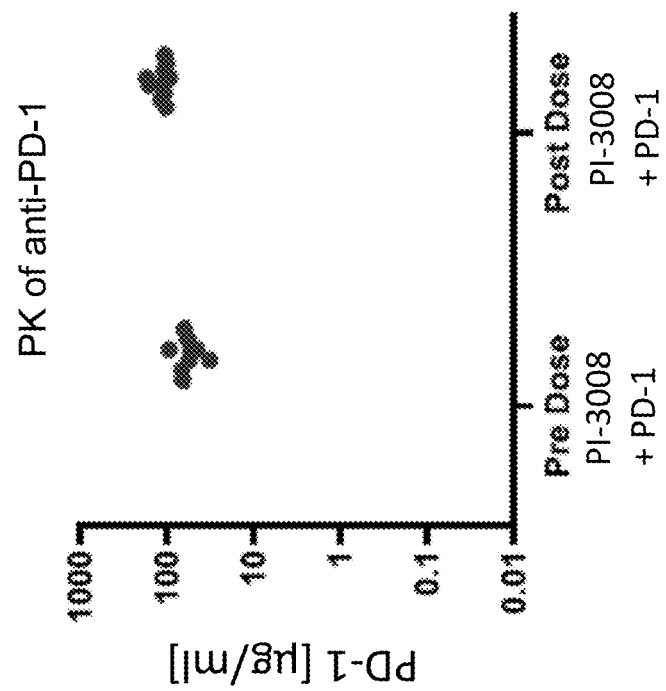
FIG. 40B provides the PD-1 antibody serum concentrations in combination experiments.
Figure 40A:
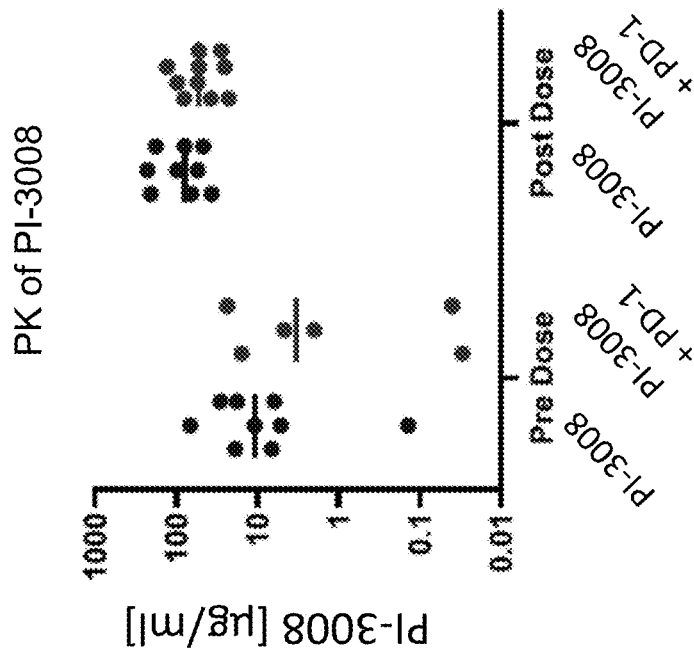
FIG. 40A provides the PI-3008 serum concentrations in mono and combination experiments with PD-1 antibody.

The serum concentrations of anti-PD-1 when combined with PI-3008 were also in the expected exposure range as seen in previous studies when dosed as single agent (FIGS. 40A and 40B). FIG. 40A provides the PI-3008 concentrations in mono and combination experiments with PD-1 antibody, while FIG. 40B provides the PD-1 concentrations in combination experiments.

PI-3008 also activated intra-tumoral immunity in the E0771 model, as seen by an increase in CD8+ T cells and NK cells in the TME after administration of the antibody. FIG. 41A provides IHC images of CD8 T cells and NCR1 (NK cells) stained with DAB after administration of isotype control or PI-3008. FIG. 41B provides quantification of the cytotoxic CD8+ T cells and NK cells in the tumor area by HALO image analysis of the IHC staining. PI-3008 promoted changes in the TME indicative of improved anti-tumor response. The anti-MARCO antibody increased MHCII$^{High}$ Ly6C+ monocytes, DC infiltration, and NK1.1 NK cells in the TME by flow cytometry (FIG. 41C). Without wishing to be bound by theory, increases in these cells may increase intra-tumoral immune activation and improve antigen presentation in the TME.

Figure 41D:
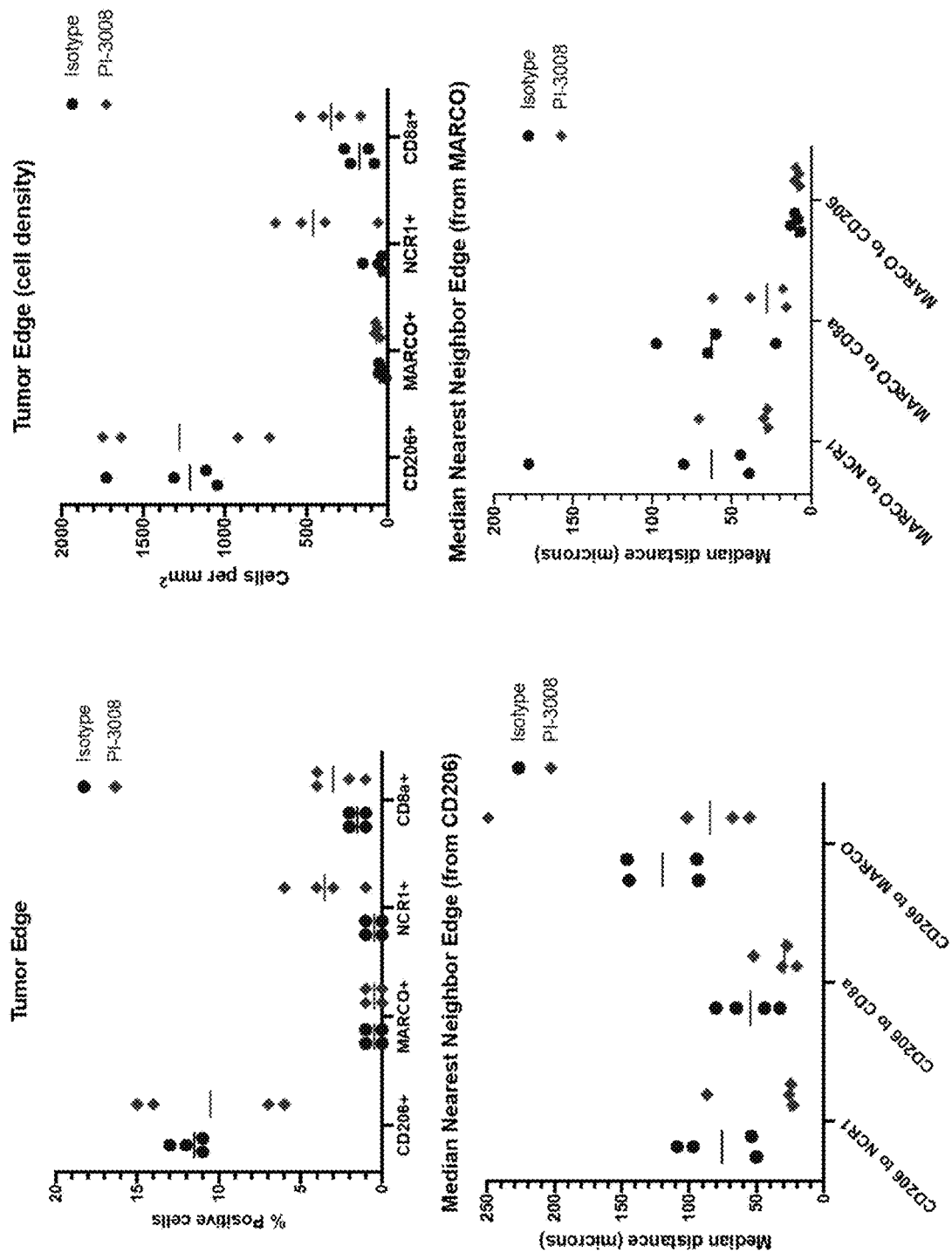
FIG. 41D provides quantification of CD206+, cells, MARCO+ cells, NCR1+ cells, and CD8a+ cells at the indicated region.

Increases in CD8+ T cells and NK cells in the TME were also observed by multiplex IF. FIG. 41D provides quantification of CD206+, cells, MARCO+ cells, NCR1+ cells, and CD8a+ cells at the tumor edge, the cell density of the indicated cell at the tumor edge, the median distance to the nearest neighbor from CD206 and the indicated cell types, and the median distance to the nearest neighbor from MARCO and the indicated cell types in mice after treatment with isotype antibody or PI-3008. Data for isotype antibody is provided on the left of each data pair with circle icons, while data for PI-3008 is provided on the right of each data pair with diamond icons. This multiplex analysis showed that NK cells and CD8T cells are increased in the tumors after anti-MARCO treatment. The spatial mapping showed a closer distance of CD8+ T cells and NK cells with MARCO+ cells in the TME in the PI-3008 treated tumors compared to isotype.

Figure 42A:
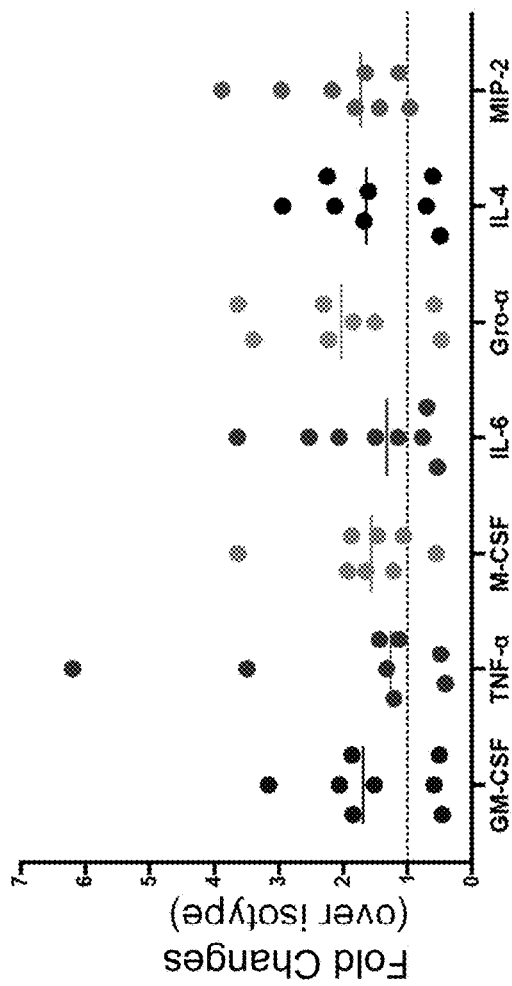
FIG. 42A provides expression levels of the indicated proinflammatory cytokines and chemokines induced by PI-3008 in the E0771 model tumor supernatants.
Figure 42B:
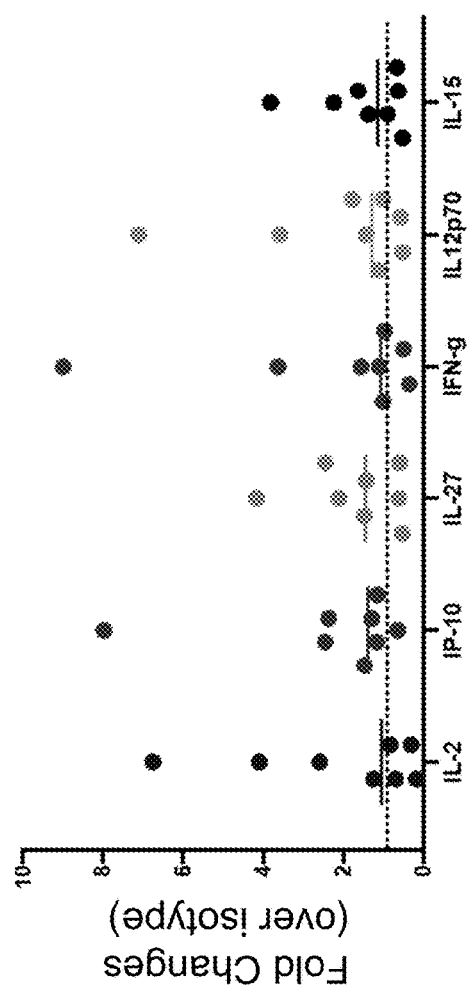
FIG. 42B provides expression levels of the indicated cytokines associated with T-cell activation and NK cells activation observed at Day 1 post-dose 2 in the tumor supernatants.

Proinflammatory cytokines and chemokines induced by PI-3008 in the E0771 model tumor supernatants were also assessed (FIG. 42A). PI-3008 treatment induced cytokines and chemokines in the tumor supernatants in the E0771 model. The same cytokines were induced in the E0771 model as identified via RNAseq in the CT26 study. Cytokines associated with T-cell activation and NK cells activation were also observed at Day 1 post-dose 2 in the tumor supernatants (FIG. 42B).

Figure 43:
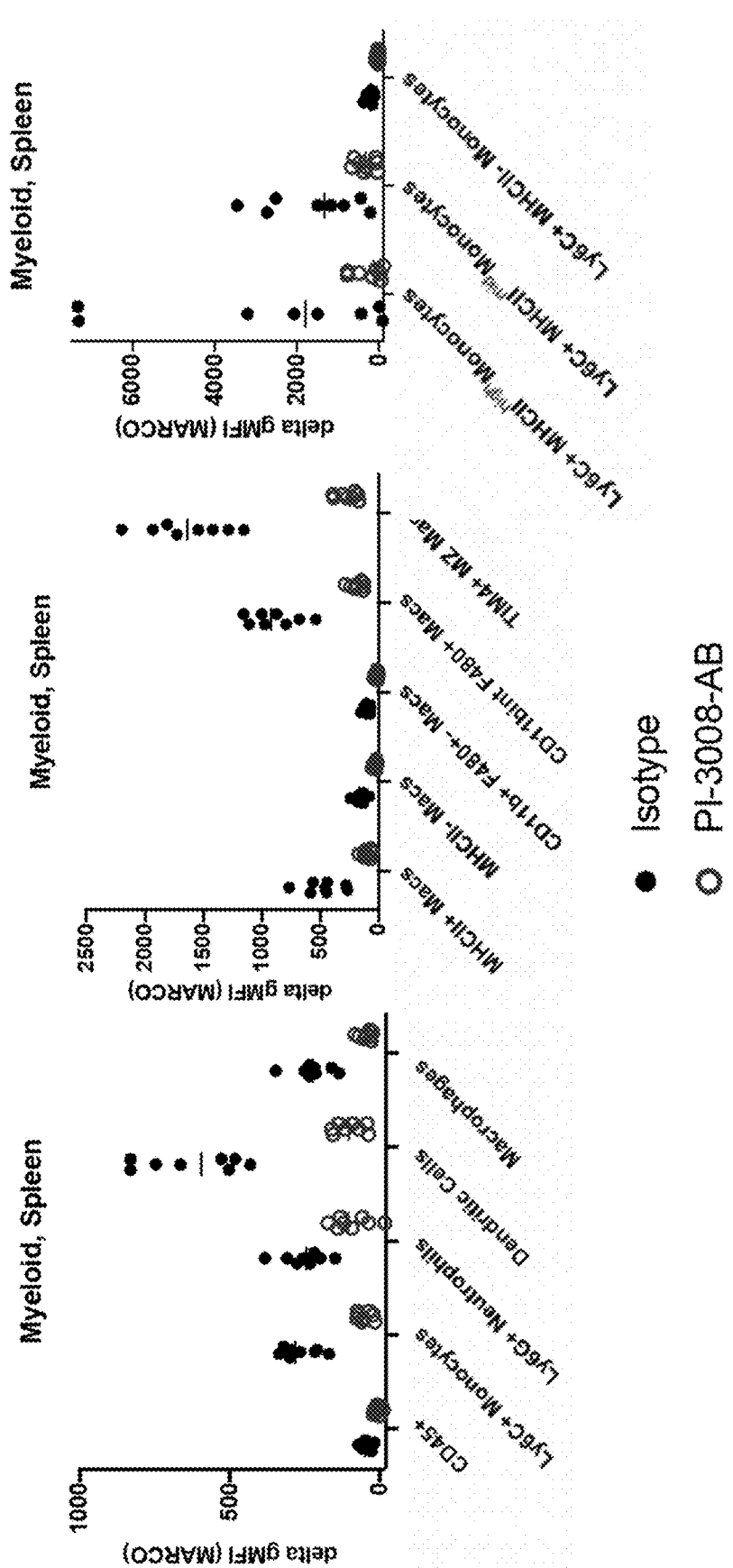
FIG. 43 provides the results of the receptor occupancy assay.

MARCO is highly expressed in the spleen, primarily on marginal zone macrophages, monocytes and dendritic cells (FIG. 43). The samples from mice treated with isotype antibody are provided on the left of each sample pair, the samples from mice treated with PI-3008 antibody are provided on the right of each sample pair. The data in FIG. 43 is plotted based on the delta gMFI between the PI-3008-PE and the mIgG2a-PE isotype antibody used in the flow cytometry analysis. In this assay, the MARCO flow antibody competes with the previously administered therapeutic PI-3008 for binding on the MARCO+ cells in the samples. Thus, receptor occupancy and competition were expected and observed in the samples from the PI-3008 treated mice, provided on the right side of the sample pairs, as evidenced by the low delta gMFI levels indicating low anti-MARCO binding in the flow assay (FIG. 43). No receptor occupancy and competition for MARCO staining in the flow cytometry assay was observed in the isotype treated mice samples, provided on the left side of the sample pairs, as evidence by high delta gMFI levels indicating high anti-MARCO binding in the flow assay (FIG. 43). Higher RO and lower gMFI in PI-3008 treated samples as compared to isotype treated samples for each myeloid target population confirmed the expression of MARCO on each specific population. The isotype treated group thus shows MARCO expression (using the PI-3008 flow antibody) to detect MARCO levels on the myeloid target population when no therapeutic antibody is present. MARCO expression was observed on dendritic cells, CD11bint F480+ macrophages, TM4+ marginal macrophages, Ly6C+MHCII$^{High}$ monocytes, and Ly6C+MHCI-I$^{mid}$ monocytes. MARCO expression was highest on the marginal zone macrophages, identified by CD11bintF480+ and TIM4+ marginal zone macrophages. MARCO was also expressed on the MHCII+ monocytes. Receptor occupancy was achieved in the PI-3008 antibody treated group (24 hours following $2^{nd}$ dose) in those myeloid populations.

In sum, FIG. 43 shows that the delta gMFI in the isotype group showed expression of MARCO receptor in the spleen and the delta gMFI on the PI-3008 treated groups confirmed that PI-3008 was bound on the MARCO positive myeloid cells and thus could not be detected with the PI-3008 flow antibody. The samples from mice treated with isotype antibody are provided on the left of each sample pair, the samples from mice treated with PI-3008 antibody are provided on the right of each sample pair.

PI-3008 did not affect the myeloid populations in the spleen but potentially affected B-cells 24 hours after the second dose. As shown in FIGS. 44A, 44B, and 44C, PI-3008 treatment did not alter the MARCO+ myeloid or lymphoid cell populations in the spleen. However, PI-3008 treatment did result in a decrease of CD19+ B-cells and plasma B-cells in the spleen (FIG. 44D). The samples from mice treated with isotype antibody are provided on the left of each sample pair, the samples from mice treated with PI-3008 antibody are provided on the right of each sample pair.

Figure 45:
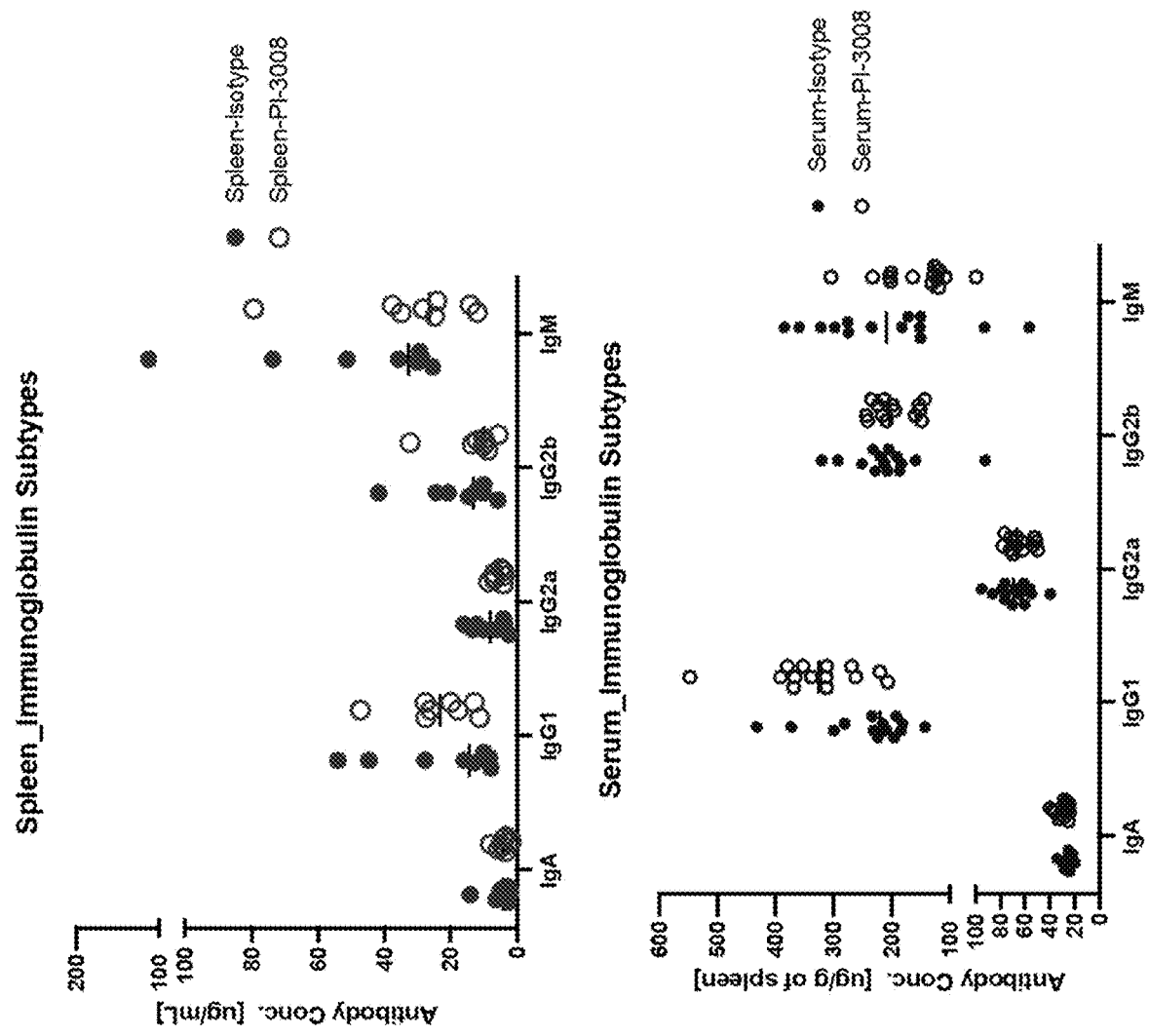
FIG. 45 provides quantification of the indicated immunoglobulin types in the spleen and serum after treatment with isotype control antibody or PI-3008.

PI-3008 treatment decreased IgM production and increased IgG production in the spleen and serum at Dose 2 (FIG. 45).

Figure 46:
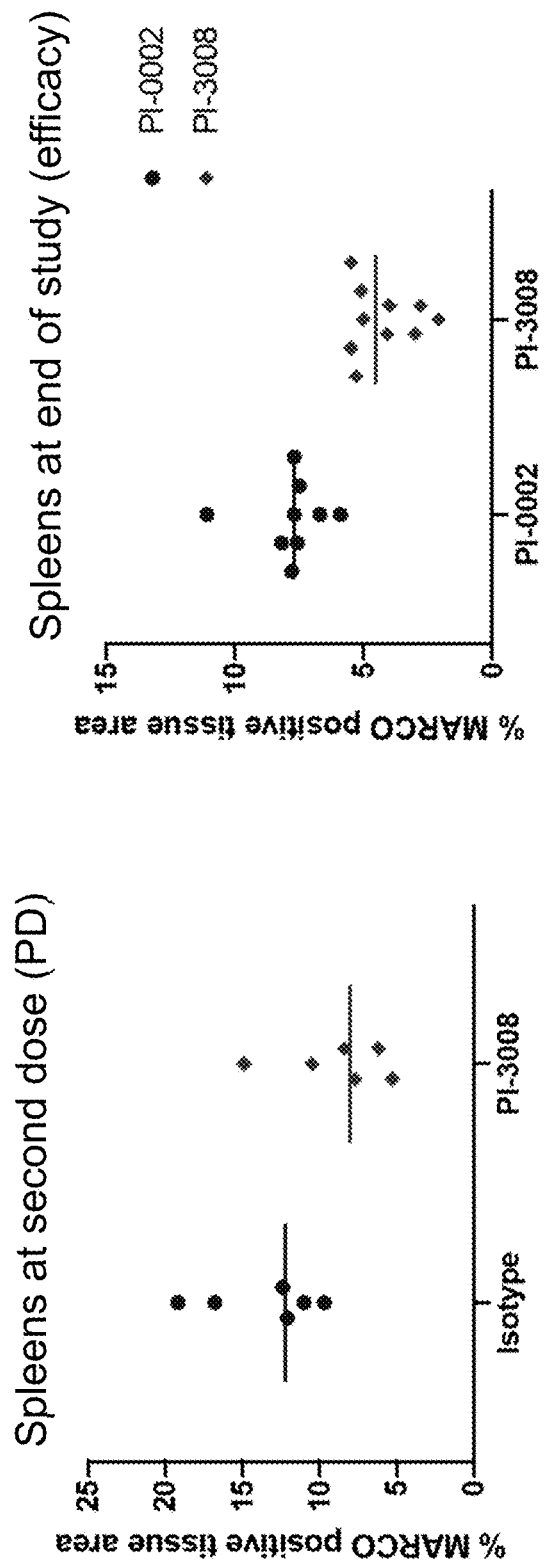
FIG. 46 provides quantification of MARCO positive cells in the spleens after the second dose and at the end of the study after treatment with isotype control antibody or PI-3008.
Figure 47A:
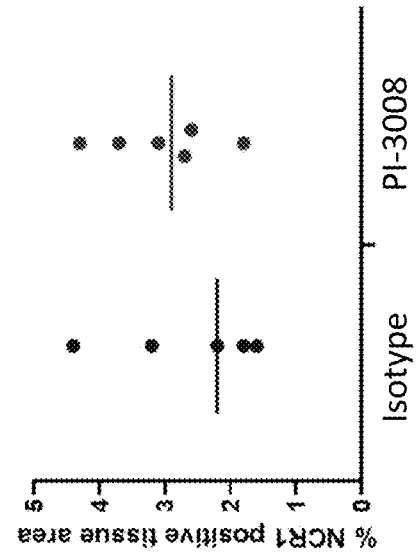
FIG. 47A provides quantification of the indicated cell type in the spleen after treatment with isotype control antibody or PI-3008.
Figure 47B:
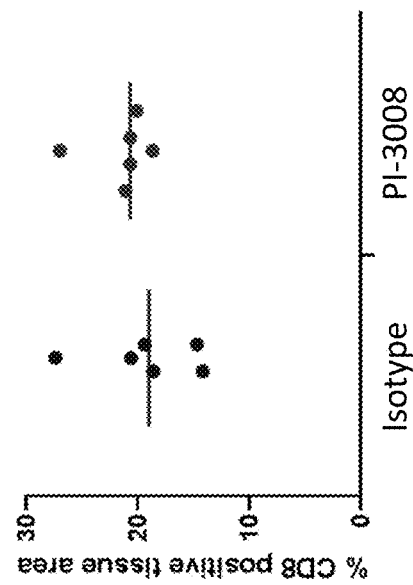
FIG. 47B provides quantification of the indicated cell type in the spleen after treatment with isotype control antibody or PI-3008.
Figure 47C:
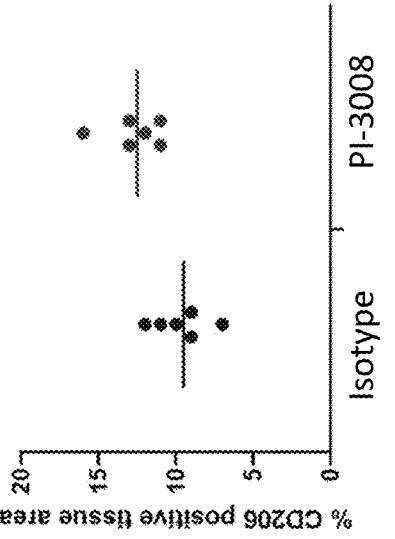
FIG. 47C provides quantification of the indicated cell type in the spleen after treatment with isotype control antibody or PI-3008.
Figure 47D:
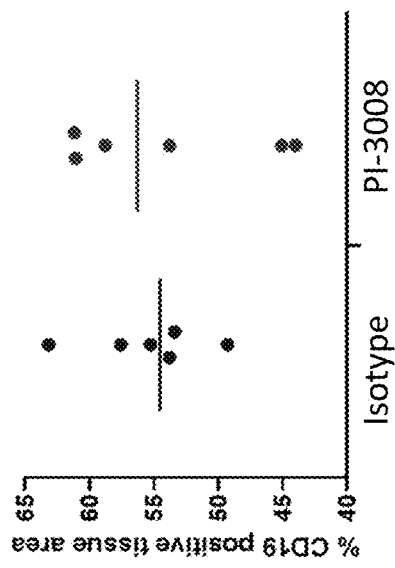
FIG. 47D provides quantification of the indicated cell type in the spleen after treatment with isotype control antibody or PI-3008.

MARCO expression on the marginal zone macrophages decreased with PI-3008 treatment in spleen when measured by IHC (FIG. 46). MARCO+ cells in the spleen were assessed at the second dose and at the end of the study. PI-3008 mice showed a decreased number of MARCO+ marginal zone macrophages as compared to isotype antibody treated mice. Monoplex IHC was also used to determine changes in the spleen after PI-3008 treatment (FIG. 47A-D). An increase in CD8+ T cells and NK cells was observed in the total area after PI-3008 treatment (FIGS. 47A and 47B). The CD19+ cell population was variable and challenging to measure by IHC (FIG. 47C). A significant increase in CD206 (red pulp macrophages) was observed after PI-3008 treatment (FIG. 47D). The samples from mice treated with isotype antibody are provided on the left of each sample pair, the samples from mice treated with PI-3008 antibody are provided on the right of each sample pair.

The percentage positive cells per tissue compartment after treatment with isotype antibody and PI-3008 was determined via image analysis of multiplex IF (FIG. 48A-D). A decrease in MARCO in the red pulp after PI-3008 therapy and in total areas was observed (FIG. 48A). A small decrease in CD19 across all tissue compartments was observed in the total area after PI-3008 treatment (FIG. 48B). An increase in CD8a across all tissue compartments was observed after PI-3008 treatment (FIG. 48C). A small increase in CD206 in the red pulp was observed after PI-3008 treatment (FIG. 48D). The samples from mice treated with isotype antibody are provided on the left of each sample pair, the samples from mice treated with PI-3008 antibody are provided on the right of each sample pair.

Day 2 and Day 5 PD Sample Analysis

Figure 59:
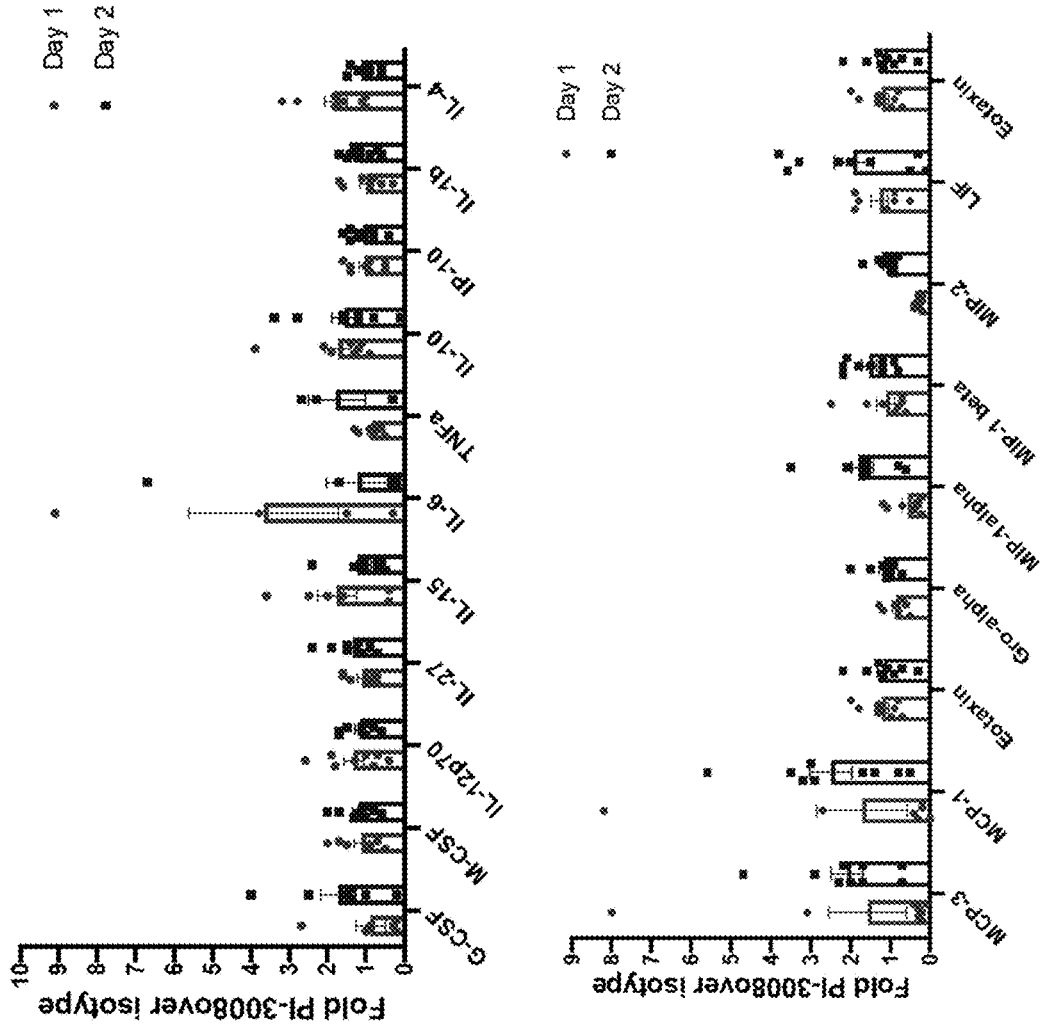
FIG. 59 shows that PI-3008 treatment induced the indicated cytokines and chemokines in the spleen in the E0771 model at early timepoints.

Digested supernatants and plasma from tumors, spleen and blood sampled at 2 days and 5 days post antibody treatment were analyzed via Luminex. Anti-MARCO treatment induced cytokines and chemokines in the tumor supernatants in the E0771 model at early timepoints (FIG. 58 and FIG. 59). Samples from Day 2 are shown on the right, samples from Day 5 are shown on the left. Changes in cytokines and chemokines were observed at both timepoints, G-CSF, IL27, IL10, and TNFα increased at day 2, IL12p70, IL10, IL6, and IL4 increased at day 5. Chemokines involved in migration and chemotaxis were increased in the spleen at day 2 after the first antibody dose.

Anti-MARCO treatment also modulated IgG1 production in the mouse tumor (Table 28).

TABLE 28

| | IgA | IgG1 | IgG2a | IgG2b | IgM | Total IgG |
|---|---|---|---|---|---|---|
| Day 2 | | | | | | |
| Isotype (µg/ml) | 1.22 | 14.67 | 2.39 | 9.58 | 4.83 | 26.65 |
| PI-3008 (µg/ml) | 1.12 | 19.42 | 2.48 | 8.48 | 4.57 | 30.38 |
| Day 5 | | | | | | |
| Isotype (µg/ml) | 1.10 | 20.61 | 1.69 | 13.56 | 6.54 | 35.86 |
| PI-3008 (µg/ml) | 1.20 | 15.52 | 2.25 | 12.34 | 6.59 | 30.12 |

Anti-MARCO treatment decreased IgM production at day 2 and IgG1 decreased slightly at day 5 in the spleen (Table 29).

TABLE 29

| | IgA | IgG1 | IgG2a | IgG2b | IgM | Total IgG |
|---|---|---|---|---|---|---|
| Day 2 | | | | | | |
| Isotype (µg/ml) | 4.36 | 15.50 | 5.08 | 12.73 | 43.58 | 33.31 |
| PI-3008 (µg/ml) | 3.65 | 14.02 | 3.18 | 10.69 | 28.13 | 27.88 |
| Day 5 | | | | | | |
| Isotype (µg/ml) | 1.90 | 14.58 | 1.46 | 7.74 | 18.37 | 23.77 |
| PI-3008 (µg/ml) | 2.43 | 10.99 | 2.01 | 9.63 | 17.22 | 22.62 |

Anti-MARCO treatment decreased IgG1 and IgG2b in the plasma after PI-3008 treatment (Table 30).

TABLE 30

| | IgA | IgG1 | IgG2a | IgG2b | IgM | Total IgG |
|---|---|---|---|---|---|---|
| Isotype (µg/ml) | 21 | 16 | 13 | 45 | 6 | 74 |
| PI-3008 (µg/ml) | 18 | 6 | 13 | 37 | 6 | 56 |

Figure 60:
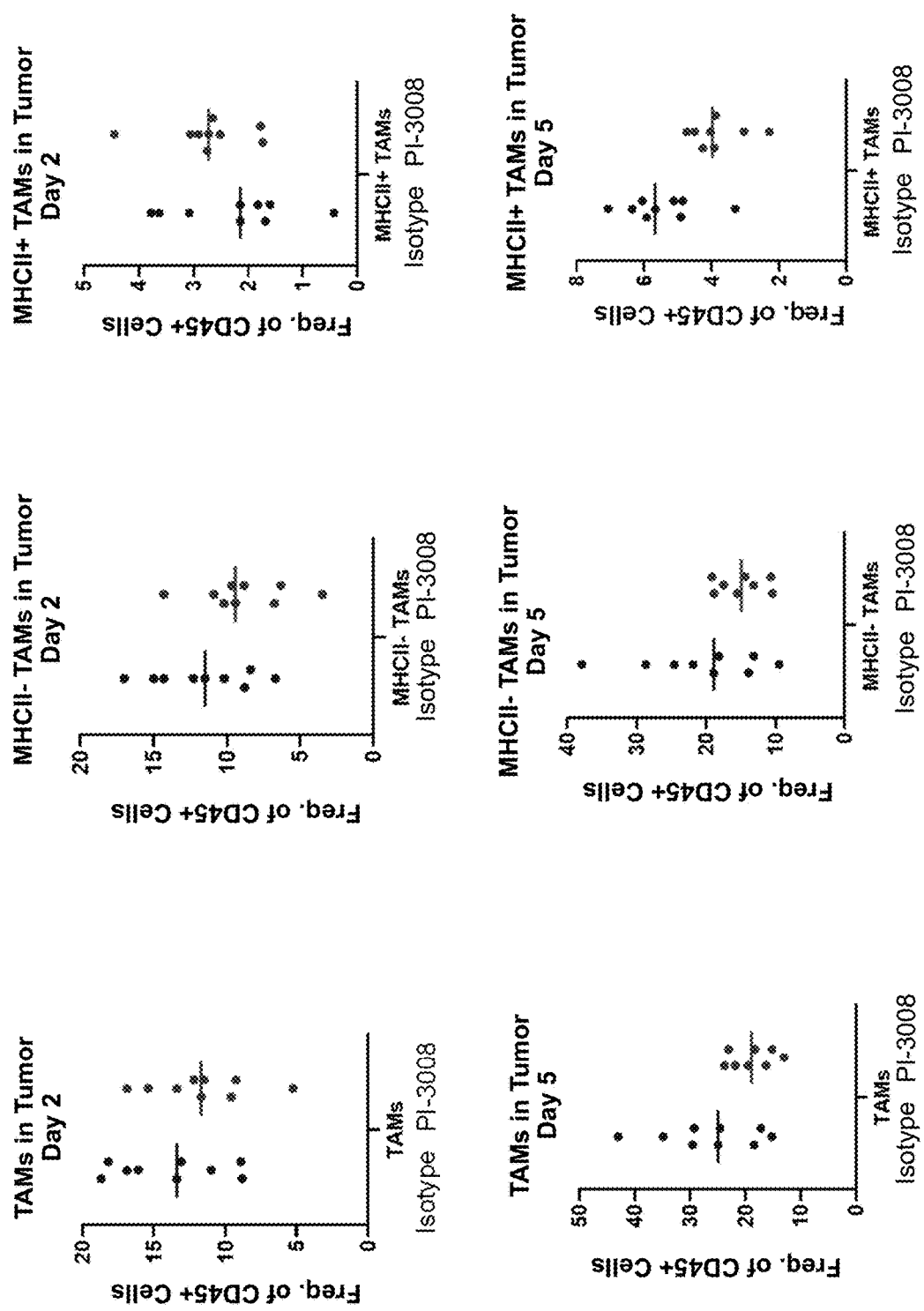
FIG. 60 provides quantification of the indicated tumor myeloid cell types at Day 2 and Day 5 post-administration of a isotype control antibody or PI-3008.
Figure 61:
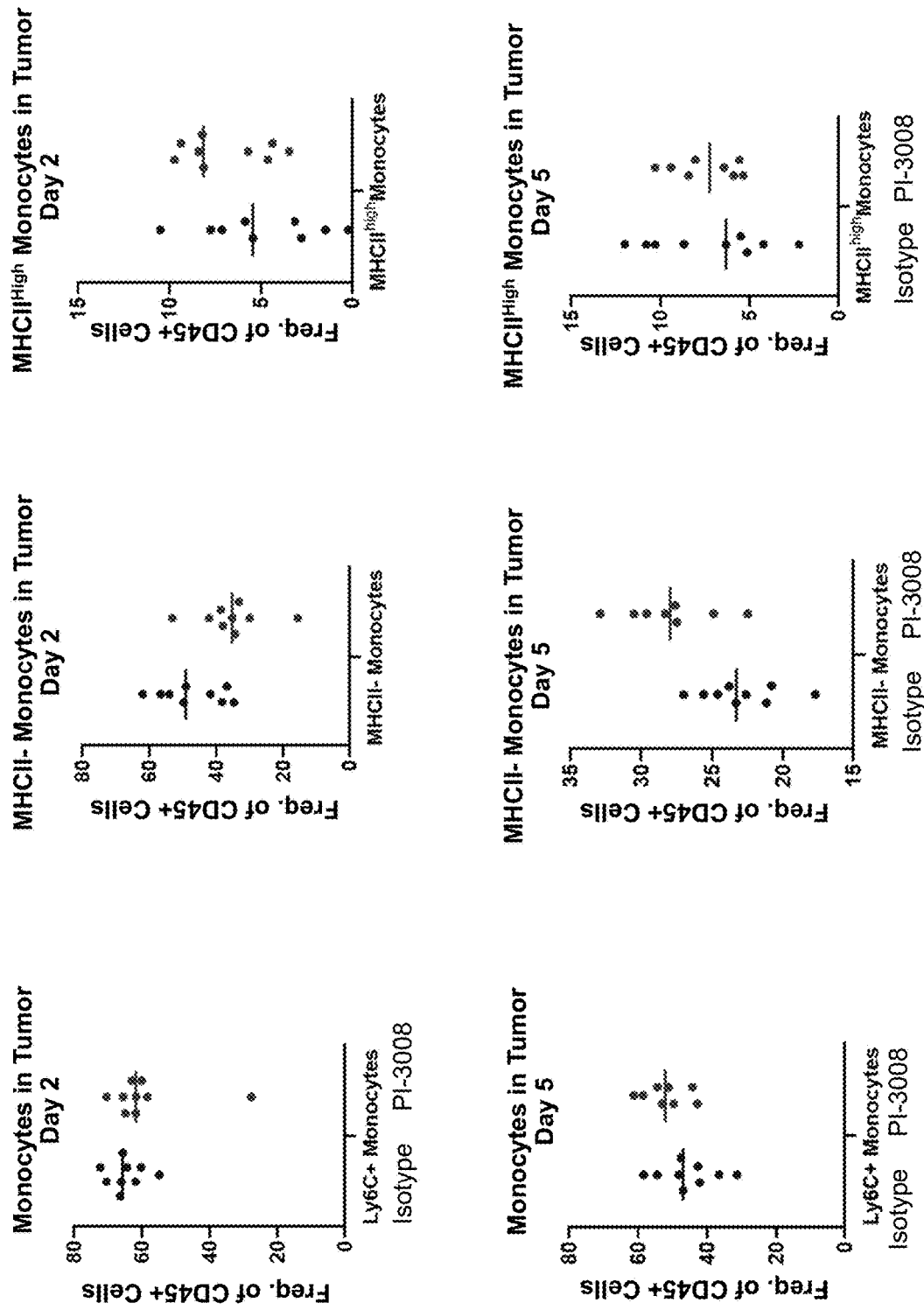
FIG. 61 provides quantification of the indicated tumor myeloid cell types at Day 2 and Day 5 post-administration of a isotype control antibody or PI-3008.

First, tumor myeloid cells were assessed at Days 2 and 5 after one does of MARCO antibody treatment. Anti-MARCO affected the total number of TAMs (decreased, FIG. 60) and monocytes (increased, FIG. 61) in tumors at D2 and D5. Anti-MARCO also reprogramed TAMs from immunosuppressive MHCII− to pro-inflammatory MHCII+ at day 2 (FIG. 60) and monocytes from immunosuppressive MHCII− to proinflammatory MHCII+ at D2 (FIG. 61).

Figure 62:
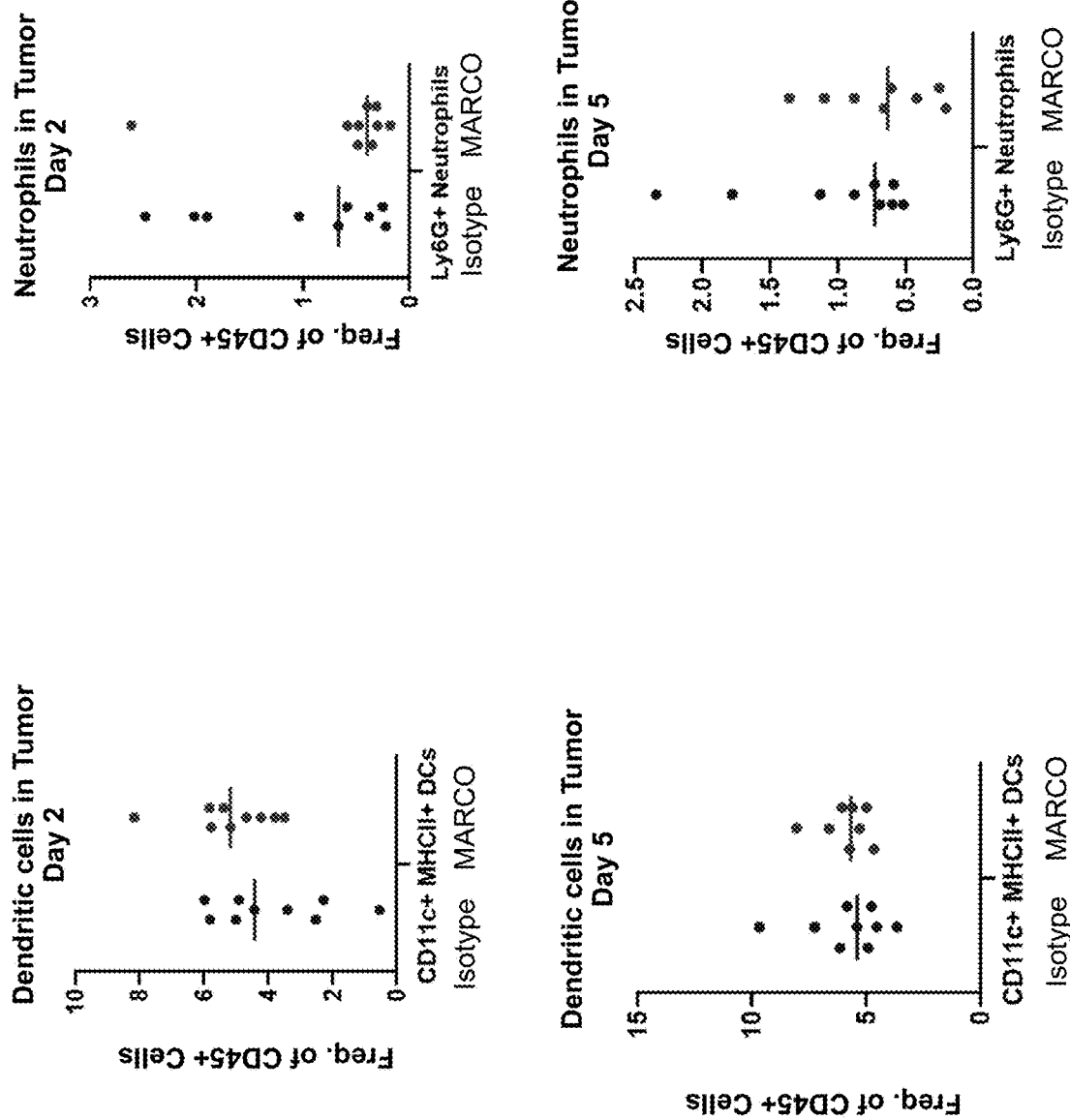
FIG. 62 provides quantification of the indicated tumor myeloid cell types at Day 2 and Day 5 post-administration of a isotype control antibody or PI-3008.

Anti-MARCO increased CD11c+ MHCII+ DCs at D2 and D5, and slightly decreased Ly6G+ neutrophils at D2 and D5 (FIG. 62). In summary, in the tumor myeloid cells, anti-MARCO antibody increased pro-inflammatory monocytes and DCs, and decreased tumor associated neutrophils (TANs) and TAMs. In addition, 2 days after first dose, anti-MARCO reprogrammed MHCII− TAMs to MHCII+ TAMs, and MHCII− monocytes to MHCII+ monocytes.

Figure 63:
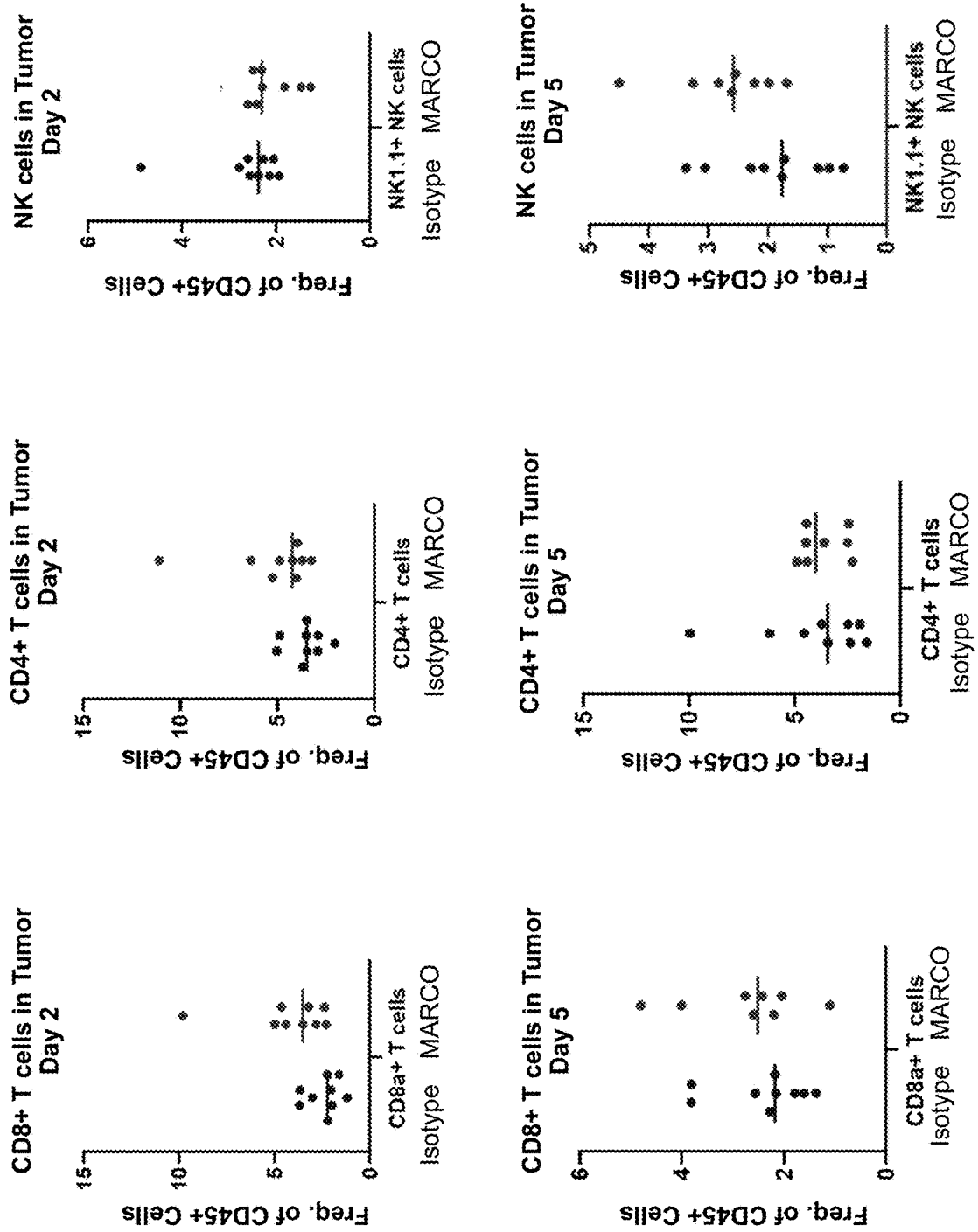
FIG. 63 provides quantification of the indicated tumor lymphoid cell types at Day 2 and Day 5 post-administration of a isotype control antibody or PI-3008.

Next, tumor lymphoid cells were assessed at Days 2 and 5 after one dose of MARCO antibody treatment. Anti-MARCO increased CD8+ T cells and CD4+ T at day 2 and 5 in the tumors (FIG. 63). Anti-MARCO also increased NK1.1 NK cells at day 5 in the tumors (FIG. 63).

Figure 64:
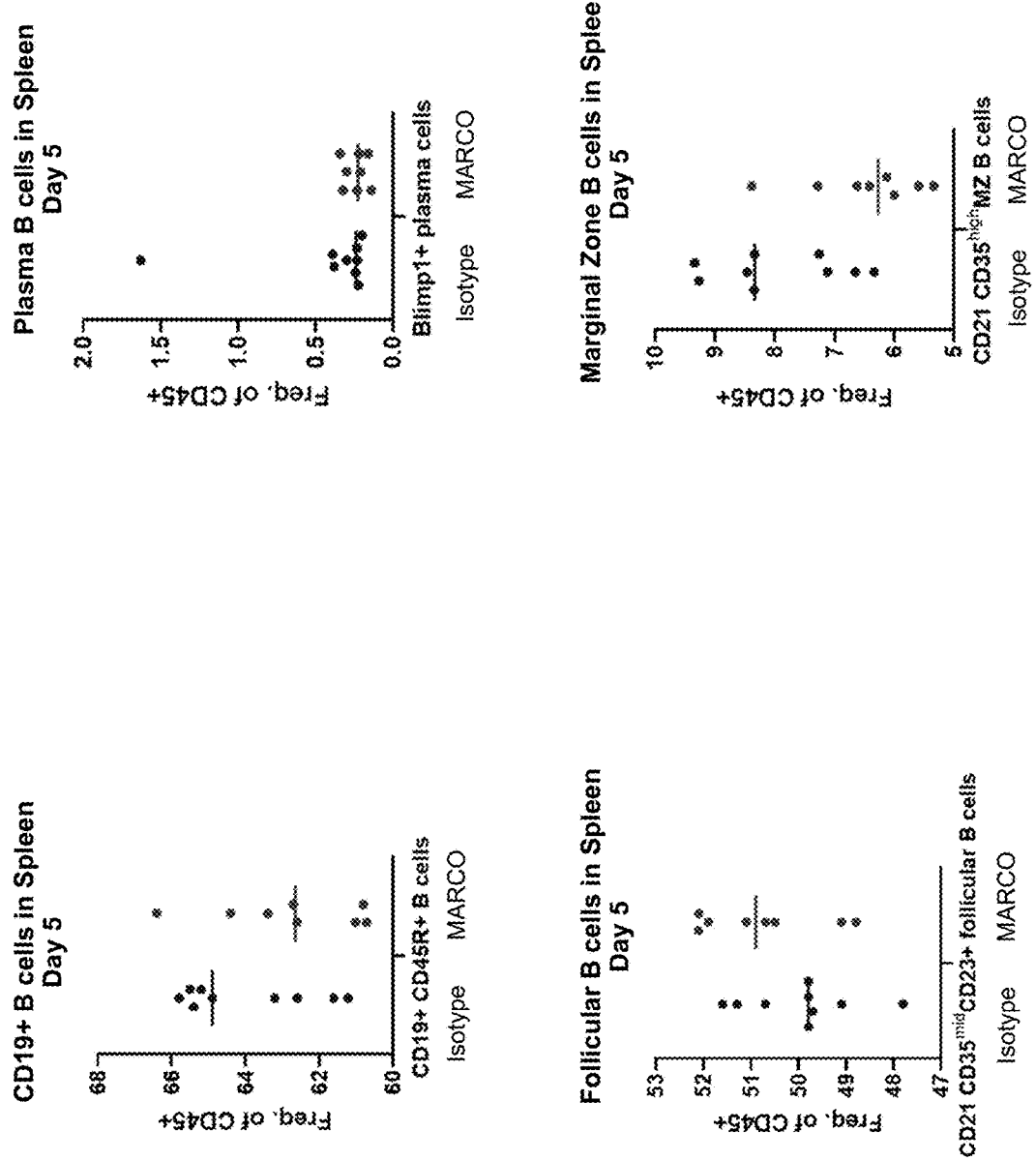
FIG. 64 provides quantification of the indicated spleen lymphoid cell types at Day 5 post-administration of a isotype control antibody or PI-3008.
Figure 65:
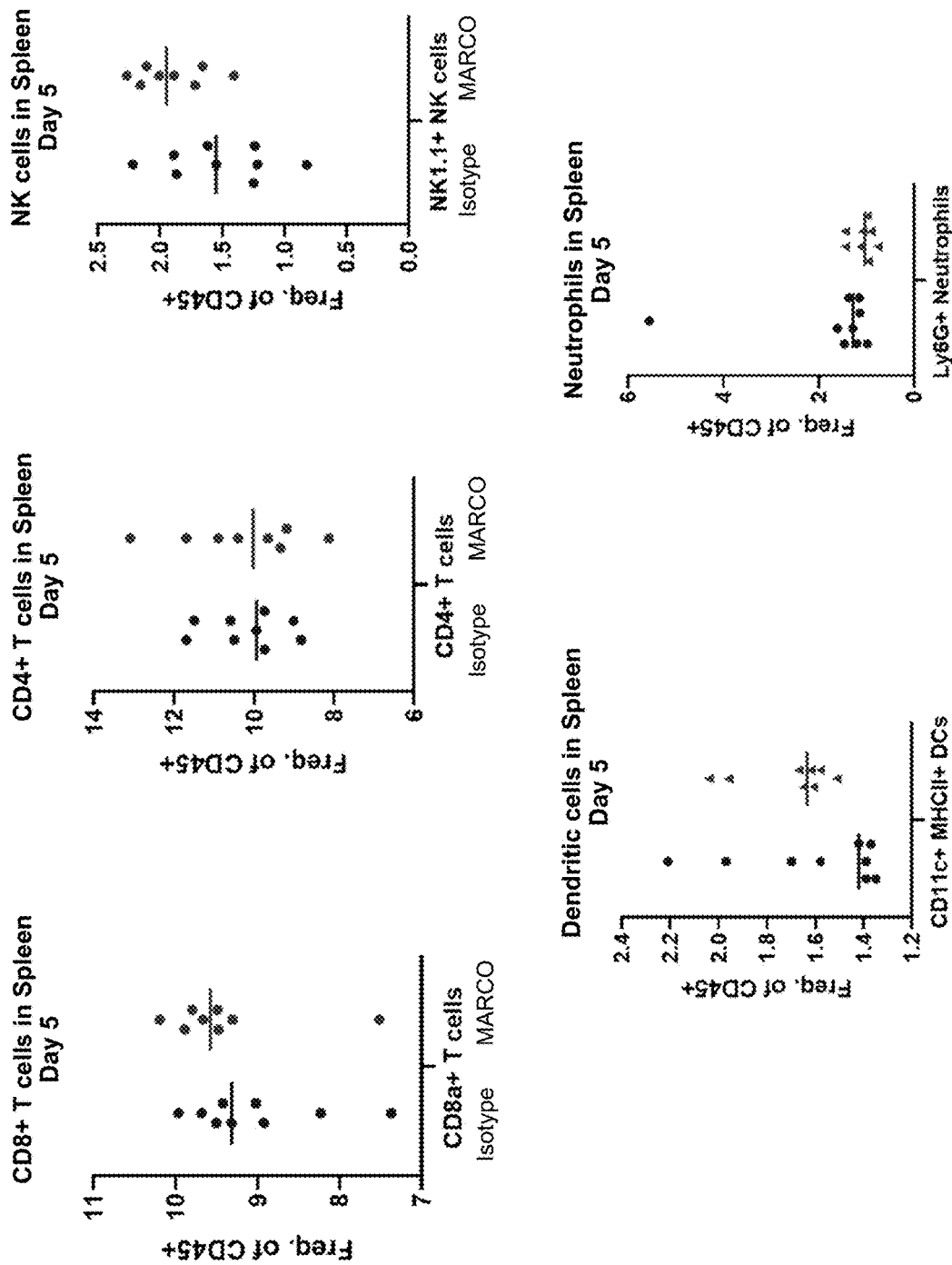
FIG. 65 provides quantification of the indicated spleen lymphoid or myeloid cell types at Day 5 post-administration of a isotype control antibody or PI-3008.

Next, spleen lymphoid cells were assessed at Days 2 and 5 after 1 dose of MARCO antibody treatment. Anti-MARCO decreased CD19+ B cells at both days and did not change Plasma B Cells (FIG. 64 and data not shown). Anti-MARCO increased follicular B cells and decreased marginal zone B cells at day 5 in the spleen (FIG. 64). Anti-MARCO affected B-cell populations in the spleen by decreasing CD19+ B-cells, decreasing marginal zone B-cells, and increasing follicular B cells at day 5 (FIG. 64). Anti-MARCO increased splenic CD8+ and CD4+ T cells at both days (FIG. 65 and data not shown). Anti-MARCO did not change NK1.1 NK cells at day 2, but increased them at day 5 (FIG. 65 and data not shown). Anti-MARCO also increased splenic DCs, and did not alter neutrophil levels in the spleen (FIG. 65).

Figure 66:
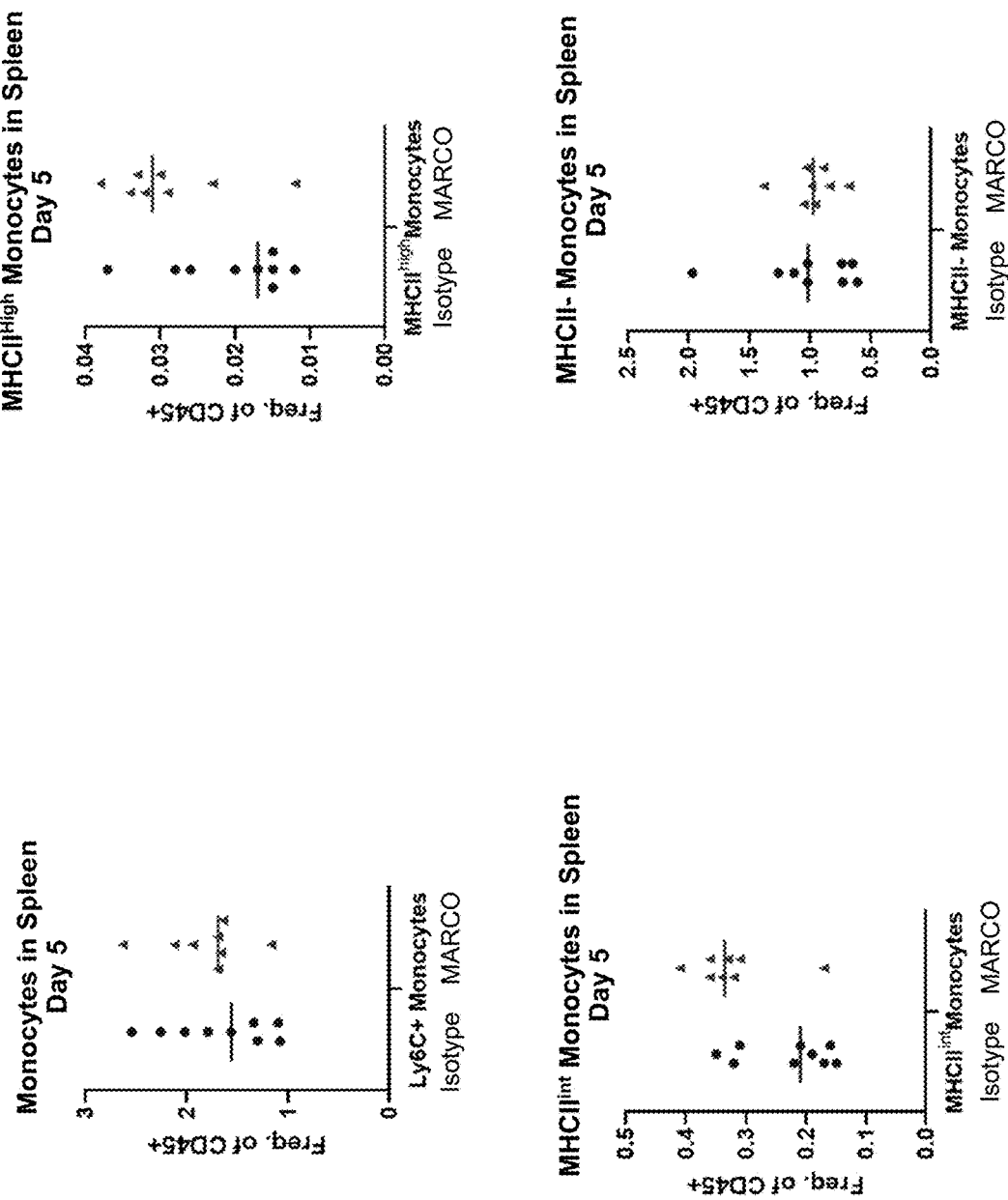
FIG. 66 provides quantification of the indicated spleen myeloid cell types at Day 5 post-administration of a isotype control antibody or PI-3008.
Figure 67:
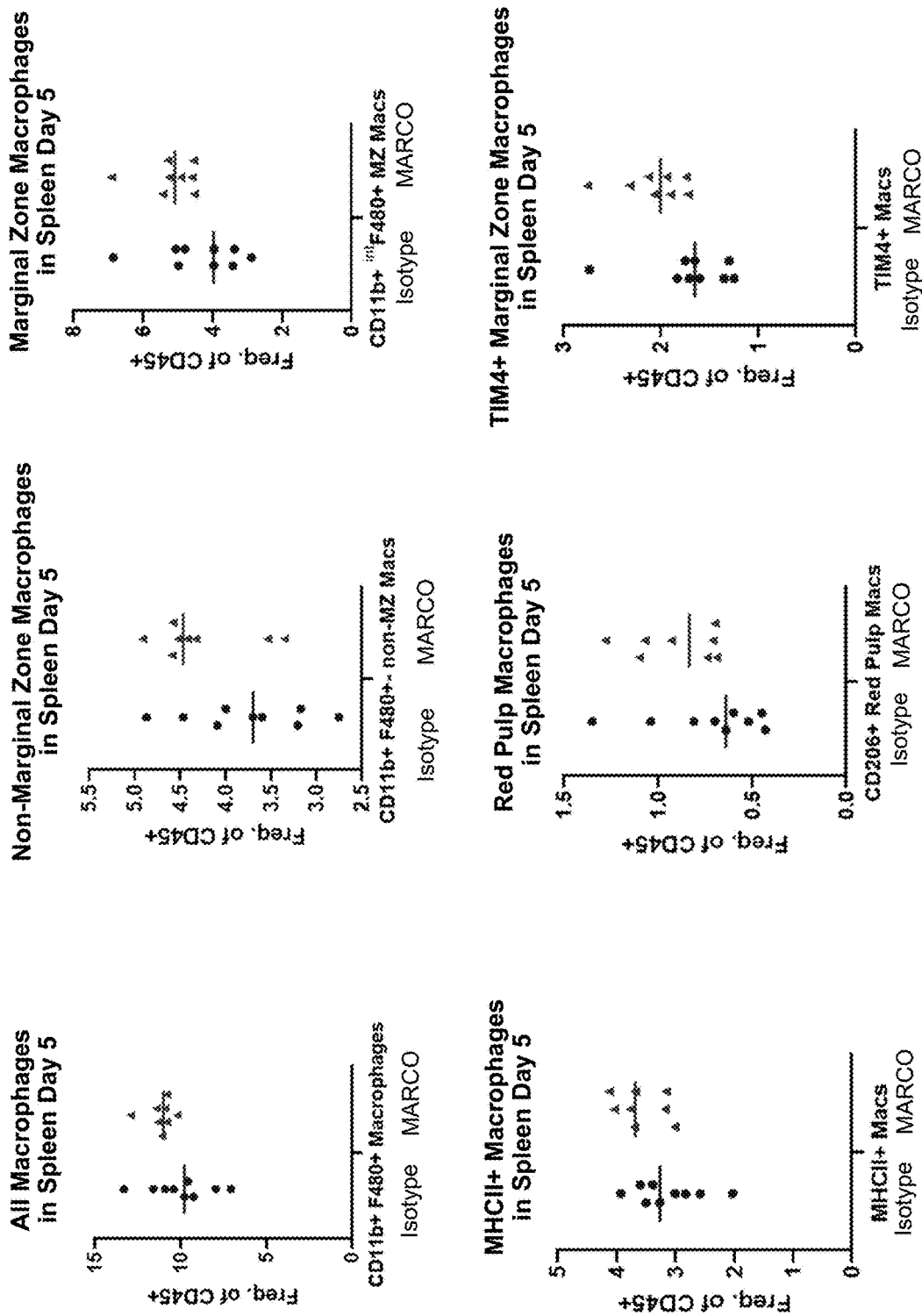
FIG. 67 provides quantification of the indicated spleen myeloid cell types at Day 5 post-administration of a isotype control antibody or PI-3008.
Figure 68:
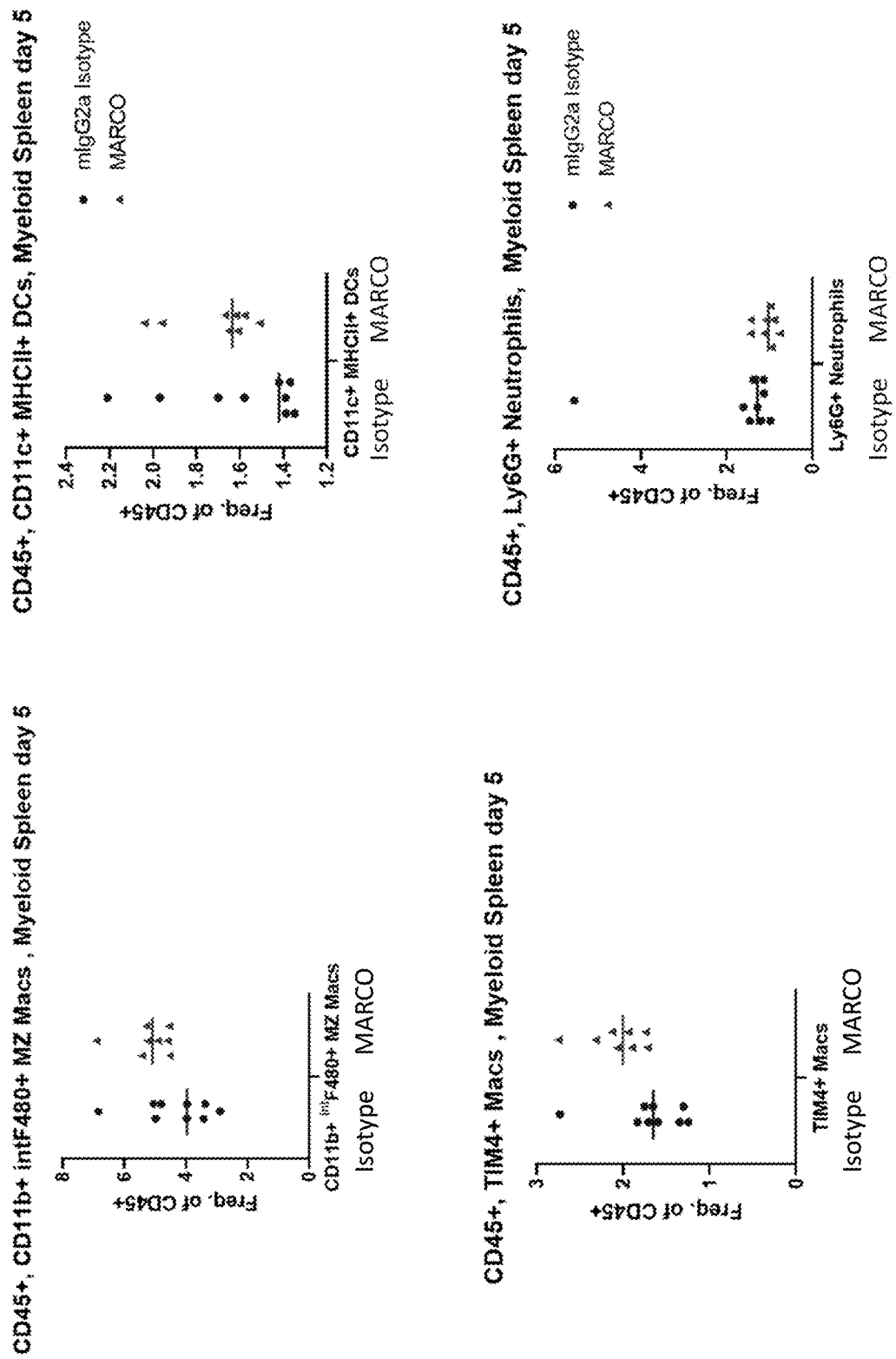
FIG. 68 provides quantification of the indicated spleen myeloid cell types at Day 5 post-administration of a isotype control antibody or PI-3008.

Spleen myeloid cells were also assessed at Day 5 after one dose of MARCO antibody treatment. Anti-MARCO decreased MHCII− monocytes and increased MHCII+ monocytes (high and intermediate) at day 5 by subtyping Ly6C+ monocytes into various MHCII level cells (FIG. 66). Anti-MARCO increased the number of total macrophages in the spleen at D2 and D5, including red pulp macrophages (FIG. 67 and data not shown). Anti-MARCO also increased the number of Marginal Zone Macrophages (MZMs) at D5, MHCII+ DCs, and increased the non-marginal zone macrophages at D5 (FIGS. 67 and 68).

Figure 69:
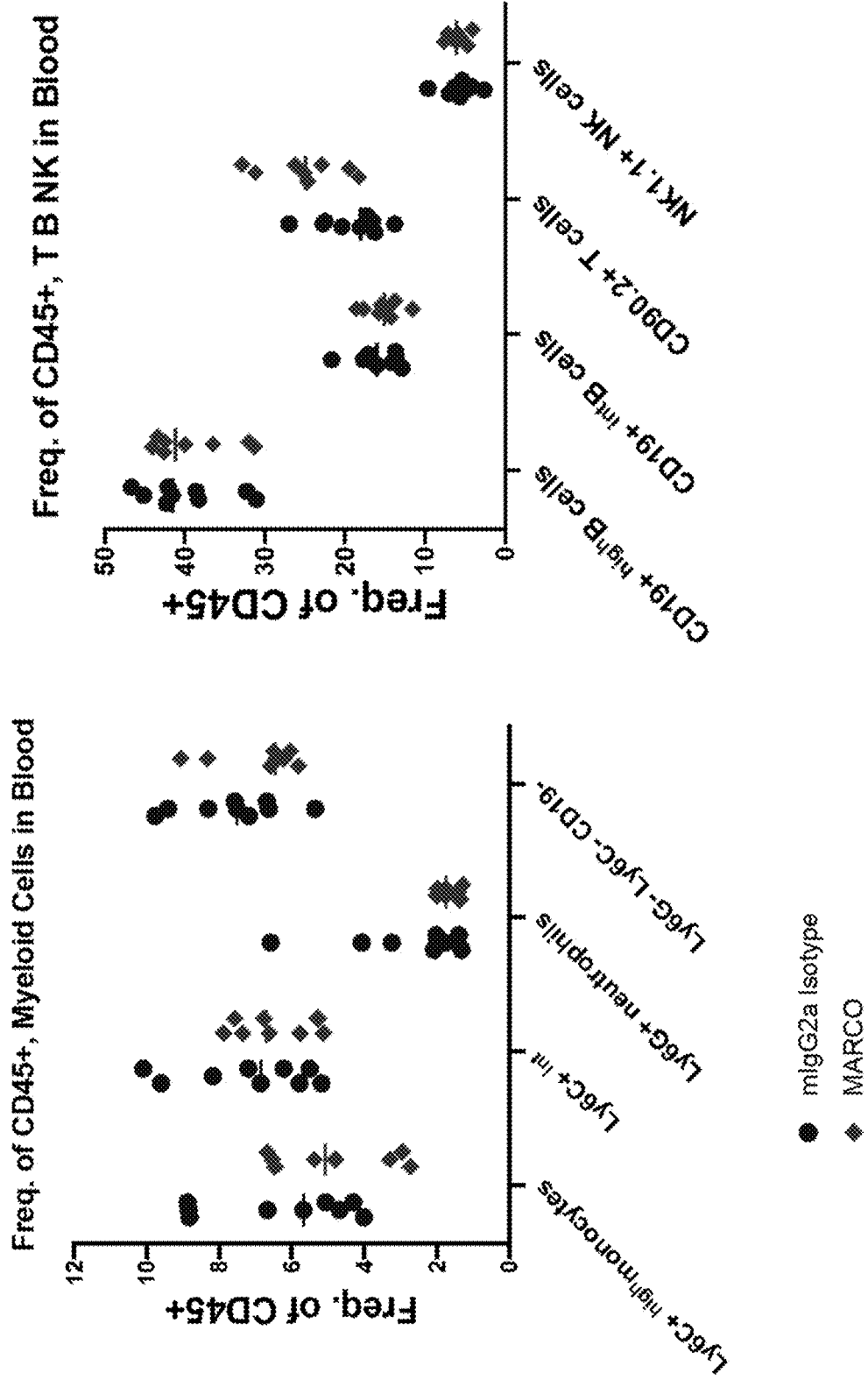
FIG. 69 provides quantification of the indicated cell types in the blood at Day 5 post-administration of a isotype control antibody or PI-3008.

Blood was also profiled by flow cytometry at Day 5. A slight decrease in $Ly6C^{high}$ monocytes and DCs at day 5 and an increase in T-cells was observed. No change in B-cells was observed. (FIG. 69).

Figure 70:
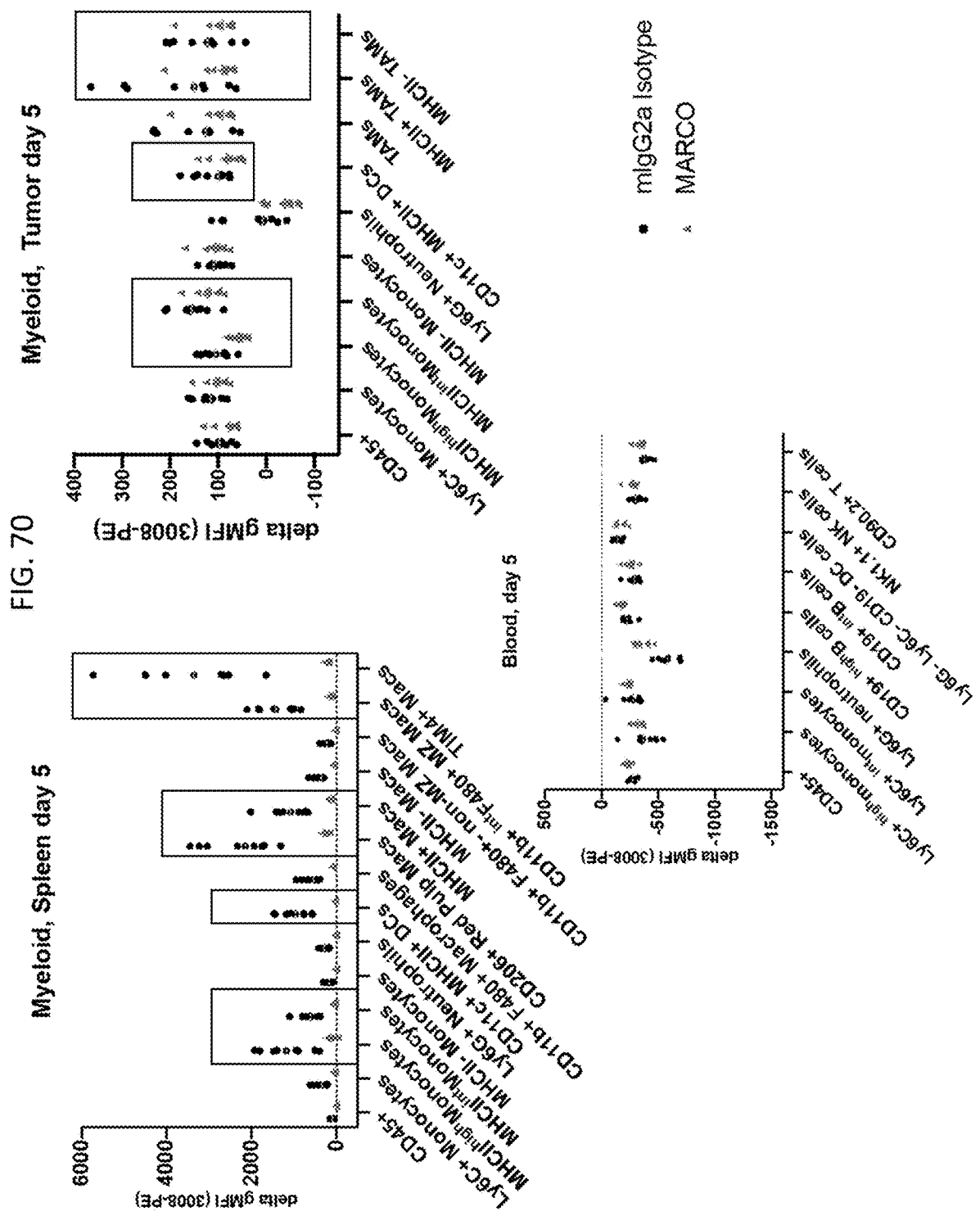
FIG. 70 shows that Receptor Occupancy of the therapeutic MARCO antibody was achieved in the MARCO expressing cells in the spleen and tumors.

MARCO expression and Receptor Occupancy in mouse spleens, E0771 tumors, and blood (FIG. 70) at Day 5 was also assessed. As shown in FIG. 70, MARCO was expressed at high levels in the spleen, in particular on the marginal zone (MZ) macrophages gated by $CD11b^{int}$ F480+ and TIM4+ Macs. MARCO was not expressed on the non-Marginal zone macrophages (non-MZ), as evidenced by the MARCO flow cytometry staining of the mIgG2a isotype samples, in which the flow cytometry MARCO antibody did not compete with prior MARCO antibody for binding to cells. MARCO was expressed on MHCII+ monocytes ($MHCII^{high}$ and $MHCII^{inter}$) and on DCs. MARCO was also expressed on CD206+ red pulp macrophages outside the marginal zone and on MHCII+ Macs. Receptor Occupancy of the therapeutic MARCO antibody was achieved in the positive MARCO expressing cells of FIG. 70 listed above, as evidenced by the lack of MARCO flow cytometry staining of the MARCO samples, in which the flow cytometry MARCO antibody was out competed for binding to cells by the prior therapeutic MARCO antibody.

In the E0771 tumors, MARCO was expressed at low levels inside the tumors. Receptor Occupancy could not be accurately measured at day 2 but was achieved in $MHCII^{high}$ and intermediate monocytes; MHCII+ DCs; and both MHCII+ TAMs and MHCII− TAMs at day 5 (FIG. 70). No MARCO expression was observed on blood immune cells (FIG. 70).

In sum, PI-3008 induced motility and/or phagocytosis changes in the tumor, as evidenced by altered gene expression in cytoskeletal, actin and muscle, migration, and cell-adhesion and migration related pathways. PI-3008 also induced immune activation as evidenced by NK cell activation, T cell activation, and myeloid cell differentiation. In the lymph nodes, PI-3008 altered gene expression in pathways associated with cell signaling, cell-adhesion, cytoskeletal, and motility genes. In the spleen, PI-3008 altered gene expression in pathways associated with cell signaling, cell-adhesion, cytoskeletal, chemotaxis, and motility genes as well as B cell activation. Without wishing to be bound by theory, taken together, this data indicates that anti-MARCO antibodies activate intra-tumor immunity at least by mediating repolarization of MARCO+ myeloid M2-like TAMs to M1-like TAMs, and repolarization of mMDSCs to pro-inflammatory monocytes. This repolarization leads to production of cytokines, chemokines, and activation receptors, which in turn leads to activation of T and NK cells. The repolarization of myeloid M2-like TAMs and mMDSCs and activation of T and NK cells then leads to tumor destruction mediated by NK cells, CD8 cells, and M1-like macrophages. Further, without wishing to be bound by theory, potential binding of the anti-MARCO antibody to medullary cord macrophages (MCMs) may induce changes in adhesion and motility in the lymph node, and potential binding of the anti-MARCO antibody to marginal zone macrophages (MZMs) in the spleen may lead to changes in adhesion and motility, leading to potential B cell activation.

Example 12: Pharmacodynamic Assay in CT26 In Vivo Model

Methods

A PD study was conducted in CT26 tumor bearing mice. Eight to ten-week old female BALB/c mice (Taconic) were implanted with subconfluent CT26.WT cells (ATCC, banked at Pionyr) grown in log-phase. One million tumor cells resuspended in serum-free media were implanted subcutaneously on the right ventral flank of the mice under isoflurane anesthesia. For the pilot CT26 PD study, mice with tumor volumes of 150-200 mm3, were dosed once intravenously with 10 mg/kg of PI-3008-AB or PI-0002-AB (isotype) and tumors and spleens were collected 4 days after treatment inn 10% formalin for IHC staining with anti-mouse MARCO, anti-CD8, and anti-granzyme B. HALO image analysis software (Indica Labs) was used to quantify the percentage of CD8+ T cells and Granzyme B+ cells over the whole tumor area. Spleens were stained with a non-PI-3008 competing anti-mouse MARCO IHC compatible antibody.

Results

Figure 49:
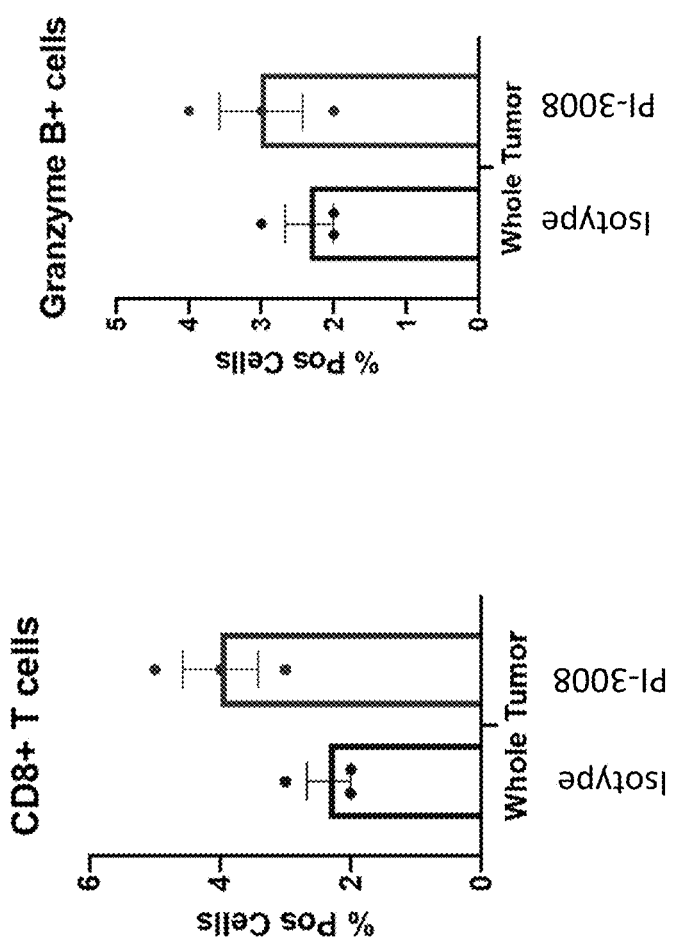
FIG. 49 shows that PI-3008 induced an increase in CD8+ T-cells and the cytotoxic marker granzyme B as measured by IHC compared to isotype control treated tumors.

The anti-MARCO antibody PI-3008 induced an increase in CD8+ T-cells and the cytotoxic marker granzyme B in tumors as compared to isotype control treated tumors (FIG. 49). Data is presented as mean percentage values from 3 mice within each treatment group of ±standard error of the mean (SEM).

Figure 50:
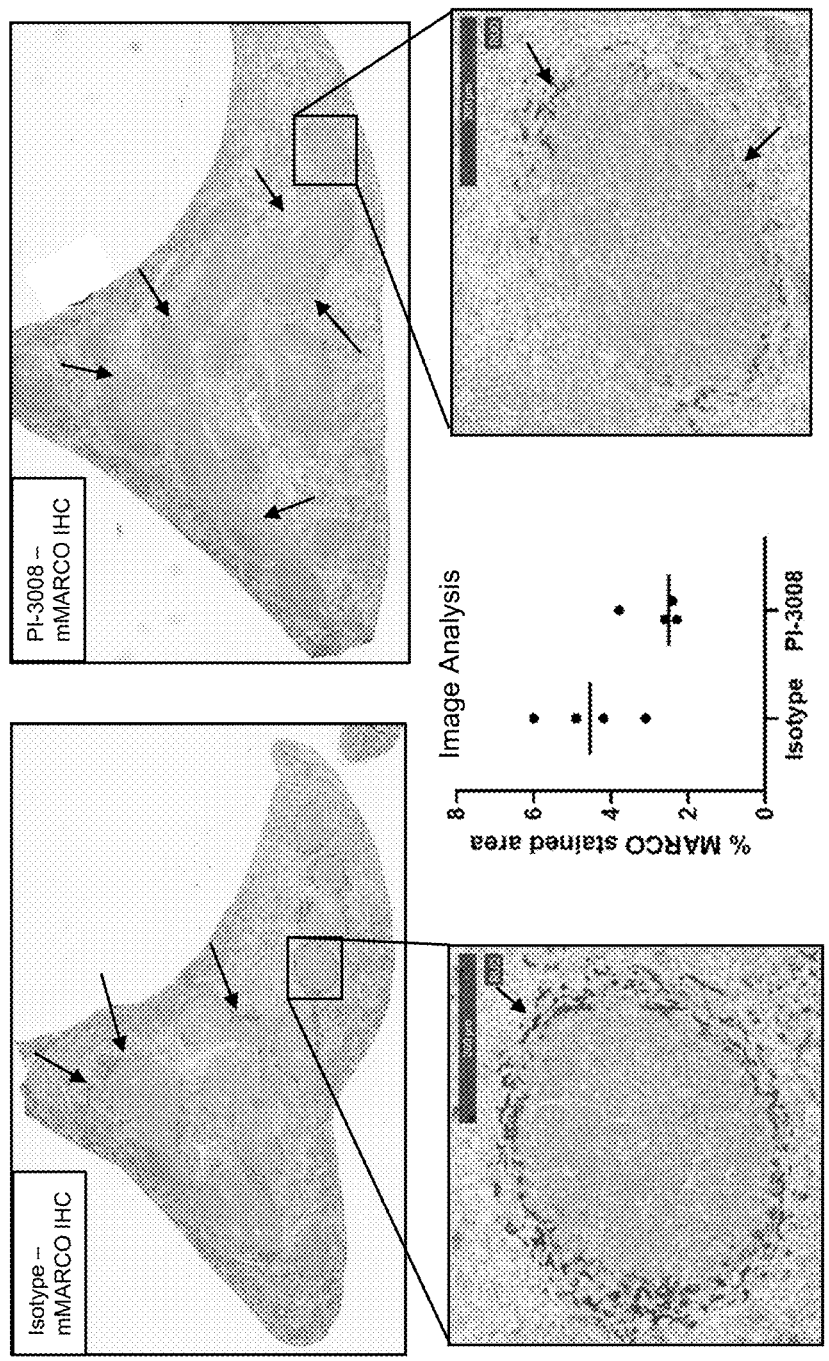
FIG. 50 shows changes in MARCO levels on the marginal zone macrophages in the spleen, with noticeable gaps in the marginal zone area when stained with a non-PI-3008 competing anti-mouse MARCO IHC compatible antibody.

In the spleen, changes in MARCO levels on the marginal zone macrophages were observed with noticeable gaps in the marginal zone area (FIG. 50). Control spleens showed several layers of MARCO+ stained cells in the marginal zone. Layers continue around most of the periarteriolar lymphoid sheath (PALS) and B cell follicle caps. Spleens from PI-3008 treated mice showed much less MARCO+ staining that include fewer cells and layers. There were also gaps in the coverage of the PALS and B cell caps. Thus, there was a decrease in MARCO-positive cells in the splenic marginal zone of animals treated with PI-3008. Without wishing to be bound by theory, these data suggest that anti-MARCO induces proinflammatory actuation within the TME and leads to changes in adhesion and motility as seen in the spleen.

Example 13: Immunohistochemistry MARCO Assay

To identify a suitable anti-human MARCO IHC antibody to profile MARCO expression in human FFPE tissues, 15 commercial and internal antibodies were screened. The primary screening comprised staining FFPE embedded MARCO over-expressing (CL3010), endogenous (L1236), and negative control (HEK-293T cells and Jurkat cells that do not express MARCO) cell pellets. Antibodies that passed the primary screen were included in the secondary screen, in which lung cancer and colon cancer FFPE sections, identified as having high RNA expression by in situ hybridization (ISH), were stained using different IHC staining conditions (different antibody concentrations, incubation times, and antigen retrieval). Two potential human MARCO specific off the shelf IHC antibodies from R&D, RDM5 (clone #858428.11, catalog CUST017MABP) and RDM9 (clone #858423.11, catalog CUST017MABP), were identified. RDM5 was slightly superior to RDM9 and thus was selected for further optimization of IHC assay conditions on additional control tissues. RDM5 demonstrated specific, strong, and sensitive labeling of MARCO-positive cells when used at 2.5 µg/mL with a high pH antigen retrieval (ER2), on an automated Leica platform (FIG. 51A). The staining was validated on normal and tumor tissue microarrays (TMAs) and MARCO specificity was confirmed by a certified-board pathologist. In addition, MARCO expression in normal tissues was restricted to the tissue resident macrophages in the lung, liver, and spleen, confirming the previous RNA data.

Next, further profiling of MARCO expression was explored on 20 tissue microarrays (TMA) from 17 different tumor indications and contained duplicate cores per subject with different diagnoses (Pathology, Grade, and TNM stage). The TMA at Reveal Biosciences was made by acquiring tissues that were fixed in 10% neutral buffer formalin for 24 hours and processed using identical SOPs. Sections were picked onto Superfrost Plus or Startfrost Adhesive slides and all TMAs were cut fresh in 4 um serial sections upon ordering and stored at 4degC prior to IHC staining.

Figures 51B, 51C:
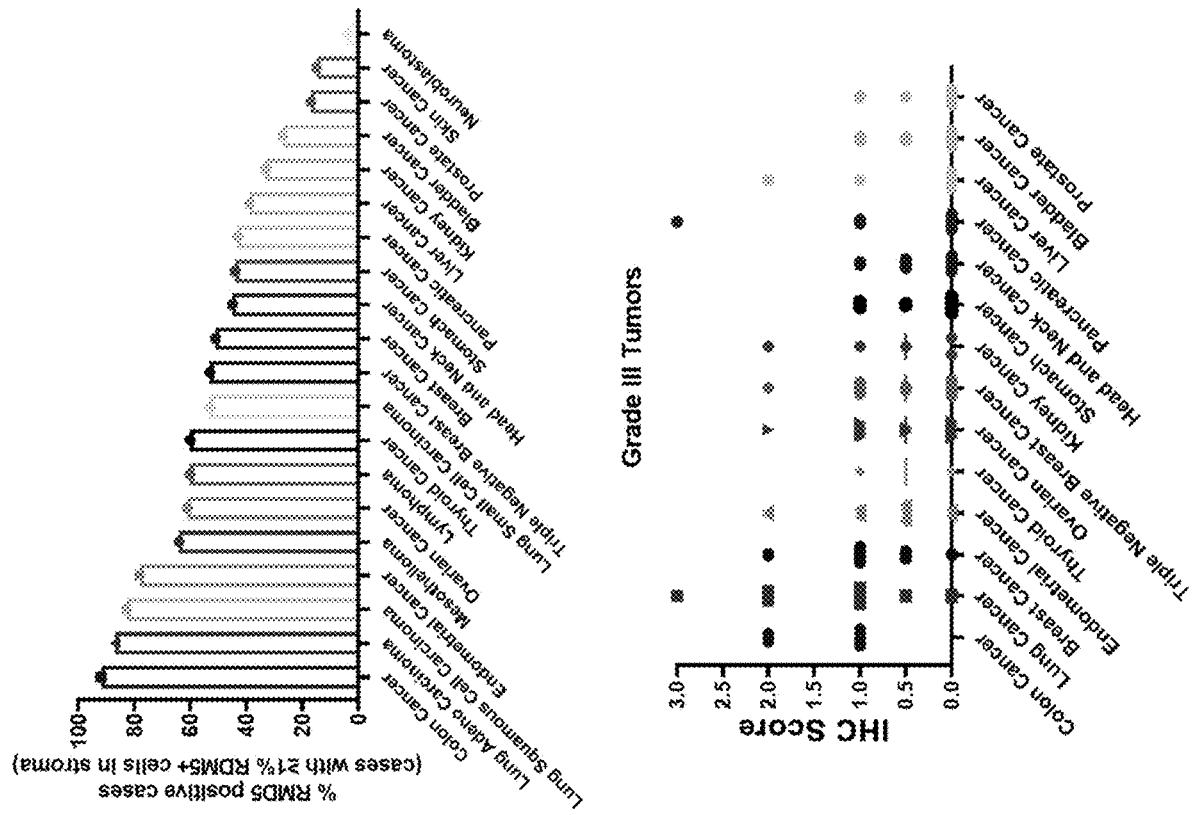
FIG. 51B shows the percentage of positive MARCO cancer cases in the indicated cancer type after IHC staining with the RDM5 antibody.
FIG. 51C shows the IHC score in the indicated cancer type after IHC staining with the RDM5 antibody.

After whole slide scanning of each TMA at 40× using the Aperio AT2 Scanner, quantification of the MARCO+ cells in the tumor intervening stroma were assessed by a board-certified pathologist using the following scoring system: 0=<1% positive cells, 0.5=1-10% positive cells, 1=10-25% positive cells, 1.5=25-50% positive cells, 2=approximately 50% positive cells, 2.5=50-75% positive cells, 3=approximately 75% positive cells, and 3.5=>75% positive cells over stroma. Lost or folded cores with more than half of the area distorted were removed from the analysis and not scored. The staining for each patient was considered positive if MARCO+ cells were expressed at 1% or above 1% over stroma. Each dot represents one case, and the median for each indication is depicted as a line The percentage of positive cases, with a cutoff at 1% MARCO+ cells in the stroma, was highest in colon cancer (92%), followed by lung cancer (87%), endometrial cancer (78%), mesothelioma (64%), ovarian cancer (61%), lymphoma (60%), thyroid cancer (60%), TNBC (53%), breast cancer (51%), head and neck cancer (45%), stomach cancer (44%), pancreatic cancer (43%), liver cancer (39%), and kidney cancer (33%) (FIG. 51B). The median MARCO IHC scores were highest with a score of 1 in colon, lung, thyroid, and mesothelioma, followed by a median score of 0.75 in lymphoma and endometrial cancer for all tumor grades (data not shown). When focusing only on the advanced grade III tumors, the median MARCO IHC scores increased from 0.5 to 1 in breast cancer and from 0 to 0.5 in kidney cancer, indicating that increased MARCO expression is correlated to higher tumor grade in these tumor indications (FIG. 51C). Moreover, the MARCO IHC score in normal tissues was highest in normal liver, lung, spleen, colon, ovary and nerve tissue, corroborating previously described MARCO RNA expression data. Thus, based on MARCO IHC scoring using the RDM5 antibody, colon cancer, lung cancer, mesothelioma, lymphoma, thyroid cancer, endometrial cancer, and ovarian cancer have the highest IHC scores and number of MARCO positive cases.

Example 14: Cell Line Development for MARCO Antibody Production

Two independent transfections were performed per double gene vector, with three static 96-shallow well plates per transfection. A transfer to suspension culture in 96-deep well plates occurs, then four transfection pools are generated from top cultures. All cultures maintained viabilities of ≥97% throughout 6 days of culture.

Evaluation of the transfection pool product quality was performed following partial purification (i.e., MabSelect™ SuRe™ affinity chromatography and sample neutralization to pH 7). Lonza performed product quality evaluation by gel permeation high performance liquid chromatography (GP-HPLC), sodium dodecyl sulfate (SDS) electrophoresis (reduced and non-reduced) and imaged capillary isoelectric focusing (iCIEF). Aggregation data for PI-3030.41 was significantly elevated compared to the other candidates. The results of the transfection pool analysis are shown in Tables 31 through 36 below.

TABLE 31

Transfection Pool Concentration Data

| Transfection Pool | Partially Purified Concentration (mg/mL) | Partially Purified Volume (μL) | Total Quantity (mg) |
|---|---|---|---|
| 3010.15 (1) | 0.818 | 650 | 0.53 |
| 3010.15 (2) | 0.959 | 645 | 0.62 |
| 3010.15 (3) | 1.372 | 650 | 0.89 |
| 3010.15 (4) | 1.150 | 750 | 0.86 |
| 3010.25 (1) | 1.248 | 740 | 0.92 |
| 3010.25 (2) | 0.936 | 655 | 0.61 |
| 3010.25 (3) | 1.243 | 590 | 0.73 |
| 3010.25 (4) | 1.271 | 605 | 0.77 |
| 3030.41 (1) | 0.972 | 650 | 0.63 |
| 3030.41 (2) | 1.073 | 655 | 0.70 |
| 3030.41 (3) | 1.025 | 655 | 0.67 |
| 3030.41 (4) | 0.871 | 650 | 0.57 |

TABLE 32

Transfection Pool Aggregation by GP-HPLC Data

| Transfection Pool | Fragments (Iv) | Monomer (%) | | Aggregates (%) | |
|---|---|---|---|---|---|
| 3010.15 (1) | <0.10 | 89.98 | 90.0-92.1 | 10.02 | 7.9-10.0 |
| 3010.15 (2) | <0.10 | 91.52 | | 8.48 | |
| 3010.15 (3) | <0.10 | 92.06 | | 7.94 | |
| 3010.15 (4) | <0.10 | 91.63 | | 8.37 | |
| 3010.25 (1) | <0.10 | 95.15 | 90.2-95.2 | 4.85 | 4.9-9.8 |
| 3010.25 (2) | <0.10 | 90.20 | | 9.80 | |
| 3010.25 (3) | <0.10 | 94.47 | | 5.53 | |
| 3010.25 (4) | <0.10 | 92.49 | | 7.51 | |
| 3030.41 (1) | <0.10 | 80.83 | 80.3-82.5 | 19.17 | 17.5-19.7 |
| 3030.41 (2) | <0.10 | 81.69 | | 18.31 | |
| 3030.41 (3) | <0.10 | 82.46 | | 17.54 | |
| 3030.41 (4) | <0.10 | 80.33 | | 19.67 | |

TABLE 33

Transfection Pool SDS Electrophoresis (Reduced) Data

| Transfection Pool | LC Size (kDa) | | LC Purity (%) | | HC Size (kDa) | | HC Purity (%) | | LC + HC Purity (%) | |
|---|---|---|---|---|---|---|---|---|---|---|
| 3010.15 (1) | 27.36 | 27.3- | 42.11 | 41.8- | 62.47 | 62.2- | 57.66 | 56.4- | 99.77 | 99.8 |
| 3010.15 (2) | 27.27 | 27.6 | 43.33 | 43.3 | 62.24 | 62.8 | 56.42 | 58.0 | 99.75 | |
| 3010.15 (3) | 27.61 | | 41.77 | | 62.82 | | 58.02 | | 99.80 | |
| 3010.15 (4)* | 27.52 | | 36.73 | | 62.61 | | 57.55 | | 94.27 | |
| 3010.25 (1)* | 27.02 | 26.5- | 26.93 | 39.8- | 63.01 | 61.5- | 32.45 | 58.1- | 59.38 | 99.6- |
| 3010.25 (2) | 26.70 | 27.0 | 41.47 | 41.5 | 62.09 | 63.0 | 58.13 | 59.9 | 99.60 | 99.7 |
| 3010.25 (3) | 26.48 | | 40.72 | | 61.48 | | 58.95 | | 99.67 | |
| 3010.25 (4) | 26.59 | | 39.77 | | 61.55 | | 59.89 | | 99.65 | |
| 3030.41 (1) | 26.51 | 26.5- | 43.32 | 42.5- | 61.65 | 61.7- | 56.47 | 56.0- | 99.79 | 98.7- |
| 3030.41 (2) | 26.48 | 26.8 | 43.53 | 43.5 | 61.78 | 62.2 | 56.27 | 57.3 | 99.80 | 99.8 |
| 3030.41 (3) | 26.72 | | 42.71 | | 62.24 | | 56.01 | | 98.72 | |
| 3030.41 (4) | 26.75 | | 42.49 | | 62.21 | | 57.30 | | 99.79 | |

*Difference in value may be due to not fully reduced samples (supported by reduced electropherogram and sample non-reduced data). Small amount of higher molecular weight species for 3010.15 (4) and significant amount of higher molecular weight species for 3010.25 (1). These values were excluded in the purity ranges for per candidate.

TABLE 34

Transfection Pool SDS Electrophoresis (Non-Reduced) Data

| Transfection Pool | IgG Size (kDa) | | IgG Purity (%) | |
|---|---|---|---|---|
| 3010.15 (1) | 170.16 | 167.8-170.2 | 96.04 | 95.8-97.0 |
| 3010.15 (2) | 169.62 | | 95.83 | |
| 3010.15 (3) | 167.81 | | 96.67 | |
| 3010.15 (4) | 168.09 | | 96.99 | |
| 3010.25 (1) | 168.83 | 167.7-169.2 | 96.72 | 95.7-96.7 |
| 3010.25 (2) | 168.47 | | 96.53 | |
| 3010.25 (3) | 169.19 | | 96.43 | |
| 3010.25 (4) | 167.72 | | 95.70 | |
| 3030.41 (1) | 165.78 | 165.0-167.5 | 96.04 | 95.2-96.0 |
| 3030.41 (2) | 164.99 | | 95.59 | |
| 3030.41 (3) | 167.45 | | 95.90 | |
| 3030.41 (4) | 166.61 | | 95.24 | |

TABLE 35

Transfection Pool iCIEF Isoform Data

| | Peak Area (%) * | | | | | | | | |
|---|---|---|---|---|---|---|---|---|---|
| | Acidic Variant Peaks | | | | Main Peak | | Basic Variant Peaks | | |
| Transfection Pool | Isoform 5 | | Isoform 4 | | Isoform 3 | | Isoform 2 | | Isoform 1 |
| 3010.15 (1) | 5.7 | <LOQ- | 18.4 | 17-20 | 67.7 | 67-71 | 6.8 | 6-7 | <LOQ <LOQ |
| 3010.15 (2) | 5.3 | 6 | 17.3 | | 69.2 | | 6.9 | | <LOQ |

TABLE 35-continued

Transfection Pool iCIEF Isoform Data

| Transfection Pool | Acidic Variant Peaks | | Main Peak | Basic Variant Peaks | |
|---|---|---|---|---|---|
| | Isoform 5 | Isoform 4 | Isoform 3 | Isoform 2 | Isoform 1 |
| 3010.15 (3) | 5.1 | 20.1 | 67.4 | 6.4 | <LOQ |
| 3010.15 (4) | <LOQ | 19.2 | 70.6 | 5.8 | <LOQ |
| 3010.25 (1) | <LOQ  <LOQ | 15.9  15-16 | 72.8  72-73 | 6.6  7 | <LOQ  <LOQ |
| 3010.25 (2) | <LOQ | 15.9 | 72.3 | 6.8 | <LOQ |
| 3010.25 (3) | <LOQ | 15.4 | 72.9 | 6.7 | <LOQ |
| 3010.25 (4) | <LOQ | 16.2 | 71.9 | 6.7 | <LOQ |
| 3030.41 (1) | 5.4  5-7 | 19.4  19-21 | 69.5  68-70 | <LOQ  <LOQ-5 | <LOQ  <LOQ |
| 3030.41 (2) | 7.0 | 20.0 | 67.8 | <LOQ | <LOQ |
| 3030.41 (3) | 5.8 | 20.5 | 68.9 | <LOQ | <LOQ |
| 3030.41 (4) | 6.5 | 20.2 | 67.6 | 5.0 | <LOQ |

* LOQ is 4.9%.

3010.15: calculated pI: 9.1; Isoform 5: pI 8.87 to 8.89; Isoform 4: pI 8.96; Isoform 3: pI 9.04 to 9.05; Isoform 2: pI 9.15 to 9.16; Isoform 1: pI 9.24 to 9.25.
3010.25: calculated pI: 8.8; Isoform 5: pI 8.30 to 8.31; Isoform 4: pI 8.46 to 8.47; Isoform 3: pI 8.61 to 8.62; Isoform 2: pI 8.75; Isoform 1: pI 8.90.
3030.41: calculated pI: 9.1; Isoform 5: pI 8.80 to 8.82; Isoform 4: pI 8.89; Isoform 3: pI 8.99 to 9.00; Isoform 2: pI 9.10 to 9.11; Isoform 1: pI 9.20.

TABLE 36

Transfection Pool iCIEF Summarized Data

| Transfection Pool | Acidic Variant Peaks | | Main Peak | | Basic Variant Peaks | |
|---|---|---|---|---|---|---|
| 3010.15 (1) | 24.1 | 23-25 | 67.7 | 67-71 | 8.2 | 7-8 |
| 3010.15 (2) | 22.6 | | 69.2 | | 8.2 | |
| 3010.15 (3) | 25.2 | | 67.4 | | 7.5 | |
| 3010.15 (4) | 22.6 | | 70.6 | | 6.8 | |
| 3010.25 (1) | 19.8 | 20-21 | 72.8 | 72-73 | 7.4 | 7-8 |
| 3010.25 (2) | 20.0 | | 72.3 | | 7.7 | |
| 3010.25 (3) | 19.6 | | 72.9 | | 7.4 | |
| 3010.25 (4) | 20.6 | | 71.9 | | 7.5 | |
| 3030.41 (1) | 24.8 | 25-27 | 69.5 | 68-70 | 5.7 | 5-6 |
| 3030.41 (2) | 27.0 | | 67.8 | | 5.2 | |
| 3030.41 (3) | 26.3 | | 68.9 | | 4.8 | |
| 3030.41 (4) | 26.7 | | 67.6 | | 5.7 | |

Figure 53:
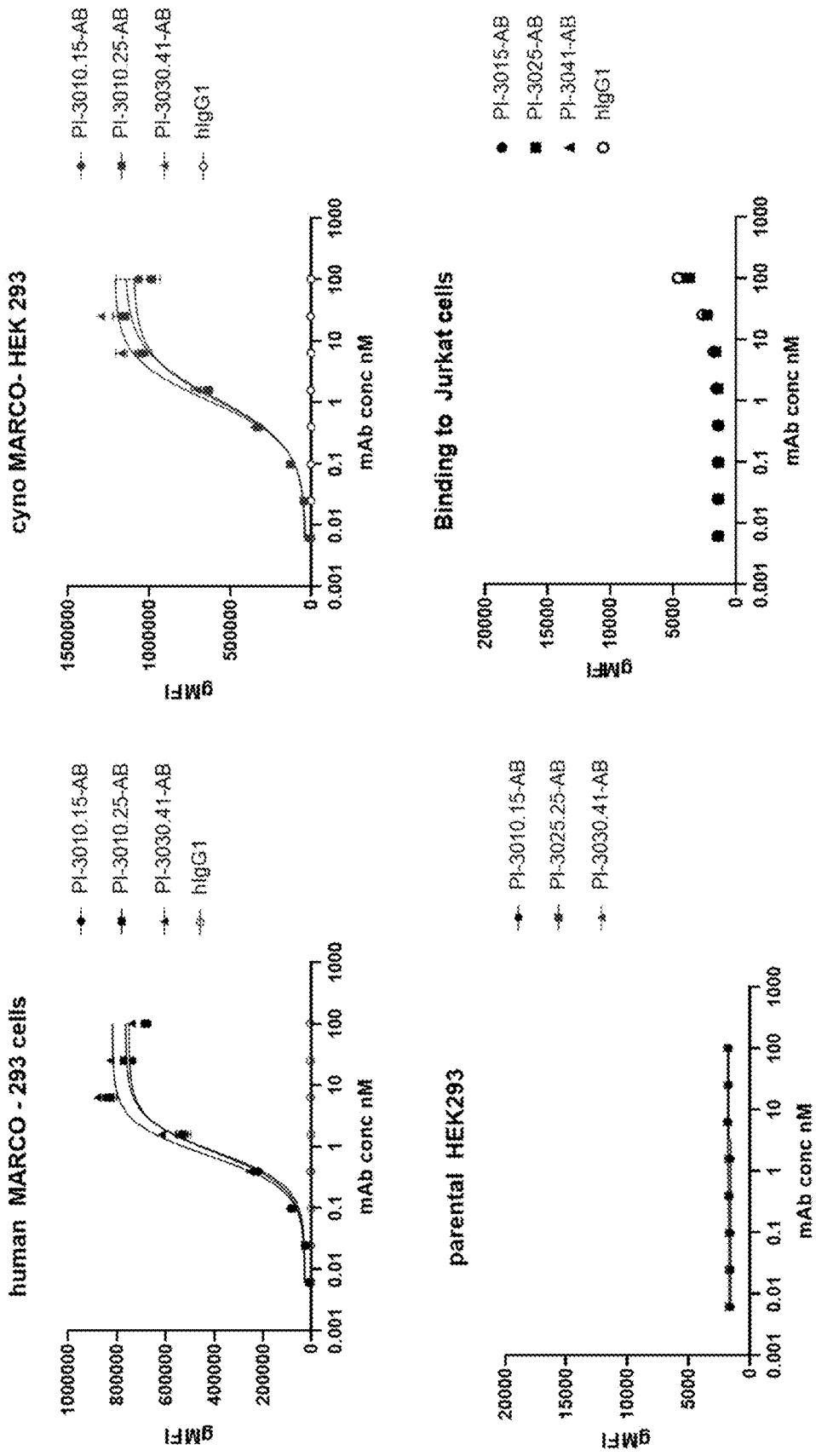
FIG. 53 shows binding of the indicated MARCO antibody to human and cynomolgus MARCO expressing cell lines.
Figure 54:
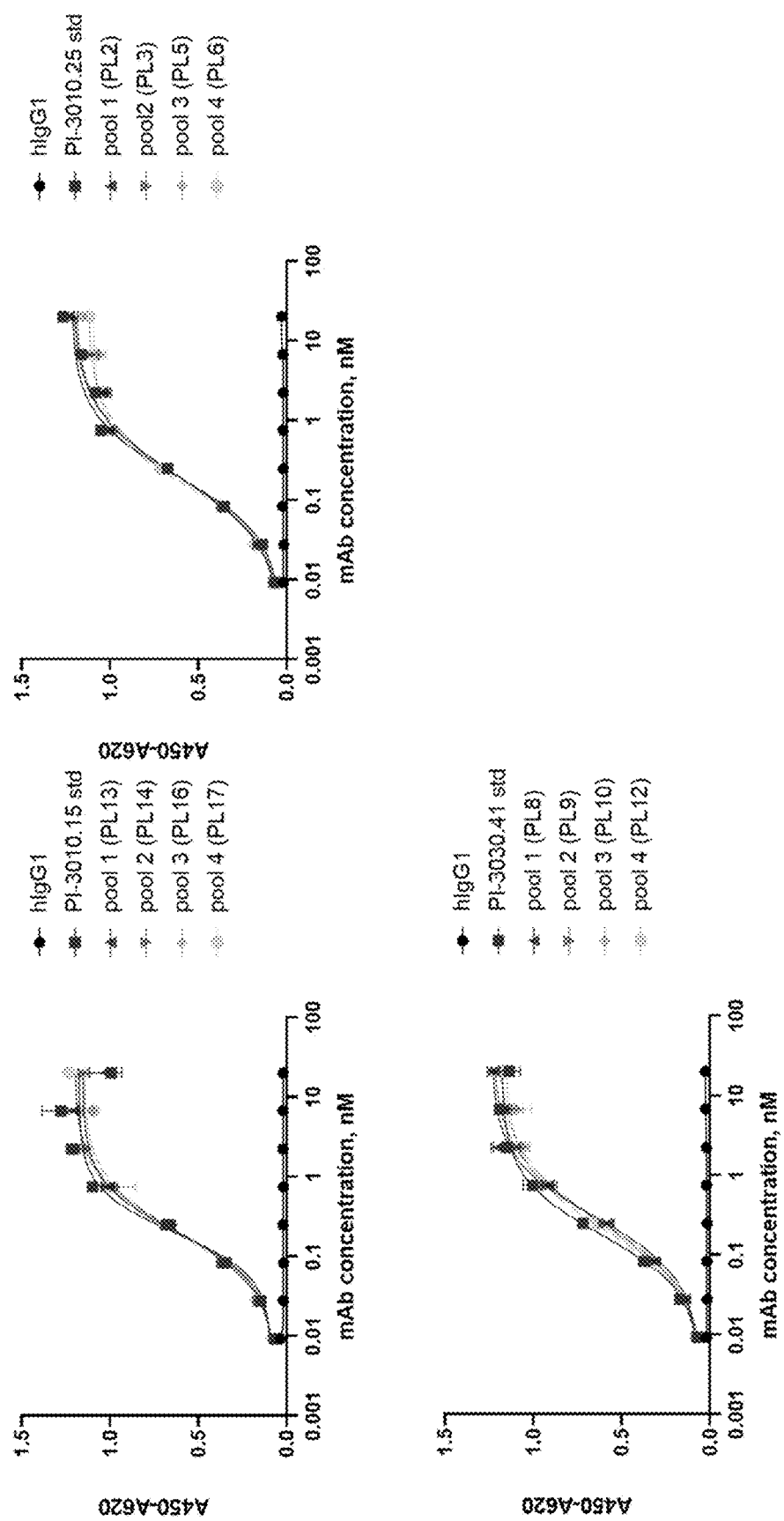
FIG. 54 shows binding of antibodies produced by the stable transfection method to MARCO expressing cells as compared to reference antibodies made via transient transfection.

Transfection pools for the 3 antibodies were tested for binding by ELISA and flow cytometry on MARCO transfectant cells. The binding of the pool material was compared to reference antibodies produced by transient transfection in CHO-S cells. Antibodies produced by the stable transfection method demonstrated comparable binding to the reference antibodies made via transient transfection (FIG. 53).

Example 15: Soluble MARCO Assay

Materials and Methods

A streptavidin MSD Plate (MSD, Catalog #L15SA-1) was coated with biotinylated anti-MARCO antibody (PI-3041-AB, Pionyr) at 2 µg/mL. The plate was incubated at room temperature for 60 min and then washed.

Protein standards (RG-3000A, Atum) and serum samples (BioVT) were diluted in buffer (PBS/0.5% BSA/0.05% Tween+Ca2+/Mg2+) and added to the coated plate in D43 diluent (MSD, Catalog #R50AG-2) with 2 mM Ca2+. The plate was incubated for 90 min at room temperature and washed. 1 µg/mL of the detection antibody, anti-MARCO (PI-3071-AB, Pionyr) was added, and the plate incubated for 60 min at room temperature. The plate was washed and 1× Read Buffer [MSD, Catalog #R92TC-1) was added to the MSD plate. The plate was read on an MSD Sector Imager.

Results

Figure 55B:
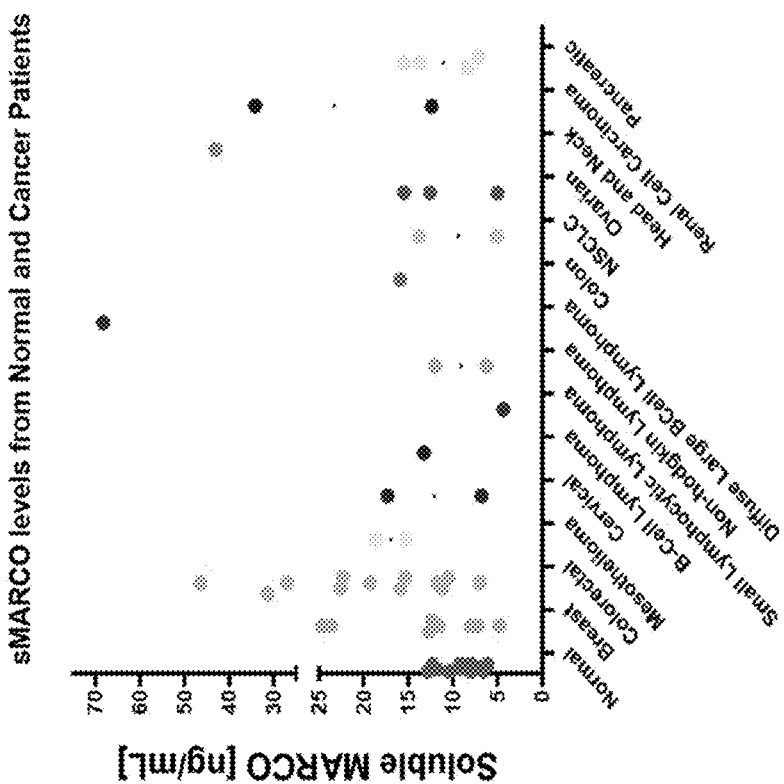
FIG. 55B shows the sMARCO levels in normal and cancer serum samples.
Figure 55A:
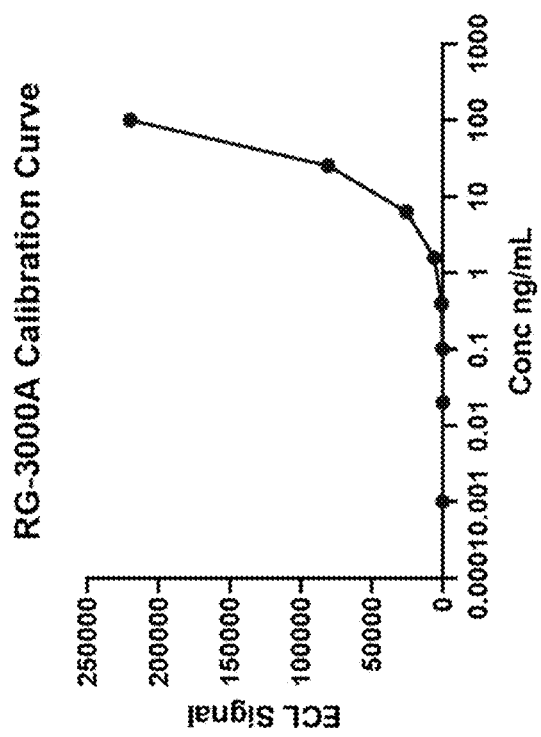
FIG. 55A shows the sMARCO calibration curve for RG-3000A.

The sMARCO assay range was 0.1 ng/mL to 100 ng/mL. The LLOQ was 0.1 ng/mL and the ULOQ was 100 ng/mL. The sMARCO calibration curve for RG-3000A is shown in FIG. 55A and Table 37.

TABLE 37

| Nominal Conc. ng/ml | Detected Mean Conc. (ng/ml) | % Recovery Mean |
|---|---|---|
| 100 | 102.2 | 102.2 |
| 25.0 | 23.5 | 94.0 |
| 6.25 | 7.09 | 113.4 |
| 1.56 | 1.76 | 113.0 |
| 0.39 | 0.32 | 83.1 |
| 0.10 | 0.10 | 100.0 |

The sMARCO levels in normal human serum samples ranged from 9 ng/mL to 13 ng/mL. The sMARCO levels in cancer serum samples ranged from 6 ng/mL to 22 ng/mL. The sMARCO levels are shown in FIG. 55B.

An immunoassay to detect sMARCO from serum samples (human, cynomolgus monkey and mouse) was successfully developed. The sMARCO assay was qualified for its specificity, sensitivity, dilution linearity and selectivity and accurately determined sMARCO levels in patient serum samples obtained from commercial sources. sMARCO levels were observed to be higher in patients diagnosed with breast, colorectal, mesothelioma, cervical, small lymphocytic lymphoma, and non-Hodgkin lymphoma (FIG. 55B).

Example 16: In Vivo B-Cell Deficient Mouse Study

Methods

Balb/c mice with J B-cell mutation were obtained from Taconic. The mouse experiment was set up as described in Example 4. Briefly, IP dosing was initiated when CT26 tumors reached a median of ~100 mm3. Mice were dosed with 10 mg/kg PI-3008 or 5 mg/kg PD-1 antibody at Q5dx4. WT mice were used as a control.

Results

Figure 56:
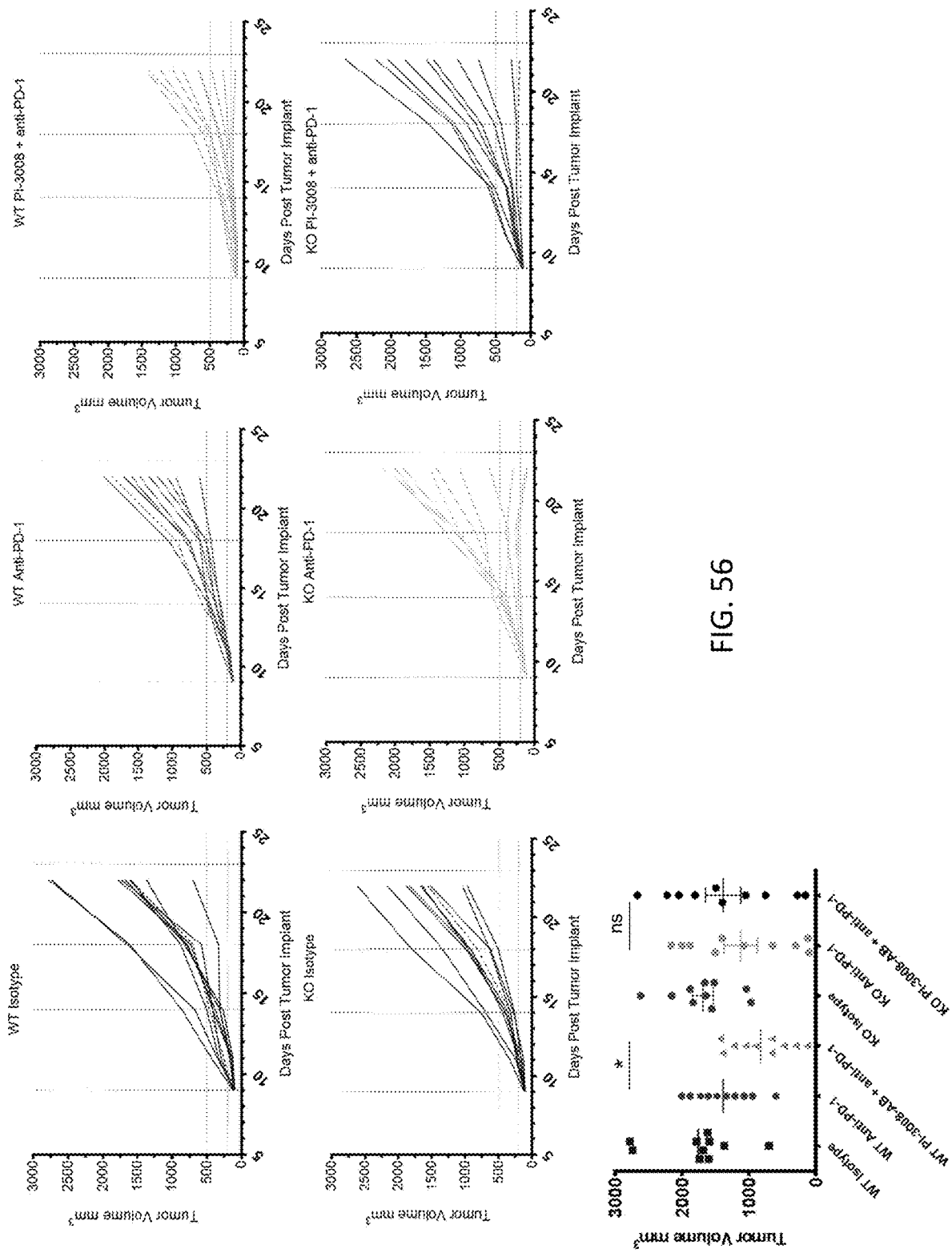
FIG. 56 shows the tumor volumes in B-cell deficient mice after MARCO antibody, PD-1 antibody, combination, or isotype antibody treatment.

The absence of B-cells dampened the combination efficacy of PI-3008 with anti-PD1 in CT26 tumors (FIG. 56). PI-3008 antibody in combination with PD-1 antibody resulted in greater tumor reduction in WT mice (top row) as compared to the combination treatment in the B-cell knock out mice (middle row). The bottom graph provides tumor volumes in individual mice in each condition.

Example 17: PI-3010.15 Induces NF-kB Signaling Pathway

Materials and Methods

THP1-Blue™ NF-κB cells were obtained from Invivogen and cultured in RPMI 1640 medium (Gibco) supplemented with 10% Fetal Bovine Serum (Gibco), 25 mM HEPES (Gibco), 1× GlutaMax (Gibco), 100 ug/ml Normacin (Gibco), 10 ug/mL Blasticidin (ThermoFisher). Approximately 50,000 cells were transduced with lentivirus containing the full-length MARCO construct (CL #3010) at MOI 10 in 500 ul media containing 8 ug/mL polybrene per well of 24-well plate. After overnight incubation at 37° C. with 5% $CO_2$, cells were washed in PBS and plated in 6-well plate in complete growth media. After 2-3 days, media was replaced with growth media containing 0.3 ug/ml puromycin (Invitrogen) for stable cell selection, and pooled cells were cultured and expanded For the reporter assay, 300,000 cells were plated per well of 96-well U-bottom plate and co-incubated with a dose titration of PI-3010.15 or isotype antibody control and 10e6/ml of HKLM (Invivogen) or 10 ng/ml of FALSTup (Invivogen) agonist and incubated for 4 hours or overnight at 37° C. with 5% $CO_2$. After incubation, 20 ul of supernatant was transferred to a new 96-well plate and incubated with 180 ul/well of QuantiBlue Solution (Invivogen) for 30-60 minutes at 37° C. with 5% $CO_2$. Alkaline Phosphatase activity was calculated by measuring the optical density (OD) at 650 nm using the Tecan microplate reader.

The THP-1 MARCO overexpressing cells were also used to validate the biomarker signature of pro-inflammatory genes activated after PI-3010.15 treatment. 1×10^6 cells in 1 ml of media were plated per well in a 24 well plate. PI-3010.15 and PI-0003 (corresponding hIgG1 isotype) were added to the cells at 1 µg/ml, 5 µg/ml, and 10 µg/ml for 4 hours and 24 hours. Cells were lysed with RLT buffer and RNA extracted for qPCR testing using the human primers to measure TNFα, IL-6, IL-1β, IL-10, CCL24, CXCL8, IL-1α, IL-18, and CCL20 expression.

Results

Figure 57:
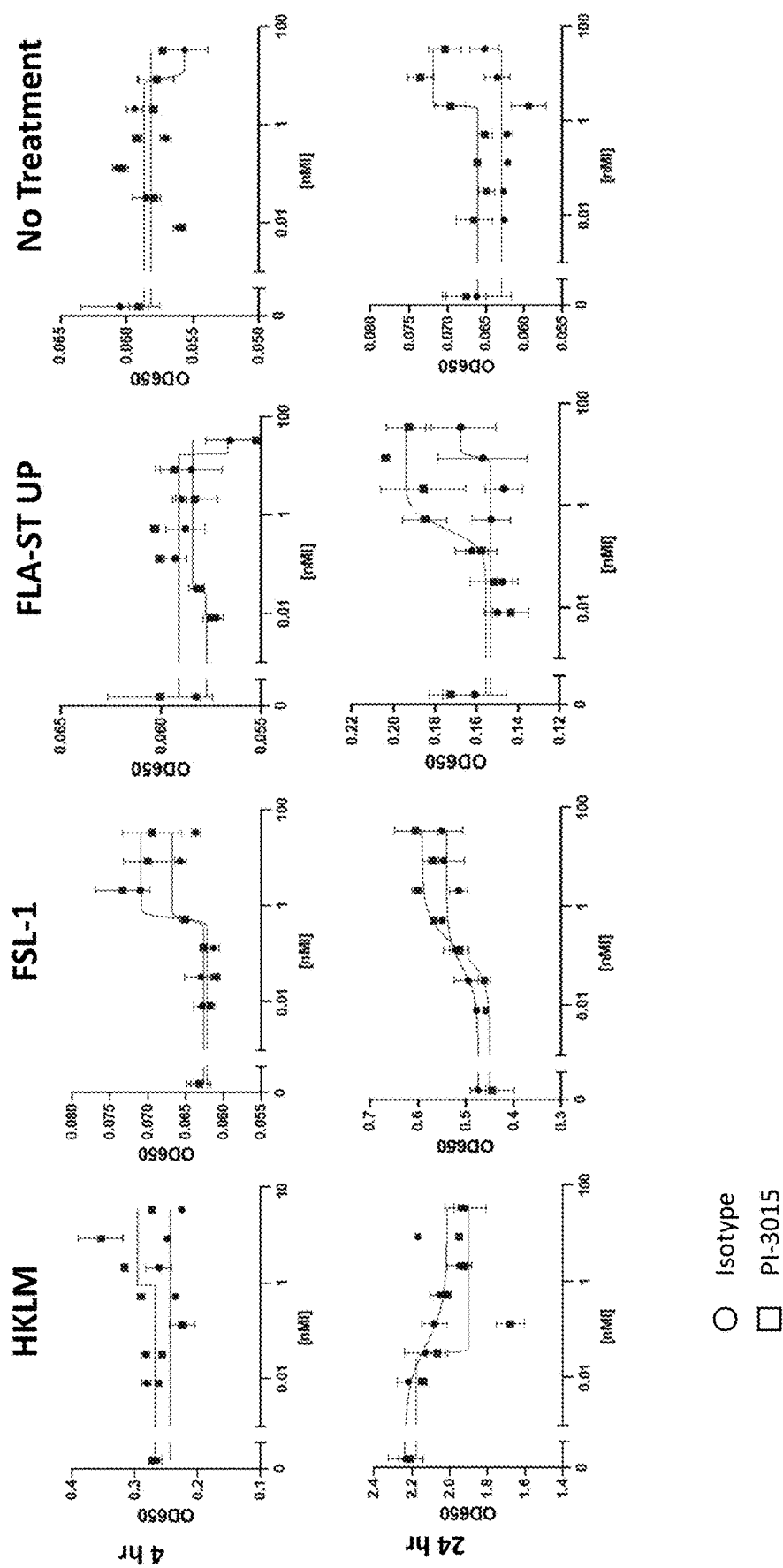
FIG. 57 shows the NF-kB reporter activity induced by PI-3010.15 or isotype antibody in combination with the indicated agonist at 4 hrs or 24 hrs.

PI-3010.15 induced the NF-kB signaling pathway after 4 hrs with the addition of HKLM, FSL-1, and FLA-ST UP after 24 hrs. PI-3010.15 also induced the NF-κB pathway in non-treated cells after 24 hrs (FIG. 57).

Figure 71:
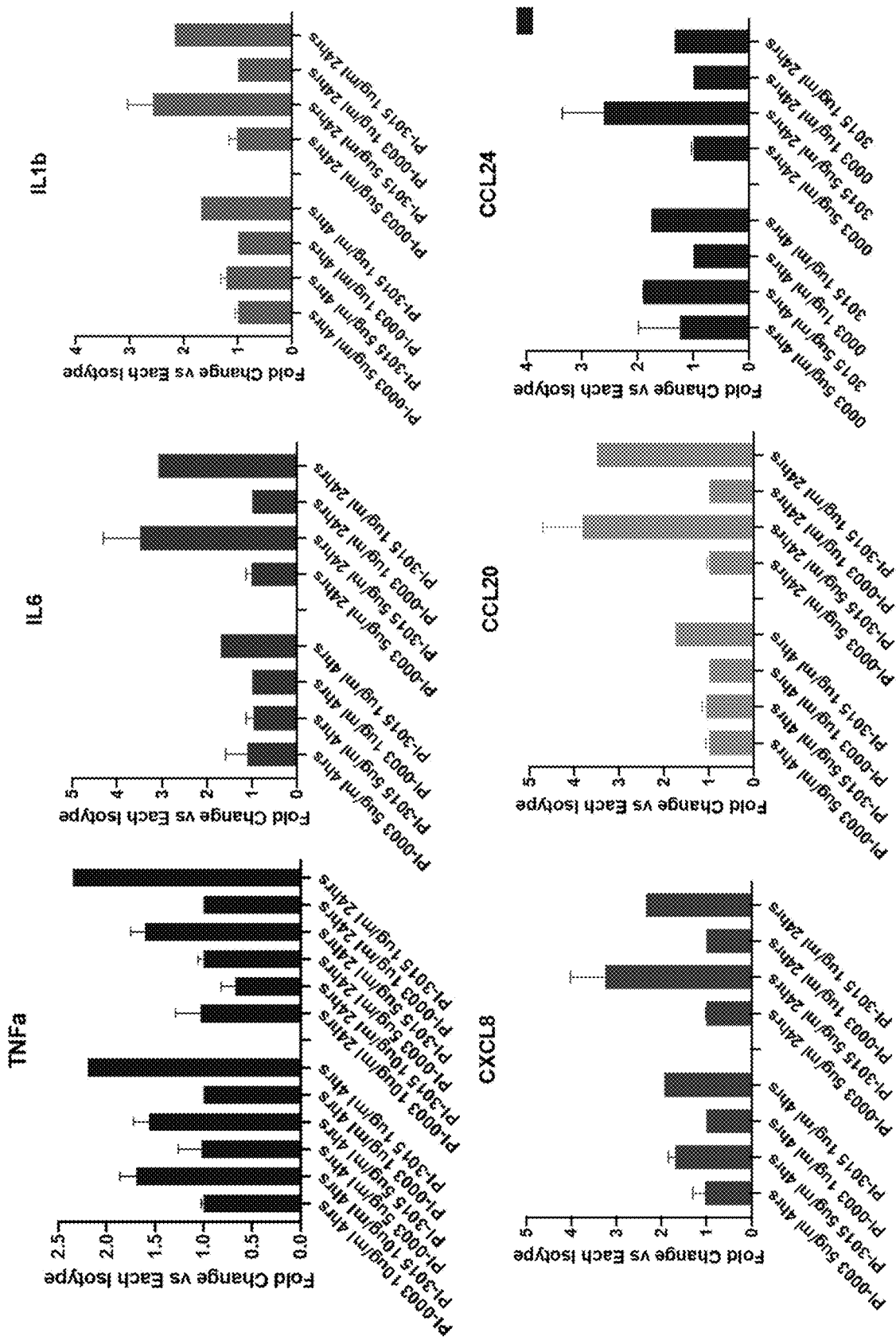
FIG. 71 shows that PI-3010.15 induced expression of the indicated pro-inflammatory cytokines.

The THP-1 OVX cells were also used as a surrogate for primary hMDMs cells to test pro-inflammatory cytokine activation by MARCO antibody PI-3010.15. Cells were incubated with PI-3010.15 or isotype antibody at 1 µg/ml, 5 µg/ml, or 10 µg/ml (TNFα only) for 4 hrs or 24 hrs. Cells were collected and assessed for TNFα, IL-6, IL-10, CXCL8, CCL20, CCL24, and IL-18 gene expression via qRT-PCR. PI-3010.15 induced TNFα gene expression after 4 h and 24 h at all antibody concentrations tested (FIG. 71). PI-3010.15 also induced expression of pro-inflammatory cytokines IL-6, IL1P, and CXCL8 at 4 hrs and 24 hrs (FIG. 71). The 5 µg/ml dosage of PI-3010.15 also induced pro-inflammatory cytokines such as CCL20, CCL24, and IL18 at 24 hrs (FIG. 71).

Example 18: Phospho Array Assay in hMDMs

Methods

A phospho array assay was performed using the Full Moon Biosystems Phospho Explorer Antibody Array on primary human monocyte derived macrophages (hMDMs) polarized with IL10 (2 donors).

Two frozen human peripheral blood CD14+ monocytes isolated from peripheral blood mononuclear cells using negative immunomagnetic selection (StemCell Technologies) were thawed and cultured in RPMI 1640 medium supplemented with 10% (v/v) heat-inactivated FBS (HyClone), 1 mM sodium pyruvate, non-essential amino-acids, 2 mM L-glutamine, 55 uM 2-mercaptoethanol and antimycotic antibiotic (all from Gibco). Monocytes were differentiated into macrophages by culturing in complete RPMI 1640 medium in the presence of 50 ng/ml human macrophage colony-stimulating factor (M-CSF) (PeproTech) at a density of 500,000 cells per well in 24 well plates. At day 3 of differentiation, media was replenished with the addition of fresh M-CSF. Differentiated human macrophages were polarized on day 6 by adding 25 ng/ml of recombinant human IL-10 (M2 condition) for 24 hours at 37° C. On day 7, the media was aspirated and cells washed gently. 500 µl of incubation medium (1×RPMI with 0.5% BSA) was added to the wells with 5 µg/ml of PI-3010.15 or hIgG1 isotype control (PI-0003). Treatment was terminated after 5 minutes and 15 minutes by washing with ice cold PBS and lysing cells with 300 µl of mPer and 1:100 HALT proteases and phosphatase inhibitors. Approximately 300 µg of protein lysate was sent to Full Moon Biosystems to perform the Phospho Explorer Antibody Array. Full Moon Biosystems used their standard protocol to label, couple, and detect the Average Signal Intensity of Replicate Spots, for each pair of site-specific antibody and phospho site-specific antibody, and determine the Signal Ratio of the paired antibodies. Fold changes between control and control samples were calculated using the following formula: Treatment Sample/Control Sample (hIgG1 treated or untreated).

Phospho hits were considered significant when the fold change was less than 0.6 or greater than 1.8 for both PI-3010.15/isotype and PI-3010.15/untreated ratio analysis. In addition, few hits were included if the isotype by itself had a substantial effect over the untreated due to Fc mediated signaling changes in the hMDMs (less than 0.75 fold decrease or greater than 1.5 fold increase compared to untreated). For those hits, a ratio of PI-3010.15/untreated was considered significant when below 0.75 fold decrease and above 1.5 fold increase if the ratio of PI-3010.15/isotype fell in the significant range (<0.6 and above 1.8 fold).

Results

Table 38 shows significant phosphorylation in PI-3010.15 vs. Isotype treated cells and PI-3010.15 vs. untreated (UT) cells at 5 minutes.

TABLE 38

| Gene | 3015 vs. Isotype (5 minutes) | 3015 vs. UT (5 minutes) |
|---|---|---|
| UP (>1.8 FC) | | |
| Cyclin B1 (Phospho-Ser147) | 5.084445769 | 2.561147785 |
| IRS-1 (Phospho-Ser794) | 4.447939568 | 2.871815775 |
| PDGFR alpha (Phospho-Tyr849) | 3.247023728 | 2.0112109 |
| Elk1 (Phospho-Ser389) | 2.650795969 | 1.93843226 |
| HSP27 (Phospho-Ser78) | 2.618765237 | 2.781365032 |
| CDK1/CDC2 (Phospho-Tyr15) | 2.495918288 | 2.915628441 |
| CDK5 (Phospho-Tyr15) | 2.495088042 | 3.772464066 |
| IL-2RA/CD25 (Phospho-Ser268) | 2.385317047 | 2.26149298 |
| Raf1 (Phospho-Ser259) | 2.345569464 | 2.986531327 |
| GluR1 (Phospho-Ser863) | 2.218294441 | 2.416141632 |
| LYN (Phospho-Tyr507)- Src pathway | 2.16499766 | 1.97114872 |
| Ezrin (Phospho-Thr566) | 2.148744088 | 2.992168753 |
| Lamin A/C (Phospho-Ser392) | 2.141294348 | 2.948772441 |
| BAD (Phospho-Ser91/128) | 2.011033931 | 2.461349555 |
| Tau (Phospho-Ser396) | 1.955441551 | 1.918036855 |
| MAP3K8/COT (Phospho-Thr290) | 1.943373784 | 1.967650786 |
| HDAC5 (Phospho-Ser259) | 1.922487843 | 2.088809947 |
| PAK3 (Phospho-Ser154) | 1.910328132 | 2.017578127 |
| mTOR (Phospho-Thr2446) | 1.8 | 2.42 |
| DOWN (<0.6 FC) | | |
| 14-3-3 beta/zeta (Phospho-Ser186/184) | 0.528463565 | 0.574004751 |
| Synapsin (Phospho-Ser9) | 0.468698508 | 0.444984245 |
| PKC delta (Phospho-Ser645) | 0.452312753 | 0.359573251 |
| 14-3-3 zeta (Phospho-Ser58) | 0.446714092 | 0.3453927 |
| Abl1 (Phospho-Thr754/735) | 0.399803417 | 0.334055031 |
| AKT1 (Phospho-Ser246) | 0.38984194 | 0.479793736 |
| Smad1 (Phospho-Ser187) | 0.380264132 | 0.442638779 |

Table 39 provides additional hits for the 5 minute samples that fell outside the first filtering bucket.

TABLE 39

| Gene | 3015 vs. Isotype | 3015 vs. Untreated | Iso vs. Untreated |
|---|---|---|---|
| ATF2 (Phospho-Ser62/44) | 2.13 | 1.59 | 0.75 |
| Claudin 3 (Phospho-Tyr219) | 0.22 | 0.68 | 3.04 |
| Connexin 43 (Phospho-Ser367) | 0.29 | 0.67 | 2.32 |
| LCK (Phospho-Tyr192) | 0.30 | 0.63 | 2.06 |
| Src (Phospho-Tyr529) | 0.32 | 0.78 | 2.45 |
| IKK-beta (Phospho-Tyr188) | 0.42 | 0.77 | 1.84 |
| PLD1 (Phospho-Ser561) | 0.42 | 0.78 | 1.86 |

Table 40 provides additional hits for the 5 minute samples where the isotype decreased the signal (below <0.6 fold over untreated) and PI-3010.15 rescued the effect with a biological significance. The fold increase over PI-3010.15/untreated could be >0.9.

TABLE 40

| Gene | 3015 vs. Isotype | 3015 vs. Untreated | Iso vs. Untreated |
|---|---|---|---|
| CaMK1-alpha (Phospho-Thr177) | 4.58 | 1.13 | 0.25 |
| p27Kip1 (Phospho-Thr187) | 3.35 | 0.95 | 0.28 |
| Cortactin (Phospho-Tyr421) | 3.00 | 1.29 | 0.43 |
| Keratin 18 (Phospho-Ser52) | 2.36 | 0.96 | 0.41 |
| FAK (Phospho-Tyr397) | 2.19 | 0.88 | 0.40 |
| IkB-beta (Phospho-Thr19) | 2.13 | 1.10 | 0.52 |
| PLC beta3 (Phospho-Ser1105) | 2.11 | 1.10 | 0.52 |

Table 41 shows the significant phosphorylation in PI-3010.15 vs. Isotype treated cells and PI-3010.15 vs. untreated (UT) cells at 15 minutes.

TABLE 41

| Gene | Gene | Gene |
|---|---|---|
| UP (>1.8 FC) | | |
| SYK (Phospho-Tyr525) | 3.763491432 | 2.629401334 |
| Dok-1 (Phospho-Tyr398) | 3.086467586 | 2.609649844 |
| IKK-alpha/beta (Phospho-Ser180/181) | 2.959202923 | 1.934873037 |
| HSP90B (Phospho-Ser226) | 2.870020923 | 3.546965968 |
| GluR1 (Phospho-Ser863) | 2.609270653 | 2.21995696 |
| Synaptotagmin (Phospho-Ser309) | 2.600941915 | 2.136658796 |
| SHP-2 (Phospho-Tyr580) | 2.597416517 | 2.242046774 |
| Filamin A (Phospho-Ser2152) | 2.335627516 | 1.996061335 |
| CaMK4 (Phospho-Thr196/200) | 2.279954736 | 1.893568987 |
| Synuclein alpha (Phospho-Tyr133) | 2.131004882 | 1.874499543 |
| HDAC5 (Phospho-Ser498) | 2.110924432 | 2.744099757 |
| P70S6K (Phospho-Ser424) | 2.076974184 | 1.870856295 |
| 4E-BP1 (Phospho-Ser65) | 2.06037659 | 2.827767866 |
| Calmodulin (Phospho-Thr79/Ser81) | 2.046380319 | 2.662693319 |
| MKK4/SEK1 (Phospho-Thr261) | 2.035499973 | 3.040392853 |
| IL-2RA/CD25 (Phospho-Ser268) | 1.973584034 | 2.080305927 |
| Synaptotagmin (Phospho-Ser202) | 1.930362488 | 1.991073071 |
| Rb (Phospho-Ser780) | 1.874035219 | 1.974833058 |
| Tyrosine Hydroxylase (Phospho-Ser40) | 1.852127179 | 1.934979677 |
| DOWN (>0.6 FC) | | |
| PLCG2 (Phospho-Tyr1217) | 0.591517857 | 0.563418522 |
| Kv1.3/KCNA3 (Phospho-Tyr135) | 0.57141834 | 0.586825891 |
| DARPP-32 (Phospho-Thr34) | 0.55741993 | 0.41127774 |
| Claudin 7 (Phospho-Tyr210) | 0.556173961 | 0.597139861 |
| Rel (Phospho-Ser503) | 0.554992754 | 0.509612791 |
| Ezrin (Phospho-Tyr478) | 0.535586574 | 0.508394478 |
| LKB1 (Phospho-Ser428) | 0.531130409 | 0.520111023 |
| AurA (Phospho-Ser342) | 0.527800917 | 0.49832997 |
| p130Cas (Phospho-Tyr165) | 0.519493014 | 0.521059511 |
| Cortactin (Phospho-Tyr421) | 0.474466269 | 0.464638242 |
| Dok-1 (Phospho-Tyr362) | 0.456406193 | 0.482008648 |
| Keratin 18 (Phospho-Ser33) | 0.417597114 | 0.288197731 |
| CaMK2-beta/gamma/delta (Phospho-Thr287) | 0.410587574 | 0.537483464 |
| ETK (Phospho-Tyr40) | 0.409259434 | 0.437316317 |
| NFkB-p65 (Phospho-Thr435) | 0.400460795 | 0.344387917 |
| p27Kip1 (Phospho-Ser10) | 0.383076583 | 0.540101088 |
| NFkB-p100/p52 (Phospho-Ser869) | 0.37145326 | 0.532229421 |
| VEGFR2 (Phospho-Tyr1175) | 0.368651283 | 0.39699714 |
| PKC delta (Phospho-Ser645) | 0.3449432 | 0.538228023 |
| Estrogen Receptor-alpha (Phospho-Ser118) | 0.322713977 | 0.305382748 |
| HSL (Phospho-Ser554) | 0.31391716 | 0.411180773 |
| CD3Z (Phospho-Tyr142) | 0.309319341 | 0.377863121 |
| PAK3 (Phospho-Ser154) | 0.288315803 | 0.472978229 |
| Raf1 (Phospho-Ser296) | 0.241201384 | 0.310819568 |
| CDK1/CDC2 (Phospho-Thr14) | 0.232456135 | 0.311120574 |

Table 42 provides additional hits that fell outside the first filtering bucket for the 15 minute samples.

TABLE 42

| Gene | 3015 vs. Isotype | 3015 vs. Untreated | Iso vs. Untreated |
|---|---|---|---|
| PKC epsilon (Phospho-Ser729) | 0.34 | 0.75 | 2.19 |
| EGFR (Phospho-Tyr1110) | 0.41 | 0.71 | 1.71 |
| ASK1 (Phospho-Ser966) | 0.42 | 0.67 | 1.58 |
| c-Jun (Phospho-Ser63) | 0.43 | 0.76 | 1.78 |
| TOP2A/DNA topoisomerase II (Phospho-Ser1106) | 0.45 | 0.77 | 1.72 |
| STAT6 (Phospho-Thr645) | 0.48 | 0.74 | 1.53 |

Based on the phospho array screen, the pathways down-regulated after 5 minutes were: Cell adhesion: Claudin 3, Connexin 43, Syapsin; 14-3-3 beta and zeta: adaptor that modulates multiple inflammatory pathways; PI3K master regulator pathway: AKT1; PKC delta (upstream of Src); TGFb signaling: Smad1; c-Abl signaling (modulates STAT signaling); and Src pathway: LCK, Src (cytoskeletal rearrangement, phagocytosis and survival).

The pathways upregulated after 5 minutes were: Cell cycle: Cyclin B1, CDK1/CDC2, CDK5, PAK3; IRS-1: insulin receptor activated by Insulin and IL-4, upstream of AKT; PDGFR: platelet derived factor receptor activates Ras/ERK to regulate angiogenesis, proliferation, migration genes; ELK1: transcription factor downstream of ERK/PDGFR and Rac/JNK during inflammasome; Raf1: activated by LPS or mCSF and upstream of ERK1/2 activation for proliferation and activation; LYN: activated by LDL on CD36 and BCR, and phosphorylates AKT and SYK among others (metabolic reprogramming); IL-2RA/CD25: activates JAK/STAT, PI3K and Ras signaling; Lamin A/C, Ezrin, PAK3 (group 1 PAK downstream effectors of Ras-related Rho GTPase Cdc42 and Rac, and AKT), cytoskeletal rearrangement; MAPK38 (TPL2): (MAP3 K) activated downstream of TNFαR, IL1R, TLR, CD40, IL17R. TPL2 regulates the MEK1/2 and ERK1/2 pathways to regulate a cascade of inflammatory responses; BAD: Survival, downstream of AKT; and Chromatin modification: HDAC5.

The pathways upregulated after 15 minutes were: Regulation: Calmodulin, GLUR1, HSP90; Induction of Enzymatic activity: SYK, GLUR1, SHP-2, MKK4, CAMK4; Molecular Association: DOK1, GLUR1, SHP-2, HSP90; Cell motility and cytoskeletal Reorganization: Filamin A, IKKa/b, SHP-2; Activation of transcription: IKKa/b, CAMK4, MKK4; IL2 Receptor activation; mTOR and Translation modification: P70S6K, 4E-BP1; and Calcium signaling, endocytosis, exocytosis, Synapses, microtubules: Synaptogamin, CAMK4, Synuclein alpha.

The pathways downregulated after 15 minutes were: Regulation (survival): Raf1, VEGFR2, PKC delta, EGFR, STAT6; Molecular Association: DOK1, GLUR1, SHP-2, HSP90; Cell motility and cytoskeletal reorganization: Claudin 7, Cortactin, PKC delta, p130Cas, Ezrin, PAK3; NfkB pathway regulation: NFkb p100, Re1, Nfkb-p65; Cell Cycle progression: CDK1, p27Kip1, AurA, PKC, CAMK2; Calcium signaling: PKC, CaMK2; TCR signaling: CD3z is downstream of LCK signaling and upstream of ZAP70.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

```
                              Sequence listing

SEQ
ID
NO   Name             Sequence

1   HX-3031          QVQLKESGPGLVQPSQTLSLTCTVSGFSLTSYHVSWVRQPPGKGLEWMGAIWTGGSIAYNSLLKSRL
     Heavy Chain      SISRDTSKSQVFLKMNSLQTEDTATYYCARDLSDYYSSYTSFDYWGQGVMVTVST
     Variable

2   HX-3031          GFSLTSYHVS
     CDR-H1

3   HX-3031          AIWTGGSIA
     CDR-H2

4   HX-3031          DLSDYYSSYTSFDY
     CDR-H3

5   HX-3031          QVQLKESGPGLVQPSQTLSLTCTVSGFSLTSYHVSWVRQPPGKGLEWMGAIWTGGSIAYNSLLKSRL
     Heavy chain      SISRDTSKSQVFLKMNSLQTEDTATYYCARDLSDYYSSYTSFDYWGQGVMVTVSTAETTAPSVYPLA
                      PGTALKSNSMVTLGCLVKGYFPEPVTVTWNSGALSSGVHTFPAVLQSGLYTLTSSVTVPSSTWSSQA
                      VTCNVAHPASSTKVDKKIVPRECNPCGCTGSEVSSVFIFPPKTKDVLTITLTPKVTCVVVDISQNDP
                      EVRFSWFIDDVEVHTAQTHAPEKQSNSTLRSVSELPIVHRDWLNGKTFKCKVNSGAFPAPIEKSISK
                      PEGTPRGPQVYTMAPPKEEMTQSQVSITCMVKGFYPPDIYTEWKMNGQPQENYKNTPPTMDTDGSYF
                      LYSKLNVKKETWQQGNTFTCSVLHEGLHNHHTEKSLSHSP*

6   HX-3031          DIQMTQSPASLSTSLGETVSIECLASEGISNDLAWYQQKSGKSPQLLIYAASRLQDGVPSRFSGSGS
     Light Chain      GTRYSLKISGMQPEDEADYFCQQSYKYPLTFGSGTKLEIK
     Variable

7   HX-3031          LASEGISNDLA
     CDR-L1

8   HX-3031          AASRLQD
     CDR-L2

9   HX-3031          QQSYKYPLT
     CDR-L3

10   HX-3031          DIQMTQSPASLSTSLGETVSIECLASEGISNDLAWYQQKSGKSPQLLIYAASRLQDGVPSRFSGSGS
     Light chain      GTRYSLKISGMQPEDEADYFCQQSYKYPLTFGSGTKLEIKRADAAPTVSIFPPSTEQLATGGASVVC
                      LMNNFYPRDISVKWKIDGTERRDGVLDSVTDQDSKDSTYSMSSTLSLTKADYESHNLYTCEVVHKTS
                      SSPVVKSFNRNEC*

11   PI-3010-AB       QVQLKESGPGLVQPSQTLSLTCTVSGFSLTSYHVSWVRQPPGKGLEWMGAIWTGGSIAYNSLLKSRL
     Heavy Chain      SISRDTSKSQVFLKMNSLQTEDTATYYCARDLSDYYSSYTSFDYWGQGVMVTVST
     Variable
```

-continued

| SEQ ID NO | Name | Sequence |
|---|---|---|
| 12 | PI-3010-AB CDR-H1 | GFSLTSYHVS |
| 13 | PI-3010-AB CDR-H2 | AIWTGGSIA |
| 14 | PI-3010-AB CDR-H3 | DLSDYYSSYTSFDY |
| 15 | PI-3010-AB Heavy chain | QVQLKESGPGLVQPSQTLSLTCTVSGFSLTSYHVSWVRQPPGKGLEWMGAIWTGGSIAYNSLLKSRL SISRDTSKSQVFLKMNSLQTEDTATYYCARDLSDYYSSYTSFDYWGQGVMVTVSTASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 16 | PI-3010-AB Light Chain Variable | DIQMTQSPASLSTSLGETVSIECLASEGISNDLAWYQQKSGKSPQLLIYAASRLQDGVPSRFSGSGS GTRYSLKISGMQPEDEADYFCQQSYKYPLTFGSGTKLEIK |
| 17 | PI-3010-AB CDR-L1 | LASEGISNDLA |
| 18 | PI-3010-AB CDR-L2 | AASRLQD |
| 19 | PI-3010-AB CDR-L3 | QQSYKYPLT |
| 20 | PI-3010-AB Light chain | DIQMTQSPASLSTSLGETVSIECLASEGISNDLAWYQQKSGKSPQLLIYAASRLQDGVPSRFSGSGS GTRYSLKISGMQPEDEADYFCQQSYKYPLTFGSGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 21 | PI-3011-AB Heavy Chain Variable | QVQLQESGPGLVKPSETLSLTCTVSGFSLTSYHVSWIRQPPGKGLEWIGAIWTGGSIAYNPSLKSRV TISVDTSKNQFSLKLSSVTAADTAVYYCARDLSDYYSSYTSFDYWGQGTLVTVSS |
| 22 | PI-3011-AB CDR-H1 | GFSLTSYHVS |
| 23 | PI-3011-AB CDR-H2 | AIWTGGSIA |
| 24 | PI-3011-AB CDR-H3 | DLSDYYSSYTSFDY |
| 25 | PI-3011-AB Heavy chain | QVQLQESGPGLVKPSETLSLTCTVSGFSLTSYHVSWIRQPPGKGLEWIGAIWTGGSIAYNPSLKSRV TISVDTSKNQFSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 26 | PI-3011-AB Light Chain Variable | DIQMTQSPSSLSASVGDRVTITCRASEGISNDLAWYQQKPGKAPKLLIYAASRLQSGVPSRFSGSGS GTDFTLTISSLQPEDFATYYCQQSYKYPLTFGQGTKLEIK |
| 27 | PI-3011-AB CDR-L1 | RASEGISNDLA |
| 28 | PI-3011-AB CDR-L2 | AASRLQD |
| 29 | PI-3011-AB CDR-L3 | QQSYKYPLT |
| 30 | PI-3011-AB Light chain | DIQMTQSPSSLSASVGDRVTITCRASEGISNDLAWYQQKPGKAPKLLIYAASRLQSGVPSRFSGSGS GTDFTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |

-continued

| SEQ ID NO | Name | Sequence |
|---|---|---|
| 31 | PI-3012-AB Heavy Chain Variable | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 32 | PI-3012-AB CDR-H1 | GFSLTSYHVS |
| 33 | PI-3012-AB CDR-H2 | AIWTGGSIA |
| 34 | PI-3012-AB CDR-H3 | DLSDYYSSYTSFDY |
| 35 | PI-3012-AB Heavy chain | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 36 | PI-3012-AB Light Chain Variable | DIQMTQSPSSLSASVGDRVTITCRASEGISNDLAWYQQKPGKAPKLLIYAASRLQSGVPSRFSGSGS GTDYTLTISSLQPEDFATYYCQQSYKYPLTFGQGTKLEIK |
| 37 | PI-3012-AB CDR-L1 | RASEGISNDLA |
| 38 | PI-3012-AB CDR-L2 | AASRLQD |
| 39 | PI-3012-AB CDR-L3 | QQSYKYPLT |
| 40 | PI-3012-AB Light chain | DIQMTQSPSSLSASVGDRVTITCRASEGISNDLAWYQQKPGKAPKLLIYAASRLQSGVPSRFSGSGS GTDYTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 41 | PI-3013-AB Heavy Chain Variable | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 42 | PI-3013-AB CDR-H1 | GFSLTSYHVS |
| 43 | PI-3013-AB CDR-H2 | AIWTGGSIA |
| 44 | PI-3013-AB CDR-H3 | DLSDYYSSYTSFDY |
| 45 | PI-3013-AB Heavy chain | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 46 | PI-3013-AB Light Chain Variable | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIK |
| 47 | PI-3013-AB CDR-L1 | RASEGISNDLA |
| 48 | PI-3013-AB CDR-L2 | AASRLQD |
| 49 | PI-3013-AB CDR-L3 | QQSYKYPLT |

| SEQ ID NO | Name | Sequence |
|---|---|---|
| 50 | PI-3013-AB Light chain | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 51 | PI-3014-AB Heavy Chain Variable | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSS |
| 52 | PI-3014-AB CDR-H1 | GFSLTSYHVS |
| 53 | PI-3014-AB CDR-H2 | AIWTGGSIA |
| 54 | PI-3014-AB CDR-H3 | DLSDYYSSYTSFDY |
| 55 | PI-3014-AB Heavy chain | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 56 | PI-3014-AB Light Chain Variable | DIQMTQSPSSLSASVGDRVTITCRASEGISNDLAWYQQKPGKAPKLLIYAASRLQSGVPSRFSGSGS GTDYTLTISSLQPEDFATYYCQQSYKYPLTFGQGTKLEIK |
| 57 | PI-3014-AB CDR-L1 | RASEGISNDLA |
| 58 | PI-3014-AB CDR-L2 | AASRLQD |
| 59 | PI-3014-AB CDR-L3 | QQSYKYPLT |
| 60 | PI-3014-AB Light chain | DIQMTQSPSSLSASVGDRVTITCRASEGISNDLAWYQQKPGKAPKLLIYAASRLQSGVPSRFSGSGS GTDYTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 61 | PI-3015-AB Heavy Chain Variable | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSS |
| 62 | PI-3015-AB CDR-H1 | GFSLTSYHVS |
| 63 | PI-3015-AB CDR-H2 | AIWTGGSIA |
| 64 | PI-3015-AB CDR-H3 | DLSDYYSSYTSFDY |
| 65 | PI-3015-AB Heavy chain | QVQLQESGPGLVKPSETLSLTCTVSGFSLTSYHVSWVRQPPGKGLEWMGAIWTGGSIAYNPSLKSRL TISRDTSKNQVSLKMSSLTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 66 | PI-3015-AB Light Chain Variable | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIK |
| 67 | PI-3015-AB CDR-L1 | RASEGISNDLA |

| SEQ ID NO | Name | Sequence |
|---|---|---|
| 68 | PI-3015-AB CDR-L2 | AASRLQD |
| 69 | PI-3015-AB CDR-L3 | QQSYKYPLT |
| 70 | PI-3015-AB Light chain | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 71 | PI-3020-AB Heavy Chain Variable | QVQLKESGPGLVQPSQTLSLTCTVSGFSLTSYHVSWVRQPPGKGLEWMGAIWTGGSIAYNSLLKSRL SISRDTSKSQVFLKMNSLQTEDTATYYCARDLSDYYSSYTSFDYWGQGVMVTVST |
| 72 | PI-3020-AB CDR-H1 | GFSLTSYHVS |
| 73 | PI-3020-AB CDR-H2 | AIWTGGSIA |
| 74 | PI-3020-AB CDR-H3 | DLSDYYSSYTSFDY |
| 75 | PI-3020-AB Heavy chain | QVQLKESGPGLVQPSQTLSLTCTVSGFSLTSYHVSWVRQPPGKGLEWMGAIWTGGSIAYNSLLKSRL SISRDTSKSQVFLKMNSLQTEDTATYYCARDLSDYYSSYTSFDYWGQGVMVTVSTASTKGPSVFPLA PCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPSCPAPEFLGGPSVFLFPPKPKDTLMISRTPEVTCVVVDV SQEDPEVQFNWYVDGVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK* |
| 76 | PI-3020-AB Light Chain Variable | DIQMTQSPASLSTSLGETVSIECLASEGISNDLAWYQQKSGKSPQLLIYAASRLQDGVPSRFSGSGS GTRYSLKISGMQPEDEADYFCQQSYKYPLTFGSGTKLEIK |
| 77 | PI-3020-AB CDR-L1 | LASEGISNDLA |
| 78 | PI-3020-AB CDR-L2 | AASRLQD |
| 79 | PI-3020-AB CDR-L3 | QQSYKYPLT |
| 80 | PI-3020-AB Light chain | DIQMTQSPASLSTSLGETVSIECLASEGISNDLAWYQQKSGKSPQLLIYAASRLQDGVPSRFSGSGS GTRYSLKISGMQPEDEADYFCQQSYKYPLTFGSGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 81 | PI-3022-AB Heavy Chain Variable | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 82 | PI-3022-AB CDR-H1 | GFSLTSYHVS |
| 83 | PI-3022-AB CDR-H2 | AIWTGGSIA |
| 84 | PI-3022-AB CDR-H3 | DLSDYYSSYTSFDY |
| 85 | PI-3022-AB Heavy chain | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 86 | PI-3022-AB Light Chain | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIK |

Sequence listing

| SEQ ID NO | Name | Sequence |
|---|---|---|
| 87 | PI-3022-AB CDR-L1 Variable | RASEGISNDLA |
| 88 | PI-3022-AB CDR-L2 | AASRLQD |
| 89 | PI-3022-AB CDR-L3 | QQSYKYPLT |
| 90 | PI-3022-AB Light chain | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 91 | PI-3023-AB Heavy Chain Variable | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 92 | PI-3023-AB CDR-H1 | GFSLTSYHVS |
| 93 | PI-3023-AB CDR-H2 | AIWTGGSIA |
| 94 | PI-3023-AB CDR-H3 | DLSDYYSSYTSFDY |
| 95 | PI-3023-AB Heavy chain | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 96 | PI-3023-AB Light Chain Variable | DIQMTQSPSSLSTSVGDRVTITCRASEGISNDLAWYQQKPGKSPKLLIYAASRLQSGVPSRFSGSGS GTDYTLTISSLQPEDFATYFCQQSYKYPLTFGQGTKLEIK |
| 97 | PI-3023-AB CDR-L1 | RASEGISNDLA |
| 98 | PI-3023-AB CDR-L2 | AASRLQD |
| 99 | PI-3023-AB CDR-L3 | QQSYKYPLT |
| 100 | PI-3023-AB Light chain | DIQMTQSPSSLSTSVGDRVTITCRASEGISNDLAWYQQKPGKSPKLLIYAASRLQSGVPSRFSGSGS GTDYTLTISSLQPEDFATYFCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 101 | PI-3024-AB Heavy Chain Variable | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 102 | PI-3024-AB CDR-H1 | GFSLTSYHVS |
| 103 | PI-3024-AB CDR-H2 | AIWTGGSIA |
| 104 | PI-3024-AB CDR-H3 | DLSDYYSSYTSFDY |
| 105 | PI-3024-AB Heavy chain | QVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA |

-continued

| SEQ ID NO | Name | Sequence |
|---|---|---|
| | | PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 106 | PI-3024-AB Light Chain Variable | DIQMTQSPSSLSTSVGDRVTITCRASEGISNDLAWYQQKPGKSPKLLIYAASRLQDGVPSRFSGSGS GTDYTLTISSLQPEDEATYFCQQSYKYPLTFGQGTKLEIK |
| 107 | PI-3024-AB CDR-L1 | RASEGISNDLA |
| 108 | PI-3024-AB CDR-L2 | AASRLQD |
| 109 | PI-3024-AB CDR-L3 | QQSYKYPLT |
| 110 | PI-3024-AB Light chain | DIQMTQSPSSLSTSVGDRVTITCRASEGISNDLAWYQQKPGKSPKLLIYAASRLQDGVPSRFSGSGS GTDYTLTISSLQPEDEATYFCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 111 | PI-3025-AB Heavy Chain Variable | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 112 | PI-3025-AB CDR-H1 | GFSLTSYHVS |
| 113 | PI-3025-AB CDR-H2 | AIWTGGSIA |
| 114 | PI-3025-AB CDR-H3 | DLSDYYSSYTSFDY |
| 115 | PI-3025-AB Heavy chain | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 116 | PI-3025-AB Light Chain Variable | DIQMTQSPSSLSTSVGDRVTITCRASEGISNDLAWYQQKPGKSPKLLIYAASRLQDGVPSRFSGSGS GTDYTLTISSLQPEDEATYFCQQSYKYPLTFGQGTKLEIK |
| 117 | PI-3025-AB CDR-L1 | RASEGISNDLA |
| 118 | PI-3025-AB CDR-L2 | AASRLQD |
| 119 | PI-3025-AB CDR-L3 | QQSYKYPLT |
| 120 | PI-3025-AB Light chain | DIQMTQSPSSLSTSVGDRVTITCRASEGISNDLAWYQQKPGKSPKLLIYAASRLQDGVPSRFSGSGS GTDYTLTISSLQPEDEATYFCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 121 | PI-3026-AB Heavy Chain Variable | VQLQESGPGLVKPSETLSLTCTVSGFSLTSYHVSWVRQPPGKGLEWIGAIWTGGSIAYNPSLKSRVT ISRDTSKNQVSLKLSSVTAADTAVYYCARDLSDYYSSYTSFDYWGQGTLVTVSS |
| 122 | PI-3026-AB CDR-H1 | GFSLTSYHVS |
| 123 | PI-3026-AB CDR-H2 | AIWTGGSIA |
| 124 | PI-3026-AB CDR-H3 | DLSDYYSSYTSFDY |

-continued

| SEQ ID NO | Name | Sequence |
|---|---|---|
| 125 | PI-3026-AB Heavy chain | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 126 | PI-3026-AB Light Chain Variable | DIQMTQSPSSLSTSVGDRVTITCRASEGISNDLAWYQQKPGKSPKLLIYAASRLQSGVPSRFSGSGS GTDYTLTISSLQPEDFATYFCQQSYKYPLTFGQGTKLEIK |
| 127 | PI-3026-AB CDR-L1 | RASEGISNDLA |
| 128 | PI-3026-AB CDR-L2 | AASRLQD |
| 129 | PI-3026-AB CDR-L3 | QQSYKYPLT |
| 130 | PI-3026-AB Light chain | DIQMTQSPSSLSTSVGDRVTITCRASEGISNDLAWYQQKPGKSPKLLIYAASRLQSGVPSRFSGSGS GTDYTLTISSLQPEDFATYFCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 131 | PI-3027-AB Heavy Chain Variable | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSS |
| 132 | PI-3027-AB CDR-H1 | GFSLTSYHVS |
| 133 | PI-3027-AB CDR-H2 | AIWTGGSIA |
| 134 | PI-3027-AB CDR-H3 | DLSDYYSSYTSFDY |
| 135 | PI-3027-AB Heavy chain | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PSSKSTSGGTAALGCLVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK* |
| 136 | PI-3027-AB Light Chain Variable | DIQMTQSPSSLSTSVGDRVTITCRASEGISNDLAWYQQKPGKSPKLLIYAASRLQDGVPSRFSGSGS GTDYTLTISSLQPEDEATYFCQQSYKYPLTFGQGTKLEIK |
| 137 | PI-3027-AB CDR-L1 | RASEGISNDLA |
| 138 | PI-3027-AB CDR-L2 | AASRLQD |
| 139 | PI-3027-AB CDR-L3 | QQSYKYPLT |
| 140 | PI-3027-AB Light chain | DIQMTQSPSSLSTSVGDRVTITCRASEGISNDLAWYQQKPGKSPKLLIYAASRLQDGVPSRFSGSGS GTDYTLTISSLQPEDEATYFCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 141 | HX-3061 Heavy Chain Variable | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSS |
| 142 | HX-3061 CDR-H1 | KFTFSNYGMN |
| 143 | HX-3061 | LIYYNSNNKY |

| SEQ ID NO | Name | Sequence |
|---|---|---|
| | CDR-H2 | |
| 144 | HX-3061 CDR-H3 | SLTGGSDYFDS |
| 145 | HX-3061 Heavy chain | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSSAETTAPSVYPLAPG TALKSNSMVTLGCLVKGYFPEPVTVTWNSGALSSGVHTFPAVLQSGLYTLSSSVTVPSSTWPSQTVT CNVAHPASSTKVDKKIVPRNCGGDCKPCICTGSEVSSVFIFPPKPKDVLTITLTPKVTCVVVDISQD DPEVHFSWFVDDVEVHTAQTRPPEEQFNSTFRSVSELPILHQDWLNGRTFRCKVTSAAFPSPIEKTI SKPEGRTQVPHVYTMSPTKEEMTQNEVSITCMVKGFYPPDIYVEWQMNGQPQENYKNTPPTMDTDGS YFLYSKLNVKKEKWQQGNTFTCSVLHEGLHNHHTEKSLSHSP* |
| 146 | HX-3061 Light Chain Variable | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIK |
| 147 | HX-3061 CDR-L1 | KASKSIGTFLA |
| 148 | HX-3061 CDR-L2 | SGSTLQS |
| 149 | HX-3061 CDR-L3 | QQHDEYPFT |
| 150 | HX-3061 Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSTEQLATGGASVVC LMNNFYPRDISVKWKIDGTERRDGVLDSVTDQDSKDSTYSMSSTLSLTKADYESHNLYTCEVVHKTS SSPVVKSFNRNEC* |
| 151 | PI-3016-AB Heavy Chain Variable | EVQLVESGGGLVQPGGSLRLSCAASKFTFSNYGMNWVRQAPGKGLEWVSLIYYNSNNKYYADSVKGR FTISRDNSKNTLYLQMNSLRAEDTAVYYCAKSLTGGSDYFDSWGQGTLVTVSS |
| 152 | PI-3016-AB CDR-H1 | KFTFSNYGMN |
| 153 | PI-3016-AB CDR-H2 | LIYYNSNNKY |
| 154 | PI-3016-AB CDR-H3 | SLTGGSDYFDS |
| 155 | PI-3016-AB Heavy chain | EVQLVESGGGLVQPGGSLRLSCAASKFTFSNYGMNWVRQAPGKGLEWVSLIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 156 | PI-3016-AB Light Chain Variable | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIK |
| 157 | PI-3016-AB CDR-L1 | RASKSIGTFLA |
| 158 | PI-3016-AB CDR-L2 | SGSTLQS |
| 159 | PI-3016-AB CDR-L3 | QQHDEYPFT |
| 160 | PI-3016-AB Light chain | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 161 | PI-3017-AB Heavy Chain Variable | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |

| SEQ ID NO | Name | Sequence |
|---|---|---|
| 162 | PI-3017-AB CDR-H1 | KFTFSNYGMN |
| 163 | PI-3017-AB CDR-H2 | LIYYNSNNKY |
| 164 | PI-3017-AB CDR-H3 | SLTGGSDYFDS |
| 165 | PI-3017-AB Heavy chain | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 166 | PI-3017-AB Light Chain Variable | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIK |
| 167 | PI-3017-AB CDR-L1 | RASKSIGTFLA |
| 168 | PI-3017-AB CDR-L2 | SGSTLQS |
| 169 | PI-3017-AB CDR-L3 | QQHDEYPFT |
| 170 | PI-3017-AB Light chain | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 171 | PI-3018-AB Heavy Chain Variable | EVQLVESGGGLVQPGGSLRLSCAASGFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |
| 172 | PI-3018-AB CDR-H1 | KFTFSNYGMN |
| 173 | PI-3018-AB CDR-H2 | LIYYNSNNKY |
| 174 | PI-3018-AB CDR-H3 | SLTGGSDYFDS |
| 175 | PI-3018-AB Heavy chain | EVQLVESGGGLVQPGGSLRLSCAASGFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 176 | PI-3018-AB Light Chain Variable | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIK |
| 177 | PI-3018-AB CDR-L1 | RASKSIGTFLA |
| 178 | PI-3018-AB CDR-L2 | SGSTLQS |
| 179 | PI-3018-AB CDR-L3 | QQHDEYPFT |
| 180 | PI-3018-AB Light chain | DIQMTQSPSSLSASVGDRVTITCRASKSIGTFLAWYQQKPGKAPKLLIYSGSTLQSGVPSRFSGSGS GTDFTLTISSLQPEDFATYYCQQHDEYPFTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL |

| SEQ ID NO | Name | Sequence |
|---|---|---|
| | | SSPVTKSFNRGEC* |
| 181 | PI-3019-AB Heavy Chain Variable | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSS |
| 182 | PI-3019-AB CDR-H1 | KFTFSNYGMN |
| 183 | PI-3019-AB CDR-H2 | LIYYNSNNKY |
| 184 | PI-3019-AB CDR-H3 | SLTGGSDYFDS |
| 185 | PI-3019-AB Heavy chain | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSSAKTTAPSVYPLAPV CGDTTGSSVTLGCLVKGYFPEPVTLTWNSGSLSSGVHTFPAVLQSDLYTLSSSVTVTSSTWPSQSIT CNVAHPASSTKVDKKIEPRGPTIKPCPPCKCPAPNLLGGPSVFIFPPKIKDVLMISLSPIVTCVVVD VSEDDPDVQISWFVNNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGKTELNYKNTEPVLD SDGSYFMYSKLRVEKKNWVERNSYSCSVVHEGLHNHHTTKSFSRTPGK* |
| 186 | PI-3019-AB Light Chain Variable | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIK |
| 187 | PI-3019-AB CDR-L1 | KASKSIGTFLA |
| 188 | PI-3019-AB CDR-L2 | SGSTLQS |
| 189 | PI-3019-AB CDR-L3 | QQHDEYPFT |
| 190 | PI-3019-AB Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSSEQLTSGGASVVC FLNNFYPKDINVKWKIDGSERQNGVLNSWTDQDSKDSTYSMSSTLTLTKDEYERHNSYTCEATHKTS TSPIVKSFNRNEC* |
| 191 | PI-3028-AB Heavy Chain Variable | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSS |
| 192 | PI-3028-AB CDR-H1 | KFTFSNYGMN |
| 193 | PI-3028-AB CDR-H2 | LIYYNSNNKY |
| 194 | PI-3028-AB CDR-H3 | SLTGGSDYFDS |
| 195 | PI-3028-AB Heavy chain | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSSAKTTAPSVYPLAPV CGDTTGSSVTLGCLVKGYFPEPVTLTWNSGSLSSGVHTFPAVLQSDLYTLSSSVTVTSSTWPSQSIT CNVAHPASSTKVDKKIEPRGPTIKPCPPCKCPAPNLLGGPSVFIFPPKIKDVLMISLSPIVTCVVVD VSEDDPDVQISWFVNNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGKTELNYKNTEPVLD SDGSYFMYSKLRVEKKNWVERNSYSCSVVHEGLHNHHTTKSFSRTPGK* |
| 196 | PI-3028-AB Light Chain Variable | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIK |
| 197 | PI-3028-AB CDR-L1 | KASKSIGTFLA |
| 198 | PI-3028-AB CDR-L2 | SGSTLQS |
| 199 | PI-3028-AB CDR-L3 | QQHDEYPFT |

-continued

Sequence listing

| SEQ ID NO | Name | Sequence |
|---|---|---|
| | CDR-L3 | |
| 200 | PI-3028-AB Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSSEQLTSGGASVVC FLNNFYPKDINVKWKIDGSERQNGVLNSWTDQDSKDSTYSMSSTLTLTKDEYERHNSYTCEATHKTS TSPIVKSFNRNEC* |
| 201 | PI-3029-AB Heavy Chain Variable | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSS |
| 202 | PI-3029-AB CDR-H1 | KFTFSNYGMN |
| 203 | PI-3029-AB CDR-H2 | LIYYNSNNKY |
| 204 | PI-3029-AB CDR-H3 | SLTGGSDYFDS |
| 205 | PI-3029-AB Heavy chain | EVQLVESGGGLVQPGSSLKLSCVASKFTFSNYGMNWIRQAPKKGLEWIALIYYNSNNKYYADSVKGR FTISRDNSKNTLYLEMNSLRSEDTAMYYCAKSLTGGSDYFDSWGQGVMVTVSSAKTTAPSVYPLAPV CGDTTGSSVTLGCLVKGYFPEPVTLTWNSGSLSSGVHTFPAVLQSDLYTLSSSVTVTSSTWPSQSIT CNVAHPASSTKVDKKIEPRGPTIKPCPPCKCPAPNLLGGPSVFIFPPKIKDVLMISLSPIVTCVVVD VSEDDPDVQISWFVNNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGKTELNYKNTEPVLD SDGSYFMYSKLRVEKKNWVERNSYSCSVVHEGLHNHHTTKSFSRTPGK* |
| 206 | PI-3029-AB Light Chain Variable | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIK |
| 207 | PI-3029-AB CDR-L1 | KASKSIGTFLA |
| 208 | PI-3029-AB CDR-L2 | SGSTLQS |
| 209 | PI-3029-AB CDR-L3 | QQHDEYPFT |
| 210 | PI-3029-AB Light chain | DVQMTQSPSYLAASPGESVSISCKASKSIGTFLAWYQEKPEKTNKLLIYSGSTLQSGTPSRFSGSGS GTDFTLTIRNLEPEDFAVYYCQQHDEYPFTFGSGTKLEIKRADAAPTVSIFPPSSEQLTSGGASVVC FLNNFYPKDINVKWKIDGSERQNGVLNSWTDQDSKDSTYSMSSTLTLTKDEYERHNSYTCEATHKTS TSPIVKSFNRNEC* |
| 211 | PI-3032-AB Heavy Chain Variable | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSS |
| 212 | PI-3032-AB CDR-H1 | KFTFSNYGMN |
| 213 | PI-3032-AB CDR-H2 | LIYYNSNNKY |
| 214 | PI-3032-AB CDR-H3 | SLTGGSDYFDS |
| 215 | PI-3032-AB Heavy chain | EVQLVESGGGLVQPGGSLRLSCAASKFTFSNYGMNWIRQAPGKGLEWIALIYYNSNNKYYADSVKGR FTISRDNSKNTLYLQMNSLRAEDTAVYYCAKSLTGGSDYFDSWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 216 | PI-3032-AB Light Chain Variable | DIQMTQSPSSLSASVGDRVTITCRASKSIGTFLAWYQQKPGKAPKLLIYSGSTLESGVPSRFSGSGS GTDFTLTISSLQPEDFATYYCQQHDEYPFTFGQGTKLEIK |
| 217 | PI-3032-AB CDR-L1 | KASKSIGTFLA |

-continued

| SEQ ID NO | Name | Sequence |
|---|---|---|
| 218 | PI-3032-AB CDR-L2 | SGSTLQS |
| 219 | PI-3032-AB CDR-L3 | QQHDEYPFT |
| 220 | PI-3032-AB Light chain | DIQMTQSPSSLSASVGDRVTITCRASKSIGTFLAWYQQKPGKAPKLLIYSGSTLESGVPSRFSGSGS<br>GTDFTLTISSLQPEDFATYYCQQHDEYPFTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |
| 221 | PI-3033-AB Heavy Chain Variable | EVQLVESGGGLVQPGGSLRLSCAASKFTFSNYGMNWIRQAPGKGLEWIALIYYNSNNKYYADSVKGR<br>FTISRDNSKNTLYLQMNSLRAEDTAVYYCAKSLTGGSDYFDSWGQGTLVTVSS |
| 222 | PI-3033-AB CDR-H1 | KFTFSNYGMN |
| 223 | PI-3033-AB CDR-H2 | LIYYNSNNKY |
| 224 | PI-3033-AB CDR-H3 | SLTGGSDYFDS |
| 225 | PI-3033-AB Heavy chain | EVQLVESGGGLVQPGGSLRLSCAASKFTFSNYGMNWIRQAPGKGLEWIALIYYNSNNKYYADSVKGR<br>FTISRDNSKNTLYLQMNSLRAEDTAVYYCAKSLTGGSDYFDSWGQGTLVTVSSASTKGPSVFPLAPS<br>SKSTSGGTAALGCLVKDYFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK* |
| 226 | PI-3033-AB Light Chain Variable | DIQMTQSPSSLSASVGDRVTITCRASKSIGTFLAWYQQKPGKAPKLLIYDASSLESGVPSRFSGSGS<br>GTDFTLTISSLQPEDFATYYCQQHDEYPFTFGQGTKLEIK |
| 227 | PI-3033-AB CDR-L1 | KASKSIGTFLA |
| 228 | PI-3033-AB CDR-L2 | SGSTLQS |
| 229 | PI-3033-AB CDR-L3 | QQHDEYPFT |
| 230 | PI-3033-AB Light chain | DIQMTQSPSSLSASVGDRVTITCRASKSIGTFLAWYQQKPGKAPKLLIYDASSLESGVPSRFSGSGS<br>GTDFTLTISSLQPEDFATYYCQQHDEYPFTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC* |
| 231 | HX-3011 Heavy Chain Variable | QIQLVQSGPELKKPGESVKISCKASGYTFTDYAVNWVKQAPGNGLKWMGWINTQTGKPTYADDFKQR<br>FVFSLETSASTSFLQINNLNIEDTATYFCTRDSYYYSSSLDYWGQGVMVTVSS |
| 232 | HX-3011 CDR-H1 | GYTFTDYAVN |
| 233 | HX-3011 CDR-H2 | WINTQTGKPT |
| 234 | HX-3011 CDR-H3 | DSYYYSSSLDY |
| 235 | HX-3011 Heavy chain | QIQLVQSGPELKKPGESVKISCKASGYTFTDYAVNWVKQAPGNGLKWMGWINTQTGKPTYADDFKQR<br>FVFSLETSASTSFLQINNLNIEDTATYFCTRDSYYYSSSLDYWGQGVMVTVSSAETTAPSVYPLAPG<br>TALKSNSMVTLGCLVKGYFPEPVTVTWNSGALSSGVHTFPAVLQSGLYTLTSSVTVPSSTWSSQAVT<br>CNVAHPASSTKVDKKIVPRECNPCGCTGSEVSSVFIFPPKTKDVLTITLTPKVTCVVVDISQNDPEV<br>RFSWFIDDVEVHTAQTHAPEKQSNSTLRSVSELPIVHRDWLNGKTFKCKVNSGAFPAPIEKSISKPE<br>GTPRGPQVYTMAPPKEEMTQSQVSITCMVKGFYPPDIYTEWKMNGQPQENYKNTPPTMDTDGSYFLY<br>SKLNVVKKETWQQGNTFTCSVLHEGLHNHHTEKSLSHSP* |
| 236 | HX-3011 | DIQMTQSPASLSASLGETVSIECLASAGISNDLAWYQQKSGKSPQLLIYAASRLQDGVPSRFSGSGS |

-continued

| SEQ ID NO | Name | Sequence |
|---|---|---|
| | Light Chain Variable | GTRFSLKISDMQPEDEADYFCQQSYKYPWTFGGGTKLELK |
| 237 | HX-3011 CDR-L1 | LASAGISNDLA |
| 238 | HX-3011 CDR-L2 | AASRLQD |
| 239 | HX-3011 CDR-L3 | QQSYKYPWT |
| 240 | HX-3011 Light chain | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELKRADAAPTVSIFPPSTEQLATGGASVVC LMNNFYPRDISVKWKIDGTERRDGVLDSVTDQDSKDSTYSMSSTLSLTKADYESHNLYTCEVVHKTS SSPVVKSFNRNEC* |
| 241 | PI-3030-AB Heavy Chain Variable | QIQLVQSGPELKKPGESVKISCKASGYTFTDYAVNWVKQAPGNGLKWMGWINTQTGKPTYADDFKQR FVFSLETSASTSFLQINNLNIEDTATYFCTRDSYYYSSSLDYWGQGVMVTVSS |
| 242 | PI-3030-AB CDR-H1 | GYTFTDYAVN |
| 243 | PI-3030-AB CDR-H2 | WINTQTGKPT |
| 244 | PI-3030-AB CDR-H3 | DSYYYSSSLDY |
| 245 | PI-3030-AB Heavy chain | QIQLVQSGPELKKPGESVKISCKASGYTFTDYAVNWVKQAPGNGLKWMGWINTQTGKPTYADDFKQR FVFSLETSASTSFLQINNLNIEDTATYFCTRDSYYYSSSLDYWGQGVMVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 246 | PI-3030-AB Light Chain Variable | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELK |
| 247 | PI-3030-AB CDR-L1 | LASAGISNDLA |
| 248 | PI-3030-AB CDR-L2 | AASRLQD |
| 249 | PI-3030-AB CDR-L3 | QQSYKYPWT |
| 250 | PI-3030-AB Light chain | DIQMTQSPASLSASLGETVSIECLASAGISNDLAWYQQKSGKSPQLLIYAASRLQDGVPSRFSGSGS GTRFSLKISDMQPEDEADYFCQQSYKYPWTFGGGTKLELKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 251 | HX-3043 Heavy Chain Variable | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSS |
| 252 | HX-3043 CDR-H1 | GYTFTDYYLH |
| 253 | HX-3043 CDR-H2 | YINPNNAYTS |
| 254 | HX-3043 CDR-H3 | DTTDYYNLHFAY |
| 255 | HX-3043 Heavy chain | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSSAETTAPSVYPLAP GTALKSNSMVTLGCLVKGYFPEPVTVTWNSGALSSGVHTFPAVLQSGLYTLSSSVTVPSSTWSSQAV TCNVAHPASSTKVDKKIVPRECNPCGCTGSEVSSVFIFPPKTKDVLTITLTPKVTCVVVDISQNDPE |

| SEQ ID NO | Name | Sequence |
|---|---|---|
| | | VRFSWFIDDVEVHTAQTHAPEKQSNSTLRSVSELPIVHRDWLNGKTFKCKVNSGAFPAPIEKSISKP EGTPRGPQVYTMAPPKEEMTQSQVSITCMVKGFYPPDIYTEWKMNGQPQENYKNTPPTMDTDGSYFL YSKLNVKKETWQQGNTFTCSVLHEGLHNHHTEKSLSHSP* |
| 256 | HX-3043 Light Chain Variable | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIK |
| 257 | HX-3043 CDR-L1 | LTSEGISNDLA |
| 258 | HX-3043 CDR-L2 | DASRLED |
| 259 | HX-3043 CDR-L3 | QQSYKYPLT |
| 260 | HX-3043 Light chain | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIKRADAAPTVSIFPPSTEQLATGGASVVC LMNNFYPRDISVKWKIDGTERRDGVLDSVTDQDSKDSTYSMSSTLSLTKADYESHNLYTCEVVHKTS SSPVVKSFNRNEC* |
| 261 | PI-3031-AB Heavy Chain Variable | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSS |
| 262 | PI-3031-AB CDR-H1 | GYTFTDYYLH |
| 263 | PI-3031-AB CDR-H2 | YINPNNAYTS |
| 264 | PI-3031-AB CDR-H3 | DTTDYYNLHFAY |
| 265 | PI-3031-AB Heavy chain | QVNLLQSRAALVKPGASVKLSCKASGYTFTDYYLHWVKQSHAKSLEWIGYINPNNAYTSYNEKFKSK ATLTVDKSTNTAYMELSRLTSADSATYYCARDTTDYYNLHFAYWGQGTLVTVSSASTKGPSVFPLAP SSKSTSGGTAALGCLVKDYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK* |
| 266 | PI-3031-AB Light Chain Variable | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIK |
| 267 | PI-3031-AB CDR-L1 | LTSEGISNDLA |
| 268 | PI-3031-AB CDR-L2 | DASRLED |
| 269 | PI-3031-AB CDR-L3 | QQSYKYPLT |
| 270 | PI-3031-AB Light chain | DIQMTQSPASLSASLGETVSIECLTSEGISNDLAWYQQKSGKSPQLLIYDASRLEDGVPSRFSGSGS GTRYSLKISGMQTEDEADYFCQQSYKYPLTFGSGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 271 | PI-3006-AB Heavy Chain Variable | EVQLVESGGGLVKPGASLKLSCVASGFTFSDYWMNWVRQTPGKTMEWIGDIKDDGSYTNYTPSLKNR FTISRDNAKSTLYLQMNNVRSEDTGTYYCTSGGVFDYWGQGVMVTVSS |
| 272 | PI-3006-AB CDR-H1 | GFTFSDYW |
| 273 | PI-3006-AB CDR-H2 | IKDDGSYT |
| 274 | PI-3006-AB CDR-H3 | TSGGVFDY |

-continued

Sequence listing

| SEQ ID NO | Name | Sequence |
|---|---|---|
| 275 | PI-3006-AB Heavy chain | EVQLVESGGGLVKPGASLKLSCVASGFTFSDYWMNWVRQTPGKTMEWIGDIKDDGSYTNYTPSLKNR FTISRDNAKSTLYLQMNNVRSEDTGTYYCTSGGVFDYWGQGVMVTVSSAKTTAPSVYPLAPVCGDTT GSSVTLGCLVKGYFPEPVTLTWNSGSLSSGVHTFPAVLQSDLYTLSSSVTVTSSTWPSQSITCNVAH PASSTKVDKKIEPRGPTIKPCPPCKCPAPNLLGGPSVFIFPPKIKDVLMISLSPIVTCVVVDVSEDD PDVQISWFVNNVEVHTAQTQTHREDYNSTLRVVSALPIQHQDWMSGKEFKCKVNNKDLPAPIERTIS KPKGSVRAPQVYVLPPPEEEMTKKQVTLTCMVTDFMPEDIYVEWTNNGKTELNYKNTEPVLDSDGSY FMYSKLRVEKKNWVERNSYSCSVVHEGLHNHHTTKSFSRTPGK* |
| 276 | PI-3006-AB Light Chain Variable | EIVLTQSPTTMAASPGEMVTITCRASSSVNYMHWFQQKSGTSPKPWIYDTSKLASGVPDRFSGSGSG TSYSLTISSMEAEDAASYYCLQRSTFPPTFGAGTKLELK |
| 277 | PI-3006-AB CDR-L1 | SSVNY |
| 278 | PI-3006-AB CDR-L2 | DTS |
| 279 | PI-3006-AB CDR-L3 | LQRSTFPPT |
| 280 | PI-3006-AB Light chain | EIVLTQSPTTMAASPGEMVTITCRASSSVNYMHWFQQKSGTSPKPWIYDTSKLASGVPDRFSGSGSG TSYSLTISSMEAEDAASYYCLQRSTFPPTFGAGTKLELKRADAAPTVSIFPPSSEQLTSGGASVVCF LNNFYPKDINVKWKIDGSERQNGVLNSWTDQDSKDSTYSMSSTLTLTKDEYERHNSYTCEATHKTST SPIVKSFNRNEC* |
| 281 | PI-3007-AB Heavy Chain Variable | QVRLVQSGTALVRPGASVRMSCTASGYSFTDYWVSWVKQSHGQSLEWIGEIYPNSGTTNFNEKFEGK ATLTVDKSTSTAYMELSRLTSEDSAIYYCTGEGTFDYWGQGVMVTVSS |
| 282 | PI-3007-AB CDR-H1 | GYSFTDYW |
| 283 | PI-3007-AB CDR-H2 | IYPNSGTT |
| 284 | PI-3007-AB CDR-H3 | TGEGTFDY |
| 285 | PI-3007-AB Heavy chain | QVRLVQSGTALVRPGASVRMSCTASGYSFTDYWVSWVKQSHGQSLEWIGEIYPNSGTTNFNEKFEGK ATLTVDKSTSTAYMELSRLTSEDSAIYYCTGEGTFDYWGQGVMVTVSSAKTTAPSVYPLAPVCGDTT GSSVTLGCLVKGYFPEPVTLTWNSGSLSSGVHTFPAVLQSDLYTLSSSVTVTSSTWPSQSITCNVAH PASSTKVDKKIEPRGPTIKPCPPCKCPAPNLLGGPSVFIFPPKIKDVLMISLSPIVTCVVVDVSEDD PDVQISWFVNNVEVHTAQTQTHREDYNSTLRVVSALPIQHQDWMSGKEFKCKVNNKDLPAPIERTIS KPKGSVRAPQVYVLPPPEEEMTKKQVTLTCMVTDFMPEDIYVEWTNNGKTELNYKNTEPVLDSDGSY FMYSKLRVEKKNWVERNSYSCSVVHEGLHNHHTTKSFSRTPGK* |
| 286 | PI-3007-AB Light Chain Variable | EIVLTQSPTTMAASPGEKVTITCRPSSSLSNMHWFQQKSGTSPKPWIYDTSKLASGVPDRFSGSGSG TSYSLTISSMEAEDAATYYCLQRSSYPPTFGAGTKLELK |
| 287 | PI-3007-AB CDR-L1 | SSLSN |
| 288 | PI-3007-AB CDR-L2 | DTS |
| 289 | PI-3007-AB CDR-L3 | LQRSSYPPT |
| 290 | PI-3007-AB Light chain | EIVLTQSPTTMAASPGEKVTITCRPSSSLSNMHWFQQKSGTSPKPWIYDTSKLASGVPDRFSGSGSG TSYSLTISSMEAEDAATYYCLQRSSYPPTFGAGTKLELKRADAAPTVSIFPPSSEQLTSGGASVVCF LNNFYPKDINVKWKIDGSERQNGVLNSWTDQDSKDSTYSMSSTLTLTKDEYERHNSYTCEATHKTST SPIVKSFNRNEC* |
| 291 | PI-3008-AB Heavy Chain Variable | EVQLVESGGGLVKPGASLKLSCVASGFTFSDDWMNWVRQTPGKAMEWIGDIKYDGSYTNYVPSLKNR LTISRDNAKNTLYLQMTNVRSEDTATYYCTSGGVFDYWGQGVMVTVSS |
| 292 | PI-3008-AB CDR-H1 | GFTFSDDW |

| SEQ ID NO | Name | Sequence |
|---|---|---|
| 293 | PI-3008-AB CDR-H2 | IKYDGSYT |
| 294 | PI-3008-AB CDR-H3 | TSGGVFDY |
| 295 | PI-3008-AB Heavy chain | EVQLVESGGGLVKPGASLKLSCVASGFTFSDDWMNWVRQTPGKAMEWIGDIKYDGSYTNYVPSLKNR LTISRDNAKNTLYLQMTNVRSEDTATYYCTSGGVFDYWGQGVMVTVSSAKTTAPSVYPLAPVCGDTT GSSVTLGCLVKGYFPEPVTLTWNSGSLSSGVHTFPAVLQSDLYTLSSSVTVTSSTWPSQSITCNVAH PASSTKVDKKIEPRGPTIKPCPPCKCPAPNLLGGPSVFIFPPKIKDVLMISLSPIVTCVVVDVSEDD PDVQISWFVNNVEVHTAQTQTHREDYNSTLRVVSALPIQHQDWMSGKEFKCKVNNKDLPAPIERTIS KPKGSVRAPQVYVLPPPEEEMTKKQVTLTCMVTDFMPEDIYVEWTNNGKTELNYKNTEPVLDSDGSY FMYSKLRVEKKNWVERNSYSCSVVHEGLHNHHTTKSFSRTPGK* |
| 296 | PI-3008-AB Light Chain Variable | EIVLSQSPTTMAASPGEKVTITCRASSSVSYMHWFQQKSGTSPKPWIYDTSKLASGVPDRFSGSGSG TSYSLTISSMEAEDAATYYCLQRSGYPPTFGAGTKLEVK |
| 297 | PI-3008-AB CDR-L1 | SSVSY |
| 298 | PI-3008-AB CDR-L2 | DTS |
| 299 | PI-3008-AB CDR-L3 | LQRSGYPPT |
| 300 | PI-3008-AB Light chain | EIVLSQSPTTMAASPGEKVTITCRASSSVSYMHWFQQKSGTSPKPWIYDTSKLASGVPDRFSGSGSG TSYSLTISSMEAEDAATYYCLQRSGYPPTFGAGTKLEVKRADAAPTVSIFPPSSEQLTSGGASVVCF LNNFYPKDINVKWKIDGSERQNGVLNSWTDQDSKDSTYSMSSTLTLTKDEYERHNSYTCEATHKTST SPIVKSFNRNEC* |
| 301 | PI-3009-AB Heavy Chain Variable | EVQLVESGGGLVQPGRSLKFSCSASGFTFSAYSMAWVRQAPKTGLEWVATIIYDGSSTYYRDSVKGR FTISRDNAKNTLYLQMDSLRSEDTATYYCARLGYSGHYFDYWGQGVMVTVSS |
| 302 | PI-3009-AB CDR-H1 | GFTFSAYS |
| 303 | PI-3009-AB CDR-H2 | IIYDGSST |
| 304 | PI-3009-AB CDR-H3 | ARLGYSGHYFDY |
| 305 | PI-3009-AB Heavy chain | EVQLVESGGGLVQPGRSLKFSCSASGFTFSAYSMAWVRQAPKTGLEWVATIIYDGSSTYYRDSVKGR FTISRDNAKNTLYLQMDSLRSEDTATYYCARLGYSGHYFDYWGQGVMVTVSSAKTTAPSVYPLAPVC GDTTGSSVTLGCLVKGYFPEPVTLTWNSGSLSSGVHTFPAVLQSDLYTLSSSVTVTSSTWPSQSITC NVAHPASSTKVDKKIEPRGPTIKPCPPCKCPAPNLLGGPSVFIFPPKIKDVLMISLSPIVTCVVVDV SEDDPDVQISWFVNNVEVHTAQTQTHREDYNSTLRVVSALPIQHQDWMSGKEFKCKVNNKDLPAPIE RTISKPKGSVRAPQVYVLPPPEEEMTKKQVTLTCMVTDFMPEDIYVEWTNNGKTELNYKNTEPVLDS DGSYFMYSKLRVEKKNWVERNSYSCSVVHEGLHNHHTTKSFSRTPGK* |
| 306 | PI-3009-AB Light Chain Variable | DTVLTQSPALAVSLGQRVTISCQASESVSSSLHSYLHWYQQKPGQQPKLLIYRASNLESGVPARFSG SGSGTDFTLNIDPVEADDIATYFCQQSWNDPRTFGGGTKLELK |
| 307 | PI-3009-AB CDR-L1 | ESVSSSLHSY |
| 308 | PI-3009-AB CDR-L2 | RAS |
| 309 | PI-3009-AB CDR-L3 | QQSWNDPRT |
| 310 | PI-3009-AB Light chain | DTVLTQSPALAVSLGQRVTISCQASESVSSSLHSYLHWYQQKPGQQPKLLIYRASNLESGVPARFSG SGSGTDFTLNIDPVEADDIATYFCQQSWNDPRTFGGGTKLELKRADAAPTVSIFPPSSEQLTSGGAS VVCFLNNFYPKDINVKWKIDGSERQNGVLNSWTDQDSKDSTYSMSSTLTLTKDEYERHNSYTCEATH KTSTSPIVKSFNRNEC* |
| 311 | PI-3036-AB Heavy Chain | VQLVQSGAEVKKPGASVKVSCKASGYTFTDYAVNWVRQAPGQGLEWMGWINTQTGKPTYAQKFQGRV TMTRDTSTSTVYMELSSLRSEDTAVYYCARDSYYYSSSLDYWGQGTLVTVSS |

| SEQ ID NO | Name | Sequence |
|---|---|---|
| | Variable | |
| 312 | PI-3036-AB CDR-H1 | GYTFTDYAVN |
| 313 | PI-3036-AB CDR-H2 | WINTQTGKPT |
| 314 | PI-3036-AB CDR-H3 | DSYYYSSSLDY |
| 315 | PI-3036-AB Heavy chain | QVQLVQSGAEVKKPGASVKVSCKASGYTFTDYAVNWVRQAPGQGLEWMGWINTQTGKPTYAQKFQGR VTMTRDTSTSTVYMELSSLRSEDTAVYYCARDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 316 | PI-3036-AB Light Chain Variable | DIQMTQSPSSLSASVGDRVTITCRASAGISNDLAWYQQKPGKAPKLLIYAASRLQDGVPSRFSGSGS GTDFTLTISSLQPEDFATYYCQQSYKYPWTFGQGTKLEIK |
| 317 | PI-3036-AB CDR-L1 | RASAGISNDLA |
| 318 | PI-3036-AB CDR-L2 | AASRLQD |
| 319 | PI-3036-AB CDR-L3 | QQSYKYPWT |
| 320 | PI-3036-AB Light chain | DIQMTQSPSSLSASVGDRVTITCRASAGISNDLAWYQQKPGKAPKLLIYAASRLQDGVPSRFSGSGS GTDFTLTISSLQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 321 | PI-3037-AB Heavy Chain Variable | QVQLVQSGAEVKKPGASVKVSCKASGYTFTDYAVNWVRQAPGQGLEWMGWINTQTGKPTYAQKFQGR VTMTLDTSTSTAYMELSSLRSEDTAVYYCTRDSYYYSSSLDYWGQGTLVTVSS |
| 322 | PI-3037-AB CDR-H1 | GYTFTDYAVN |
| 323 | PI-3037-AB CDR-H2 | WINTQTGKPT |
| 324 | PI-3037-AB CDR-H3 | DSYYYSSSLDY |
| 325 | PI-3037-AB Heavy chain | QVQLVQSGAEVKKPGASVKVSCKASGYTFTDYAVNWVRQAPGQGLEWMGWINTQTGKPTYAQKFQGR VTMTLDTSTSTAYMELSSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 326 | PI-3037-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 327 | PI-3037-AB CDR-L1 | RASAGISNDLA |
| 328 | PI-3037-AB CDR-L2 | AASRLQD |
| 329 | PI-3037-AB CDR-L3 | QQSYKYPWT |
| 330 | PI-3037-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC |

| SEQ ID NO | Name | Sequence |
|---|---|---|
| | | LLNNFYPREAKVQWKVDNALQSGNSQESVTEQDSKDSTYSLSSTLTLSKADYEKHKVYACEVTHQGL SSPVTKSFNRGEC* |
| 331 | PI-3038-AB Heavy Chain Variable | QVQLVQSGAEVKKPGASVKISCKASGYTFTDYAVNWVRQAPGQGLEWMGWINTQTGKPTYAQKFQGR FTFTLDTSTSTAYLEISSLRSEDTAVYYCTRDSYYYSSSLDYWGQGTLVTVSS |
| 332 | PI-3038-AB CDR-H1 | GYTFTDYAVN |
| 333 | PI-3038-AB CDR-H2 | WINTQTGKPT |
| 334 | PI-3038-AB CDR-H3 | DSYYYSSSLDY |
| 335 | PI-3038-AB Heavy chain | QVQLVQSGAEVKKPGASVKISCKASGYTFTDYAVNWVRQAPGQGLEWMGWINTQTGKPTYAQKFQGR FTFTLDTSTSTAYLEISSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 336 | PI-3038-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 337 | PI-3038-AB CDR-L1 | RASAGISNDLA |
| 338 | PI-3038-AB CDR-L2 | AASRLQD |
| 339 | PI-3038-AB CDR-L3 | QQSYKYPWT |
| 340 | PI-3038-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 341 | PI-3039-AB Heavy Chain Variable | QVQLVQSGAEVKKPGASVKVSCKASGYTFTDYAVNWVRQAPGQGLEWMGWINTQTGKPTYAQKFQGR VTMTLDTSTSTSYMELSSLRSEDTAVYYCTRDSYYYSSSLDYWGQGTLVTVSS |
| 342 | PI-3039-AB CDR-H1 | GYTFTDYAVN |
| 343 | PI-3039-AB CDR-H2 | WINTQTGKPT |
| 344 | PI-3039-AB CDR-H3 | DSYYYSSSLDY |
| 345 | PI-3039-AB Heavy chain | QVQLVQSGAEVKKPGASVKVSCKASGYTFTDYAVNWVRQAPGQGLEWMGWINTQTGKPTYAQKFQGR VTMTLDTSTSTSYMELSSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 346 | PI-3039-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 347 | PI-3039-AB CDR-L1 | RASAGISNDLA |
| 348 | PI-3039-AB CDR-L2 | AASRLQD |

| SEQ ID NO | Name | Sequence |
|---|---|---|
| 349 | PI-3039-AB CDR-L3 | QQSYKYPWT |
| 350 | PI-3039-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 351 | PI-3040-AB Heavy Chain Variable | QVQLVQSGAEVKKPGASVKISCKASGYTFTDYAVNWVRQAPGQGLEWMGWINTQTGKPTYAQKFQGR FTFTLDTSTSTSYLEISSLRSEDTAVYYCTRDSYYYSSSLDYWGQGTLVTVSS |
| 352 | PI-3040-AB CDR-H1 | GYTFTDYAVN |
| 353 | PI-3040-AB CDR-H2 | WINTQTGKPT |
| 354 | PI-3040-AB CDR-H3 | DSYYYSSSLDY |
| 355 | PI-3040-AB Heavy chain | QVQLVQSGAEVKKPGASVKISCKASGYTFTDYAVNWVRQAPGQGLEWMGWINTQTGKPTYAQKFQGR FTFTLDTSTSTSYLEISSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK* |
| 356 | PI-3040-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 357 | PI-3040-AB CDR-L1 | RASAGISNDLA |
| 358 | PI-3040-AB CDR-L2 | AASRLQD |
| 359 | PI-3040-AB CDR-L3 | QQSYKYPWT |
| 360 | PI-3040-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC* |
| 361 | PI-HX-3092 Heavy Chain Variable | QVQLKESGPGLVQPSQTLSLTCTVSGFSLTSYTLSWVRQPPGKGLEWIGAIWGGDNTDYNSALKSRL SITWDTSKSQVLLKMNSLQTEDTAIYFCTRELGGSFDYWGQGVMVTVSS |
| 362 | PI-HX-3092 CDR-H1 | GFSLTSYTLS |
| 363 | PI-HX-3092 CDR-H2 | AIWGGDNTD |
| 364 | PI-HX-3092 CDR-H3 | ELGGSFDY |
| 365 | PI-HX-3092 Heavy chain | QVQLKESGPGLVQPSQTLSLTCTVSGFSLTSYTLSWVRQPPGKGLEWIGAIWGGDNTDYNSALKSRL SITWDTSKSQVLLKMNSLQTEDTAIYFCTRELGGSFDYWGQGVMVTVSSAETTAPSVYPLAPGTALK SNSMVTLGCLVKGYFPEPVTVTWNSGALSSGVHTFPAVLQSGLYTLTSSVTVPSSTWSSQAVTCNVA HPASSTKVDKKIVPRECNPCGCTGSEVSSVFIFPPKTKDVLTITLTPKVTCVVVDISQNDPEVRFSW FIDDVEVHTAQTHAPEKQSNSTLRSVSELPIVHRDWLNGKTFKCKVNSGAFPAPIEKSISKPEGTPR GPQVYTMAPPKEEMTQSVSITCMVKGFYPPDIYTEWKMNGQPQENYKNTPPTMDTDGSYFLYSKLN VKKETWQQGNTFTCSVLHEGLHNHHTEKSLSHSP* |
| 366 | PI-HX-3092 Light Chain Variable | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELK |
| 367 | PI-HX-3092 | KTSQNINKKLD |

| SEQ ID NO | Name | Sequence |
|---|---|---|
| | CDR-L1 | |
| 368 | PI-HX-3092 CDR-L2 | YTNNLQT |
| 369 | PI-HX-3092 CDR-L3 | YQYDSGFT |
| 370 | PI-HX-3092 Light chain | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELKRADAAPTVSIFPPSTEQLATGGASVVCL MNNFYPRDISVKWKIDGTERRDGVLDSVTDQDSKDSTYSMSSTLSLTKADYESHNLYTCEVVHKTSS SPVVKSFNRNEC |
| 371 | PI-3035-AB Heavy Chain Variable | QVQLKESGPGLVQPSQTLSLTCTVSGFSLTSYTLSWVRQPPGKGLEWIGAIWGGDNTDYNSALKSRL SISRDTSKSQVLLKMNSLQTEDTAIYFCTRELGGSFDYWGQGVMVTVSS |
| 372 | PI-3035-AB CDR-H1 | GFSLTSYTLS |
| 373 | PI-3035-AB CDR-H2 | AIWGGDNTD |
| 374 | PI-3035-AB CDR-H3 | ELGGSFDY |
| 375 | PI-3035-AB Heavy chain | QVQLKESGPGLVQPSQTLSLTCTVSGFSLTSYTLSWVRQPPGKGLEWIGAIWGGDNTDYNSALKSRL SISRDTSKSQVLLKMNSLQTEDTAIYFCTRELGGSFDYWGQGVMVTVSSAKTTAPSVYPLAPVCGDT TGSSVTLGCLVKGYFPEPVTLTWNSGSLSSGVHTFPAVLQSDLYTLSSSVTVTSSTWPSQSITCNVA HPASSTKVDKKIEPRGPTIKPCPPCKCPAPNLLGGPSVFIFPPKIKDVLMISLSPIVTCVVVDVSED DPDVQISWFVNNVEVHTAQTQTHREDYNSTLRVVSALPIQHQDWMSGKEFKCKVNNKDLPAPIERTI SKPKGSVRAPQVYVLPPPEEEMTKKQVTLTCMVTDFMPEDIYVEWTNNGKTELNYKNTEPVLDSDGS YFMYSKLRVEKKNWVERNSYSCSVVHEGLHNHHTTKSFSRTPGK* |
| 376 | PI-3035-AB Light Chain Variable | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELK |
| 377 | PI-3035-AB CDR-L1 | KTSQNINKKLD |
| 378 | PI-3035-AB CDR-L2 | YTNNLQT |
| 379 | PI-3035-AB CDR-L3 | YQYDSGFT |
| 380 | PI-3035-AB Light chain | DIQMTQSPPVLSASVGDRVTLSCKTSQNINKKLDWYQQKHGEAPKLLIYYTNNLQTGIPSRFSGSGS GTDFTLTISTLQPEDVATYYCYQYDSGFTFGAGTKLELKRADAAPTVSIFPPSSEQLTSGGASVVCF LNNFYPKDINVKWKIDGSERQNGVLNSWTDQDSKDSTYSMSSTLTLTKDEYERHNSYTCEATHKTST SPIVKSFNRNEC |
| 381 | HX-3011 CDR-L1 Consensus sequence | XASAGISNDLA |
| 382 | HX-3061 CDR-L1 Consensus sequence | XASKSIGTFLA |
| 383 | HX-3031 CDR-L1 Consensus sequence | XASEGISNDLA |
| 384 | Human MARCO protein UNIPROT Q9UEW3 | MRNKKILKEDELLSETQQAAFHQIAMEPFEINVPKPKRRNGVNFSLAVVVIYLILLTAGAGLLVVQV LNLQARLRVLEMYFLNDTLAAEDSPSFSLLQSAHPGEHLAQGASRLQVLQAQLTWRVSHEHLLQRV DNFTQNPGMFRIKGEQGAPGLQGHKGAMGMPGAPGPPGPPAEKGAKGAMGRDGATGPSGPQGPPGVK GEAGLQGPQGAPGKQGATGTPGPQGEKGSKGDGGLIGPKGETGTKGEKGDLGLPGSKGDRGMKGDAG VMGPPGAQGSKGDFGRPGPPGLAGFPGAKGDQGQPGLQGVPGPPGAVGHPGAKGEPGSAGSPGRAGL PGSPGSPGATGLKGSKGDTGLQGQQGRKGESGVPGPAGVKGEQGSPGLAGPKGAPGQAGQKGDQGVK |

| SEQ ID NO | Name | Sequence |
|---|---|---|
| | | GSSGEQGVKGEKGERGENSVSVRIVGSSNRGRAEVYYSGTWGTICDDEWQNSDAIVFCRMLGYSKGR<br>ALYKVGAGTGQIWLDNVQCRGTESTLWSCTKNSWGHHDCSHEEDAGVECSV |
| 385 | PI-3010-AB HC cDNA | ATGGATTGGACTTGGCGCTTCTTGTTTGTGGTGGCGGCGGCTACTGGAGTGCAGTCACAAGTGCAAC<br>TTAAGGAATCCGGACCGGGACTCGTGCAGCCGTCACAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATG<br>GGTGCCATTTGGACTGGGGGATCCATTGCGTATAACTCGCTGCTGAAGTCGCGCTTGTCCATTTCGA<br>GAGATACCTCCAAGTCCCAAGTGTTTCTGAAGATGAACTCCCTGCAAACTGAAGATACTGCCACTTA<br>CTACTGTGCCCGCGATCTGTCCGACTATTACTCGAGTTACACCTCGTTCGATTACTGGGGACAGGGT<br>GTAATGGTCACTGTGTCGACTGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 386 | PI-3010-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCGCCTCGCTTTCAACCTCCCTGGGAGAAACCGTGTCCATCGAATG<br>CCTGGCTTCCGAAGGGATTTCCAACGATCTGGCCTGGTACCAGCAGAAGTCCGGAAAGTCACCTCAG<br>CTCCTGATCTACGCGGCCAGCCGGCTGCAGGACGGCGTGCCTTCCCGCTTTTCCGGTTCGGGATCAG<br>GGACTCGGTACTCGCTGAAGATTTCCGGGATGCAGCCTGAGGACGAAGCGGACTACTTCTGCCAACA<br>ATCCTACAAGTACCCGCTGACCTTCGGCTCCGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 387 | PI-3011-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGATCAGACAGCCTCCTGGAAAGGGACTGGAATGGATC<br>GGTGCCATTTGGACTGGGGGATCCATTGCGTATAACCCGTCCCTGAAGTCGCGCGTGACTATTTCGG<br>TGGATACCTCCAAGAACCAATTCAGCCTGAAGTTGTCCTCCGTGACTGCCGCCGATACTGCCGTATA<br>CTACTGTGCCCGCGATCTGTCCGACTATTACTCGAGTTACACCTCGTTCGATTACTGGGGACAGGGT<br>ACTCTGGTCACTGTGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 388 | PI-3011-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCGGAAAGGCCCCTAAG<br>CTCCTGATCTACGCGGCCAGCCGGCTGCAGTCCGGCGTGCCTTCCCGCTTTTCCGGTTCGGGATCAG<br>GGACTGACTTCACCCTGACCATTTCCAGCCTGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |

| SEQ ID NO | Name | Sequence |
|---|---|---|
| 389 | PI-3012-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 390 | PI-3012-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCGGAAAGGCCCCTAAG<br>CTCCCTGATCTACGCGGCCAGCCGGCTGCAGTCCGGCGTGCCTTCCCGCTTTTCCGGTTCGGGATCAG<br>GGACTGACTACACCCTGACCATTTCCAGCCTGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 391 | PI-3013-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCGTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 392 | PI-3013-AB LC cDNA | ATGGATATGCGGGTGCCGGCCCAGCTTCTGGGCCTGTTGCTGCTCTGGCTCTCGGAGCGCGCTGTG<br>ACATCCAAATGACTCAGTCCCCCTCATCGCTTTCAGCCTCCGTGGGAGACAGAGTGACCATCACTTG<br>CCGGGCTTCCGAAGGGATTTCCAACGATCTGGCCTGGTACCAGCAGAAGCCGGAAAGGCCCCTAAG<br>CTCCCTGATCTACGCGGCCAGCCGGCTGCAGTCCGGCGTGCCTTCCCGCTTTTCCGGTTCGGGATCAG<br>GGACTGACTACACCCTGACCATTTCCAGCATGCAGCCTGAGGACTTCGCGACCTACTACTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 393 | PI-3014-AB HC cDNA | ATGGATTGGACTTGGCGCTTCTTGTTTGTGGTGGCGGCGGCTACTGGAGTGCAGTCACAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATG |

| SEQ ID NO | Name | Sequence |
|---|---|---|
| | | GGTGCCATTTGGACTGGGGGATCCATTGCGTATAACCCGTCCCTGAAGTCGCGCTTGACTATTTCGA GAGATACCTCCAAGAACCAAGTGTCGCTGAAGATGTCCTCCCTGACTGCCGCCGATACTGCCGTATA CTACTGTGCCCGCGATCTGTCCGACTATTACTCGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAGCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 394 | PI-3014-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTTCAACGATCTGGCCTGGTACCAGCAGAAGCCCGGAAAGGCCCCTAAG CTCCTGATCTACGCGGCCAGCCGGCTGCAGTCCGGCGTGCCTTCCCGCTTTTCCGGTTCGGGATCAG GGACTGACTACACCCTGACCATTTCCAGCCTGCAGCCTGAGGACTTCGCGACCTACTACTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 395 | PI-3015-AB HC cDNA | ATGGATTGGACTTGGCGCTTCTTGTTTGTGGTGGCGGCGGCTACTGGAGTGCAGTCACAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGACAGCCTCCTGGAAAGGGACTGGAATGGATG GGTGCCATTTGGACTGGGGGATCCATTGCGTATAACCCGTCCCTGAAGTCGCGCTTGACTATTTCGA GAGATACCTCCAAGAACCAAGTGTCGCTGAAGATGTCCTCCCTGACTGCCGCCGATACTGCCGTATA CTACTGTGCCCGCGATCTGTCCGACTATTACTCGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAGCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 396 | PI-3015-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTTCAACGATCTGGCCTGGTACCAGCAGAAGCCCGGAAAGGCCCCTAAG CTCCTGATCTACGCGGCCAGCCGGCTGCAGTCCGGCGTGCCTTCCCGCTTTTCCGGTTCGGGATCAG GGACTGACTACACCCTGACCATTTCCAGCATGCAGCCTGAGGACTTCGCGACCTACTACTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 397 | PI-3022-AB HC cDNA | ATGGATTGGACTTGGCGCTTCTTGTTTGTGGTGGCGGCGGCTACTGGAGTGCAGTCACAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGACAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTCGAGTTACACCTCGTTCGATTACTGGGGACAGGGT |

Sequence listing

| SEQ ID NO | Name | Sequence |
|---|---|---|
| | | ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAGCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 398 | PI-3022-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTCCAACGATCTGGCCTGGTACCAGCAGAAGCCCGGAAAGGCCCCTAAG CTCCTGATCTACGCGGCCAGCCGGCTGCAGGACGGCGTGCCCTTCCCGCTTTTCCGGTTCGGGATCAG GGACTGACTACACCCTGACCATTTCCAGCCTGCAGCCTGAGGACTTCGCGACCTACTACTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 399 | PI-3023-AB HC cDNA | ATGGATTGGACTTGGCGCTTCTTGTTTGTGGTGGCGGCGGCTACTGGAGTGCAGTCACAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGCAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTCGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAGCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 400 | PI-3023-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTCCAACGATCTGGCCTGGTACCAGCAGAAGCCCGGAAAGTCGCCTAAG CTCCTGATCTACGCGGCCAGCCGGCTGCAGTCCGGCGTGCCTTCCCGCTTTTCCGGTTCGGGATCAG GGACTGACTACACCCTGACCATTTCCAGCCTGCAGCCTGAGGACTTCGCGACCTACTTCTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 401 | PI-3024-AB HC cDNA | ATGGATTGGACTTGGCGCTTCTTGTTTGTGGTGGCGGCGGCTACTGGAGTGCAGTCACAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGCAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTCGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA |

Sequence listing

| SEQ ID NO | Name | Sequence |
|---|---|---|
| | | GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAGCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 402 | PI-3024-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAACCTCCGTGGGAGACAGAGTGACCATCACTTG CCGGGCTTCCGAAGGGATTTCCAACGATCTGGCCTGGTACCAGCAGAAGCCCGGAAAGTCCCCTAAG CTCCTGATCTACGCGGCCAGCCGGCTGCAGGACGGCGTGCCTTCCCGCTTTTCCGGTTCGGGATCAG GGACTGACTACACCCTGACCATTTCCAGCCTGCAGCCTGAGGACGAAGCGACCTACTTCTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 403 | PI-3025-AB HC cDNA | ATGGATTGGACTTGGCGCTTCTTGTTTGTGGTGGCGGCGGCTACTGGAGTGCAGTCAGAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGACAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTCGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGACGTGA GCCACGAAGACCCTGAGGTCAAGTTCAACTGGTACGTGGACGGCGTGGAGGTGCATAATGCCAAGAC AAAGCCGCGGGAGGAGCAGTACAACAGCACGTACCGGGTGGTCAGCGTCCTCACCGTCCTGCACCAG GACTGGCTGAATGGCAAGGAGTACAAGTGCAAGGTCAGCAACAAAGCCCTCCCAGCCCCCATCGAGA AAACCATCTCCAAAGCCAAAGGGCAGCCCCGAGAACCACAGGTGTACACCCTGCCCCCATCCCGGGA TGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGTCCCTCTCCCTGTCTCCG GGTAAATAG |
| 404 | PI-3025-AB LC cDNA | ATGGATATGCGGGTGCCGGCCCAGCTTCTGGGCCTGTTGCTGCTCTGGCTCTCCGGAGCGCGCTGTG ACATCCAAATGACTCAGTCCCCCTCATCGCTTTCAGCCTCCGTGGGAGACAGAGTGACCATCACTTG CCGGGCTTCCGAAGGGATTTCCAACGATCTGGCCTGGTACCAGCAGAAGCCCGGAAAGGCCCCTAAG CTCCTGATCTACGCGGCCAGCCGGCTGCAGGACGGCGTGCCTTCCCGCTTTTCCGGTTCGGGATCAG GGACTGACTACACCCTGACCATTTCCAGCCTGCAGCCTGAGGACTTCGCGACCTACTACTGCCAACA ATCCTACAAGTACCCGCTGACCTTCGGCCAAGGCACCAAGCTCGAAATCAAGCGAACTGTGGCTGCA CCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGGG TAACTCCCAGGAGAGTGTCACAGAGCAGGACAGCAAGGACAGCACCTACAGCCTCAGCAGCACCCTG ACGCTGAGCAAAGCAGACTACGAGAAACACAAAGTCTACGCCTGCGAAGTCACCCATCAGGGCCTGA GCTCGCCCGTCACAAAGAGCTTCAACAGGGGAGAGTGTTAA |
| 405 | PI-3026-AB HC cDNA | ATGGATTGGACTTGGCGCTTCTTGTTTGTGGTGGCGGCGGCTACTGGAGTGCAGTCAGAAGTGCAAC TTCAAGAATCCGGACCGGGACTCGTGAAGCCGTCAGAAACTCTTTCGCTTACCTGTACCGTGTCCGG ATTTTCCCTGACTTCCTACCATGTGTCCTGGGTCAGACAGCCTCCTGGAAAGGGACTGGAATGGATC GGTGCCATTTGGACTGGGGGATCCATTGCGTATAACCCGTCCCTGAAGTCGCGCGTAACTATTTCGA GAGATACCTCCAAGAACCAAGTGTCCCTGAAGCTGTCGTCCGTGACTGCCGCCGATACTGCCGTGTA CTACTGTGCCCGCGATCTGTCCGACTATTACTCGAGTTACACCTCGTTCGATTACTGGGGACAGGGT ACTCTGGTCACTGTGTCGTCGGCCAGCACCAAGGGCCCATCGGTCTTCCCCCTGGCACCCTCCTCCA AGAGCACCTCTGGGGGCACAGCGGCCCTGGGCTGCCTGGTCAAGGACTACTTCCCCGAACCGGTGAC GGTGTCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTACATCT GCAACGTGAATCACAAGCCCAGCAACACCAAGGTGGACAAGAAAGTTGAGCCCAAATCTTGTGACAA AACTCACACATGCCCACCGTGCCCAGCACCTGAACTCCTGGGGGGACCGTCAGTCTTCCTCTTCCCC |

| SEQ ID NO | Name | Sequence |
|---|---|---|
| | | CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 406 | PI-3026-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAACCTCCGTGGGAGACAGAGTGACCATCACTTG<br>CCGGGCTTCCAAGGGATTTCCAACGATCTGGCTGGTACCAGCAGAAGCCCGGAAAGTCGCCTAAG<br>CTCCTGATCTACGCGGCCAGCCGGCTGCAGTCCGGCGTGCCTTCCCGCTTTTCCGGTTCGGGATCAG<br>GGACTGACTACACCCTGACCATTTCCAGCCTGCAGCCTGAGGACTTCGCGACCTACTTCTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 407 | PI-3027-AB HC cDNA | ATGGATTGGACTTGGCGCTTCTTGTTTGTGGTGGCGGCGGCTACTGGAGTGCAGTCAGAAGTGCAAC<br>TTCAAGAATCCGGACCGGGACTCGTGAAGCCGTCAGAAACTCTTTCGCTTACCTGTACCGTGTCCGG<br>ATTTTCCCTGACTTCCTACCATGTGTCCTGGGTCAGACAGCCTCCTGGAAAGGGACTGGAATGGATC<br>GGTGCCATTTGGACTGGGGGATCCATTGCTATAACCCGTCCCTGAAGTCGCGCGTAACTATTTCGA<br>GAGATACCTCCAAGAACCAAGTGTCCCTGAAGCTGTCGTCCGTGACTGCCGCCGATACTGCCGTGTA<br>CTACTGTGCCCGCGATCTGTCCGACTATTACTCGAGTTACACCTCGTTCGATTACTGGGGACAGGGT<br>ACTCTGGTCACTGTGTCGTCGGCCAGCACCAAGGGCCCATCGGTCTTCCCCCTGGCACCCTCCTCCA<br>AGAGCACCTCTGGGGGCACAGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAAGTTGAGCCCAAATCTTGTGACAA<br>AACTCACACATGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACCGTCCTGCACCAG<br>GACTGGCTGAATGGCAAGGAGTACAAGTGCAAGGTCAGCAACAAAGCCCTCCCAGCCCCCATCGAGA<br>AAACCATCTCCAAAGCCAAAGGGCAGCCCCGAGAACCACAGGTGTACACCCTGCCCCCATCCCGGGA<br>TGAGCTGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGACTCCG<br>ACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGTCCCTCTCCCTGTCTCCG<br>GGTAAATAG |
| 408 | PI-3027-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCCTCATCGCTTTCAACCTCCGTGGGAGACAGAGTGACCATCACTTG<br>CCGGGCTTCCAAGGGATTTCCAACGATCTGGCTGGTACCAGCAGAAGCCCGGAAAGTCCCCTAAG<br>CTCCTGATCTACGCGGCCAGCCGGCTGCAGGACGGCGTGCCTTCCCGCTTTTCCGGTTCGGGATCAG<br>GGACTGACTACACCCTGACCATTTCCAGCCTGCAGCCTGAGGACGAAGCGACCTACTTCTGCCAACA<br>ATCCTACAAGTACCCGCTGACCTTCGGCCAAGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 409 | PI-3030-AB HC cDNA | ATGGATTGGACTTGGCGCTTCTTGTTTGTGGTGGCGGCGGCTACTGGAGTGCAGTCACAAATCCAGC<br>TCGTGCAGTCCGGGCCAGAGCTGAAAAAGCCCGGAGAATCCGTCAAGATTAGCTGCAAGGCCTCCGG<br>CTACACCTTCACCGACTACGCAGTGAACTGGGTCAAGCAGGCCCCGGGAAATGGTCTGAAGTGGATG<br>GGCTGGATTAACACGCAGACCGGGAAGCCTACCTACGCCGACGACTTCAAGCAACGGTTCGTGTTCT<br>CGCTTGAAACTAGCGCCTCGACCTCGTTCCTGCAAATCAACAACCTGAACATCGAGGACACCGCCAC<br>CTACTTCTGCACAAGAGACTCCTACTATTACTCATCCTCCCTCGATTACTGGGGACAGGGCGTGATG<br>GTCACTGTGTCCAGCGCCAGCACCAAGGGCCCATCGGTCTTCCCCCTGGCACCCTCCTCCAAGAGCA<br>CCTCTGGGGGCACAGCGGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAATCTTGTGACAAAACTCA<br>CACATGCCCACCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGACGTGAGCCACG<br>AAGACCCTGAGGTCAAGTTCAACTGGTACGTGGACGGCGTGGAGGTGCATAATGCCAAGACAAAGCC<br>GCGGGAGGAGCAGTACAACAGCACGTACCGGGTGGTCAGCGTCCTCACCGTCCTGCACCAGGACTGG |

| SEQ ID NO | Name | Sequence |
|---|---|---|
| | | CTGAATGGCAAGGAGTACAAGTGCAAGGTCAGCAACAAAGCCCTCCCAGCCCCCATCGAGAAAACCA<br>TCTCCAAAGCCAAAGGGCAGCCCCGAGAACCACAGGTGTACACCCTGCCCCCATCCCGGGATGAGCT<br>GACCAAGAACCAGGTCAGCCTGACCTGCCTGGTCAAAGGCTTCTATCCCAGCGACATCGCCGTGGAG<br>TGGGAGAGCAATGGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAACGTCTTCTCATG<br>CTCCGTGATGCATGAGGCTCTGCACAACCACTACACGCAGAAGTCCCTCTCCCTGTCTCCGGGTAAA<br>TAG |
| 410 | PI-3030-AB LC cDNA | ATGGATATGCGGGTGCCGGCCCAGCTTCTGGGCCTGTTGCTGCTCTGGCTCTCCGGAGCGCGCTGTG<br>ACATCCAAATGACTCAGTCCCCTGCATCCCTGAGCGCGAGCCTGGGGGAGACTGTGTCCATTGAATG<br>CCTCGCCTCCGCCGGAATTTCTAACGACCTGGCCTGGTACCAGCAGAAGTCCGGAAAGTCGCCCCAG<br>CTGCTGATCTACGCCCTTCGAGGCTTCAGGATGGTGTCCCGTCACGGTTTAGCGGATCAGGATCCG<br>GCACCAGATTCTCCCTGCAAAATCAGCGACATGCAGCCAGAGGACGAAGCCGACTACTTCTGCCAACA<br>ATCGTACAAGTATCCCTGGACCTTCGGCGGGGGCACCAAGCTCGAACTGAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 411 | PI-3036-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAGTGTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGGTCACCATGA<br>CCCGCGACACCAGCACCTCCACCGTGTACATGGAATTGAGCAGCCTGCGGTCCGAAGATACAGCCGT<br>GTACTATTGTGCGAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |
| 412 | PI-3036-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCGTCAGCATCCGTCTGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 413 | PI-3038-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAGTGTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGGTCACCATGA<br>CCCTGGACACCAGCACCTCCACCGCATACATGGAATTGAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCGTGACGGTGTC<br>CTGGAACTCCGGGGCCCTGACCTCGGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA |

| SEQ ID NO | Name | Sequence |
|---|---|---|
| | | TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |
| 414 | PI-3038-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 415 | PI-3039-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAATCTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGTTCACCTTTA<br>CCTTGGACACCAGCACCTCCACCGCGTACTTGGAAATTAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCCAAAG<br>CCCAAGGATACTCTGATGATTTCGCGGACTCCTGAAGTGACCTGTGTGGTCGTCGATGTGCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |
| 416 | PI-3039-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 417 | PI-3040-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAGTGTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGGTCACCATGA<br>CCTTGGACACCAGCACCTCCACCTCCTACATGGAATTGAGCAGCCTGCGGTCCGAAGATACAGCCGT<br>GTACTATTGTACTAGGGACTCCTACTACTACTCATCCTCGCTCGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGGAGTGCACACTTTCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCCAAAG<br>CCCAAGGATACTCTGATGATTTCGCGGACTCCTGAAGTGACCTGTGTGGTCGTCGATGTGCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGCCCTGCCTGCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA |

-continued

Sequence listing

| SEQ ID NO | Name | Sequence |
|---|---|---|
| | | TAA |
| 418 | PI-3040-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 419 | PI-3041-AB HC cDNA | ATGGACTGGACCTGGAGATTTTTATTCGTCGTCGCTGCCGCCACCGGAGTGCAATCACAAGTACAAC<br>TGGTGCAGAGCGGGGCCGAAGTCAAGAAGCCCGGCGCCTCCGTGAAAATCTCGTGCAAAGCCTCGGG<br>TTACACATTCACTGACTACGCAGTGAACTGGGTCAGACAGGCACCGGGCCAGGGACTCGAGTGGATG<br>GGCTGGATCAACACTCAGACTGGGAAGCCCACCTATGCTCAGAAGTTCCAGGGAAGGTTTACCTTCA<br>CCCTCGACACCAGCACCTCCACCTCCTACTTGGAAATTAGCAGCCTGCGGTCCGAAGATACAGCCGT<br>GTACTATTGTACTAGGGACTCCTACTACTACTCATCGTCGCTGACTACTGGGGCCAGGGTACCCTC<br>GTGACCGTTAGCTCGGCCTCTACTAAGGGTCCGTCCGTGTTCCCGTTGGCCCCGAGCTCGAAGTCCA<br>CCTCCGGGGGAACCGCTGCGCTTGGATGCCTGGTCAAGGACTACTTCCCCGAGCCCGTGACGGTGTC<br>CTGGAACTCCGGGGCCCTGACCTCGGAGTGCACACTTTCCCTGCGGTGCTGCAGAGCTCAGGACTG<br>TACAGCCTCAGCTCCGTCGTGACCGTGCCTTCGTCCTCGCTGGGCACCCAGACCTACATCTGCAACG<br>TGAACCACAAGCCGAGCAACACCAAGGTCGACAAGAAAGTCGAGCCGAAGTCATGCGACAAGACTCA<br>CACTTGCCCGCCGTGCCCCGCGCCTGAGCTTCTTGGCGGGCCCTCCGTGTTCCTGTTTCCGCCAAAG<br>CCCAAGGATACTCTGATGATTTCGCGGACTCCTGAAGTGACCTGTGTGGTCGTCGATGTGTCCCATG<br>AGGACCCCGAGGTCAAGTTCAATTGGTACGTGGACGGCGTGGAGGTCCACAATGCCAAGACGAAGCC<br>GCGGGAAGAACAGTACAACTCCACTTATCGCGTGGTGTCCGTGCTCACCGTGCTGCATCAGGACTGG<br>CTGAACGGAAAGGAGTACAAGTGCAAAGTGTCCAACAAGGGCCTGCCTGCCCAATTGAAAAGACCA<br>TCTCAAAAGCGAAGGGCCAGCCGCGCGAACCACAAGTGTACACCCTGCCTCCTTCCCGGGATGAACT<br>GACCAAGAACCAAGTGTCCCTGACTTGCCTCTCGTGAAGGGTTTCTACCCGTCCGACATCGCCGTGGAA<br>TGGGAGAGCAACGGACAGCCCGAGAACAATTACAAGACTACCCCACCCGTGCTCGATTCGGACGGCA<br>GCTTCTTCCTGTACTCCAAGCTGACCGTGGATAAGTCCCGCTGGCAACAGGGAAACGTGTTCAGTTG<br>TTCCGTGATGCACGAAGCCCTGCACAACCACTACACCCAGAAGTCACTGTCCCTGTCTCCGGGAAAA<br>TAA |
| 420 | PI-3041-AB LC cDNA | ATGGATATGAGAGTGCCTGCACAACTTCTTGGATTACTGCTGCTTTGGTTGTCGGGAGCCAGATGCG<br>ATATCCAGATGACCCAGTCCCCGTCGAGCCTGTCAGCTTCCGTGGGCGACCGGGTCACCATTACTTG<br>TCGCGCCTCGGCCGGTATTAGCAATGACTTGGCCTGGTACCAGCAGAAGCCTGGGAAGGCCCCCAAG<br>CTCCTCATCTACGCGGCTTCCCGCCTGCAAGACGGCGTGCCGTCAAGGTTCAGCGGTTCGGGCTCCG<br>GAACTGACTTCACCCTCACTATCTCGTCCCTGCAACCCGAAGATTTCGCAACCTACTACTGCCAGCA<br>GTCCTATAAGTACCCCTGGACTTTCGGACAAGGCACCAAGCTCGAGATCAAGCGGACCGTGGCCGCC<br>CCGAGCGTGTTTATCTTCCCGCCATCTGACGAACAGCTGAAGTCCGGGACAGCGTCCGTGGTCTGCC<br>TGCTCAACAACTTCTACCCCCGCGAGGCCAAAGTGCAGTGGAAAGTCGATAACGCGCTGCAGTCCGG<br>AAACAGCCAGGAAAGCGTGACTGAGCAAGACTCCAAGGACTCCACCTACTCCCTGTCATCCACCCTG<br>ACGCTGTCCAAGGCCGACTACGAAAAGCACAAGGTCTACGCCTGCGAAGTGACCCATCAGGGCCTGT<br>CAAGCCCTGTGACCAAGTCGTTCAACCGGGGAGAGTGTTAA |
| 421 | PI-3028-AB HC cDNA | ATGGATTGGACTTGGAGATTTTTGTTTGTGGTGGCGGCGGCCACTGGAGTGCAATCCGAAGTGCAAT<br>TGGTGGAATCGGGTGGTGGACTTGTGCAGCCTGGATCGTCACTTAAGCTGTCCTGTGTGGCCTCGAA<br>GTTTACCTTCTCCAACTATGGGATGAACTGGATTAGACAAGCCCCGAAGAAGGGACTGGAATGGATT<br>GCGCTGATCTATTACAACTCGAACAACAAGTACTACGCTGATTCCGTGAAGGGTCGCTTCACTATTT<br>CCCGCGACAACTCGAAGAACACTCTGTACCTTGAGATGAACTCCCTGCGCTCGGAAGATACTGCCAT<br>GTACTACTGTGCCAAGTCGCTGACTGGCGGATCCGATTACTTCGATTCCTGGGGACAAGGAGTGATG<br>GTCACTGTATCCAGTGCCAGCACCAAGGGCCCATCGGTCTTCCCCCTGGCACCCTCCTCCAAGAGCA<br>CCTCTGGGGGCACAGCGGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAGACCTACATCTGCAACG<br>TGAATCACAAGCCCAGCAACACCAAGGTGGACAAGAAAGTTGAGCCCAAATCTTGTGACAAAACTCA<br>CACATGCCCACCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGACGTGAGCCACG<br>AAGACCCTGAGGTCAAGTTCAACTGGTACGTGGACGGCGTGGAGGTGCATAATGCCAAGACAAAGCC<br>GCGGGAGGAGCAGTACAACAGCACGTACCGGGTGGTCAGCGTCCTCACCGTCCTGCACCAGGACTGG<br>CTGAATGGCAAGGAGTACAAGTGCAAGGTCAGCAACAAAGCCCTCCCAGCCCCCATCGAGAAAACCA<br>TCTCCAAAGCCAAAGGGCAGCCCCGAGAACCACAGGTGTACACCCTGCCCCCATCCCGGGATGAGCT<br>GACCAAGAACCAGGTCAGCCTGACCTGCCTGGTCAAAGGCTTCTATCCCAGCGACATCGCCGTGGAG<br>TGGGAGAGCAATGGGCAGCCGGAGAACAACTACAAGACCACGCCTCCCGTGCTGGACTCCGACGGCT<br>CCTTCTTCCTCTACAGCAAGCTCACCGTGGACAAGAGCAGGTGGCAGCAGGGGAACGTCTTCTCATG<br>CTCCGTGATGCATGAGGCTCTGCACAACCACTACACGCAGAAGTCCCTCTCCCTGTCTCCGGGTAAA<br>TAG |
| 422 | PI-3028-AB | ATGGACATGCGCGTGCCTGCGCAATTGCTGGGGCTGCTTCTCCTGTGGCTTTCGGGAGCCCGCTGCG |

| SEQ ID NO | Name | Sequence |
|---|---|---|
| | LC cDNA | ACGTGCAGATGACCCAGTCCCCTTCCTACCTGGCTGCGTCACCGGGAGAATCAGTGTCCATCAGCTG<br>CAAGGCCTCCAAGTCCATTGGTACCTTCCTGGCCTGGTACCAAGAGAAGCCTGAAAAGACCAACAAG<br>CTCCTGATCTACTCGGGATCAACCCTGCAATCCGGCACTCCGTCGCGGTTCTCCGGATCCGGGTCCG<br>GCACCGACTTTACTCTGACCATTCGGAACCTGGAACCCGAAGATTTCGCCGTGTACTACTGTCAGCA<br>GCACGACGAATACCCGTTTACTTTCGGCTCCGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 423 | PI-3029-AB HC cDNA | ATGGATTGGACTTGGAGATTTTTGTTTGTGGTGGCGGCGGCCACTGGAGTGCAATCCGAAGTGCAAT<br>TGGTGGAATCGGGTGGTGGACTTGTGCAGCCTGGATCGTCACTTAAGCTGTCCTGTGTGGCCTCGAA<br>GTTTTACCTTCTCCAACTATGGGATGAACTGGATTAGACAAGCCCCGAAGAAGGGACTGGAATGGATT<br>GCGCTGATCTATTACAACTCGAACAACAAGTACTACGCTGATTCCGTGAAGGGTCGCTTCACTATTT<br>CCCGCGACAACTCGAAGAACACTCTGTACCTTGAGATGAACTCCCTGCGCTCGGAAGATACTGCCAT<br>GTACTACTGTGCCAAGTCGCTGACTGGCGGATCCGATTACTTCGATTCCTGGGGACAAGGAGTGATG<br>GTCACTGTATCCAGTGCCAGCACAAAGGGCCCATCCGTCTTCCCCCTGGCGCCCTGCTCCAGGAGCA<br>CCTCCGAGAGCACAGCCGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACGAAGACCTACACCTGCAACG<br>TAGATCACAAGCCCAGCAACACCAAGGTGGACAAGAGAGTTGAGTCCAAATATGGTCCCCCATGCCC<br>ATCCTGCCCAGCACCTGAGTTCCTGGGGGGACCATCAGTCTTCCTGTTCCCCCCAAAACCCAAGGAC<br>ACTCTCATGATCTCCCGGACCCCTGAGGTCACGTGCGTGGTGGTGGACGTGAGCCAGGAAGACCCCG<br>AGGTCCAGTTCAACTGGTACGTGGATGGCGTGGAGGTGCATAATGCCAAGACAAAGCCGCGGGAGGA<br>GCAGTTCAACAGCACGTACCGTGTGGTCAGCGTCCTCACCGTCCTGCACCAGGACTGGCTGAACGGC<br>AAGGAGTACAAGTGCAAGGTCAGCAACAAAGCCCTCCCGTCCTCCATCGAGAAAACCATCTCCAAAG<br>CCAAAGGGCAGCCCCGAGAGCCACAGGTGTACACCCTGCCCCCATCCCAGGAGGAGATGACCAAGAA<br>CCAGGTCAGCCTGACCTGCCTGGTCAAAGGCTTCTACCCCAGCGACATCGCCGTGGAGTGGGAGAGC<br>AATGGGCAGCCGGAGAACAACTACAAGACCACGCCTCCCGTGCTGGACTCCGACGGCTCCTTCTTCC<br>TCTACAGCAGGCTAACCGTGGACAAGAGCAGGTGGCAGGAGGGGAATGTCTTCTCATGCTCCGTGAT<br>GCATGAGGCTCTGCACAACCACTACACAGAAGTCCCTCTCCCTGTCTCTGGGTAAATAG |
| 424 | PI-3029-AB LC cDNA | ATGGACATGCGCGTGCCTGCGCAATTGCTGGGGCTGCTTCTCCTGTGGCTTTCGGGAGCCCGCTGCG<br>ACGTGCAGATGACCCAGTCCCCTTCCTACCTGGCTGCGTCACCGGGAGAATCAGTGTCCATCAGCTG<br>CAAGGCCTCCAAGTCCATTGGTACCTTCCTGGCCTGGTACCAAGAGAAGCCTGAAAAGACCAACAAG<br>CTCCTGATCTACTCGGGATCAACCCTGCAATCCGGCACTCCGTCGCGGTTCTCCGGATCCGGGTCCG<br>GCACCGACTTTACTCTGACCATTCGGAACCTGGAACCCGAAGATTTCGCCGTGTACTACTGTCAGCA<br>GCACGACGAATACCCGTTTACTTTCGGCTCCGGCACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 425 | PI-3031-AB HC cDNA | ATGGATTGGACTTGGCGCTTCTTGTTTGTGGTGGCGGCGGCTACTGGAGTGCAGTCACAAGTCAACC<br>TTCTGCAATCCCGGGCAGCACTCGTGAAGCCCGGTGCTTCAGTGAAGCTGAGCTGCAAGGCCTCCGG<br>GTACACCTTCACCGACTACTATCTGCATTGGGTCAAGCAGTCCCACGCCAAGAGCCTGGAGTGGATT<br>GGCTACATCAACCCGAACAACGCCTACACCTCGTACAATGAGAAGTTCAAGTCCAAAGCGACCCTGA<br>CCGTGGATAAGTCCACTAACACCGCCTACATGGAACTGTCCAGACTCACGTCCGCCGACTCGGCCAC<br>CTATTACTGTGCCCGGGACACCCAGACTACTACAACCTCCACTTCGCCTACTGGGGCCAGGGAACT<br>CTGGTCACCGTGTCGAGCGCCAGCACCAAGGGCCCATCGGTCTTCCCCCTGGCACCCTCCTCCAAGA<br>GCACCTCTGGGGGCACAGCGGCCCTGGGCTGCCTGGTCAAGGACTACTTCCCCGAACCGGTGACGGT<br>GTCGTGGAACTCAGGCGCCCTGACCAGCGGCGTGCACACCTTCCCGGCTGTCCTACAGTCCTCAGGA<br>CTCTACTCCCTCAGCAGCGTGGTGACCGTGCCCTCCAGCAGCTTGGGCACCCAGACCTACATCTGCA<br>ACGTGAATCACAAGCCCAGCAACACCAAGGTGGACAAGAAAGTTGAGCCCAAATCTTGTGACAAAAC<br>TCACACATGCCCACCGTGCCCAGCACCTGAACTCCTGGGGGGACCGTCAGTCTTCCTCTTCCCCCCA<br>AAACCCAAGGACACCCTCATGATCTCCCGGACCCCTGAGGTCACATGCGTGGTGGTGGACGTGAGCC<br>ACGAAGACCCTGAGGTCAAGTTCAACTGGTACGTGGACGGCGTGGAGGTGCATAATGCCAAGACAAA<br>GCCGCGGGAGGAGCAGTACAACAGCACGTACCGGGTGGTCAGCGTCCTCACCGTCCTGCACCAGGAC<br>TGGCTGAATGGCAAGGAGTACAAGTGCAAGGTCAGCAACAAAGCCCTCCCAGCCCCCATCGAGAAAA<br>CCATCTCCAAAGCCAAAGGGCAGCCCCGAGAACCACAGGTGTACACCCTGCCCCCATCCCGGGATGA<br>GCTGACCAAGAACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTGGACTCCGACG<br>GCTCCTTCTTCCTCTACAGCAAGCTCACCGTGGACAAGAGCAGGTGGCAGCAGGGGAACGTCTTCTC<br>ATGCTCCGTGATGCATGAGGCTCTGCACAACCACTACACGCAGAAGTCCCTCTCCCTGTCTCCGGGT<br>AAATAG |
| 426 | PI-3031-AB LC cDNA | ATGGATATGCGGGTGCCGGCCCAGCTTCTGGGGCTGTTGCTGCTCTGGCTCTCGGGAGCGCGCTGTG<br>ACATTCAAATGACCCAGTCCCCTGCATCACTGAGCGCCTCACTGGGGGAAACTGTCAGCATTGAGTG<br>CCTGACCTCCGAGGGAATCTCGAACGACCTGGCCTGGTATCAGCAGAAGTCCGGAAAGTCGCCGCAG<br>CTGCTTATCTACGACGCCAGCAGACTCGAGGACGGCGTGCCCTCCCGCTTTTCCGGCTCTGGTTCCG<br>GCACTCGGTACAGCCTGAAGATCTCCGGAATGCAGACCGAAGATGAAGCTGACTACTTCTGCCAACA |

| SEQ ID NO | Name | Sequence |
|---|---|---|
| | | ATCGTACAAATACCCACTGACCTTCGGTTCCGGGACCAAGCTCGAAATCAAGCGAACTGTGGCTGCA<br>CCATCTGTCTTCATCTTCCCGCCATCTGATGAGCAGTTGAAATCTGGAACTGCCTCTGTTGTGTGCC<br>TGCTGAATAACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCAGCACCCTG<br>ACGCTGAGCAAAGCAGACTACGAGAAACACAAAGTCTACGCCTGCGAAGTCACCCATCAGGGCCTGA<br>GCTCGCCCGTCACAAAGAGCTTCAACAGGGGAGAGTGTTAA |
| 427 | HC signal peptide sequence | ATGGATTGGACTTGGCGCTTCTTGTTTGTGGTGGCGGCGGCTACTGGAGTGCAGTCA |
| 428 | HC signal peptide sequence | MDWTWRFLFVVAAATGVQS |
| 429 | LC signal peptide sequence | MDMRVPAQLLGLLLLWLSGARC |
| 430 | LC signal peptide sequence | ATGGATATGCGGGTGCCGGCCCAGCTTCTGGGCCTGTTGCTGCTCTGGCTCTCCGGAGCGCGCTGT |
| 431 | CDR L1 | ASEGISNDLA |
| 432 | CDR L1 | ASAGISNDLA |
| 433 | CDR L1 | ASKSIGTFLA |
| 434 | PI-3025-AB2 Heavy Chain Variable | EVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSS |
| 435 | PI-3025-AB2 CDR-H1 | GFSLTSYHVS |
| 436 | PI-3025-AB2 CDR-H2 | AIWTGGSIA |
| 437 | PI-3025-AB2 CDR-H3 | DLSDYYSSYTSFDY |
| 438 | PI-3025-AB2 Heavy chain | EVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 439 | PI-3025-AB2 Light Chain Variable | DIQMTQSPSSLSASVGDRVTITCRASEGISNDLAWYQQKPGKAPKLLIYAASRLQDGVPSRFSGSGS<br>GTDYTLTISSLQPEDFATYYCQQSYKYPLTFGQGTKLEIK |
| 440 | PI-3025-AB2 CDR-L1 | RASEGISNDLA |
| 441 | PI-3025-AB2 CDR-L2 | AASRLQD |
| 442 | PI-3025-AB2 CDR-L3 | QQSYKYPLT |
| 443 | PI-3025-AB Light chain | DIQMTQSPSSLSASVGDRVTITCRASEGISNDLAWYQQKPGKAPKLLIYAASRLQDGVPSRFSGSGS<br>GTDYTLTISSLQPEDFATYYCQQSYKYPLTFGQGTKLEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC |
| 444 | PI-3048-AB Heavy Chain Variable | EVQLQESGPGLVKPSETLSLTCTVSGFSLTSYHVSWVRQPPGKGLEWIGAIWTGGSIAYNPSLKSRV<br>TISRDTSKNQVSLKLSSVTAADTAVYYCARDLSDYYSSYTSFDYWGQGTLVTVSS |
| 445 | PI-3048-AB | GFSLTSYHVS |

-continued

Sequence listing

| SEQ ID NO | Name | Sequence |
|---|---|---|
| 446 | PI-3048-AB CDR-H1 | AIWTGGSIA |
| 447 | PI-3048-AB CDR-H2 | DLSDYYSSYTSFDY |
| 448 | PI-3048-AB CDR-H3 Heavy chain | EVQLQESGPGLVKPSETLSLTCTVSGFSLTSYHVSWVRQPPGKGLEWIGAIWTGGSIAYNPSLKSRV TISRDTSKNQVSLKLSSVTAADTAVYYCARDLSDYYSSYTSFDYWGQGTLVTVSSASTKGPSVFPLA PCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 449 | PI-3048-AB Light Chain Variable | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIK |
| 450 | PI-3048-AB CDR-L1 | RASEGISNDLA |
| 451 | PI-3048-AB CDR-L2 | AASRLQD |
| 452 | PI-3048-AB CDR-L3 | QQSYKYPLT |
| 453 | PI-3048-AB Light chain | DIQMTQSPSSLSASVGDRVTITCRASEGISNDLAWYQQKPGKAPKLLIYAASRLQDGVPSRFSGSGS GTDYTLTISSLQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |
| 454 | PI-3041-AB Heavy Chain Variable | QVQLVQSGAEVKKPGASVKISCKASGYTFTDYAVNWVRQAPGQGLEWMGWINTQTGKPTYAQKFQGR FTFTLDTSTSTSYLEISSLRSEDTAVYYCTRDSYYYSSSLDYWGQGTLVTVSS |
| 455 | PI-3041-AB CDR-H1 | GYTFTDYAVN |
| 456 | PI-3041-AB CDR-H2 | WINTQTGKPT |
| 457 | PI-3041-AB CDR-H3 | DSYYYSSSLDY |
| 458 | PI-3041-AB Heavy chain | QVQLVQSGAEVKKPGASVKISCKASGYTFTDYAVNWVRQAPGQGLEWMGWINTQTGKPTYAQKFQGR FTFTLDTSTSTSYLEISSLRSEDTAVYYCTRDSYYYSSSLDYWGQGTLVTVSSASTKGPSVFPLAPS SKSTSGGTAALGCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |
| 459 | PI-3041-AB Light Chain Variable | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIK |
| 460 | PI-3041-AB CDR-L1 | RASAGISNDLA |
| 461 | PI-3041-AB CDR-L2 | AASRLQD |
| 462 | PI-3041-AB CDR-L3 | QQSYKYPWT |
| 463 | PI-3041-AB Light chain | DIQMTQSPSSLSASVGDRVTITCRASAGISNDLAWYQQKPGKAPKLLIYAASRLQDGVPSRFSGSGS GTDFTLTISSMQPEDFATYYCQQSYKYPWTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |

| SEQ ID NO | Name | Sequence |
|---|---|---|
| 464 | PI-3047-AB Heavy Chain Variable | EVQLVQSGAEVKKPGASVKISCKASGYTFTDYAVNWVRQAPGQGLEWMGWINTQTGKPTYAQKFQGRFTFTLDTSTSTSYLEISSLRSEDTAVYYCTRDSYYYSSSLDYWGQGTLVTVSS |
| 465 | PI-3047-AB CDR-H1 | GYTFTDYAVN |
| 466 | PI-3047-AB CDR-H2 | WINTQTGKPT |
| 467 | PI-3047-AB CDR-H3 | DSYYYSSSLDY |
| 468 | PI-3047-AB Heavy chain | EVQLVQSGAEVKKPGASVKISCKASGYTFTDYAVNWVRQAPGQGLEWMGWINTQTGKPTYAQKFQGRFTFTLDTSTSTSYLEISSLRSEDTAVYYCTRDSYYYSSSLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 469 | PI-3047-AB Light Chain Variable | DIQMTQSPSSLSASVGDRVTITCRASAGISNDLAWYQQKPGKAPKLLIYAASRLQDGVPSRFSGSGSGTDFTLTISSMQPEDFATYYCQQSYKYPWTFGQGTKLEIK |
| 470 | PI-3047-AB CDR-L1 | RASAGISNDLA |
| 471 | PI-3047-AB CDR-L2 | AASRLQD |
| 472 | PI-3047-AB CDR-L3 | QQSYKYPWT |
| 473 | PI-3047-AB Light chain | DIQMTQSPSSLSASVGDRVTITCRASAGISNDLAWYQQKPGKAPKLLIYAASRLQDGVPSRFSGSGSGTDFTLTISSMQPEDFATYYCQQSYKYPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 474 | PI-3046-AB Heavy Chain Variable | EVQLQESGPGLVKPSETLSLTCTVSGFSLTSYHVSWVRQPPGKGLEWMGAIWTGGSIAYNPSLKSRLTISRDTSKNQVSLKMSSLTAADTAVYYCARDLSDYYSSYTSFDYWGQGTLVTVSS |
| 475 | PI-3046-AB CDR-H1 | GFSLTSYHVS |
| 476 | PI-3046-AB CDR-H2 | AIWTGGSIA |
| 477 | PI-3046-AB CDR-H3 | DLSDYYSSYTSFDY |
| 478 | PI-3046-AB Heavy chain | EVQLQESGPGLVKPSETLSLTCTVSGFSLTSYHVSWVRQPPGKGLEWMGAIWTGGSIAYNPSLKSRLTISRDTSKNQVSLKMSSLTAADTAVYYCARDLSDYYSSYTSFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 479 | PI-3046-AB Light Chain Variable | DIQMTQSPSSLSASVGDRVTITCRASEGISNDLAWYQQKPGKAPKLLIYAASRLQSGVPSRFSGSGSGTDYTLTISSMQPEDFATYYCQQSYKYPLTFGQGTKLEIK |
| 480 | PI-3046-AB CDR-L1 | RASEGISNDLA |
| 481 | PI-3046-AB CDR-L2 | AASRLQD |
| 482 | PI-3046-AB CDR-L3 | QQSYKYPLT |

-continued

| SEQ ID NO | Name | Sequence |
|---|---|---|
| 483 | PI-3046-AB Light chain | DIQMTQSPSSLSASVGDRVTITCRASEGISNDLAWYQQKPGKAPKLLIYAASRLQSGVPSRFSGSGS GTDYTLTISSMQPEDFATYYCQQSYKYPLTFGQGTKLEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |
| 528 | CDR-L2 | AASRLQS |

SEQUENCE LISTING

```
Sequence total quantity: 528
SEQ ID NO: 1            moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 1
QVQLKESGPG LVQPSQTLSL TCTVSGFSLT SYHVSWVRQP PGKGLEWMGA IWTGGSIAYN    60
SLLKSRLSIS RDTSKSQVFL KMNSLQTEDT ATYYCARDLS DYYSSYTSFD YWGQGVMVTV   120
ST                                                                 122

SEQ ID NO: 2            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 2
GFSLTSYHVS                                                          10

SEQ ID NO: 3            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 3
AIWTGGSIA                                                            9

SEQ ID NO: 4            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 4
DLSDYYSSYT SFDY                                                     14

SEQ ID NO: 5            moltype = AA  length = 442
FEATURE                 Location/Qualifiers
REGION                  1..442
                        note = Description of Artificial Sequence: Synthetic
                         polypeptide
source                  1..442
                        mol_type = protein
                        organism = synthetic construct
SEQUENCE: 5
QVQLKESGPG LVQPSQTLSL TCTVSGFSLT SYHVSWVRQP PGKGLEWMGA IWTGGSIAYN    60
SLLKSRLSIS RDTSKSQVFL KMNSLQTEDT ATYYCARDLS DYYSSYTSFD YWGQGVMVTV   120
STAETTAPSV YPLAPGTALK SNSMVTLGCL VKGYFPEPVT VTWNSGALSS GVHTFPAVLQ   180
SGLYTLTSSV TVPSSTWSSQ AVTCNVAHPA SSTKVDKKIV PRECNPCGCT GSEVSSVFIF   240
PPKTKDVLTI TLTPKVTCVV VDISQNDPEV RFSWFIDDVE VHTAQTHAPE KQSNSTLRSV   300
SELPIVHRDW LNGKTFKCKV NSGAFPAPIE KSISKPEGTP RGPQVYTMAP PKEEMTQSQV   360
SITCMVKGFY PPDIYTEWKM NGQPQENYKN TPPTMDTDGS YFLYSKLNVK KETWQQGNTF   420
TCSVLHEGLH NHHTEKSLSH SP                                           442
```

```
SEQ ID NO: 6              moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 6
DIQMTQSPAS LSTSLGETVS IECLASEGIS NDLAWYQQKS GKSPQLLIYA ASRLQDGVPS    60
RFSGSGSGTR YSLKISGMQP EDEADYFCQQ SYKYPLTFGS GTKLEIK                 107

SEQ ID NO: 7              moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 7
LASEGISNDL A                                                         11

SEQ ID NO: 8              moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 8
AASRLQD                                                               7

SEQ ID NO: 9              moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 9
QQSYKYPLT                                                             9

SEQ ID NO: 10             moltype = AA  length = 214
FEATURE                   Location/Qualifiers
REGION                    1..214
                          note = Description of Artificial Sequence: Synthetic
                           polypeptide
source                    1..214
                          mol_type = protein
                          organism = synthetic construct
SEQUENCE: 10
DIQMTQSPAS LSTSLGETVS IECLASEGIS NDLAWYQQKS GKSPQLLIYA ASRLQDGVPS    60
RFSGSGSGTR YSLKISGMQP EDEADYFCQQ SYKYPLTFGS GTKLEIKRAD AAPTVSIFPP   120
STEQLATGGA SVVCLMNNFY PRDISVKWKI DGTERRDGVL DSVTDQDSKD STYSMSSTLS   180
LTKADYESHN LYTCEVVHKT SSSPVVKSFN RNEC                               214

SEQ ID NO: 11             moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 11
QVQLKESGPG LVQPSQTLSL TCTVSGFSLT SYHVSWVRQP PGKGLEWMGA IWTGGSIAYN    60
SLLKSRLSIS RDTSKSQVFL KMNSLQTEDT ATYYCARDLS DYYSSYTSFD YWGQGVMVTV   120
ST                                                                  122

SEQ ID NO: 12             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 12
GFSLTSYHVS                                                           10
```

```
SEQ ID NO: 13            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 13
AIWTGGSIA                                                                9

SEQ ID NO: 14            moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 14
DLSDYYSSYT SFDY                                                         14

SEQ ID NO: 15            moltype = AA  length = 452
FEATURE                  Location/Qualifiers
REGION                   1..452
                         note = Description of Artificial Sequence: Synthetic
                          polypeptide
source                   1..452
                         mol_type = protein
                         organism = synthetic construct
SEQUENCE: 15
QVQLKESGPG LVQPSQTLSL TCTVSGFSLT SYHVSWVRQP PGKGLEWMGA IWTGGSIAYN    60
SLLKSRLSIS RDTSKSQVFL KMNSLQTEDT ATYYCARDLS DYYSSYTSFD YWGQGVMVTV   120
STASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 16            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 16
DIQMTQSPAS LSTSLGETVS IECLASEGIS NDLAWYQQKS GKSPQLLIYA ASRLQDGVPS    60
RFSGSGSGTR YSLKISGMQP EDEADYFCQQ SYKYPLTFGS GTKLEIK                 107

SEQ ID NO: 17            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 17
LASEGISNDL A                                                            11

SEQ ID NO: 18            moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 18
AASRLQD                                                                  7

SEQ ID NO: 19            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 19
```

```
QQSYKYPLT                                                                         9

SEQ ID NO: 20           moltype = AA   length = 214
FEATURE                 Location/Qualifiers
REGION                  1..214
                        note = Description of Artificial Sequence: Synthetic
                          polypeptide
source                  1..214
                        mol_type = protein
                        organism = synthetic construct
SEQUENCE: 20
DIQMTQSPAS LSTSLGETVS IECLASEGIS NDLAWYQQKS GKSPQLLIYA ASRLQDGVPS  60
RFSGSGSGTR YSLKISGMQP EDEADYFCQQ SYKYPLTFGS GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                             214

SEQ ID NO: 21           moltype = AA   length = 122
FEATURE                 Location/Qualifiers
REGION                  1..122
                        note = Description of Artificial Sequence: Synthetic
                          polypeptide
source                  1..122
                        mol_type = protein
                        organism = synthetic construct
SEQUENCE: 21
QVQLQESGPG LVKPSETLSL TCTVSGFSLT SYHVSWIRQP PGKGLEWIGA IWTGGSIAYN  60
PSLKSRVTIS VDTSKNQFSL KLSSVTAADT AVYYCARDLS DYYSSYTSFD YWGQGTLVTV 120
SS                                                                122

SEQ ID NO: 22           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 22
GFSLTSYHVS                                                                       10

SEQ ID NO: 23           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 23
AIWTGGSIA                                                                         9

SEQ ID NO: 24           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 24
DLSDYYSSYT SFDY                                                                  14

SEQ ID NO: 25           moltype = AA   length = 452
FEATURE                 Location/Qualifiers
REGION                  1..452
                        note = Description of Artificial Sequence: Synthetic
                          polypeptide
source                  1..452
                        mol_type = protein
                        organism = synthetic construct
SEQUENCE: 25
QVQLQESGPG LVKPSETLSL TCTVSGFSLT SYHVSWIRQP PGKGLEWIGA IWTGGSIAYN  60
PSLKSRVTIS VDTSKNQFSL KLSSVTAADT AVYYCARDLS DYYSSYTSFD YWGQGTLVTV 120
SSASTKGPSV FPLAPSSKST SGGTAALGCL VKDYFPEPVT VSWNSGALTS GVHTFPAVLQ 180
SSGLYSLSSV VTVPSSSLGT QTYICNVNHK PSNTKVDKKV EPKSCDKTHT CPPCPAPELL 240
GGPSVFLFPP KPKDTLMISR TPEVTCVVVD VSHEDPEVKF NWYVDGVEVH NAKTKPREEQ 300
YNSTYRVVSV LTVLHQDWLN GKEYKCKVSN KALPAPIEKT ISKAKGQPRE PQVYTLPPSR 360
DELTKNQVSL TCLVKGFYPS DIAVEWESNG QPENNYKTTP PVLDSDGSFF LYSKLTVDKS 420
RWQQGNVFSC SVMHEALHNH YTQKSLSLSP GK                               452

SEQ ID NO: 26           moltype = AA   length = 107
FEATURE                 Location/Qualifiers
```

```
REGION              1..107
                    note = Description of Artificial Sequence: Synthetic
                     polypeptide
source              1..107
                    mol_type = protein
                    organism = synthetic construct
SEQUENCE: 26
DIQMTQSPSS LSASVGDRVT ITCRASEGIS NDLAWYQQKP GKAPKLLIYA ASRLQSGVPS    60
RFSGSGSGTD FTLTISSLQP EDFATYYCQQ SYKYPLTFGQ GTKLEIK                 107

SEQ ID NO: 27       moltype = AA   length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 27
RASEGISNDL A                                                         11

SEQ ID NO: 28       moltype = AA   length = 7
FEATURE             Location/Qualifiers
REGION              1..7
                    note = Description of Artificial Sequence: Synthetic peptide
source              1..7
                    mol_type = protein
                    organism = synthetic construct
SEQUENCE: 28
AASRLQD                                                               7

SEQ ID NO: 29       moltype = AA   length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 29
QQSYKYPLT                                                             9

SEQ ID NO: 30       moltype = AA   length = 214
FEATURE             Location/Qualifiers
REGION              1..214
                    note = Description of Artificial Sequence: Synthetic
                     polypeptide
source              1..214
                    mol_type = protein
                    organism = synthetic construct
SEQUENCE: 30
DIQMTQSPSS LSASVGDRVT ITCRASEGIS NDLAWYQQKP GKAPKLLIYA ASRLQSGVPS    60
RFSGSGSGTD FTLTISSLQP EDFATYYCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 31       moltype = AA   length = 122
FEATURE             Location/Qualifiers
REGION              1..122
                    note = Description of Artificial Sequence: Synthetic
                     polypeptide
source              1..122
                    mol_type = protein
                    organism = synthetic construct
SEQUENCE: 31
QVQLQESGPG LVKPSETLSL TCTVSGFSLT SYHVSWVRQP PGKGLEWIGA IWTGGSIAYN    60
PSLKSRVTIS RDTSKNQVSL KLSSVTAADT AVYYCARDLS DYYSSYTSFD YWGQGTLVTV   120
SS                                                                 122

SEQ ID NO: 32       moltype = AA   length = 10
FEATURE             Location/Qualifiers
REGION              1..10
                    note = Description of Artificial Sequence: Synthetic peptide
source              1..10
                    mol_type = protein
                    organism = synthetic construct
SEQUENCE: 32
GFSLTSYHVS                                                           10

SEQ ID NO: 33       moltype = AA   length = 9
FEATURE             Location/Qualifiers
```

```
REGION                  1..9
                        note = Description of Artificial Sequence: Synthetic peptide
source                  1..9
                        mol_type = protein
                        organism = synthetic construct
SEQUENCE: 33
AIWTGGSIA                                                                           9

SEQ ID NO: 34           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 34
DLSDYYSSYT SFDY                                                                    14

SEQ ID NO: 35           moltype = AA   length = 452
FEATURE                 Location/Qualifiers
REGION                  1..452
                        note = Description of Artificial Sequence: Synthetic
                         polypeptide
source                  1..452
                        mol_type = protein
                        organism = synthetic construct
SEQUENCE: 35
QVQLQESGPG LVKPSETLSL TCTVSGFSLT SYHVSWVRQP PGKGLEWIGA IWTGGSIAYN    60
PSLKSRVTIS RDTSKNQVSL KLSSVTAADT AVYYCARDLS DYYSSYTSFD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 36           moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 36
DIQMTQSPSS LSASVGDRVT ITCRASEGIS NDLAWYQQKP GKAPKLLIYA ASRLQSGVPS    60
RFSGSGSGTD YTLTISSLQP EDFATYYCQQ SYKYPLTFGQ GTKLEIK                 107

SEQ ID NO: 37           moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 37
RASEGISNDL A                                                                       11

SEQ ID NO: 38           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 38
AASRLQD                                                                             7

SEQ ID NO: 39           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 39
QQSYKYPLT                                                                           9

SEQ ID NO: 40           moltype = AA   length = 214
```

| | | |
|---|---|---|
| FEATURE | Location/Qualifiers | |
| REGION | 1..214<br>note = Description of Artificial Sequence: Synthetic<br>polypeptide | |
| source | 1..214<br>mol_type = protein<br>organism = synthetic construct | |
| SEQUENCE: 40 | | |
| DIQMTQSPSS LSASVGDRVT | ITCRASEGIS NDLAWYQQKP | GKAPKLLIYA ASRLQSGVPS 60 |
| RFSGSGSGTD YTLTISSLQP | EDFATYYCQQ SYKYPLTFGQ | GTKLEIKRTV AAPSVFIFPP 120 |
| SDEQLKSGTA SVVCLLNNFY | PREAKVQWKV DNALQSGNSQ | ESVTEQDSKD STYSLSSTLT 180 |
| LSKADYEKHK VYACEVTHQG | LSSPVTKSFN RGEC | 214 |
| | | |
| SEQ ID NO: 41 | moltype = AA   length = 122 | |
| FEATURE | Location/Qualifiers | |
| REGION | 1..122<br>note = Description of Artificial Sequence: Synthetic<br>polypeptide | |
| source | 1..122<br>mol_type = protein<br>organism = synthetic construct | |
| SEQUENCE: 41 | | |
| QVQLQESGPG LVKPSETLSL | TCTVSGFSLT SYHVSWVRQP | PGKGLEWIGA IWTGGSIAYN 60 |
| PSLKSRVTIS RDTSKNQVSL | KLSSVTAADT AVYYCARDLS | DYYSSYTSFD YWGQGTLVTV 120 |
| SS | | 122 |
| | | |
| SEQ ID NO: 42 | moltype = AA   length = 10 | |
| FEATURE | Location/Qualifiers | |
| REGION | 1..10<br>note = Description of Artificial Sequence: Synthetic peptide | |
| source | 1..10<br>mol_type = protein<br>organism = synthetic construct | |
| SEQUENCE: 42 | | |
| GFSLTSYHVS | | 10 |
| | | |
| SEQ ID NO: 43 | moltype = AA   length = 9 | |
| FEATURE | Location/Qualifiers | |
| REGION | 1..9<br>note = Description of Artificial Sequence: Synthetic peptide | |
| source | 1..9<br>mol_type = protein<br>organism = synthetic construct | |
| SEQUENCE: 43 | | |
| AIWTGGSIA | | 9 |
| | | |
| SEQ ID NO: 44 | moltype = AA   length = 14 | |
| FEATURE | Location/Qualifiers | |
| REGION | 1..14<br>note = Description of Artificial Sequence: Synthetic peptide | |
| source | 1..14<br>mol_type = protein<br>organism = synthetic construct | |
| SEQUENCE: 44 | | |
| DLSDYYSSYT SFDY | | 14 |
| | | |
| SEQ ID NO: 45 | moltype = AA   length = 452 | |
| FEATURE | Location/Qualifiers | |
| REGION | 1..452<br>note = Description of Artificial Sequence: Synthetic<br>polypeptide | |
| source | 1..452<br>mol_type = protein<br>organism = synthetic construct | |
| SEQUENCE: 45 | | |
| QVQLQESGPG LVKPSETLSL | TCTVSGFSLT SYHVSWVRQP | PGKGLEWIGA IWTGGSIAYN 60 |
| PSLKSRVTIS RDTSKNQVSL | KLSSVTAADT AVYYCARDLS | DYYSSYTSFD YWGQGTLVTV 120 |
| SSASTKGPSV FPLAPSSKST | SGGTAALGCL VKDYFPEPVT | VSWNSGALTS GVHTFPAVLQ 180 |
| SSGLYSLSSV VTVPSSSLGT | QTYICNVNHK PSNTKVDKKV | EPKSCDKTHT CPPCPAPELL 240 |
| GGPSVFLFPP KPKDTLMISR | TPEVTCVVVD VSHEDPEVKF | NWYVDGVEVH NAKTKPREEQ 300 |
| YNSTYRVVSV LTVLHQDWLN | GKEYKCKVSN KALPAPIEKT | ISKAKGQPRE PQVYTLPPSR 360 |
| DELTKNQVSL TCLVKGFYPS | DIAVEWESNG QPENNYKTTP | PVLDSDGSFF LYSKLTVDKS 420 |
| RWQQGNVFSC SVMHEALHNH | YTQKSLSLSP GK | 452 |
| | | |
| SEQ ID NO: 46 | moltype = AA   length = 107 | |
| FEATURE | Location/Qualifiers | |
| REGION | 1..107<br>note = Description of Artificial Sequence: Synthetic<br>polypeptide | |

```
                        source              1..107
                                            mol_type = protein
                                            organism = synthetic construct
SEQUENCE: 46
DIQMTQSPSS LSASVGDRVT ITCRASEGIS NDLAWYQQKP GKAPKLLIYA ASRLQSGVPS    60
RFSGSGSGTD YTLTISSMQP EDFATYYCQQ SYKYPLTFGQ GTKLEIK                 107

SEQ ID NO: 47           moltype = AA    length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 47
RASEGISNDL A                                                         11

SEQ ID NO: 48           moltype = AA    length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 48
AASRLQD                                                               7

SEQ ID NO: 49           moltype = AA    length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 49
QQSYKYPLT                                                             9

SEQ ID NO: 50           moltype = AA    length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 50
DIQMTQSPSS LSASVGDRVT ITCRASEGIS NDLAWYQQKP GKAPKLLIYA ASRLQSGVPS    60
RFSGSGSGTD YTLTISSMQP EDFATYYCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 51           moltype = AA    length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 51
QVQLQESGPG LVKPSETLSL TCTVSGFSLT SYHVSWVRQP PGKGLEWMGA IWTGGSIAYN    60
PSLKSRLTIS RDTSKNQVSL KMSSLTAADT AVYYCARDLS DYYSSYTSFD YWGQGTLVTV   120
SS                                                                  122

SEQ ID NO: 52           moltype = AA    length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 52
GFSLTSYHVS                                                           10

SEQ ID NO: 53           moltype = AA    length = 9
FEATURE                 Location/Qualifiers
REGION                  1..9
                        note = Description of Artificial Sequence: Synthetic peptide
source                  1..9
```

```
                        mol_type = protein
                        organism = synthetic construct
SEQUENCE: 53
AIWTGGSIA                                                               9

SEQ ID NO: 54           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 54
DLSDYYSSYT SFDY                                                        14

SEQ ID NO: 55           moltype = AA   length = 452
FEATURE                 Location/Qualifiers
REGION                  1..452
                        note = Description of Artificial Sequence: Synthetic
                         polypeptide
source                  1..452
                        mol_type = protein
                        organism = synthetic construct
SEQUENCE: 55
QVQLQESGPG LVKPSETLSL TCTVSGFSLT SYHVSWVRQP PGKGLEWMGA IWTGGSIAYN        60
PSLKSRLTIS RDTSKNQVSL KMSSLTAADT AVYYCARDLS DYYSSYTSFD YWGQGTLVTV       120
SSASTKGPSV FPLAPSSKST SGGTAALGCL VKDYFPEPVT VSWNSGALTS GVHTFPAVLQ       180
SSGLYSLSSV VTVPSSSLGT QTYICNVNHK PSNTKVDKKV EPKSCDKTHT CPPCPAPELL       240
GGPSVFLFPP KPKDTLMISR TPEVTCVVVD VSHEDPEVKF NWYVDGVEVH NAKTKPREEQ       300
YNSTYRVVSV LTVLHQDWLN GKEYKCKVSN KALPAPIEKT ISKAKGQPRE PQVYTLPPSR       360
DELTKNQVSL TCLVKGFYPS DIAVEWESNG QPENNYKTTP PVLDSDGSFF LYSKLTVDKS       420
RWQQGNVFSC SVMHEALHNH YTQKSLSLSP GK                                    452

SEQ ID NO: 56           moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 56
DIQMTQSPSS LSASVGDRVT ITCRASEGIS NDLAWYQQKP GKAPKLLIYA ASRLQSGVPS        60
RFSGSGSGTD YTLTISSLQP EDFATYYCQQ SYKYPLTFGQ GTKLEIK                     107

SEQ ID NO: 57           moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 57
RASEGISNDL A                                                           11

SEQ ID NO: 58           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 58
AASRLQD                                                                 7

SEQ ID NO: 59           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 59
QQSYKYPLT                                                               9

SEQ ID NO: 60           moltype = AA   length = 214
FEATURE                 Location/Qualifiers
REGION                  1..214
                        note = Description of Artificial Sequence: Synthetic
```

```
                              polypeptide
source                        1..214
                              mol_type = protein
                              organism = synthetic construct
SEQUENCE: 60
DIQMTQSPSS LSASVGDRVT ITCRASEGIS NDLAWYQQKP GKAPKLLIYA ASRLQSGVPS    60
RFSGSGSGTD YTLTISSLQP EDFATYYCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 61                 moltype = AA   length = 122
FEATURE                       Location/Qualifiers
REGION                        1..122
                              note = Description of Artificial Sequence: Synthetic
                              polypeptide
source                        1..122
                              mol_type = protein
                              organism = synthetic construct
SEQUENCE: 61
QVQLQESGPG LVKPSETLSL TCTVSGFSLT SYHVSWVRQP PGKGLEWMGA IWTGGSIAYN    60
PSLKSRLTIS RDTSKNQVSL KMSSLTAADT AVYYCARDLS DYYSSYTSFD YWGQGTLVTV   120
SS                                                                  122

SEQ ID NO: 62                 moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 62
GFSLTSYHVS                                                           10

SEQ ID NO: 63                 moltype = AA   length = 9
FEATURE                       Location/Qualifiers
REGION                        1..9
                              note = Description of Artificial Sequence: Synthetic peptide
source                        1..9
                              mol_type = protein
                              organism = synthetic construct
SEQUENCE: 63
AIWTGGSIA                                                             9

SEQ ID NO: 64                 moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 64
DLSDYYSSYT SFDY                                                      14

SEQ ID NO: 65                 moltype = AA   length = 452
FEATURE                       Location/Qualifiers
REGION                        1..452
                              note = Description of Artificial Sequence: Synthetic
                              polypeptide
source                        1..452
                              mol_type = protein
                              organism = synthetic construct
SEQUENCE: 65
QVQLQESGPG LVKPSETLSL TCTVSGFSLT SYHVSWVRQP PGKGLEWMGA IWTGGSIAYN    60
PSLKSRLTIS RDTSKNQVSL KMSSLTAADT AVYYCARDLS DYYSSYTSFD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 66                 moltype = AA   length = 107
FEATURE                       Location/Qualifiers
REGION                        1..107
                              note = Description of Artificial Sequence: Synthetic
                              polypeptide
source                        1..107
                              mol_type = protein
                              organism = synthetic construct
```

```
SEQUENCE: 66
DIQMTQSPSS LSASVGDRVT ITCRASEGIS NDLAWYQQKP GKAPKLLIYA ASRLQSGVPS    60
RFSGSGSGTD YTLTISSMQP EDFATYYCQQ SYKYPLTFGQ GTKLEIK                107

SEQ ID NO: 67            moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 67
RASEGISNDL A                                                        11

SEQ ID NO: 68            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 68
AASRLQD                                                              7

SEQ ID NO: 69            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 69
QQSYKYPLT                                                            9

SEQ ID NO: 70            moltype = AA   length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 70
DIQMTQSPSS LSASVGDRVT ITCRASEGIS NDLAWYQQKP GKAPKLLIYA ASRLQSGVPS    60
RFSGSGSGTD YTLTISSMQP EDFATYYCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 71            moltype = AA   length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 71
QVQLKESGPG LVQPSQTLSL TCTVSGFSLT SYHVSWVRQP PGKGLEWMGA IWTGGSIAYN    60
SLLKSRLSIS RDTSKSQVFL KMNSLQTEDT ATYYCARDLS DYYSSYTSFD YWGQGVMVTV   120
ST                                                                 122

SEQ ID NO: 72            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 72
GFSLTSYHVS                                                          10

SEQ ID NO: 73            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 73
```

```
AIWTGGSIA                                                              9

SEQ ID NO: 74           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 74
DLSDYYSSYT SFDY                                                        14

SEQ ID NO: 75           moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 75
QVQLKESGPG LVQPSQTLSL TCTVSGFSLT SYHVSWVRQP PGKGLEWMGA IWTGGSIAYN       60
SLLKSRLSIS RDTSKSQVFL KMNSLQTEDT ATYYCARDLS DYYSYTSFD YWGQGVMVTV       120
STASTKGPSV FPLAPCSRST SESTAALGCL VKDYFPEPVT VSWNSGALTS GVHTFPAVLQ      180
SSGLYSLSSV VTVPSSSLGT KTYTCNVDHK PSNTKVDKRV ESKYGPPCPS CPAPEFLGGP      240
SVFLFPPKPK DTLMISRTPE VTCVVVDVSQ EDPEVQFNWY VDGVEVHNAK TKPREEQFNS      300
TYRVVSVLTV LHQDWLNGKE YKCKVSNKGL PSSIEKTISK AKGQPREPQV YTLPPSQEEM      360
TKNQVSLTCL VKGFYPSDIA VEWESNGQPE NNYKTTPPVL DSDGSFFLYS RLTVDKSRWQ      420
EGNVFSCSVM HEALHNHYTQ KSLSLSLGK                                        449

SEQ ID NO: 76           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 76
DIQMTQSPAS LSTSLGETVS IECLASEGIS NDLAWYQQKS GKSPQLLIYA ASRLQDGVPS       60
RFSGSGSGTR YSLKISGMQP EDEADYFCQQ SYKYPLTFGS GTKLEIK                    107

SEQ ID NO: 77           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 77
LASEGISNDL A                                                           11

SEQ ID NO: 78           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 78
AASRLQD                                                                7

SEQ ID NO: 79           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 79
QQSYKYPLT                                                              9

SEQ ID NO: 80           moltype = AA  length = 214
FEATURE                 Location/Qualifiers
REGION                  1..214
                        note = Description of Artificial Sequence: Synthetic
                         polypeptide
source                  1..214
                        mol_type = protein
```

```
                        organism = synthetic construct
SEQUENCE: 80
DIQMTQSPAS LSTSLGETVS IECLASEGIS NDLAWYQQKS GKSPQLLIYA ASRLQDGVPS      60
RFSGSGSGTR YSLKISGMQP EDEADYFCQQ SYKYPLTFGS GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 81           moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 81
QVQLQESGPG LVKPSETLSL TCTVSGFSLT SYHVSWVRQP PGKGLEWIGA IWTGGSIAYN      60
PSLKSRVTIS RDTSKNQVSL KLSSVTAADT AVYYCARDLS DYYSSYTSFD YWGQGTLVTV     120
SS                                                                    122

SEQ ID NO: 82           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 82
GFSLTSYHVS                                                             10

SEQ ID NO: 83           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 83
AIWTGGSIA                                                               9

SEQ ID NO: 84           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 84
DLSDYYSSYT SFDY                                                        14

SEQ ID NO: 85           moltype = AA  length = 452
FEATURE                 Location/Qualifiers
REGION                  1..452
                        note = Description of Artificial Sequence: Synthetic
                         polypeptide
source                  1..452
                        mol_type = protein
                        organism = synthetic construct
SEQUENCE: 85
QVQLQESGPG LVKPSETLSL TCTVSGFSLT SYHVSWVRQP PGKGLEWIGA IWTGGSIAYN      60
PSLKSRVTIS RDTSKNQVSL KLSSVTAADT AVYYCARDLS DYYSSYTSFD YWGQGTLVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 86           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 86
DIQMTQSPSS LSASVGDRVT ITCRASEGIS NDLAWYQQKP GKAPKLLIYA ASRLQDGVPS      60
RFSGSGSGTD YTLTISSLQP EDFATYYCQQ SYKYPLTFGQ GTKLEIK                   107
```

```
SEQ ID NO: 87            moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 87
RASEGISNDL A                                                                11

SEQ ID NO: 88            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 88
AASRLQD                                                                     7

SEQ ID NO: 89            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 89
QQSYKYPLT                                                                   9

SEQ ID NO: 90            moltype = AA   length = 214
FEATURE                  Location/Qualifiers
REGION                   1..214
                         note = Description of Artificial Sequence: Synthetic
                           polypeptide
source                   1..214
                         mol_type = protein
                         organism = synthetic construct
SEQUENCE: 90
DIQMTQSPSS LSASVGDRVT ITCRASEGIS NDLAWYQQKP GKAPKLLIYA ASRLQDGVPS   60
RFSGSGSGTD YTLTISSLQP EDFATYYCQQ SYKYPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 91            moltype = AA   length = 122
FEATURE                  Location/Qualifiers
REGION                   1..122
                         note = Description of Artificial Sequence: Synthetic
                           polypeptide
source                   1..122
                         mol_type = protein
                         organism = synthetic construct
SEQUENCE: 91
QVQLQESGPG LVKPSETLSL TCTVSGFSLT SYHVSWVRQP PGKGLEWIGA IWTGGSIAYN   60
PSLKSRVTIS RDTSKNQVSL KLSSVTAADT AVYYCARDLS DYYSSYTSFD YWGQGTLVTV  120
SS                                                                 122

SEQ ID NO: 92            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 92
GFSLTSYHVS                                                                 10

SEQ ID NO: 93            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 93
AIWTGGSIA                                                                   9

SEQ ID NO: 94            moltype = AA   length = 14
```

| | |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 94
DLSDYYSSYT SFDY                                                                14

| | |
|---|---|
| SEQ ID NO: 95 | moltype = AA   length = 452 |
| FEATURE | Location/Qualifiers |
| REGION | 1..452 |
| | note = Description of Artificial Sequence: Synthetic polypeptide |
| source | 1..452 |
| | mol_type = protein |
| | organism = synthetic construct |

SEQUENCE: 95
```
QVQLQESGPG LVKPSETLSL TCTVSGFSLT SYHVSWVRQP PGKGLEWIGA IWTGGSIAYN  60
PSLKSRVTIS RDTSKNQVSL KLSSVTAADT AVYYCARDLS DYYSSYTSFD YWGQGTLVTV 120
SSASTKGPSV FPLAPSSKST SGGTAALGCL VKDYFPEPVT VSWNSGALTS GVHTFPAVLQ 180
SSGLYSLSSV VTVPSSSLGT QTYICNVNHK PSNTKVDKKV EPKSCDKTHT CPPCPAPELL 240
GGPSVFLFPP KPKDTLMISR TPEVTCVVVD VSHEDPEVKF NWYVDGVEVH NAKTKPREEQ 300
YNSTYRVVSV LTVLHQDWLN GKEYKCKVSN KALPAPIEKT ISKAKGQPRE PQVYTLPPSR 360
DELTKNQVSL TCLVKGFYPS DIAVEWESNG QPENNYKTTP PVLDSDGSFF LYSKLTVDKS 420
RWQQGNVFSC SVMHEALHNH YTQKSLSLSP GK                               452
```

| | |
|---|---|
| SEQ ID NO: 96 | moltype = AA   length = 107 |
| FEATURE | Location/Qualifiers |
| REGION | 1..107 |
| | note = Description of Artificial Sequence: Synthetic polypeptide |
| source | 1..107 |
| | mol_type = protein |
| | organism = synthetic construct |

SEQUENCE: 96
```
DIQMTQSPSS LSTSVGDRVT ITCRASEGIS NDLAWYQQKP GKSPKLLIYA ASRLQSGVPS  60
RFSGSGSGTD YTLTISSLQP EDFATYFCQQ SYKYPLTFGQ GTKLEIK              107
```

| | |
|---|---|
| SEQ ID NO: 97 | moltype = AA   length = 11 |
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 97
RASEGISNDL A                                                                   11

| | |
|---|---|
| SEQ ID NO: 98 | moltype = AA   length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |

SEQUENCE: 98
AASRLQD                                                                         7

| | |
|---|---|
| SEQ ID NO: 99 | moltype = AA   length = 9 |
| FEATURE | Location/Qualifiers |
| REGION | 1..9 |
| | note = Description of Artificial Sequence: Synthetic peptide |
| source | 1..9 |
| | mol_type = protein |
| | organism = synthetic construct |

SEQUENCE: 99
QQSYKYPLT                                                                       9

| | |
|---|---|
| SEQ ID NO: 100 | moltype = AA   length = 214 |
| FEATURE | Location/Qualifiers |
| REGION | 1..214 |
| | note = Description of Artificial Sequence: Synthetic polypeptide |
| source | 1..214 |
| | mol_type = protein |
| | organism = synthetic construct |

SEQUENCE: 100
DIQMTQSPSS LSTSVGDRVT ITCRASEGIS NDLAWYQQKP GKSPKLLIYA ASRLQSGVPS  60

```
RFSGSGSGTD YTLTISSLQP EDFATYFCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 101          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 101
QVQLQESGPG LVKPSETLSL TCTVSGFSLT SYHVSWVRQP PGKGLEWIGA IWTGGSIAYN   60
PSLKSRVTIS RDTSKNQVSL KLSSVTAADT AVYYCARDLS DYYSSYTSFD YWGQGTLVTV   120
SS                                                                 122

SEQ ID NO: 102          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 102
GFSLTSYHVS                                                         10

SEQ ID NO: 103          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 103
AIWTGGSIA                                                          9

SEQ ID NO: 104          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 104
DLSDYYSSYT SFDY                                                    14

SEQ ID NO: 105          moltype = AA  length = 452
FEATURE                 Location/Qualifiers
REGION                  1..452
                        note = Description of Artificial Sequence: Synthetic
                         polypeptide
source                  1..452
                        mol_type = protein
                        organism = synthetic construct
SEQUENCE: 105
QVQLQESGPG LVKPSETLSL TCTVSGFSLT SYHVSWVRQP PGKGLEWIGA IWTGGSIAYN   60
PSLKSRVTIS RDTSKNQVSL KLSSVTAADT AVYYCARDLS DYYSSYTSFD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 106          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 106
DIQMTQSPSS LSTSVGDRVT ITCRASEGIS NDLAWYQQKP GKSPKLLIYA ASRLQDGVPS   60
RFSGSGSGTD YTLTISSLQP EDEATYFCQQ SYKYPLTFGQ GTKLEIK                107

SEQ ID NO: 107          moltype = AA  length = 11
FEATURE                 Location/Qualifiers
```

```
REGION                  1..11
                        note = Description of Artificial Sequence: Synthetic peptide
source                  1..11
                        mol_type = protein
                        organism = synthetic construct
SEQUENCE: 107
RASEGISNDL A                                                                      11

SEQ ID NO: 108          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 108
AASRLQD                                                                            7

SEQ ID NO: 109          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 109
QQSYKYPLT                                                                          9

SEQ ID NO: 110          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 110
DIQMTQSPSS LSTSVGDRVT ITCRASEGIS NDLAWYQQKP GKSPKLLIYA ASRLQDGVPS    60
RFSGSGSGTD YTLTISSLQP EDEATYFCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 111          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 111
EVQLQESGPG LVKPSETLSL TCTVSGFSLT SYHVSWVRQP PGKGLEWIGA IWTGGSIAYN    60
PSLKSRVTIS RDTSKNQVSL KLSSVTAADT AVYYCARDLS DYYSSYTSFD YWGQGTLVTV   120
SS                                                                 122

SEQ ID NO: 112          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 112
GFSLTSYHVS                                                                        10

SEQ ID NO: 113          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 113
AIWTGGSIA                                                                          9

SEQ ID NO: 114          moltype = AA  length = 14
FEATURE                 Location/Qualifiers
REGION                  1..14
                        note = Description of Artificial Sequence: Synthetic peptide
```

```
source                    1..14
                          mol_type = protein
                          organism = synthetic construct
SEQUENCE: 114
DLSDYYSSYT SFDY                                                          14

SEQ ID NO: 115            moltype = AA  length = 452
FEATURE                   Location/Qualifiers
REGION                    1..452
                          note = Description of Artificial Sequence: Synthetic
                           polypeptide
source                    1..452
                          mol_type = protein
                          organism = synthetic construct
SEQUENCE: 115
EVQLQESGPG LVKPSETLSL TCTVSGFSLT SYHVSWVRQP PGKGLEWIGA IWTGGSIAYN          60
PSLKSRVTIS RDTSKNQVSL KLSSVTAADT AVYYCARDLS DYYSSYTSFD YWGQGTLVTV         120
SSASTKGPSV FPLAPSSKST SGGTAALGCL VKDYFPEPVT VSWNSGALTS GVHTFPAVLQ         180
SSGLYSLSSV VTVPSSSLGT QTYICNVNHK PSNTKVDKKV EPKSCDKTHT CPPCPAPELL         240
GGPSVFLFPP KPKDTLMISR TPEVTCVVVD VSHEDPEVKF NWYVDGVEVH NAKTKPREEQ         300
YNSTYRVVSV LTVLHQDWLN GKEYKCKVSN KALPAPIEKT ISKAKGQPRE PQVYTLPPSR         360
DELTKNQVSL TCLVKGFYPS DIAVEWESNG QPENNYKTTP PVLDSDGSFF LYSKLTVDKS         420
RWQQGNVFSC SVMHEALHNH YTQKSLSLSP GK                                      452

SEQ ID NO: 116            moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 116
DIQMTQSPSS LSTSVGDRVT ITCRASEGIS NDLAWYQQKP GKSPKLLIYA ASRLQDGVPS          60
RFSGSGSGTD YTLTISSLQP EDEATYFCQQ SYKYPLTFGQ GTKLEIK                      107

SEQ ID NO: 117            moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 117
RASEGISNDL A                                                             11

SEQ ID NO: 118            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 118
AASRLQD                                                                   7

SEQ ID NO: 119            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 119
QQSYKYPLT                                                                 9

SEQ ID NO: 120            moltype = AA  length = 214
FEATURE                   Location/Qualifiers
REGION                    1..214
                          note = Description of Artificial Sequence: Synthetic
                           polypeptide
source                    1..214
                          mol_type = protein
                          organism = synthetic construct
SEQUENCE: 120
DIQMTQSPSS LSTSVGDRVT ITCRASEGIS NDLAWYQQKP GKSPKLLIYA ASRLQDGVPS          60
RFSGSGSGTD YTLTISSLQP EDEATYFCQQ SYKYPLTFGQ GTKLEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                    214
```

```
SEQ ID NO: 121          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 121
VQLQESGPGL VKPSETLSLT CTVSGFSLTS YHVSWVRQPP GKGLEWIGAI WTGGSIAYNP    60
SLKSRVTISR DTSKNQVSLK LSSVTAADTA VYYCARDLSD YYSSYTSFDY WGQGTLVTVS   120
S                                                                   121

SEQ ID NO: 122          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 122
GFSLTSYHVS                                                           10

SEQ ID NO: 123          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 123
AIWTGGSIA                                                             9

SEQ ID NO: 124          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 124
DLSDYYSSYT SFDY                                                      14

SEQ ID NO: 125          moltype = AA   length = 452
FEATURE                 Location/Qualifiers
REGION                  1..452
                        note = Description of Artificial Sequence: Synthetic
                         polypeptide
source                  1..452
                        mol_type = protein
                        organism = synthetic construct
SEQUENCE: 125
EVQLQESGPG LVKPSETLSL TCTVSGFSLT SYHVSWVRQP PGKGLEWIGA IWTGGSIAYN    60
PSLKSRVTIS RDTSKNQVSL KLSSVTAADT AVYYCARDLS DYYSSYTSFD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 126          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 126
DIQMTQSPSS LSTSVGDRVT ITCRASEGIS NDLAWYQQKP GKSPKLLIYA ASRLQSGVPS    60
RFSGSGSGTD YTLTISSLQP EDFATYFCQQ SYKYPLTFGQ GTKLEIK                 107

SEQ ID NO: 127          moltype = AA   length = 11
FEATURE                 Location/Qualifiers
REGION                  1..11
                        note = Description of Artificial Sequence: Synthetic peptide
source                  1..11
```

```
                        mol_type = protein
                        organism = synthetic construct
SEQUENCE: 127
RASEGISNDL A                                                          11

SEQ ID NO: 128          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 128
AASRLQD                                                               7

SEQ ID NO: 129          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 129
QQSYKYPLT                                                             9

SEQ ID NO: 130          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 130
DIQMTQSPSS LSTSVGDRVT ITCRASEGIS NDLAWYQQKP GKSPKLLIYA ASRLQSGVPS      60
RFSGSGSGTD YTLTISSLQP EDFATYFCQQ SYKYPLTFGQ GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 131          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 131
EVQLQESGPG LVKPSETLSL TCTVSGFSLT SYHVSWVRQP PGKGLEWIGA IWTGGSIAYN      60
PSLKSRVTIS RDTSKNQVSL KLSSVTAADT AVYYCARDLS DYYSSYTSFD YWGQGTLVTV     120
SS                                                                   122

SEQ ID NO: 132          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 132
GFSLTSYHVS                                                            10

SEQ ID NO: 133          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 133
AIWTGGSIA                                                             9

SEQ ID NO: 134          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 134
DLSDYYSSYT SFDY                                                             14

SEQ ID NO: 135          moltype = AA  length = 452
FEATURE                 Location/Qualifiers
REGION                  1..452
                        note = Description of Artificial Sequence: Synthetic
                          polypeptide
source                  1..452
                        mol_type = protein
                        organism = synthetic construct
SEQUENCE: 135
EVQLQESGPG LVKPSETLSL TCTVSGFSLT SYHVSWVRQP PGKGLEWIGA IWTGGSIAYN   60
PSLKSRVTIS RDTSKNQVSL KLSSVTAADT AVYYCARDLS DYYSSYTSFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 136          moltype = AA  length = 107
FEATURE                 Location/Qualifiers
REGION                  1..107
                        note = Description of Artificial Sequence: Synthetic
                          polypeptide
source                  1..107
                        mol_type = protein
                        organism = synthetic construct
SEQUENCE: 136
DIQMTQSPSS LSTSVGDRVT ITCRASEGIS NDLAWYQQKP GKSPKLLIYA ASRLQDGVPS   60
RFSGSGSGTD YTLTISSLQP EDEATYFCQQ SYKYPLTFGQ GTKLEIK                107

SEQ ID NO: 137          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 137
RASEGISNDL A                                                                11

SEQ ID NO: 138          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 138
AASRLQD                                                                      7

SEQ ID NO: 139          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 139
QQSYKYPLT                                                                    9

SEQ ID NO: 140          moltype = AA  length = 214
FEATURE                 Location/Qualifiers
REGION                  1..214
                        note = Description of Artificial Sequence: Synthetic
                          polypeptide
source                  1..214
                        mol_type = protein
                        organism = synthetic construct
SEQUENCE: 140
DIQMTQSPSS LSTSVGDRVT ITCRASEGIS NDLAWYQQKP GKSPKLLIYA ASRLQDGVPS   60
RFSGSGSGTD YTLTISSLQP EDEATYFCQQ SYKYPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 141          moltype = AA  length = 120
FEATURE                 Location/Qualifiers
```

```
REGION                  1..120
                        note = Description of Artificial Sequence: Synthetic
                        polypeptide
source                  1..120
                        mol_type = protein
                        organism = synthetic construct
SEQUENCE: 141
EVQLVESGGG LVQPGSSLKL SCVASKFTFS NYGMNWIRQA PKKGLEWIAL IYYNSNNKYY    60
ADSVKGRFTI SRDNSKNTLY LEMNSLRSED TAMYYCAKSL TGGSDYFDSW GQGVMVTVSS   120

SEQ ID NO: 142          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 142
KFTFSNYGMN                                                           10

SEQ ID NO: 143          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 143
LIYYNSNNKY                                                           10

SEQ ID NO: 144          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 144
SLTGGSDYFD S                                                         11

SEQ ID NO: 145          moltype = AA  length = 444
FEATURE                 Location/Qualifiers
REGION                  1..444
                        note = Description of Artificial Sequence: Synthetic
                        polypeptide
source                  1..444
                        mol_type = protein
                        organism = synthetic construct
SEQUENCE: 145
EVQLVESGGG LVQPGSSLKL SCVASKFTFS NYGMNWIRQA PKKGLEWIAL IYYNSNNKYY    60
ADSVKGRFTI SRDNSKNTLY LEMNSLRSED TAMYYCAKSL TGGSDYFDSW GQGVMVTVSS   120
AETTAPSVYP LAPGTALKSN SMVTLGCLVK GYFPEPVTVT WNSGALSSGV HTFPAVLQSG   180
LYTLTSSVTV PSSTWPSQTV TCNVAHPASS TKVDKKIVPR NCGGDCKPCI CTGSEVSSVF   240
IFPPKPKDVL TITLTPKVTC VVVDISQDDP EVHFSWFVDD VEVHTAQTRP PEEQFNSTFR   300
SVSELPILHQ DWLNGRTFRC KVTSAAFPSP IEKTISKPEG RTQVPHVYTM SPTKEEMTQN   360
EVSITCMVKG FYPPDIYVEW QMNGQPQENY KNTPPTMDTD GSYFLYSKLN VKKEKWQQGN   420
TFTCSVLHEG LHNHHTEKSL SHSP                                         444

SEQ ID NO: 146          moltype = AA  length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 146
DVQMTQSPSY LAASPGESVS ISCKASKSIG TFLAWYQEKP EKTNKLLIYS GSTLQSGTPS    60
RFSGSGSGTD FTLTIRNLEP EDFAVYYCQQ HDEYPFTFGS GTKLEIK                 107

SEQ ID NO: 147          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 147
KASKSIGTFL A                                                         11
```

```
SEQ ID NO: 148            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 148
SGSTLQS                                                                    7

SEQ ID NO: 149            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 149
QQHDEYPFT                                                                  9

SEQ ID NO: 150            moltype = AA   length = 214
FEATURE                   Location/Qualifiers
REGION                    1..214
                          note = Description of Artificial Sequence: Synthetic
                           polypeptide
source                    1..214
                          mol_type = protein
                          organism = synthetic construct
SEQUENCE: 150
DVQMTQSPSY LAASPGESVS ISCKASKSIG TFLAWYQEKP EKTNKLLIYS GSTLQSGTPS   60
RFSGSGSGTD FTLTIRNLEP EDFAVYYCQQ HDEYPFTFGS GTKLEIKRAD AAPTVSIFPP  120
STEQLATGGA SVVCLMNNFY PRDISVKWKI DGTERRDGVL DSVTDQDSKD STYSMSSTLS  180
LTKADYESHN LYTCEVVHKT SSSPVVKSFN RNEC                              214

SEQ ID NO: 151            moltype = AA   length = 120
FEATURE                   Location/Qualifiers
REGION                    1..120
                          note = Description of Artificial Sequence: Synthetic
                           polypeptide
source                    1..120
                          mol_type = protein
                          organism = synthetic construct
SEQUENCE: 151
EVQLVESGGG LVQPGGSLRL SCAASKFTFS NYGMNWVRQA PGKGLEWVSL IYYNSNNKYY   60
ADSVKGRFTI SRDNSKNTLY LQMNSLRAED TAVYYCAKSL TGGSDYFDSW GQGTLVTVSS  120

SEQ ID NO: 152            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 152
KFTFSNYGMN                                                                10

SEQ ID NO: 153            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 153
LIYYNSNNKY                                                                10

SEQ ID NO: 154            moltype = AA   length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 154
SLTGGSDYFD S                                                              11

SEQ ID NO: 155            moltype = AA   length = 450
FEATURE                   Location/Qualifiers
```

```
REGION                        1..450
                              note = Description of Artificial Sequence: Synthetic
                                  polypeptide
source                        1..450
                              mol_type = protein
                              organism = synthetic construct
SEQUENCE: 155
EVQLVESGGG LVQPGGSLRL SCAASKFTFS NYGMNWVRQA PGKGLEWVSL IYYNSNNKYY    60
ADSVKGRFTI SRDNSKNTLY LQMNSLRAED TAVYYCAKSL TGGSDYFDSW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 156                moltype = AA   length = 107
FEATURE                       Location/Qualifiers
REGION                        1..107
                              note = Description of Artificial Sequence: Synthetic
                                  polypeptide
source                        1..107
                              mol_type = protein
                              organism = synthetic construct
SEQUENCE: 156
DIQMTQSPSS LSASVGDRVT ITCRASKSIG TFLAWYQQKP GKAPKLLIYS GSTLQSGVPS    60
RFSGSGSGTD FTLTISSLQP EDFATYYCQQ HDEYPFTFGQ GTKLEIK                107

SEQ ID NO: 157                moltype = AA   length = 11
FEATURE                       Location/Qualifiers
REGION                        1..11
                              note = Description of Artificial Sequence: Synthetic peptide
source                        1..11
                              mol_type = protein
                              organism = synthetic construct
SEQUENCE: 157
RASKSIGTFL A                                                        11

SEQ ID NO: 158                moltype = AA   length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 158
SGSTLQS                                                              7

SEQ ID NO: 159                moltype = AA   length = 9
FEATURE                       Location/Qualifiers
REGION                        1..9
                              note = Description of Artificial Sequence: Synthetic peptide
source                        1..9
                              mol_type = protein
                              organism = synthetic construct
SEQUENCE: 159
QQHDEYPFT                                                            9

SEQ ID NO: 160                moltype = AA   length = 214
FEATURE                       Location/Qualifiers
REGION                        1..214
                              note = Description of Artificial Sequence: Synthetic
                                  polypeptide
source                        1..214
                              mol_type = protein
                              organism = synthetic construct
SEQUENCE: 160
DIQMTQSPSS LSASVGDRVT ITCRASKSIG TFLAWYQQKP GKAPKLLIYS GSTLQSGVPS    60
RFSGSGSGTD FTLTISSLQP EDFATYYCQQ HDEYPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 161                moltype = AA   length = 120
FEATURE                       Location/Qualifiers
REGION                        1..120
                              note = Description of Artificial Sequence: Synthetic
                                  polypeptide
source                        1..120
                              mol_type = protein
```

```
                                organism = synthetic construct
SEQUENCE: 161
EVQLVESGGG LVQPGGSLRL SCAASKFTFS NYGMNWIRQA PGKGLEWIAL IYYNSNNKYY     60
ADSVKGRFTI SRDNSKNTLY LQMNSLRAED TAVYYCAKSL TGGSDYFDSW GQGTLVTVSS    120

SEQ ID NO: 162          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 162
KFTFSNYGMN                                                            10

SEQ ID NO: 163          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 163
LIYYNSNNKY                                                            10

SEQ ID NO: 164          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 164
SLTGGSDYFD S                                                          11

SEQ ID NO: 165          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 165
EVQLVESGGG LVQPGGSLRL SCAASKFTFS NYGMNWIRQA PGKGLEWIAL IYYNSNNKYY     60
ADSVKGRFTI SRDNSKNTLY LQMNSLRAED TAVYYCAKSL TGGSDYFDSW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 166          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 166
DIQMTQSPSS LSASVGDRVT ITCRASKSIG TFLAWYQQKP GKAPKLLIYS GSTLQSGVPS     60
RFSGSGSGTD FTLTISSLQP EDFATYYCQQ HDEYPFTFGQ GTKLEIK                  107

SEQ ID NO: 167          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 167
RASKSIGTFL A                                                          11

SEQ ID NO: 168          moltype = AA   length = 7
FEATURE                 Location/Qualifiers
REGION                  1..7
                        note = Description of Artificial Sequence: Synthetic peptide
```

```
source                    1..7
                          mol_type = protein
                          organism = synthetic construct
SEQUENCE: 168
SGSTLQS                                                                        7

SEQ ID NO: 169            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 169
QQHDEYPFT                                                                      9

SEQ ID NO: 170            moltype = AA  length = 214
FEATURE                   Location/Qualifiers
REGION                    1..214
                          note = Description of Artificial Sequence: Synthetic
                           polypeptide
source                    1..214
                          mol_type = protein
                          organism = synthetic construct
SEQUENCE: 170
DIQMTQSPSS LSASVGDRVT ITCRASKSIG TFLAWYQQKP GKAPKLLIYS GSTLQSGVPS    60
RFSGSGSGTD FTLTISSLQP EDFATYYCQQ HDEYPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 171            moltype = AA  length = 120
FEATURE                   Location/Qualifiers
REGION                    1..120
                          note = Description of Artificial Sequence: Synthetic
                           polypeptide
source                    1..120
                          mol_type = protein
                          organism = synthetic construct
SEQUENCE: 171
EVQLVESGGG LVQPGGSLRL SCAASGFTFS NYGMNWIRQA PGKGLEWIAL IYYNSNNKYY    60
ADSVKGRFTI SRDNSKNTLY LQMNSLRAED TAVYYCAKSL TGGSDYFDSW GQGTLVTVSS   120

SEQ ID NO: 172            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 172
KFTFSNYGMN                                                                    10

SEQ ID NO: 173            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 173
LIYYNSNNKY                                                                    10

SEQ ID NO: 174            moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 174
SLTGGSDYFD S                                                                  11

SEQ ID NO: 175            moltype = AA  length = 450
FEATURE                   Location/Qualifiers
REGION                    1..450
                          note = Description of Artificial Sequence: Synthetic
                           polypeptide
source                    1..450
                          mol_type = protein
```

```
                        organism = synthetic construct
SEQUENCE: 175
EVQLVESGGG LVQPGGSLRL SCAASGFTFS NYGMNWIRQA PGKGLEWIAL IYYNSNNKYY       60
ADSVKGRFTI SRDNSKNTLY LQMNSLRAED TAVYYCAKSL TGGSDYFDSW GQGTLVTVSS      120
ASTKGPSVFP LAPSSKSTSG GTAALGCLVK DYFPEPVTVS WNSGALTSGV HTFPAVLQSS      180
GLYSLSSVVT VPSSSLGTQT YICNVNHKPS NTKVDKKVEP KSCDKTHTCP PCPAPELLGG      240
PSVFLFPPKP KDTLMISRTP EVTCVVVDVS HEDPEVKFNW YVDGVEVHNA KTKPREEQYN      300
STYRVVSVLT VLHQDWLNGK EYKCKVSNKA LPAPIEKTIS KAKGQPREPQ VYTLPPSRDE      360
LTKNQVSLTC LVKGFYPSDI AVEWESNGQP ENNYKTTPPV LDSDGSFFLY SKLTVDKSRW      420
QQGNVFSCSV MHEALHNHYT QKSLSLSPGK                                      450

SEQ ID NO: 176          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 176
DIQMTQSPSS LSASVGDRVT ITCRASKSIG TFLAWYQQKP GKAPKLLIYS GSTLQSGVPS       60
RFSGSGSGTD FTLTISSLQP EDFATYYCQQ HDEYPFTFGQ GTKLEIK                   107

SEQ ID NO: 177          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 177
RASKSIGTFL A                                                           11

SEQ ID NO: 178          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 178
SGSTLQS                                                                 7

SEQ ID NO: 179          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 179
QQHDEYPFT                                                               9

SEQ ID NO: 180          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 180
DIQMTQSPSS LSASVGDRVT ITCRASKSIG TFLAWYQQKP GKAPKLLIYS GSTLQSGVPS       60
RFSGSGSGTD FTLTISSLQP EDFATYYCQQ HDEYPFTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                 214

SEQ ID NO: 181          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 181
EVQLVESGGG LVQPGSSLKL SCVASKFTFS NYGMNWIRQA PKKGLEWIAL IYYNSNNKYY       60
ADSVKGRFTI SRDNSKNTLY LEMNSLRSED TAMYYCAKSL TGGSDYFDSW GQGVMVTVSS      120
```

```
SEQ ID NO: 182            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 182
KFTFSNYGMN                                                                     10

SEQ ID NO: 183            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 183
LIYYNSNNKY                                                                     10

SEQ ID NO: 184            moltype = AA   length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 184
SLTGGSDYFD S                                                                   11

SEQ ID NO: 185            moltype = AA   length = 450
FEATURE                   Location/Qualifiers
REGION                    1..450
                          note = Description of Artificial Sequence: Synthetic
                           polypeptide
source                    1..450
                          mol_type = protein
                          organism = synthetic construct
SEQUENCE: 185
EVQLVESGGG LVQPGSSLKL SCVASKFTFS NYGMNWIRQA PKKGLEWIAL IYYNSNNKYY   60
ADSVKGRFTI SRDNSKNTLY LEMNSLRSED TAMYYCAKSL TGGSDYFDSW GQGVMVTVSS  120
AKTTAPSVYP LAPVCGDTTG SSVTLGCLVK GYFPEPVTLT WNSGSLSSGV HTFPAVLQSD  180
LYTLSSSVTV TSSTWPSQSI TCNVAHPASS TKVDKKIEPR GPTIKPCPPC KCPAPNLLGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LPAPIERTIS KPKGSVRAPQ VYVLPPPEEE  360
MTKKQVTLTC MVTDFMPEDI YVEWTNNGKT ELNYKNTEPV LDSDGSYFMY SKLRVEKKNW  420
VERNSYSCSV VHEGLHNHHT TKSFSRTPGK                                   450

SEQ ID NO: 186            moltype = AA   length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 186
DVQMTQSPSY LAASPGESVS ISCKASKSIG TFLAWYQEKP EKTNKLLIYS GSTLQSGTPS   60
RFSGSGSGTD FTLTIRNLEP EDFAVYYCQQ HDEYPFTFGS GTKLEIK                 107

SEQ ID NO: 187            moltype = AA   length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 187
KASKSIGTFL A                                                                   11

SEQ ID NO: 188            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 188
SGSTLQS                                                                         7
```

```
SEQ ID NO: 189          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 189
QQHDEYPFT                                                                   9

SEQ ID NO: 190          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 190
DVQMTQSPSY LAASPGESVS ISCKASKSIG TFLAWYQEKP EKTNKLLIYS GSTLQSGTPS        60
RFSGSGSGTD FTLTIRNLEP EDFAVYYCQQ HDEYPFTFGS GTKLEIKRAD AAPTVSIFPP        120
SSEQLTSGGA SVVCFLNNFY PKDINVKWKI DGSERQNGVL NSWTDQDSKD STYSMSSTLT        180
LTKDEYERHN SYTCEATHKT STSPIVKSFN RNEC                                    214

SEQ ID NO: 191          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 191
EVQLVESGGG LVQPGSSLKL SCVASKFTFS NYGMNWIRQA PKKGLEWIAL IYYNSNNKYY        60
ADSVKGRFTI SRDNSKNTLY LEMNSLRSED TAMYYCAKSL TGGSDYFDSW GQGVMVTVSS        120

SEQ ID NO: 192          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 192
KFTFSNYGMN                                                                  10

SEQ ID NO: 193          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 193
LIYYNSNNKY                                                                  10

SEQ ID NO: 194          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 194
SLTGGSDYFD S                                                                11

SEQ ID NO: 195          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 195
EVQLVESGGG LVQPGSSLKL SCVASKFTFS NYGMNWIRQA PKKGLEWIAL IYYNSNNKYY        60
ADSVKGRFTI SRDNSKNTLY LEMNSLRSED TAMYYCAKSL TGGSDYFDSW GQGVMVTVSS        120
AKTTAPSVYP LAPVCGDTTG SSVTLGCLVK GYFPEPVTLT WNSGSLSSGV HTFPAVLQSD        180
```

```
LYTLSSSVTV TSSTWPSQSI TCNVAHPASS TKVDKKIEPR GPTIKPCPPC KCPAPNLLGG    240
PSVFIFPPKI KDVLMISLSP IVTCVVVDVS EDDPDVQISW FVNNVEVHTA QTQTHREDYN    300
STLRVVSALP IQHQDWMSGK EFKCKVNNKD LPAPIERTIS KPKGSVRAPQ VYVLPPPEEE    360
MTKKQVTLTC MVTDFMPEDI YVEWTNNGKT ELNYKNTEPV LDSDGSYFMY SKLRVEKKNW    420
VERNSYSCSV VHEGLHNHHT TKSFSRTPGK                                    450

SEQ ID NO: 196          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 196
DVQMTQSPSY LAASPGESVS ISCKASKSIG TFLAWYQEKP EKTNKLLIYS GSTLQSGTPS     60
RFSGSGSGTD FTLTIRNLEP EDFAVYYCQQ HDEYPFTFGS GTKLEIK                 107

SEQ ID NO: 197          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 197
KASKSIGTFL A                                                         11

SEQ ID NO: 198          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 198
SGSTLQS                                                               7

SEQ ID NO: 199          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 199
QQHDEYPFT                                                             9

SEQ ID NO: 200          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 200
DVQMTQSPSY LAASPGESVS ISCKASKSIG TFLAWYQEKP EKTNKLLIYS GSTLQSGTPS     60
RFSGSGSGTD FTLTIRNLEP EDFAVYYCQQ HDEYPFTFGS GTKLEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                               214

SEQ ID NO: 201          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 201
EVQLVESGGG LVQPGSSLKL SCVASKFTFS NYGMNWIRQA PKKGLEWIAL IYYNSNNKYY     60
ADSVKGRFTI SRDNSKNTLY LEMNSLRSED TAMYYCAKSL TGGSDYFDSW GQGVMVTVSS    120

SEQ ID NO: 202          moltype = AA  length = 10
FEATURE                 Location/Qualifiers
REGION                  1..10
                        note = Description of Artificial Sequence: Synthetic peptide
source                  1..10
```

```
                        mol_type = protein
                        organism = synthetic construct
SEQUENCE: 202
KFTFSNYGMN                                                                  10

SEQ ID NO: 203          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 203
LIYYNSNNKY                                                                  10

SEQ ID NO: 204          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 204
SLTGGSDYFD S                                                                11

SEQ ID NO: 205          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 205
EVQLVESGGG LVQPGSSLKL SCVASKFTFS NYGMNWIRQA PKKGLEWIAL IYYNSNNKYY           60
ADSVKGRFTI SRDNSKNTLY LEMNSLRSED TAMYYCAKSL TGGSDYFDSW GQGVMVTVSS          120
AKTTAPSVYP LAPVCGDTTG SSVTLGCLVK GYFPEPVTLT WNSGSLSSGV HTFPAVLQSD          180
LYTLSSSVTV TSSTWPSQSI TCNVAHPASS TKVDKKIEPR GPTIKPCPPC KCPAPNLLGG          240
PSVFIFPPKI KDVLMISLSP IVTCVVVDVS EDDPDVQISW FVNNVEVHTA QTQTHREDYN          300
STLRVVSALP IQHQDWMSGK EFKCKVNNKD LPAPIERTIS KPKGSVRAPQ VYVLPPPEEE          360
MTKKQVTLTC MVTDFMPEDI YVEWTNNGKT ELNYKNTEPV LDSDGSYFMY SKLRVEKKNW          420
VERNSYSCSV VHEGLHNHHT TKSFSRTPGK                                          450

SEQ ID NO: 206          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 206
DVQMTQSPSY LAASPGESVS ISCKASKSIG TFLAWYQEKP EKTNKLLIYS GSTLQSGTPS           60
RFSGSGSGTD FTLTIRNLEP EDFAVYYCQQ HDEYPFTFGS GTKLEIK                        107

SEQ ID NO: 207          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 207
KASKSIGTFL A                                                                11

SEQ ID NO: 208          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 208
SGSTLQS                                                                     7

SEQ ID NO: 209          moltype = AA   length = 9
FEATURE                 Location/Qualifiers
REGION                  1..9
                        note = Description of Artificial Sequence: Synthetic peptide
```

```
source                  1..9
                        mol_type = protein
                        organism = synthetic construct
SEQUENCE: 209
QQHDEYPFT                                                                  9

SEQ ID NO: 210          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 210
DVQMTQSPSY LAASPGESVS ISCKASKSIG TFLAWYQEKP EKTNKLLIYS GSTLQSGTPS   60
RFSGSGSGTD FTLTIRNLEP EDFAVYYCQQ HDEYPFTFGS GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 211          moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 211
EVQLVESGGG LVQPGGSLRL SCAASKFTFS NYGMNWIRQA PGKGLEWIAL IYYNSNNKYY   60
ADSVKGRFTI SRDNSKNTLY LQMNSLRAED TAVYYCAKSL TGGSDYFDSW GQGTLVTVSS  120

SEQ ID NO: 212          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 212
KFTFSNYGMN                                                                10

SEQ ID NO: 213          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 213
LIYYNSNNKY                                                                10

SEQ ID NO: 214          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 214
SLTGGSDYFD S                                                              11

SEQ ID NO: 215          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 215
EVQLVESGGG LVQPGGSLRL SCAASKFTFS NYGMNWIRQA PGKGLEWIAL IYYNSNNKYY   60
ADSVKGRFTI SRDNSKNTLY LQMNSLRAED TAVYYCAKSL TGGSDYFDSW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450
```

```
SEQ ID NO: 216          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 216
DIQMTQSPSS LSASVGDRVT ITCRASKSIG TFLAWYQQKP GKAPKLLIYS GSTLESGVPS   60
RFSGSGSGTD FTLTISSLQP EDFATYYCQQ HDEYPFTFGQ GTKLEIK                107

SEQ ID NO: 217          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 217
KASKSIGTFL A                                                       11

SEQ ID NO: 218          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 218
SGSTLQS                                                            7

SEQ ID NO: 219          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 219
QQHDEYPFT                                                          9

SEQ ID NO: 220          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 220
DIQMTQSPSS LSASVGDRVT ITCRASKSIG TFLAWYQQKP GKAPKLLIYS GSTLESGVPS   60
RFSGSGSGTD FTLTISSLQP EDFATYYCQQ HDEYPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 221          moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 221
EVQLVESGGG LVQPGGSLRL SCAASKFTFS NYGMNWIRQA PGKGLEWIAL IYYNSNNKYY   60
ADSVKGRFTI SRDNSKNTLY LQMNSLRAED TAVYYCAKSL TGGSDYFDSW GQGTLVTVSS  120

SEQ ID NO: 222          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 222
KFTFSNYGMN                                                         10
```

```
SEQ ID NO: 223          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 223
LIYYNSNNKY                                                                        10

SEQ ID NO: 224          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 224
SLTGGSDYFD S                                                                      11

SEQ ID NO: 225          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 225
EVQLVESGGG LVQPGGSLRL SCAASKFTFS NYGMNWIRQA PGKGLEWIAL IYYNSNNKYY    60
ADSVKGRFTI SRDNSKNTLY LQMNSLRAED TAVYYCAKSL TGGSDYFDSW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 226          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 226
DIQMTQSPSS LSASVGDRVT ITCRASKSIG TFLAWYQQKP GKAPKLLIYD ASSLESGVPS    60
RFSGSGSGTD FTLTISSLQP EDFATYYCQQ HDEYPFTFGQ GTKLEIK                 107

SEQ ID NO: 227          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 227
KASKSIGTFL A                                                                      11

SEQ ID NO: 228          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 228
SGSTLQS                                                                            7

SEQ ID NO: 229          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 229
QQHDEYPFT                                                                          9
```

```
SEQ ID NO: 230          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 230
DIQMTQSPSS LSASVGDRVT ITCRASKSIG TFLAWYQQKP GKAPKLLIYD ASSLESGVPS    60
RFSGSGSGTD FTLTISSLQP EDFATYYCQQ HDEYPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 231          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 231
QIQLVQSGPE LKKPGESVKI SCKASGYTFT DYAVNWVKQA PGNGLKWMGW INTQTGKPTY    60
ADDFKQRFVF SLETSASTSF LQINNLNIED TATYFCTRDS YYYSSSLDYW GQGVMVTVSS   120

SEQ ID NO: 232          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 232
GYTFTDYAVN                                                           10

SEQ ID NO: 233          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 233
WINTQTGKPT                                                           10

SEQ ID NO: 234          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 234
DSYYYSSSLD Y                                                         11

SEQ ID NO: 235          moltype = AA  length = 440
FEATURE                 Location/Qualifiers
REGION                  1..440
                        note = Description of Artificial Sequence: Synthetic
                         polypeptide
source                  1..440
                        mol_type = protein
                        organism = synthetic construct
SEQUENCE: 235
QIQLVQSGPE LKKPGESVKI SCKASGYTFT DYAVNWVKQA PGNGLKWMGW INTQTGKPTY    60
ADDFKQRFVF SLETSASTSF LQINNLNIED TATYFCTRDS YYYSSSLDYW GQGVMVTVSS   120
AETTAPSVYP LAPGTALKSN SMVTLGCLVK GYFPEPVTVT WNSGALSSGV HTFPAVLQSG   180
LYTLTSSVTV PSSTWSSQAV TCNVAHPASS TKVDKKIVPR ECNPCGCTGS EVSSVFIFPP   240
KTKDVLTITL TPKVTCVVVD ISQNDPEVRF SWFIDDVEVH TAQTHAPEKQ SNSTLRSVSE   300
LPIVHRDWLN GKTFKCKVNS GAFPAPIEKS ISKPEGTPRG PQVYTMAPPK EEMTQSQVSI   360
TCMVKGFYPP DIYTEWKMNG QPQENYKNTP PTMDTDGSYF LYSKLNVKKE TWQQGNTFTC   420
SVLHEGLHNH HTEKSLSHSP                                               440

SEQ ID NO: 236          moltype = AA  length = 107
FEATURE                 Location/Qualifiers
REGION                  1..107
                        note = Description of Artificial Sequence: Synthetic
```

```
                              polypeptide
source                        1..107
                              mol_type = protein
                              organism = synthetic construct
SEQUENCE: 236
DIQMTQSPAS LSASLGETVS IECLASAGIS NDLAWYQQKS GKSPQLLIYA ASRLQDGVPS    60
RFSGSGSGTR FSLKISDMQP EDEADYFCQQ SYKYPWTFGG GTKLELK                 107

SEQ ID NO: 237               moltype = AA  length = 11
FEATURE                      Location/Qualifiers
REGION                       1..11
                             note = Description of Artificial Sequence: Synthetic peptide
source                       1..11
                             mol_type = protein
                             organism = synthetic construct
SEQUENCE: 237
LASAGISNDL A                                                        11

SEQ ID NO: 238               moltype = AA  length = 7
FEATURE                      Location/Qualifiers
REGION                       1..7
                             note = Description of Artificial Sequence: Synthetic peptide
source                       1..7
                             mol_type = protein
                             organism = synthetic construct
SEQUENCE: 238
AASRLQD                                                             7

SEQ ID NO: 239               moltype = AA  length = 9
FEATURE                      Location/Qualifiers
REGION                       1..9
                             note = Description of Artificial Sequence: Synthetic peptide
source                       1..9
                             mol_type = protein
                             organism = synthetic construct
SEQUENCE: 239
QQSYKYPWT                                                           9

SEQ ID NO: 240               moltype = AA  length = 214
FEATURE                      Location/Qualifiers
REGION                       1..214
                             note = Description of Artificial Sequence: Synthetic
                              polypeptide
source                       1..214
                             mol_type = protein
                             organism = synthetic construct
SEQUENCE: 240
DIQMTQSPAS LSASLGETVS IECLASAGIS NDLAWYQQKS GKSPQLLIYA ASRLQDGVPS    60
RFSGSGSGTR FSLKISDMQP EDEADYFCQQ SYKYPWTFGG GTKLELKRAD AAPTVSIFPP   120
STEQLATGGA SVVCLMNNFY PRDISVKWKI DGTERRDGVL DSVTDQDSKD STYSMSSTLS   180
LTKADYESHN LYTCEVVHKT SSSPVVKSFN RNEC                               214

SEQ ID NO: 241               moltype = AA  length = 120
FEATURE                      Location/Qualifiers
REGION                       1..120
                             note = Description of Artificial Sequence: Synthetic
                              polypeptide
source                       1..120
                             mol_type = protein
                             organism = synthetic construct
SEQUENCE: 241
QIQLVQSGPE LKKPGESVKI SCKASGYTFT DYAVNWVKQA PGNGLKWMGW INTQTGKPTY    60
ADDFKQRFVF SLETSASTSF LQINNLNIED TATYFCTRDS YYYSSSLDYW GQGVMVTVSS   120

SEQ ID NO: 242               moltype = AA  length = 10
FEATURE                      Location/Qualifiers
REGION                       1..10
                             note = Description of Artificial Sequence: Synthetic peptide
source                       1..10
                             mol_type = protein
                             organism = synthetic construct
SEQUENCE: 242
GYTFTDYAVN                                                          10

SEQ ID NO: 243               moltype = AA  length = 10
FEATURE                      Location/Qualifiers
REGION                       1..10
                             note = Description of Artificial Sequence: Synthetic peptide
source                       1..10
```

```
                        mol_type = protein
                        organism = synthetic construct
SEQUENCE: 243
WINTQTGKPT                                                             10

SEQ ID NO: 244          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 244
DSYYYSSSLD Y                                                           11

SEQ ID NO: 245          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 245
QIQLVQSGPE LKKPGESVKI SCKASGYTFT DYAVNWVKQA PGNGLKWMGW INTQTGKPTY       60
ADDFKQRFVF SLETSASTSF LQINNLNIED TATYFCTRDS YYYSSSLDYW GQGVMTVSS       120
ASTKGPSVFP LAPSSKSTSG GTAALGCLVK DYFPEPVTVS WNSGALTSGV HTFPAVLQSS      180
GLYSLSSVVT VPSSSLGTQT YICNVNHKPS NTKVDKKVEP KSCDKTHTCP PCPAPELLGG      240
PSVFLFPPKP KDTLMISRTP EVTCVVVDVS HEDPEVKFNW YVDGVEVHNA KTKPREEQYN      300
STYRVVSVLT VLHQDWLNGK EYKCKVSNKA LPAPIEKTIS KAKGQPREPQ VYTLPPSRDE      360
LTKNQVSLTC LVKGFYPSDI AVEWESNGQP ENNYKTTPPV LDSDGSFFLY SKLTVDKSRW      420
QQGNVFSCSV MHEALHNHYT QKSLSLSPGK                                      450

SEQ ID NO: 246          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 246
DIQMTQSPAS LSASLGETVS IECLASAGIS NDLAWYQQKS GKSPQLLIYA ASRLQDGVPS       60
RFSGSGSGTR FSLKISDMQP EDEADYFCQQ SYKYPWTFGG GTKLELK                   107

SEQ ID NO: 247          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 247
LASAGISNDL A                                                           11

SEQ ID NO: 248          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 248
AASRLQD                                                                 7

SEQ ID NO: 249          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 249
QQSYKYPWT                                                               9

SEQ ID NO: 250          moltype = AA  length = 214
FEATURE                 Location/Qualifiers
REGION                  1..214
                        note = Description of Artificial Sequence: Synthetic
```

```
                         polypeptide
source                   1..214
                         mol_type = protein
                         organism = synthetic construct
SEQUENCE: 250
DIQMTQSPAS LSASLGETVS IECLASAGIS NDLAWYQQKS GKSPQLLIYA ASRLQDGVPS    60
RFSGSGSGTR FSLKISDMQP EDEADYFCQQ SYKYPWTFGG GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 251           moltype = AA   length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 251
QVNLLQSRAA LVKPGASVKL SCKASGYTFT DYYLHWVKQS HAKSLEWIGY INPNNAYTSY    60
NEKFKSKATL TVDKSTNTAY MELSRLTSAD SATYYCARDT TDYYNLHFAY WGQGTLVTVS   120
S                                                                   121

SEQ ID NO: 252           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 252
GYTFTDYYLH                                                           10

SEQ ID NO: 253           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 253
YINPNNAYTS                                                           10

SEQ ID NO: 254           moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 254
DTTDYYNLHF AY                                                        12

SEQ ID NO: 255           moltype = AA   length = 441
FEATURE                  Location/Qualifiers
REGION                   1..441
                         note = Description of Artificial Sequence: Synthetic
                          polypeptide
source                   1..441
                         mol_type = protein
                         organism = synthetic construct
SEQUENCE: 255
QVNLLQSRAA LVKPGASVKL SCKASGYTFT DYYLHWVKQS HAKSLEWIGY INPNNAYTSY    60
NEKFKSKATL TVDKSTNTAY MELSRLTSAD SATYYCARDT TDYYNLHFAY WGQGTLVTVS   120
SAETTAPSVY PLAPGTALKS NSMVTLGCLV KGYFPEPVTV TWNSGALSSG VHTFPAVLQS   180
GLYTLTSSVT VPSSTWSSQA VTCNVAHPAS STKVDKKIVP RECNPCGCTG SEVSSVFIFP   240
PKTKDVLTIT LTPKVTCVVV DISQNDPEVR FSWFIDDVEV HTAQTHAPEK QSNSTLRSVS   300
ELPIVHRDWL NGKTFKCKVN SGAFPAPIEK SISKPEGTPR GPQVYTMAPP KEEMTQSQVS   360
ITCMVKGFYP PDIYTEWKMN GQPQENYKNT PPTMDTDGSY FLYSKLNVKK ETWQQGNTFT   420
CSVLHEGLHN HHTEKSLSHS P                                             441

SEQ ID NO: 256           moltype = AA   length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
```

```
SEQUENCE: 256
DIQMTQSPAS LSASLGETVS IECLTSEGIS NDLAWYQQKS GKSPQLLIYD ASRLEDGVPS    60
RFSGSGSGTR YSLKISGMQT EDEADYFCQQ SYKYPLTFGS GTKLEIK                 107

SEQ ID NO: 257          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 257
LTSEGISNDL A                                                         11

SEQ ID NO: 258          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 258
DASRLED                                                              7

SEQ ID NO: 259          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 259
QQSYKYPLT                                                            9

SEQ ID NO: 260          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 260
DIQMTQSPAS LSASLGETVS IECLTSEGIS NDLAWYQQKS GKSPQLLIYD ASRLEDGVPS    60
RFSGSGSGTR YSLKISGMQT EDEADYFCQQ SYKYPLTFGS GTKLEIKRAD AAPTVSIFPP   120
STEQLATGGA SVVCLMNNFY PRDISVKWKI DGTERRDGVL DSVTDQDSKD STYSMSSTLS   180
LTKADYESHN LYTCEVVHKT SSSPVVKSFN RNEC                               214

SEQ ID NO: 261          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 261
QVNLLQSRAA LVKPGASVKL SCKASGYTFT DYYLHWVKQS HAKSLEWIGY INPNNAYTSY    60
NEKFKSKATL TVDKSTNTAY MELSRLTSAD SATYYCARDT TDYYNLHFAY WGQGTLVTVS   120
S                                                                   121

SEQ ID NO: 262          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 262
GYTFTDYYLH                                                           10

SEQ ID NO: 263          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 263
```

```
YINPNNAYTS                                                                  10

SEQ ID NO: 264          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 264
DTTDYYNLHF AY                                                               12

SEQ ID NO: 265          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 265
QVNLLQSRAA LVKPGASVKL SCKASGYTFT DYYLHWVKQS HAKSLEWIGY INPNNAYTSY           60
NEKFKSKATL TVDKSTNTAY MELSRLTSAD SATYYCARDT TDYYNLHFAY WGQGTLVTVS           120
SASTKGPSVF PLAPSSKSTS GGTAALGCLV KDYFPEPVTV SWNSGALTSG VHTFPAVLQS           180
SGLYSLSSVV TVPSSSLGTQ TYICNVNHKP SNTKVDKKVE PKSCDKTHTC PPCPAPELLG           240
GPSVFLFPPK PKDTLMISRT PEVTCVVVDV SHEDPEVKFN WYVDGVEVHN AKTKPREEQY           300
NSTYRVVSVL TVLHQDWLNG KEYKCKVSNK ALPAPIEKTI SKAKGQPREP QVYTLPPSRD           360
ELTKNQVSLT CLVKGFYPSD IAVEWESNGQ PENNYKTTPP VLDSDGSFFL YSKLTVDKSR           420
WQQGNVFSCS VMHEALHNHY TQKSLSLSPG K                                          451

SEQ ID NO: 266          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 266
DIQMTQSPAS LSASLGETVS IECLTSEGIS NDLAWYQQKS GKSPQLLIYD ASRLEDGVPS           60
RFSGSGSGTR YSLKISGMQT EDEADYFCQQ SYKYPLTFGS GTKLEIK                         107

SEQ ID NO: 267          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 267
LTSEGISNDL A                                                                11

SEQ ID NO: 268          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 268
DASRLED                                                                     7

SEQ ID NO: 269          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 269
QQSYKYPLT                                                                   9

SEQ ID NO: 270          moltype = AA  length = 214
FEATURE                 Location/Qualifiers
REGION                  1..214
                        note = Description of Artificial Sequence: Synthetic
                         polypeptide
source                  1..214
                        mol_type = protein
```

-continued

```
                            organism = synthetic construct
SEQUENCE: 270
DIQMTQSPAS LSASLGETVS IECLTSEGIS NDLAWYQQKS GKSPQLLIYD ASRLEDGVPS    60
RFSGSGSGTR YSLKISGMQT EDEADYFCQQ SYKYPLTFGS GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 271          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 271
EVQLVESGGG LVKPGASLKL SCVASGFTFS DYWMNWVRQT PGKTMEWIGD IKDDGSYTNY    60
TPSLKNRFTI SRDNAKSTLY LQMNNVRSED TGTYYCTSGG VFDYWGQGVM VTVSS        115

SEQ ID NO: 272          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 272
GFTFSDYW                                                              8

SEQ ID NO: 273          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 273
IKDDGSYT                                                              8

SEQ ID NO: 274          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 274
TSGGVFDY                                                              8

SEQ ID NO: 275          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 275
EVQLVESGGG LVKPGASLKL SCVASGFTFS DYWMNWVRQT PGKTMEWIGD IKDDGSYTNY    60
TPSLKNRFTI SRDNAKSTLY LQMNNVRSED TGTYYCTSGG VFDYWGQGVM VTVSSAKTTA   120
PSVYPLAPVC GDTTGSSVTL GCLVKGYFPE PVTLTWNSGS LSSGVHTFPA VLQSDLYTLS   180
SSVTVTSSTW PSQSITCNVA HPASSTKVDK KIEPRGPTIK PCPPCKCPAP NLLGGPSVFI   240
FPPKIKDVLM ISLSPIVTCV VVDVSEDDPD VQISWFVNNV EVHTAQTQTH REDYNSTLRV   300
VSALPIQHQD WMSGKEFKCK VNNKDLPAPI ERTISKPKGS VRAPQVYVLP PPEEEMTKKQ   360
VTLTCMVTDF MPEDIYVEWT NNGKTELNYK NTEPVLDSDG SYFMYSKLRV EKKNWVERNS   420
YSCSVVHEGL HNHHTTKSFS RTPGK                                         445

SEQ ID NO: 276          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 276
EIVLTQSPTT MAASPGEMVT ITCRASSSVN YMHWFQQKSG TSPKPWIYDT SKLASGVPDR    60
FSGSGSGTSY SLTISSMEAE DAASYYCLQR STFPPTFGAG TKLELK                  106
```

```
SEQ ID NO: 277            moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 277
SSVNY                                                                      5

SEQ ID NO: 278            moltype =   length =
SEQUENCE: 278
000

SEQ ID NO: 279            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 279
LQRSTFPPT                                                                  9

SEQ ID NO: 280            moltype = AA   length = 213
FEATURE                   Location/Qualifiers
REGION                    1..213
                          note = Description of Artificial Sequence: Synthetic
                           polypeptide
source                    1..213
                          mol_type = protein
                          organism = synthetic construct
SEQUENCE: 280
EIVLTQSPTT MAASPGEMVT ITCRASSSVN YMHWFQQKSG TSPKPWIYDT SKLASGVPDR  60
FSGSGSGTSY SLTISSMEAE DAASYYCLQR STFPPTFGAG TKLELKRADA APTVSIFPPS 120
SEQLTSGGAS VVCFLNNFYP KDINVKWKID GSERQNGVLN SWTDQDSKDS TYSMSSTLTL 180
TKDEYERHNS YTCEATHKTS TSPIVKSFNR NEC                              213

SEQ ID NO: 281            moltype = AA   length = 115
FEATURE                   Location/Qualifiers
REGION                    1..115
                          note = Description of Artificial Sequence: Synthetic
                           polypeptide
source                    1..115
                          mol_type = protein
                          organism = synthetic construct
SEQUENCE: 281
QVRLVQSGTA LVRPGASVRM SCTASGYSFT DYWVSWVKQS HGQSLEWIGE IYPNSGTTNF  60
NEKFEGKATL TVDKSTSTAY MELSRLTSED SAIYYCTGEG TFDYWGQGVM VTVSS      115

SEQ ID NO: 282            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 282
GYSFTDYW                                                                   8

SEQ ID NO: 283            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 283
IYPNSGTT                                                                   8

SEQ ID NO: 284            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 284
TGEGTFDY                                                                   8
```

```
SEQ ID NO: 285         moltype = AA   length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 285
QVRLVQSGTA LVRPGASVRM SCTASGYSFT DYWVSWVKQS HGQSLEWIGE IYPNSGTTNF    60
NEKFEGKATL TVDKSTSTAY MELSRLTSED SAIYYCTGEG TFDYWGQGVM VTVSSAKTTA   120
PSVYPLAPVC GDTTGSSVTL GCLVKGYFPE PVTLTWNSGS LSSGVHTFPA VLQSDLYTLS   180
SSVTVTSSTW PSQSITCNVA HPASSTKVDK KIEPRGPTIK PCPPCKCPAP NLLGGPSVFI   240
FPPKIKDVLM ISLSPIVTCV VVDVSEDDPD VQISWFVNNV EVHTAQTQTH REDYNSTLRV   300
VSALPIQHQD WMSGKEFKCK VNNKDLPAPI ERTISKPKGS VRAPQVYVLP PPEEEMTKKQ   360
VTLTCMVTDF MPEDIYVEWT NNGKTELNYK NTEPVLDSDG SYFMYSKLRV EKKNWVERNS   420
YSCSVVHEGL HNHHTTKSFS RTPGK                                        445

SEQ ID NO: 286         moltype = AA   length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 286
EIVLTQSPTT MAASPGEKVT ITCRPSSSLS NMHWFQQKSG TSPKPWIYDT SKLASGVPDR    60
FSGSGSGTSY SLTISSMEAE DAATYYCLQR SSYPPTFGAG TKLELK                 106

SEQ ID NO: 287         moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 287
SSLSN                                                                5

SEQ ID NO: 288         moltype =      length =
SEQUENCE: 288
000

SEQ ID NO: 289         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 289
LQRSSYPPT                                                            9

SEQ ID NO: 290         moltype = AA   length = 213
FEATURE                Location/Qualifiers
REGION                 1..213
                       note = Description of Artificial Sequence: Synthetic
                        polypeptide
source                 1..213
                       mol_type = protein
                       organism = synthetic construct
SEQUENCE: 290
EIVLTQSPTT MAASPGEKVT ITCRPSSSLS NMHWFQQKSG TSPKPWIYDT SKLASGVPDR    60
FSGSGSGTSY SLTISSMEAE DAATYYCLQR SSYPPTFGAG TKLELKRADA APTVSIFPPS   120
SEQLTSGGAS VVCFLNNFYP KDINVKWKID GSERQNGVLN SWTDQDSKDS TYSMSSTLTL   180
TKDEYERHNS YTCEATHKTS TSPIVKSFNR NEC                                213

SEQ ID NO: 291         moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 291
EVQLVESGGG LVKPGASLKL SCVASGFTFS DDWMNWVRQT PGKAMEWIGD IKYDGSYTNY    60
```

```
VPSLKNRLTI SRDNAKNTLY LQMTNVRSED TATYYCTSGG VFDYWGQGVM VTVSS            115

SEQ ID NO: 292          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 292
GFTFSDDW                                                                 8

SEQ ID NO: 293          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 293
IKYDGSYT                                                                 8

SEQ ID NO: 294          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 294
TSGGVFDY                                                                 8

SEQ ID NO: 295          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 295
EVQLVESGGG LVKPGASLKL SCVASGFTFS DDWMNWVRQT PGKAMEWIGD IKYDGSYTNY         60
VPSLKNRLTI SRDNAKNTLY LQMTNVRSED TATYYCTSGG VFDYWGQGVM VTVSSAKTTA        120
PSVYPLAPVC GDTTGSSVTL GCLVKGYFPE PVTLTWNSGS LSSGVHTFPA VLQSDLYTLS        180
SSVTVTSSTW PSQSITCNVA HPASSTKVDK KIEPRGPTIK PCPPCKCPAP NLLGGPSVFI        240
FPPKIKDVLM ISLSPIVTCV VVDVSEDDPD VQISWFVNNV EVHTAQTQTH REDYNSTLRV        300
VSALPIQHQD WMSGKEFKCK VNNKDLPAPI ERTISKPKGS VRAPQVYVLP PPEEEMTKKQ        360
VTLTCMVTDF MPEDIYVEWT NNGKTELNYK NTEPVLDSDG SYFMYSKLRV EKKNWVERNS        420
YSCSVVHEGL HNHHTTKSFS RTPGK                                             445

SEQ ID NO: 296          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 296
EIVLSQSPTT MAASPGEKVT ITCRASSSVS YMHWFQQKSG TSPKPWIYDT SKLASGVPDR         60
FSGSGSGTSY SLTISSMEAE DAATYYCLQR SGYPPTFGAG TKLEVK                      106

SEQ ID NO: 297          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 297
SSVSY                                                                    5

SEQ ID NO: 298          moltype =     length =
SEQUENCE: 298
000

SEQ ID NO: 299          moltype = AA  length = 9
FEATURE                 Location/Qualifiers
REGION                  1..9
```

```
                        note = Description of Artificial Sequence: Synthetic peptide
source                  1..9
                        mol_type = protein
                        organism = synthetic construct
SEQUENCE: 299
LQRSGYPPT                                                                          9

SEQ ID NO: 300          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 300
EIVLSQSPTT MAASPGEKVT ITCRASSSVS YMHWFQQKSG TSPKPWIYDT SKLASGVPDR   60
FSGSGSGTSY SLTISSMEAE DAATYYCLQR SGYPPTFGAG TKLEVKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 301          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 301
EVQLVESGGG LVQPGRSLKF SCSASGFTFS AYSMAWVRQA PKTGLEWVAT IIYDGSSTYY   60
RDSVKGRFTI SRDNAKNTLY LQMDSLRSED TATYYCARLG YSGHYFDYWG QGVMVTVSS   119

SEQ ID NO: 302          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 302
GFTFSAYS                                                                           8

SEQ ID NO: 303          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 303
IIYDGSST                                                                           8

SEQ ID NO: 304          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 304
ARLGYSGHYF DY                                                                     12

SEQ ID NO: 305          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 305
EVQLVESGGG LVQPGRSLKF SCSASGFTFS AYSMAWVRQA PKTGLEWVAT IIYDGSSTYY   60
RDSVKGRFTI SRDNAKNTLY LQMDSLRSED TATYYCARLG YSGHYFDYWG QGVMVTVSSA  120
KTTAPSVYPL APVCGDTTGS SVTLGCLVKG YFPEPVTLTW NSGSLSSGVH TFPAVLQSDL  180
YTLSSSVTVT SSTWPSQSIT CNVAHPASST KVDKKIEPRG PTIKPCPPCK CPAPNLLGGP  240
SVFIFPPKIK DVLMISLSPI VTCVVVDVSE DDPDVQISWF VNNVEVHTAQ TQTHREDYNS  300
TLRVVSALPI QHQDWMSGKE FKCKVNNKDL PAPIERTISK PKGSVRAPQV YVLPPPEEEM  360
TKKQVTLTCM VTDFMPEDIY VEWTNNGKTE LNYKNTEPVL DSDGSYFMYS KLRVEKKNWV  420
```

```
ERNSYSCSVV HEGLHNHHTT KSFSRTPGK                                              449

SEQ ID NO: 306          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 306
DTVLTQSPAL AVSLGQRVTI SCQASESVSS SLHSYLHWYQ QKPGQQPKLL IYRASNLESG   60
VPARFSGSGS GTDFTLNIDP VEADDIATYF CQQSWNDPRT FGGGTKLELK             110

SEQ ID NO: 307          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 307
ESVSSSLHSY                                                         10

SEQ ID NO: 308          moltype =   length =
SEQUENCE: 308
000

SEQ ID NO: 309          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 309
QQSWNDPRT                                                          9

SEQ ID NO: 310          moltype = AA  length = 217
FEATURE                 Location/Qualifiers
REGION                  1..217
                        note = Description of Artificial Sequence: Synthetic
                         polypeptide
source                  1..217
                        mol_type = protein
                        organism = synthetic construct
SEQUENCE: 310
DTVLTQSPAL AVSLGQRVTI SCQASESVSS SLHSYLHWYQ QKPGQQPKLL IYRASNLESG   60
VPARFSGSGS GTDFTLNIDP VEADDIATYF CQQSWNDPRT FGGGTKLELK RADAAPTVSI   120
FPPSSEQLTS GGASVVCFLN NFYPKDINVK WKIDGSERQN GVLNSWTDQD SKDSTYSMSS   180
TLTLTKDEYE RHNSYTCEAT HKTSTSPIVK SFNRNEC                           217

SEQ ID NO: 311          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 311
VQLVQSGAEV KKPGASVKVS CKASGYTFTD YAVNWVRQAP GQGLEWMGWI NTQTGKPTYA   60
QKFQGRVTMT RDTSTSTVYM ELSSLRSEDT AVYYCARDSY YSSSLDYWG QGTLVTVSS    119

SEQ ID NO: 312          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 312
GYTFTDYAVN                                                         10

SEQ ID NO: 313          moltype = AA  length = 10
FEATURE                 Location/Qualifiers
REGION                  1..10
                        note = Description of Artificial Sequence: Synthetic peptide
source                  1..10
```

```
                        mol_type = protein
                        organism = synthetic construct
SEQUENCE: 313
WINTQTGKPT                                                              10

SEQ ID NO: 314          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 314
DSYYYSSSLD Y                                                            11

SEQ ID NO: 315          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 315
QVQLVQSGAE VKKPGASVKV SCKASGYTFT DYAVNWVRQA PGQGLEWMGW INTQTGKPTY    60
AQKFQGRVTM TRDTSTSTVY MELSSLRSED TAVYYCARDS YYYSSSLDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 316          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 316
DIQMTQSPSS LSASVGDRVT ITCRASAGIS NDLAWYQQKP GKAPKLLIYA ASRLQDGVPS    60
RFSGSGSGTD FTLTISSLQP EDFATYYCQQ SYKYPWTFGQ GTKLEIK                 107

SEQ ID NO: 317          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 317
RASAGISNDL A                                                            11

SEQ ID NO: 318          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 318
AASRLQD                                                                  7

SEQ ID NO: 319          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 319
QQSYKYPWT                                                                9

SEQ ID NO: 320          moltype = AA   length = 214
FEATURE                 Location/Qualifiers
REGION                  1..214
                        note = Description of Artificial Sequence: Synthetic
```

```
                                polypeptide
source                          1..214
                                mol_type = protein
                                organism = synthetic construct
SEQUENCE: 320
DIQMTQSPSS LSASVGDRVT ITCRASAGIS NDLAWYQQKP GKAPKLLIYA ASRLQDGVPS    60
RFSGSGSGTD FTLTISSLQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 321                  moltype = AA   length = 120
FEATURE                         Location/Qualifiers
REGION                          1..120
                                note = Description of Artificial Sequence: Synthetic
                                 polypeptide
source                          1..120
                                mol_type = protein
                                organism = synthetic construct
SEQUENCE: 321
QVQLVQSGAE VKKPGASVKV SCKASGYTFT DYAVNWVRQA PGQGLEWMGW INTQTGKPTY    60
AQKFQGRVTM TLDTSTSTAY MELSSLRSED TAVYYCTRDS YYYSSSLDYW GQGTLVTVSS   120

SEQ ID NO: 322                  moltype = AA   length = 10
FEATURE                         Location/Qualifiers
REGION                          1..10
                                note = Description of Artificial Sequence: Synthetic peptide
source                          1..10
                                mol_type = protein
                                organism = synthetic construct
SEQUENCE: 322
GYTFTDYAVN                                                           10

SEQ ID NO: 323                  moltype = AA   length = 10
FEATURE                         Location/Qualifiers
REGION                          1..10
                                note = Description of Artificial Sequence: Synthetic peptide
source                          1..10
                                mol_type = protein
                                organism = synthetic construct
SEQUENCE: 323
WINTQTGKPT                                                           10

SEQ ID NO: 324                  moltype = AA   length = 11
FEATURE                         Location/Qualifiers
REGION                          1..11
                                note = Description of Artificial Sequence: Synthetic peptide
source                          1..11
                                mol_type = protein
                                organism = synthetic construct
SEQUENCE: 324
DSYYYSSSLD Y                                                         11

SEQ ID NO: 325                  moltype = AA   length = 450
FEATURE                         Location/Qualifiers
REGION                          1..450
                                note = Description of Artificial Sequence: Synthetic
                                 polypeptide
source                          1..450
                                mol_type = protein
                                organism = synthetic construct
SEQUENCE: 325
QVQLVQSGAE VKKPGASVKV SCKASGYTFT DYAVNWVRQA PGQGLEWMGW INTQTGKPTY    60
AQKFQGRVTM TLDTSTSTAY MELSSLRSED TAVYYCTRDS YYYSSSLDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 326                  moltype = AA   length = 107
FEATURE                         Location/Qualifiers
REGION                          1..107
                                note = Description of Artificial Sequence: Synthetic
                                 polypeptide
source                          1..107
                                mol_type = protein
                                organism = synthetic construct
SEQUENCE: 326
```

```
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIK                 107

SEQ ID NO: 327          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 327
RASAGISNDL A                                                         11

SEQ ID NO: 328          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 328
AASRLQD                                                              7

SEQ ID NO: 329          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 329
QQSYKYPWT                                                            9

SEQ ID NO: 330          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 330
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 331          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 331
QVQLVQSGAE VKKPGASVKI SCKASGYTFT DYAVNWVRQA PGQGLEWMGW INTQTGKPTY    60
AQKFQGRFTF TLDTSTSTAY LEISSLRSED TAVYYCTRDS YYYSSSLDYW GQGTLVTVSS   120

SEQ ID NO: 332          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 332
GYTFTDYAVN                                                           10

SEQ ID NO: 333          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 333
WINTQTGKPT                                                           10
```

| | | |
|---|---|---|
| SEQ ID NO: 334 | moltype = AA  length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |
| SEQUENCE: 334 | | |
| DSYYSSSLD Y | | 11 |
| | | |
| SEQ ID NO: 335 | moltype = AA  length = 450 | |
| FEATURE | Location/Qualifiers | |
| REGION | 1..450 | |
| | note = Description of Artificial Sequence: Synthetic polypeptide | |
| source | 1..450 | |
| | mol_type = protein | |
| | organism = synthetic construct | |

SEQUENCE: 335
```
QVQLVQSGAE VKKPGASVKI SCKASGYTFT DYAVNWVRQA PGQGLEWMGW INTQTGKPTY    60
AQKFQGRFTF TLDTSTSTAY LEISSLRSED TAVYYCTRDS YYYSSSLDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450
```

| | | |
|---|---|---|
| SEQ ID NO: 336 | moltype = AA  length = 107 | |
| FEATURE | Location/Qualifiers | |
| REGION | 1..107 | |
| | note = Description of Artificial Sequence: Synthetic polypeptide | |
| source | 1..107 | |
| | mol_type = protein | |
| | organism = synthetic construct | |

SEQUENCE: 336
```
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIK                107
```

| | | |
|---|---|---|
| SEQ ID NO: 337 | moltype = AA  length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |
| SEQUENCE: 337 | | |
| RASAGISNDL A | | 11 |
| | | |
| SEQ ID NO: 338 | moltype = AA  length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 338 | | |
| AASRLQD | | 7 |
| | | |
| SEQ ID NO: 339 | moltype = AA  length = 9 | |
| FEATURE | Location/Qualifiers | |
| REGION | 1..9 | |
| | note = Description of Artificial Sequence: Synthetic peptide | |
| source | 1..9 | |
| | mol_type = protein | |
| | organism = synthetic construct | |
| SEQUENCE: 339 | | |
| QQSYKYPWT | | 9 |
| | | |
| SEQ ID NO: 340 | moltype = AA  length = 214 | |
| FEATURE | Location/Qualifiers | |
| REGION | 1..214 | |
| | note = Description of Artificial Sequence: Synthetic polypeptide | |
| source | 1..214 | |
| | mol_type = protein | |
| | organism = synthetic construct | |
| SEQUENCE: 340 | | |

```
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 341         moltype = AA   length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 341
QVQLVQSGAE VKKPGASVKV SCKASGYTFT DYAVNWVRQA PGQGLEWMGW INTQTGKPTY    60
AQKFQGRVTM TLDTSTSTSY MELSSLRSED TAVYYCTRDS YYYSSSLDYW GQGTLVTVSS   120

SEQ ID NO: 342         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 342
GYTFTDYAVN                                                          10

SEQ ID NO: 343         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 343
WINTQTGKPT                                                          10

SEQ ID NO: 344         moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 344
DSYYYSSSLD Y                                                        11

SEQ ID NO: 345         moltype = AA   length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 345
QVQLVQSGAE VKKPGASVKV SCKASGYTFT DYAVNWVRQA PGQGLEWMGW INTQTGKPTY    60
AQKFQGRVTM TLDTSTSTSY MELSSLRSED TAVYYCTRDS YYYSSSLDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 346         moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 346
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIK                 107

SEQ ID NO: 347         moltype = AA   length = 11
FEATURE                Location/Qualifiers
```

```
REGION                  1..11
                        note = Description of Artificial Sequence: Synthetic peptide
source                  1..11
                        mol_type = protein
                        organism = synthetic construct
SEQUENCE: 347
RASAGISNDL A                                                                    11

SEQ ID NO: 348          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 348
AASRLQD                                                                         7

SEQ ID NO: 349          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 349
QQSYKYPWT                                                                       9

SEQ ID NO: 350          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 350
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 351          moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 351
QVQLVQSGAE VKKPGASVKI SCKASGYTFT DYAVNWVRQA PGQGLEWMGW INTQTGKPTY    60
AQKFQGRFTF TLDTSTSTSY LEISSLRSED TAVYYCTRDS YYYSSSLDYW GQGTLVTVSS   120

SEQ ID NO: 352          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 352
GYTFTDYAVN                                                                      10

SEQ ID NO: 353          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 353
WINTQTGKPT                                                                      10

SEQ ID NO: 354          moltype = AA   length = 11
FEATURE                 Location/Qualifiers
REGION                  1..11
                        note = Description of Artificial Sequence: Synthetic peptide
source                  1..11
```

```
                        mol_type = protein
                        organism = synthetic construct
SEQUENCE: 354
DSYYYSSSLD Y                                                         11

SEQ ID NO: 355          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 355
QVQLVQSGAE VKKPGASVKI SCKASGYTFT DYAVNWVRQA PGQGLEWMGW INTQTGKPTY    60
AQKFQGRFTF TLDTSTSTSY LEISSLRSED TAVYYCTRDS YYYSSSLDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 356          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 356
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIK                 107

SEQ ID NO: 357          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 357
RASAGISNDL A                                                         11

SEQ ID NO: 358          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 358
AASRLQD                                                               7

SEQ ID NO: 359          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 359
QQSYKYPWT                                                             9

SEQ ID NO: 360          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 360
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

| | | |
|---|---|---|
| SEQ ID NO: 361 | moltype = AA length = 116 | |
| FEATURE | Location/Qualifiers | |
| REGION | 1..116 | |
| | note = Description of Artificial Sequence: Synthetic polypeptide | |
| source | 1..116 | |
| | mol_type = protein | |
| | organism = synthetic construct | |

SEQUENCE: 361
```
QVQLKESGPG LVQPSQTLSL TCTVSGFSLT SYTLSWVRQP PGKGLEWIGA IWGGDNTDYN   60
SALKSRLSIT WDTSKSQVLL KMNSLQTEDT AIYFCTRELG GSFDYWGQGV MVTVSS      116
```

| | | |
|---|---|---|
| SEQ ID NO: 362 | moltype = AA length = 10 | |
| FEATURE | Location/Qualifiers | |
| REGION | 1..10 | |
| | note = Description of Artificial Sequence: Synthetic peptide | |
| source | 1..10 | |
| | mol_type = protein | |
| | organism = synthetic construct | |

SEQUENCE: 362
```
GFSLTSYTLS                                                          10
```

| | | |
|---|---|---|
| SEQ ID NO: 363 | moltype = AA length = 9 | |
| FEATURE | Location/Qualifiers | |
| REGION | 1..9 | |
| | note = Description of Artificial Sequence: Synthetic peptide | |
| source | 1..9 | |
| | mol_type = protein | |
| | organism = synthetic construct | |

SEQUENCE: 363
```
AIWGGDNTD                                                            9
```

| | | |
|---|---|---|
| SEQ ID NO: 364 | moltype = AA length = 8 | |
| FEATURE | Location/Qualifiers | |
| REGION | 1..8 | |
| | note = Description of Artificial Sequence: Synthetic peptide | |
| source | 1..8 | |
| | mol_type = protein | |
| | organism = synthetic construct | |

SEQUENCE: 364
```
ELGGSFDY                                                             8
```

| | | |
|---|---|---|
| SEQ ID NO: 365 | moltype = AA length = 436 | |
| FEATURE | Location/Qualifiers | |
| REGION | 1..436 | |
| | note = Description of Artificial Sequence: Synthetic polypeptide | |
| source | 1..436 | |
| | mol_type = protein | |
| | organism = synthetic construct | |

SEQUENCE: 365
```
QVQLKESGPG LVQPSQTLSL TCTVSGFSLT SYTLSWVRQP PGKGLEWIGA IWGGDNTDYN   60
SALKSRLSIT WDTSKSQVLL KMNSLQTEDT AIYFCTRELG GSFDYWGQGV MVTVSSAETT  120
APSVYPLAPG TALKSNSMVT LGCLVKGYFP EPVTVTWNSG ALSSGVHTFP AVLQSGLYTL  180
TSSVTVPSST WSSQAVTCNV AHPASSTKVD KKIVPRECNP CGCTGSEVSS VFIFPPKTKD  240
VLTITLTPKV TCVVVDISQN DPEVRFSWFI DDVEVHTAQT HAPEKQSNST LRSVSELPIV  300
HRDWLNGKTF KCKVNSGAFP APIEKSISKP EGTPRGPQVY TMAPPKEEMT QSQVSITCMV  360
KGFYPPDIYT EWKMNGQPQE NYKNTPPTMD TDGSYFLYSK LNVKKETWQQ GNTFTCSVLH  420
EGLHNHHTEK SLSHSP                                                  436
```

| | | |
|---|---|---|
| SEQ ID NO: 366 | moltype = AA length = 106 | |
| FEATURE | Location/Qualifiers | |
| REGION | 1..106 | |
| | note = Description of Artificial Sequence: Synthetic polypeptide | |
| source | 1..106 | |
| | mol_type = protein | |
| | organism = synthetic construct | |

SEQUENCE: 366
```
DIQMTQSPPV LSASVGDRVT LSCKTSQNIN KKLDWYQQKH GEAPKLLIYY TNNLQTGIPS   60
RFSGSGSGTD FTLTISTLQP EDVATYYCYQ YDSGFTFGAG TKLELK                 106
```

| | | |
|---|---|---|
| SEQ ID NO: 367 | moltype = AA length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |

```
SEQUENCE: 367
KTSQNINKKL D                                                              11

SEQ ID NO: 368          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 368
YTNNLQT                                                                   7

SEQ ID NO: 369          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 369
YQYDSGFT                                                                  8

SEQ ID NO: 370          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 370
DIQMTQSPPV LSASVGDRVT LSCKTSQNIN KKLDWYQQKH GEAPKLLIYY TNNLQTGIPS          60
RFSGSGSGTD FTLTISTLQP EDVATYYCYQ YDSGFTFGAG TKLELKRADA APTVSIFPPS         120
TEQLATGGAS VVCLMNNFYP RDISVKWKID GTERRDGVLD SVTDQDSKDS TYSMSSTLSL         180
TKADYESHNL YTCEVVHKTS SSPVVKSFNR NEC                                     213

SEQ ID NO: 371          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 371
QVQLKESGPG LVQPSQTLSL TCTVSGFSLT SYTLSWVRQP PGKGLEWIGA IWGGDNTDYN          60
SALKSRLSIS RDTSKSQVLL KMNSLQTEDT AIYFCTRELG GSFDYWGQGV MVTVSS             116

SEQ ID NO: 372          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 372
GFSLTSYTLS                                                               10

SEQ ID NO: 373          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 373
AIWGGDNTD                                                                 9

SEQ ID NO: 374          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 374
ELGGSFDY                                                                  8
```

```
SEQ ID NO: 375              moltype = AA  length = 446
FEATURE                     Location/Qualifiers
REGION                      1..446
                            note = Description of Artificial Sequence: Synthetic
                             polypeptide
source                      1..446
                            mol_type = protein
                            organism = synthetic construct
SEQUENCE: 375
QVQLKESGPG LVQPSQTLSL TCTVSGFSLT SYTLSWVRQP PGKGLEWIGA IWGGDNTDYN   60
SALKSRLSIS RDTSKSQVLL KMNSLQTEDT AIYFCTRELG GSFDYWGQGV MVTVSSAKTT  120
APSVYPLAPV CGDTTGSSVT LGCLVKGYFP EPVTLTWNSG SLSSGVHTFP AVLQSDLYTL  180
SSSVTVTSST WPSQSITCNV AHPASSTKVD KKIEPRGPTI KPCPPCKCPA PNLLGGPSVF  240
IFPPKIKDVL MISLSPIVTC VVVDVSEDDP DVQISWFVNN VEVHTAQTQT HREDYNSTLR  300
VVSALPIQHQ DWMSGKEFKC KVNNKDLPAP IERTISKPKG SVRAPQVYVL PPPEEEMTKK  360
QVTLTCMVTD FMPEDIYVEW TNNGKTELNY KNTEPVLDSD GSYFMYSKLR VEKKNWVERN  420
SYSCSVVHEG LHNHHTTKSF SRTPGK                                      446

SEQ ID NO: 376              moltype = AA  length = 106
FEATURE                     Location/Qualifiers
REGION                      1..106
                            note = Description of Artificial Sequence: Synthetic
                             polypeptide
source                      1..106
                            mol_type = protein
                            organism = synthetic construct
SEQUENCE: 376
DIQMTQSPPV LSASVGDRVT LSCKTSQNIN KKLDWYQQKH GEAPKLLIYY TNNLQTGIPS   60
RFSGSGSGTD FTLTISTLQP EDVATYYCYQ YDSGFTFGAG TKLELK                 106

SEQ ID NO: 377              moltype = AA  length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 377
KTSQNINKKL D                                                        11

SEQ ID NO: 378              moltype = AA  length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 378
YTNNLQT                                                             7

SEQ ID NO: 379              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 379
YQYDSGFT                                                            8

SEQ ID NO: 380              moltype = AA  length = 213
FEATURE                     Location/Qualifiers
REGION                      1..213
                            note = Description of Artificial Sequence: Synthetic
                             polypeptide
source                      1..213
                            mol_type = protein
                            organism = synthetic construct
SEQUENCE: 380
DIQMTQSPPV LSASVGDRVT LSCKTSQNIN KKLDWYQQKH GEAPKLLIYY TNNLQTGIPS   60
RFSGSGSGTD FTLTISTLQP EDVATYYCYQ YDSGFTFGAG TKLELKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 381              moltype = AA  length = 11
FEATURE                     Location/Qualifiers
REGION                      1..11
                            note = Description of Artificial Sequence: Synthetic peptide
source                      1..11
```

```
                        mol_type = protein
                        organism = synthetic construct
VARIANT                 1
                        note = X can be R or L
SEQUENCE: 381
XASAGISNDL A                                                              11

SEQ ID NO: 382          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
VARIANT                 1
                        note = X can be R or K
SEQUENCE: 382
XASKSIGTFL A                                                              11

SEQ ID NO: 383          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
VARIANT                 1
                        note = X can be R or L
SEQUENCE: 383
XASEGISNDL A                                                              11

SEQ ID NO: 384          moltype = AA  length = 520
FEATURE                 Location/Qualifiers
source                  1..520
                        mol_type = protein
                        organism = Homo sapiens
SEQUENCE: 384
MRNKKILKED ELLSETQQAA FHQIAMEPFE INVPKPKRRN GVNFSLAVVV IYLILLTAGA          60
GLLVVQVLNL QARLRVLEMY FLNDTLAAED SPSFSLLQSA HPGEHLAQGA SRLQVLQAQL         120
TWVRVSHEHL LQRVDNFTQN PGMFRIKGEQ GAPGLQGHKG AMGMPGAPGP PGPPAEKGAK         180
GAMGRDGATG PSGPQGPPGV KGEAGLQGPQ GAPGKQGATG TPGPQGEKGS KGDGGLIGPK         240
GETGTKGEKG DLGLPGSKGD RGMKGDAGVM GPPGAQGSKG DFGRPGPPGL AGFPGAKGDQ         300
GQPGLQGVPG PPGAVGHPGA KGEPGSAGSP GRAGLPGSPG SPGATGLKGS KGDTGLQGQQ         360
GRKGESGVPG PAGVKGEQGS PGLAGPKGAP GQAGQKGDQG VKGSSGEQGV KGEKGERGEN         420
SVSVRIVGSS NRGAEVYYS  GTWGTICDDE WQNSDAIVFC RMLGYSKGRA LYKVGAGTGQ         480
IWLDNVQCRG TESTLWSCTK NSWGHHDCSH EEDAGVECSV                              520

SEQ ID NO: 385          moltype = DNA  length = 1416
FEATURE                 Location/Qualifiers
misc_feature            1..1416
                        note = Description of Artificial Sequence: Synthetic
                         polynucleotide
source                  1..1416
                        mol_type = other DNA
                        organism = synthetic construct
SEQUENCE: 385
atggattgga cttggcgctt cttgtttgtg gtggcggcgg ctactggagt gcagtcacaa          60
gtgcaactta aggaatccgg accgggactc gtgcagccgt cacaaactct ttcgcttacc         120
tgtaccgtgt ccggatttc  cctgacttcc taccatgtgt cctgggtcag acagcctcct         180
ggaaagggac tggaatggat gggtgccatt tggactgggg gatccattgc gtataactcg         240
ctgctgaagt cgcgcttgtc catttcgaga gatacctcca agtcccaagt gtttctgaag         300
atgaactccc tgcaaactga agatactgcc acttactact gtgcccgcga tctgtccgac         360
tattactcga gttacacctc gttcgattac tggggacagg gtgtaatggt cactgtgtcg         420
actgccagca ccaagggccc atcggtcttc cccctgcac  cctcctccaa gagcacctct         480
gggggcacag cggccctggg ctgcctggtc aaggactact ccccgaacc  ggtgacggtg         540
tcgtggaact caggcgccct gaccagcggc gtgcacacct cccgcctgt  cctacagtcc         600
tcaggactct actccctcag cagcgtggtg accgtgccct ccagcagctt gggcacccag         660
acctacatct gcaacgtgaa tcacaagccc agcaacaca  aggtggacaa gaaagttgag         720
cccaaatctt gtgacaaaac tcacacatgc ccaccgtgcc cagcacctga actcctgggg         780
ggaccgtcag tcttcctctt ccccccaaaa cccaaggaca ccctcatgat ctcccggacc         840
cctgaggtca catgcgtggt ggtggacgtg agccacgaag accctgaggt caagttcaac         900
tggtacgtgg acggcgtgga ggtgcataat gccaagaca  agccgcggga ggagcagtac         960
aacagcacgt accgggtggt cagcgtcctc accgtcctgc accaggactg gctgaatggc        1020
aaggagtaca agtgcaaggt cagcaacaaa gccctcccag cccccatcga gaaaaccatc        1080
tccaaagcca aagggcagcc ccgagaacca caggtgtaca cctgccccc  atcccgggat        1140
gagctgacca agaaccaggt cagcctgacc tgcctggtca aaggcttcta tcccagcgac        1200
atcgccgtgg agtgggagag caatgggcag ccggagaaca actacaagac cacgcctccc        1260
gtgctggact ccgacggctc cttcttcctc tacagcaagc tcaccgtgga caagagcagg        1320
tggcagcagg ggaacgtctt ctcatgctcc gtgatgcatg aggctctgca caaccactac        1380
```

```
acgcagaagt ccctctccct gtctccgggt aaatag                              1416

SEQ ID NO: 386          moltype = DNA  length = 711
FEATURE                 Location/Qualifiers
misc_feature            1..711
                        note = Description of Artificial Sequence: Synthetic
                         polynucleotide
source                  1..711
                        mol_type = other DNA
                        organism = synthetic construct
SEQUENCE: 386
atggatatgc gggtgccggc ccagcttctg ggcctgttgc tgctctggct ctccggagcg  60
cgctgtgaca tccaaatgac tcagtccccc gcctcgcttt caacctccct gggagaaacc  120
gtgtccatcg aatgcctggc ttccgaaggg atttccaacg atctggcctg gtaccagcag  180
aagtccggaa agtcacctca gctcctgatc tacgcggcca gccggctgca ggacggcgtg  240
ccttcccgct tttccggttc gggatcaggg actcggtact cgctgaagat ttccgggatg  300
cagcctgagg acgaagcgga ctacttctgc caacaatcct acaagtaccc gctgaccttc  360
ggctccggca ccaagctcga aatcaagcga actgtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata cgccctcca atcgggtaac   540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta a           711

SEQ ID NO: 387          moltype = DNA  length = 1416
FEATURE                 Location/Qualifiers
misc_feature            1..1416
                        note = Description of Artificial Sequence: Synthetic
                         polynucleotide
source                  1..1416
                        mol_type = other DNA
                        organism = synthetic construct
SEQUENCE: 387
atggattgga cttggcgctt cttgtttgtg gtggcggcgg ctactggagt gcagtcacaa  60
gtgcaacttc aagaatccgg accgggactc gtgaagccgt cagaaactct ttcgcttacc  120
tgtaccgtgt ccggatttc cctgacttcc taccatgtgt cctggatcag acagcctcct  180
ggaaagggac tggaatggat cggtgccatt tggactgggg gatccattgc gtataacccg  240
tccctgaagt cgcgcgtgac tatttcggtg gatacctcca agaaccaatt cagcctgaag  300
ttgtcctccg tgactgccgc cgatactgcc gtatactact gtgcccgcga tctgtccgac  360
tattactcga gttacaccct cgttcgattac tggggacagg gtactctggt cactgtgtcg  420
tcggccagca ccaagggccc atcggtcttc cccctggcac cctcctccaa gagcacctct  480
gggggcacag cggccctggg ctgcctggtc aaggactact ccccgaacc ggtgacggtg   540
tcgtggaact caggcgccct gaccagcggc gtgcacaccat tcccggctgt cctacagtcc  600
tcaggactct actccctcag cagcgtggtg accgtgccct ccagcagctt gggcacccag  660
acctacatct gcaacgtgaa tcacaagccc agcaacacca aggtggacaa gaaagttgag  720
cccaaatctt gtgacaaaac tcacacatgc ccaccgtgcc cagcacctga actcctgggg  780
ggaccgtcag tcttcctctt ccccccaaaa cccaaggaca cctcatgat ctcccggacc   840
cctgaggtca catgcgtggt ggtggacgtg agccacgaag accctgaggt caagttcaac  900
tggtacgtgg acggcgtgga ggtgcataat gccaagacaa agccgcggga ggagcagtac  960
aacagcacgt accgggtggt cagcgtcctc accgtcctgc accaggactg gctgaatggc  1020
aaggagtaca agtgcaaggt cagcaacaaa gccctcccag cccccatcga gaaaaccatc  1080
tccaaagcca aagggcagcc ccgagaacca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaagt ccctctccct gtctccgggt aaatag                            1416

SEQ ID NO: 388          moltype = DNA  length = 711
FEATURE                 Location/Qualifiers
misc_feature            1..711
                        note = Description of Artificial Sequence: Synthetic
                         polynucleotide
source                  1..711
                        mol_type = other DNA
                        organism = synthetic construct
SEQUENCE: 388
atggatatgc gggtgccggc ccagcttctg ggcctgttgc tgctctggct ctccggagcg  60
cgctgtgaca tccaaatgac tcagtccccc tcatcgcttt cagcctccgt gggagacaga  120
gtgaccatca cttgccgggc ttccgaaggg atttccaacg atctggcctg gtaccagcag  180
aagcccggaa aggcccctaa gctcctgatc tacgcggcca gccggctgca gtccggcgtg  240
ccttcccgct tttccggttc gggatcaggg actgacttca ccctgaccat ttccagcctg  300
cagcctgagg acttcgcgac ctactactgc caacaatcct acaagtaccc gctgaccttc  360
ggccaaggca ccaagctcga aatcaagcga actgtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata cgccctcca atcgggtaac   540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgtta a           711
```

| SEQ ID NO: 389 | moltype = DNA length = 1416 |
| --- | --- |
| FEATURE | Location/Qualifiers |
| misc_feature | 1..1416 |
| | note = Description of Artificial Sequence: Synthetic polynucleotide |
| source | 1..1416 |
| | mol_type = other DNA |
| | organism = synthetic construct |

SEQUENCE: 389

```
atggattgga cttggcgctt cttgtttgtg gtggcggcgg ctactggagt gcagtcacaa   60
gtgcaacttc aagaatccgg accgggactc gtgaagccgt cagaaactct ttcgcttacc  120
tgtaccgtgt ccggattttc cctgacttcc taccatgtgt cctgggtcag acagcctcct  180
ggaaagggac tggaatggat cggtgccatt tggactgggg atccattgc gtataaccgg   240
tccctgaagt cgcgcgtaac tatttcgaga gatacctcca agaaccaagt gtccctgaag  300
ctgtcgtccg tgactgccgc cgatactgcc gtgtactact gtgcccgcga tctgtccgac  360
tattactcga gttacacctc gttcgattac tggggacagg gtactctggt cactgtgtcg  420
tcggccagca ccaagggccc atcggtcttc cccctggcac cctcctccaa gagcacctct  480
gggggcacag cggccctggg ctgcctggtc aaggactact tccccgaacc ggtgacggtg  540
tcgtggaact caggcgccct gaccagcggc gtgcacacct tcccggctgt cctacagtcc  600
tcaggactct actccctcag cagcgtggtg accgtgccct ccagcagctt gggcacccag  660
acctacatct gcaacgtgaa tcacaagccc agcaacacca aggtggacaa gaaagttgag  720
cccaaatctt gtgacaaaac tcacacatgc ccaccgtgcc cagcacctga actcctgggg  780
ggaccgtcag tcttcctctt ccccccaaaa cccaaggaca cctcatgat ctccggacc    840
cctgaggtca catgcgtggt ggtggacgtg agccacgaag accctgaggt caagttcaac  900
tggtacgtgg acggcgtgga ggtgcataat gccaagacaa agccgcgggg ggagcagtac  960
aacagcacgt accgggtggt cagcgtcctc accgtcctgc accaggactg gctgaatggc 1020
aaggagtaca agtgcaaggt cagcaacaaa gccctcccag cccccatcga gaaaaccatc 1080
tccaaagcca aagggcagcc ccgagaacca caggtgtaca ccctgccccc atcccgggat 1140
gagctgacca agaaccaggt cagcctgacc tgcctggtca aaggcttcta tcccagcgac 1200
atcgccgtgg agtgggagag caatgggcag ccggagaaca actacaagac cacgcctccc 1260
gtgctggact ccgacggctc cttcttcctc tacagcaagc tcaccgtgga caagagcagg 1320
tggcagcagg ggaacgtctt ctcatgctcc gtgatgcatg aggctctgca caaccactac 1380
acgcagaagt ccctctccct gtctccgggt aaatag                           1416
```

| SEQ ID NO: 390 | moltype = DNA length = 711 |
| --- | --- |
| FEATURE | Location/Qualifiers |
| misc_feature | 1..711 |
| | note = Description of Artificial Sequence: Synthetic polynucleotide |
| source | 1..711 |
| | mol_type = other DNA |
| | organism = synthetic construct |

SEQUENCE: 390

```
atggatatgc gggtgccggc ccagcttctg ggcctgttgc tgctctggct ctccggagcg   60
cgctgtgaca tccaaatgac tcagtccccc tcatcgcttt cagcctccgt gggagacaga  120
gtgaccatca cttgccgggc ttccgaaggg atttccaacg atctggcctg gtaccagcag  180
aagcccggaa aggcccctaa gctcctgatc tacgcggcca gcggctgca gtccggcgtg   240
ccttcccgct tttccggttc gggatcaggg actgactaca ccctgaccat ttccagcctg  300
cagcctgagg acttcgcgac ctactactgc caacaatcct acaagtaccc gctgacctgc  360
ggccaaggca ccaagctcga aatcaagcga actgtgctg caccatctgt cttcatcttc   420
ccgccatctg atgagcagtt gaaatctgga actgcctctg ttgtgtgcct gctgaataac 480
ttctatccca gagaggccaa agtacagtgg aaggtggata acgccctcca atcgggtaac 540
tcccaggaga gtgtcacaga gcaggacagc aaggacagca cctacagcct cagcagcacc 600
ctgacgctga gcaaagcaga ctacgagaaa cacaaagtct acgcctgcga agtcacccat 660
cagggcctga gctcgcccgt cacaaagagc ttcaacaggg gagagtgtta a            711
```

| SEQ ID NO: 391 | moltype = DNA length = 1416 |
| --- | --- |
| FEATURE | Location/Qualifiers |
| misc_feature | 1..1416 |
| | note = Description of Artificial Sequence: Synthetic polynucleotide |
| source | 1..1416 |
| | mol_type = other DNA |
| | organism = synthetic construct |

SEQUENCE: 391

```
atggattgga cttggcgctt cttgtttgtg gtggcggcgg ctactggagt gcagtcacaa   60
gtgcaacttc aagaatccgg accgggactc gtgaagccgt cagaaactct ttcgcttacc  120
tgtaccgtgt ccggattttc cctgacttcc taccatgtgt cctgggtcag acagcctcct  180
ggaaagggac tggaatggat cggtgccatt tggactgggg atccattgc gtataacccg   240
tccctgaagt cgcgcgtaac tatttcgaga gatacctcca agaaccaagt gtccctgaag  300
ctgtcgtccg tgactgccgc cgatactgcc gtgtactact gtgcccgcga tctgtccgac  360
tattactcga gttacacctc gttcgattac tggggacagg gtactctggt cactgtgtcg  420
tcggccagca ccaagggccc atcggtcttc cccctggcac cctcctccaa gagcacctct  480
gggggcacag cggccctggg ctgcctggtc aaggactact tccccgaacc ggtgacggtg  540
tcgtggaact caggcgccct gaccagcggc gtgcacacct tcccggctgt cctacagtcc  600
tcaggactct actccctcag cagcgtggtg accgtgccct ccagcagctt gggcacccag  660
acctacatct gcaacgtgaa tcacaagccc agcaacacca aggtggacaa gaaagttgag  720
cccaaatctt gtgacaaaac tcacacatgc ccaccgtgcc cagcacctga actcctgggg  780
```

```
ggaccgtcag tcttcctctt cccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc   1020
aaggagtaca agtgcaaggt cagcaacaaa gccctcccag cccccatcga gaaaaccatc   1080
tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaagt ccctctccct gtctccgggt aaatag                             1416

SEQ ID NO: 392           moltype = DNA  length = 711
FEATURE                  Location/Qualifiers
misc_feature             1..711
                         note = Description of Artificial Sequence: Synthetic
                         polynucleotide
source                   1..711
                         mol_type = other DNA
                         organism = synthetic construct
SEQUENCE: 392
atggatatgc gggtgccggc ccagcttctg ggcctgttgc tgctctggct ctccggagcg     60
cgctgtgaca tccaaatgac tcagtccccc tcatcgcttt cagcctccgt gggagacaga   120
gtgaccatca cttgccgggc ttccgaaggg atttccaacg atctggcctg gtaccagcag   180
aagcccggaa aggcccctaa gctcctgatc tacgcggcca gccggctgca gtccggcgtg   240
ccttcccgct tttccggttc gggatcaggg actgactaca cctgaccat ttccagcatg   300
cagcctgagg acttcgcgac ctactactgc caacaatcct acaagtaccc gctgaccttc   360
ggccaaggca ccaagctcga aatcaagcga actgtggctg caccatcgt cttcatcttc   420
ccgccatctg atgagcagtt gaaatctgga actgcctctg ttgtgtgcct gctgaataac   480
ttctatcca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a             711

SEQ ID NO: 393           moltype = DNA  length = 1416
FEATURE                  Location/Qualifiers
misc_feature             1..1416
                         note = Description of Artificial Sequence: Synthetic
                         polynucleotide
source                   1..1416
                         mol_type = other DNA
                         organism = synthetic construct
SEQUENCE: 393
atggattgga cttggcgctt cttgtttgtg gtggcggcgg ctactggagt gcagtcacaa     60
gtgcaacttc aagaatccgg accgggactc gtgaagccgt cagaaactct ttcgcttacc   120
tgtaccgtgt ccggattttc cctgacttcc taccatgtgt cctgggtcag acagcctcct   180
ggaaagggac tggaatggat gggtgccatt tggactgggg gatccattgc gtataacccg   240
tccctgaagt cgcgcttgac tatttcgaga gataccttcca agaaccaagt gtcgctgaag   300
atgtcctccc tgactgccgc cgatactgcc gtatactact gtgcccgcga tctgtccgac   360
tattactcga gttacacctc gttcgattac tgggacaggg tactctggt cactgtgtcg   420
tcggccagca ccaagggccc atcggtcttc cccctgcac cctcctccaa gagcacctct   480
gggggcacag cggccctggg ctgcctggtc aaggactact ccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt cccccaaaa cccaaggaca ccctcatgat ctcccggacc   840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgggtggt cagcgtcctc accgtcctgc accaggactg gctgaatggc  1020
aaggagtaca agtgcaaggt cagcaacaaa gccctcccag cccccatcga gaaaaccatc  1080
tccaaagcca aagggcagcc ccgagaacca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaagt ccctctccct gtctccgggt aaatag                            1416

SEQ ID NO: 394           moltype = DNA  length = 711
FEATURE                  Location/Qualifiers
misc_feature             1..711
                         note = Description of Artificial Sequence: Synthetic
                         polynucleotide
source                   1..711
                         mol_type = other DNA
                         organism = synthetic construct
SEQUENCE: 394
atggatatgc gggtgccggc ccagcttctg ggcctgttgc tgctctggct ctccggagcg     60
cgctgtgaca tccaaatgac tcagtccccc tcatcgcttt cagcctccgt gggagacaga   120
```

```
gtgaccatca cttgccgggc ttccgaaggg atttccaacg atctggcctg gtaccagcag    180
aagcccggaa aggcccctaa gctcctgatc tacgcggcca gccggctgca gtccggcgtg    240
ccttcccgct tttccggttc gggatcaggg actgactaca ccctgaccat ttccagcctg    300
cagcctgagg acttcgcgac ctactactgc aacaatcct acaagtaccc gctgaccttc     360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac     540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
SEQ ID NO: 395          moltype = DNA  length = 1416
FEATURE                 Location/Qualifiers
misc_feature            1..1416
                        note = Description of Artificial Sequence: Synthetic
                        polynucleotide
source                  1..1416
                        mol_type = other DNA
                        organism = synthetic construct
SEQUENCE: 395
atggattgga cttggcgctt cttgtttgtg gtggcggcgg ctactggagt gcagtcacaa    60
gtgcaacttc aagaatccgg accgggactc gtgaagccgt cagaaactct ttcgcttacc    120
tgtaccgtgt ccggattttc cctgacttcc taccatgtgt cctgggtcag acagcctcct    180
ggaaagggac tggaatggat gggtgccatt tggactgggg gatccattgc gtataacccg    240
tccctgaagt cgcgcttgac tatttcgaga gatacctcca agaaccaagt gtcgctgaag    300
atgtcctccc tgactgccgc cgatactgcc gtatactgcg tgcccgcga tctgtccgga    360
tattactcga gttacacctc gttcgattac tggggacagg gtactctggt cactgtgtcg    420
tcggccagca ccaagggccc atcggtcttc cccctggcac cctcctccaa gagcacctct    480
gggggcacag cggccctggg ctgcctggtc aaggactact cccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcaccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca cctcatgat ctccoggacc     840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc    1020
aaggagtaca agtgcaaggt cagcaacaaa gccctcccag cccccatcga gaaaaccatc    1080
tccaaagcca aagggcagcc ccgagaacca caggtgtaca ccctgcccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaagt ccctctccct gtctccgggt aaatag                              1416
SEQ ID NO: 396          moltype = DNA  length = 711
FEATURE                 Location/Qualifiers
misc_feature            1..711
                        note = Description of Artificial Sequence: Synthetic
                        polynucleotide
source                  1..711
                        mol_type = other DNA
                        organism = synthetic construct
SEQUENCE: 396
atggatatgc gggtgccggc ccagcttctg ggcctgttgc tgctctggct ctccggagcg    60
cgctgtgaca tccaaatgac tcagtccccc tcatcgcttt cagcctccgt gggagacaga    120
gtgaccatca cttgccgggc ttccgaaggg atttccaacg atctggcctg gtaccagcag    180
aagcccggaa aggcccctaa gctcctgatc tacgcggcca gccggctgca gtccggcgtg    240
ccttcccgct tttccggttc gggatcaggg actgactaca ccctgaccat ttccagcatg    300
cagcctgagg acttcgcgac ctactactgc aacaatcct acaagtaccc gctgaccttc     360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac     540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
SEQ ID NO: 397          moltype = DNA  length = 1416
FEATURE                 Location/Qualifiers
misc_feature            1..1416
                        note = Description of Artificial Sequence: Synthetic
                        polynucleotide
source                  1..1416
                        mol_type = other DNA
                        organism = synthetic construct
SEQUENCE: 397
atggattgga cttggcgctt cttgtttgtg gtggcggcgg ctactggagt gcagtcacaa    60
gtgcaacttc aagaatccgg accgggactc gtgaagccgt cagaaactct ttcgcttacc    120
tgtaccgtgt ccggattttc cctgacttcc taccatgtgt cctgggtcag acagcctcct    180
```

```
ggaaagggac tggaatggat cggtgccatt tggactgggg gatccattgc gtataacccg    240
tccctgaagt cgcgcgtaac tatttcgaga gatacctcca agaaccaagt gtccctgaag    300
ctgtcgtccg tgactgccgc cgatactgcc gtgtactact gtgcccgcga tctgtccgac    360
tattactcga gttacacctc gttcgattac tggggacagg gtactctggt cactgtgtcg    420
tcggccagca ccaagggccc atcggtcttc ccctcctcaa gagcacctct                480
ggggcacag cggccctggg ctgcctggtc aaggactact ccccgaacc ggtgacggtg       540
tcgtggaact caggcgccct gaccagcggc gtgcacacct cccggctgt cctacagtcc      600
tcaggactct actccctcag cagcgtggtg accgtgccct ccagcagctt gggcacccag     660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt cccccaaaa cccaaggaca ccctcatgat ctcccggacc     840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgggtggt cagcgtcctc accgtcctgc accaggactg gctgaatggc   1020
aaggagtaca agtgcaaggt cagcaacaaa gccctcccag cccccatcga gaaaaccatc   1080
tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaagt ccctctccct gtctccgggt aaatag                             1416

SEQ ID NO: 398           moltype = DNA   length = 711
FEATURE                  Location/Qualifiers
misc_feature             1..711
                         note = Description of Artificial Sequence: Synthetic
                          polynucleotide
source                   1..711
                         mol_type = other DNA
                         organism = synthetic construct
SEQUENCE: 398
atggatatgc gggtgccggc ccagcttctg ggcctgttgc tgctctggct ctccggagcg    60
cgctgtgaca tccaaatgac tcagtccccc tcatcgcttt cagcctccgt gggagacaga   120
gtgaccatca cttgccgggc ttccgaaggg atttccaacg atctggctg gtaccagcag    180
aagcccggaa aggccctaa gctcctgatc tacgcgggca gccggctgca ggacaggctg   240
ccttcccgct tttccggttc gggatcaggg actgactaca ccctgaccat ttccagcctg   300
cagcctgagg acttcgcgac ctactactgc caacaatcct acaagtaccc gctgaccttc   360
ggccaaggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711

SEQ ID NO: 399           moltype = DNA   length = 1416
FEATURE                  Location/Qualifiers
misc_feature             1..1416
                         note = Description of Artificial Sequence: Synthetic
                          polynucleotide
source                   1..1416
                         mol_type = other DNA
                         organism = synthetic construct
SEQUENCE: 399
atggattgga cttggcgctt cttgtttgtg gtggcggcgg ctactggagt gcagtcacaa    60
gtgcaacttc aagaatccgg accgggactc gtgaagccgt cagaaactct ttcgcttacc   120
tgtaccgtgt ccggattttc cctgacttcc taccatggta cctggggtcag acagcctcct   180
ggaaagggac tggaatggat cggtgccatt tggactgggg gatccattgc gtataacccg   240
tccctgaagt cgcgcgtaac tatttcgaga gatacctcca agaaccaagt gtccctgaag   300
ctgtcgtccg tgactgccgc cgatactgcc gtgtactact gtgcccgcga tctgtccgac   360
tattactcga gttacacctc gttcgattac tggggacagg gtactctggt cactgtgtcg   420
tcggccagca ccaagggccc atcggtcttc ccctggcac cctcctcaa gagcacctct    480
ggggcacag cggccctggg ctgcctggtc aaggactact ccccgaacc ggtgacggtg    540
tcgtggaact caggcgccct gaccagcggc gtgcacacct cccggctgt cctacagtcc   600
tcaggactct actccctcag cagcgtggtg accgtgccct ccagcagctt gggcacccag    660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt cccccaaaa cccaaggaca ccctcatgat ctcccggacc    840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgggtggt cagcgtcctc accgtcctgc accaggactg gctgaatggc  1020
aaggagtaca agtgcaaggt cagcaacaaa gccctcccag cccccatcga gaaaaccatc  1080
tccaaagcca aagggcagcc ccgagaacca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaagt ccctctccct gtctccgggt aaatag                            1416

SEQ ID NO: 400           moltype = DNA   length = 711
```

```
FEATURE            Location/Qualifiers
misc_feature       1..711
                   note = Description of Artificial Sequence: Synthetic
                   polynucleotide
source             1..711
                   mol_type = other DNA
                   organism = synthetic construct
SEQUENCE: 400
atggatatgc gggtgccggc ccagcttctg ggcctgttgc tgctctggct ctccggagcg    60
cgctgtgaca tccaaatgac tcagtccccc tcatcgcttt caacctccgt gggagacaga   120
gtgaccatca cttgccgggc ttccgaaggg atttccaacg atctggcctg gtaccagcag   180
aagcccggaa agtcgcctaa gctcctgatc tacgcggcca gccggctgca gtccggcgtg   240
ccttcccgct tttccggttc gggatcaggg actgactaca ccctgaccat ttccagcctg   300
cagcctgagg acttcgcgac ctacttctgc aacaatctc  acaagtaccc gctgaccttc   360
ggccaaggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711

SEQ ID NO: 401     moltype = DNA   length = 1416
FEATURE            Location/Qualifiers
misc_feature       1..1416
                   note = Description of Artificial Sequence: Synthetic
                   polynucleotide
source             1..1416
                   mol_type = other DNA
                   organism = synthetic construct
SEQUENCE: 401
atggattgga cttggcgctt cttgtttgtg gtggcggcgg ctactggagt gcagtcacaa    60
gtgcaacttc aagaatccgg accgggactc gtgaagccgt cagaaactct ttcgcttacc   120
tgtaccgtgt ccggattttc cctgacttcc taccatgtgt cctgggtcag acagcctcct   180
ggaaagggac tggaatggat cggtgccatt tggactgggg gatccattgc gtataaccga   240
tccctgaagt cgcgcgtaac tatttcgaga gatacctcca agaaccaagt gtccctgaag   300
ctgtcgtccg tgactgccgc cgatactgcc gtgtactact gtgcccgcga tctgtccgac   360
tattactcga gttacacctc gttcgattac tggggacagg gtactctggt cactgtgtcg   420
tcggccagca ccaagggccc atcggtcttc ccccctggcac cctcctccaa gagcacctct   480
gggggcacag cggcctgggg ctgcctggtc aaggactact tccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt ccccccaaaa cccaaggaca cccctcatgat ctcccggacc   840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgtgtggt cagcgtcctc accgtcctgc accaggactg gctgaatggc  1020
aaggagtaca agtgcaaggt cagcaacaaa gccctcccag cccccatcga gaaaaccatc  1080
tccaaagcca aagggcagcc ccgagaacca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaagt ccctctccct gtctccgggt aaatag                            1416

SEQ ID NO: 402     moltype = DNA   length = 711
FEATURE            Location/Qualifiers
misc_feature       1..711
                   note = Description of Artificial Sequence: Synthetic
                   polynucleotide
source             1..711
                   mol_type = other DNA
                   organism = synthetic construct
SEQUENCE: 402
atggatatgc gggtgccggc ccagcttctg ggcctgttgc tgctctggct ctccggagcg    60
cgctgtgaca tccaaatgac tcagtccccc tcatcgcttt caacctccgt gggagacaga   120
gtgaccatca cttgccgggc ttccgaaggg atttccaacg atctggcctg gtaccagcag   180
aagcccggaa agtcccctaa gctcctgatc tacgcggcca gccggctgca ggacggcgtg   240
ccttcccgct tttccggttc gggatcaggg actgactaca ccctgaccat ttccagcctg   300
cagcctgagg acgaagcgac ctacttctgc aacaatcct  acaagtaccc gctgaccttc   360
ggccaaggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711

SEQ ID NO: 403     moltype = DNA   length = 1416
FEATURE            Location/Qualifiers
```

```
misc_feature          1..1416
                      note = Description of Artificial Sequence: Synthetic
                      polynucleotide
source                1..1416
                      mol_type = other DNA
                      organism = synthetic construct
SEQUENCE: 403
atggattgga cttggcgctt cttgtttgtg gtggcggcgg ctactggagt gcagtcagaa    60
gtgcaacttc aagaatccgg accgggactc gtgaagccgt cagaaactct ttcgcttacc   120
tgtaccgtgt ccggattttc cctgacttcc taccatgtgt cctgggtcag acagcctcct   180
ggaaagggac tggaatggat cggtgccatt tggactgggg gatccattgc gtataacccg   240
tccctgaagt cgcgcgtaac tatttcgaga gatacctcca agaaccaagt gtccctgaag   300
ctgtcgtccg tgactgccgc cgatactgcc gtgtactact gtgcccgcga tctgtccgac   360
tattactcga gttacacctc gttcgattac tggggacagg gtactctggt cactgtgtcg   420
tcggccagca ccaagggccc atcggtcttc ccctggcac cctcctccaa gagcacctct    480
ggggcacag cggccctggg ctgcctggtc aaggactact ccccgaacc ggtgacggtg     540
tcgtggaact caggcgccct gaccagcggc gtgcacacct tccggctgt cctacagtcc    600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt ccccccaaaa cccaaggaca cctcatgat ctcccggacc    840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgggtggt cagcgtcctc accgtcctgc accaggactg gctgaatggc  1020
aaggagtaca agtgcaaggt cagcaacaaa gccctcccag cccccatcga gaaaaccatc  1080
tccaaagcca aagggcagcc ccgagaacca caggtgtaca cctgccccc atcccgggat   1140
gagctgacca gaaccaggt cagcctgacc tgcctggtca aaggcttcta tcccagcgac   1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaagt ccctctccct gtctccgggt aaatag                            1416

SEQ ID NO: 404         moltype = DNA  length = 711
FEATURE                Location/Qualifiers
misc_feature           1..711
                       note = Description of Artificial Sequence: Synthetic
                       polynucleotide
source                 1..711
                       mol_type = other DNA
                       organism = synthetic construct
SEQUENCE: 404
atggatatgc gggtgccggc ccagcttctg ggcctgttgc tgctctggct ctccggagcg    60
cgctgtgaca tccaaatgac tcagtccccc tcatcgctt cagcctccgt gggagacaga   120
gtgaccatca cttgccgggc ttccgaaggg atttccaacg atctggcctg gtaccagcag   180
aagcccggaa aggcccctaa gctcctgatc tacgcggcca gccggctgca ggacggcgtg   240
ccttcccgct tttccggttc gggatcaggg actgactaca ccctgaccat ttccagcctg   300
cagcctgacg acttcgcgac ctactactgc caacaatcct acaagtaccc gctgaccttc   360
ggccaaggca ccaagctcga aatcaagcga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta a            711

SEQ ID NO: 405         moltype = DNA  length = 1416
FEATURE                Location/Qualifiers
misc_feature           1..1416
                       note = Description of Artificial Sequence: Synthetic
                       polynucleotide
source                 1..1416
                       mol_type = other DNA
                       organism = synthetic construct
SEQUENCE: 405
atggattgga cttggcgctt cttgtttgtg gtggcggcgg ctactggagt gcagtcagaa    60
gtgcaacttc aagaatccgg accgggactc gtgaagccgt cagaaactct ttcgcttacc   120
tgtaccgtgt ccggattttc cctgacttcc taccatgtgt cctgggtcag acagcctcct   180
ggaaagggac tggaatggat cggtgccatt tggactgggg gatccattgc gtataacccg   240
tccctgaagt cgcgcgtaac tatttcgaga gatacctcca agaaccaagt gtccctgaag   300
ctgtcgtccg tgactgccgc cgatactgcc gtgtactact gtgcccgcga tctgtccgac   360
tattactcga gttacacctc gttcgattac tggggacagg gtactctggt cactgtgtcg   420
tcggccagca ccaagggccc atcggtcttc ccctggcac cctcctccaa gagcacctct    480
ggggcacag cggccctggg ctgcctggtc aaggactact ccccgaacc ggtgacggtg     540
tcgtggaact caggcgccct gaccagcggc gtgcacacct tccggctgt cctacagtcc    600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt ccccccaaaa cccaaggaca cctcatgat ctcccggacc    840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
```

-continued

```
aacagcacgt accgggtggt cagcgtcctc accgtcctgc accaggactg gctgaatggc 1020
aaggagtaca agtgcaaggt cagcaacaaa gccctcccag cccccatcga gaaaaccatc 1080
tccaaagcca aagggcagcc ccgagaacca caggtgtaca ccctgccccc atcccgggat 1140
gagctgacca agaaccaggt cagcctgacc tgcctggtca aaggcttcta tcccagcgac 1200
atcgccgtgg agtgggagag caatgggcag ccggagaaca actacaagac cacgcctccc 1260
gtgctggact ccgacggctc cttcttcctc tacagcaagc tcaccgtgga caagagcagg 1320
tggcagcagg ggaacgtctt ctcatgctcc gtgatgcatg aggctctgca caaccactac 1380
acgcagaagt ccctctcccc gtctccgggt aaatag                         1416
```

```
SEQ ID NO: 406           moltype = DNA   length = 711
FEATURE                  Location/Qualifiers
misc_feature             1..711
                         note = Description of Artificial Sequence: Synthetic
                          polynucleotide
source                   1..711
                         mol_type = other DNA
                         organism = synthetic construct
SEQUENCE: 406
atggatatgc gggtgccggc ccagcttctg ggcctgttgc tgctctggct ctccggagcg 60
cgctgtgaca tccaaatgac tcagtccccc tcatcgcttt caacctccgt gggagacaga 120
gtgaccatca cttgccgggc ttccgaaggg atttccaacg atctggcctg gtaccagcag 180
aagcccggaa agtcgcctaa gctcctgatc tacgcggcca gccggctgca gtccggcgtg 240
ccttcccgct tttccggttc gggatcaggg actgactaca ccctgaccat ttccagcctg 300
cagcctgagg acttcgcgac ctacttctgc caacaatcct acaagtaccc gctgaccttc 360
ggccaaggca ccaagctcga aatcaagcga actgtggctg caccatctgt cttcatcttc 420
ccgccatctg atgagcagtt gaaatctgga actgcctctg ttgtgtgcct gctgaataac 480
ttctatccca gagaggccaa agtacagtgg aaggtggata acgccctcca atcgggtaac 540
tcccaggaga gtgtcacaga gcaggacagc aaggacagca cctacagcct cagcagcacc 600
ctgacgctga gcaaagcaga ctacgagaaa cacaaagtct acgcctgcga agtcacccat 660
cagggcctga gctcgcccgt cacaaagagc ttcaacaggg gagagtgtta a           711
```

```
SEQ ID NO: 407           moltype = DNA   length = 1416
FEATURE                  Location/Qualifiers
misc_feature             1..1416
                         note = Description of Artificial Sequence: Synthetic
                          polynucleotide
source                   1..1416
                         mol_type = other DNA
                         organism = synthetic construct
SEQUENCE: 407
atggattgga cttggcgctt cttgtttgtg gtggcggcgg ctactggagt gcagtcagaa 60
gtgcaacttg aagaatccgg accgggactc gtgaagccgt cagaaactct ttcgcttacc 120
tgtaccgtgt ccggattttc cctgacttcc taccatgtgt cctgggtcag acagcctcct 180
ggaaagggac tggaatggat cggtgccatt tggactgggg gatccattgc gtataacccg 240
tccctgaagt cgcgcgtaac tatttcgaga gataccgcca agaaccaagt gtccctgaag 300
ctgtcgtccg tgactgccgc cgatactgcc gtgtactact gtgcccgcga tctgtccgac 360
tattactcga gttacacctc gttcgattac tggggacagg gtactctggt cactgtgtcg 420
tcggccagca ccaagggccc atcggtcttc cccctggcac cctcctccaa gagcacctct 480
gggggcacag cggccctggg ctgcctggtc aaggactact tccccgaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacccag 660
acctacatct gcaacgtgaa tcacaagccc agcaacacca aggtggacaa gaaagttgag 720
cccaaatctt gtgacaaaac tcacacatgc ccaccgtgcc cagcacctga actcctgggg 780
ggaccgtcag tcttcctctt ccccccaaaa cccaaggaca cctcatgat ctcccggacc 840
cctgaggtca catgcgtggt ggtggacgtg agccacgaag accctgaggt caagttcaac 900
tggtacgtgg acggcgtgga ggtgcataat gccaagacaa agccgcggga ggagcagtac 960
aacagcacgt accgggtggt cagcgtcctc accgtcctgc accaggactg gctgaatggc 1020
aaggagtaca agtgcaaggt cagcaacaaa gccctcccag cccccatcga gaaaaccatc 1080
tccaaagcca aagggcagcc ccgagaacca caggtgtaca ccctgccccc atcccgggat 1140
gagctgacca agaaccaggt cagcctgacc tgcctggtca aaggcttcta tcccagcgac 1200
atcgccgtgg agtgggagag caatgggcag ccggagaaca actacaagac cacgcctccc 1260
gtgctggact ccgacggctc cttcttcctc tacagcaagc tcaccgtgga caagagcagg 1320
tggcagcagg ggaacgtctt ctcatgctcc gtgatgcatg aggctctgca caaccactac 1380
acgcagaagt ccctctcccc gtctccgggt aaatag                         1416
```

```
SEQ ID NO: 408           moltype = DNA   length = 711
FEATURE                  Location/Qualifiers
misc_feature             1..711
                         note = Description of Artificial Sequence: Synthetic
                          polynucleotide
source                   1..711
                         mol_type = other DNA
                         organism = synthetic construct
SEQUENCE: 408
atggatatgc gggtgccggc ccagcttctg ggcctgttgc tgctctggct ctccggagcg 60
cgctgtgaca tccaaatgac tcagtccccc tcatcgcttt caacctccgt gggagacaga 120
gtgaccatca cttgccgggc ttccgaaggg atttccaacg atctggcctg gtaccagcag 180
aagcccggaa agtcccctaa gctcctgatc tacgcggcca gccggctgca ggacggcgtg 240
ccttcccgct tttccggttc gggatcaggg actgactaca ccctgaccat ttccagcctg 300
```

-continued

```
cagcctgagg acgaagcgac ctacttctgc caacaatcct acaagtaccc gctgaccttc    360
ggccaaggca ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac     540
tcccaggaga gtgtcacaga gcaggacagc aaggacagcc cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

```
SEQ ID NO: 409         moltype = DNA   length = 1410
FEATURE                Location/Qualifiers
misc_feature           1..1410
                       note = Description of Artificial Sequence: Synthetic
                         polynucleotide
source                 1..1410
                       mol_type = other DNA
                       organism = synthetic construct
SEQUENCE: 409
atggattgga cttggcgctt cttgtttgtg gtggcggcgg ctactggagt gcagtcacaa    60
atccagctcg tgcagtccgg gccagagctg aaaaagcccg gagaatccgt caagattagc    120
tgcaaggcct ccggctacac cttcaccgac tacgcagtga actgggtcaa gcaggccccg    180
ggaaatggtc tgaagtggat gggctggatt aacacgcaga ccgggaagcc tacctacgcc    240
gacgacttca gcaacggtt cgtgttctct cttgaaacta gcgcctcgac ctcgttcctg    300
caaatcaaca acctgaacat cgaggacacc gccacctact tctgcacaag agactcctac    360
tattactcat cctccctcga ttactgggga caggcgtga tggtcactgt gtccagcgcc    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct gggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccggg tggtcagcgt cctcaccgtc ctgcaccagg actggctgaa tggcaaggag    1020
tacaagtgca aggtcagcaa caaagcctc ccagccccca tcgagaaaac catctccaaa    1080
gccaaagggc agccccgaga accacaggtg tacaccctgc cccatcccg ggatgagctg    1140
accaagaacc aggtcagcct gacctgctg gtcaaaggct tctatccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagtccctct ccctgtctcc gggtaaatag                                     1410
```

```
SEQ ID NO: 410         moltype = DNA   length = 711
FEATURE                Location/Qualifiers
misc_feature           1..711
                       note = Description of Artificial Sequence: Synthetic
                         polynucleotide
source                 1..711
                       mol_type = other DNA
                       organism = synthetic construct
SEQUENCE: 410
atggatatgc gggtgccggc ccagcttctg ggcctgttgc tgctctggct ctccggagcg    60
cgctgtgaca tccaaatgac tcagtcccct gcatccctga gcgcgagcct gggggagact    120
gtgtccattg aatgcctcgc ctccgccgga atttctaacg acctggcctg gtaccagcag    180
aagtccggaa agtcgcccca gctgctgatc tacgccgctt cgaggcttca ggatggtgtc    240
ccgtcacggt ttagcggatc aggatccggc accagattct ccctgaaaat cagcgacatg    300
cagcctgagg acgaagccga ctacttctgc caacaatcgt acaagtatcc ctggaccttc    360
ggcgggggca ccaagctcga actgaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac    540
tcccaggaga gtgtcacaga gcaggacagc aaggacagcc cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

```
SEQ ID NO: 411         moltype = DNA   length = 1410
FEATURE                Location/Qualifiers
misc_feature           1..1410
                       note = Description of Artificial Sequence: Synthetic
                         polynucleotide
source                 1..1410
                       mol_type = other DNA
                       organism = synthetic construct
SEQUENCE: 411
atggactgga cctggagatt tttattcgtc gtcgctgccg ccaccggagt gcaatcacaa    60
gtacaactgg tgcagagcgg ggccgaagtc aagaagcccg gcgcctccgt gaaagtgtcg    120
tgcaaagcct cgggttacac attcactgac tacgcagtga actgggtcag acaggcaccg    180
ggccaggggac tcgagtggat gggctggatc aacactcaga ctgggaagcc cacctatgct    240
cagaagttcc agggaagggt caccatgacc cgcgacacca gcacctccac cgtgtacatg    300
gaattgagca gcctgcggtc cgaagataca gccgtgtact attgtgcgag ggactcctac    360
```

```
tactactcat cctcgctcga ctactggggc cagggtaccc tcgtgaccgt tagctcggcc    420
tctactaagg gtccgtccgt gttcccgttg gccccgagct cgaagtccac ctccggggga    480
accgctgcgc ttggatgcct ggtcaaggac tacttccccg agcccgtgac ggtgtcctgg    540
aactccgggg ccctgacctc gggagtgcac actttcctg cggtgctgca gagctcagga    600
ctgtacagcc tcagctccgt cgtgaccgtg ccttcgtcct cgctgggcac ccagacctac    660
atctgcaacg tgaaccacaa gccgagcaac accaaggtcg acaagaaagt cgagccgaag    720
tcatgcgaca agactcacac ttgcccgccg tgccccgcgc ctgagcttct tggcgggccc    780
tccgtgttcc tgtttccgcc aaagcccaag gatactctga tgatttcgcg gactcctgaa    840
gtgacctgtg tggtcgtcga tgtgtcccat gaggacccg aggtcaagtt caattggtac    900
gtggacggcg tggaggtcca caatgccaag acgaagccgc gggaagaaca gtacaactcc    960
acttatcgcg tggtgtccgt gctcaccgtg ctgcatcagg actggctgaa cggaaaggag   1020
tacaagtgca aagtgtccaa caaggccctg cctgccccaa ttgaaaagac catctcaaaa   1080
gcgaaggggc agccgcgcga accacaagtg tacaccctgc ctccttcccg ggatgaactg   1140
accaagaacc aagtgtccct gacttgcctc gtgaagggtt tctacccgtc cgacatcgcc   1200
gtggaatggg agagcaacgg acagcccgag aacaattaca agactacccc acccgtgctc   1260
gattcggacg gcagcttctt cctgtactcc aagctgaccg tggataagtc ccgctggcaa   1320
cagggaaacg tgttcagttg ttccgtgatg cacgaagccc tgcacaacca ctacacccag   1380
aagtcactgt ccctgtctcc gggaaaataa                                     1410

SEQ ID NO: 412            moltype = DNA   length = 711
FEATURE                   Location/Qualifiers
misc_feature              1..711
                          note = Description of Artificial Sequence: Synthetic
                          polynucleotide
source                    1..711
                          mol_type = other DNA
                          organism = synthetic construct
SEQUENCE: 412
atggatatga gagtgcctgc acaacttctt ggattactgc tgctttggtt gtcgggagcc     60
agatgcgata tccagatgac ccagtccccg tcgagcctgt cagcttccgt gggcgaccgg    120
gtcaccatta cttgtcgcgc ctcggccggt attagcaatg acttggcctg gtaccagcag    180
aagcctggga aggcccccaa gctcctcatc tacgcggctt cccgcctgca agacggcgtg    240
ccgtcaaggt tcagcggttc gggctccgga actgacttca ccctcactat ctcgtccctg    300
caacccgaag atttcgcaac ctactactgc cagcagtcta ataagtaccc ctggactttc    360
ggacaaggca ccaagctcga gatcaagcgg accgtggccg ccccgagcgt gtttatcttc    420
ccgccatctg acgaacagct gaagtccggg acagcgtccg tggtctgcct gctcaacaac    480
ttctacccc gcgaggccaa agtgcagtgg aagtcgata acgcgctgca gtccggaaac    540
agccaggaaa gcgtgactga gcaagactcc aaggactcca cctactccct gtcatccacc    600
ctgacgctgt ccaaggccga ctacgaaaag cacaaggtct acgcctgcga agtgacccat    660
cagggcctgt caagccctgt gaccaagtcg ttcaaccggg gagagtgtta a             711

SEQ ID NO: 413            moltype = DNA   length = 1410
FEATURE                   Location/Qualifiers
misc_feature              1..1410
                          note = Description of Artificial Sequence: Synthetic
                          polynucleotide
source                    1..1410
                          mol_type = other DNA
                          organism = synthetic construct
SEQUENCE: 413
atggactgga cctggagatt tttattcgtc gtcgctgccg ccaccggagt gcaatcacaa     60
gtacaactgg tgcagagcgg ggccgaagtc aagaagcccg gcgcctccgt gaaagtgtcg    120
tgcaaagcct cgggttacac attcactgac tacgcagtga actgggtcag acaggcaccg    180
ggccaggac tcgagtggat gggctggatc aacactcaga ctgggaagcc cacctatgct    240
cagaagttcc agggaagggt caccatgacc ctggacacca gcatcactac cgcatacatg    300
gaattgagca gcctgcgtc cgaagataca gccgtgtact attgtactag ggactcctac    360
tactactcat cctcgctcga ctactggggc cagggtaccc tcgtgaccgt tagctcggcc    420
tctactaagg gtccgtccgt gttcccgttg gccccgagct cgaagtccac ctccggggga    480
accgctgcgc ttggatgcct ggtcaaggac tacttccccg agcccgtgac ggtgtcctgg    540
aactccgggg ccctgacctc gggagtgcac actttcctg cggtgctgca gagctcagga    600
ctgtacagcc tcagctccgt cgtgaccgtg ccttcgtcct cgctgggcac ccagacctac    660
atctgcaacg tgaaccacaa gccgagcaac accaaggtcg acaagaaagt cgagccgaag    720
tcatgcgaca agactcacac ttgcccgccg tgccccgcgc ctgagcttct tggcgggccc    780
tccgtgttcc tgtttccgcc aaagcccaag gatactctga tgatttcgcg gactcctgaa    840
gtgacctgtg tggtcgtcga tgtgtcccat gaggacccg aggtcaagtt caattggtac    900
gtggacggcg tggaggtcca caatgccaag acgaagccgc gggaagaaca gtacaactcc    960
acttatcgcg tggtgtccgt gctcaccgtg ctgcatcagg actggctgaa cggaaaggag   1020
tacaagtgca aagtgtccaa caaggccctg cctgccccaa ttgaaaagac catctcaaaa   1080
gcgaaggggc agccgcgcga accacaagtg tacaccctgc ctccttcccg ggatgaactg   1140
accaagaacc aagtgtccct gacttgcctc gtgaagggtt tctacccgtc cgacatcgcc   1200
gtggaatggg agagcaacgg acagcccgag aacaattaca agactacccc acccgtgctc   1260
gattcggacg gcagcttctt cctgtactcc aagctgaccg tggataagtc ccgctggcaa   1320
cagggaaacg tgttcagttg ttccgtgatg cacgaagccc tgcacaacca ctacacccag   1380
aagtcactgt ccctgtctcc gggaaaataa                                     1410

SEQ ID NO: 414            moltype = DNA   length = 711
FEATURE                   Location/Qualifiers
misc_feature              1..711
                          note = Description of Artificial Sequence: Synthetic
```

```
                        polynucleotide
source                  1..711
                        mol_type = other DNA
                        organism = synthetic construct
SEQUENCE: 414
atggatatga gagtgcctgc acaacttctt ggattactgc tgctttggtt gtcgggagcc    60
agatgcgata tccagatgac ccagtccccg tcgagcctgt cagcttccgt gggcgaccgg   120
gtcaccatta cttgtcgcgc ctcggccggt attagcaatg acttggcctg gtaccagcag   180
aagcctggga aggcccccaa gctcctcatc tacgcggctt cccgcctgca agacggcgtg   240
ccgtcaaggt tcagcggttc gggctccgga actgacttca ccctcactat ctcgtccctg   300
caacccgaag atttcgcaac ctactactgc cagcagtcct ataagtaccc ctggactttc   360
ggacaaggca ccaagctcga gatcaagcgg accgtggccg ccccgagcgt gtttatcttc   420
ccgccatctg acgaacagct gaagtccggg acagcgtccg tggtctgcct gctcaacaac   480
ttctaccccc gcgaggccaa agtgcagtgg aaagtcgata acgcgctgca gtccggaaac   540
agccaggaaa gcgtgactga gcaagactcc aaggactcca cctactccct gtcatccacc   600
ctgacgctgt ccaaggccga ctacgaaaag cacaaggtct acgcctgcga agtgacccat   660
cagggcctgt caagccctgt gaccaagtcg ttcaaccggg gagagtgtta a            711

SEQ ID NO: 415          moltype = DNA  length = 1410
FEATURE                 Location/Qualifiers
misc_feature            1..1410
                        note = Description of Artificial Sequence: Synthetic
                        polynucleotide
source                  1..1410
                        mol_type = other DNA
                        organism = synthetic construct
SEQUENCE: 415
atggactgga cctggagatt tttattcgtc gtcgctgccg ccaccggagt gcaatcacaa    60
gtacaactgt gcagagcgg ggccgaagtc aagaagcccg gcgcctccgt gaaaatctcg    120
tgcaaagcct cgggttacac attcactgac tacgcagtga actgggtcag acaggcaccg   180
ggccagggac tcgagtggat gggctggatc aacactcaga ctgggaagcc cacctatgct   240
cagaagttcc agggaaggtt caccttacc ttggacacca gcacctccac cgcgtacttg   300
gaaattagca gcctgcggtc cgaagataca gccgtgtact attgtactag ggactcctac   360
tactactcat cctcgctcga ctactgggc cagggtaccc tcgtgaccgt tagctcggcc   420
tctactaagg gtccgtcccgt gttccgttg gcccgaagct cgaagtccac ctccggggga   480
accgctgcgc ttgatgcct ggtcaaggac tacttcccg agcccgtgac ggtgtcctgg   540
aactccgggg ccctgacctc gggagtgcac actttcctg cggtgctgca gagctcagga   600
ctgtacagcc tcagctccgt cgtgaccgtg ccttcgtcct cgctgggcac ccagacctac   660
atctgcaacg tgaaccacaa gccgagcaac accaaggtcg acaagaaagt cgagccgaag   720
tcatgcgaca agactcacac ttgcccgccg tgccccgcgc tgagcttct ggcgggccc    780
tccgtgttcc tgtttccgcc aaagcccaag gatactctga tgatttcgcg gactcctgaa   840
gtgacctgtg tggtcgtcga tgtgtcccat gaggaccccg aggtcaagtt caattggtac   900
gtggacggcg tggaggtcca caatgccaag acgaagccgg gggaagaaca gtacaactcg   960
acttatcgcg tggtgtccgt gctcaccgtg ctgcatcagg actggctgaa cggaaaggag  1020
tacaagtgca agtgtccaa caaggccctg cctgccccaa ttgaaaagac catctcaaaa  1080
gcgaaggggc agccgcgcga accacaagtg tacaccctgc ctccttccg ggatgaactg   1140
accaagaacc aagtgtccct gacttgcctc gtgaaggtt tctacccgtc cgacatcgcc  1200
gtggaatggg agagcaacgg acagcccgag aacaattaca agactacccc accgtgtctc   1260
gattcggacg gcagcttctt cctgtactcc aagctgaccg tggataagtc ccgctggcaa  1320
cagggaaacg tgttcagttg ttccgtgatg cacgaagccc tgcacaacca ctacacccag  1380
aagtcactgt ccctgtctcc gggaaaataa                                   1410

SEQ ID NO: 416          moltype = DNA  length = 711
FEATURE                 Location/Qualifiers
misc_feature            1..711
                        note = Description of Artificial Sequence: Synthetic
                        polynucleotide
source                  1..711
                        mol_type = other DNA
                        organism = synthetic construct
SEQUENCE: 416
atggatatga gagtgcctgc acaacttctt ggattactgc tgctttggtt gtcgggagcc    60
agatgcgata tccagatgac ccagtccccg tcgagcctgt cagcttccgt gggcgaccgg   120
gtcaccatta cttgtcgcgc ctcggccggt attagcaatg acttggcctg gtaccagcag   180
aagcctggga aggcccccaa gctcctcatc tacgcggctt cccgcctgca agacggcgtg   240
ccgtcaaggt tcagcggttc gggctccgga actgacttca ccctcactat ctcgtccctg   300
caacccgaag atttcgcaac ctactactgc cagcagtcct ataagtaccc ctggactttc   360
ggacaaggca ccaagctcga gatcaagcgg accgtggccg ccccgagcgt gtttatcttc   420
ccgccatctg acgaacagct gaagtccggg acagcgtccg tggtctgcct gctcaacaac   480
ttctaccccc gcgaggccaa agtgcagtgg aaagtcgata acgcgctgca gtccggaaac   540
agccaggaaa gcgtgactga gcaagactcc aaggactcca cctactccct gtcatccacc   600
ctgacgctgt ccaaggccga ctacgaaaag cacaaggtct acgcctgcga agtgacccat   660
cagggcctgt caagccctgt gaccaagtcg ttcaaccggg gagagtgtta a            711

SEQ ID NO: 417          moltype = DNA  length = 1410
FEATURE                 Location/Qualifiers
misc_feature            1..1410
                        note = Description of Artificial Sequence: Synthetic
                        polynucleotide
```

```
source                  1..1410
                        mol_type = other DNA
                        organism = synthetic construct
SEQUENCE: 417
atggactgga cctggagatt tttattcgtc gtcgctgccg ccaccggagt gcaatcacaa    60
gtacaactgg tgcagagcgg ggccgaagtc aagaagcccg gcgcctccgt gaaagtgtcg   120
tgcaaagcct cgggttacac attcactgac tacgcagtga actgggtcag acaggcaccg   180
ggccaggac tcgagtggat gggctggatc aacactcaga ctgggaagcc cacctatgct   240
cagaagttcc agggaagggt caccatgacc ttggacacca gcacctccac ctcctacatg   300
gaattgagca gcctgcggtc cgaagataca gccgtgtact attgtactag ggactcctac   360
tactactcat cctcgctcga ctactggggc cagggtaccc tcgtgaccgt tagctcggcc   420
tctactaagg gtccgtccgt gttcccgttg gccccgagct cgaagtccac ctccggggga   480
accgctgcgc ttggatgcct ggtcaaggac tacttcccg agcccgtgac ggtgtcctgg    540
aactccgggg ccctgacctc gggagtgcac actttccctg cggtgctgca gagctcagga   600
ctgtacagcc tcagctccgt cgtgaccgtg ccttcgtcct cgctgggcac ccagacctac   660
atctgcaacg tgaaccacaa gccgagcaac accaaggtcg acaagaaagt cgagccgaag   720
tcatgcgaca agactcacac ttgccgccg tgccccgcgc ctgagcttct tggcgggccc    780
tccgtgttcc tgtttccgcc aaagcccaag gatactctga tgatttcgcg gactcctgaa   840
gtgacctgtg tggtcgtcga tgtgtcccat gaggaccccg aggtcaagtt caattggtac   900
gtggacggcg tggaggtcca caatgccaag acgaagccgc gggaagaaca gtacaactcc   960
acttatcgcg tggtgtccgt gctcaccgtg ctgcatcagg actggctgaa cggaaaggag  1020
tacaagtgca aagtgtccaa caaggccctg cctgcccaa ttgaaaagac catctcaaaa   1080
gcgaagggcc agccgcgcga accacaagtg tacaccctgc ctccttcccg ggatgaactg  1140
accaagaacc aagtgtccct gacttgcctc gtgaagggtt tctacccgtc cgacatcgcc  1200
gtggaatggg agagcaacgg acagcccgag aacaattaca agactacccc acccgtgctc  1260
gattcggacg gcagcttctt cctgtactcc aagctgaccg tggataagtc ccgctggcaa  1320
cagggaaacg tgttcagttg ttccgtgatg cacgaagccc tgcacaacca ctacacccag  1380
aagtcactgt ccctgtctcc gggaaaataa                                   1410

SEQ ID NO: 418          moltype = DNA  length = 711
FEATURE                 Location/Qualifiers
misc_feature            1..711
                        note = Description of Artificial Sequence: Synthetic
                        polynucleotide
source                  1..711
                        mol_type = other DNA
                        organism = synthetic construct
SEQUENCE: 418
atggatatga gagtgcctgc acaacttctt ggattactgc tgctttggtt gtcgggagcc    60
agatgcgata tccagatgac ccagtccccg tcgagcctgt cagcttccgt gggcgaccgg   120
gtcaccatta cttgtcgcgc ctcggccggt attagcaatg acttggcctg gtaccagcag   180
aagcctggga aggcccccaa gctcctcatc tacgcggctt cccgcctgca agacggcgtg   240
ccgtcaaggt tcagcggttc gggctccgga actgacttca ccctcactat ctcgtccctg   300
caacccgaag atttcgcaac ctactactgc cagcagtcct ataagtaccc ctggactttg   360
ggacaaggca ccaagctcga gatcaagcgg accgtggccg ccccgagcgt gtttatcttc   420
ccgccatctg acgaacagct gaagtccggg acagcgtccg tggtctgcct gctcaacaac   480
ttctacccc gcgaggccaa agtgcagtgg aaagtcgata actcccggga atccggaaac    540
agccaggaaa gcgtgactga gcaagactcc aaggactcca cctactccct gtcatccacc   600
ctgacgctgt ccaaggccga ctacgaaaag cacaaggtct acgcctgcga agtgacccat   660
cagggcctgt caagccctgt gaccaagtcg ttcaaccggg gagagtgtta a            711

SEQ ID NO: 419          moltype = DNA  length = 1410
FEATURE                 Location/Qualifiers
misc_feature            1..1410
                        note = Description of Artificial Sequence: Synthetic
                        polynucleotide
source                  1..1410
                        mol_type = other DNA
                        organism = synthetic construct
SEQUENCE: 419
atggactgga cctggagatt tttattcgtc gtcgctgccg ccaccggagt gcaatcacaa    60
gtacaactgg tgcagagcgg ggccgaagtc aagaagcccg gcgcctccgt gaaaatctcg   120
tgcaaagcct cgggttacac attcactgac tacgcagtga actgggtcag acaggcaccg   180
ggccaggac tcgagtggat gggctggatc aacactcaga ctgggaagcc cacctatgct   240
cagaagttcc agggaaggtt taccttcacc ctcgacacca gcacctccac ctcctacttg   300
gaaattagca gcctgcggtc cgaagataca gccgtgtact attgtactag ggactcctac   360
tactactcat cctcgctcga ctactggggc cagggtaccc tcgtgaccgt tagctcggcc   420
tctactaagg gtccgtccgt gttcccgttg gccccgagct cgaagtccac ctccggggga   480
accgctgcgc ttggatgcct ggtcaaggac tacttcccg agcccgtgac ggtgtcctgg    540
aactccgggg ccctgacctc gggagtgcac actttccctg cggtgctgca gagctcagga   600
ctgtacagcc tcagctccgt cgtgaccgtg ccttcgtcct cgctgggcac ccagacctac   660
atctgcaacg tgaaccacaa gccgagcaac accaaggtcg acaagaaagt cgagccgaag   720
tcatgcgaca agactcacac ttgccgccg tgccccgcgc ctgagcttct tggcgggccc    780
tccgtgttcc tgtttccgcc aaagcccaag gatactctga tgatttcgcg gactcctgaa   840
gtgacctgtg tggtcgtcga tgtgtcccat gaggaccccg aggtcaagtt caattggtac   900
gtggacggcg tggaggtcca caatgccaag acgaagccgc gggaagaaca gtacaactcc   960
acttatcgcg tggtgtccgt gctcaccgtg ctgcatcagg actggctgaa cggaaaggag  1020
tacaagtgca aagtgtccaa caaggccctg cctgcccaa ttgaaaagac catctcaaaa   1080
gcgaagggcc agccgcgcga accacaagtg tacaccctgc ctccttcccg ggatgaactg  1140
```

```
accaagaacc aagtgtccct gacttgcctc gtgaagggtt tctacccgtc cgacatcgcc   1200
gtggaatggg agagcaacgg acagcccgag aacaattaca agactacccc acccgtgctc   1260
gattcggacg gcagcttctt cctgtactcc aagctgaccg tggataagtc ccgctggcaa   1320
cagggaaacg tgttcagttg ttccgtgatg cacgaagccc tgcacaacca ctacacccag   1380
aagtcactgt ccctgtctcc gggaaaataa                                    1410
```

```
SEQ ID NO: 420          moltype = DNA   length = 711
FEATURE                 Location/Qualifiers
misc_feature            1..711
                        note = Description of Artificial Sequence: Synthetic
                         polynucleotide
source                  1..711
                        mol_type = other DNA
                        organism = synthetic construct
SEQUENCE: 420
atggatatga gagtgcctgc acaacttctt ggattactgc tgctttggtt gtcgggagcc    60
agatgcgata tccagatgac ccagtccccg tcgagcctgt cagcttccgt gggcgaccgg   120
gtcaccatta cttgtcgcgc ctcggccggt attagcaatg acttggcctg gtaccagcag   180
aagcctggga aggcccccaa gctcctcatc tacgcggctt cccgcctgca agacggcgtg   240
ccgtcaaggt tcagcggttc gggctccgga actgacttca ccctcactat ctcgtccctg   300
caacccgaag atttcgcaac ctactactgc cagcagtcct ataagtaccc ctggactttc   360
ggacaaggca ccaagctcga gatcaagcgg accgtggccc cccgagcgt gtttatcttc    420
ccgccatctg acgaacagct gaagtccggg acagcgtccg tggtctgcct gctcaacaac   480
ttctaccccc gcgaggccaa agtgcagtgg aaagtcgata cgcgctgca gtccggaaac    540
agccaggaaa gcgtgactga gcaagactcc aaggactcca cctactccct gtcatccacc   600
ctgacgctgt ccaaggccga ctacgaaaag cacaaggtct acgcctgcga agtgacccat   660
cagggcctgt caagccctgt gaccaagtcg ttcaaccggg gagagtgtta a             711
```

```
SEQ ID NO: 421          moltype = DNA   length = 1410
FEATURE                 Location/Qualifiers
misc_feature            1..1410
                        note = Description of Artificial Sequence: Synthetic
                         polynucleotide
source                  1..1410
                        mol_type = other DNA
                        organism = synthetic construct
SEQUENCE: 421
atggattgga cttggagatt tttgtttgtg gtggcggcgg ccactggagt gcaatccgaa    60
gtgcaattgg tggaatcggg tggtggactt gtgcagcctg gatcgtcact taagctgtcc   120
tgtgtggcct cgaagtttac cttctccaac tatgggatga actggattag acaagcccg    180
aagaagggac tggaatggat tgcgctgatc tattacaact cgaacaacaa gtactacgct   240
gattccgtga agggtcgctt cactatttcc cgcgacaact cgaagaacac tctgtacctt   300
gagatgaact ccctgcgctc ggaagatact gccatgtact actgtgccaa gtcgctgact   360
ggcggatccg attacttcga ttcctgggga caaggagtga tggtcactgt atccagtgcc   420
agcaccaagg gcccatcggt cttccccctg gcacctcct ccaagagcac ctctgggggc    480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccggg tggtcagcgt cctcaccgtc ctgcaccagg actggctgaa tggcaaggag  1020
tacaagtgca aggtctccaa caaagccctc ccagcccca tcgagaaaac catctccaaa   1080
gccaaagggc agccccgaga accacaggtg tacaccctgc ccccatcccg ggatgagctg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagtccctct ccctgtctcc gggtaaatag                                    1410
```

```
SEQ ID NO: 422          moltype = DNA   length = 711
FEATURE                 Location/Qualifiers
misc_feature            1..711
                        note = Description of Artificial Sequence: Synthetic
                         polynucleotide
source                  1..711
                        mol_type = other DNA
                        organism = synthetic construct
SEQUENCE: 422
atggacatgc gcgtgcctgc gcaattgctg ggctgcttc tcctgtggct ttcgggagcc     60
cgctgcgacg tgcagatgac ccagtcccct tcctacctgg ctcgtcacc gggagaatca   120
gtgtccatca gctgcaaggc ctccaagtcc attggtacct tcctggcctg gtaccaagag   180
aagcctgaaa agaccaacaa gctcctgatc tactcgggat caaccctgca atccggcact   240
ccgtcgcggt tctccggatc cgggtccggc accgacttta ctctgaccat tcggaacctg   300
gaacccgaag atttcgccgt gtactactgt cagcagcacg acgaataccc gtttactttc   360
ggctccggca ccaagctcga aatcaagcga actgtggctg caccatcgtg cttcatcttc   420
ccgccatctg atgagcagtt gaaatctgga actgcctctg ttgtgtgcct gctgaataac   480
```

```
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711

SEQ ID NO: 423          moltype = DNA   length = 1401
FEATURE                 Location/Qualifiers
misc_feature            1..1401
                        note = Description of Artificial Sequence: Synthetic
                         polynucleotide
source                  1..1401
                        mol_type = other DNA
                        organism = synthetic construct
SEQUENCE: 423
atggattgga cttggagatt tttgtttgtg gtggcggcgg ccactggagt gcaatccgaa    60
gtgcaattgg tggaatcggg tggtggactt gtgcagcctg gatcgtcact taagctgtcc    120
tgtgtggcct cgaagtttac cttctccaac tatgggatga actggattag acaagccccg    180
aagaaggac tggaatggat tgcgctgatc tattacaact cgaacaacaa gtactacgct    240
gattccgtga agggtcgctt cactatttcc cgcgacaact cgaagaacac tctgtacctt    300
gagatgaact ccctgcgctc ggaagatact gccatgtact actgtgccaa gtcgctgact    360
ggcggatccg attacttcga ttcctgggga caaggagtga tggtcactgt atccagtgcc    420
agcacaaagg gcccatccgt cttcccccctg gcgccctgct ccaggagcac ctccgagagc    480
acagccgccc tgggctgcct ggtcaaggac tacttcccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac gaagacctac    660
acctgcaacg tagatcacaa gcccagcaac accaaggtg acaagagagt tgagtccaaa    720
tatggtcccc catgcccatc ctgcccagca cctgagttcc tggggggacc atcagtcttc    780
ctgttccccc caaaacccaa ggacactctc atgatctccc ggaccctga ggtcacgtgc    840
gtggtggtgg acgtgagcca ggaagacccc gaggtccagt tcaactggta cgtggatggc    900
gtggaggtgc ataatgccaa gacaaagccg cgggaggagc agttcaacag cacgtaccgt    960
gtggtcagcg tcctcaccgt cctgcaccag gactggctga acggcaagga gtacaagtgc    1020
aaggtcagca caaaggcct cccgtcctcc atcgagaaaa ccatctccaa agccaaaggg    1080
cagccccgag agccacaggt gtacaccctg cccccatccc aggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacgc ctcccgtgct ggactccgac    1260
ggctccttct cctctacag caggctaacc gtggacaaga gcaggtggca ggaggggaat    1320
gtcttctcat gctccgtgat gcatgaggct ctgcacaacc actacacaca gaagtccctc    1380
tccctgtctc tgggtaaata g                                               1401

SEQ ID NO: 424          moltype = DNA   length = 711
FEATURE                 Location/Qualifiers
misc_feature            1..711
                        note = Description of Artificial Sequence: Synthetic
                         polynucleotide
source                  1..711
                        mol_type = other DNA
                        organism = synthetic construct
SEQUENCE: 424
atggacatgc gcgtgcctgc gcaattgctg gggctgcttc tcctgtggct ttcgggagcc    60
cgctgcgacg tgcagatgac ccagtcccct tcctacctgg ctgcgtcacc gggagaatca    120
gtgtccatca gctgcaaggc ctccaagtcc attggtacct tcctggcctg gtaccaagga    180
aagcctgaaa agaccaacaa gctcctgatc tactcgggat caaccctgca atccggcact    240
ccgtcgcggt tctccggatc cgggtccggc accgactta ctctgaccat tcggaacctg    300
gaacccgaag atttcgccgt gtactactgt cagcagcacg acgaataccc gtttactttc    360
ggctccggca ccaagctcga aatcaagcga actgtgctg caccatctgt cttcatcttc    420
ccgccatctg atgagcagtt gaaatctgga actgctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711

SEQ ID NO: 425          moltype = DNA   length = 1413
FEATURE                 Location/Qualifiers
misc_feature            1..1413
                        note = Description of Artificial Sequence: Synthetic
                         polynucleotide
source                  1..1413
                        mol_type = other DNA
                        organism = synthetic construct
SEQUENCE: 425
atggattgga cttggcgctt cttgtttgtg gtggcggcgg ctactggagt gcagtcacaa    60
gtcaaccttc tgcaatcccg ggcagcactc gtgaagcccg tgcttcagt gaagctgagc    120
tgcaaggcct ccgggtacac cttcaccgac tactatctgc attgggtcaa gcagtccac    180
gccaagagcc tggagtggat tggctacatc aacccgaaca acgctacgc tcgtacaat    240
gagaagttca gtccaaagc gaccctgacc gtgataagt ccactaacac cgcctacatg    300
gaactgtcca gactcacgtc cgccgactcg gccacctatt actgtgcccg gacaccaca    360
gactactaca acctccactt cgcctactgg ggccagggaa ctctggtcac cgtgtcgagc    420
gccagcacca agggcccatc ggtcttcccc ctggcaccct cctccaagag cacctctggg    480
ggcacagcgg ccctgggctg cctggtcaag gactacttcc ccgaaccggt gacggtgtcg    540
```

```
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gggtggtcag cgtcctcacc gtcctgcacc aggactggct gaatggcaag   1020
gagtacaagt gcaaggtcag caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagtccc tctccctgtc tccgggtaaa tag                                1413

SEQ ID NO: 426         moltype = DNA  length = 711
FEATURE                Location/Qualifiers
misc_feature           1..711
                       note = Description of Artificial Sequence: Synthetic
                        polynucleotide
source                 1..711
                       mol_type = other DNA
                       organism = synthetic construct
SEQUENCE: 426
atggatatgc gggtgccggc ccagcttctg ggcctgttgc tgctctggct ctccggagcg     60
cgctgtgaca ttcaaatgac ccagtcccct gcatcactga gcgcctcact ggggggaaact   120
gtcagcattg agtgcctgac ctccgaggga atctcgaacg acctggcctg gtatcagcag    180
aagtccggaa agtcgccgca gctgcttatc tacgacgcca gcagactcga ggacggcgtg    240
ccctcccgct tttccggctc tggttccggc actcggtaca gcctgaagat ctccggaatg    300
cagaccgaag atgaagctga ctacttctgc caacaatcgt acaaataccc actgaccttc    360
ggttccggga ccaagctcga aatcaagcga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711

SEQ ID NO: 427         moltype = DNA  length = 57
FEATURE                Location/Qualifiers
misc_feature           1..57
                       note = Description of Artificial Sequence: Synthetic
                        oligonucleotide
source                 1..57
                       mol_type = other DNA
                       organism = synthetic construct
SEQUENCE: 427
atggattgga cttggcgctt cttgtttgtg gtggcggcgg ctactggagt gcagtca        57

SEQ ID NO: 428         moltype = AA   length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 428
MDWTWRFLFV VAAATGVQS                                                  19

SEQ ID NO: 429         moltype = AA   length = 22
FEATURE                Location/Qualifiers
REGION                 1..22
                       note = Description of Artificial Sequence: Synthetic peptide
source                 1..22
                       mol_type = protein
                       organism = synthetic construct
SEQUENCE: 429
MDMRVPAQLL GLLLLWLSGA RC                                              22

SEQ ID NO: 430         moltype = DNA  length = 66
FEATURE                Location/Qualifiers
misc_feature           1..66
                       note = Description of Artificial Sequence: Synthetic
                        oligonucleotide
source                 1..66
                       mol_type = other DNA
                       organism = synthetic construct
SEQUENCE: 430
atggatatgc gggtgccggc ccagcttctg ggcctgttgc tgctctggct ctccggagcg     60
```

```
SEQ ID NO: 431           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 431
ASEGISNDLA                                                                      10

SEQ ID NO: 432           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 432
ASAGISNDLA                                                                      10

SEQ ID NO: 433           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 433
ASKSIGTFLA                                                                      10

SEQ ID NO: 434           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 434
EVQLQESGPG LVKPSETLSL TCTVSGFSLT SYHVSWVRQP PGKGLEWIGA IWTGGSIAYN              60
PSLKSRVTIS RDTSKNQVSL KLSSVTAADT AVYYCARDLS DYYSSYTSFD YWGQGTLVTV             120
SS                                                                            122

SEQ ID NO: 435           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 435
GFSLTSYHVS                                                                      10

SEQ ID NO: 436           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 436
AIWTGGSIA                                                                        9

SEQ ID NO: 437           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 437
DLSDYYSSYT SFDY                                                                 14

SEQ ID NO: 438           moltype = AA  length = 452
FEATURE                  Location/Qualifiers
REGION                   1..452
                         note = Description of Artificial Sequence: Synthetic
```

|  |  |  |
|---|---|---|
| source | 1..452<br>mol_type = protein<br>organism = synthetic construct | |

SEQUENCE: 438

```
EVQLQESGPG LVKPSETLSL TCTVSGFSLT SYHVSWVRQP PGKGLEWIGA IWTGGSIAYN     60
PSLKSRVTIS RDTSKNQVSL KLSSVTAADT AVYYCARDLS DYYSSYTSFD YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452
```

| SEQ ID NO: 439<br>FEATURE<br>REGION | moltype = AA length = 107<br>Location/Qualifiers<br>1..107<br>note = Description of Artificial Sequence: Synthetic<br>polypeptide |  |
|---|---|---|
| source | 1..107<br>mol_type = protein<br>organism = synthetic construct | |

SEQUENCE: 439

```
DIQMTQSPSS LSASVGDRVT ITCRASEGIS NDLAWYQQKP GKAPKLLIYA ASRLQDGVPS     60
RFSGSGSGTD YTLTISSLQP EDFATYYCQQ SYKYPLTFGQ GTKLEIK                  107
```

| SEQ ID NO: 440<br>FEATURE<br>REGION | moltype = AA length = 11<br>Location/Qualifiers<br>1..11<br>note = Description of Artificial Sequence: Synthetic peptide |  |
|---|---|---|
| source | 1..11<br>mol_type = protein<br>organism = synthetic construct | |

SEQUENCE: 440

```
RASEGISNDL A                                                          11
```

| SEQ ID NO: 441<br>FEATURE<br>REGION | moltype = AA length = 7<br>Location/Qualifiers<br>1..7<br>note = Description of Artificial Sequence: Synthetic peptide |  |
|---|---|---|
| source | 1..7<br>mol_type = protein<br>organism = synthetic construct | |

SEQUENCE: 441

```
AASRLQD                                                                7
```

| SEQ ID NO: 442<br>FEATURE<br>REGION | moltype = AA length = 9<br>Location/Qualifiers<br>1..9<br>note = Description of Artificial Sequence: Synthetic peptide |  |
|---|---|---|
| source | 1..9<br>mol_type = protein<br>organism = synthetic construct | |

SEQUENCE: 442

```
QQSYKYPLT                                                              9
```

| SEQ ID NO: 443<br>FEATURE<br>REGION | moltype = AA length = 214<br>Location/Qualifiers<br>1..214<br>note = Description of Artificial Sequence: Synthetic<br>polypeptide |  |
|---|---|---|
| source | 1..214<br>mol_type = protein<br>organism = synthetic construct | |

SEQUENCE: 443

```
DIQMTQSPSS LSASVGDRVT ITCRASEGIS NDLAWYQQKP GKAPKLLIYA ASRLQDGVPS     60
RFSGSGSGTD YTLTISSLQP EDFATYYCQQ SYKYPLTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

| SEQ ID NO: 444<br>FEATURE<br>REGION | moltype = AA length = 122<br>Location/Qualifiers<br>1..122<br>note = Description of Artificial Sequence: Synthetic<br>polypeptide |  |
|---|---|---|
| source | 1..122<br>mol_type = protein<br>organism = synthetic construct | |

SEQUENCE: 444

```
EVQLQESGPG LVKPSETLSL TCTVSGFSLT SYHVSWVRQP PGKGLEWIGA IWTGGSIAYN    60
PSLKSRVTIS RDTSKNQVSL KLSSVTAADT AVYYCARDLS DYYSSYTSFD YWGQGTLVTV   120
SS                                                                  122

SEQ ID NO: 445          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 445
GFSLTSYHVS                                                           10

SEQ ID NO: 446          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 446
AIWTGGSIA                                                             9

SEQ ID NO: 447          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 447
DLSDYYSSYT SFDY                                                      14

SEQ ID NO: 448          moltype = AA   length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 448
EVQLQESGPG LVKPSETLSL TCTVSGFSLT SYHVSWVRQP PGKGLEWIGA IWTGGSIAYN    60
PSLKSRVTIS RDTSKNQVSL KLSSVTAADT AVYYCARDLS DYYSSYTSFD YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLGK                                    449

SEQ ID NO: 449          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 449
DIQMTQSPSS LSASVGDRVT ITCRASEGIS NDLAWYQQKP GKAPKLLIYA ASRLQDGVPS    60
RFSGSGSGTD YTLTISSLQP EDFATYYCQQ SYKYPLTFGQ GTKLEIK                 107

SEQ ID NO: 450          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 450
RASEGISNDL A                                                         11

SEQ ID NO: 451          moltype = AA   length = 7
FEATURE                 Location/Qualifiers
REGION                  1..7
                        note = Description of Artificial Sequence: Synthetic peptide
source                  1..7
```

```
                        mol_type = protein
                        organism = synthetic construct
SEQUENCE: 451
AASRLQD                                                                   7

SEQ ID NO: 452          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 452
QQSYKYPLT                                                                 9

SEQ ID NO: 453          moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 453
DIQMTQSPSS LSASVGDRVT ITCRASEGIS NDLAWYQQKP GKAPKLLIYA ASRLQDGVPS  60
RFSGSGSGTD YTLTISSLQP EDFATYYCQQ SYKYPLTFGQ GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                             214

SEQ ID NO: 454          moltype = AA   length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 454
QVQLVQSGAE VKKPGASVKI SCKASGYTFT DYAVNWVRQA PGQGLEWMGW INTQTGKPTY  60
AQKFQGRFTF TLDTSTSTSY LEISSLRSED TAVYYCTRDS YYYSSSLDYW GQGTLVTVSS 120

SEQ ID NO: 455          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 455
GYTFTDYAVN                                                               10

SEQ ID NO: 456          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 456
WINTQTGKPT                                                               10

SEQ ID NO: 457          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 457
DSYYYSSSLD Y                                                             11

SEQ ID NO: 458          moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
```

```
SEQUENCE: 458
QVQLVQSGAE VKKPGASVKI SCKASGYTFT DYAVNWVRQA PGQGLEWMGW INTQTGKPTY    60
AQKFQGRFTF TLDTSTSTSY LEISSLRSED TAVYYCTRDS YYYSSSLDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 459         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 459
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIK                 107

SEQ ID NO: 460         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 460
RASAGISNDL A                                                        11

SEQ ID NO: 461         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 461
AASRLQD                                                              7

SEQ ID NO: 462         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 462
QQSYKYPWT                                                            9

SEQ ID NO: 463         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 463
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 464         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 464
EVQLVQSGAE VKKPGASVKI SCKASGYTFT DYAVNWVRQA PGQGLEWMGW INTQTGKPTY    60
AQKFQGRFTF TLDTSTSTSY LEISSLRSED TAVYYCTRDS YYYSSSLDYW GQGTLVTVSS   120

SEQ ID NO: 465         moltype = AA  length = 10
```

```
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 465
GYTFTDYAVN                                                                    10

SEQ ID NO: 466           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 466
WINTQTGKPT                                                                    10

SEQ ID NO: 467           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 467
DSYYYSSSLD Y                                                                  11

SEQ ID NO: 468           moltype = AA   length = 447
FEATURE                  Location/Qualifiers
REGION                   1..447
                         note = Description of Artificial Sequence: Synthetic
                          polypeptide
source                   1..447
                         mol_type = protein
                         organism = synthetic construct
SEQUENCE: 468
EVQLVQSGAE VKKPGASVKI SCKASGYTFT DYAVNWVRQA PGQGLEWMGW INTQTGKPTY    60
AQKFQGRFTF TLDTSTSTSY LEISSLRSED TAVYYCTRDS YYYSSSLDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 469           moltype = AA   length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 469
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIK                 107

SEQ ID NO: 470           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 470
RASAGISNDL A                                                                  11

SEQ ID NO: 471           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 471
AASRLQD                                                                        7
```

-continued

```
SEQ ID NO: 472          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 472
QQSYKYPWT                                                                 9

SEQ ID NO: 473          moltype = AA   length = 214
FEATURE                 Location/Qualifiers
REGION                  1..214
                        note = Description of Artificial Sequence: Synthetic
                        polypeptide
source                  1..214
                        mol_type = protein
                        organism = synthetic construct
SEQUENCE: 473
DIQMTQSPSS LSASVGDRVT ITCRASAGIS NDLAWYQQKP GKAPKLLIYA ASRLQDGVPS    60
RFSGSGSGTD FTLTISSMQP EDFATYYCQQ SYKYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 474          moltype = AA   length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 474
EVQLQESGPG LVKPSETLSL TCTVSGFSLT SYHVSWVRQP PGKGLEWMGA IWTGGSIAYN    60
PSLKSRLTIS RDTSKNQVSL KMSSLTAADT AVYYCARDLS DYYSSYTSFD YWGQGTLVTV   120
SS                                                                  122

SEQ ID NO: 475          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 475
GFSLTSYHVS                                                               10

SEQ ID NO: 476          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 476
AIWTGGSIA                                                                 9

SEQ ID NO: 477          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 477
DLSDYYSSYT SFDY                                                          14

SEQ ID NO: 478          moltype = AA   length = 449
FEATURE                 Location/Qualifiers
REGION                  1..449
                        note = Description of Artificial Sequence: Synthetic
                        polypeptide
source                  1..449
                        mol_type = protein
                        organism = synthetic construct
SEQUENCE: 478
EVQLQESGPG LVKPSETLSL TCTVSGFSLT SYHVSWVRQP PGKGLEWMGA IWTGGSIAYN    60
PSLKSRLTIS RDTSKNQVSL KMSSLTAADT AVYYCARDLS DYYSSYTSFD YWGQGTLVTV   120
SSASTKGPSV FPLAPCSRST SESTAALGCL VKDYFPEPVT VSWNSGALTS GVHTFPAVLQ   180
```

```
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGK                                     449

SEQ ID NO: 479          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 479
DIQMTQSPSS LSASVGDRVT ITCRASEGIS NDLAWYQQKP GKAPKLLIYA ASRLQSGVPS    60
RFSGSGSGTD YTLTISSMQP EDFATYYCQQ SYKYPLTFGQ GTKLEIK                 107

SEQ ID NO: 480          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 480
RASEGISNDL A                                                         11

SEQ ID NO: 481          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 481
AASRLQD                                                               7

SEQ ID NO: 482          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 482
QQSYKYPLT                                                             9

SEQ ID NO: 483          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 483
DIQMTQSPSS LSASVGDRVT ITCRASEGIS NDLAWYQQKP GKAPKLLIYA ASRLQSGVPS    60
RFSGSGSGTD YTLTISSMQP EDFATYYCQQ SYKYPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 484          moltype = AA  length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 484
HHHHHHHHGE RGSPGPKGAP GAPGIPGLPG PAAEKGEKGA AGRDGTPGVQ GPQGPPGSKG    60
EAGLQGLTGA PGKQGATGAP GPRGEKGSKG DIGLTGPKGE HGTKGDKGDL GLPGNKGDMG   120
MKGDTGPMGS PGAQGGKGDA GKPGLPGLAG SPGVKGDQGK PGVQGVPGPQ GAPGLSGAKG   180
EPGRTGLPGP AGPPGIAGNP GIAGVKGSKG DTGIQGQKGT KGESGVPGLV GRKGDTGSPG   240
LAGPKGEPGR VGQKGDPGMK GSSGQQGQKG EKGQKGESFQ RVRIMGGTNR GRAEVYYNNE   300
WGTICDDDWD NNDATVFCRM LGYSRGRALS SYGGGSGNIW LDNVNCRGTE NSLWDCSKNS   360
WGNHNCVHNE DAGVECS                                                  377
```

```
SEQ ID NO: 485              moltype = AA   length = 379
FEATURE                     Location/Qualifiers
REGION                      1..379
                            note = Description of Artificial Sequence: Synthetic
                             polypeptide
source                      1..379
                            mol_type = protein
                            organism = synthetic construct
SEQUENCE: 485
HHHHHHHHKG ERGSPGPKGA PGAPGIPGLP GPAAEKGEKG AAGRDGTPGV QGPQGPPGSK    60
GEAGLQGLTG APGKQGATGA PGPRGEKGSK GDIGLTGPKG EHGTKGDKGD LGLPGNKGDM   120
GMKGDTGPMG SPGAQGGKGD AGKPGLPGLA GSPGVKGDQG KPGVQGVPGP QGAPGLSGAK   180
GEPGRTGLPG PAGPPGIAGN PGIAGVKGSK GDTGIQGQKG TKGESGVPGL VGRKGDTGSP   240
GLAGPKGEPG RVGQKGDPGM KGSSGQQGQK GEKGQKGENS VSVRIVGSSN RGRAEVYYSG   300
TWGTICDDEW QNSDAIVFCR MLGYSKGRAL YKVGAGTGQI WLDNVQCRGT ESTLWSCTKN   360
SWGHHDCSHE EDAGVECSV                                               379

SEQ ID NO: 486              moltype = AA   length = 379
FEATURE                     Location/Qualifiers
REGION                      1..379
                            note = Description of Artificial Sequence: Synthetic
                             polypeptide
source                      1..379
                            mol_type = protein
                            organism = synthetic construct
SEQUENCE: 486
HHHHHHKGEQ GAPGLQGHKG AMGMPGAPGP PGPPAEKGAK GAMGRDGATG PSGPQGPPGV    60
KGEAGLQGPQ GAPGKQGATG TPGPQGEKGS KGDGGLIGPK GETGTKGEKG DLGLPGSKGD   120
RGMKGDAGVM GPPGAQGSKG DFGRPGPPGL AGFPGAKGDQ GQPGLQGVPG PPGAVGHPGA   180
KGEPGSAGSP GRAGLPGSPG SPGATGLKGS KGDTGLQGQG GRKGESGVPG PAGVKGEQGS   240
PGLAGPKGAP GQAGQKGDQG VKGSSGEQGV KGEKGERGES FQRVRIMGGT NRGRAEVYYN   300
NEWGTICDDD WDNNDATVFC RMLGYSRGRA LSSYGGGSGN IWLDNVNCRG TENSLWDCSK   360
NSWGNHNCVH NEDAGVECS                                               379

SEQ ID NO: 487              moltype = DNA   length = 22
FEATURE                     Location/Qualifiers
misc_feature                1..22
                            note = Description of Artificial Sequence: Synthetic primer
source                      1..22
                            mol_type = other DNA
                            organism = synthetic construct
SEQUENCE: 487
ttgtcgttca ctgccatcaa tc                                            22

SEQ ID NO: 488              moltype = DNA   length = 24
FEATURE                     Location/Qualifiers
misc_feature                1..24
                            note = Description of Artificial Sequence: Synthetic primer
source                      1..24
                            mol_type = other DNA
                            organism = synthetic construct
SEQUENCE: 488
acattgatgt ctttggggta gaag                                          24

SEQ ID NO: 489              moltype = DNA   length = 20
FEATURE                     Location/Qualifiers
misc_feature                1..20
                            note = Description of Artificial Sequence: Synthetic primer
source                      1..20
                            mol_type = other DNA
                            organism = synthetic construct
SEQUENCE: 489
agctgggaag gtgtgcacac                                               20

SEQ ID NO: 490              moltype = DNA   length = 20
FEATURE                     Location/Qualifiers
misc_feature                1..20
                            note = Description of Artificial Sequence: Synthetic primer
source                      1..20
                            mol_type = other DNA
                            organism = synthetic construct
SEQUENCE: 490
gggatccaga gttccaggtc                                               20

SEQ ID NO: 491              moltype = DNA   length = 23
FEATURE                     Location/Qualifiers
misc_feature                1..23
                            note = Description of Artificial Sequence: Synthetic primer
source                      1..23
```

```
                        mol_type = other DNA
                        organism = synthetic construct
SEQUENCE: 491
gtgaggatga tgtcttatga aca                                       23

SEQ ID NO: 492          moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 492
gccatcaatc ttccacttga cac                                       23

SEQ ID NO: 493          moltype = DNA   length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 493
gagatgstttt tctcgatggg                                          20

SEQ ID NO: 494          moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 494
gsgggaagat gaagacagat g                                         21

SEQ ID NO: 495          moltype = AA    length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 495
HHHHHHKGEQ GAPGLQGHKG AMGMPGAPGP PGPPAEKGAK GAMGRDGATG PSGPQGPPGV  60
KGEAGLQGPQ GAPGKQGATG TPGPQGEKGS KGDGGLIGPK GETGTKGEKG DLGLPGSKGD 120
RGMKGDAGVM GPPGAQGSKG DFGRPGPPGL AGFPGAKGDQ GQPGLQGVPG PPGAVGHPGA 180
KGEPGSAGSP GRAGLPGSPG SPGATGLKGS KGDTGLQGQQ GRKGESGVPG PAGVKGEQGS 240
PGLAGPKGAP GQAGQKGDQG VKGSSGEQGV KGEKGERGEN SVSVRIVGSS NRGRAEVYYS 300
GTWGTICDDE WQNSDAIVFC RMLGYSKGRA LYKVGAGTGQ IWLDNVQCRG TESTLWSCTK 360
NSWGHHDCSH EEDAGVECSV                                           380

SEQ ID NO: 496          moltype = AA    length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 496
HHHHHHKGEQ GAPGLQGHKG AMGMPGAPGP PGPPAEKGAK GAMGRDGATG PSGPQGPPGV  60
KGEAGLQGPQ GAPGKQGATG TPGPQGEKGS KGDGGLIGPK GETGTKGEKG DLGLPGSKGD 120
RGMKGDAGVM GPPGAQGSKG DFGRPGPPGL AGFPGAKGDQ GQPGLQGVPG PPGAVGHPGA 180
KGEPGSAGSP GRAGLPGSPG SPGATGLKGS KGDTGLQGQQ GRKGESGVPG PAGVKGEQGS 240
PGLAGPKGAP GQAGQKGDQG VKGSSGEQGV KGEKGERGEN SVSVRIVGSS NRGRAEVYYN 300
NEWGTICDDE WQNSDAIVFC RMLGYSKGRA LYKVGAGTGQ IWLDNVQCRG TESTLWSCTK 360
NSWGHHDCSH EEDAGVECSV                                           380

SEQ ID NO: 497          moltype = AA    length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 497
HHHHHHKGEQ GAPGLQGHKG AMGMPGAPGP PGPPAEKGAK GAMGRDGATG PSGPQGPPGV  60
```

```
KGEAGLQGPQ GAPGKQGATG TPGPQGEKGS KGDGGLIGPK GETGTKGEKG DLGLPGSKGD   120
RGMKGDAGVM GPPGAQGSKG DFGRPGPPGL AGFPGAKGDQ GQPGLQGVPG PPGAVGHPGA   180
KGEPGSAGSP GRAGLPGSPG SPGATGLKGS KGDTGLQGQQ GRKGESGVPG PAGVKGEQGS   240
PGLAGPKGAP GQAGQKGDQG VKGSSGEQGV KGEKGERGEN SVSVRIVGSS NRGRAEVYYS   300
GTWGTICDDD WDNNDAIVFC RMLGYSRGRA LYKVGAGTGQ IWLDNVQCRG TESTLWSCTK   360
NSWGHHDCSH EEDAGVECSV                                              380

SEQ ID NO: 498          moltype = AA  length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 498
HHHHHHKGEQ GAPGLQGHKG AMGMPGAPGP PGPPAEKGAK GAMGRDGATG PSGPQGPPGV    60
KGEAGLQGPQ GAPGKQGATG TPGPQGEKGS KGDGGLIGPK GETGTKGEKG DLGLPGSKGD   120
RGMKGDAGVM GPPGAQGSKG DFGRPGPPGL AGFPGAKGDQ GQPGLQGVPG PPGAVGHPGA   180
KGEPGSAGSP GRAGLPGSPG SPGATGLKGS KGDTGLQGQQ GRKGESGVPG PAGVKGEQGS   240
PGLAGPKGAP GQAGQKGDQG VKGSSGEQGV KGEKGERGEN SVSVRIVGSS NRGRAEVYYS   300
GTWGTICDDE WDNSDAIVFC RMLGYSKGRA LSSVGAGTGQ IWLDNVQCRG TESTLWSCTK   360
NSWGHHDCSH EEDAGVECSV                                              380

SEQ ID NO: 499          moltype = AA  length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 499
HHHHHHKGEQ GAPGLQGHKG AMGMPGAPGP PGPPAEKGAK GAMGRDGATG PSGPQGPPGV    60
KGEAGLQGPQ GAPGKQGATG TPGPQGEKGS KGDGGLIGPK GETGTKGEKG DLGLPGSKGD   120
RGMKGDAGVM GPPGAQGSKG DFGRPGPPGL AGFPGAKGDQ GQPGLQGVPG PPGAVGHPGA   180
KGEPGSAGSP GRAGLPGSPG SPGATGLKGS KGDTGLQGQQ GRKGESGVPG PAGVKGEQGS   240
PGLAGPKGAP GQAGQKGDQG VKGSSGEQGV KGEKGERGEN SVSVRIVGSS NRGRAEVYYS   300
GTWGTICDDE WQNSDAIVFC RMLGYSKGRA LYKVGAGTGQ IWLDNVQCRG TENSLWDCSK   360
NSWGHHDCSH EEDAGVECSV                                              380

SEQ ID NO: 500          moltype = AA  length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 500
HHHHHHKGEQ GAPGLQGHKG AMGMPGAPGP PGPPAEKGAK GAMGRDGATG PSGPQGPPGV    60
KGEAGLQGPQ GAPGKQGATG TPGPQGEKGS KGDGGLIGPK GETGTKGEKG DLGLPGSKGD   120
RGMKGDAGVM GPPGAQGSKG DFGRPGPPGL AGFPGAKGDQ GQPGLQGVPG PPGAVGHPGA   180
KGEPGSAGSP GRAGLPGSPG SPGATGLKGS KGDTGLQGQQ GRKGESGVPG PAGVKGEQGS   240
PGLAGPKGAP GQAGQKGDQG VKGSSGEQGV KGEKGERGEN SVSVRIVGSS NRGRAEVYYS   300
GTWGTICDDE WQNSDAIVFC RMLGYSKGRA LYKVGAGTGQ IWLDNVQCRG TESTLWSCTK   360
NSWGNHNCVH NEDAGVECSV                                              380

SEQ ID NO: 501          moltype = AA  length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 501
HHHHHHKGEQ GAPGLQGHKG AMGMPGAPGP PGPPAEKGAK GAMGRDGATG PSGPQGPPGV    60
KGEAGLQGPQ GAPGKQGATG TPGPQGEKGS KGDGGLIGPK GETGTKGEKG DLGLPGSKGD   120
RGMKGDAGVM GPPGAQGSKG DFGRPGPPGL AGFPGAKGDQ GQPGLQGVPG PPGAVGHPGA   180
KGEPGSAGSP GRAGLPGSPG SPGATGLKGS KGDTGLQGQQ GRKGESGVPG PAGVKGEQGS   240
PGLAGPKGAP GQAGQKGDQG VKGSSGEQGV KGEKGERGEN SVSVRIVGSS NRGRAEVYYS   300
GTWGTICDDD WDNSDAIVFC RMLGYSKGRA LYKVGAGTGQ IWLDNVNCRG TESTLWSCSK   360
NSWGHHDCSH EEDAGVECSV                                              380

SEQ ID NO: 502          moltype = AA  length = 380
FEATURE                 Location/Qualifiers
REGION                  1..380
                        note = Description of Artificial Sequence: Synthetic
```

-continued

```
                         polypeptide
source                  1..380
                        mol_type = protein
                        organism = synthetic construct
SEQUENCE: 502
HHHHHHKGEQ GAPGLQGHKG AMGMPGAPGP PGPPAEKGAK GAMGRDGATG PSGPQGPPGV  60
KGEAGLQGPQ GAPGKQGATG TPGPQGEKGS KGDGGLIGPK GETGTKGEKG DLGLPGSKGD  120
RGMKGDAGVM GPPGAQGSKG DFGRPGPPGL AGFPGAKGDQ GQPGLQGVPG PPGAVGHPGA  180
KGEPGSAGSP GRAGLPGSPG SPGATGLKGS KGDTGLQGQQ GRKGESGVPG PAGVKGEQGS  240
PGLAGPKGAP GQAGQKGDQG VKGSSGEQGV KGEKGERGES FQRVRIVGGT NRGRAEVYYS  300
GTWGTICDDE WQNSDAIVFC RMLGYSKGRA LYKVGAGTGQ IWLDNVQCRG TESTLWSCTK  360
NSWGHHDCSH EEDAGVECSV                                            380

SEQ ID NO: 503          moltype = AA  length = 101
FEATURE                 Location/Qualifiers
REGION                  1..101
                        note = Description of Artificial Sequence: Synthetic
                         polypeptide
source                  1..101
                        mol_type = protein
                        organism = synthetic construct
SEQUENCE: 503
SFQRVRIVGG TNRGRAEVYY SGTWGTICDD EWQNSDAIVF CRMLGYSKGR ALYKVGAGTG  60
QIWLDNVQCR GTESTLWSCT KNSWGHHDCS HEEDAGVECS V                    101

SEQ ID NO: 504          moltype = AA  length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 504
HHHHHHHHGE RGSPGPKGAP GAPGIPGLPG PAAEKGEKGA AGRDGTPGVQ GPQGPPGSKG  60
EAGLQGLTGA PGKQGATGAP GPRGEKGSKG DIGLTGPKGE HGTKGDKGDL GLPGNKGDMG  120
MKGDTGPMGS PGAQGGKGDA GKPGLPGLAG SPGVKGDQGK PGVQGVPGPQ GAPGLSGAKG  180
EPGRTGLPGP AGPPGIAGNP GIAGVKGSKG DTGIQGQKGT KGESGVPGLV GRKGDTGSPG  240
LAGPKGEPGR VGQKGDPGMK GSSGQQGQKG EKGQKGESFQ RVRIMGGTNR GRAEVYYSGT  300
WGTICDDDWD NNDATVFCRM LGYSRGRALS SYGGGSGNIW LDNVNCRGTE NSLWDCSKNS  360
WGNHNCVHNE DAGVECS                                               377

SEQ ID NO: 505          moltype = AA  length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 505
HHHHHHHHGE RGSPGPKGAP GAPGIPGLPG PAAEKGEKGA AGRDGTPGVQ GPQGPPGSKG  60
EAGLQGLTGA PGKQGATGAP GPRGEKGSKG DIGLTGPKGE HGTKGDKGDL GLPGNKGDMG  120
MKGDTGPMGS PGAQGGKGDA GKPGLPGLAG SPGVKGDQGK PGVQGVPGPQ GAPGLSGAKG  180
EPGRTGLPGP AGPPGIAGNP GIAGVKGSKG DTGIQGQKGT KGESGVPGLV GRKGDTGSPG  240
LAGPKGEPGR VGQKGDPGMK GSSGQQGQKG EKGQKGESFQ RVRIMGGTNR GRAEVYYNNE  300
WGTICDDEWQ NSDATVFCRM LGYSKGRALS SYGGGSGNIW LDNVNCRGTE NSLWDCSKNS  360
WGNHNCVHNE DAGVECS                                               377

SEQ ID NO: 506          moltype = AA  length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 506
HHHHHHHHGE RGSPGPKGAP GAPGIPGLPG PAAEKGEKGA AGRDGTPGVQ GPQGPPGSKG  60
EAGLQGLTGA PGKQGATGAP GPRGEKGSKG DIGLTGPKGE HGTKGDKGDL GLPGNKGDMG  120
MKGDTGPMGS PGAQGGKGDA GKPGLPGLAG SPGVKGDQGK PGVQGVPGPQ GAPGLSGAKG  180
EPGRTGLPGP AGPPGIAGNP GIAGVKGSKG DTGIQGQKGT KGESGVPGLV GRKGDTGSPG  240
LAGPKGEPGR VGQKGDPGMK GSSGQQGQKG EKGQKGESFQ RVRIMGGTNR GRAEVYYNNE  300
WGTICDDDWQ NNDATVFCRM LGYSRGRALY KYGGGSGNIW LDNVNCRGTE NSLWDCSKNS  360
WGNHNCVHNE DAGVECS                                               377

SEQ ID NO: 507          moltype = AA  length = 377
FEATURE                 Location/Qualifiers
REGION                  1..377
```

```
                        note = Description of Artificial Sequence: Synthetic
                         polypeptide
source                  1..377
                        mol_type = protein
                        organism = synthetic construct
SEQUENCE: 507
HHHHHHHHGE RGSPGPKGAP GAPGIPGLPG PAAEKGEKGA AGRDGTPGVQ GPQGPPGSKG     60
EAGLQGLTGA PGKQGATGAP GPRGEKGSKG DIGLTGPKGE HGTKGDKGDL GLPGNKGDMG    120
MKGDTGPMGS PGAQGGKGDA GKPGLPGLAG SPGVKGDQGK PGVQGVPGPQ GAPGLSGAKG    180
EPGRTGLPGP AGPPGIAGNP GIAGVKGSKG DTGIQGQKGT KGESGVPGLV GRKGDTGSPG    240
LAGPKGEPGR VGQKGDPGMK GSSGQQGQKG EKGQKGESFQ RVRIMGGTNR GRAEVYYNNE    300
WGTICDDDWD NNDATVFCRM LGYSRGRALS SYGGGSGNIW LDNVNCRGTE STLWSCTKNS    360
WGNHNCVHNE DAGVECS                                                  377

SEQ ID NO: 508          moltype = AA length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 508
HHHHHHHHGE RGSPGPKGAP GAPGIPGLPG PAAEKGEKGA AGRDGTPGVQ GPQGPPGSKG     60
EAGLQGLTGA PGKQGATGAP GPRGEKGSKG DIGLTGPKGE HGTKGDKGDL GLPGNKGDMG    120
MKGDTGPMGS PGAQGGKGDA GKPGLPGLAG SPGVKGDQGK PGVQGVPGPQ GAPGLSGAKG    180
EPGRTGLPGP AGPPGIAGNP GIAGVKGSKG DTGIQGQKGT KGESGVPGLV GRKGDTGSPG    240
LAGPKGEPGR VGQKGDPGMK GSSGQQGQKG EKGQKGESFQ RVRIMGGTNR GRAEVYYNNE    300
WGTICDDDWD NNDATVFCRM LGYSRGRALS SYGGGSGNIW LDNVNCRGTE NSLWDCSKNS    360
WGHHDCSHEE DAGVECS                                                  377

SEQ ID NO: 509          moltype = AA length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 509
HHHHHHHHGE RGSPGPKGAP GAPGIPGLPG PAAEKGEKGA AGRDGTPGVQ GPQGPPGSKG     60
EAGLQGLTGA PGKQGATGAP GPRGEKGSKG DIGLTGPKGE HGTKGDKGDL GLPGNKGDMG    120
MKGDTGPMGS PGAQGGKGDA GKPGLPGLAG SPGVKGDQGK PGVQGVPGPQ GAPGLSGAKG    180
EPGRTGLPGP AGPPGIAGNP GIAGVKGSKG DTGIQGQKGT KGESGVPGLV GRKGDTGSPG    240
LAGPKGEPGR VGQKGDPGMK GSSGQQGQKG EKGQKGESFQ RVRIMGGTNR GRAEVYYNNE    300
WGTICDDEWQ NNDATVFCRM LGYSRGRALS SYGGGSGNIW LDNVQCRGTE NSLWDCTKNS    360
WGNHNCVHNE DAGVECS                                                  377

SEQ ID NO: 510          moltype = AA length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 510
HHHHHHHHGE RGSPGPKGAP GAPGIPGLPG PAAEKGEKGA AGRDGTPGVQ GPQGPPGSKG     60
EAGLQGLTGA PGKQGATGAP GPRGEKGSKG DIGLTGPKGE HGTKGDKGDL GLPGNKGDMG    120
MKGDTGPMGS PGAQGGKGDA GKPGLPGLAG SPGVKGDQGK PGVQGVPGPQ GAPGLSGAKG    180
EPGRTGLPGP AGPPGIAGNP GIAGVKGSKG DTGIQGQKGT KGESGVPGLV GRKGDTGSPG    240
LAGPKGEPGR VGQKGDPGMK GSSGQQGQKG EKGQKGENSV SVRIMGSSNR GRAEVYYNNE    300
WGTICDDDWD NNDATVFCRM LGYSRGRALS SYGGGSGNIW LDNVNCRGTE NSLWDCSKNS    360
WGNHNCVHNE DAGVECS                                                  377

SEQ ID NO: 511          moltype = AA length = 109
FEATURE                 Location/Qualifiers
source                  1..109
                        mol_type = protein
                        organism = Homo sapiens
SEQUENCE: 511
EVQLVESGGG LVQPGGSLRL SCAASGFTFS SYAMSWVRQA PGKGLEWVSA ISGSGGSTYY     60
ADSVKGRFTI SRDNSKNTLY LQMNSLRAED TAVYYCAKWG QGTLVTVSS               109

SEQ ID NO: 512          moltype = AA length = 106
FEATURE                 Location/Qualifiers
source                  1..106
                        mol_type = protein
                        organism = Homo sapiens
```

```
SEQUENCE: 512
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ SYSTPPFGQG TKLEIK                   106

SEQ ID NO: 513           moltype = AA  length = 101
FEATURE                  Location/Qualifiers
source                   1..101
                         mol_type = protein
                         organism = Homo sapiens
SEQUENCE: 513
NSVSVRIVGS SNRGRAEVYY SGTWGTICDD EWQNSDAIVF CRMLGYSKGR ALYKVGAGTG     60
QIWLDNVQCR GTESTLWSCT KNSWGHHDCS HEEDAGVECS V                        101

SEQ ID NO: 514           moltype = AA  length = 100
FEATURE                  Location/Qualifiers
source                   1..100
                         mol_type = protein
                         organism = Mus musculus
SEQUENCE: 514
SFQRVRIMGG TNRGRAEVYY NNEWGTICDD DWDNNDATVF CRMLGYSRGR ALSSYGGGSG     60
NIWLDNVNCR GTENSLWDCS KNSWGNHNCV HNEDAGVECS                          100

SEQ ID NO: 515           moltype = AA  length = 100
FEATURE                  Location/Qualifiers
REGION                   1..100
                         note = Description of Artificial Sequence: Synthetic
                          polypeptide
source                   1..100
                         mol_type = protein
                         organism = synthetic construct
SEQUENCE: 515
SFQRVRIMGG TNRGRAEVYY SGTWGTICDD DWDNNDATVF CRMLGYSRGR ALSSYGGGSG     60
NIWLDNVNCR GTENSLWDCS KNSWGNHNCV HNEDAGVECS                          100

SEQ ID NO: 516           moltype = AA  length = 100
FEATURE                  Location/Qualifiers
REGION                   1..100
                         note = Description of Artificial Sequence: Synthetic
                          polypeptide
source                   1..100
                         mol_type = protein
                         organism = synthetic construct
SEQUENCE: 516
SFQRVRIMGG TNRGRAEVYY NNEWGTICDD EWQNSDATVF CRMLGYSKGR ALSSYGGGSG     60
NIWLDNVNCR GTENSLWDCS KNSWGNHNCV HNEDAGVECS                          100

SEQ ID NO: 517           moltype = AA  length = 100
FEATURE                  Location/Qualifiers
REGION                   1..100
                         note = Description of Artificial Sequence: Synthetic
                          polypeptide
source                   1..100
                         mol_type = protein
                         organism = synthetic construct
SEQUENCE: 517
SFQRVRIMGG TNRGRAEVYY NNEWGTICDD DWQNNDATVF CRMLGYSRGR ALYKYGGGSG     60
NIWLDNVNCR GTENSLWDCS KNSWGNHNCV HNEDAGVECS                          100

SEQ ID NO: 518           moltype = AA  length = 100
FEATURE                  Location/Qualifiers
REGION                   1..100
                         note = Description of Artificial Sequence: Synthetic
                          polypeptide
source                   1..100
                         mol_type = protein
                         organism = synthetic construct
SEQUENCE: 518
SFQRVRIMGG TNRGRAEVYY NNEWGTICDD DWDNNDATVF CRMLGYSRGR ALSSYGGGSG     60
NIWLDNVNCR GTESTLWSCT KNSWGNHNCV HNEDAGVECS                          100

SEQ ID NO: 519           moltype = AA  length = 100
FEATURE                  Location/Qualifiers
REGION                   1..100
                         note = Description of Artificial Sequence: Synthetic
                          polypeptide
source                   1..100
                         mol_type = protein
                         organism = synthetic construct
SEQUENCE: 519
```

```
SFQRVRIMGG TNRGRAEVYY NNEWGTICDD DWDNNDATVF CRMLGYSRGR ALSSYGGGSG    60
NIWLDNVNCR GTENSLWDCS KNSWGHHDCS HEEDAGVECS                        100

SEQ ID NO: 520          moltype = AA  length = 100
FEATURE                 Location/Qualifiers
REGION                  1..100
                        note = Description of Artificial Sequence: Synthetic
                         polypeptide
source                  1..100
                        mol_type = protein
                        organism = synthetic construct
SEQUENCE: 520
SFQRVRIMGG TNRGRAEVYY NNEWGTICDD EWQNNDATVF CRMLGYSRGR ALSSYGGGSG    60
NIWLDNVQCR GTENSLWDCT KNSWGNHNCV HNEDAGVECS                        100

SEQ ID NO: 521          moltype = AA  length = 100
FEATURE                 Location/Qualifiers
REGION                  1..100
                        note = Description of Artificial Sequence: Synthetic
                         polypeptide
source                  1..100
                        mol_type = protein
                        organism = synthetic construct
SEQUENCE: 521
NSVSVRIMGS SNRGRAEVYY NNEWGTICDD DWDNNDATVF CRMLGYSRGR ALSSYGGGSG    60
NIWLDNVNCR GTENSLWDCS KNSWGNHNCV HNEDAGVECS                        100

SEQ ID NO: 522          moltype = AA  length = 101
FEATURE                 Location/Qualifiers
REGION                  1..101
                        note = Description of Artificial Sequence: Synthetic
                         polypeptide
source                  1..101
                        mol_type = protein
                        organism = synthetic construct
SEQUENCE: 522
NSVSVRIVGS SNRGRAEVYY NNEWGTICDD EWQNSDAIVF CRMLGYSKGR ALYKVGAGTG    60
QIWLDNVQCR GTESTLWSCT KNSWGHHDCS HEEDAGVECS V                      101

SEQ ID NO: 523          moltype = AA  length = 101
FEATURE                 Location/Qualifiers
REGION                  1..101
                        note = Description of Artificial Sequence: Synthetic
                         polypeptide
source                  1..101
                        mol_type = protein
                        organism = synthetic construct
SEQUENCE: 523
NSVSVRIVGS SNRGRAEVYY SGTWGTICDD DWDNNDAIVF CRMLGYSRGR ALYKVGAGTG    60
QIWLDNVQCR GTESTLWSCT KNSWGHHDCS HEEDAGVECS V                      101

SEQ ID NO: 524          moltype = AA  length = 101
FEATURE                 Location/Qualifiers
REGION                  1..101
                        note = Description of Artificial Sequence: Synthetic
                         polypeptide
source                  1..101
                        mol_type = protein
                        organism = synthetic construct
SEQUENCE: 524
NSVSVRIVGS SNRGRAEVYY SGTWGTICDD EWDNSDAIVF CRMLGYSKGR ALSSVGAGTG    60
QIWLDNVQCR GTESTLWSCT KNSWGHHDCS HEEDAGVECS V                      101

SEQ ID NO: 525          moltype = AA  length = 101
FEATURE                 Location/Qualifiers
REGION                  1..101
                        note = Description of Artificial Sequence: Synthetic
                         polypeptide
source                  1..101
                        mol_type = protein
                        organism = synthetic construct
SEQUENCE: 525
NSVSVRIVGS SNRGRAEVYY SGTWGTICDD EWQNSDAIVF CRMLGYSKGR ALYKVGAGTG    60
QIWLDNVQCR GTENSLWDCS KNSWGHHDCS HEEDAGVECS V                      101

SEQ ID NO: 526          moltype = AA  length = 101
FEATURE                 Location/Qualifiers
REGION                  1..101
                        note = Description of Artificial Sequence: Synthetic
```

```
                          polypeptide
source                    1..101
                          mol_type = protein
                          organism = synthetic construct
SEQUENCE: 526
NSVSVRIVGS SNRGRAEVYY SGTWGTICDD EWQNSDAIVF CRMLGYSKGR ALYKVGAGTG   60
QIWLDNVQCR GTESTLWSCT KNSWGNHNCV HNEDAGVECS V                     101

SEQ ID NO: 527            moltype = AA   length = 101
FEATURE                   Location/Qualifiers
REGION                    1..101
                          note = Description of Artificial Sequence: Synthetic
                          polypeptide
source                    1..101
                          mol_type = protein
                          organism = synthetic construct
SEQUENCE: 527
NSVSVRIVGS SNRGRAEVYY SGTWGTICDD DWDNSDAIVF CRMLGYSKGR ALYKVGAGTG   60
QIWLDNVNCR GTESTLWSCS KNSWGHHDCS HEEDAGVECS V                     101

SEQ ID NO: 528            moltype = AA   length = 7
FEATURE                   Location/Qualifiers
source                    1..7
                          mol_type = protein
                          organism = synthetic construct
SEQUENCE: 528
AASRLQS                                                             7
```

The invention claimed is:

1. A method of treating cancer in a subject, comprising administering to the subject an antibody or antigen binding fragment thereof that binds to human MARCO (SEQ ID NO: 384) comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
   a. CDR-H1 comprises the sequence GFSLTSYHVS (SEQ ID NO: 2),
   b. CDR-H2 comprises the sequence AIWTGGSIA (SEQ ID NO: 3),
   c. CDR-H3 comprises the sequence DLSDYYS-SYTSFDY (SEQ ID NO: 4),
   d. CDR-L1 comprises the sequence ASEGISNDLA (SEQ ID NO: 431) or XASEGISNDLA (SEQ ID NO: 383), wherein X is arginine (R) or leucine (L),
   e. CDR-L2 comprises the sequence AASRLQS (SEQ ID NO: 528) or AASRLQD (SEQ ID NO: 8), and
   f. CDR-L3 comprises the sequence QQSYKYPLT (SEQ ID NO: 9).

2. The method of claim 1, wherein the cancer is a solid cancer or a liquid cancer.

3. The method of claim 2, wherein the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

4. The method of claim 3, wherein the cancer is colon cancer, breast cancer, basal-like breast cancer, ovarian cancer, or gastric cancer.

5. The method of claim 1, wherein the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator.

6. The method of claim 5, wherein the immunotherapy is an anti-PD1 antibody, an anti-PDL1 antibody, or an anti-CTLA4 antibody.

7. The method of claim 1, wherein MARCO is expressed at a higher level on a tumor immune cell as compared to a non-tumor immune cell.

8. The method of claim 7, wherein IL-10 is expressed at a higher level on a tumor immune cell as compared to a non-tumor immune cell.

9. The method of claim 1, wherein CDR-L2 comprises the sequence AASRLQS (SEQ ID NO: 528) and CDR-L1 comprises the sequence RASEGISNDLA (SEQ ID NO: 27).

10. The method of claim 1, wherein the VH sequence comprises the VH sequence set forth in SEQ ID NO: 61; and the VL sequence comprises the VL sequence set forth in SEQ ID NO: 66.

11. The method of claim 1, wherein the VH sequence comprises the VH sequence set forth in SEQ ID NO: 434; and the and the VL sequence comprises the VL sequence set forth in SEQ ID NO: 439.

12. The method of claim 1, wherein the antibody comprises a heavy chain and a light chain, wherein the sequence of the heavy chain comprises the heavy chain sequence set forth in SEQ ID NO: 65 and the sequence of the light chain comprises the light chain sequence set forth in SEQ ID NO: 70.

13. The method of claim 1, wherein the antibody comprises a heavy chain and a light chain, wherein the sequence of the heavy chain comprises the heavy chain sequence set forth in SEQ ID NO: 438 and the sequence of the light chain comprises the light chain sequence set forth in SEQ ID NO: 443.

14. A method of increasing an immune response in a subject, comprising administering to the subject an antibody or antigen binding fragment thereof that binds to human MARCO (SEQ ID NO: 384) comprising a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
  a. CDR-H1 comprises the sequence GFSLTSYHVS (SEQ ID NO: 2),
  b. CDR-H2 comprises the sequence AIWTGGSIA (SEQ ID NO: 3),
  c. CDR-H3 comprises the sequence DLSDYYSYTSFDY (SEQ ID NO: 4),
  d. CDR-L1 comprises the sequence ASEGISNDLA (SEQ ID NO: 431) or XASEGISNDLA (SEQ ID NO: 383), wherein X is arginine (R) or leucine (L),
  e. CDR-L2 comprises the sequence AASRLQS (SEQ ID NO: 528) or AASRLQD (SEQ ID NO: 8), and
  f. CDR-L3 comprises the sequence QQSYKYPLT (SEQ ID NO: 9).

15. The method of claim 14, wherein the subject is human.

16. The method of claim 14, wherein the subject has cancer.

17. The method of claim 16, wherein the cancer is a solid cancer or a liquid cancer.

18. The method of claim 17, wherein the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

19. The method of claim 18, wherein the cancer is colon cancer, breast cancer, basal-like breast cancer, ovarian cancer, or gastric cancer.

20. The method of claim 14, wherein the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator.

21. The method of claim 20, wherein the immunotherapy is an anti-PD1 antibody, an anti-PDL1 antibody, or an anti-CTLA4 antibody.

22. The method of claim 14, wherein MARCO is expressed at a higher level on a tumor immune cell as compared to a non-tumor immune cell.

23. The method of claim 14, wherein IL-10 is expressed at a higher level on a tumor immune cell as compared to a non-tumor immune cell.

24. The method of claim 14, wherein CDR-L2 comprises the sequence AASRLQS (SEQ ID NO: 528) and CDR-L1 comprises the sequence RASEGISNDLA (SEQ ID NO: 27).

25. The method of claim 14, wherein the VH sequence comprises the VH sequence set forth in SEQ ID NO: 61; and the VL sequence comprises the VL sequence set forth in SEQ ID NO: 66.

26. The method of claim 14, wherein the VH sequence comprises the VH sequence set forth in SEQ ID NO: 434; and the and the VL sequence comprises the VL sequence set forth in SEQ ID NO: 439.

27. The method of claim 14, wherein the antibody comprises a heavy chain and a light chain, wherein the sequence of the heavy chain comprises the heavy chain sequence set forth in SEQ ID NO: 65 and the sequence of the light chain comprises the light chain sequence set forth in SEQ ID NO: 70.

28. A method of treating cancer in a subject or increasing an immune response in a subject, comprising administering to the subject an antibody or antigen binding fragment thereof that binds to human MARCO (SEQ ID NO: 384), comprising three heavy chain complementarity determining regions (CDRs) (CDR-H1, CDR-H2, and CDR-H3) and three light chain complementarity determining regions (CDRs) (CDR-L1, CDR-L2, and CDR-L3), wherein the CDR-H1, CDR-H2, and CDR-H3 are from a heavy chain variable domain (VH) comprising the amino acid sequence set forth in SEQ ID NO: 61; and wherein the CDR-L1, CDR-L2, and CDR-L3 are from a light chain variable domain (VL) comprising the amino acid sequence set forth in SEQ ID NO: 66.

29. The method of claim 28, wherein the VH sequence comprises the VH sequence set forth in SEQ ID NO: 61; and the VL sequence comprises the VL sequence set forth in SEQ ID NO: 66.

30. The method of claim 28, wherein the antibody comprises a heavy chain and a light chain, wherein the sequence of the heavy chain comprises the heavy chain sequence set forth in SEQ ID NO: 65 and the sequence of the light chain comprises the light chain sequence set forth in SEQ ID NO: 70.

31. The method of claim 28, wherein the cancer is selected from the group consisting of: lung cancer, lung adeno carcinoma, lung squamous cell carcinoma, lung small cell carcinoma, kidney cancer, liver cancer, renal cell carcinoma, cervical cancer, ovarian cancer, colorectal cancer, colon cancer, neuroblastoma, breast cancer, triple negative breast cancer, basal-like breast cancer, gastric cancer, stomach cancer, bladder cancer, prostate cancer, skin cancer, lymphoma, Diffuse large B-cell lymphoma (DLBCL), small lymphocytic lymphoma, non-Hodgkin lymphoma, mesothelioma, pancreatic cancer, thyroid cancer, endometrial cancer, head and neck cancer, or head and neck squamous carcinoma (HNSC) cancer.

* * * * *